(12) United States Patent
White et al.

(10) Patent No.: US 8,426,447 B2
(45) Date of Patent: Apr. 23, 2013

(54) SPIRO-TRICYCLIC RING COMPOUNDS AS BETA-SECRETASE MODULATORS AND METHODS OF USE

(75) Inventors: Ryan White, Somerville, MA (US); Albert Amegadzie, Moorpark, CA (US); Marian C. Bryan, West Hills, CA (US); Jian Jeffrey Chen, Camarillo, CA (US); Alan C. Cheng, Cambridge, MA (US); Thomas Dineen, Somerville, MA (US); Oleg Epstein, Belmont, MA (US); Vijay Keshav Gore, Thousand Oaks, CA (US); Zihao Hua, Tewksbury, MA (US); Jason Brooks Human, Boston, MA (US); Hongbing Huang, Lexington, MA (US); Charles Kreiman, Watertown, MA (US); Daniel La, Brookline, MA (US); Qingyian Liu, Camarillo, CA (US); Vu Van Ma, Simi Valley, CA (US); Isaac Marx, Cambridge, MA (US); Vinod F Patel, Acton, MA (US); Wenyuan Qian, Camarillo, CA (US); Matthew Weiss, Boston, MA (US); Chester Chenguang Yuan, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 342 days.

(21) Appl. No.: 12/558,426

(22) Filed: Sep. 11, 2009

(65) Prior Publication Data
US 2010/0087429 A1 Apr. 8, 2010

Related U.S. Application Data

(60) Provisional application No. 61/096,082, filed on Sep. 11, 2008.

(51) Int. Cl.
*A61K 31/44* (2006.01)
*C07D 311/82* (2006.01)
*C07D 401/00* (2006.01)
*C07D 413/00* (2006.01)

(52) U.S. Cl.
USPC ............... 514/336; 546/268.1; 546/271.4; 549/223

(58) Field of Classification Search .......... 514/336; 546/268.1, 271.4; 549/223
See application file for complete search history.

(56) References Cited

U.S. PATENT DOCUMENTS

| 5,441,870 A | 8/1995 | Seubert et al. |
| 5,712,130 A | 1/1998 | Hajko et al. |
| 5,942,400 A | 8/1999 | Anderson |
| 6,835,565 B1 | 12/2004 | Gurney et al. |
| 6,864,290 B2 | 3/2005 | Schostarez et al. |
| 6,962,934 B2 | 11/2005 | Warpehoski et al. |
| 6,982,264 B2 | 1/2006 | John et al. |
| 6,992,103 B2 | 1/2006 | Faller et al. |
| 7,034,182 B2 | 4/2006 | Fang et al. |
| 7,067,542 B2 | 6/2006 | Schostarez et al. |
| 7,074,799 B2 | 7/2006 | Bakthavatchalam et al. |
| 7,109,217 B2 | 9/2006 | Coburn et al. |
| 7,115,652 B2 | 10/2006 | Yang et al. |
| 7,132,568 B2 | 11/2006 | Yang et al. |
| 7,176,242 B2 | 2/2007 | John et al. |
| 7,223,774 B2 | 5/2007 | Aquino et al. |
| 7,244,725 B2 | 7/2007 | John et al. |
| 7,244,755 B2 | 7/2007 | Fisher et al. |
| 7,253,198 B2 | 8/2007 | Demont et al. |
| 7,291,620 B2 | 11/2007 | Coburn et al. |
| 7,312,360 B2 | 12/2007 | TenBrink et al. |

(Continued)

FOREIGN PATENT DOCUMENTS

| EP | 01942105 A1 | 9/2008 |
| EP | 02305672 A1 | 6/2011 |

(Continued)

OTHER PUBLICATIONS

Joachim et al., *Alz. Dis. Assoc. Dis.*, 6:7-34 (1992).
Selkoe, Neuron, 6:487 (1991).
Seubert et al., Nature, 359:325-327 (1992).
Citron, Trends in Pharmacological Sciences, 25(2):92-97 (2004).
Nature Medicine (Jun. 22, 2008).
Nature, 402:537-554 (1999) (p. 510).
Sabbagh, M. et al., *Alz. Dis. Rev.* 3:1-19 (1997).

(Continued)

*Primary Examiner* — Susannah Chung
(74) *Attorney, Agent, or Firm* — G. Prabhakar Reddy

(57) ABSTRACT

The present invention comprises a new class of compounds useful for the modulation of Beta-secretase enzyme activity and for the treatment of Beta-secretase mediated diseases, including Alzheimer's disease (AD) and related conditions. In one embodiment, the compounds have a general Formula I

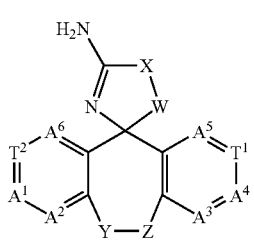

wherein $A^1$, $A^2$, $A^3$, $A^4$, $A^5$, $A^6$, $T^1$, $T^2$, W, X, Y and Z of Formula I are defined herein. The invention also includes use of these compounds in pharmaceutical compositions for treatment, prophylactic or therapeutic, of disorders and conditions related to the activity of beta-secretase protein. Such disorders include, for example, Alzheimer's Disease, cognitive deficits, cognitive impairment, schizophrenia and other central nervous system conditions related to and/or caused by the formation and/or deposition of plaque on the brain. The invention also comprises further embodiments of Formula I, intermediates and processes useful for the preparation of compounds of Formula I.

22 Claims, No Drawings

U.S. PATENT DOCUMENTS

| | | |
|---|---|---|
| 7,348,448 B2 | 3/2008 | Nantermet et al. |
| 7,371,853 B2 | 5/2008 | Coburn et al. |
| 7,582,650 B2 * | 9/2009 | DeCorte et al. ............. 514/299 |
| 7,592,348 B2 | 9/2009 | Zhu et al. |
| 2003/0109559 A1 | 6/2003 | Gailunas et al. |
| 2005/0038019 A1 | 2/2005 | Beck |
| 2005/0054690 A1 | 3/2005 | Aquino et al. |
| 2005/0282825 A1 | 12/2005 | Malamas et al. |
| 2006/0111370 A1 | 5/2006 | Zhu et al. |
| 2006/0211740 A1 | 9/2006 | Demont et al. |
| 2006/0241133 A1 | 10/2006 | Shearman et al. |
| 2006/0287297 A1 * | 12/2006 | DeCorte et al. ............. 514/216 |
| 2007/0004786 A1 | 1/2007 | Malamas et al. |
| 2007/0027199 A1 | 2/2007 | Malamas et al. |
| 2007/0072925 A1 | 3/2007 | Malamas et al. |
| 2007/0203116 A1 | 8/2007 | Quagliato et al. |
| 2007/0287692 A1 | 12/2007 | Wu et al. |
| 2008/0200445 A1 | 8/2008 | Zhu et al. |
| 2009/0082560 A1 | 3/2009 | Kobayashi et al. |
| 2009/0209529 A1 | 8/2009 | Andreini et al. |
| 2009/0209755 A1 | 8/2009 | Suzuki et al. |
| 2009/0306047 A1 | 12/2009 | Zhu et al. |
| 2010/0075957 A1 | 3/2010 | Tamura et al. |
| 2010/0160290 A1 | 6/2010 | Kobayashi et al. |

FOREIGN PATENT DOCUMENTS

| | | |
|---|---|---|
| WO | 01/70671 A2 | 9/2001 |
| WO | 03/002518 A1 | 1/2003 |
| WO | 03/030886 A2 | 4/2003 |
| WO | 04/000821 A1 | 12/2003 |
| WO | 2004/099376 A2 | 11/2004 |
| WO | 2005058311 A1 | 6/2005 |
| WO | 2005097767 A1 | 10/2005 |
| WO | 2006041404 A1 | 4/2006 |
| WO | 2006076284 A2 | 7/2006 |
| WO | 2006138230 A2 | 12/2006 |
| WO | 2006138265 A2 | 12/2006 |
| WO | 2007011810 A1 | 1/2007 |
| WO | 2007011833 A1 | 1/2007 |
| WO | 2007038271 A1 | 4/2007 |
| WO | WO2007114771 A1 | 10/2007 |
| WO | WO2007120096 A1 | 10/2007 |
| WO | WO2007145571 A1 | 12/2007 |
| WO | WO2007149033 A1 | 12/2007 |
| WO | 2008054698 A1 | 5/2008 |
| WO | WO2008076045 A1 | 6/2008 |
| WO | WO2008076046 A1 | 6/2008 |
| WO | 2008103351 A2 | 8/2008 |
| WO | WO2008092785 A1 | 8/2008 |
| WO | 2008118379 A2 | 10/2008 |
| WO | WO2008150217 A1 | 12/2008 |
| WO | 2009131974 A1 | 10/2009 |
| WO | 2009131975 A1 | 10/2009 |
| WO | 2009134617 A1 | 11/2009 |
| WO | 2010010014 A1 | 1/2010 |

OTHER PUBLICATIONS

Cole, S.L., Vasser, R., Molecular Degeneration 2:22, 2007.
Luo et al., Nature Neuroscience, 4:231-232 (2001).
Bioorganic & Medicinal Chemistry Letters 20 (2010) 2068-2073.
J. Med. Chem. 2009.
Alzheimer's Research & Therapy 2009.
Expert Opin. Emerging Drugs (2008) 13(2):255-271.
J. Med. Chem. 2008, 51, 6259-6262.
Chem. Soc. Rev., 2009, 38, 2698-2715.
Sabbagh_ClinicalDev_2009.
J. Neurosci., Oct. 14, 2009 • 29(41):12787-12794.
Zhou_et_al_ARKIVOC_2010_vi_84-88.
Nowak_Bioorganic_Medicinal_Chemistry_Letters_2009.
Malamas_Bioorganic_Medicinal_Chemistry_Letters_2009.
Zhou_Bioorganic_Medicinal_Chemistry_Letters_2010.
Malamas_JMedChem_2009.

* cited by examiner

SPIRO-TRICYCLIC RING COMPOUNDS AS BETA-SECRETASE MODULATORS AND METHODS OF USE

RELATED APPLICATIONS

This application claims the benefit of U.S. Provisional Patent Application No. 61/096,082 filed on Sep. 11, 2008, which is hereby incorporated herein by reference in its entirety.

FIELD OF THE INVENTION

The invention relates generally to pharmaceutically active compounds, pharmaceutical compositions and methods of use thereof, to treat Beta-Secretase mediated diseases and conditions, including, without limitation, Alzheimer's disease, plaque formation on the brain and related disorders.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., Alz. Dis. Assoc. Dis., 6:7-34 (1992).

Several lines of evidence indicate that progressive cerebral deposition of A-beta plays a seminal role in the pathogenisis of AD and can precede cognitive symptoms by years or even decades. Selkoe, Neuron, 6:487 (1991). Release of A-beta from neuronal cells grown in culture and the presence of A-beta in cerebrospinal fluid (CSF) of both normal individuals and AD patients has been demonstrated. Seubert et al., Nature, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits in the brains of Alzheimer's Disease patients. Citron, Trends in Pharmacological Sciences, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the two-molecule, soluble form of the peptide is a causative agent in the development of Alzheimer's and that the two-molecule form is the smallest synaptotoxic species of soluble amyloid beta oligomer. Shnakar, G. M., Nature Medicine (Jun. 22, 2008) online doi 10:1038 nm 1782.

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., Nature, 402:537-554 (1999) (p 510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., Alz. Dis. Rev. 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., Molecular Degeneration 2:22, 2007. When crossed with transgenic mice that over express APP, the progeny of BACE deficient mice show reduced amounts of A-beta in brain extracts as compares with control animals (Luo et al., Nature Neuroscience, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, WO 04/094384, WO 04/094413, WO 03/006423, WO 03/050073, WO 03/029169 and WO 04/000821, describe inhibitors of BACE, useful for treating AD and other beta-secretase mediated disorders.

BRIEF DESCRIPTION OF THE INVENTION

The present invention provides a new class of compounds useful for the modulation of beta secretase activity. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

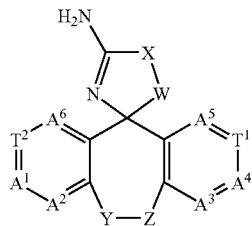

wherein $A^1$, $A^2$, $A^3$, $A^4$, $A^5$, $A^6$, $T^1$, $T^2$, W, X, Y and Z of Formula I are described below. The invention also provides procedures for making compounds of Formula I, II, III, IV and sub-Formulas A-D thereof, as well as intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are generally defined by the compound of Formula I:

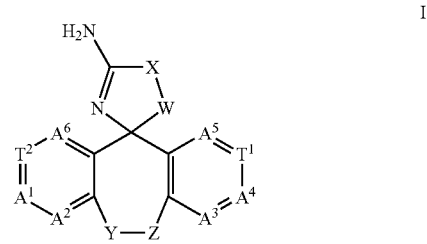

wherein
$A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N;
$T^1$ is $CR^2$ or N;
$T^2$ is $CR^7$ or N, provided that (1) when $T^1$ is N then $A^5$ is $CR^1$; and (2) no more than four of $A^1$, $A^2$, $A^3$, $A^4$, $A^5$, $A^6$, $T^1$ and $T^2$ is N;

each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$ $C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_o$ $C_{1-6}$-alkyl, —$NHC_{1-6}$-alkyl and —$C(O)C_{1-6}$-alkyl are optionally substituted with 1-3 substituents of F, oxo or OH;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2$ $NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CR^1R^1$;

X is O or S;

Y is absent or Y is $CR^1R^1$, $C(=O)$, O, $NR^1$, or $S(O)_o$;

Z is absent or Z is $CR^1R^1$, $C(=O)$, O, $NR^1$, or $S(O)_o$; and each o independently, is 0, 1 or 2, provided that both Y and Z are not absent, —O— or —$S(O)_o$—.

In another embodiment of the present invention, the compounds are defined by Formula I-A

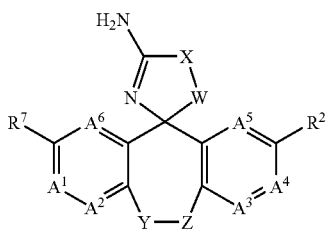

I-A wherein $A^1$ is $CR^6$ or N;

$A^1$ is $CR^6$ or N;
$A^2$ is $CR^5$ or N;
$A^3$ is $CR^4$ or N;
$A^4$ is $CR^3$ or N;
$A^5$ is $CR^1$ or N;
$A^6$ is $CR^8$ or N; provided that no more than four of $A^1$, $A^2$, $A^3$, $A^4$, $A^5$ and $A^6$ is N;

each of $R^1$, $R^4$, $R^5$ and $R^8$, independently, is H, F, Cl, Br, $CF_3$, $OCF_3$, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $S(O)_oC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CR^1R^1$;

X is O or S;

Y is absent or Y is $CR^{10}R^{10}$, $C(=O)$, O, $NR^{10}$, or $S(O)_o$ wherein o is 0, 1 or 2; and Z is absent or Z is $CR^{10}R^{10}$, $C(=O)$, O, $NR^{10}$, or $S(O)_o$; and each o independently, is 0, 1 or 2, provided that both Y and Z are not absent, —O— or —$S(O)_o$—.

In one embodiment of the invention, the compounds, including stereoisomers, tautomers, solvates, pharmaceutically acceptable salts, derivatives or prodrugs thereof, are generally defined by Formula II

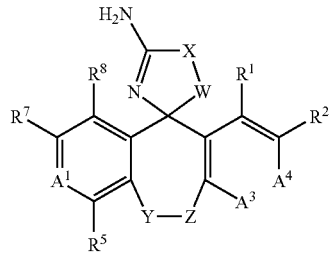

II wherein
$A^1$ is $CR^6$ or N;
$A^3$ is $CR^4$ or N;
$A^4$ is $CR^3$ or N; provided no more than one of $A^1$, $A^3$ and $A^4$ is N;

each of $R^1$, $R^4$, $R^5$ and $R^8$, independently, is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CR^1R^1$;

X is O or S;

Y is absent or Y is $CR^{10}R^{10}$, $C(=O)$, O, $NR^{10}$, or $S(O)_o$ wherein o is 0, 1 or 2; and Z is absent or Z is $CR^{10}R^{10}$, $C(=O)$, O, $NR^{10}$, or $S(O)_o$ wherein o is 0, 1 or 2, provided that both Y and Z are not —O— or —$S(O)_o$—.

In another embodiment of the invention, the compounds, including stereoisomers, tautomers, solvates, pharmaceutically acceptable salts, derivatives or prodrugs thereof, are generally defined by Formula II-A

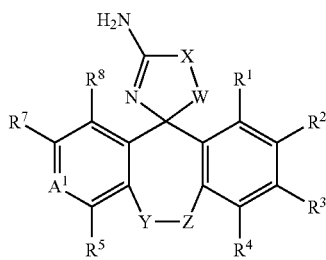

II-A $A^1$ is $CR^6$ or N;

each of $R^1$, $R^4$, $R^5$ and $R^8$, independently, is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHC_{1-3}$alkyl;

X is O or S;

Y is absent or Y is $CR^{10}R^{10}$, $C(=O)$, O, $NR^{10}$, or $S(O)_o$ wherein o is 0, 1 or 2; and Z is absent or Z is $CR^{10}R^{10}$, $C(=O)$, O, $NR^{10}$, or $S(O)_o$ wherein o is 0, 1 or 2, provided that both Y and Z are not —O— or —$S(O)_o$—.

In another embodiment of the invention, the compounds, including stereoisomers, tautomers, solvates, pharmaceutically acceptable salts, derivatives or prodrugs thereof, are generally defined by Formula II-B

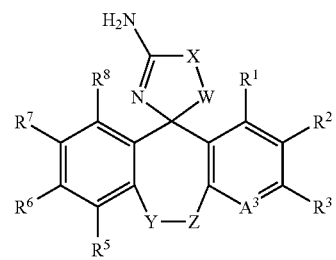

II-B $A^3$ is $CR^4$ or N;

each of $R^1$, $R^4$, $R^5$ and $R^8$, independently, is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is $-C(O)R^{10}$, $-S(O)_2R^{10}$, $-C(O)NHR^{10}$, $-NHC(O)R^{10}$, $-NHC(O)NHR^{10}$, $-S(O)_2NHR^{10}$ or $-NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, $-CHF$ or $-CHC_{1-3}$alkyl;

X is O or S;

Y is absent or Y is $CR^{10}R^{10}$, $C(=O)$, O, $NR^{10}$, or $S(O)_o$ wherein o is 0, 1 or 2; and Z is absent or Z is $CR^{10}R^{10}$, $C(=O)$, O, $NR^{10}$, or $S(O)_o$ wherein o is 0, 1 or 2, provided that both Y and Z are not $-O-$ or $-S(O)_o-$.

In another embodiment of the invention, the compounds, including stereoisomers, tautomers, solvates, pharmaceutically acceptable salts, derivatives or prodrugs thereof, are generally defined by Formula II-C

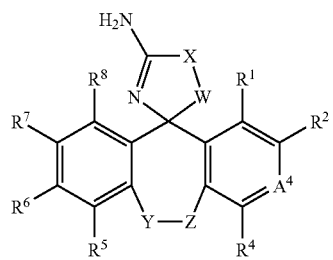

II-C $A^4$ is $CR^3$ or N;

each of $R^1$, $R^4$, $R^5$ and $R^8$, independently, is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is $-C(O)R^{10}$, $-S(O)_2R^{10}$, $-C(O)NHR^{10}$, $-NHC(O)R^{10}$, $-NHC(O)NHR^{10}$, $-S(O)_2NHR^{10}$ or $-NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, $-CHF$ or $-CHC_{1-3}$alkyl;

X is O or S;

Y is absent or Y is $CR^{10}R^{10}$, $C(=O)$, O, $NR^{10}$, or $S(O)_o$ wherein o is 0, 1 or 2; and Z is absent or Z is $CR^{10}R^{10}$, $C(=O)$, O, $NR^{10}$, or $S(O)_o$ wherein o is 0, 1 or 2, provided that both Y and Z are not $-O-$ or $-S(O)_o-$.

In another embodiment, the invention provides compounds, and pharmaceutically acceptable salt forms thereof, having a general Formula III:

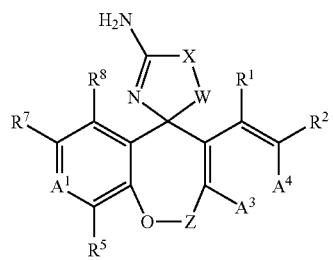

III wherein $A^1$ is $CR^6$ or N;

$A^3$ is $CR^4$ or N;

$A^4$ is $CR^3$ or N; provided no more than one of $A^1$, $A^3$ and $A^4$ is N;

each of $R^1$, $R^4$, $R^5$ and $R^8$, independently, is H, F, Cl, Br, $CF_3$, $OCF_3$, $CH_3$, $C_2H_5$, CN, OH, $OCH_3$;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHC_{1-3}$alkyl;

X is O or S; and

Z is absent or $CR^{10}R^{10}$.

In another embodiment, the invention provides compounds, and pharmaceutically acceptable salt forms thereof, having a general Formula III-A:

III-A wherein $A^1$ is $CR^6$ or N;

$A^3$ is $CR^4$ or N;

$A^4$ is $CR^3$ or N; provided no more than one of $A^1$, $A^3$ and $A^4$ is N;

each of $R^1$, $R^4$, $R^5$ and $R^8$, independently, is H, F, Cl, Br, $CF_3$, $OCF_3$, $CH_3$, $C_2H_5$, CN, OH, $OCH_3$;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$ each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$ —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHC_{1-3}$ alkyl;

X is O or S; and

Y is absent or $CR^{10}R^{10}$.

In another embodiment, the invention provides compounds, and solvates, stereoisomers, tautomers and pharmaceutically acceptable salt forms thereof, having a general Formula IV:

IV wherein $A^1$ is $CR^6$ or N;

$A^3$ is $CR^4$ or N;

$A^4$ is $CR^3$ or N; provided no more than one of $A^1$, $A^3$ and $A^4$ is N;

each of $R^1$, $R^4$, $R^5$ and $R^8$, independently, is H, F, Cl, Br, $CF_3$, $OCF_3$, $CH_3$, $C_2H_5$, CN, OH, $OCH_3$;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHC_{1-3}$ alkyl; and

X is O or S; and

Y is O, S or $CR^{10}R^{10}$.

In another embodiment, the invention provides compounds, and solvates, stereoisomers, tautomers and pharmaceutically acceptable salt forms thereof, having a general Formula IV-A:

IV-A wherein $A^1$ is $CR^6$ or N;

$A^3$ is $CR^4$ or N;

$A^4$ is $CR^3$ or N; provided no more than one of $A^1$, $A^3$ and $A^4$ is N;

each of $R^1$, $R^4$, $R^5$ and $R^8$, independently, is H, F, Cl, Br, $CF_3$, $OCF_3$, $CH_3$, $C_2H_5$, CN, OH, $OCH_3$;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHC_{1-3}$ alkyl; and

X is O or S.

In another embodiment, the invention provides compounds, and solvates, stereoisomers, tautomers and pharmaceutically acceptable salt forms thereof, having a general Formula IV-B:

IV-B wherein each of $R^1$, $R^4$, $R^5$ and $R^8$, independently, is H, F, Cl, Br, $CF_3$, $OCF_3$, $CH_3$, $C_2H_5$, CN, OH, $OCH_3$;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —C(O)$R^{10}$, —S(O)$_2R^{10}$, —C(O)NH$R^{10}$, —NHC(O)$R^{10}$ —NHC(O)NH$R^{10}$, —S(O)$_2$NH$R^{10}$ or —NHS(O)$_2R^{10}$;

each $R^{10}$, independently, is H, halo, haloalkyl, CN, OH, NO$_2$, NH$_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is CH$_2$, —CHF or —CHC$_{1-3}$ alkyl; and

X is O or S.

In another embodiment, the invention provides compounds, and solvates, stereoisomers, tautomers and pharmaceutically acceptable salt forms thereof, having a general Formula IV-C:

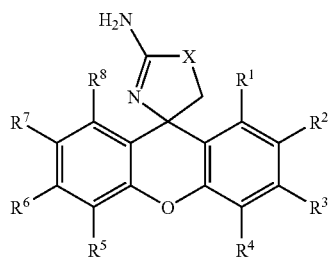

wherein each of $R^1$, $R^4$, $R^5$ and $R^8$, independently, is H, F, Cl, Br, CF$_3$, OCF$_3$, CH$_3$, C$_2$H$_5$, CN, OH, OCH$_3$;

each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, O$R^{10}$, S$R^{10}$, N$R^{10}R^{10}$, C(O)$R^{10}$, S(O)$_2R^{10}$, N$R^{10}$C(O)$R^{10}$, C(O)N$R^{10}R^{10}$, N$R^{10}$S(O)$_2R^{10}$, S(O)$_2$N$R^{10}$, N$R^{10}$C(O)N$R^{10}R^{10}$, or a 5- or 6-membered monocyclic or 8-, 9- or 10-membered bicyclic heterocyclic, aryl or heteroaryl ring, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-substituents of $R^9$ or $R^{10}$;

each of $R^3$ and $R^6$, independently, is H, halo, haloalkyl, haloalkoxyl, $C_{1-6}$-alkyl, CN, OH, OC$_{1-6}$-alkyl, SC$_{1-6}$-alkyl, NHC$_{1-6}$-alkyl or C(O)C$_{1-6}$-alkyl;

each $R^9$, independently, is —C(O)$R^{10}$, —S(O)$_2R^{10}$, —C(O)NH$R^{10}$, —NHC(O)$R^{10}$, —NHC(O)NH$R^{10}$, —S(O)$_2$NH$R^{10}$ or —NHS(O)$_2R^{10}$;

each $R^{10}$, independently, is H, halo, haloalkyl, CN, OH, NO$_2$, NH$_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a 5- or 6-membered monocyclic or 7- to 11-membered bicyclic heterocyclic, aryl or heteroaryl ring, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, NO$_2$, NH$_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl; and X is O or S.

The present invention contemplates that the various different embodiments below of each individual variable $A^1$, $A^2$, $A^3$, $A^4$, $A^5$, $A^6$, $T^1$, $T^2$, W, X, Y and Z, as described below, may be applied "in conjunction with any of the other {above and below} embodiments" to create various embodiments of general Formulas I, II, III and IV and each sub-formula thereof described hereinabove, which are not literally described herein.

In another embodiment, the invention includes compounds wherein $A^1$ is C$R^6$, in conjunction with any of the above or below embodiments.

In another embodiment, the invention includes compounds wherein $A^1$ is N, in conjunction with any of the above or below embodiments.

In another embodiment, the invention includes compounds wherein $A^2$ is C$R^5$, in conjunction with any of the above or below embodiments.

In another embodiment, the invention includes compounds wherein $A^2$ is N, in conjunction with any of the above or below embodiments.

In another embodiment, the invention includes compounds wherein $A^3$ is C$R^4$, in conjunction with any of the above or below embodiments.

In another embodiment, the invention includes compounds wherein $A^3$ is N, in conjunction with any of the above or below embodiments.

In another embodiment, the invention includes compounds wherein $A^4$ is C$R^3$, in conjunction with any of the above or below embodiments.

In another embodiment, the invention includes compounds wherein $A^4$ is N, in conjunction with any of the above or below embodiments.

In another embodiment, the invention includes compounds wherein $A^5$ is C$R^1$, in conjunction with any of the above or below embodiments.

In another embodiment, the invention includes compounds wherein $A^5$ is N, in conjunction with any of the above or below embodiments.

In another embodiment, the invention includes compounds wherein $A^6$ is C$R^8$, in conjunction with any of the above or below embodiments.

In another embodiment, the invention includes compounds wherein $A^6$ is N, in conjunction with any of the above or below embodiments.

In another embodiment, the invention includes compounds wherein one of $A^1$, $A^2$, $A^3$, $A^4$, $A^5$ and $A^6$ is N and the other five of $A^1$, $A^2$, $A^3$, $A^4$, $A^5$ and $A^6$ is C as defined in Formula I, in conjunction with any of the above or below embodiments.

In another embodiment, the invention includes compounds wherein each of $A^1$, $A^2$, $A^3$, $A^4$, $A^5$ and $A^6$ is C as defined in Formula I, in conjunction with any of the above or below embodiments.

In another embodiment, the invention includes compounds wherein each of $R^1$, $R^4$, $R^5$ and $R^8$, independently, is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein $R^1$ is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein $R^4$ is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein $R^5$ is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein $R^8$ is H, F, Cl, Br, $CF_3$, $OCF_3$, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^1$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^4$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein $R^8$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment, the invention includes compounds wherein each of $R^1$, $R^4$, $R^5$ and $R^8$, independently, is H, F, Cl, $CF_3$, methyl, CN, OH, $OCH_3$, $SCH_3$ or $NHCH_3$, in conjunction with any of the above or below embodiments.

In another embodiment, the invention includes compounds wherein each of $R^1$, $R^4$, $R^5$ and $R^8$, independently, is H, F, methyl, CN or OH, in conjunction with any of the above or below embodiments.

In another embodiment, the invention includes compounds wherein each of $R^1$, $R^4$, $R^5$ and $R^8$, independently, is H or F, in conjunction with any of the above or below embodiments.

In another embodiment, the invention includes compounds wherein each of $R^1$, $R^4$, $R^5$ and $R^8$, independently, is H, in conjunction with any of the above or below embodiments.

In another embodiment, the invention includes compounds wherein $R^2$ is H, halo, haloalkyl, haloalkoxyl, $C_{1-6}$-alkyl, $C_{2-6}$ alkenyl, $C_{2-6}$-alkynyl, $C_{3-8}$-cycloalkyl, $OR^{10}$, $SR^{10}$ or $NR^{10}R^{10}$, wherein the $C_{1-6}$-alkyl, $C_{2-6}$-alkenyl, $C_{2-6}$-alkynyl and $C_{3-8}$-cycloalkyl are optionally substituted with 1-5 substituents of $R^9$ or $R^{10}$, in conjunction with any of the above or below embodiments.

In another embodiment, the invention includes compounds wherein $R^2$ is halo, haloalkyl, haloalkoxyl, $C_{1-6}$-alkyl, $C_{2-6}$ alkenyl, $C_{2-6}$-alkynyl, $OR^{10}$ or $SR^{10}$, wherein the $C_{1-6}$-alkyl, $C_{2-6}$-alkenyl, $C_{2-6}$-alkynyl and $C_{3-8}$-cycloalkyl are optionally substituted, independently, with 1-5 substituents of $R^9$ or $R^{10}$, in conjunction with any of the above or below embodiments.

In another embodiment, the invention includes compounds wherein $R^2$ is F, $CF_3$, $OCF_3$, $C_{1-6}$-alkyl or $OR^{10}$, wherein the $C_{1-6}$-alkyl is optionally substituted, independently, with 1-5 substituents of $R^9$ or $R^{10}$, in conjunction with any of the above or below embodiments.

In another embodiment, the invention includes compounds wherein $R^2$ is F, $CF_3$, $OCF_3$, $C_{1-6}$-alkyl or $OR^{10}$, in conjunction with any of the above or below embodiments.

In another embodiment, the invention includes compounds wherein $R^2$ is a 4-, 5-, 6- or 7-membered monocyclic or 6-12-membered bicyclic heterocyclic, aryl or heteroaryl ring, said ring optionally substituted, independently, with 1-5 substituents of $R^9$ or $R^{10}$, in conjunction with any of the above or below embodiments.

In another embodiment, the invention includes compounds wherein $R^2$ is a 5- or 6-membered monocyclic heterocyclic, aryl or heteroaryl ring, said ring optionally substituted, independently, with 1-5 substituents of $R^9$ or $R^{10}$, in conjunction with any of the above or below embodiments.

In another embodiment, the invention includes compounds wherein $R^2$ is a 5- or 6-membered monocyclic or 8-, 9- or 10-membered bicyclic heterocyclic, aryl or heteroaryl ring, said ring optionally substituted, independently, with 1-5 substituents of $R^9$ or $R^{10}$, in conjunction with any of the above or below embodiments.

In another embodiment, the invention includes compounds wherein $R^2$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of $R^9$ or $R^{10}$, in conjunction with any of the above or below embodiments.

In another embodiment, the invention includes compounds wherein $R^2$ is a ring selected from phenyl, pyridyl, pyrimidyl, pyridazinyl, pyrazinyl, triazinyl, thiophenyl, furyl, dihydrofuranyl, pyrrolyl, pyrazolyl, imidazolyl, imidazopyridiyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl, pyranyl, tetrahydropyranyl, duhydropyranyl, 2-oxo-5-aza-bicycloheptanyl, azetetinyl, pyridinonyl, pyrrolidinonyl, cyclopropyl, cyclobutyl, cyclopentyl, cyclohenxyl, cyclohexenyl, tetrahydropyridinyl, dihydropyridinyl, thiopyranyl, dihydrothiopyranyl, benzofuranyl, dihydrobenzofuranyl, benzimidazolyl, benzopyrazolyl, said ring optionally substituted, independently, with 1-5 substituents of $R^9$ or $R^{10}$, in conjunction with any of the above or below embodiments.

In another embodiment, the invention includes compounds wherein $R^2$ is halo, haloalkyl, haloalkoxyl, $C_{1-6}$-alkyl, $C_{2-6}$ alkenyl, $C_{2-6}$-alkynyl, $C_{3-8}$-cycloalkyl, $OR^{10}$, $SR^{10}$, $NR^{10}R^{10}$ or a ring selected from phenyl, pyridine, pyrimidine, dihydropyran, morpholine, oxazole, isoxazole, azetidine, pyran, pyrazole and imidazole, wherein the $C_{1-6}$-alkyl, $C_{2-6}$-alkenyl, $C_{2-6}$-alkynyl, $C_{3-8}$-cycloalkyl and ring are optionally substituted with 1-5 substituents of $R^9$ or $R^{10}$, in conjunction with any of the above or below embodiments.

In another embodiment, the invention includes compounds wherein each of $R^2$ and $R^7$, independently, is H, halo, haloalkyl, haloalkoxyl, $C_{1-6}$-alkyl, $C_{2-6}$ alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 6-12-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$, in conjunction with any of the above or below embodiments.

In another embodiment, the invention includes compounds wherein each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, in conjunction with any of the above or below embodiments.

In another embodiment, the invention includes compounds wherein each of $R^2$ and $R^7$, independently, is a fully saturated or partially or fully unsaturated 4-, 5-, 6- or 7-membered monocyclic or 7-, 8-, 9- or 10-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$, in conjunction with any of the above or below embodiments.

In another embodiment, the invention includes compounds wherein one of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-10}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, and the other of $R^2$ and $R^7$, independently, is a fully saturated or partially or fully unsaturated 4-, 5-, 6- or 7-membered monocyclic or 8-, 9-, or 10-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$, in conjunction with any of the above or below embodiments.

In another embodiment, the invention includes compounds wherein one of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, and the other of $R^2$ and $R^7$, independently, is a 4-, 5-, 6- or 7-membered monocyclic or 7- to 11-membered bicyclic heterocyclic, aryl or heteroaryl ring, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$, in conjunction with any of the above or below embodiments.

In another embodiment, the invention includes compounds wherein $R^7$ is a 5- or 6-membered monocyclic or 7- to 11-membered bicyclic heterocyclic, aryl or heteroaryl ring, said ring optionally substituted, independently, with 1-5 substituents of $R^9$ or $R^{10}$, in conjunction with any of the above or below embodiments.

In another embodiment, the invention includes compounds wherein $R^7$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of $R^9$ or $R^{10}$, in conjunction with any of the above or below embodiments.

In another embodiment, the invention includes compounds wherein $R^7$ is a ring selected from phenyl, naphthyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, quinolinyl, isoquinolinyl, naphthyridinyl, benzofuranyl, benzimidazolyl, benzopyrazolyl, morpholinyl, piperidinyl, piperazinyl and pyranyl, said ring optionally substituted, independently, with 1-5 substituents of $R^9$ or $R^{10}$, in conjunction with any of the above or below embodiments.

In another embodiment, the invention includes compounds wherein $R^7$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, or $R^7$ is —$OC_{1-10}$alkyl, said ring and —$OC_{1-10}$alkyl optionally substituted, independently, with 1-5 substituents of $R^9$ or $R^{10}$, in conjunction with any of the above or below embodiments.

In another embodiment, the invention includes compounds wherein $R^2$ is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, and $R^7$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of $R^9$ or $R^{10}$, in conjunction with any of the above or below embodiments.

In another embodiment, the invention includes compounds wherein $R^7$ is a ring selected from phenyl, pyridyl, pyrimidyl, pyridazinyl, pyrazinyl, triazinyl or thiophenyl, said ring optionally substituted, independently, with 1-5 substituents of $R^9$ or $R^{10}$, in conjunction with any of the above or below embodiments.

In another embodiment, the invention includes compounds wherein $R^7$ is a ring selected from phenyl, pyridyl, pyrimidyl, pyridazinyl or pyrazinyl, said ring optionally substituted, independently, with 1-5 substituents of $R^9$ or $R^{10}$, in conjunction with any of the above or below embodiments.

In another embodiment, the invention includes compounds wherein $R^7$ is phenyl, pyridyl or pyrimidyl, each of which is optionally substituted with 1-5 substituents of F, Cl, Br, I, $CF_3$, $C_2F_5$, haloalkoxyl, $C_{1-6}$-alkyl, CN, OH, $OC_{1-6}$-alkyl, $SC_{1-6}$-alkyl, $SC_{1-6}$-alkyl, $S(O)_oC_{1-6}$-alkyl wherein o is 0, 1 or 2, $NHC_{1-6}$-alkyl or $C(O)C_{1-6}$-alkyl, in conjunction with any of the above or below embodiments.

In another embodiment, the invention includes compounds wherein $R^7$ is pyridyl, pyrimidyl, pyridazinyl, pyrazinyl or triazinyl, each of which is optionally substituted with 1-5 substituents of F, Cl, Br, I, $CF_3$, $C_2F_5$, haloalkoxyl, $C_{1-6}$-alkyl, CN, OH, $OC_{1-6}$-alkyl, $SC_{1-6}$-alkyl, $SC_{1-6}$-alkyl, $S(O)_oC_{1-6}$-alkyl wherein o is 0, 1 or 2, $NHC_{1-6}$-alkyl or $C(O)C_{1-6}$-alkyl, in conjunction with any of the above or below embodiments.

In another embodiment, the invention includes compounds wherein each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein each of $R^3$ and $R^6$, independently, is H, F, Cl, $CF_3$, $CH_3$, CN, OH, $OCH_3$, $SCH_3$ or $NHCH_3$, in conjunction with any of the above or below embodiments.

In another embodiment, the invention includes compounds wherein each of $R^3$ and $R^6$, independently, is H, F or methyl, in conjunction with any of the above or below embodiments.

In another embodiment, the invention includes compounds wherein each of $R^3$ and $R^6$, independently, is H, in conjunction with any of the above or below embodiments.

In another embodiment, the invention includes compounds wherein $R^3$ is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein $R^6$ is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein W is $CR^1R^1$, in conjunction with any of the above or below embodiments.

In another embodiment, the invention includes compounds wherein W is $CH_2$, —CHF or —$CHC_{1-3}$alkyl, in conjunction with any of the above or below embodiments.

In another embodiment, the invention includes compounds wherein W is $CH_2$, —CHF or —$CHCH_3$, in conjunction with any of the above or below embodiments.

In another embodiment, the invention includes compounds wherein X is O or S, in conjunction with any of the above or below embodiments.

In another embodiment, the invention includes compounds wherein X is O, in conjunction with any of the above or below embodiments.

In another embodiment, the invention includes compounds wherein X is S, in conjunction with any of the above or below embodiments.

In another embodiment, the invention includes compounds wherein Y is absent or Y is $CR^{10}R^{10}$, $C(=O)$, O, $NR^{10}$, or $S(O)_o$ wherein o is 0, 1 or 2; in conjunction with any of the above or below embodiments.

In another embodiment, the invention includes compounds wherein Y is absent; in conjunction with any of the above or below embodiments.

In another embodiment, the invention includes compounds wherein Y is $CR^{10}R^{10}$, $C(=O)$, O, $NR^{10}$, or $S(O)_o$ wherein o is 0, 1 or 2, in conjunction with any of the above or below embodiments.

In another embodiment, the invention includes compounds wherein Y is $CR^{10}R^{10}$, O, $NR^{10}$ or $S(O)_o$ wherein o is 0, 1 or 2, in conjunction with any of the above or below embodiments.

In another embodiment, the invention includes compounds wherein Y is $CR^{10}R^{10}$ or O, in conjunction with any of the above or below embodiments.

In another embodiment, the invention includes compounds wherein Y is O, in conjunction with any of the above or below embodiments.

In another embodiment, the invention includes compounds wherein Y is $CR^{10}R^{10}$, in conjunction with any of the above or below embodiments.

In another embodiment, the invention includes compounds wherein Z is absent or Z is $CR^{10}R^{10}$, $C(=O)$, O, $NR^{10}$, or $S(O)_o$ wherein o is 0, 1 or 2; in conjunction with any of the above or below embodiments.

In another embodiment, the invention includes compounds wherein Z is absent; in conjunction with any of the above or below embodiments.

In another embodiment, the invention includes compounds wherein Z is $CR^{10}R^{10}$, $C(=O)$, O, $NR^{10}$, or $S(O)_o$ wherein o is 0, 1 or 2, in conjunction with any of the above or below embodiments.

In another embodiment, the invention includes compounds wherein Z is $CR^{10}R^{10}$, O, $NR^{10}$, or $S(O)_o$ wherein o is 0, 1 or 2, in conjunction with any of the above or below embodiments.

In another embodiment, the invention includes compounds wherein Z is $CR^{10}R^{10}$ or O, in conjunction with any of the above or below embodiments.

In another embodiment, the invention includes compounds wherein Z is O, in conjunction with any of the above or below embodiments.

In another embodiment, the invention includes compounds wherein Z is $CR^{10}R^{10}$, in conjunction with any of the above or below embodiments.

In another embodiment, the invention includes compounds wherein Y is absent and Z is $CR^{10}R^{10}$, $C(=O)$, O, $NR^{10}$ or $S(O)_o$ wherein o is 0, 1 or 2, in conjunction with any of the above or below embodiments.

In another embodiment, the invention includes compounds wherein Y is absent and Z is $CR^{10}R^{10}$, O, $NR^{10}$ or $S(O)_o$ wherein o is 0, 1 or 2, in conjunction with any of the above or below embodiments.

In another embodiment, the invention includes compounds wherein Y is absent and Z is $CR^{10}R^{10}$ or O, in conjunction with any of the above or below embodiments.

In another embodiment, the invention includes compounds wherein Y is O and Z is absent or $CR^{10}R^{10}$, in conjunction with any of the above or below embodiments.

In another embodiment, the invention includes compounds wherein Y is O and Z is absent, in conjunction with any of the above or below embodiments.

In another embodiment, the invention includes compounds wherein X is O, Y is O and Z is absent or $CR^{10}R^{10}$, in conjunction with any of the above or below embodiments.

In another embodiment, the invention includes compounds wherein X is O, Y is O and Z is absent, in conjunction with any of the above or below embodiments.

In another embodiment, the invention includes compounds wherein Z is absent and Y is $CR^{10}R^{10}$ or O, in conjunction with any of the above or below embodiments.

In another embodiment, the invention includes compounds wherein Y is $CR^{10}R^{10}$ and Z is $CR^{10}R^{10}$, $C(=O)$, O, $NR^{10}$, or $S(O)_o$ wherein o is 0, 1 or 2, in conjunction with any of the above or below embodiments.

In another embodiment, the invention includes compounds wherein Y is $CR^{10}R^{10}$, $C(=O)$, O, $NR^{10}$, or $S(O)_o$ wherein o is 0, 1 or 2 and Z is $CR^{10}R^{10}$, in conjunction with any of the above or below embodiments.

In another embodiment, the compounds of Formula I or I-A includes compounds wherein each of Y and Z, independently, is $CR^{10}R^{10}$, in conjunction with any of the above or below embodiments.

In another embodiment, the invention includes compounds wherein each of Y and Z, independently, is absent or $CR^{10}R^{10}$, $C(=O)$, O, $NR^{10}$, or $S(O)_o$ wherein o is 0, 1 or 2; provided that both Y and Z are not absent, —O— or —$S(O)_o$—, in conjunction with any of the above or below embodiments.

In another embodiment, the invention includes compounds wherein one of $R^2$ and $R^7$, independently, is a fully saturated or partially or fully unsaturated 5- or 6-membered monocyclic or 9- or 10-membered bicyclic ring formed of carbon atoms, said ring optionally including 1-4 heteroatoms selected from O, N, or S and optionally substituted, independently with 1-5 substituents of $R^9$ or $R^{10}$;

the other of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, wherein the $C_{1-6}$-alkyl, $C_{2-6}$-alkenyl, $C_{2-6}$-alkynyl, $C_{3-8}$-cycloalkyl, $C_{4-8}$-cycloalkenyl are optionally substituted, independently, with 1-5 substituents of $R^9$ or $R^{10}$; and each of $R^1$, $R^4$, $R^5$ and $R^8$, independently, is H, F, Cl, $CF_3$, $OCF_3$, methyl, ethyl, CN, OH, $OCH_3$, $SCH_3$, $NHCH_3$ or $C(O)CH_3$; and each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl, in conjunction with any of the above or below embodiments.

In another embodiment, the invention includes compounds wherein $R^2$ is H, halo, haloalkyl, haloalkoxyl, $C_{1-6}$-alkyl, $C_{2-6}$alkenyl, $C_{2-6}$-alkynyl, $C_{3-8}$-cycloalkyl, $OR^{10}$, $SR^{10}$ or $NR^{10}R^{10}$, wherein the $C_{1-6}$-alkyl, $C_{2-6}$-alkenyl, $C_{2-6}$-alkynyl and $C_{3-8}$-cycloalkyl are optionally substituted with 1-5 substituents of $R^9$ or $R^{10}$; and each of $R^1$, $R^4$, $R^5$ and $R^8$, independently, is H, F, Cl, $CF_3$, methyl, CN, OH, $OCH_3$, $SCH_3$ or $NHCH_3$; and each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl; $R^7$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of $R^9$ or $R^{10}$;

Y is O; and

Z is absent or $CR^{10}R^{10}$, in conjunction with any of the above or below embodiments.

In another embodiment, the compounds of Formula I or I-A includes compounds wherein $R^2$ is halo, haloalkyl, haloalkoxyl, $C_{1-6}$-alkyl, $C_{2-6}$alkenyl, $C_{2-6}$-alkynyl, $OR^{10}$ or $SR^{10}$, wherein the $C_{1-6}$-alkyl, $C_{2-6}$-alkenyl, $C_{2-6}$-alkynyl and $C_{3-8}$-cycloalkyl are optionally substituted, independently, with 1-5 substituents of $R^9$ or $R^{10}$;

each of $R^1$, $R^4$, $R^5$ and $R^8$, independently, is H, F, methyl, CN or OH;

each of $R^3$ and $R^6$, independently, is H, F, Cl, $CF_3$, methyl, CN, OH, $OCH_3$, $SCH_3$ or $NHCH_3$;

$R^7$ is a ring selected from phenyl, pyridyl, pyrimidyl, pyridazinyl, pyrazinyl, triazinyl or thiophenyl, said ring optionally substituted, independently, with 1-5 substituents of $R^9$ or $R^{10}$;

W is $CH_2$, —CHF or —$CCH_3$;

X is O;

Y is O; and

Z is absent or $CR^{10}R^{10}$, in conjunction with any of the above or below embodiments.

In another embodiment, the invention includes compounds wherein $R^2$ is F, $CF_3$, $OCF_3$, $C_{1-6}$-alkyl or $OR^{10}$, wherein the $C_{1-6}$-alkyl is optionally substituted, independently, with 1-5 substituents of $R^9$ or $R^{10}$;

each of $R^1$, $R^4$, $R^5$ and $R^8$, independently, is H or F;

each of $R^3$ and $R^6$, independently, is H, F or methyl;

$R^7$ is a ring selected from phenyl, pyridyl, pyrimidyl, pyridazinyl or pyrazinyl, said ring optionally substituted, independently, with 1-5 substituents of $R^9$ or $R^{10}$;

W is $CH_2$, —CHF or —$CCH_3$;

X is O;

Y is O; and

Z is absent or $CR^{10}R^{10}$, in conjunction with any of the above or below embodiments.

In another embodiment, the invention includes compounds, and stereoisomers, tautomers and pharmaceutically acceptable salt thereof, wherein $A^1$ is $CR^6$;

$A^3$ is $CR^4$;

$A^4$ is $CR^3$;

each of $R^1$, $R^4$, $R^5$ and $R^8$, independently, is H, F, Cl, Br, $CF_3$, $OCF_3$, $CH_3$, $C_2H_5$, CN, OH, $OCH_3$;

$R^2$ is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a 5- or 6-membered monocyclic or 7- to 11-membered bicyclic heterocyclic, aryl or heteroaryl ring, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

$R^7$ is phenyl, pyridyl or pyrimidyl, each of which is optionally substituted with 1-5 substituents of F, Cl, Br, I, $CF_3$, $C_2F_5$, haloalkoxyl, $C_{1-6}$-alkyl, CN, OH, $OC_{1-6}$-alkyl, $SC_{1-6}$-alkyl, $SC_{1-6}$-alkyl, $S(O)_oC_{1-6}$-alkyl wherein o is 0, 1 or 2, $NHC_{1-6}$-alkyl or $C(O)C_{1-6}$-alkyl.

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a 5- or 6-membered monocyclic or 7- to 11-membered bicyclic heterocyclic, aryl or heteroaryl ring, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHCH_3$; and

X is O, in conjunction with any of the above or below embodiments.

In another embodiment, the invention provides the compound of Formula I, or a pharmaceutically acceptable salt thereof, selected from 2'-(2,2-dimethylpropoxy)-7'-(5-pyrimidinyl)spiro[1,3-oxazole-4,9'-xanthen]-2-amine;

(4S)-2'-propoxy-7'-(5-pyrimidinyl)spiro[1,3-oxazole-4,9'-xanthen]-2-amine;
2'-(2-methylpropoxy)-7'-(5-pyrimidinyl)spiro[1,3-oxazole-4,9'-xanthen]-2-amine;
2'-propoxy-7'-(5-pyrimidinyl)spiro[1,3-oxazole-4,9'-xanthen]-2-amine;
(4S)-2'-methoxy-7'-(5-pyrimidinyl)spiro[1,3-oxazole-4,9'-xanthen]-2-amine;
(4R)-2'-propoxy-7'-(5-pyrimidinyl)spiro[1,3-oxazole-4,9'-xanthen]-2-amine;
(4S)-2'-(5-chloro-2-fluorophenyl)-7'-methoxyspiro[1,3-oxazole-4,9'-xanthen]-2-amine trifluoroacetic acid;
2'-chloro-7'-(5-pyrimidinyl)spiro[1,3-oxazole-4,9'-xanthen]-2-amine;
2'-methoxy-7'-(5-pyrimidinyl)spiro[1,3-oxazole-4,9'-xanthen]-2-amine;
2'-(2-fluoro-5-methoxyphenyl)-7'-methoxyspiro[1,3-oxazole-4,9'-xanthen]-2-amine;
2'-(2-fluoro-3-pyridinyl)-7'-methoxyspiro[1,3-oxazole-4,9'-xanthen]-2-amine;
2'-(2-fluoro-3-methoxyphenyl)-7'-methoxyspiro[1,3-oxazole-4,9'-xanthen]-2-amine;
2'-(3-chloro-2-fluorophenyl)-7'-methoxyspiro[1,3-oxazole-4,9'-xanthen]-2-amine;
2'-(2-fluoro-5-methoxyphenyl)-6'-methylspiro[1,3-oxazole-4,9'-xanthen]-2-amine;
2'-methoxy-7'-(3-methylphenyl)spiro[1,3-oxazole-4,9'-xanthen]-2-amine;
2'-(2-chloro-3-pyridinyl)-7'-methoxyspiro[1,3-oxazole-4,9'-xanthen]-2-amine trifluoroacetic acid;
2'-methoxy-7'-(3-(trifluoromethoxy)phenyl)spiro[1,3-oxazole-4,9'-xanthen]-2-amine;
2'-(5-chloro-2-fluoro-4-methylphenyl)-7'-methoxyspiro[1,3-oxazole-4,9'-xanthen]-2-amine;
(4S)-6'-methyl-2'-(3-(trifluoromethoxy)phenyl)spiro[1,3-oxazole-4,9'-xanthen]-2-amine;
2'-(3-chlorophenyl)-6'-methylspiro[1,3-oxazole-4,9'-xanthen]-2-amine;
2'-(3-chloro-2-fluorophenyl)-6'-methylspiro[1,3-oxazole-4,9'-xanthen]-2-amine;
2'-methoxy-7'-(4-(trifluoromethoxy)phenyl)spiro[1,3-oxazole-4,9'-xanthen]-2-amine;
2'-(2-chlorophenyl)-7'-methoxyspiro[1,3-oxazole-4,9'-xanthen]-2-amine;
2'-(2-chlorophenyl)-6'-methylspiro[1,3-oxazole-4,9'-xanthen]-2-amine;
2'-(2-fluoro-3-methoxyphenyl)-6'-methylspiro[1,3-oxazole-4,9'-xanthen]-2-aminel;
(4R)-2'-methoxy-7'-(5-pyrimidinyl)spiro[1,3-oxazole-4,9'-xanthen]-2-amine;
2'-methoxy-7'-(2-methylphenyl)spiro[1,3-oxazole-4,9'-xanthen]-2-amine;
6'-methyl-2'-(3-methylphenyl)spiro[1,3-oxazole-4,9'-xanthen]-2-amine;
6'-methyl-2'-(2-methylphenyl)spiro[1,3-oxazole-4,9'-xanthen]-2-amine;
2'-bromo-7'-methoxyspiro[1,3-oxazole-4,9'-xanthen]-2-amine; and
6'-methyl-2'-(4-(trifluoromethoxy)phenyl)spiro[1,3-oxazole-4,9'-xanthen]-2-amine.

In another embodiment, the invention provides the following compounds, or pharmaceutically acceptable salt or stereoisomer thereof, selected from (4S)-2'-(2,2-dimethylpropoxy)-7'-(5-pyrimidinyl)spiro[1,3-oxazole-4,9'-xanthen]-2-amine;
(4S)-2'-(2-methylpropoxy)-7'-(5-pyrimidinyl)spiro[1,3-oxazole-4,9'-xanthen]-2-amine;
(4S)-2'-(5-pyrimidinyl)-7'-(2,2,2-trifluoroethoxy)spiro[1,3-oxazole-4,9'-xanthen]-2-amine;
(4R)-2'-(3,3-dimethylbutyl)-7'-(5-pyrimidinyl)spiro[1,3-oxazole-4,9'-xanthen]-2-amine;
(4S)-2'-(cyclopropylmethoxy)-7'-(5-pyrimidinyl)spiro[1,3-oxazole-4,9'-xanthen]-2-amine;
(4R)-2'-(3,3-dimethyl-1-butyn-1-yl)-7'-(5-pyrimidinyl)spiro[1,3-oxazole-4,9'-xanthen]-2-amine;
(4S)-2'-(((1S)-2,2-difluorocyclopropyl)methoxy)-7'-(5-pyrimidinyl)spiro[1,3-oxazole-4,9'-xanthen]-2-amine;
(4S)-2'-(((1R)-2,2-difluorocyclopropyl)methoxy)-7'-(5-pyrimidinyl)spiro[1,3-oxazole-4,9'-xanthen]-2-amine;
(5S)-7-(2,2-dimethylpropoxy)-3-(3-pyridinyl)spiro[chromeno[2,3-b]pyridine-5,4'-[1,3]oxazol]-2'-amine;
(4S)-2'-(2-fluoro-2-methylpropoxy)-7'-(5-pyrimidinyl)spiro[1,3-oxazole-4,9'-xanthen]-2-amine;
(4S)-2'-(2-methoxy-2-methylpropoxy)-7'-(5-pyrimidinyl)spiro[1,3-oxazole-4,9'-xanthen]-2-amine;
3-(((4S)-2-amino-7'-(3-pyridinyl)spiro[1,3-oxazole-4,9'-xanthen]-2'-yl)oxy)-2,2-dimethylpropanenitrile;
(4S)-2'-((3-methyl-3-oxetanyl)methoxy)-7'-(3-pyridinyl)spiro[1,3-oxazole-4,9'-xanthen]-2-amine;
(5S)-7-((3-methyl-3-oxetanyl)methoxy)-3-phenylspiro[chromeno[2,3-b]pyridine-5,4'-[1,3]oxazol]-2'-amine;
(5S)-3-(3,3-dimethyl-1-butyn-1-yl)-7-(3-pyridinyl)spiro[chromeno[2,3-b]pyridine-5,4'-[1,3]oxazol]-2'-amine;
3-(((5S)-2'-amino-3-(5-pyrimidinyl)spiro[chromeno[2,3-b]pyridine-5,4'-[1,3]oxazol]-7-yl)oxy)-2,2-dimethylpropanenitrile;
(4R)-2'-(3,6-dihydro-2H-pyran-4-yl)-7'-(5-pyrimidinyl)spiro[1,3-oxazole-4,9'-xanthen]-2-amine;
(4R)-2'-(3-methoxy-3-methyl-1-butyn-1-yl)-7'-(5-pyrimidinyl)spiro[1,3-oxazole-4,9'-xanthen]-2-amine;
(5S)-3-(3,3-dimethyl-1-butyn-1-yl)-7-(5-pyrimidinyl)spiro[chromeno[2,3-b]pyridine-5,4'-[1,3]oxazol]-2'-amine;
1-(((4R)-2-amino-7'-(5-pyrimidinyl)spiro[1,3-oxazole-4,9'-xanthen]-2'-yl)ethynyl)cyclobutanol;
N-(3-((4S)-2-amino-4-methyl-5,6-dihydro-4H-1,3-thiazin-4-yl)-4-fluorophenyl)-5-methyl-2-pyrazinecarboxamide;
N-(3-((4S)-2-amino-4-methyl-5,6-dihydro-4H-1,3-thiazin-4-yl)-4-fluorophenyl)-5-methoxy-2-pyrazinecarboxamide;
3-(((5S)-2'-amino-3-phenylspiro[chromeno[2,3-b]pyridine-5,4'-[1,3]oxazol]-7-yl)oxy)-2,2-dimethylpropanenitrile;
(5S)-7-(2,2-dimethylpropoxy)-3-(4-pyridinyl)spiro[chromeno[2,3-b]pyridine-5,4'-[1,3]oxazol]-2'-amine;
(5S)-3-(3,3-dimethyl-1-butyn-1-yl)-7-(2-fluoro-3-pyridinyl)spiro[chromeno[2,3-b]pyridine-5,4'-[1,3]oxazol]-2'-amine;
(4S)-2'-(2,2-dimethyl-4-morpholinyl)-7'-(5-pyrimidinyl)spiro[1,3-oxazole-4,9'-xanthen]-2-amine;
(4S)-2'-(2,2-dimethyl-4-morpholinyl)-7'-(3-pyridinyl)spiro[1,3-oxazole-4,9'-xanthen]-2-amine;
(4S)-2'-((2R,6S)-2,6-dimethyl-4-morpholinyl)-7'-(3-pyridinyl)spiro[1,3-oxazole-4,9'-xanthen]-2-amine;
(4R)-2'-(6,6-dimethyl-3,6-dihydro-2H-pyran-4-yl)-7'-(5-pyrimidinyl)spiro[1,3-oxazole-4,9'-xanthen]-2-amine;
(4S)-4'-fluoro-2'-(3-methoxy-3-methyl-1-butyn-1-yl)-7'-(5-pyrimidinyl)spiro[1,3-oxazole-4,9'-xanthen]-2-amine;
(5S)-3-(3,3-dimethyl-1-butyn-1-yl)-7-(3-pyridinyl)spiro[chromeno[2,3-b]pyridine-5,4'-[1,3]oxazol]-2'-amine;
(4S)-2'-(3,6-dihydro-2H-pyran-4-yl)-4'-fluoro-7'-(3-pyridinyl)spiro[1,3-oxazole-4,9'-xanthen]-2-amine;
(5S)-7-(5-chloro-2-fluorophenyl)-3-(3,6-dihydro-2H-pyran-4-yl)spiro[chromeno[2,3-b]pyridine-5,4'-[1,3]oxazol]-2'-amine;

(4S)-2'-(3,6-dihydro-2H-pyran-4-yl)-4'-fluoro-7'-(5-pyrimidinyl)spiro[1,3-oxazole-4,9'-xanthen]-2-amine;

(5S)-3-(3,6-dihydro-2H-pyran-4-yl)-7-phenylspiro[chromeno[2,3-c]pyridine-5,4'-[1,3]oxazol]-2'-amine;

(5S)-3-(3,6-dihydro-2H-pyran-4-yl)-7-(2-fluoro-3-pyridinyl)spiro[chromeno[2,3-c]pyridine-5,4'-[1,3]oxazol]-2'-amine;

(5S)-3-(3-methoxy-3-methyl-1-butyn-1-yl)-7-(2-pyrazinyl)spiro[chromeno[2,3-b]pyridine-5,4'-[1,3]oxazol]-2'-amine;

(4S)-2'-(2-fluoro-3-pyridinyl)-7'-(3-methyl-5-isoxazolyl)spiro[1,3-oxazole-4,9'-xanthen]-2-amine;

(5S)-3-(2,2-dimethylpropoxy)-7-(3-pyridinyl)spiro[chromeno[2,3-b]pyridine-5,4'-[1,3]oxazol]-2'-amine;

(4S)-4'-fluoro-2'-(2-fluoro-2-methylpropoxy)-7'-(5-pyrimidinyl)spiro[1,3-oxazole-4,9'-xanthen]-2-amine;

(4S)-2'-(3,3-difluoro-1-azetidinyl)-7'-(3-pyridinyl)spiro[1,3-oxazole-4,9'-xanthen]-2-amine;

(4S)-2'-(3,6-dihydro-2H-pyran-4-yl)-3'-fluoro-7'-(5-pyrimidinyl)spiro[1,3-oxazole-4,9'-xanthen]-2-amine;

(4S)-3'-fluoro-2'-(1-methyl-1H-pyrazol-4-yl)-7'-(3-pyridinyl)spiro[1,3-oxazole-4,9'-xanthen]-2-amine;

(5S)-3-((1E)-3,3-dimethyl-1-buten-1-yl)-7-(5-pyrimidinyl)spiro[chromeno[2,3-c]pyridine-5,4'-[1,3]oxazol]-2'-amine;

(4S)-2'-(2,2-dimethyl-4-morpholinyl)-7'-(2-fluoro-3-pyridinyl)spiro[1,3-oxazole-4,9'-xanthen]-2-amine;

(5S)-7-(2-fluoro-3-pyridinyl)-3-(3-pyridinyl)spiro[chromeno[2,3-c]pyridine-5,4'-[1,3]oxazol]-2'-amine;

(5S)-7-(2-fluoro-3-pyridinyl)-3-(4-pyridinyl)spiro[chromeno[2,3-c]pyridine-5,4'-[1,3]oxazol]-2'-amine;

(4S)-2'-(2-fluoro-3-pyridinyl)-7'-(4-morpholinyl)spiro[1,3-oxazole-4,9'-xanthen]-2-amine;

(5S)-7-(2-fluoro-3-pyridinyl)-3-(tetrahydro-2H-pyran-4-yl)spiro[chromeno[2,3-c]pyridine-5,4'-[1,3]oxazol]-2'-amine;

(5S)-3-(2,2-dimethyl-4-morpholinyl)-7-(3-pyridinyl)spiro[chromeno[2,3-c]pyridine-5,4'-[1,3]oxazol]-2'-amine;

(5S)-7-(2-fluoro-3-pyridinyl)-3-((3-methyl-3-oxetanyl)ethynyl)spiro[chromeno[2,3-b]pyridine-5,4'-[1,3]oxazol]-2'-amine;

3-(((4S)-2-amino-4'-fluoro-7'-(2-fluoro-3-pyridinyl)spiro[1,3-oxazole-4,9'-xanthen]-2'-yl)oxy)-2,2-dimethylpropanenitrile;

(5S)-3-(3,6-dihydro-2H-pyran-4-yl)-7-(2-fluoro-5-methyl-3-pyridinyl)spiro[chromeno[2,3-c]pyridine-5,4'-[1,3]oxazol]-2'-amine;

(4S)-4'-fluoro-7'-(2-fluoro-3-pyridinyl)-2'-((3-methyl-3-oxetanyl)methoxy)spiro[1,3-oxazole-4,9'-xanthen]-2-amine;

(5S)-7-(5-chloro-2-fluorophenyl)-3-((3-methyl-3-oxetanyl)ethynyl)spiro[chromeno[2,3-b]pyridine-5,4'-[1,3]oxazol]-2'-amine;

(5S)-7-(3-chlorophenyl)-3-(3,6-dihydro-2H-pyran-4-yl)spiro[chromeno[2,3-c]pyridine-5,4'-[1,3]oxazol]-2'-amine;

(4S)-4'-fluoro-2'-(1-methyl-1H-pyrazol-4-yl)-7'-(3-pyridinyl)spiro[1,3-oxazole-4,9'-xanthen]-2-amine;

(4S)-2'-(3,6-dihydro-2H-pyran-4-yl)-4'-fluoro-7'-(2-fluoro-3-pyridinyl)spiro[1,3-oxazole-4,9'-xanthen]-2-amine;

(5S)-3-(3,6-dihydro-2H-pyran-4-yl)-7-(5-fluoro-3-pyridinyl)spiro[chromeno[2,3-c]pyridine-5,4'-[1,3]oxazol]-2'-amine;

(5S)-3-(6,6-dimethyl-3,6-dihydro-2H-pyran-4-yl)-7-(3-pyridinyl)spiro[chromeno[2,3-c]pyridine-5,4'-[1,3]oxazol]-2'-amine;

(5S)-3-(3,6-dihydro-2H-pyran-4-yl)-7-(6-fluoro-3-pyridinyl)spiro[chromeno[2,3-c]pyridine-5,4'-[1,3]oxazol]-2'-amine;

(4S)-4'-fluoro-7'-(2-fluoro-3-pyridinyl)-2'-(tetrahydro-2H-pyran-4-yl)spiro[1,3-oxazole-4,9'-xanthen]-2-amine;

(4S)-4'-fluoro-7'-(2-fluoro-3-pyridinyl)-2'-(1-methyl-1H-pyrazol-4-yl)spiro[1,3-oxazole-4,9'-xanthen]-2-amine;

(4S)-3'-fluoro-2'-(2-fluoro-2-methylpropoxy)-7'-(3-pyridinyl)spiro[1,3-oxazole-4,9'-xanthen]-2-amine; and (5S)-3-(3,3-dimethyl-1-butyn-1-yl)-7-(5-pyrimidinyl)spiro[chromeno[2,3-c]pyridine-5,4'-[1,3]oxazol]-2'-amine.

In another embodiment, Formulas II, III and IV include any sub-formulas, such as Formula II-A. All of the possible embodiments described herein for various of the R groups of the compounds of Formula I may be applied, as appropriate, to compounds of Formulas II, III and IV and any sub-formulas thereof.

In another embodiment, the invention provides each of the Exemplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the invention described herein.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having α to β number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from α and β. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from α and β. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$ CH=CHCH$_3$ and the like. Similar examples exist for such "alkynyl" radicals, as appreciated by those skilled in the art.

The term "$C_{\alpha-\beta}$alkoxyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane. Carbocyclic may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

Thus, the term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-iso-quinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The phrase "a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S" as used herein is intended to encompass all monocyclic and bicyclic rings as small as three atoms to as large as 12 atoms in size, including both carbocyclic rings and heterocyclic, aromatic and non-aromatic rings. The non-aromatic rings may be partially or fully saturated in nature.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "Formula I" includes any sub formulas, such as Formulas I-A, II, II-A, II-B, II-C, III, III-A, IV, IV-A and IV-B.

The term "pharmaceutically-acceptable" when used with reference to a compound of Formulas I-IV is intended to refer to a form of the compound that is safe for administration. For example, a salt form, a solvate, a hydrate, a prodrug or derivative form of a compound of Formulas I-IV, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-IV are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-IV may be prepared from an inorganic acid or from an organic acid. Examples of such inorganic acids are hydrochloric, hydrobromic, hydroiodic, hydrofluoric, nitric, carbonic, sulfuric and phosphoric acid.

Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-IV include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-IV. A "pharmaceutically-acceptable prodrug" as used herein, denotes a prodrug which is pharmaceutically acceptable. Pharmaceutically acceptable modifications to the compounds of Formula I-IV are readily appreciated by those of ordinary skill in the art.

The compound(s) of Formulas I-IV may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-IV. The compounds of Formulas I-IV can be synthesized according to the procedures described in the following Schemes 1, 2, 3a, 3b, 4 and 5, wherein the substituents are as defined for Formulas I-IV above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DIC—1,3-diisopropylcarbodiimide
DIEA, DIPEA—diisopropylethylamine
DME—dimethoxyethane
DMF—dimethylformamide
DMAP—4-dimethylaminopyridine
DMS—dimethylsulfide
DMSO—dimethylsulfoxide
EDC, EDCI—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen
$NaCNBH_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
PBS—phosphate buffered saline
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone) dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium fluoride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light Scheme 1

-continued

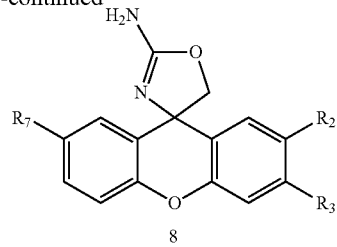

8

Scheme 1 describes an exemplary method for preparing compounds 8 of Formulas I-II, wherein X is O, one of Y and Z is O while the other of Y and Z is absent, $A^1$ is $CR^6$ and $R^1$, $R^4$, $R^5$, $R^6$ and $R^8$ are each H, respectively. As shown, a bromo-benzoic acid 1 can be coupled to a bromo-phenol 2 using a copper reagent in conjunction with a suitable base, such cesium carbonate, under suitable conditions. The coupled ether 3 can then be treated with an acid, such as sulfuric acid, to effect ring closure to the corresponding bromo-xanthene 4. The ketone of xanthene 4 can be converted to the corresponding ene group as shown under suitable conditions, such as using TMS-methyllithuim or triphenylphosphoniummethyl bromide under suitable reaction conditions, respectively, such as in the presence of a suitable base to afford the ene compound 5. Intermediate 5 can be reacted with cyanotosilver in the presence of iodine and ammonium hydroxide to provide the amino-oxazoline intermediate 6. The bromide of compound 6 can then be converted to desired compounds 8 via coupling at the site of the bromide, such as by a Suzuki or Suzuki-like aromatic-halogen exchange reaction, which reaction generally employs a boronic acid moiety, a phosphine reagent and a base.

The boronic ester intermediates 7 may be prepared by methods described in the following references: (1) PCT Int. Patent Appl. No. WO 2005073189, titled "Preparation of fused heteroaryl derivatives as p38 kinase inhibitors" or (2) PCT Int. Patent Appl. No. WO 2006094187, titled "Preparation of phthalazine, aza- and diaza-phthalazine compounds as protein kinase, especially p38 kinase, inhibitors for treating inflammation and related conditions". Also, desired boronic acids may be purchases commercially in catalogs, or specially made by the vendor.

The Suzuki method is a reaction using a borane reagent, such as a boronic acid 7 or ester such as a dioxaborolane (not shown), and a suitable leaving group containing reagent, such as the Br-xanthene 6 (Br is a suitable halogen leaving group "LG"). As appreciated to one of ordinary skill in the art, Suzuki reactions also utilize a palladium catalyst. Suitable palladium catalysts include, without limitation, $Pd(PPh_3)_4$, $Pd(OAc)_2$ or $Pd(dppf)Cl_2$. Where LG is a halide, the halide may be an iodide, a bromide or even a chloride. Chloropyridyl rings (where $A^1$=N) undergo Suzuki reactions in the presence of $Pd(OAc)_2$. Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular bromide 6 and/or boronic acid or ester 7, as appreciated by those skilled in the art. In addition, where the bromide is an aromatic moiety, such as phenyl, the reaction may be complete in a short period of time with heat.

Other methods of installing the boronate on a desired aromatic ring are known. For example metal coupling chemistry, such Stille, Kumada, Negishi coupling methods, and the like, may be employed to the xanthene cores 6 prepare desired cyclic products 8.

Scheme 2

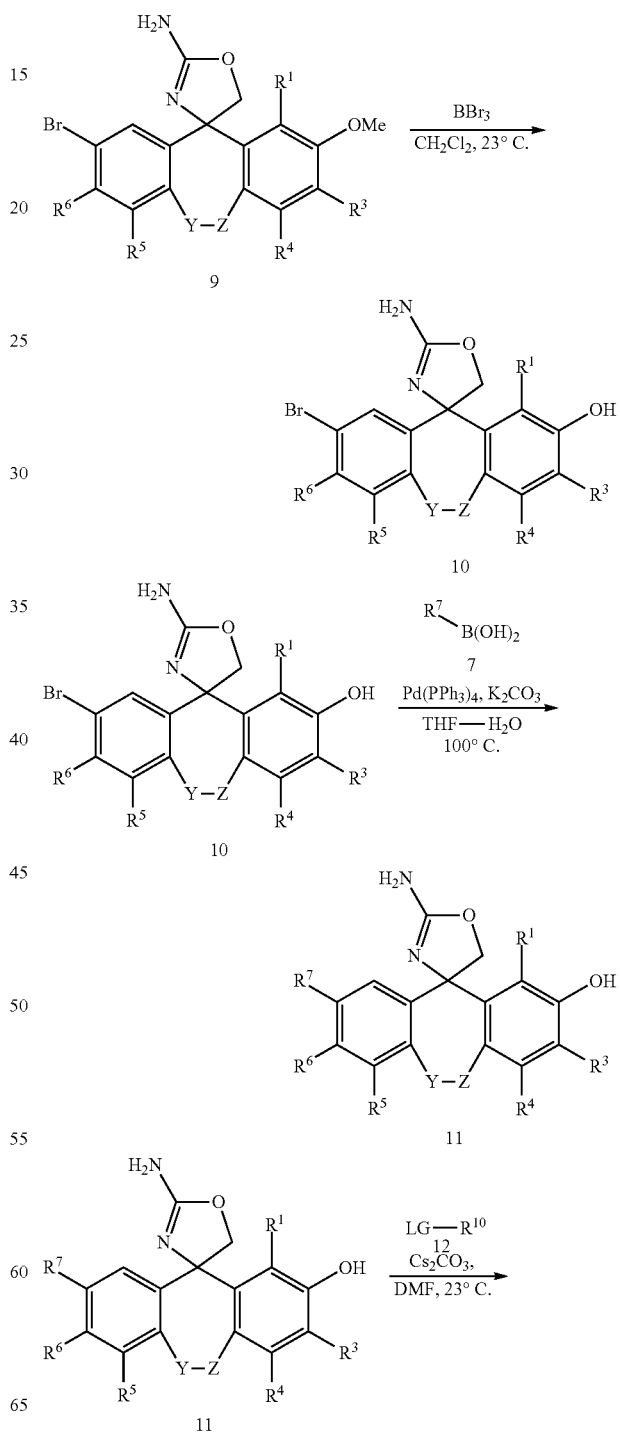

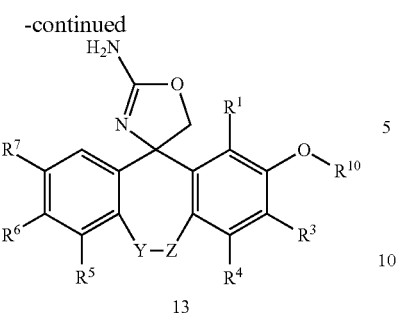

13

Desired compounds 13 of Formulas I, II, II-A, III-A and III-B, wherein the $R^2$ group is —$OR^{10}$ may be made as generally described in Scheme 2. As shown, bromo-methoxy intermediate 9 can be O-demethylate using known reagents, such as borontribromide to afford the alcohol adduct 10. The bromide of alcohol 10 can be coupled as described above in scheme 1 to provide the desired $R^7$ group intermediate 11. The alcohol of intermediate 11 can be functionalized as desired, such as by alkylation as shown, by reaction with an alkyl halide in the presence of a suitable base, such as cesium carbonate as shown, under solvent conditions to afford the finally desired product 13.

"LG" in this instance is a "leaving group" which may be a halide such as an iodide, bromide, chloride or fluoride. LG may also be a non-halide moiety such as an alkylsulfonate or other known groups which generally form an electrophilic species ($E^+$). Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

Scheme 3a

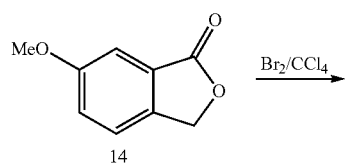

14

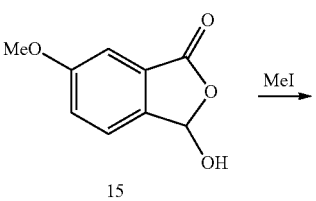

15

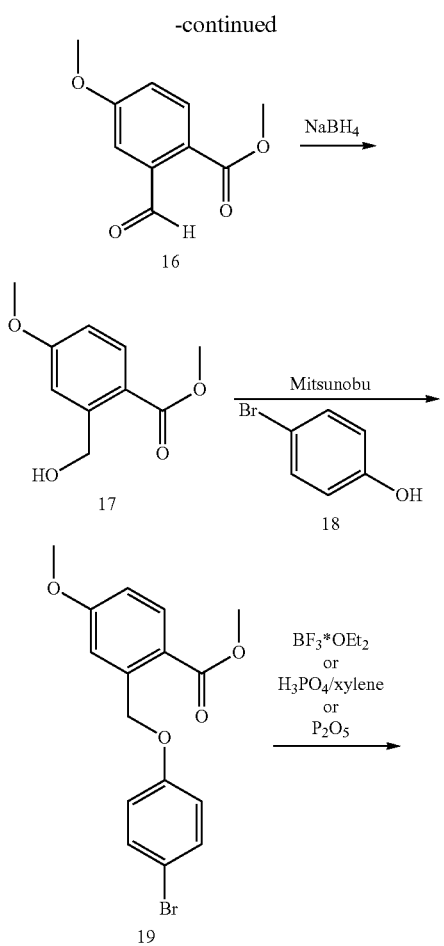

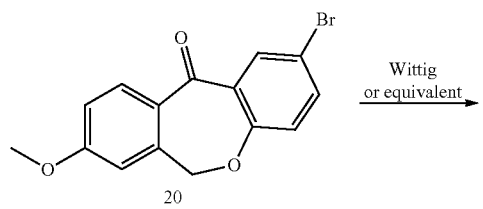

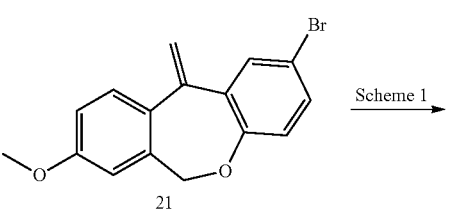

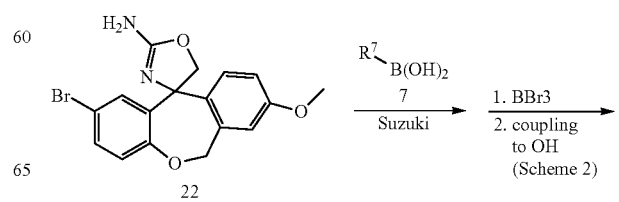

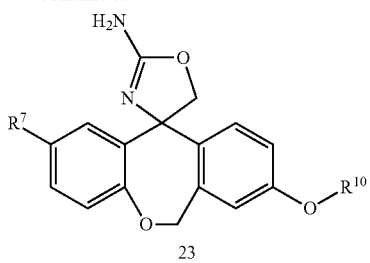

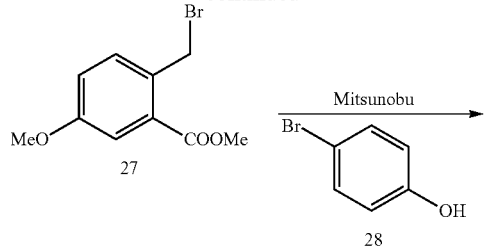

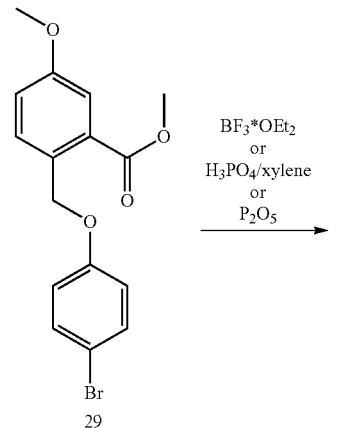

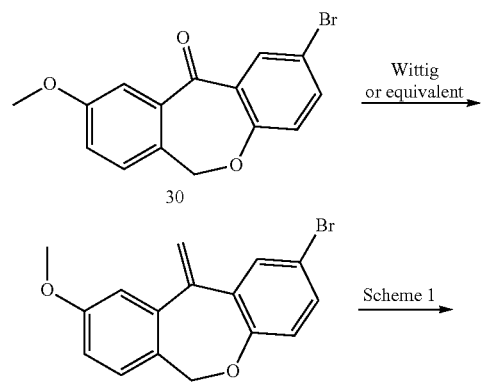

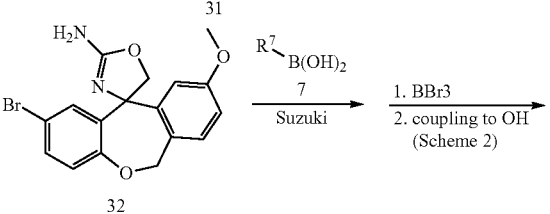

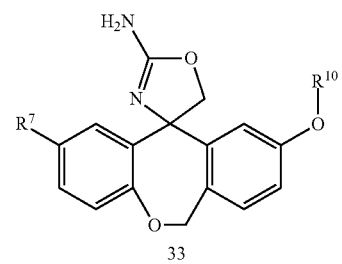

Desired compounds 23 of Formula I, wherein the $R^3$ group is —$OR^{10}$ and Y is O and Z is $CH_2$ may be made as generally described in Scheme 3a. As shown, methoxy-benzolactone 14 (commercially available) can be converted to the corresponding alcohol 15 in the presence of bromine, as known in the art. Such reactions are described in greater detail in literature reference, *Org. Prep. and Proc. Int.* 11(1), 27-32, 1979. Alcohol 15 can be treated with methyliodide to open the ring of compound 15, and afford the aldehyde 16. Such reactions are described in greater detail in literature reference, *Aus. J. Chem.* 34(1), 151-162, 1981. Aldehyde 16 can be reduced with a suitable reducing reagent, such as a borohydride as shown, to provide the corresponding alcohol 17. Alcohol 17 can then be reacted with bromo-phenol in a Mitsunobu type reaction involving use of a phosphine reagent (typically triphenylphosphine), to produce the coupled adduct 19. Intermediate 19 can be treated with a strong acid, such as phosphoric acid or borontrifluoride.etherate to afford the ring closed ketone 20. Ketone 20 can then be treated in a manner similar to that described in scheme 1 to convert the ketone to the ene group 21, and react the ene 21 with cyanatosilver in the presence of iodine (see scheme 1) to afford the amino-oxazoline 22. Amino-oxazoline 22 can be functionalized as described above in scheme 2 to prepare the desired compounds 23 of Formula I.

Scheme 3b

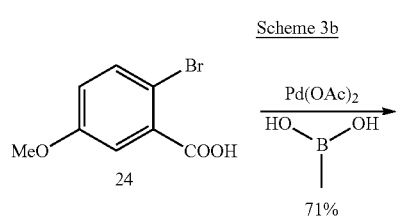

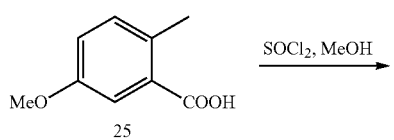

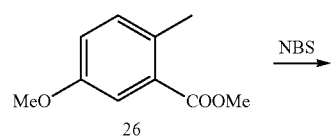

Desired compounds 33 of Formula I, wherein the R group is —$OR^{10}$ and Y is O and Z is $CH_2$ may be made as generally described in Scheme 3b. As shown, bromo-methoxy-benzoic acid 24 (commercially available) can be methylate to the corresponding methyl benzoic acid adduct 25 using a source of methyl such as shown in the presence of an appropriate catalyst, such as palladium, in a Suzuki reaction, as shown. Such reactions are described in greater detail in literature reference, *JACS*, 129(12), 3510-3511; 2007. Acid 25 can be converted to the corresponding methyl ester 26 with thionyl chloride and methanol. The methyl of ester 26 can be brominated using NBS to provide the corresponding bromo-methyl adduct 27. Bromide 27 can then be reacted with bromophenol in a Mitsunobu type reaction involving use of a phosphine reagent (typically triphenylphosphine), to produce the coupled adduct 29. Intermediate 29 can be treated with a strong acid, such as phosphoric acid or borontrifluoride.etherate to afford the ring closed ketone 30. Ketone 30 can then be treated in a manner similar to that described in scheme 1 to convert the ketone to the ene group 31, and react the ene 31 with cyanatosilver in the presence of iodine (see scheme 1) to afford the amino-oxazoline 32. Amino-oxazoline 32 can be functionalized as described above in scheme 2 to prepare the desired compounds 33 of Formula I.

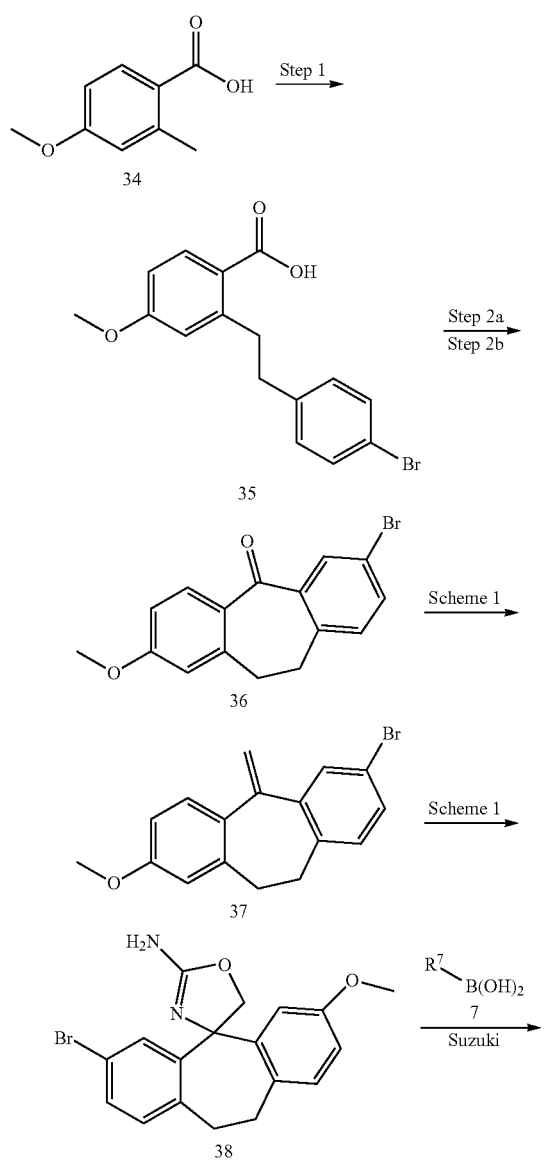

Scheme 4

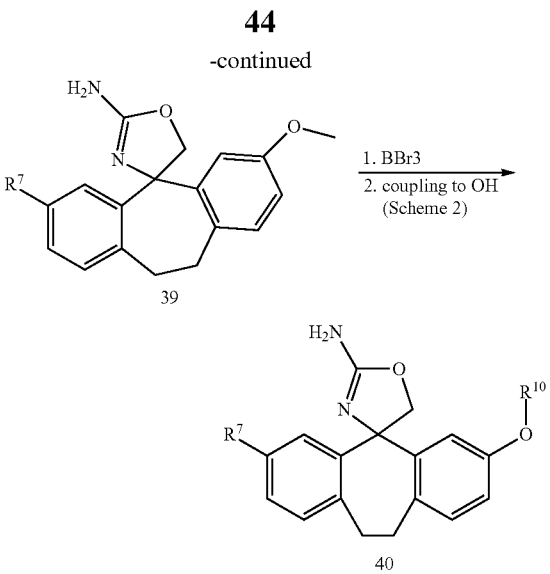

Desired compounds 40 of Formula I, wherein the $R^2$ group is $-OR^{10}$ and Y and Z are both $CH_2$ may be made as generally described in Scheme 4. As shown, methoxy-methyl benzoic acid 34 (commercially available from Aldrich) can be reacted with bromomethyl-bromo benzene in the presence of a strong base, such as sBuLi to prepare intermediate 35. Intermediate 35 may be treated with oxalyl chloride in the presence if DMF and heat to close the ring of compound 36, while deprotecting the methoxy to the alcohol (step 2a, intermediate not shown). Step 2b involves treating the alcohol with a suitable base, such as sodium hydride, in the presence of a methylating reagent, such as methyl iodide to prepare the methoxyl adduct 36. Alternatively, intermediate 35 may be treated with a strong acid such as chloro-sulfonic acid to afford the ring closed adduct ketone 36. Ketone 36 can then be treated in a manner similar to that described in scheme 1 to convert the ketone to the ene group, and react the ene 37 with cyanatosilver in the presence of iodine (see scheme 1) to afford the amino-oxazoline 38. Amino-oxazoline 38 can be functionalized as described above in scheme 2 to prepare the desired compounds 40 of Formula I.

In an analogous fashion, compounds of Formula I where $R^2$ is $-O-R^{10}$ can be prepared using the above general synthesis, but starting with meta-methoxy-ortho-methyl benzoic acid instead of para-methoxy starting material 34 shown above.

Scheme 5

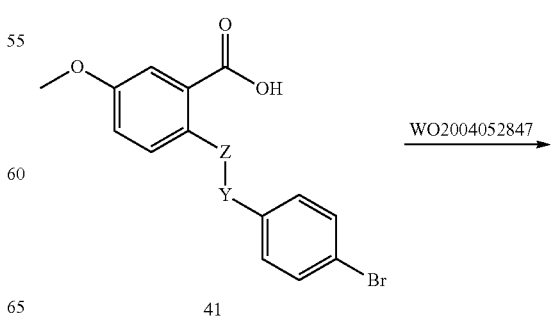

-continued

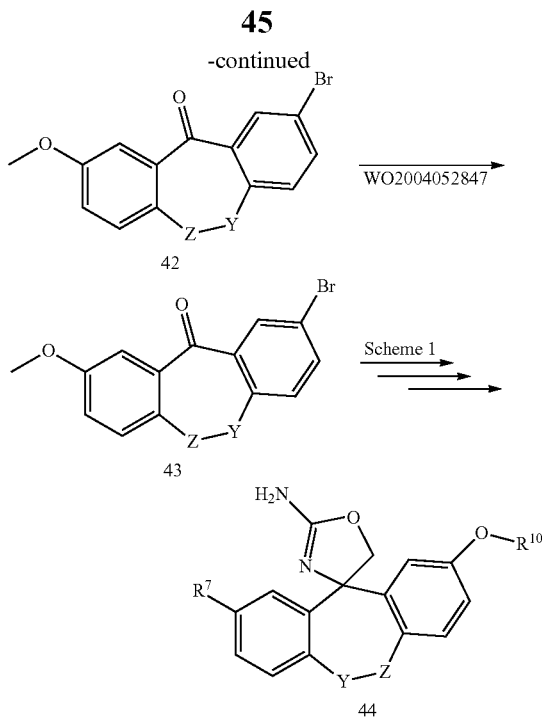

Desired compounds 44 of Formula I, wherein the $R^2$ group is —$OR^{10}$ and Y and Z each, independently, may be either S, SO, $SO_2$, CO or NH may be made as generally described in Scheme 5. As shown, intermediate 41 (commercially available or may be prepared separately) wherein one of Y and Z is —C(O-protected alcohol)— or —S— can be converted to intermediate 43 via ketone 42 using procedures described in PCT published patent application WO 2004052847, beginning on pg 280 (eg no 261) to pg 288 (eg 274), and on pgs 326 (preparation 56, see also J. Med. Chem., 33. pg 3095, 1990), pgs 190-192 (eg 90); pg 223 (eg 158), each of which are hereby incorporated herein by reference. One can envision deprotecting the alcohol group and oxidizing it up to the corresponding ketone either before or after final ring closure of compounds 43 or 44. Regarding either of Y or Z being —N (protecting group)-, intermediates 41 may be prepared using the methods described in Tetrahedron Letters, 48, 8174-8177, 2007. Such Y and Z groups may also be prepared (Y or Z=N) by the methods described in U.S. Pat. No. 7,312,209, and specifically in schemes 1-10 therein (cols. 38-45), which are also hereby incorporated herein by reference, to prepare intermediates like compound 42 as shown, where one of Y and Z is NH and the other of Y and Z is absent. The ene intermediate 43 may then be treated in a manner described in schemes 3a, 3b or 4 above to prepare the targeted or desired amino-oxazolines 44.

To enhance the understanding and appreciation of the present invention, the following specific examples (starting reagents, intermediates and compounds of Formulas I-III) are set forth. The following analytical methods were used to purify and/or characterize the compounds, and intermediates, described in the examples below.

Chromatography: Unless otherwise indicated, crude product-containing residues were purified by passing the crude material or concentrate through an ISCO brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 8.0 software, available in Chem Office, or (2) by the ISIS database software (Advanced Chemistry Design Labs or ACD software). In some instances, compounds were named with the term "spirocarbocycle" inserted where appropriate. For example, where the chroman is substituted with 2,2-spirocyclobutyl, "2,2-spirocyclobutyl" have been added to the Chem-Draw nomenclature in the appropriate place.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I-III. It should be appreciated that the general methods above and specific examples below are illustrative only, for the purpose of assistance and of understanding the present invention, and should not be construed as limiting the scope of the present invention in any manner.

Example 1

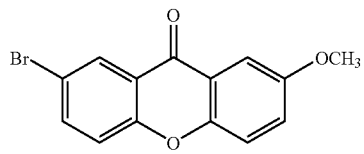 [SMILES: COc1ccc2oc3ccc(Br)cc3c(=O)c2c1]

Synthesis of 2-Bromo-7-methoxy-9H-xanthen-9-one

Step 1: 2-(4-Bromophenoxy)-5-methoxybenzoic acid

4-Bromophenol (8.7 g, 50 mmol), Cs₂CO₃ (16 g, 50 mmol), CuOTf toluene complex (2:1) (0.625 mmol, 5 mol % Cu, 150 mg), ethyl acetate (0.25 ml, 2.5 mmol) were added to a solution of 2-bromo-5-methoxybenzoic acid (11.6 g, 50 mmol) in toluene (40 mL) in a sealed tube. The reaction mixture was purged with N₂, and was heated to 110° C. until the aryl halide was consumed as determined by LC-MS (48 h). After cooling to rt, the mixture was filtered through a Celite plug. The Celite plug was washed with EtOAc. The mixture was acidified by 1N HCl, and extracted w/EtOAc. The combined organic phases were washed with brine, dried over anhydrous sodium sulfate, filtered, and concentrated. This residue was purified via column chromatography on silica gel (gradient elution with 0-10% MeOH/DCM) to afford 2-(4-bromophenoxy)-5-methoxybenzoic acid. MS m/z=324.9 [M+H]⁺. Calc'd for C₁₄H₁₁BrO₄: 323.1.

Step 2: 2-Bromo-7-methoxy-9H-xanthen-9-one

Sulfuric acid (41 ml, 765 mmol) was added to 2-(4-bromophenoxy)-5-methoxybenzoic acid (3750 mg, 12 mmol) at RT. The reaction mixture was stirred at 60° C. for 60 min. LCMS showed complete reaction. The reaction mixture was cooled to rt and poured slowly over stirred mixture of ice and water (100 ml). The tan precipitate was filtered and washed with water (3×30 ml), twice with 30 ml of 0.5N NaOH, and with water again. The residue was recrystallized from 40 ml THF to give the title compound. MS m/z=307.2 [M+H]⁺. Calc'd for C₁₄H₉BrO₃: 305.1.

Example 2

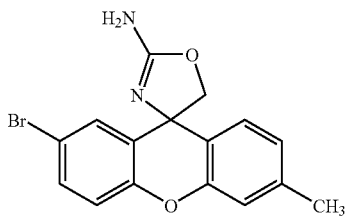 [SMILES: Cc1ccc2c(c1)Oc1ccc(Br)cc1C21COC(N)=N1]

Synthesis of 2'-Bromo-6'-methylspiro[1,3-oxazole-4,9'-xanthen]-2-amine

Step 1: 2-(4-Bromophenoxy)-4-methylbenzoic acid

4-Bromophenol (0.87 g, 5 mmol), Cs₂CO₃ (1.6 g, 5 mmol), CuOTf toluene complex (2:1) (0.0625 mmol, 5 mol % Cu, 33 mg), ethyl acetate (0.013 ml, 0.125 mmol) were added to a solution of 2-bromo-4-methylbenzoic acid (0.86 g, 5 mmol) in toluene (2 mL) in a sealed tube. The reaction mixture was purged with N₂, and was heated to 110° C. until the aryl halide was consumed as determined by LC-MS (48 h). After cooling to rt, the mixture was filtered through a Celite plug. The Celite plug was washed with EtOAc. The mixture was acidified by 1N HCl, and extracted w/EtOAc. The combined organic phases were washed with brine, dried over anhydrous sodium sulfate, filtered, and concentrated. This residue was purified via column chromatography on silica gel (gradient elution with 0-10% MeOH/DCM) to afford 2-(4-bromophenoxy)-4-methylbenzoic acid, MS m/z=309.1 [M+H]⁺. Calc'd for C₁₄H₁₁BrO₃: 307.1.

Step 2: 2-Bromo-6-methyl-9H-xanthen-9-one

Sulfuric acid (5 ml, 93 mmol) was added to 2-(4-bromophenoxy)-4-methylbenzoic acid (200 mg, 0.62 mmol) at rt. The reaction mixture was heated to 80° C. for 30 min. LCMS showed complete reaction. The reaction mixture was cooled to rt and poured over ice water. The gray suspension was filtered, and the gray solid was washed with water. The residue was dissolved in EtOAc, and washed w/Sat. NaCl. After concentration in vacuo, the brown solid was used without further purification. MS m/z=291.1 [M+H]⁺. Calc'd for C₁₄H₉BrO₂: 289.1.

Step 3: 2-Bromo-6-methyl-9-methylene-9H-xanthene

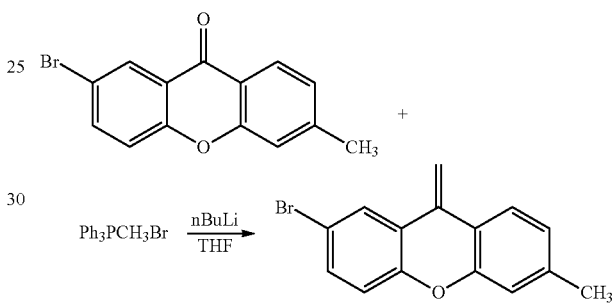

To a solution of methyltriphenylphosphonium bromide (2664 mg, 7457 µmol) in THF (19 ml) at 0° C. was added butyllithium (1.6 M in Hexanes, 3995 µl, 6392 µmol) dropwise. After stirring at 0° C. for 30 minutes, a solution of 2-bromo-6-methyl-9H-xanthen-9-one (1540 mg, 5326 µmol) in THF (5 ml) was added dropwise. The solution was allowed to warm to RT and stirred for 1 hour. The reaction mixture was quenched with water and the aqueous layer was washed 3× with EtOAc. The organic layers were combined, dried with MgSO₄, filtered and concentrated to an oil. The crude product was flashed with the MPLC (100% hexanes to 10% EtOAc in hexanes to 30% EtOAc in hexanes) MS m/z=289.1 [M+H]⁺. Calc'd for C₁₅H₁₁BrO₂: 287.1.

Step 4: 2'-Bromo-6'-methylspiro[1,3-oxazole-4,9'-xanthen]-2-amine

To a solution of 2-bromo-6-methyl-9-methylene-9H-xanthene (1383 mg, 4816 µmol) in ethoxyethane (24081 µl, 4816 µmol) was added cyanatosilver (2166 mg, 14449 µmol) at RT. The resulting mixture was cooled to −6° C. and solid iodine (1222 mg, 4816 µmol) was added in one portion and the solution stirred for 1.5 hours. The solution was then filtered through a cotton/celite plug and concentrated to oil. The residue was immediately dissolved in acetone (16057 µl, 4817 µmol) at RT. To the resulting solution, was added ammonium hydroxide (3018 µl, 14452 µmol) by syringe. The resulting mixture was stirred overnight. The resulting mixture was transferred to a separation funnel containing water and the aqueous layer was washed 3× with DCM. The organic layers were combined, dried with MgSO4, filtered and concentrated to oil. The product was purified with the MPLC (100% DCM to 40% 90:10:1 DCM:MeOH:NH$_4$OH) MS m/z=347.2 [M+H]$^+$. Calc'd for C$_{16}$H$_{13}$BrN$_2$O$_2$: 345.2.

Example 3

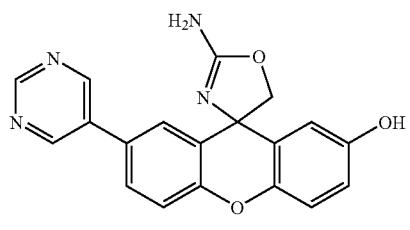 [SMILES: NC1=NC2(CO1)c1cc(O)ccc1Oc1ccc(-c3cncnc3)cc12]

Synthesis of 2'-Hydroxy-7'-(5-pyrimidinyl)spiro[1,3-oxazole-4,9'-xanthen]-2-amine

Step 1: 2-Bromo-7-methoxy-9-methylene-9H-xanthene

A solution of 2-bromo-7-methoxy-9H-xanthen-9-one (2.035 g, 6.7 mmol) in THF (67 ml) contained in a 250-mL RBF was cooled in a dry ice/acetone bath for 10 min to give a milky-white mixture. Trimethylsilyl methyllithium (10 ml of a 1.0 M solution in pentane, 10 mmol) was added dropwise over 5 min to give a clear orange solution. The mixture was stirred for 15 min, then acetyl chloride (0.76 ml, 11 mmol) was added dropwise, resulting in the formation of a clear, bright-yellow solution. The mixture was warmed to RT for 3 h, then an additional portion of acetyl chloride (0.25 mL) was added. The mixture was stirred for an additional 30 min before being diluted with saturated aqueous sodium bicarbonate solution (100 mL). The biphasic mixture was extracted with EtOAc (2×50 mL), and the combined organic extracts were dried over sodium sulfate, filtered, and evaporated to give a yellow solid that was used without further purification. MS m/z=303.0 [M+H]$^+$. Calc'd for C$_{15}$H$_{12}$BrO$_2$: 303.0.

Step 2: 2'-Bromo-7'-methoxyspiro[1,3-oxazole-4,9'-xanthen]-2-amine

Crude 2-bromo-7-methoxy-9-methylene-9H-xanthene was suspended in ether (33 ml). silver cyanate (3.0 g, 20 mmol) and iodine (1.7 g, 6.7 mmol) were added in sequence, resulting in a brown mixture. After stirring for 40 min at RT, the reaction mixture was filtered through celite with the aid of ether, and the filtrate was evaporated. The residue was dissolve in a mixture of THF (26 mL) and ammonium hydroxide (2.6 mL) and stirred for 15 h. The reaction mixture was partitioned between water (100 mL) and DCM (70 mL). The layers were separated, and the aqueous layer was extracted with DCM (2×70 mL). The combined organic extracts were dried over sodium sulfate, filtered, and evaporated. The residue was purified by chromatography on silica gel (eluting with 0-40% of a 90:10:1 DCM/MeOH/NH$_4$OH in DCM) to give 2'-bromo-7'-methoxyspiro[1,3-oxazole-4,9'-xanthen]-2-amine as a pale yellow foam. MS m/z=361.2 [M+H]$^+$. Calc'd for C$_{16}$H$_{14}$BrN$_2$O$_3$: 361.2.

Step 3: 2'-Bromo-7'-hydroxyspiro[1,3-oxazole-4,9'-xanthen]-2-amine

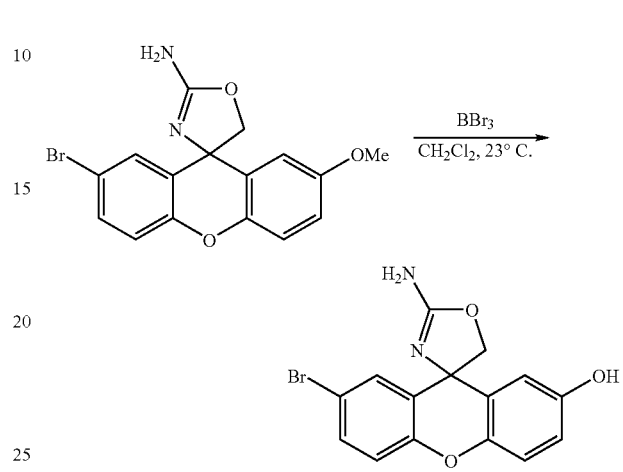

A solution of 2'-bromo-7'-methoxyspiro[1,3-oxazole-4,9'-xanthen]-2-amine (1.034 g, 2863 μmol) in DCM (29 mL) contained in a 100-mL RBF was cooled in an ice-bath for min. A solution of boron tribromide (8.5 mL of a 1.0 M solution in DCM, 8588 μmol) was added dropwise over 5 min, resulting in a dark brown solution at The ice-bath was removed, and the mixture was stirred for 1.5 h. The reaction mixture was carefully quenched with saturated aqueous sodium bicarbonate solution (30 mL). The mixture was partitioned between water (50 mL) and DCM (50 mL). The aqueous layer was extracted with DCM (2×25 mL), and the combined organic extracts were dried over sodium sulfate. The solution was filtered, and the filter cake was washed successively with 10% MeOH/DCM. The combined filtrates were concentrated in vacuo. The residue was purified by chromatography on silica gel (eluting with 0-70% of a 90:10:1 DCM/MeOH/NH$_4$OH solution in DCM) to give 2'-bromo-7'-hydroxyspiro[1,3-oxazole-4,9'-xanthen]-2-amine. MS m/z=347.0 [M+H]$^+$. Calc'd for C$_{15}$H$_{12}$BrN$_2$O$_3$: 347.0.

Step 4: 2'-Hydroxy-7'-(5-pyrimidinyl)spiro[1,3-oxazole-4,9'-xanthen]-2-amine

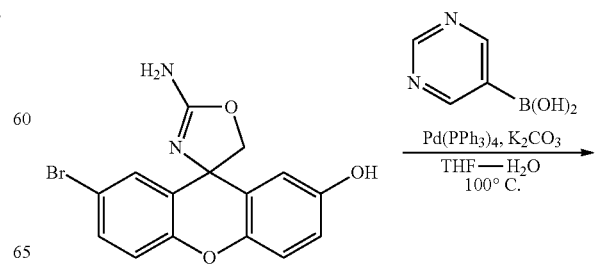

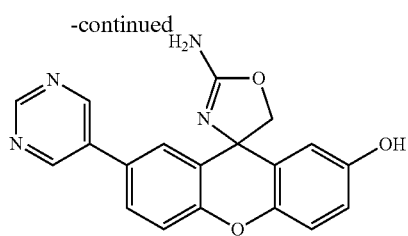

A 150-mL pressure vessel was charged with 2'-bromo-7'-hydroxyspiro[1,3-oxazole-4,9'-xanthen]-2-amine (845 mg, 2434 µmol) in THF (24 mL), pyrimidin-5-ylboronic acid (754 mg, 6085 µmol), tetrakis(triphenylphosphine)palladium(0) (281 mg, 243 µmol), and potassium carbonate (10.1 mL of a 1.2 M aqueous solution, 12.1 mmol). The vessel was sealed and placed in a 100° C. oil bath at for 4 h. The reaction mixture was cooled to RT and partitioned between EtOAc (50 mL) and water (50 mL). The aqueous layer was extracted with EtOAc (50 mL), and the combined organic extracts were dried over sodium sulfate, filtered, and evaporated. The crude material was purified by chromatography on silica gel (eluting with 30-100% of a 90:10:1 DCM/MeOH/NH$_4$OH solution in DCM) to give 2'-hydroxy-7'-(5-pyrimidinyl)spiro[1,3-oxazole-4,9'-xanthen]-2-amine as an off-white solid. MS m/z=347.2 [M+H]$^+$. Calc'd for $C_{19}H_{15}N_4O_3$: 347.1.

Example 4

Synthesis of 2'-Bromo-7'-chlorospiro[1,3-oxazole-4,9'-xanthen]-2-amine

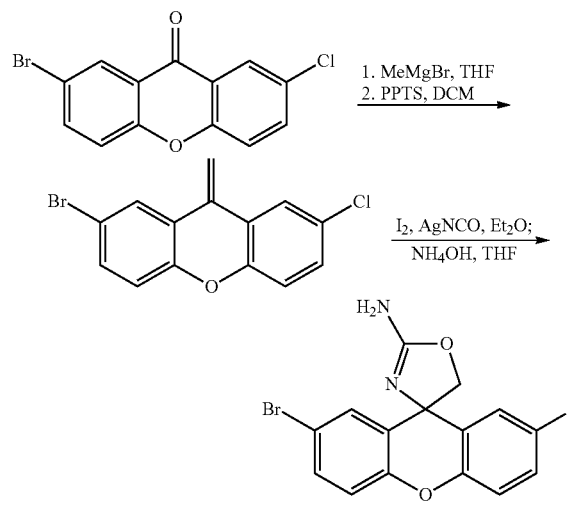

Step 1: Synthesis of 2'-Bromo-7'-chlorospiro[1,3-oxazole-4,9'-xanthen]-2-amine

2-Bromo-7-chloro-9H-xanthen-9-one (prepared as described in example 1 using 4-bromophenol and 2-bromo-5-chlorobenzoic acid) (12.78 g, 41 mmol) was treated with 100 ml of dry THF. The mixture was stirred for 10 min at room temperature and the resulting suspension was placed in water-ice bath for another 10 min. MeMgBr (23 ml, 70 mmol) (3M in THF) was added dropwise under argon using syringe. As addition progressed major amount of solid dissolved to form reddish solution. The mixture was stirred another 5 min at 0° C. then was removed from the bath and allowed to reach room temperature. The flask was recooled to 0° C. and ~20 ml of saturated ammonium chloride solution was added dropwise slowly (CAREFUL: gas evolution!). The mixture was diluted with ether, organic layer was separated, washed with brine, dried and concentrated to afford an oil. The oil was dissolved in 100 ml of DCM, PPTS (0.2 g, 0.8 mmol) was added and the mixture was heated to reflux for 5 min and left overnight at room temperature. The precipitate was filtered and rinsed with ether, the filtrate was concentrated in vacuo and treated with hot methanol (~30 ml) and allowed to crystallize at room temperature. The crystalline material was filtered off and dried in vacuo. These two batches gave 2-bromo-7-chloro-9-methylene-9H-xanthene (8.69 g, 68% yield). m/z=307.5 [M+H]$^+$. Calc'd for $C_{14}H_8BrClO$: 307.5

Step 2: 2'-Bromo-7'-chlorospiro[1,3-oxazole-4,9'-xanthen]-2-amine

A suspension of 2-bromo-7-chloro-9-methylene-9H-xanthene (244.0 mg, 793 µmol) in ether (7.9 mL) was treated sequentially with silver cyanate (357 mg, 2380 µmol) and iodine (201 mg, 793 µmol). The mixture was stirred for 6 h, then filtered through celite with the aid of ether. The filtrate was evaporated, and the residue was dissolved in THF (4.0 mL) and ammonium hydroxide (0.4 mL). The resulting mixture, which quickly developed a thick precipitate, was stirred for 1 h. Silica gel was added, and the solvent was evaporated to adsorb the crude product. The silica gel was loaded into a silica gel column and eluted with 0-40% of a 90:10:1 DCM/MeOH/NH$_4$OH mixture in DCM to give 2'-bromo-7'-chlorospiro[1,3-oxazole-4,9'-xanthen]-2-amine as an off-white solid. MS m/z=365.0 [M+H]$^+$. Calc'd for $C_{15}H_{11}BrClN_2O_2$: 365.0.

Example 5

Method A

Synthesis of 2'-Propoxy-7'-(5-pyrimidinyl)spiro[1,3-oxazole-4,9'-xanthen]-2-amine

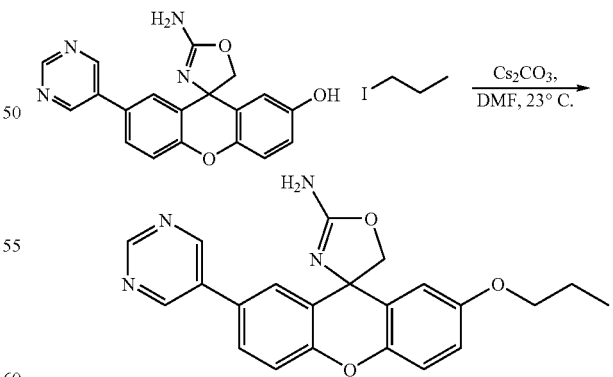

Step 1: 2'-Propoxy-7'-(5-pyrimidinyl)spiro[1,3-oxazole-4,9'-xanthen]-2-amine

A glass vial was charged with 2'-hydroxy-7'-(5-pyrimidinyl)spiro[1,3-oxazole-4,9'-xanthen]-2-amine (prepared as described in Example 3; 53.68 mg, 155 μmol), cesium carbonate (75.7 mg, 232 μmol), DMF (0.62 mL), and 1-iodopropane (16.6 μl, 170 μmol). The mixture was stirred at RT for 18 h, then poured into water (10 mL) and extracted with EtOAc (3×7 mL). The combined organic extracts were dried over sodium sulfate, filtered, and evaporated. The residue was purified by chromatography on silica gel (eluting with 0-80% of a 90:10:1 DCM/MeOH/NH$_4$OH solution in DCM) to give 2'-(1-propyloxy)-7'-(5-pyrimidinyl)spiro[1,3-oxazole-4,9'-xanthen]-2-amine as a white solid. MS m/z=389.2 [M+H]$^+$. Calc'd for C$_{22}$H$_{21}$N$_4$O$_3$: 389.2.

Step 2: Chiral separation of racemic 2'-propoxy-7'-(5-pyrimidinyl)spiro[1,3-oxazole-4,9'-xanthen]-2-amine 2'-Propoxy-7'-(5-pyrimidinyl)spiro[1,3-oxazole-4,9'-xanthen]-2-amine (40 mg) was subjected to chromatography using 15:85:0.2 MeOH:CO$_2$:DEA at 80 ml/min on a 20×250 mm, 5 μm ChiralPak AS-H column and 100-bar system pressure. The first peak (RT=3.5 min) provided (R)-2'-propoxy-7'-(5-pyrimidinyl)spiro[1,3-oxazole-4,9'-xanthen]-2-amine (13.0 mg, >99% ee), and the second peak (RT=4.3 min) provided (S)-2'-propoxy-7'-(5-pyrimidinyl)spiro[1,3-oxazole-4,9'-xanthen]-2-amine (12.8 mg, >99% ee).

Example 6

Method B

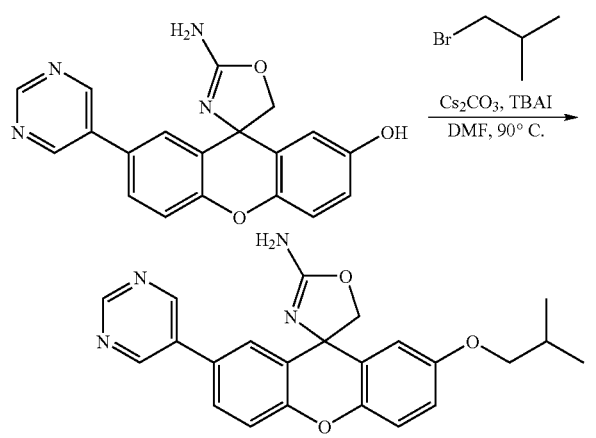

Synthesis of 2'-(2-methylpropoxy)-7'-(5-pyrimidinyl) spiro[1,3-oxazole-4,9'-xanthen]-2-amine A glass vial was charged with 2'-hydroxy-7'-(5-pyrimidinyl)spiro[1,3-oxazole-4,9'-xanthen]-2-amine (prepared as described in Example 3; 41.60 mg, 120 μmol), tetrabutylammonium iodide (8.85 mg, 24.0 μmol), cesium carbonate (58.6 mg, 180 mol), DMF (0.48 mL), and isobutyl bromide (16.3 μl, 150 μmol). The vial was sealed and placed in a 90° C. oil bath for 15 h. Additional portions of cesium carbonate (40 mg) and isobutyl bromide (16 uL) were added, and the vial was heated in a Biotage Initiator microwave reactor for 1.5 h at 100° C. The mixture was then partitioned between EtOAc (10 mL) and water (20 mL). The layers were separated, and the aqueous layer was extracted with EtOAc (2×10 mL). The combined organic extracts were dried over sodium sulfate, filtered, and evaporated. The residue was purified by chromatography on silica gel (eluting with 0-80% of a 90:10:1 DCM/MeOH/NH$_4$OH solution in DCM) to give 2'-iso-butyloxy-7'-(5-pyrimidinyl)spiro[1,3-oxazole-4,9'-xanthen]-2-amine as an oily tan solid. MS m/z=403.2 [M+H]+. Calc'd for C$_{23}$H$_{23}$N$_4$O$_3$: 403.2.

Example 7

Method C

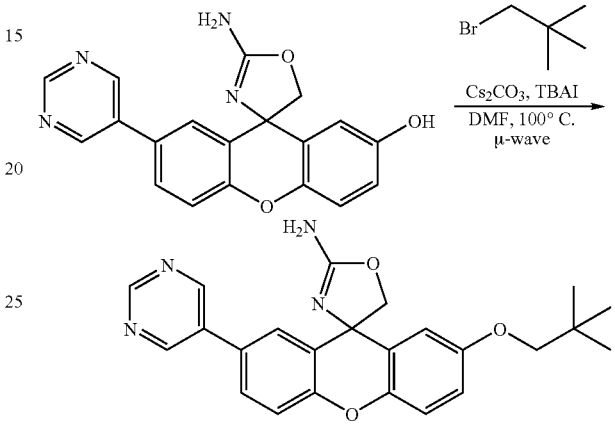

Synthesis of 2'-(2,2-dimethylpropoxy)-7'-(5-pyrimidinyl)spiro[1,3-oxazole-4,9'-xanthen]-2-amine A glass vial was charged with 2'-hydroxy-7'-(5-pyrimidinyl)spiro[1,3-oxazole-4,9'-xanthen]-2-amine (prepared as described in Example 3; 159 mg, 459 μmol), tetrabutylammonium iodide (84.8 mg, 230 μmol), cesium carbonate (374 mg, 1148 μmol), DMF (1.8 mL), and 1-bromo-2,2-dimethylpropane (175 μl, 1377 μmol). The vial was sealed and heated in a Biotage Initiator microwave reactor for 2 h at 100° C. Additional portions of tetrabutylammonium iodide (85 mg), cesium carbonate (180 mg), and 1-bromo-2,2-dimethylpropane (100 uL) were added. The vial was again heated in the microwave for 2 h at 100° C. The mixture was poured into water (10 mL) and extracted with EtOAc (3×10 mL). The combined organic extracts were dried over sodium sulfate, filtered, and evaporated. The residue was purified by chromatography on silica gel (eluting with 0-80% of a 90:10:1 DCM/MeOH/NH$_4$OH mixture in DCM) to give 2'-(2,2-dimethylpropoxy)-7'-(5-pyrimidinyl)spiro[1,3-oxazole-4,9'-xanthen]-2-amine of a pale orange glass that solidified into an off-white solid. MS m/z=417.2 [M+H]$^+$. Calc'd for C$_{24}$H$_{25}$N$_4$O$_3$: 417.2.

Chiral separation of racemic 2'-(2,2-dimethylpropoxy)-7'-(5-pyrimidinyl)spiro[1,3-oxazole-4,9'-xanthen]-2-amine 2'-(2,2-Dimethylpropoxy)-7'-(5-pyrimidinyl)spiro[1,3-oxazole-4,9'-xanthen]-2-amine (139 mg) was subjected to chromatography using 40:60:0.2 MeOH:CO$_2$:DEA at 70 ml/min on a 20×250 mm, 5 μm ChiralPak AD-H column and 100-bar system pressure. The first peak (RT=2.0 min) provided (R)-2'-(2,2-dimethylpropoxy)-7'-(5-pyrimidinyl)spiro[1,3-oxazole-4,9'-xanthen]-2-amine (50.9 mg, >99% ee), and the second peak (RT=3.9 min) provided (S)-2'-(2,2-dimethylpropoxy)-7'-(5-pyrimidinyl)spiro[1,3-oxazole-4,9'-xanthen]-2-amine (52.7 mg, >99% ee).

Example 8

Method D

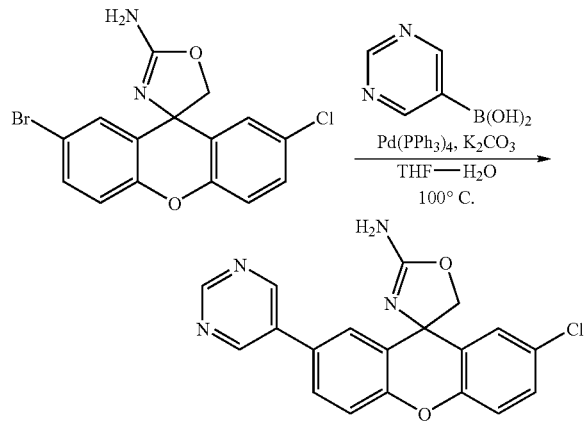

Synthesis of 2'-Chloro-7'-(5-pyrimidinyl)spiro[1,3-oxazole-4,9'-xanthen]-2-amine A microwave vial was charged with 2'-bromo-7'-chlorospiro[1,3-oxazole-4,9'-xanthen]-2-amine (prepared as described in Example 4; 106 mg, 290 µmol) in THF (3.5 mL), pyrimidin-5-ylboronic acid (43.1 mg, 348 µmol), potassium carbonate (1208 µl of a 1.2 M aqueous solution, 1450 µmol), and tetrakis(triphenylphosphine)palladium(0) (33.5 mg, 29.0 µmol). The vial was covered with a blanket of Ar (g), capped, and heated in Biotage Initiator microwave reactor for 2 h at 100° C. The layers were separated, and the aqueous layer was extracted with EtOAc (5 mL). The combined organic extracts were concentrated in vacuo, and the residue was purified by chromatography on silica gel eluting with 0-50% of a 90:10:1 DCM/MeOH/NH$_4$OH mixture in DCM to give 65 mg of a white solid that was impure by HPLC. The residue was dissolved in DMSO-MeOH and purified by reverse-phase HPLC (10-90% CH$_3$CN/H$_2$O with 0.1% TFA). The fractions containing product were poured into saturated sodium bicarbonate with the aid of methanol and extracted with DCM. The organic layer was dried over sodium sulfate, filtered, and evaporated to give 2'-chloro-7'-(5-pyrimidinyl)spiro[1,3-oxazole-4,9'-xanthen]-2-amine as a white solid. MS m/z=365.2 [M+H]+. Calc'd for C$_{19}$H$_{14}$ClN$_4$O$_2$: 365.1.

The following examples in Table I were prepared by methods and Steps analogous to those described in Examples 1-8 above. Provided also is the mass spectral data and BACE enzyme and cell-based assay data (IC$_{50}$'s in uM ranges) for each example, where available. Where the name of the exemplified compound, in each of the Tables herein, does not designate a specific (S) or (R) stereoisomer, then the Example was tested as a racemic mixture. Racemic mixture Examples were in many cases, found to be generally close to a 1:1 stereoisomer mixture.

TABLE 1

| Ex. No. | Compound Name | Method | Observed MS | BACE1 FRET assay (uM) | HEK cell assay (uM) |
|---|---|---|---|---|---|
| 7 | 2'-(2,2-dimethylpropoxy)-7'-(5-pyrimidinyl)spiro[1,3-oxazole-4,9'-xanthen]-2-amine | C | 417.2 | ++++ | ++++ |
| 5 | (4S)-2'-propoxy-7'-(5-pyrimidinyl)spiro[1,3-oxazole-4,9'-xanthen]-2-amine | A | 389.2 | ++++ | ++++ |
| 6 | 2'-(2-methylpropoxy)-7'-(5-pyrimidinyl)spiro[1,3-oxazole-4,9'-xanthen]-2-amine | B | 403.2 | ++++ | ++++ |
| 9 | 2'-propoxy-7'-(5-pyrimidinyl)spiro[1,3-oxazole-4,9'-xanthen]-2-amine | A | 389.2 | ++++ | +++ |
| 10 | (4S)-2'-methoxy-7'-(5-pyrimidinyl)spiro[1,3-oxazole-4,9'-xanthen]-2-amine | D | 361.0 | +++ | ++ |
| 11 | (4R)-2'-propoxy-7'-(5-pyrimidinyl)spiro[1,3-oxazole-4,9'-xanthen]-2-amine | A | 389.2 | +++ | ++ |
| 12 | (4S)-2'-(5-chloro-2-fluorophenyl)-7'-methoxyspiro[1,3-oxazole-4,9'-xanthen]-2-amine trifluoroacetic acid | D | 411.1 | +++ | + |
| 13 | 2'-chloro-7'-(5-pyrimidinyl)spiro[1,3-oxazole-4,9'-xanthen]-2-amine | D | 365.2 | +++ | |
| 14 | 2'-methoxy-7'-(5-pyrimidinyl)spiro[1,3-oxazole-4,9'-xanthen]-2-amine | D | 361.0 | +++ | ++ |
| 15 | 2'-(2-fluoro-5-methoxyphenyl)-7'-methoxyspiro[1,3-oxazole-4,9'-xanthen]-2-amine | D | 407.2 | ++ | + |
| 16 | 2'-(2-fluoro-3-pyridinyl)-7'-methoxyspiro[1,3-oxazole-4,9'-xanthen]-2-amine | D | 378.0 | ++ | ++ |
| 17 | 2'-(2-fluoro-3-methoxyphenyl)-7'-methoxyspiro[1,3-oxazole-4,9'-xanthen]-2-amine | D | 407.2 | ++ | ++ |
| 18 | 2'-(3-chloro-2-fluorophenyl)-7'-methoxyspiro[1,3-oxazole-4,9'-xanthen]-2-amine | D | 411.0 | ++ | + |
| 19 | 2'-(2-fluoro-5-methoxyphenyl)-6'-methylspiro[1,3-oxazole-4,9'-xanthen]-2-amine | D | 391.0 | ++ | +++ |

TABLE 1-continued

| Ex. No. | Compound Name | Method | Observed MS | BACE1 FRET assay (uM) | HEK cell assay (uM) |
|---|---|---|---|---|---|
| 20 | 2'-methoxy-7'-(3-methylphenyl)spiro[1,3-oxazole-4,9'-xanthen]-2-amine | D | 373.0 | ++ | + |
| 21 | 2'-(2-chloro-3-pyridinyl)-7'-methoxyspiro[1,3-oxazole-4,9'-xanthen]-2-amine trifluoroacetic acid | D | 394.3 | ++ | + |
| 22 | 2'-methoxy-7'-(3-(trifluoromethoxy)phenyl)spiro[1,3-oxazole-4,9'-xanthen]-2-amine | D | 443.2 | ++ | ++ |
| 23 | 2'-(5-chloro-2-fluoro-4-methylphenyl)-7'-methoxyspiro[1,3-oxazole-4,9'-xanthen]-2-amine | D | 425.0 | ++ | + |
| 24 | (4S)-6'-methyl-2'-(3-(trifluoromethoxy)phenyl)spiro[1,3-oxazole-4,9'-xanthen]-2-amine | D | 427.0 | + | ++ |
| 25 | 2'-(3-chlorophenyl)-6'-methylspiro[1,3-oxazole-4,9'-xanthen]-2-amine | D | 377.0 | + | ++ |
| 26 | 2'-(3-chloro-2-fluorophenyl)-6'-methylspiro[1,3-oxazole-4,9'-xanthen]-2-amine | D | 395.0 | + | ++ |
| 27 | 2'-methoxy-7'-(4-(trifluoromethoxy)phenyl)spiro[1,3-oxazole-4,9'-xanthen]-2-amine | D | 443.2 | + | ++ |
| 28 | 2'-(2-chlorophenyl)-7'-methoxyspiro[1,3-oxazole-4,9'-xanthen]-2-amine | D | 393.0 | + | ++ |
| 29 | 2'-(2-chlorophenyl)-6'-methylspiro[1,3-oxazole-4,9'-xanthen]-2-amine | D | 377.0 | + | + |
| 30 | 2'-(2-fluoro-3-methoxyphenyl)-6'-methylspiro[1,3-oxazole-4,9'-xanthen]-2-amine | D | 391.0 | + | + |
| 31 | (4R)-2'-methoxy-7'-(5-pyrimidinyl)spiro[1,3-oxazole-4,9'-xanthen]-2-amine | D | 361.0 | + | |
| 32 | 2'-methoxy-7'-(2-methylphenyl)spiro[1,3-oxazole-4,9'-xanthen]-2-amine | D | 373.0 | + | ++ |
| 33 | 6'-methyl-2'-(3-methylphenyl)spiro[1,3-oxazole-4,9'-xanthen]-2-amine | D | 357.0 | + | |
| 34 | 6'-methyl-2'-(2-methylphenyl)spiro[1,3-oxazole-4,9'-xanthen]-2-amine | D | 357.0 | + | |
| 35 | 2'-bromo-7'-methoxyspiro[1,3-oxazole-4,9'-xanthen]-2-amine | D | 363.1 | + | + |
| 36 | 6'-methyl-2'-(4-(trifluoromethoxy)phenyl)spiro[1,3-oxazole-4,9'-xanthen]-2-amine | D | 427.0 | + | |
| 37 | 2'-bromo-6'-methylspiro[1,3-oxazole-4,9'-xanthen]-2-amine | D | 347.2 | + | + |

The following are additional examples, representative of the present invention.

Example 38

Method E

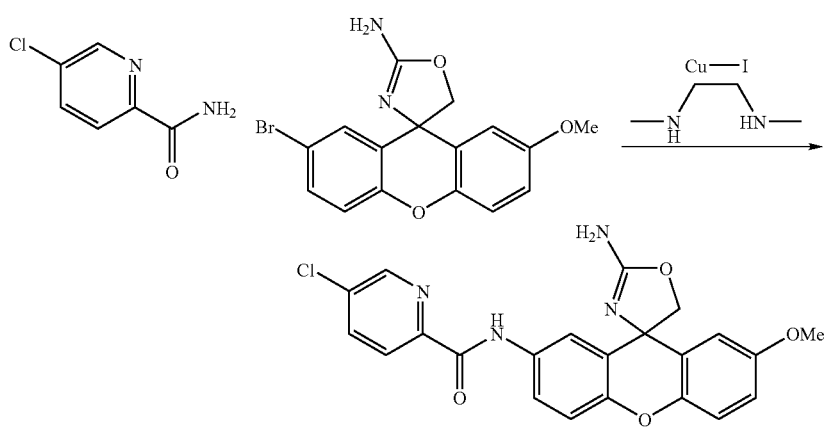

Synthesis of N-((4R)-2-amino-7'-methoxyspiro[1,3-oxazole-4,9'-xanthen]-2'-yl)-5-chloro-2-pyridinecarboxamide A vial was charged with 2'-bromo-7'-methoxyspiro[1,3-oxazole-4,9'-xanthen]-2-amine (90.0 mg, 249 µmol), 5-chloropicolinamide (59 mg, 374 µmol), cesium carbonate (244 mg, 748 µmol), copper(I) iodide (47 mg, 249 µmol), dioxane (2 mL), and N1,N2-dimethylethane-1,2-diamine (27 µl, 249 µmol). The vial was sealed under a blanket of Ar (g) and placed in a 110° C. oil bath for 5 days. The reaction mixture was then poured into a mixture of ammonium chloride solution (10 mL) and DCM (10 mL). The layers were separated, and the aqueous layer was extracted with DCM (2×5 mL). The combined organic extracts were dried over sodium sulfate, filtered, and evaporated. The residue was dissolved in DMSO and filtered, and the filtrate was purified by reverse-phase HPLC (10-90% $CH_3CN/H_2O$ with 0.1% TFA). The fractions containing the desired product were poured into saturated sodium bicarbonate solution and extracted with DCM (3×). The combined organic extracts were dried over sodium sulfate, filtered, and evaporated to give N-((4R)-2-amino-7'-methoxyspiro[1,3-oxazole-4,9'-xanthen]-2'-yl)-5-chloro-2-pyridinecarboxamide as a white solid. MS m/z=437.2 [M+H]+. Calc'd for $C_{22}H_{18}ClN_4O_4$: 437.1.

Example 39

Method F

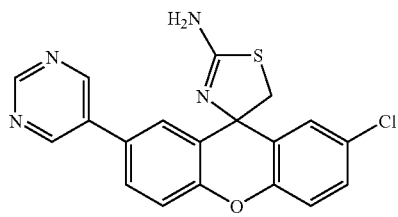 [SMILES: NC1=NC2(CS1)c1cc(Cl)ccc1Oc1ccc(-c3cncnc3)cc12]

Synthesis of Racemic 2'-chloro-7'-(5-pyrimidinyl)spiro[1,3-thiazole-4,9'-xanthen]-2-amine Step 1: Racemic-N-tert-butyl-2'-bromo-7'-chloro-spiro[1,3-thiazole-4,9'-xanthen]-2-amine A mixture of 2-bromo-7-chloro-9-methylene-9H-xanthene (950 mg, 3089 µmol) and silver thiocyanate (1538 mg, 9266 µmol) in ether (30887 µl, 3089 µmol) was treated with iodine (784 mg, 3089 µmol). After stirring for 3 h, the mixture was filtered through celite with the aid of ether. The filtrate was evaporated, and the residue was dissolved in THF (20 mL) and tert-butylamine (649 µl, 6177 µmol). The resulting mixture was stirred for 5 h, concentrated onto silica gel, and purified by chromatography on a 120-g Redi-Sep column, eluting with 0-40% EtOAc/Hexane to give racemic-N-tert-butyl-2'-bromo-7'-chloro-spiro[1,3-thiazole-4,9'-xanthen]-2-amine as a bright yellow foam. MS m/z=437.0 [M+H]+. Calc'd for $C_{19}H_{19}BrClN_2OS$: 437.0.

Step 2: Racemic-N-tert-butyl-2'-chloro-7'-(5-pyrimidinyl)spiro[1,3-thiazole-4,9'-xanthen]-2-amine A 10-20 mL microwave vial was charged with racemic-N-tert-butyl-2'-bromo-7'-chloro-spiro[1,3-thiazole-4,9'-xanthen]-2-amine (363 mg, 829 µmol), pyrimidin-5-ylboronic acid (257 mg, 2073 µmol), tetrakis(triphenylphosphine)palladium(0) (95.8 mg, 82.9 µmol), THF (8292 µl, 829 µmol), and potassium carbonate (3455 µl of a 1.2 M aqueous solution, 4146 µmol). The vial was covered with a blanket of Ar (g), capped, and heated in a Biotage Initiator microwave reactor for 1 h at 100° C. The organic layer was separated, dried over sodium sulfate, filtered, and evaporated. The residue was purified by chromatography on an 80-g Redi-Sep column, eluting with 0-50% EtOAc/Hexane to give rac-N-tert-butyl-2'-chloro-7'-(5-pyrimidinyl)spiro[1,3-thiazole-4,9'-xanthen]-2-amine as an orange-yellow solid. MS m/z=437.2 [M+H]+. Calc'd for $C_{23}H_{22}ClN_4OSS$: 437.1.

Step 3: Racemic-2'-chloro-7'-(5-pyrimidinyl)spiro[1,3-thiazole-4,9'-xanthen]-2-amine A vial was charged with rac-N-tert-butyl-2'-chloro-7'-(5-pyrimidinyl)spiro[1,3-thiazole-4,9'-xanthen]-2-amine (63.0 mg, 144 µmol) and TFA (1111 µl, 14418 µmol) resulting in a dark orange mixture. The vial was capped and placed in a 150° C. oil bath for 2 d. The reaction mixture cooled to RT, poured into 6N NaOH (aq.), and extracted with DCM (3×). The combined organic extracts were dried over sodium sulfate, filtered, and evaporated. The residue was purified by chromatography on a 12-g Redi-Sep column, eluting with 0-50% of a 90:10:1 mix of DCM/MeOH/$NH_4OH$ in DCM to give racemic-2'-chloro-7'-(5-pyrimidinyl)spiro[1,3-thiazole-4,9'-xanthen]-2-amine as an off-white solid. MS m/z=381.0 [M+H]+. Calc'd for $C_{19}H_{14}ClN_4OS$: 381.1.

Step 4: Chiral separation of racemic 2'-Chloro-7'-(5-pyrimidinyl)spiro[1,3-oxazole-4,9'-xanthen]-2-amine 2'-Chloro-7'-(5-pyrimidinyl)spiro[1,3-oxazole-4,9'-xanthen]-2-amine (440 mg) was subjected to chromatography using 20:80:0.2 MeOH:$CO_2$:DEA at 70 ml/min on a 20×150 mm, 5 m ChiralPak AD-H column and 100-bar system pressure. The first peak (RT=6.31 min) provided (4R)-2'-Chloro-7'-(5-pyrimidinyl)spiro[1,3-oxazole-4,9'-xanthen]-2-amine (98% ee), and the second peak (RT=15.7 min) provided (4S)-2'-Chloro-7'-(5-pyrimidinyl)spiro[1,3-oxazole-4,9'-xanthen]-2-amine (>99% ee).

Example 40

Method G

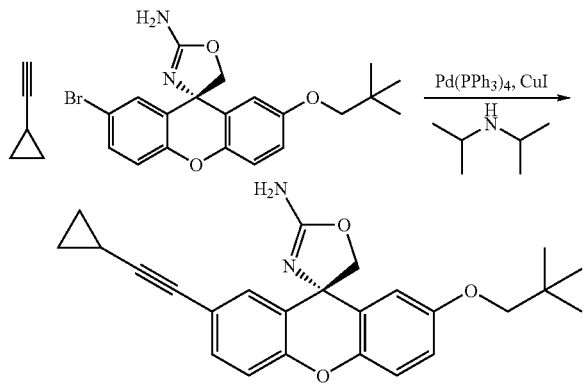

Synthesis of (4S)-2'-(cyclopropylethynyl)-7'-(2,2-dimethylpropoxy)spiro[1,3-oxazole-4,9'-xanthen]-2-amine A vial was charged with (4R)-2'-bromo-7'-(2,2-dimethylpropoxy)spiro[1,3-oxazole-4,9'-xanthen]-2-amine (52.5 mg, 126 μmol), tetrakis(triphenylphosphine)palladium(0) (14.5 mg, 12.6 μmol), copper(I) iodide (4.79 mg, 25.2 μmol), diisopropylamine (629 μl, 126 μmol), and ethynylcyclopropane (32.0 μl, 377 μmol). The vial was heated in a 50° C. oil bath for 15 h. The reaction mixture was diluted with EtOAc and filtered through celite. The filtrate was evaporated, and the crude residue was purified by chromatography on a 12-g Redi-Sep column, eluting with 0-5% MeOH/DCM to give (4S)-2'-(cyclopropylethynyl)-7'-(2,2-dimethylpropoxy)spiro[1,3-oxazole-4,9'-xanthen]-2-amine as a white solid. MS m/z=403.2 [M+H]+. Calc'd for $C_{25}H_{27}N_2O_3$: 403.2.

Example 41

Method H

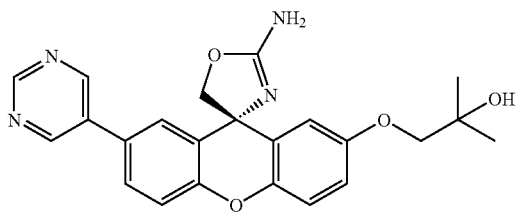 [SMILES: CC(C)(O)COc1ccc2c(c1)[C@]1(COC(N)=N1)c1cc(-c3cncnc3)ccc1O2]

Synthesis of 1-(((4S)-2-amino-7'-(5-pyrimidinyl)spiro[1,3-oxazole-4,9'-xanthen]-2'-yl)oxy)-2-methyl-2-propanol Step 1: (S)-1-(2-amino-2'-(pyrimidin-5-yl)-5H-spiro[oxazole-4,9'-xanthene]-7'-yloxy)propan-2-one A vial was charged with (S)-2-amino-7'-(pyrimidin-5-yl)-5H-spiro[oxazole-4,9'-xanthen]-2'-ol (192.0 mg, 554 μmol), cesium carbonate (271 mg, 832 μmol), and potassium iodide (92.0 mg, 554 μmol). DMF (2217 μl, 554 μmol) was added, the vial was sonicated for about 30 seconds, and the mixture was stirred vigorously for 20 min, at which time some white solid still remained. The vial was cooled in an ice-bath for 10 min, and to it chloroacetone (48.6 μl, 610 μmol) was added dropwise. The cooling bath was removed after 5 h, and the mixture was stirred for an additional 10 h. The reaction mixture was partitioned between water and EtOAc. The layers were separated and the aqueous layer was extracted with EtOAc (2×). The combined organic extracts were dried over sodium sulfate, filtered, and evaporated. The residue was purified by chromatography on a 40-g Redi-Sep column, eluting with 2.5%-10% MeOH/DCM to afford (S)-1-(2-amino-2'-(pyrimidin-5-yl)-5H-spiro[oxazole-4,9'-xanthene]-7'-yloxy)propan-2-one as a white solid. MS m/z=403.2 [M+H]+. Calc'd for $C_{22}H_{19}N_4O_4$: 403.1.

Step 2: 1-(((4S)-2-amino-7'-(5-pyrimidinyl)spiro[1,3-oxazole-4,9'-xanthen]-2'-yl)oxy)-2-methyl-2-propanol A 15-mL RBF was charged with the product from (S)-1-(2-amino-2'-(pyrimidin-5-yl)-5H-spiro[oxazole-4,9'-xanthene]-7'-yloxy)propan-2-one (104 mg, 258 μmol) in THF (2584 μl, 258 μmol). The flask was cooled in an ice-bath for 5 min, and methylmagnesium chloride, (258 μl of a 3.0 M solution in ether, 775 μmol) was added dropwise to it over 20 sec, resulting in a yellowish-white suspension. After 2 h, an additional portion of Grignard reagent (150 uL) was added and the ice-bath was removed. After 2 h, the mixture was quenched with saturated ammonium chloride solution and diluted with EtOAc and water. The layers were separated, and the aqueous layer was extracted with EtOAc (2×). The combined organic extracts were dried over sodium sulfate, filtered, and evaporated. The residue was purified by chromatography on a 40-g Redi-Sep column with 5% MeOH/DCM, then with 8% MeOH/DCM to afford 1-(((4S)-2-amino-7'-(5-pyrimidinyl)spiro[1,3-oxazole-4,9'-xanthen]-2'-yl)oxy)-2-methyl-2-propanol as a white solid. MS m/z=419.2 [M+H]+. Calc'd for $C_{23}H_{23}N_4O_4$: 419.2.

Example 42

Method I

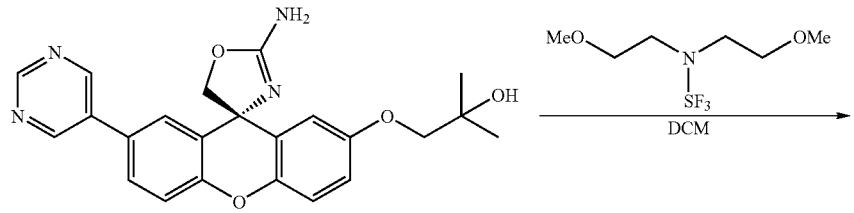

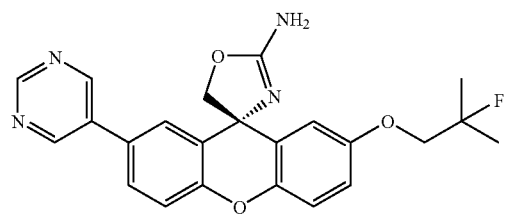

Synthesis of (4S)-2'-(2-fluoro-2-methylpropoxy)-7'-(5-pyrimidinyl)spiro[1,3-oxazole-4,9'-xanthen]-2-amine A solution of 1-(((4S)-2-amino-7'-(5-pyrimidinyl)spiro[1,3-oxazole-4,9'-xanthen]-2'-yl)oxy)-2-methyl-2-propanol (25 mg, 60 µmol) in DCM (2 mL) was cooled in a dry-ice acetone bath for 10 min, then to it Deoxo-Fluor (28 µl, 149 µmol) was added dropwise. The mixture was stirred for 1 h, then quenched by the addition of saturated sodium bicarbonate solution (aq.). The mixture was warmed to RT and partitioned between water and DCM. The aqueous layer was extracted with DCM (2×). The combined organic extracts were dried over sodium sulfate, filtered, and evaporated. The residue was purified by chromatography on a 12-g Redi-Sep column, eluting with 0-7.5% MeOH/DCM to give 20 mg of a white solid that was further purified by reverse-phase HPLC (10-90% $CH_3CN/H_2O$ with 0.1% TFA). The fractions containing product were combined in saturated sodium bicarbonate solution and extracted with DCM (2×). The combined organic extracts were dried over sodium sulfate, filtered and evaporated to give (4S)-2'-(2-fluoro-2-methylpropoxy)-7'-(5-pyrimidinyl)spiro[1,3-oxazole-4,9'-xanthen]-2-amine as a white solid. MS m/z=421.2 $[M+H]^+$. Calc'd for $C_{23}H_{22}FN_4O_3$: 421.2.

Example 43

Method J

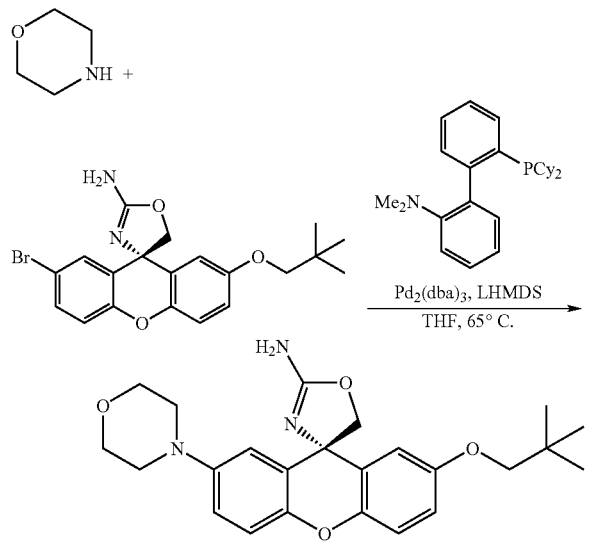

Synthesis of (4S)-2'-(2,2-dimethylpropoxy)-7'-(4-morpholinyl)spiro[1,3-oxazole-4,9'-xanthen]-2-amine A vial was charged with (4R)-2'-bromo-7'-(2,2-dimethylpropoxy)spiro[1,3-oxazole-4,9'-xanthen]-2-amine (80.0 mg, 192 µmol), DavePhos (9.05 mg, 23.0 µmol), tris(dibenzylideneacetone)dipalladium(0) (8.78 mg, 9.59 µmol), lithium bis(trimethylsilyl)amide (767 µl of a 1.0 M solution in THF, 767 µmol), and morpholine (50.1 µl, 575 µmol). The vial was sealed and heated in a 65° C. oil bath for 15 h. The reaction mixture was diluted with a saturated aqueous ammonium chloride solution (10 mL) and extracted with DCM (3×10 mL). The combined organic extracts were dried over sodium sulfate, filtered, and evaporated. The residue was purified by chromatography on a 12-g Redi-Sep column, eluting with 0-8% MeOH/DCM. The first fraction containing product was mixed and was discarded. The remaining fractions were combined and evaporated to yield (4S)-2'-(2,2-dimethylpropoxy)-7'-(4-morpholinyl)spiro[1,3-oxazole-4,9'-xanthen]-2-amine as a pale yellow solid. MS m/z=424.2 [M+H]+. Calc'd for $C_{24}H_{30}N_3O_4$: 424.2.

Method K

Compounds prepared by this Method involved procedures utilized in Method C, except employing (S)-2-amino-7'-(pyrimidin-5-yl)-5H-spiro[oxazole-4,9'-xanthen]-2'-ol as the starting material, rather than a racemic mixture.

Example 44

Method L

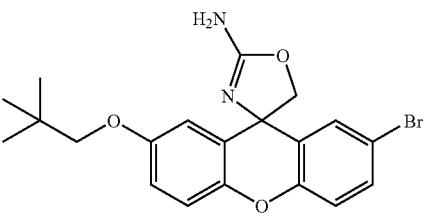 [SMILES: CC(C)(C)COc1ccc2c(c1)C1(COC(N)=N1)c1cc(Br)ccc1O2]

Synthesis of 2'-bromo-7'-(neopentyloxy)-5H-spiro[oxazole-4,9'-xanthen]-2-amine was carried out by a method similar to that described in example 3, steps 1 & 2, but using 2-bromo-9-methylene-7-(neopentyloxy)-9H-xanthene as starting material.

Method M

Compounds prepared by this Method involved procedures utilized in Method D, but employing (R)-2'-bromo-7'-(neopentyloxy)-5H-spiro[oxazole-4,9'-xanthen]-2-amine as starting material.

Example 45

Method N

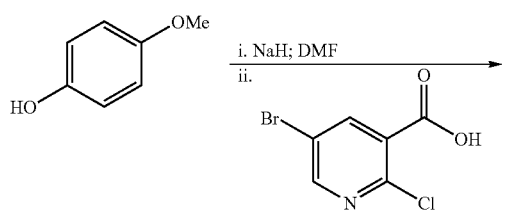

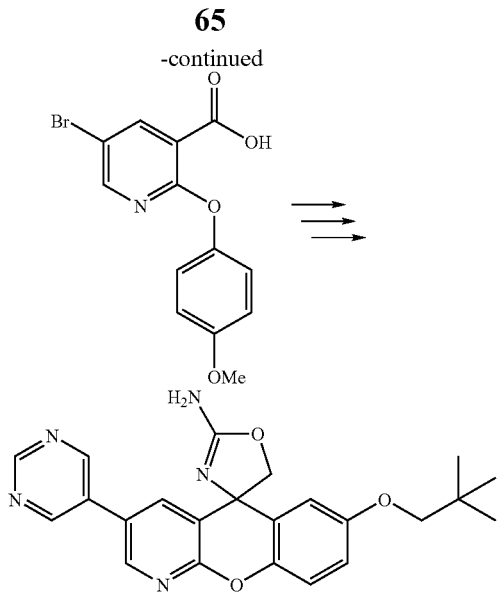

Synthesis of 7-(2,2-Dimethylpropoxy)-3-(5-pyrimidinyl)-spiro[chromeno[2,3b]pyridine]-5,4'-[1,3]oxazole]-2'-amine Step 1: 5-Bromo-2-(4-methoxyphenoxy)nicotinic acid To a 500 mL RB flask charged with sodium hydride (60% dispersion in mineral oil) (5.33 g, 133 mmol) was added DMF (127 ml, 63.4 mmol). To this slurry at 0° C. was added 4-methoxyphenol (7.88 g, 63.4 mmol) portion wise over 1 minute resulting in the evolution of large amounts of hydrogen gas. The mixture was removed from the ice batch and allowed to stir for 5 minutes, before 5-bromo-2-chloronicotinic acid (15.00 g, 63.4 mmol) was introduced portion wise over 2 minutes. The resulting green slurry was stirred at rt for 10 minutes at which point the reaction become homogeneous. The solution was then heated at 140° C. for 1 hour. The reaction was cooled to rt and diluted with 800 mL of water. The water was washed twice with ether (300 mL). The aqueous layer was acidified with acetic acid (18.2 ml, 317 mmol) and allowed to stir at rt for 12 hours to provide a fine off white solid. Filtered to provide 5-bromo-2-(4-methoxyphenoxy)nicotinic acid as an off white solid. MS m/z=324.0 [M+H]$^+$. Calc'd for $C_{13}H_{11}BrNO_4$: 324.0.

Step 2: 3-Bromo-7-methoxy-5H-chromeno[2,3-b]pyridin-5-one

A slurry of 5-bromo-2-(4-methoxyphenoxy)nicotinic acid (12.20 g, 37.6 mmol) and polyphosphoric acid (200 g) was heated at 135° C. for 1.5 hours. The reaction was cooled to rt and poured onto 300 g of ice before being basified to pH 12 with 50% aq. KOH (1.5 L). The resulting yellow slurry was filtered and washed with 100 mL of ether. The wet solid was then partitioned between water and DCM (1:1; 2000 mL). The layers were separated and the aqueous layer was extracted with DCM 5×500 mL. The combined organics were washed with brine, dried over sodium sulfate, filtered and concentrated to provide 3-bromo-7-methoxy-5H-chromeno[2,3-b]pyridin-5-one as a yellow solid. MS m/z=306.2 [M+H]$^+$. Calc'd for $C_{13}H_9BrNO_3$: 306.0.

Step 3: 3-bromo-7-methoxy-5-methylene-5H-chromeno[2,3-b]pyridine

To a solution of 3-bromo-7-methoxy-5H-chromeno[2,3-b]pyridin-5-one (4.50 g, 14.7 mmol) in THF (294 ml, 14.7 mmol) at 5° C. was added methylmagnesium bromide (1 M in butyl ether) (36.8 ml, 36.8 mmol). The reaction was removed from the ice bath and stirred for an additional 1 hour. TLC showed complete conversion to a lower Rf material. The reaction mixture was quenched with saturated ammonium chloride (250 mL) and to it DCM (100 mL) was added. The mixture was stirred vigorously for 30 minutes before being poured into a separatory funnel containing 300 mL of DCM. The layers were separated and the aqueous layer was extracted with DCM 2×100 mL. The combined organic layers were washed with brine, dried over $Na_2SO_4$ and filtered. TLC revealed tertiary alcohol and no olefin. The organics were concentrated under reduced pressure at 60° C. Flask was maintained at 60° C. on the rotovap for 1 hour at which point TLC and NMR show clean conversion to 3-bromo-7-methoxy-5-methylene-5H-chromeno[2,3-b]pyridine. MS m/z=304.2 [M+H]$^+$. Calc'd for $C_{14}H_{11}BrNO_2$: 304.0.

Step 4: 3-Bromo-7-methoxy-spiro[chromeno[2,3-b]pyridine]-5,4'-[1,3]oxazole]-2'-amine A 500 mL RBF containing iodine (3067 mg, 12083 μmol) and 60 mL of THF was cooled to −15° C. Silver cyanate (5175 mg, 34524 μmol) was added in one portion, and the mixture was stirred at −15 to −20° C. for 20 minutes, after which a solution of 3-bromo-7-methoxy-5-methylene-5H-chromeno[2,3-b]pyridine (3500 mg, 11508 μmol) in 10 mL of THF was added to the mixture followed by a 2 mL THF wash. The resulting yellow slurry was maintained at −20° C. to −10° C. for 1 hour at which point LCMS indicated the complete consumption of the starting material. The mixture was diluted with 20 mL of ether and filtered through a pad of celite. The filter cake was washed with ether and concentrated with minimal heating to provide an orange residue. This residue was taken up in 70 mL of THF and cooled to 0° C. and treated with ammonia (2 M in propanol) (17262 μl, 34524 μmol). The mixture was stirred at 0° C. for 5 minutes then removed from ice bath, warmed to rt and stirred overnight. The reaction was quenched with 10% $Na_2S_2O_3$ 250 mL and poured into ethyl acetate 250 mL. The layers were separated and the aqueous layer was extracted with ethyl acetate 2×250 mL. The combined organic layers were washed with brine, dried over $Na_2SO_4$ and filtered. The resulting crude material was purified by flash chromatography eluting with 0-100% EA in hexanes to provide 3-bromo-7-methoxy-spiro[chromeno[2,3-b]pyridine]-5,4'-[1,3]oxazole]-2'-amine as a tan foam. MS m/z=362.1 [M+H]$^+$. Calc'd for $C_{15}H_{13}BrN_3O_3$: 362.0.

Step 5: 3-Bromo-7-hydroxy-spiro[chromeno[2,3-b]pyridine]-5,4'-[1,3]oxazole]-2'-amine To a solution of 3-bromo-7-methoxy-spiro[chromeno[2,3-b]pyridine]-5,4'-[1,3]oxazole]-2'-amine (2300 mg, 6350 μmol) in DCM (127009 μl, 6350 μmol) at 0° C. was added tribromoborane (1801 μl, 19051 μmol). Immediately a thick precipitate formed. The resulting red slurry was stirred at 0° C. for 10 minutes at which point the ice bath was removed and the mixture was allowed to warm to rt and stirred at rt for 1 hour. Added another 1 mL of tribromoborane at rt and the mixture was stirred for another hour. The reaction was cooled to 0° C. and carefully quenched with saturated sodium bicarbonate 250 mL and poured into DCM 250 mL. The layers were separated and the aqueous layer was extracted with DCM 3×300 mL. The organic layers were washed with brine, dried over Na$_2$SO$_4$ and filtered. The extraction process was repeated with DCM. All organic layers were combined and concentrated under reduced pressure to provide 3-bromo-7-hydroxy-spiro[chromeno[2,3-b]pyridine]-5,4'-[1,3]oxazole]-2'-amine as a brown solid. MS m/z=348.0 [M+H]$^+$. Calc'd for C$_{14}$H$_{11}$BrN$_3$O$_3$: 348.0.

Step 6: 3-Bromo-7-(2,2-dimethylpropoxy)-spiro[chromeno[2,3-b]pyridine]-5,4'-[1,3]oxazole]-2'-amine To a solution of 3-bromo-7-hydroxy-spiro[chromeno[2,3-b]pyridine]-5,4'-[1,3]oxazole]-2'-amine (650 mg, 1867 µmol) and DMF (7468 µl, 1867 µmol) in a microwave vial were added cesium carbonate (1521 mg, 4668 µmol) and 1-iodo-2,2-dimethylpropane (495 µl, 3734 µmol). The mixture was heated in a microwave at 100° C. for 1 hour and to it was added another 400 mL of 1-iodo-2,2-dimethylpropane and heated in the microwave at 100° C. for another 1 hour. The reaction was diluted with 5 mL of water and 5 mL of ethyl acetate and stirred for 5 minutes until homogeneous. The resulting mixture was poured into 10 mL of ethyl acetate and 25 mL of saturated ammonium chloride the layers were separated. The aqueous layer was extracted with ethyl acetate 3×20 mL. The aqueous layer was then extracted with DCM 3×15 mL. The organic layers were each washed with brine, combined, dried over sodium sulfate, filtered and concentrated. The resulting oil was purified by silica gel chromatography (12 g RediSep) 0-100% EA in hexanes then repurified 0-100% EA in hexanes to provide 3-bromo-7-(2,2-dimethylpropoxy)-spiro[chromeno[2,3-b]pyridine]-5,4'-[1,3]oxazole]-2'-amine as a yellow solid. MS m/z=418.2 [M+H]$^+$. Calc'd for C$_{19}$H$_{21}$BrN$_3$O$_3$: 418.1.

Step 7: 7-(2,2-Dimethylpropoxy)-3-(5-pyrimidinyl)-spiro[chromeno[2,3-b]pyridine]-5,4'-[1,3]oxazole]-2'-amine A sealable tube was charged with 3-bromo-7-(2,2-dimethylpropoxy)-spiro[chromeno[2,3-b]pyridine]-5,4'-[1,3]oxazole]-2'-amine (0.120 g, 287 µmol), pyrimidin-5-ylboronic acid (98 mg, 789 µmol), Pd(Ph$_3$P)$_4$ (33 mg, 29 µmol) 8 mL of THF and a solution of potassium carbonate (1 M) (1434 µl, 1434 µmol). The tube was sealed and heated at 90° C. for 2.5 hours. The reaction was cooled to RT and diluted with 15 mL of water. The organics were removed and the aqueous layer was extracted with ethyl acetate 3×45 mL. The combined organics were washed with brine, dried over sodium sulfate, filtered and concentrated to provide a residue which was purified by chromatography on silica gel (40 g; 0-10% MeOH in DCM) to provide 7-(2,2-dimethylpropoxy)-3-(5-pyrimidinyl)-spiro[chromeno[2,3-b]pyridine]-5,4'-[1,3]oxazole]-2'-amine as a yellow solid. MS m/z=418.2 [M+H]$^+$. Calc'd for C$_{23}$H$_{24}$N$_5$O$_3$: 418.2.

Step 8: Chiral separation of racemic 7-(2,2-dimethylpropoxy)-3-(5-pyrimidinyl)-spiro[chromeno[2,3-b]pridine]-5,4'-[1,3]oxazole]-2'-amine Racemic 7-(2,2-dimethylpropoxy)-3-(5-pyrimidinyl)-spiro[chromeno[2,3-b]pyridine]-5,4'-[1,3]oxazole]-2'-amine (69 mg) was subjected to chromatography using 15:85:0.1 MeOH:CO$_2$:DEA at 70 ml/min on a 2×15 cm, 5 µm Chiral-Pak AD-H column and 100-bar system pressure. The first peak (RT=3.2 min) provided (S)-7-(2,2-dimethylpropoxy)-3-(5-pyrimidinyl)-spiro[chromeno[2,3-b]pyridine]-5,4'-[1,3]oxazole]-2'-amine (29 mg, >99% ee), and the second peak (RT=6.8 min) provided (R)-7-(2,2-dimethylpropoxy)-3-(5-pyrimidinyl)-spiro[chromeno[2,3-b]pyridine]-5,4'-[1,3]oxazole]-2'-amine (>99% ee).

Example 46

Method O

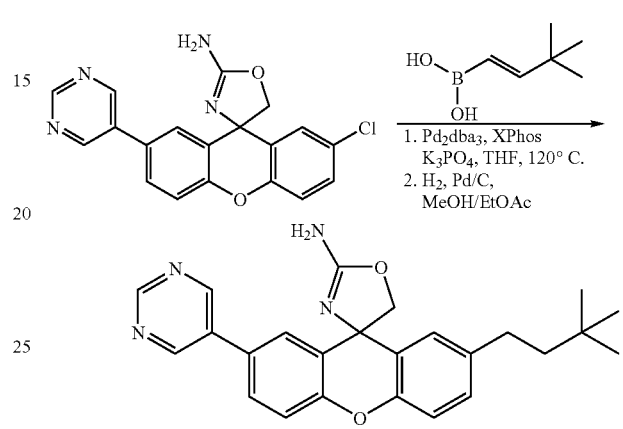

Synthesis of (rac)-2'-(3,3-dimethylbutyl)-7'-(5-pyrimidinyl)spiro[1,3-oxazole-4,9'-xanthen]-2-amine A microwave vial was charged with (rac)-2'-Chloro-7'-(5-pyrimidinyl)spiro[1,3-oxazole-4,9'-xanthen]-2-amine (prepared in a manner similar to Example 39; 90 mg, 247 µmol), Pd$_2$dba$_3$ (11 mg, 12 µmol), X-Phos (12 mg, 25 µmol), (E)-3,3-dimethylbut-1-enylboronic acid (63 mg, 493 µmol) and potassium phosphate (157 mg, 740 µmol). THF (2 mL) was added and the mixture was heated at 120° C. in microwave reactor for 2 hrs. The mixture was diluted with ethyl acetate and filtered through plug of Celite. After removal of the solvents the residue was purified by flash chromatography on silica gel (12 g Redi-Sep column, 20-100% DCM/MeOH/NH$_4$OH 90:10:1 in DCM) to give 2'-(3,3-dimethylbut-1-enyl)-7'-(pyrimidin-5-yl)-5H-spiro[oxazole-4,9'-xanthen]-2-amine (65 mg, 64% yield). This product was hydrogenated at 1 atm of H$_2$ in MeOH/EtOAc mixture using 10% palladium on carbon (53 mg, 49 µmol) for 60 hrs. The reaction mixture was filtered and concentrated in vacuo and was further purified by reverse-phase HPLC (10-90% CH$_3$CN/H$_2$O with 0.1% TFA). The fractions containing product were combined and dried overnight under high vacuum to give 2'-(3,3-dimethylbutyl)-7'-(pyrimidin-5-yl)-5H-spiro[oxazole-4,9'-xanthen]-2-amine as its TFA salt.

Step 2: Chiral separation of racemic 2'-(3,3-dimethylbutyl)-7'-(pyrimidin-5-yl)-5H-spiro[oxazole-4,9'-xanthen]-2-amine Racemic 2'-(3,3-dimethylbutyl)-7'-(pyrimidin-5-yl)-5H-spiro[oxazole-4,9'-xanthen]-2-amine (490 mg) from step 1 was subjected to chromatography using 20:80:0.1 MeOH:CO$_2$:DEA at 70 ml/min on a 20×150 mm ChiralPak AD-H column and 100-bar system pressure. The first peak (RT=1.97 min) provided (4S)-2'-(3,3-dimethylbutyl)-7'-(pyrimidin-5-yl)-5H-spiro[oxazole-4,9'-xanthen]-2-amine (210 mg, 99% ee), and the second peak (RT=4.43 min) provided (4R)-2'-(3,3-dimethylbutyl)-7'-(pyrimidin-5-yl)-5H-spiro[oxazole-4,9'-xanthen]-2-amine (>99% ee).

Example 47

Method P

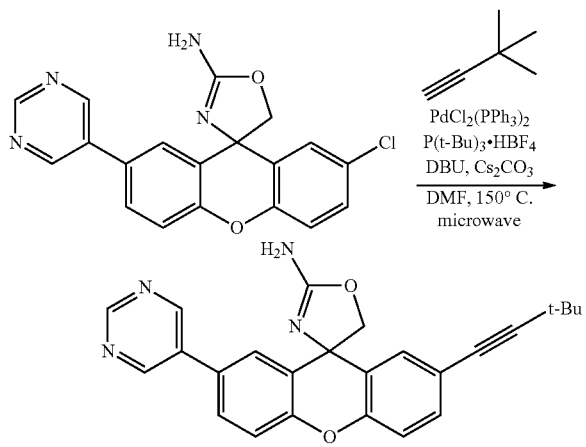

Synthesis of 2'-(3,3-dimethylbut-1-ynyl)-7'-(pyrimidin-5-yl)-5H-spiro[oxazole-4,9'-xanthen]-2-amine A microwave vial was charged with (racemic)-2'-Chloro-7'-(5-pyrimidinyl)spiro[1,3-oxazole-4,9'-xanthen]-2-amine (prepared in a manner similar to Example 39; 100 mg, 274 μmol), cesium carbonate (134 mg, 411 μmol), bis(triphenylphosphine)palladium(II) chloride (19 mg, 27 μmol) and tri-tert-butylphosphonium tetrafluoroborate (16 mg, 55 μmol). DMF (1 ml), DBU (21 μl, 137 μmol) and 3,3-dimethylbut-1-yne (167 μl, 1371 μmol) were added. The vial was sealed and heated at 150° C. in Biotage microwave oven for 60 min. The mixture was diluted with 5 ml of EtOAc, filtered through Celite and concentrated in vacuo to give brown oil, which was re-dissolved in 7 ml of EtOAc and shaken with 10 ml of 2N HCl. Acidic aqueous layer was basified with 30% ammonium hydroxide and precipitated brown oil was extracted twice with EtOAc. The organic layers were washed with brine, concentrated, dissolved in 1.5 ml of DMF, filtered through Nalgene PTFE 0.2 mkm filter and subjected to preparative reverse phase HPLC (15-90% ACN in 0.1% aq TFA). The fractions containing product were concentrated in vacuo in order to remove ACN, saturated NaHCO₃ was added and the mixture was extracted with EtOAc (15 ml). The organic layer was washed with brine, dried over MgSO₄ and concentrated to give (rac)-2'-(3,3-dimethylbut-1-ynyl)-7'-(pyrimidin-5-yl)-5H-spiro[oxazole-4,9'-xanthen]-2-amine (49% yield).

Step 2: Chiral separation of racemic 2'-(3,3-dimethylbut-1-ynyl)-7'-(pyrimidin-5-yl)-5H-spiro[oxazole-4,9'-xanthen]-2-amine Racemic 2'-(3,3-dimethylbut-1-ynyl)-7'-(pyrimidin-5-yl)-5H-spiro[oxazole-4,9'-xanthen]-2-amine (490 mg) was subjected to chromatography using 20:80:0.1 MeOH:CO₂:DEA at 65 ml/min on a 20×150 mm ChiralPak AD-H column and 100-bar system pressure. The first peak (RT=3.51 min) provided (4S)-2'-(3,3-dimethylbut-1-ynyl)-7'-(pyrimidin-5-yl)-5H-spiro[oxazole-4,9'-xanthen]-2-amine (204 mg, 99% ee), and the second peak (RT=5.44 min) provided (4R)-2'-(3,3-dimethylbut-1-ynyl)-7'-(pyrimidin-5-yl)-5H-spiro[oxazole-4,9'-xanthen]-2-amine (>99% ee).

Method Q

Compounds prepared by this Method involved procedures utilized in Method P except employing (4S)-2'-Chloro-7'-(5-pyrimidinyl)spiro[1,3-oxazole-4,9'-xanthen]-2-amine as the starting material, instead of a racemic mixture.

Example 48

Method R

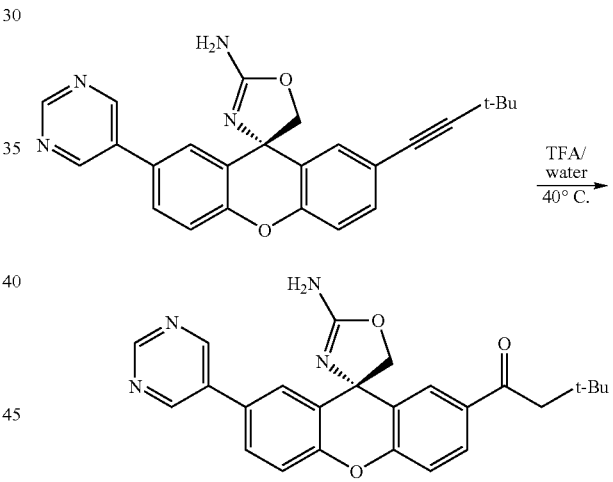

Synthesis of 1-((4S)-2-Amino-7'-(5-pyrimidinyl)spiro[1,3-oxazole-4,9'-xanthen]-2'-yl)-3,3-dimethyl-1-butanone (4R)-2'-(3,3-Dimethylbut-1-ynyl)-7'-(pyrimidin-5-yl)-5H-spiro[oxazole-4,9'-xanthen]-2-amine (70 mg, 171 μmol) was dissolved in TFA (1.31 ml) at RT and water (31 μl, 1705 μmol) was added. The mixture then was heated at 40° C. for 1 hr. TFA was removed in a stream of nitrogen and yellow residue was treated with 1.5 ml of 2N ammonia in methanol for 15 min at RT. The solution was concentrated in vacuo, residue was diluted with ethyl acetate (5 ml), the solution was washed with saturated NaHCO₃ solution, brine, dried with magnesium sulfate and concentrated to give 1-((4S)-2-amino-7'-(5-pyrimidinyl)spiro[1,3-oxazole-4,9'-xanthen]-2'-yl)-3,3-dimethyl-1-butanone.

Example 49

Method S

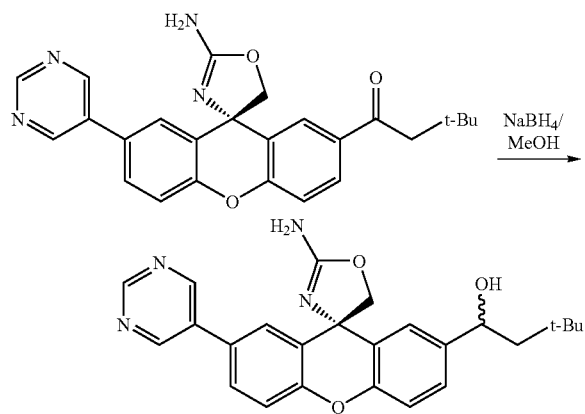

Synthesis of (1RS)-1-((4S)-2-amino-7'-(5-pyrimidinyl)spiro[1,3-oxazole-4,9'-xanthen]-2'-yl)-3,3-dimethyl-1-butanol Sodium borohydride (33.1 mg, 874 μmol) was added at RT to a solution of 1-((4S)-2-amino-7'-(5-pyrimidinyl)spiro[1,3-oxazole-4,9'-xanthen]-2'-yl)-3,3-dimethyl-1-butanone (312 mg, 728 μmol) in methanol (5 ml) and the mixture was stirred for 1 hr at ambient temperature. Saturated ammonium chloride solution (3 ml) was added, the mixture was diluted with ethyl acetate (5 ml) and water was added to dissolve solids. The organic layer was washed with brine, dried and concentrated to give pink solid which was purified by chromatography on silica gel (12 g Redi-Sep column, 15-75% DCM/MeOH/NH$_4$OH 90:10:1 in DCM) to afford (1RS)-1-((4S)-2-amino-7'-(5-pyrimidinyl)spiro[1,3-oxazole-4,9'-xanthen]-2'-yl)-3,3-dimethyl-1-butanol as white solid.

The following examples in Table II were prepared by Methods and Steps analogous to those described in Examples 3, 6-8 and 38-49 above. For example, Example no. 56 was prepared by a combination of the methods taught in methods K and C. Provided also is the mass spectral data and BACE enzyme and cell-based assay data (IC$_{50}$'s in uM ranges) for each example, where available.

TABLE 1I

| Ex. No. | Compound Name | Method | Observed MS | BACE1 FRET assay (uM) | HEK cell assay (uM) |
|---|---|---|---|---|---|
| 39 | (4R)-2'-chloro-7'-(5-pyrimidinyl)spiro[1,3-thiazole-4,9'-xanthen]-2-amine | F | 381 | +++ | + |
| 50 | (4R)-2'-(2,2-dimethylpropoxy)-7'-(5-pyrimidinyl)spiro[1,3-oxazole-4,9'-xanthen]-2-amine | C | 417.2 | ++++ | +++ |
| 51 | (4S)-2'-(2,2-dimethylpropoxy)-7'-(5-pyrimidinyl)spiro[1,3-oxazole-4,9'-xanthen]-2-amine | C | 417.2 | ++++ | ++++ |
| 52 | (4R)-2'-(3,3-dimethylbutyl)-7'-(5-pyrimidinyl)spiro[1,3-oxazole-4,9'-xanthen]-2-amine | O | 415.2 | ++++ | ++++ |
| 53 | (4S)-2'-propyl-7'-(5-pyrimidinyl)spiro[1,3-oxazole-4,9'-xanthen]-2-amine | O | 373.3 | ++++ | +++ |
| 54 | (5R)-7-methoxy-3-(5-pyrimidinyl)spiro[chromeno[2,3-b]pyridine-5,4'-[1,3]oxazol]-2'-amine | N | 362.2 | ++ | + |
| 55 | N-((4R)-2-amino-7'-methoxyspiro[1,3-oxazole-4,9'-xanthen]-2'-yl)-5-chloro-2-pyridinecarboxamide | E | 437.2 | ++++ | +++ |
| 56 | (4S)-2'-(2-methylpropoxy)-7'-(5-pyrimidinyl)spiro[1,3-oxazole-4,9'-xanthen]-2-amine | K/C | 403.2 | ++++ | ++++ |
| 57 | 2'-bromo-7'-(2,2-dimethylpropoxy)spiro[1,3-oxazole-4,9'-xanthen]-2-amine | L | 417/419 | +++ | ++ |
| 58 | (4S)-2'-(5-pyrimidinyl)-7'-(2,2,2-trifluoroethoxy)spiro[1,3-oxazole-4,9'-xanthen]-2-amine | K/C | 429.2 | ++++ | +++ |
| 59 | (4S)-2'-(3,3-dimethyl-1-butyn-1-yl)-7'-(5-pyrimidinyl)spiro[1,3-oxazole-4,9'-xanthen]-2-amine | P | 410 | ++++ | ++++ |
| 60 | (4S)-2'-(5-pyrimidinyl)-7'-(tetrahydro-2-furanylmethoxy)spiro[1,3-oxazole-4,9'-xanthen]-2-amine | K/C | 431.1 | ++++ | ++++ |
| 61 | (4S)-2'-(cyclopropylmethoxy)-7'-(5-pyrimidinyl)spiro[1,3-oxazole-4,9'-xanthen]-2-amine | K/C | 401.4 | ++++ | ++++ |
| 40 | (4S)-2'-(cyclopropylethynyl)-7'-(2,2-dimethylpropoxy)spiro[1,3-oxazole-4,9'-xanthen]-2-amine | G | 403.2 | ++++ | +++ |
| 62 | (4S)-2'-((2,2-difluorocyclopropyl)methoxy)-7'-(5-pyrimidinyl)spiro[1,3-oxazole-4,9'-xanthen]-2-amine | K/C | 437.1 | ++++ | ++++ |

TABLE 1I-continued

| Ex. No. | Compound Name | Method | Observed MS | BACE1 FRET assay (uM) | HEK cell assay (uM) |
|---|---|---|---|---|---|
| 63 | (4S)-2'-(3,3-dimethylbutyl)-7'-(5-pyrimidinyl)spiro[1,3-oxazole-4,9'-xanthen]-2-amine | O | 415.2 | ++++ | +++ |
| 64 | (4S)-2'-(3,3-dimethylbutyl)-7'-(5-pyrimidinyl)spiro[1,3-oxazole-4,9'-xanthen]-2-amine | O | 415.2 | ++++ | +++ |
| 65 | (4R)-2'-(3,3-dimethylbutyl)-7'-(5-pyrimidinyl)spiro[1,3-oxazole-4,9'-xanthen]-2-amine | O | 415.2 | ++++ | ++++ |
| 66 | (4R)-2'-(3,3-dimethylbutyl)-7'-(5-pyrimidinyl)spiro[1,3-oxazole-4,9'-xanthen]-2-amine | O | 415.2 | ++++ | ++++ |
| 67 | (5R)-7-(2,2-dimethylpropoxy)-3-(5-pyrimidinyl)spiro[chromeno[2,3-b]pyridine-5,4'-[1,3]oxazol]-2'-amine | N | 418.2 | ++++ | +++ |
| 68 | (5R)-7-(2,2-dimethylpropoxy)-3-(3-pyridinyl)spiro[chromeno[2,3-b]pyridine-5,4'-[1,3]oxazol]-2'-amine | N | 417.2 | ++++ | ++++ |
| 69 | (5R)-3-(5-chloro-2-fluorophenyl)-7-(2,2-dimethylpropoxy)spiro[chromeno[2,3-b]pyridine-5,4'-[1,3]oxazol]-2'-amine | N | 468.2 | ++++ | ++ |
| 43 | (4S)-2'-(2,2-dimethylpropoxy)-7'-(4-morpholinyl)spiro[1,3-oxazole-4,9'-xanthen]-2-amine | J | 424.2 | +++ | +++ |
| 70 | (4S)-2'-(3,3-dimethylbutoxy)-7'-(5-pyrimidinyl)spiro[1,3-oxazole-4,9'-xanthen]-2-amine | K/C | 431.4 | ++++ | +++ |
| 71 | (5S)-7-(2,2-dimethylpropoxy)-3-(5-pyrimidinyl)spiro[chromeno[2,3-b]pyridine-5,4'-[1,3]oxazol]-2'-amine | N | 418.2 | +++ | +++ |
| 72 | (5R)-7-(2,2-dimethylpropoxy)-3-(5-pyrimidinyl)spiro[chromeno[2,3-b]pyridine-5,4'-[1,3]oxazol]-2'-amine | N | 418.2 | ++++ | ++++ |
| 73 | (4S)-2'-(2,2-dimethylpropoxy)-7'-(1H-indol-5-yl)spiro[1,3-oxazole-4,9'-xanthen]-2-amine | M/D | 454.2 | +++ | ++ |
| 74 | (4S)-2'-(cyclopentylmethoxy)-7'-(5-pyrimidinyl)spiro[1,3-oxazole-4,9'-xanthen]-2-amine | K/C | 429.3 | ++++ | ++++ |
| 75 | (4S)-2'-(5-chloro-2-fluorophenyl)-7'-(2,2-dimethylpropoxy)spiro[1,3-oxazole-4,9'-xanthen]-2-amine | M/D | 467.8 | ++++ | +++ |
| 76 | (4S)-2'-(2,2-dimethylpropoxy)-7'-(3-furanyl)spiro[1,3-oxazole-4,9'-xanthen]-2-amine | M/D | 405.8 | ++++ | ++ |
| 77 | (4S)-2'-(2,2-dimethylpropoxy)-7'-(2-methoxy-3-pyridinyl)spiro[1,3-oxazole-4,9'-xanthen]-2-amine | M/D | 446.8 | ++++ | ++ |
| 78 | (4S)-2'-(2,2-dimethylpropoxy)-7'-(6-fluoro-3-pyridinyl)spiro[1,3-oxazole-4,9'-xanthen]-2-amine | M/D | 434.2 | ++++ | +++ |
| 79 | (4S)-2'-(2,2-dimethylpropoxy)-7'-(2-methyl-3-pyridinyl)spiro[1,3-oxazole-4,9'-xanthen]-2-amine | M/D | 430.2 | +++ | +++ |
| 80 | (4S)-2'-(2,2-dimethylpropoxy)-7'-(6-methyl-3-pyridinyl)spiro[1,3-oxazole-4,9'-xanthen]-2-amine | M/D | 430.2 | +++ | ++ |
| 81 | (4S)-2'-(2,2-dimethylpropoxy)-7'-(5-methyl-3-pyridinyl)spiro[1,3-oxazole-4,9'-xanthen]-2-amine | M/D | 430.2 | ++++ | ++++ |
| 45 | (5R)-3-(cyclopropylethynyl)-7-(2,2-dimethylpropoxy)spiro[chromeno[2,3-b]pyridine-5,4'-[1,3]oxazol]-2'-amine | N | 404.1 | ++++ | +++ |
| 82 | (4S)-2'-(2,2-dimethylpropoxy)-7'-(1-methyl-1H-pyrazol-4-yl)spiro[1,3-oxazole-4,9'-xanthen]-2-amine | M/D | 419.2 | +++ | ++ |
| 83 | (4S)-2'-(2,2-dimethylpropoxy)-7'-(3-pyridinyl)spiro[1,3-oxazole-4,9'-xanthen]-2-amine | M/D | 416.2 | ++++ | ++++ |
| 84 | (4S)-2'-(2,2-dimethylpropoxy)-7'-(4-pyridinyl)spiro[1,3-oxazole-4,9'-xanthen]-2-amine | M/D | 416.2 | +++ | ++ |
| 85 | (4S)-2'-(2,2-dimethylpropoxy)-7'-phenylspiro[1,3-oxazole-4,9'-xanthen]-2-amine | M/D | 415.2 | ++++ | ++ |

TABLE 1I-continued

| Ex. No. | Compound Name | Method | Observed MS | BACE1 FRET assay (uM) | HEK cell assay (uM) |
|---|---|---|---|---|---|
| 86 | (4S)-2'-(2,2-dimethylpropoxy)-7'-(4-methyl-3-pyridinyl)spiro[1,3-oxazole-4,9'-xanthen]-2-amine | M/D | 430.2 | ++++ | +++ |
| 87 | (4S)-2'-(2,2-dimethylpropoxy)-7'-(6-methoxy-3-pyridinyl)spiro[1,3-oxazole-4,9'-xanthen]-2-amine | M/D | 446.2 | +++ | ++ |
| 88 | (4S)-2'-(2,2-dimethylpropoxy)-7'-(5-fluoro-3-pyridinyl)spiro[1,3-oxazole-4,9'-xanthen]-2-amine | M/D | 434.2 | ++++ | ++++ |
| 47 | (4S)-2'-(3,3-dimethyl-1-butyn-1-yl)-7'-(5-pyrimidinyl)spiro[1,3-oxazole-4,9'-xanthen]-2-amine | P | 411 | +++ | ++ |
| 47 | (4R)-2'-(3,3-dimethyl-1-butyn-1-yl)-7'-(5-pyrimidinyl)spiro[1,3-oxazole-4,9'-xanthen]-2-amine | P | 411 | ++++ | ++++ |
| 89 | (4S)-2'-(3-(dimethylamino)-1-propyn-1-yl)-7'-(2,2-dimethylpropoxy)spiro[1,3-oxazole-4,9'-xanthen]-2-amine | G | 420.2 | +++ | +++ |
| 90 | (5S)-3-(5-chloro-2-fluorophenyl)-7-(2,2-dimethylpropoxy)spiro[chromeno[2,3-b]pyridine-5,4'-[1,3]oxazol]-2'-amine | N | 468 | ++++ | ++ |
| 91 | (5R)-3-(5-chloro-2-fluorophenyl)-7-(2,2-dimethylpropoxy)spiro[chromeno[2,3-b]pyridine-5,4'-[1,3]oxazol]-2'-amine | N | 468 | ++++ | +++ |
| 92 | (5R)-7-(2,2-dimethylpropoxy)-3-(3-pyridinyl)spiro[chromeno[2,3-b]pyridine-5,4'-[1,3]oxazol]-2'-amine | N | 417.3 | ++++ | ++++ |
| 93 | (5S)-7-(2,2-dimethylpropoxy)-3-(3-pyridinyl)spiro[chromeno[2,3-b]pyridine-5,4'-[1,3]oxazol]-2'-amine | N | 417.3 | +++ | +++ |
| 48 | 1-((4R)-2-amino-7'-(5-pyrimidinyl)spiro[1,3-oxazole-4,9'-xanthen]-2'-yl)-3,3-dimethyl-1-butanone | R | 429 | +++ | +++ |
| 48 | 1-((4S)-2-amino-7'-(5-pyrimidinyl)spiro[1,3-oxazole-4,9'-xanthen]-2'-yl)-3,3-dimethyl-1-butanone | R | 429 | ++++ | ++++ |
| 94 | (4S)-2'-(cyclohexylmethoxy)-7'-(5-pyrimidinyl)spiro[1,3-oxazole-4,9'-xanthen]-2-amine | B | 443.4 | ++++ | |
| 95 | (4R)-2'-(cyclopentylethynyl)-7'-(5-pyrimidinyl)spiro[1,3-oxazole-4,9'-xanthen]-2-amine | Q | 423 | ++++ | |
| 97 | (4S)-2'-(((1S)-2,2-difluorocyclopropyl)methoxy)-7'-(5-pyrimidinyl)spiro[1,3-oxazole-4,9'-xanthen]-2-amine | K/C | 437.1 | ++++ | |
| 98 | (4S)-2'-(((1R)-2,2-difluorocyclopropyl)methoxy)-7'-(5-pyrimidinyl)spiro[1,3-oxazole-4,9'-xanthen]-2-amine | K/C | 437.1 | ++++ | |
| 99 | (4S)-2'-(3-pyridinyl)-7'-(tetrahydro-2-furanylmethoxy)spiro[1,3-oxazole-4,9'-xanthen]-2-amine | D | 430.2 | ++++ | |
| 100 | 1-(((4S)-2-amino-7'-(5-pyrimidinyl)spiro[1,3-oxazole-4,9'-xanthen]-2'-yl)oxy)-2-methyl-2-propanol | H | 419.2 | ++++ | |
| 101 | (4R)-2'-(cyclopropylethynyl)-7'-(5-pyrimidinyl)spiro[1,3-oxazole-4,9'-xanthen]-2-amine | Q | 395 | ++++ | |
| 102 | 1-((4S)-2-amino-7'-(5-pyrimidinyl)spiro[1,3-oxazole-4,9'-xanthen]-2'-yl)-2-cyclopentylethanone | R | 441 | ++++ | |
| 103 | (4S)-2'-(cyclopropylethynyl)-7'-(tetrahydro-2-furanylmethoxy)spiro[1,3-oxazole-4,9'-xanthen]-2-amine | G | 417.2 | ++++ | |
| 104 | (4S)-2'-(2-fluoro-2-methylpropoxy)-7'-(5-pyrimidinyl)spiro[1,3-oxazole-4,9'-xanthen]-2-amine | K/C | 421.2 | ++++ | |
| 105 | (4S)-2'-(5-pyrimidinyl)-7'-((2S)-tetrahydro-2-furanylmethoxy)spiro[1,3-oxazole-4,9'-xanthen]-2-amine | K/C | 431.4 | ++++ | |
| 106 | (4S)-2'-(5-pyrimidinyl)-7'-((2R)-tetrahydro-2-furanylmethoxy)spiro[1,3-oxazole-4,9'-xanthen]-2-amine | K/C | 431.4 | ++++ | |

TABLE 1I-continued

| Ex. No. | Compound Name | Method | Observed MS | BACE1 FRET assay (uM) | HEK cell assay (uM) |
|---|---|---|---|---|---|
| 107 | (4S)-2'-(5-pyrimidinyl)-7'-(tetrahydro-2H-pyran-2-ylmethoxy)spiro[1,3-oxazole-4,9'-xanthen]-2-amine | K/C | 445.2 | ++++ | |
| 49 | (1S)-1-((4S)-2-amino-7'-(5-pyrimidinyl)spiro[1,3-oxazole-4,9'-xanthen]-2'-yl)-3,3-dimethyl-1-butanol | S | 431 | ++++ | |

The following are additional compound examples, representative of the present invention.

Example 108a

Method JBH1

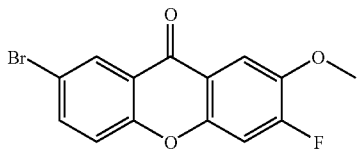 [SMILES: COc1cc2c(=O)c3cc(Br)ccc3oc2cc1F]

Synthesis of 7-Bromo-3-fluoro-2-methoxy-9H-xanthen-9-one

The titled compound was prepared in a manner similar to the procedure described in Example 1, but using 2-bromo-4-fluoro-5-methoxybenzoic acid as the starting material, which starting material was prepared as follows:

Step 1: 4-Bromo-2-fluoro-5-methylphenol 2-fluoro-5-methylphenol (23.8 g, 0.19 mol) and bromine (9.7 ml, 0.19 mol) are combined in 50 ml of glacial acetic acid and stirred at RT for one hour. Acetic acid was removed under vacuum. The liquid was diluted with ethyl acetate and washed with water. The organic layer was washed with brine, dried over anhydrous sodium sulfate, filtered and concentrated to afford 4-bromo-2-fluoro-5-methylphenol (38 g, 98% yield) as a colorless liquid. No [M+H] peak by LCMS. $^1$H NMR (400 MHz, CHLOROFORM-d) ppm 1.98 (s, 1H) 2.22 (s, 3H) 6.81 (dd, J=9.15, 0.54 Hz, 1H) 7.17 (d, J=9.88 Hz, 1H)

Step 2: 1-Bromo-5-fluoro-4-methoxy-2-methylbenzene

4-Bromo-2-fluoro-5-methylphenol (40 g, 0.19 mol), cesium carbonate (75 g, 0.23 mol), and iodomethane (15 ml, 0.23 mol) were combined in 100 ml of DMF and stirred at RT for one hour (exothermic). The solution was diluted with ethyl acetate and filtered. The solution was washed with water twice, dried with anhydrous sodium sulfate, filtered, and concentrated. The product was purified via silica gel column chromatography (RediSep 330 g column) using 0-50% ethyl acetate in hexane to afford 1-bromo-5-fluoro-4-methoxy-2-methylbenzene (38 g, 89% yield) as a colorless liquid. No [M+H] peak by LCMS. $^1$H NMR (400 MHz, CHLOROFORM-d) δ ppm 2.24 (s, 3H) 3.76 (s, 3H) 6.73 (d, J=8.80 Hz, 1H) 7.13 (d, J=10.56 Hz, 1H)

Step 3: 2-Bromo-4-fluoro-5-methoxybenzoic acid

Potassium permanganate (53 g, 3.4 mol) was added to a solution of 1-bromo-5-fluoro-4-methoxy-2-methylbenzene (37 g, 1.7 mol) in 75 ml of pyridine and 150 ml of water at 60° C. The solution was stirred at 60° C. degrees for 24 hours. The solution was filtered and the solids were washed with a solution of water/methanol (50:50). The filtrate was concentrated to approximately 100 ml, then acidified (pH 1) with concentrated HCl. The solid was collected by filtration and dried under vacuum to afford 2-bromo-4-fluoro-5-methoxybenzoic acid as an off white solid. MS m/z=248.9 [M+H].

Example 108b

Method JBH 2

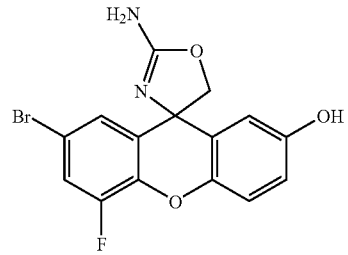

Synthesis of 2-Amino-2'-bromo-4'-fluoro-5H-spiro [oxazole-4,9'-xanthen]-7'-ol

The titled compound was prepared in a manner similar to the procedures described in scheme 1 and Examples 1 and 3, but using a fluoro-bromo-phenol (see scheme 1) as starting material 2.

Example 109

Method MM1

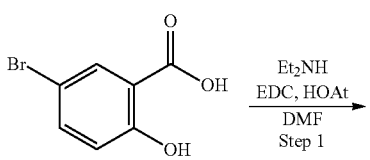

-continued

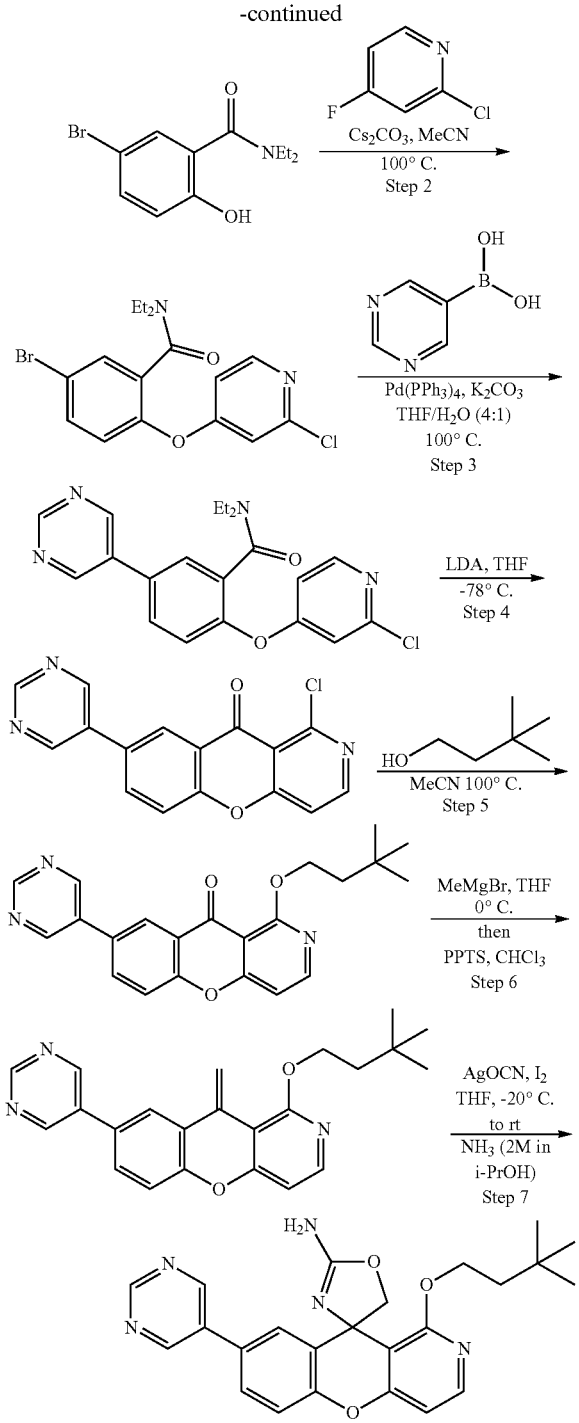

Synthesis of 1-(3,3-Dimethylbutoxy)-8-(pyrimidin-5-yl)-5'H-spiro[chromeno[3,2-c]pyridine-10,4'-oxazol]-2'-amine Step 1: 5-Bromo-N,N-diethyl-2-hydroxybenzamide Diethylamine (2.39 mL, 23.0 mmol) was added to a solution of 5-bromosalicylic acid (1.000 g, 4.61 mmol), EDC (1.33 g, 6.91 mmol), HOAt (0.627 g, 4.61 mmol) and DMF (20.0 mL) and the system was flushed with argon. The tube was sealed and the mixture stirred at 50° C. for 12 h. The reaction mixture was partitioned between ethyl acetate and water. The aqueous phase was separated and extracted with ethyl acetate. The combined organic phases were washed with brine, dried over anhydrous sodium sulfate, filtered, and concentrated to afford a brown oil. This oil was purified via column chromatography on silica gel (RediSep 40 g column, gradient elution with 0-50% ethyl acetate-hexane) to afford 5-bromo-N,N-diethyl-2-hydroxybenzamide as an off-white solid. MS m/z=272.1, 274.1 [M+H]$^+$. Calcd for $C_{11}H_{14}BrNO_2$: 272.1.

Step 2: 5-Bromo-2-(2-chloropyridin-4-yloxy)-N,N-diethylbenzamide

2-Chloro-4-fluoropyridine (0.242 g, 1.837 mmol) was added to a mixture of 5-bromo-N,N-diethyl-2-hydroxybenzamide (0.500 g, 1.837 mmol) and cesium carbonate (1.197 g, 3.67 mmol) in acetonitrile (10.0 mL). The mixture stirred at 100° C. for 8 h. The reaction mixture was partitioned between ethyl acetate and water. The aqueous phase was separated and extracted with ethyl acetate. The combined organic phases were washed with brine, dried over anhydrous sodium sulfate, filtered, and concentrated to afford a brown oil. This oil was purified via column chromatography on silica gel (RediSep 80 g column, gradient elution with 0-50% ethyl acetate-hexane) to afford 5-bromo-2-(2-chloropyridin-4-yloxy)-N,N-diethylbenzamide as a thick, yellow oil. MS m/z=383.0 [M+H]$^+$. Calcd for $C_{16}H_{16}BrClN_2O_2$: 382.0.

Step 3: 2-(2-Chloropyridin-4-yloxy)-N,N-diethyl-5-(pyrimidin-5-yl)benzamide

A resealable tube was charged with a mixture of 5-bromo-2-(2-chloropyridin-4-yloxy)-N,N-diethylbenzamide (2.500 g, 6.52 mmol), pyrimidin-5-ylboronic acid (2.018 g, 16.29 mmol), and potassium carbonate (4.50 g, 32.6 mmol) in THF (40.0 mL) and water (10.0 mL). Tetrakis(triphenylphosphine)palladium(0) (0.376 g, 0.326 mmol) was added, the system was purged with argon, and the tube was sealed. The reaction mixture was stirred at 100° C. for 4.0 h. The reaction mixture was partitioned between EtOAc and water. The aqueous phase was separated and extracted with EtOAc. The combined organic phases were washed with brine, dried over anhydrous sodium sulfate, filtered, and concentrated to afford a brown solid. This material was purified via column chromatography on silica gel (RediSep 120 g column, gradient elution with 50-100% ethyl acetate-hexane) to afford 2-(2-chloropyridin-4-yloxy)-N,N-diethyl-5-(pyrimidin-5-yl)benzamide as an off-white solid. MS m/z=383.2 [M+H]$^+$. Calcd for $C_{20}H_{19}ClN_4O_2$: 382.1.

Step 4: 1-Chloro-8-(pyrimidin-5-yl)-10H-chromeno[3,2-c]pyridin-10-one

Lithium diisopropylamide, 1.8 M in heptane/THF (5.80 mL, 10.45 mmol) was added dropwise to a −78° C. solution of 2-(2-chloropyridin-4-yloxy)-N,N-diethyl-5-(pyrimidin-5-yl)benzamide (1.000 g, 2.61 mmol) in THF (20.0 mL). The reaction mixture was stirred at −78° C. for 2.5 h. The reaction mixture was quenched with saturated aqueous ammonium chloride solution and the mixture was partitioned between EtOAc and water. The aqueous phase was separated and extracted with DCM. The combined organic phases were washed with brine, dried over anhydrous sodium sulfate, filtered, and concentrated to afford an orange solid. This material was purified via column chromatography on silica gel (RediSep 40 g column, eluting with 100% EtOAc) to afford 1-chloro-8-(pyrimidin-5-yl)-10H-chromeno[3,2-c]pyridin-10-one as an off-white solid. MS m/z=310.0 [M+H]+. Calcd for C₁₆H₈ClN₃O₂: 309.7.

Step 5: 1-(3,3-Dimethylbutoxy)-8-(pyrimidin-5-yl)-10H-chromeno[3,2-c]pyridin-10-one A resealable tube was charged with 1-chloro-8-(pyrimidin-5-yl)-10H-chromeno[3,2-c]pyridin-10-one (0.320 g, 1.033 mmol), 3,3-dimethyl-1-butanol (0.260 mL, 2.066 mmol), cesium carbonate (0.842 g, 2.58 mmol), and acetonitrile (10.0 mL). The system was flushed with argon, the tube was sealed, and the mixture stirred at 100° C. for 5 h. The material was partitioned between dichloromethane and water. The aqueous phase was separated and extracted with dichloromethane. The combined organic phases were washed with brine, dried over anhydrous sodium sulfate, filtered, and concentrated to afford a brown solid. This solid was purified via column chromatography on silica gel (RediSep 120 g column, gradient elution with 50-100% ethyl acetate-hexane) to afford 1-(3,3-dimethylbutoxy)-8-(pyrimidin-5-yl)-10H-chromeno[3,2-c]pyridin-10-one as a white solid. MS m/z=376.2 [M+H]+. Calcd for C₂₂H₂₁N₃O₃: 375.4.

Step 6: 1-(3,3-Dimethylbutoxy)-10-methylene-8-(pyrimidin-5-yl)-10H-chromeno[3,2-c]pyridine A solution of 1-(3,3-dimethylbutoxy)-8-(pyrimidin-5-yl)-10H-chromeno[3,2-c]pyridin-10-one (0.320 g, 0.852 mmol) in THF (8.00 mL) was cooled to 0° C. and methylmagnesium bromide (3.0 M in diethyl ether) (0.483 mL, 1.449 mmol) was added dropwise. The mixture stirred at 0° C. for 1 h. The mixture was quenched at 0° C. with saturated aqueous ammonium chloride solution and diluted with EtOAc. The aqueous phase was separated and extracted with EtOAc. The combined organic phases were washed with brine, dried over anhydrous sodium sulfate, filtered, and concentrated to afford a yellow film. This material was dissolved in chloroform (8.00 mL), pyridinium p-toluenesulfonate (10.71 mg, 0.043 mmol) was added, and the mixture was heated at reflux for 2 h. The reaction mixture was diluted with DCM and the solution was partitioned between DCM and saturated aqueous sodium bicarbonate solution. The aqueous phase was separated and extracted with DCM. The combined organic phases were washed with brine, dried over anhydrous sodium sulfate, filtered, and concentrated to afford 1-(3,3-dimethylbutoxy)-10-methylene-8-(pyrimidin-5-yl)-10H-chromeno[3,2-c]pyridine as a yellow solid. MS m/z=374.2 [M+H]+. Calcd for C₂₃H₂₃N₃O₂: 373.4.

Step 7: 1-(3,3-Dimethylbutoxy)-8-(pyrimidin-5-yl)-5'H-spiro[chromeno[3,2-c]pyridine-10,4'-oxazol]-2'-amine A solution of 1-(3,3-dimethylbutoxy)-10-methylene-8-(pyrimidin-5-yl)-10H-chromeno[3,2-c]pyridine (0.065 g, 0.174 mmol) and silver cyanate (0.078 g, 0.522 mmol) in THF (2.00 mL) was stirred for 10 min and then cooled to −20° C. for 15 min. Iodine (0.044 g, 0.174 mmol) was added and the mixture stirred at −20° C. for 1 h. The mixture was filtered through Celite and the filter cake was washed with diethyl ether. The combined filtrates were concentrated to afford an orange brown solid. The residue was dissolved in THF (2.00 mL) and the resulting solution was cooled in an ice bath. Ammonia (2.0 M in 2-propanol, 0.261 mL, 0.522 mmol) was added dropwise and the mixture slowly warmed to rt over 16 h. The reaction mixture was concentrated and the residue was partitioned between ethyl acetate and saturated aqueous sodium thiosulfate solution. The aqueous layer was separated and extracted with ethyl acetate. The combined organic phases were washed with brine, dried over anhydrous sodium sulfate, filtered, and concentrated to afford an orange film. This material was purified via column chromatography on silica gel (RediSep 40 g column, gradient elution with 0-100% (90:10:1, dichloromethane/methanol/ammonium hydroxide)-dichloromethane) to afford 1-(3,3-dimethylbutoxy)-8-(pyrimidin-5-yl)-5'H-spiro[chromeno[3,2-c]pyridine-10,4'-oxazol]-2'-amine as a white solid. MS m/z=432.2 [M+H]+. Calcd for C₂₄H₂₅N₅O₃: 431.5.

Example 110

Method MW1

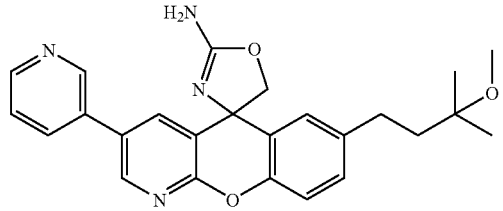 [SMILES: COC(C)(C)CCc1ccc2c(c1)C1(COC(N)=N1)c1cc(-c3cccnc3)cnc1O2]

Synthesis of rac-7-(3-methoxy-3-methylbutyl)-3-(3-pyridinyl)spiro[chromeno[2,3-b]pyridine-5,4'-[1,3]oxazol]-2'-amine Step 1: 7-(3-Hydroxy-3-methyl-1-butyn-1-yl)-3-bromo-spiro[chromeno[2,3-b]pyridine-5,4'-[1,3]oxazol]-2'-amine A resealable tube was charged with 7-iodo-3-bromo-spiro[chromeno[2,3-b]pyridine-5,4'-[1,3]oxazol]-2'-amine (0.500 g, 1.092 mmol), tetrakis(triphenylphosphine)palladium (0.126 g, 0.109 mmol) and copper iodide (0.021 g, 0.109 mmol). THF (2.183 mL, 1.092 mmol) was added followed by 2-methylbut-3-yn-2-ol (0.138 g, 1.637 mmol) and diisopropylamine (1.556 mL, 10.92 mmol). The tube was sealed and stirred at RT overnight. The reaction was diluted with water (25 mL) and poured into a separatory funnel containing ethyl acetate (50 mL). The layers were separated and the aqueous layer was extracted with ethyl acetate (3×25 mL). The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide 7-(3-hydroxy-3-methyl-1-butyn-1-yl)-3-bromo-spiro[chromeno[2,3-b]pyridine-5,4'-[1,3]oxazol]-2'-amine (374 mg, 0.903 mmol, 83% yield) (104420-10-1) as a light yellow foam. MS m/z=414.0 [M+H]+. Calc'd for C₁₉H₁₇BrN₃O₃: 414.0.

Step 2: 7-(3-Methoxy-3-methyl-1-butyn-1-yl)-3-bromo-spiro[chromeno[2,3-b]pyridine-5,4'-[1,3]oxazol]-2'-amine To a flask charged with 7-(3-hydroxy-3-methyl-1-butyn-1-yl)-3-bromo-spiro[chromeno[2,3-b]pyridine-5,4'-[1,3]oxazol]-2'-amine (340 mg, 0.821 mmol) was added methanol (9962 μL, 246 mmol) and methane sulfonic acid (533 μL, 8.21 mmol). The flask was sealed and heated at 60° C. for 3 hours. The reaction was diluted with saturated sodium bicarbonate (100 mL) and poured into a separatory funnel containing ethyl acetate (50 mL). The layers were separated and the aqueous layer was extracted with ethyl acetate (3×50 mL). The combined organic layers were washed with brine, dried over sodium sulfate, filtered and concentrated in vacuo to provide a tan solid that was purified by silica gel chromatography (Redi-Sep pre-packed silica gel column (40 g), 0-10% methanol in methylenechloride with 0.1% ammonium hydroxide) to provide 7-(3-methoxy-3-methyl-1-butyn-1-yl)-3-bromo-spiro[chromeno[2,3-b]pyridine-5,4'-[1,3]oxazol]-2'-amine (306 mg, 0.714 mmol, 87% yield) as a tan solid. MS m/z=428.0 [M+H]+. Calc'd for $C_{20}H_{19}BrN_3O_3$: 428.1.

Step 3: 7-(3-Methoxy-3-methyl-1-butyn-1-yl)-3-(3-pyridinyl)spiro[chromeno[2,3-b]pyridine-5,4'-[1,3]oxazol]-2'-amine 7-(3-Methoxy-3-methyl-1-butyn-1-yl)-3-bromo-spiro[chromeno[2,3-b]pyridine-5,4'-[1,3]oxazol]-2'-amine (300 mg, 0.700 mmol), tetrakis(triphenylphosphine)palladium (81 mg, 0.070 mmol), 3-pyridineboronic acid (172 mg, 1.401 mmol) and THF (7005 μL, 0.700 mmol) were combined in a sealable tube. Potassium carbonate (1.5 M) (1401 μL, 2.101 mmol) was added to the tube, which was then flushed with argon, sealed and heated at 110° C. for 1.5 hours. The reaction was diluted with water (50 mL) and poured into a separatory funnel containing ethyl acetate (25 mL). The layers were separated and the aqueous layer was extracted with ethyl acetate (3×25 mL). The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide 7-(3-methoxy-3-methyl-1-butyn-1-yl)-3-(3-pyridinyl)spiro[chromeno[2,3-b]pyridine-5,4'-[1,3]oxazol]-2'-amine (235 mg, 0.551 mmol, 79% yield) as a light yellow solid. MS m/z=427.2 [M+H]+. Calc'd for $C_{25}H_{23}N_4O_3$: 427.2.

Step 4: 7-(3-methoxy-3-methylbutyl)-3-(3-pyridinyl)spiro[chromeno[2,3-b]pyridine-5,4'-[1,3]oxazol]-2'-amine To a solution of 7-(3-methoxy-3-methylbut-1-ynyl)-3-(pyridin-3-yl)-5'H-spiro[chromeno[2,3-b]pyridine-5,4'-oxazol]-2'-amine (110 mg, 0.258 mmol) in 1:1 methanol ethyl acetate (10 mL) was added Pd/C (5%) (274 mg, 2.58 mmol). The resulting slurry was maintained under 1 atm of hydrogen gas for 4 hours at which point another loading of Pd/C (5%) (274 mg, 2.58 mmol) was added and the reaction was maintained under 1 atm of hydrogen gas for an additional 3 hours. The reaction was filtered through a pad of celite, washing well with methanol and ethyl acetate. The derived mixture was filtered through a 0.1 micron frit and concentrated to provide 7-(3-methoxy-3-methylbutyl)-3-(3-pyridinyl)spiro[chromeno[2,3-b]pyridine-5,4'-[1,3]oxazol]-2'-amine (55 mg, 0.128 mmol, 49.5% yield) as a light yellow solid. MS m/z=431.2 [M+H]+. Calc'd for $C_{25}H_{27}N_4O_3$: 431.2.

Example 111

Method MW2

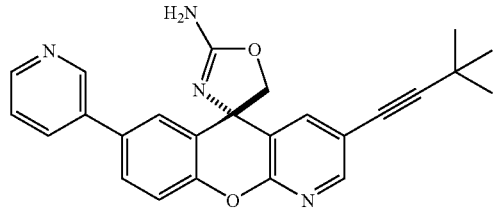

Synthesis of (5S)-3-(3,3-dimethyl-1-butyn-1-yl)-7-(3-pyridinyl)spiro[chromeno[2,3-b]pyridine-5,4'-[1,3]oxazol]-2'-amine Step 1: (5S)-3-bromo-7-(3-pyridinyl)spiro[chromeno[2,3-b]pyridine-5,4'-[1,3]oxazol]-2'-amine A sealable tube was charged with (5S)-7-iodo-3-bromo-spiro[chromeno[2,3-b]pyridine-5,4'-[1,3]oxazol]-2'-amine (350 mg, 0.764 mmol), pyridin-3-ylboronic acid (94 mg, 0.764 mmol), tetrakis(triphenylphosphine)palladium (20.04 mg, 0.076 mmol) and THF (7641 μL, 0.764 mmol). The mixture was purged with Ar for 2 minutes then a solution of potassium carbonate (1.5 M) (1019 μL, 1.528 mmol) was added and the reaction vessel was sealed and heated at 110° C. for 6 hours. The reaction was diluted with water (100 mL) and poured into a separatory funnel containing ethyl acetate (50 mL). The layers were separated and the aqueous layer was extracted with ethyl acetate (4×50 mL). The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide (5S)-3-bromo-7-(3-pyridinyl)spiro[chromeno[2,3-b]pyridine-5,4'-[1,3]oxazol]-2'-amine (175 mg, 0.428 mmol, 56.0% yield) as a brown foam. MS m/z=409.0 [M+H]+. Calc'd for $C_{19}H_{14}BrN_4O_2$: 409.0.

Step 2: (5S)-3-(3,3-dimethyl-1-butyn-1-yl)-7-(3-pyridinyl)spiro[chromeno[2,3-b]pyridine-5,4'-[1,3]oxazol]-2'-amine (5S)-3-Bromo-7-(3-pyridinyl)spiro[chromeno[2,3-b]pyridine-5,4'-[1,3]oxazol]-2'-amine (170 mg, 0.415 mmol), diisopropyl amine (2911 μL, 20.77 mmol), copper iodide (15.82 mg, 0.083 mmol), tetrakis(triphenylphosphine)palladium (48.0 mg, 0.042 mmol) and DMF (2769 μL, 0.415 mmol) were combined in a sealable tube, which was then flushed with argon and heated at 90° C. for 5 hours. After cooling to room temperature the reaction in the tube was diluted with water (25 mL) and poured into a separatory funnel containing ethyl acetate (25 mL). The layers were separated and the aqueous layer was extracted with ethyl acetate (4×50 mL). The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide (5S)-3-(3,3-dimethyl-1-butyn-1-yl)-7-(3-pyridinyl)spiro[chromeno[2,3-b]pyridine-5,4'-[1,3]oxazol]-2'-amine (110 mg, 0.268 mmol, 64.5% yield) as a brown foam. MS m/z=411.2 [M+H]+. Calc'd for $C_{25}H_{23}N_4O_3$: 411.2.

Example 112

Method MW3

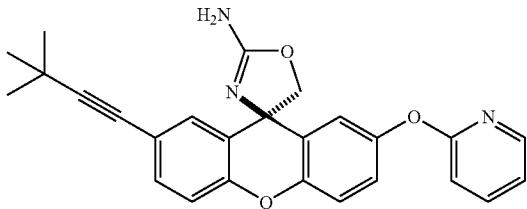

Synthesis of (4R)-2'-(3,3-dimethyl-1-butyn-1-yl)-7'-(2-pyridinyloxy)spiro[1,3-oxazole-4,9'-xanthen]-2-amine Step 1: (4S)-2'-bromo-7'-(2-pyridinyloxy)spiro[1,3-oxazole-4,9'-xanthen]-2-amine (4S)-2'-Bromo-7'-(2-pyridinyloxy)spiro[1,3-oxazole-4,9'-xanthen]-2-amine (500 mg, 1.440 mmol), cesium carbonate (469 mg, 1.440 mmol), and N,N-dimethylformamide (9602 µL, 1.440 mmol) were combined and stirred at RT for 1 minute before 2-fluoropyridine (420 mg, 4.32 mmol) was added. The resulting mixture was heated at 80° C. for 3 hours and 110° C. for 30 hrs. The reaction was diluted with water (100 mL) and poured into a separatory funnel containing ethyl acetate (50 mL). The resulting emulsion was cleared up by the addition of 25 mL of brine. The layers were separated and the aqueous layer was extracted with ethyl acetate (3×100 mL). The combined organic layers were washed with water and then brine, dried over sodium sulfate, filtered and concentrated in vacuo to provide a brown foam that was purified by silica gel chromatography (Redi-Sep pre-packed silica gel column (40 g), 0-10% methanol in methylenechloride with 0.1% ammonium hydroxide) to provide (4S)-2'-bromo-7'-(2-pyridinyloxy)spiro[1,3-oxazole-4,9'-xanthen]-2-amine (390 mg, 0.919 mmol, 63.8% yield) as an off white foam. MS m/z=424.0 [M+H]+. Calc'd for $C_{20}H_{15}BrN_3O_3$: 424.0.

Step 2: (4R)-2'-(3,3-dimethyl-1-butyn-1-yl)-7'-(2-pyridinyloxy)spiro[1,3-oxazole-4,9'-xanthen]-2-amine (4S)-2'-Bromo-7'-(2-pyridinyloxy)spiro[1,3-oxazole-4,9'-xanthen]-2-amine (380 mg, 0.896 mmol), copper(i) iodide (34.1 mg, 0.179 mmol), tetrakis(triphenylphosphine)palladium (104 mg, 0.090 mmol), 3,3-dimethylbut-1-yne (221 mg, 2.69 mmol) and DMF (3583 µL, 0.896 mmol) were combined in a sealable tube. The reaction vessel was flushed with argon then di-isopropyl amine (3766 µL, 26.9 mmol) was added and the vessel was sealed and heated at 90° C. for 2 hours. The reaction was diluted with water (50 mL) and poured into a separatory funnel containing ethyl acetate (50 mL). The layers were separated and the aqueous layer was extracted with ethyl acetate (3×50 mL). The combined organic layers were washed with water and then brine, dried over sodium sulfate, filtered and concentrated in vacuo to provide a brown foam that was purified by silica gel chromatography (Redi-Sep pre-packed silica gel column (40 g), 0-10% methanol in methylenechloride with 0.1% ammonium hydroxide) to provide (4R)-2'-(3,3-dimethyl-1-butyn-1-yl)-7'-(2-pyridinyloxy)spiro[1,3-oxazole-4,9'-xanthen]-2-amine (245 mg, 0.576 mmol, 64.3% yield) as a light yellow solid. MS m/z=426.2 [M+H]+. Calc'd for $C_{26}H_{24}N_3O_3$: 426.2.

Example 113

Method MW4

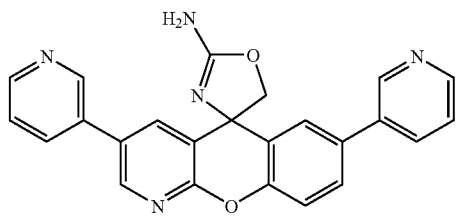 [SMILES: NC1=NC2(CO1)c1cc(-c3cccnc3)ccc1Oc1ncc(-c3cccnc3)cc12]

Synthesis of 3,7-di-3-pyridinylspiro[chromeno[2,3-b]pyridine-5,4'-[1,3]oxazol]-2'-amine A sealable tube was charged with 3-bromo-7-iodo-5'H-spiro[chromeno[2,3-b]pyridine-5,4'-[1,3]oxazol]-2'-amine (150 mg, 0.327 mmol), pyridin-3-ylboronic acid (121 mg, 0.982 mmol), Pd(PPh3)4 (8.59 mg, 0.033 mmol) and 1.5 mL of THF. The mixture was purged with argon for 2 minutes then a solution of potassium carbonate (1 M) (1637 µL, 1.637 mmol) in 1 mL of water was added. The tube was sealed and heated at 110° C. for 12 hours. The reaction was diluted with water (15 mL) and poured into a separatory funnel containing EtOAc (25 mL). The layers were separated and the aqueous layer was extracted with EtOAc (3×25 mL). The combined organic layers were washed with brine, dried over sodium sulfate, filtered and concentrated in vacuo to provide a brown oil that was purified by silica gel chromatography (Redi-Sep pre-packed silica gel column (12 g), 0-10% methanol in methylenechloride with 0.1% ammonium hydroxide) to provide 3,7-di-3-pyridinylspiro[chromeno[2,3-b]pyridine-5,4'-[1,3]oxazol]-2'-amine (68 mg, 0.167 mmol, 51.0% yield) as a brown foam. MS m/z=408.2 [M+H]+. Calc'd for $C_{24}H_{18}N_5O_2$: 408.2.

Example 114

Method MW5

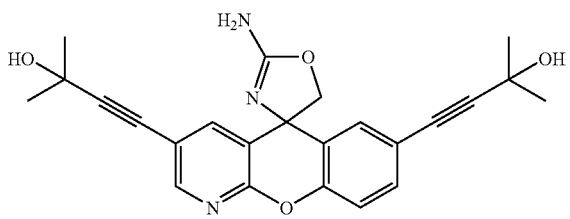 [SMILES: CC(C)(O)C#Cc1ccc2c(c1)C1(COC(N)=N1)c1cc(C#CC(C)(C)O)cnc1O2]

Synthesis of 4,4'-(–2'-aminospiro[chromeno[2,3-b]pyridine-5,4'-[1,3]oxazole]-3,7-diyl)bis(2-methyl-3-butyn-2-ol)

A resealable tube was charged with 3-bromo-7-iodo-5'H-spiro[chromeno[2,3-b]pyridine-5,4'-[1,3]oxazol]-2'-amine (0.500 g, 1.092 mmol), tetrakis(triphenylphosphine)palladium (0.126 g, 0.109 mmol) and copper iodide (0.021 g, 0.109 mmol). THF (2.183 mL, 1.092 mmol) was added followed by 2-methylbut-3-yn-2-ol (0.138 g, 1.637 mmol) and diisopropylamine (1.556 mL, 10.92 mmol). The reaction vessel was sealed and stirred at rt for 12 hours. The reaction was diluted with water (25 mL) and poured into a separatory funnel containing ethyl acetate (50 mL). The layers were separated and the aqueous layer was extracted with ethyl acetate (3×25 mL). The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide 4,4'-(-2'-aminospiro[chromeno[2,3-b]pyridine-5,4'-[1,3]oxazole]-3,7-diyl)bis(2-methyl-3-butyn-2-ol) (60 mg, 0.144 mmol, 13.17% yield) 104420-10-42 as a yellow film. MS m/z=418.2 [M+H]+. Calc'd for $C_{24}H_{24}N_3O_4$: 418.2.

Example 115

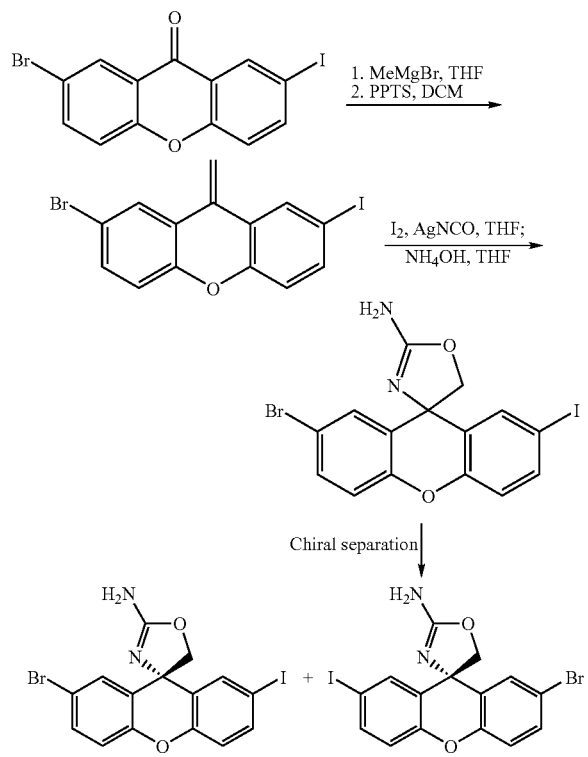

Synthesis of S)-2'-Bromo-7'-iodo-5H-spiro[1,3-oxazole-4,9'-xanthen]-2-amine and (R)-2'-Bromo-7'-iodo-5H-spiro[1,3-oxazole-4,9'-xanthen]-2-amine Step 1: Synthesis of 2-bromo-7-iodo-9-methylene-9H-xanthene 1-L RBF was charged with 2-bromo-7-iodo-9H-xanthen-9-one (42 g, 105 mmol) (prepared as described in Example 1 from 2,5-diiodobenzoic acid and 4-bromophenol) and THF (350 mL) and the suspension was stirred for 30 min at RT. The mixture was cooled to 0° C. (water-ice bath) and methylmagnesium bromide (62.4 mL, 187 mmol) was added at 0° C. dropwise through syringe. The mixture was stirred for 30 min at 0° C. Saturated $NH_4Cl$ solution was carefully added dropwise to quench the reaction. Ether (~100 ml) was added followed by water in order to achieve a clean phase separation. The organic layer was separated and washed with brine, dried over $MgSO_4$ and concentrated to give brown oil. DCM (150 mL) and PPTS (0.526 g, 2.095 mmol) were added and the resulting mixture was refluxed for 3 hrs. Upon cooling to RT the mixture crystallized. The solid was filtered, washed with DCM and dried to give 6.12 g (~15%) of the product. DCM filtrate was washed with $NaHCO_3$ and brine and concentrated. The residue was treated with 150 ml of dry ether. The precipitate was filtered off and dried to give 2-bromo-7-iodo-9-methylene-9H-xanthene as a yellowish solid. The filtrate yielded more of 2-bromo-7-iodo-9-methylene-9H-xanthene.

Step 2: 2'-Bromo-7'-iodo-5H-spiro[1,3-oxazole-4,9'-xanthen]-2-amine 500 mL RBF was charged with iodine (7.04 g, 27.7 mmol) and 210 ml of dry THF. The mixture was cooled to –20-15° C. (methanol-ice bath) and silver cyanate (11.9 g, 79 mmol) was added in one portion. The resulting brown slurry was stirred for 1 hr, then 2-bromo-7-iodo-9-methylene-9H-xanthene (10.55 g, 26.4 mmol) was added portion-wise. The mixture was then stirred at 0° C. for 1 hr and filtered through Celite with the aid of THF (50 ml). To the filtrate, ammonia (39.6 ml, 79.3 mmol) (2M in i-PrOH) was added at RT and the reaction mixture was stirred overnight. The resulting brown solution was diluted with 5% solution of $Na_2S_2O_3$ (15 ml) and sodium bicarbonate (15 ml), then 50 ml of EtOAc was added. The organic extract was washed with saturated NaCl (2×50 mL) and dried over $MgSO_4$. The solution was filtered, concentrated in vacuo and purified by chromatography through a Redi-Sep pre-packed silica gel column (120 g), eluting with a gradient of 10% to 80% DCM/MeOH/NH4OH (90:10:1) in DCM, to provide a crude product as brown glass which crystallized overnight. This crystalline material was treated with 20 ml of DCM and solid was filtered and dried to afford 3.3 g of 2'-Bromo-7'-iodo-5H-spiro[1,3-oxazole-4,9'-xanthen]-2-amine as a white solid. The filtrate was purified by chromatography through a Redi-Sep pre-packed silica gel column (80 g), eluting with a gradient of 5% to 40% DCM/MeOH/$NH_4$OH (90:10:1) in DCM, to provide additional 2'-Bromo-7'-iodo-5H-spiro[1,3-oxazole-4,9'-xanthen]-2-amine as a tan glass crystalline material.

Step 3: (S)-2'-Bromo-7'-iodo-5H-spiro[1,3-oxazole-4,9'-xanthen]-2-amine and (R)-2'-Bromo-7'-iodo-5H-spiro[1,3-oxazole-4,9'-xanthen]-2-amine Racemic 2'-Bromo-7'-iodo-5H-spiro[1,3-oxazole-4,9'-xanthen]-2-amine was purified by chromatography using a elution gradient of 20:80:0.2 MeOH:$CO_2$:DEA at 80 ml/min on a 20×250 mm ChiralPak AD-H column and 100-bar system pressure. The first peak (RT=3.4 min) provided (S)-2'-Bromo-7'-iodo-5H-spiro[1,3-oxazole-4,9'-xanthen]-2-amine (99% ee), and the second peak (RT=4.7 min) provided (R)-2'-Bromo-7'-iodo-5H-spiro[1,3-oxazole-4,9'-xanthen]-2-amine (>99% ee).

Example 116

Method OE1

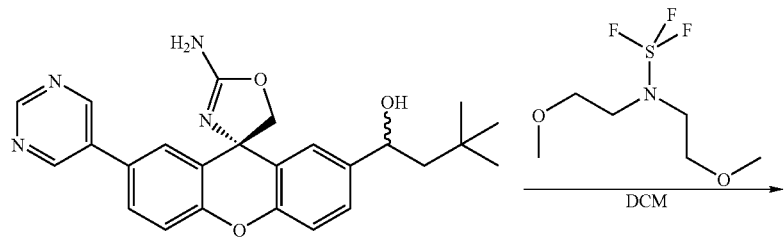

Synthesis of (4S)-2'-((1S)-1-fluoro-3,3-dimethylbutyl)-7'-(5-pyrimidinyl)spiro[1,3-oxazole-4,9'-xanthen]-2-amine and (4S)-2'-((1R)-1-fluoro-3,3-dimethylbutyl)-7'-(5-pyrimidinyl)spiro[1,3-oxazole-4,9'-xanthen]-2-amine A solution of (S)-1-(2-amino-2'-(pyrimidin-5-yl)-5H-spiro[oxazole-4,9'-xanthene]-7'-yl)-3,3-dimethylbutan-1-ol (86 mg, 0.200 mmol) in DCM (1998 μL) was cooled to −78° C. and deoxofluor (73.7 μL, 0.400 mmol) was added dropwise. The mixture was stirred for 1 hr @-78° C. and then allowed to reach RT. The reaction mixture was quenched by addition of sat NaHCO₃ (1 ml) and diluted with EtOAc. The organic extract was dried over MgSO₄. The solution was filtered and concentrated in vacuo to give the crude titled material as a tan glass-like crystalline material. The crude material was purified by chromatography through a Redi-Sep pre-packed silica gel column (12 g), eluting with a gradient of 10% to 80% DCM/MeOH/NH4OH (90:10:1) in DCM, to provide mixture of diastereomers which were separated using Chiralpack AD-H (2×15 cm) 30% MeOH/CO₂, 100 bar, 70 ml/min to afford:

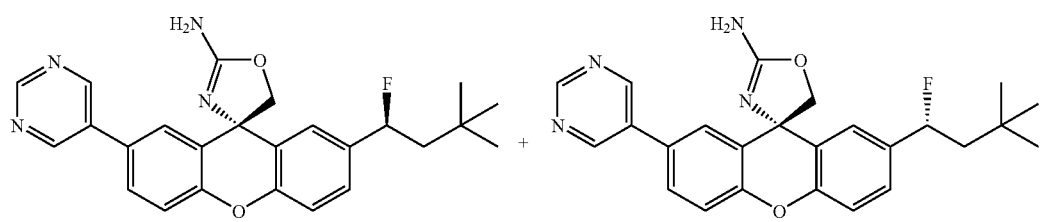

Diastereomer 1 (RT 2.48 min)-(S)-2'-((S)-1-fluoro-3,3-dimethylbutyl)-7'-(pyrimidin-5-yl)-5H-spiro[oxazole-4,9'-xanthen]-2-amine; and Diastereomer 2 (RT 3.36 min)-(S)-2'-((R)-1-fluoro-3,3-dimethylbutyl)-7'-(pyrimidin-5-yl)-5H-spiro[oxazole-4,9'-xanthen]-2-amine.

Example 117

Method OE2

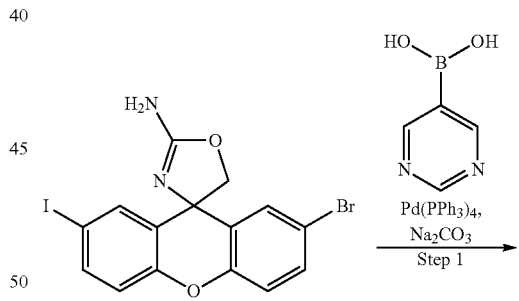

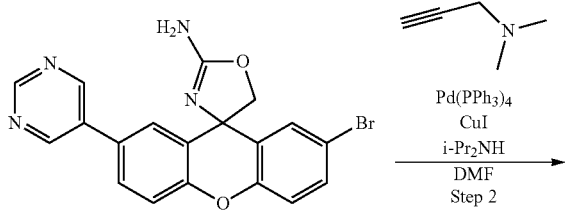

91

-continued

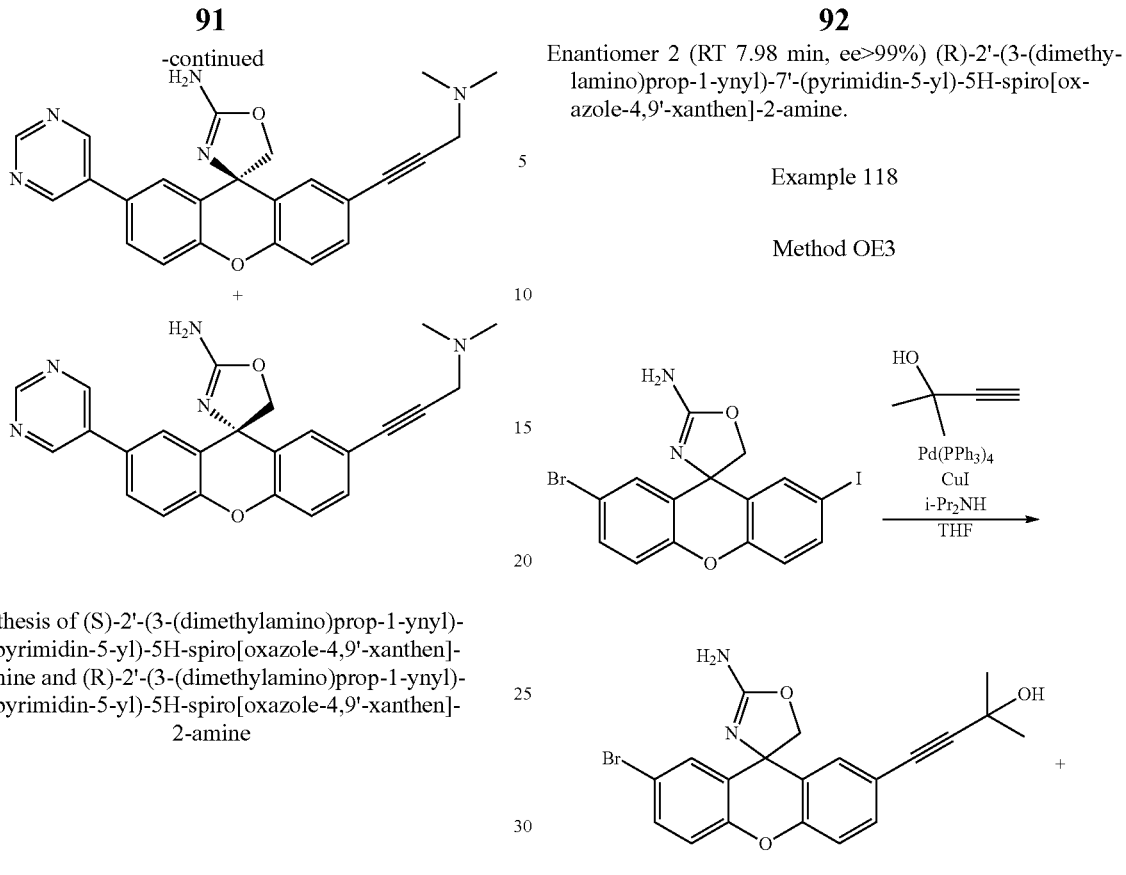

Synthesis of (S)-2'-(3-(dimethylamino)prop-1-ynyl)-
7'-(pyrimidin-5-yl)-5H-spiro[oxazole-4,9'-xanthen]-
2-amine and (R)-2'-(3-(dimethylamino)prop-1-ynyl)-
7'-(pyrimidin-5-yl)-5H-spiro[oxazole-4,9'-xanthen]-
2-amine Step 1:

50 ml Flask was charged with 2'-bromo-7'-iodo-5H-spiro [oxazole-4,9'-xanthen]-2-amine (1.000 g, 2.188 mmol), pyrimidin-5-ylboronic acid (0.380 g, 3.06 mmol), tetrakis(triphenylphosphine)palladium (0.126 g, 0.109 mmol) and DME (10 mL). Sodium carbonate (3.28 mL, 6.56 mmol) was added and the reaction mixture was stirred at 65° C. for 16 hrs. The brown mixture with precipitate was filtered and the solids were washed with DME (3 ml), water (5 ml) and methanol (5 ml), dried on air. The material was treated with 10 ml of DCM and filtered, filtrate was evaporated to afford to afford 2'-bromo-7'-(pyrimidin-5-yl)-5H-spiro[oxazole-4,9'-xanthen]-2-amine as white solid Step 2:

0.5-2 ml Glass microwave reaction vessel was charged with tetrakis(triphenylphosphine)palladium (28.2 mg, 0.024 mmol), copper(I) iodide (9.31 mg, 0.049 mmol), 2'-bromo-7'-(pyrimidin-5-yl)-5H-spiro[oxazole-4,9'-xanthen]-2-amine (100 mg, 0.244 mmol) and N,N-dimethylprop-2-yn-1-amine (0.076 ml, 0.733 mmol) and diisopropylamine (1.393 ml, 9.77 mmol) in DMF (1 ml). The reaction mixture was stirred and heated in a heating block at 80° C. for 6 hrs. The mixture was filtered through Celite with the aid of EtOAc and concentrated in vacuo at 50° C. The crude material was purified by chromatography through a Redi-Sep pre-packed silica gel column (12 g), eluting with a gradient of 10% to 100% DCM/MeOH/NH$_4$OH 90:10:1 in DCM, to provide the titled compound as a tan, solid racemic product. Chiral separation of this racemate using Chiralpack AD-H (2×15 cm) column 30% MeOH/CO$_2$, 100 bar, 70 ml/min afforded:

Enantiomer 1 (RT 4.21 min, ee>99%) (S)-2'-(3-(dimethylamino)prop-1-ynyl)-7'-(pyrimidin-5-yl)-5H-spiro[oxazole-4,9'-xanthen]-2-amine.

92

Enantiomer 2 (RT 7.98 min, ee>99%) (R)-2'-(3-(dimethylamino)prop-1-ynyl)-7'-(pyrimidin-5-yl)-5H-spiro[oxazole-4,9'-xanthen]-2-amine.

Example 118

Method OE3

Synthesis of 4-(2-amino-2'-bromo-5H-spiro[oxazole-4,9'-xanthene]-7'-yl)-2-methylbut-3-yn-2-ol and 4,4'-(2-amino-5H-spiro[oxazole-4,9'-xanthene]-2',7'-diyl)bis(2-methylbut-3-yn-2-ol)

To a 25 mL flask was added 2'-bromo-7'-iodo-5H-spiro [oxazole-4,9'-xanthen]-2-amine (536 mg, 1.173 mmol), bis (triphenylphosphine)palladium(II) chloride (82 mg, 0.117 mmol), copper(I) iodide (22.33 mg, 0.117 mmol). THF (10 ml), 2-methylbut-3-yn-2-ol (0.459 ml, 4.69 mmol) and DIPA (1.657 ml, 11.73 mmol) were added and the mixture was heated at 60° C. for 16 hrs. The mixture was filtered through Celite and concentrated. Separation on 12 g Redi-Sep column using 15-80% DCM/MeOH/NH4OH 90:10:1 in DCM gave 4-(2-amino-2'-bromo-5H-spiro[oxazole-4,9'-xanthene]-7'-yl)-2-methylbut-3-yn-2-ol (310 mg, 0.750 mmol, 64% yield) and ~200 mg of symmetric product containing impurities, which was purified again using stacker of two 12 g Redi-Sep column, eluent 45-75% DCM/MeOH/NH4OH in DCM to afford 4,4'-(2-amino-5H-spiro[oxazole-4,9'-xanthene]-2',7'-diyl)bis(2-methylbut-3-yn-2-ol).

Example 119

Method OE4

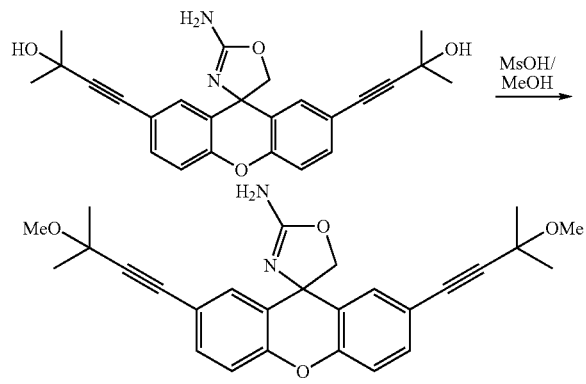

Synthesis of 2',7'-bis(3-methoxy-3-methylbut-1-ynyl)-5H-spiro[oxazole-4,9'-xanthen]-2-amine To a solution of 4,4'-(2-amino-5H-spiro[oxazole-4,9'-xanthene]-2',7'-diyl)bis(2-methylbut-3-yn-2-ol) (96 mg, 0.231 mmol) in MeOH (2 mL) methanesulfonic acid (0.150 mL, 2.305 mmol) was added at room temperature and the resulting mixture was stirred at 60° C. for 2 hrs. The reaction mixture was cooled to RT and then quenched with sat NaHCO$_3$ solution (~3 ml). The reaction mixture was extracted with EtOAc (5 ml), organic layer was separated and washed with saturated NaCl (2 mL) and dried over MgSO$_4$. The solution was filtered and concentrated in vacuo to give the crude titled product as a tan solid. The crude material was purified by chromatography through a Redi-Sep pre-packed silica gel column (12 g), eluting with a gradient of 5% to 70% of DCM/MeOH/NH$_4$OH 90:10:1 in DCM, to provide 2',7'-bis(3-methoxy-3-methylbut-1-ynyl)-5H-spiro[oxazole-4,9'-xanthen]-2-amine as off-white solid.

Example 120

Method OE5

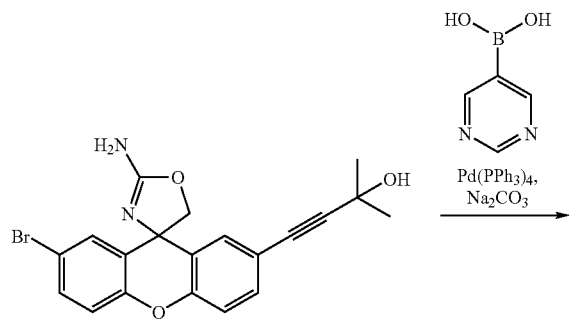

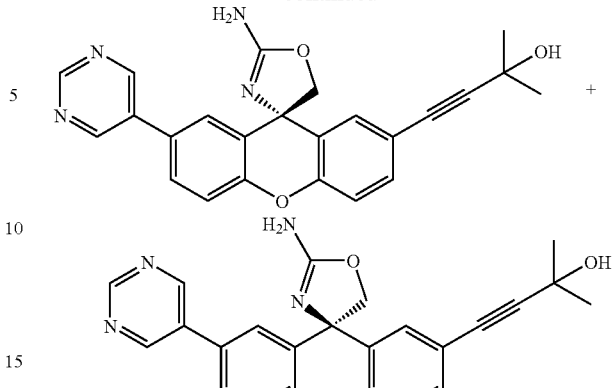

Synthesis of (S)-4-(2-amino-2'-(pyrimidin-5-yl)-5H-spiro[oxazole-4,9'-xanthene]-7'-yl)-2-methylbut-3-yn-2-ol and (R)-4-(2-amino-2'-(pyrimidin-5-yl)-5H-spiro[oxazole-4,9'-xanthene]-7'-yl)-2-methylbut-3-yn-2-ol A resealable tube was charged with tetrakis(triphenylphosphine)palladium(0) (17.62 mg, 0.015 mmol), pyrimidin-5-ylboronic acid (28.3 mg, 0.229 mmol) and 4-(2-amino-2'-bromo-5H-spiro[oxazole-4,9'-xanthene]-7'-yl)-2-methylbut-3-yn-2-ol (63.0 mg, 0.152 mmol) in DME (1 mL) was added followed by addition of sodium carbonate (0.229 mL, 0.457 mmol) (2M soln). The reaction mixture was stirred and heated in a heating block at 80° C. for 16 hrs. After workup and separation on silica gel (10-80% DCM/MeOH/NH$_4$OH in DCM) racemic 4-(2-amino-2'-(pyrimidin-5-yl)-5H-spiro[oxazole-4,9'-xanthene]-7'-yl)-2-methylbut-3-yn-2-ol was obtained. Chiral purification of the racemic product using Chiralpack AD-H (2×15 cm) column 30% MeOH/CO$_2$, 100 bar, 70 ml/min afforded:

Enantiomer 1 (RT 1.18 min): (S)-4-(2-amino-2'-(pyrimidin-5-yl)-5H-spiro[oxazole-4,9'-xanthene]-7'-yl)-2-methylbut-3-yn-2-ol; and Enantiomer 2 (RT 3.27 min): (R)-4-(2-amino-2'-(pyrimidin-5-yl)-5H-spiro[oxazole-4,9'-xanthene]-7'-yl)-2-methylbut-3-yn-2-ol.

Example 121

Method OE6

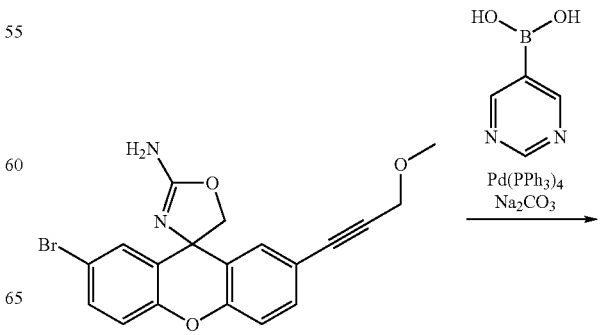

-continued

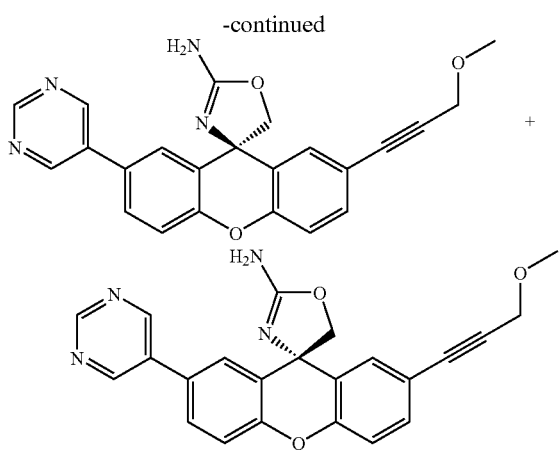

Synthesis of (S)-2'-(3-methoxyprop-1-ynyl)-7'-(pyrimidin-5-yl)-5H-spiro[oxazole-4,9'-xanthen]-2-amine and (R)-2'-(3-methoxyprop-1-ynyl)-7'-(pyrimidin-5-yl)-5H-spiro[oxazole-4,9'-xanthen]-2-amine Synthesis of (S)-2'-(3-methoxyprop-1-ynyl)-7'-(pyrimidin-5-yl)-5H-spiro[oxazole-4,9'-xanthen]-2-amine and (R)-2'-(3-methoxyprop-1-ynyl)-7'-(pyrimidin-5-yl)-5H-spiro[oxazole-4,9'-xanthen]-2-amine was carried out according to Example 120 using 2'-bromo-7'-(3-methoxyprop-1-ynyl)-5H-spiro[oxazole-4,9'-xanthen]-2-amine (prepared as described in Method OE3 using 3-methoxy-1-propyne) as the starting material. Chiral separation as described in Example 120 afforded:

Enantiomer 1 (S)-2'-(3-methoxyprop-1-ynyl)-7'-(pyrimidin-5-yl)-5H-spiro[oxazole-4,9'-xanthen]-2-amine; and Enantiomer 2 (R)-2'-(3-methoxyprop-1-ynyl)-7'-(pyrimidin-5-yl)-5H-spiro[oxazole-4,9'-xanthen]-2-amine.

Example 122

Method OE7

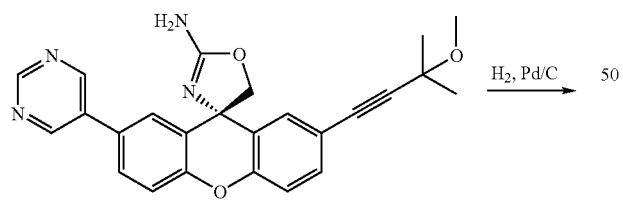

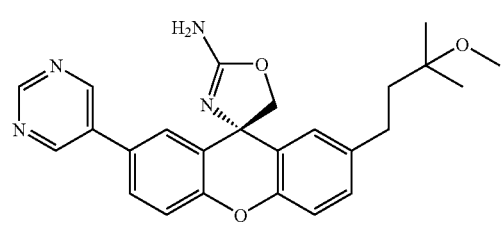

Synthesis of (R)-2'-(3-methoxy-3-methylbutyl)-7'-(pyrimidin-5-yl)-5H-spiro[oxazole-4,9'-xanthen]-2-amine To a solution of (R)-2'-(3-methoxy-3-methylbut-1-ynyl)-7'-(pyrimidin-5-yl)-5H-spiro[oxazole-4,9'-xanthen]-2-amine (23 mg, 0.054 mmol) in MeOH (1 mL) suspension of palladium on carbon (28.7 mg, 0.027 mmol) in ethyl acetate (0.5 mL) was added and the mixture was hydrogenated (1 atm) overnight at 40° C. The mixture was cooled to room temperature, filtered through plug of Celite and concentrated to give (R)-2'-(3-methoxy-3-methylbutyl)-7'-(pyrimidin-5-yl)-5H-spiro[oxazole-4,9'-xanthen]-2-amine.

Example 123

Method OE8

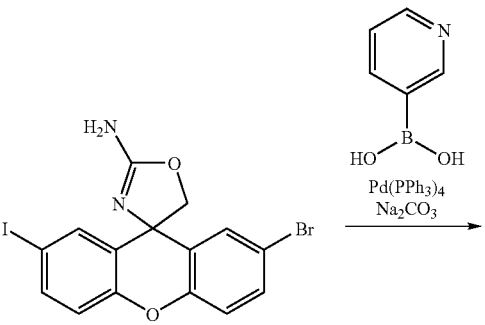

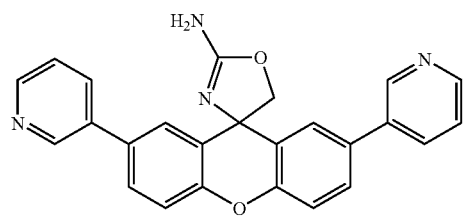

Synthesis of 2',7'-di(pyridin-3-yl)-5H-spiro[oxazole-4,9'-xanthen]-2-amine

Resealable tube was charged with 2'-bromo-7'-iodo-5H-spiro[oxazole-4,9'-xanthen]-2-amine (100 mg, 0.219 mmol), pyridin-3-ylboronic acid (81 mg, 0.656 mmol), Pd(PPh$_3$)$_4$ (50.6 mg, 0.044 mmol). DME (1 ml) and sodium carbonate (0.328 ml, 0.656 mmol) were added and the reaction mixture was capped with argon, sealed, and stirred at 95° C. for 16 hrs. The mixture was partitioned between DCM and water. The aqueous layer was removed and the organic layer was washed with brine, filtered and concentrated in vacuo. The crude residue was purified by flash chromatography on silica gel (12 g column, 15-100% DCM/MeOH/NH$_4$OH in DCM) to give material with impurity followed by second FC on silica (12 g column, 50-85% DCM/MeOH/NH₄OH) to give 2',7'-di(pyridin-3-yl)-5H-spiro[oxazole-4,9'-xanthen]-2-amine.

Example 124

Method OE9

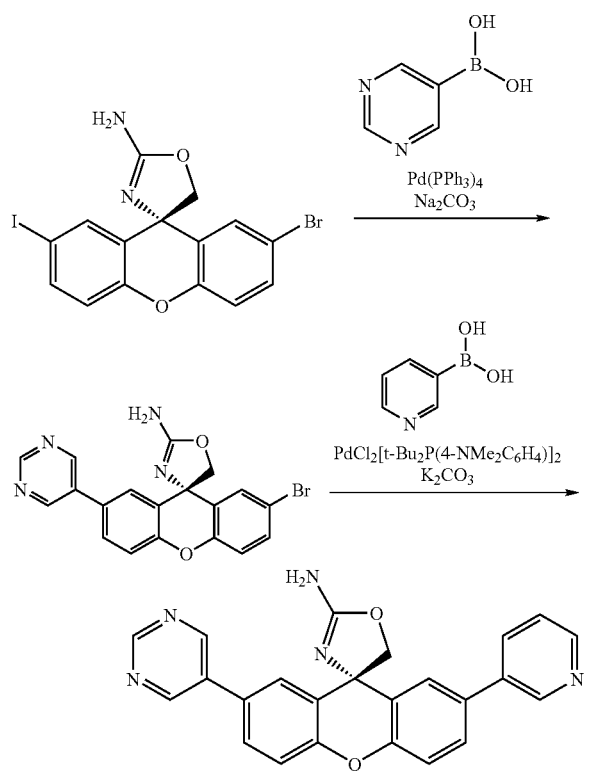

Synthesis of (R)-2'-(pyridin-3-yl)-7'-(pyrimidin-5-yl)-5H-spiro[oxazole-4,9'-xanthen]-2-amine Step 1:

100 ml RBF was charged with (R)-2'-bromo-7'-iodo-5H-spiro[oxazole-4,9'-xanthen]-2-amine (1.5 g, 3.28 mmol), pyrimidin-5-ylboronic acid (0.488 g, 3.94 mmol), tetrakis(triphenylphosphine)palladium(0) (0.284 g, 0.246 mmol). DME (23.44 mL) followed by sodium carbonate (4.92 mL, 9.85 mmol) (2M solution) were added and the mixture was heated at 65° C. for 24 h. The mixture was diluted with water and EtOAc, filtered and organic layer was separated and concentrated. The crude material was purified by flash chromatography on 40 g RediSep column using 5-70% gradient of DCM/MeOH/NH₄OH in DCM to give (S)-2'-bromo-7'-(pyrimidin-5-yl)-5H-spiro[oxazole-4,9'-xanthen]-2-amine.
Step 2.

0.5-2 ml Microwave vial was charged with (S)-2'-bromo-7'-(pyrimidin-5-yl)-5H-spiro[oxazole-4,9'-xanthen]-2-amine (100 mg, 0.244 mmol), pyridin-3-ylboronic acid (38.7 mg, 0.315 mmol), dichlorobis(di-t-butyl-4-dimethylaminophenylphosphine)palladium (II) (7.44 mg, 10.51 µmol) and potassium carbonate (87 mg, 0.630 mmol), dioxane (1 ml) and water (0.12 ml) were added and the vial was sealed and heated at 100° C. in the microwave oven (Biotage) for 1 hr. The mixture was diluted with DCM, filtered through Celite, concentrated and purified by flash chromatography on silica gel (12 g column, 20-100% DCM/MeOH/NH₄OH in DCM) to afford (R)-2'-(pyridin-3-yl)-7'-(pyrimidin-5-yl)-5H-spiro[oxazole-4,9'-xanthen]-2-amine as yellowish solid.

Example 125

Method RW1

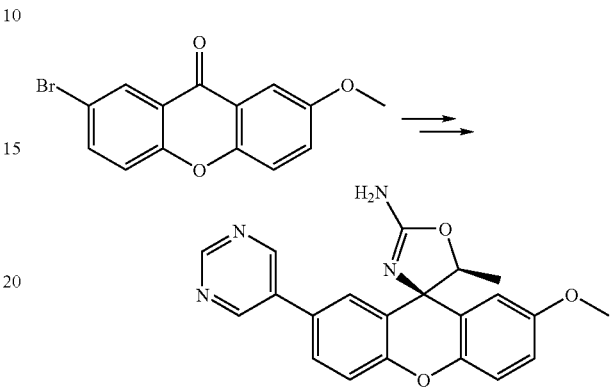

Synthesis of '(4R,5S)-2'-methoxy-5-methyl-7'-(5-pyrimidinyl)spiro[1,3-oxazole-4,9'-xanthen]-2-amine Step 1:
2-Bromo-9-ethylidene-7-methoxy-9H-xanthene A 250 mL RBF was charged with 2-bromo-7-methoxy-9H-xanthen-9-one (10.20 g, 33.4 mmol) and 100 mL dry THF. The mixture was stirred for 10 min at RT and the resulting suspension was placed in an ice-methanol bath for another 10 min. Ethylmagnesium bromide, 1.0 M in THF (43.5 mL, 43.5 mmol) was added to the mixture dropwise. After 30 min, the mixture was carefully quenched with saturated aqueous ammonium chloride (100 mL) at 0° C. and diluted with EtOAc. The organic layer was washed with brine, dried with sodium sulfate, and concentrated in vacuo. The crude material was dissolved in 100 mL of chloroform, treated with pyridine 4-methylbenzenesulfonate (0.115 g, 0.669 mmol), and heated to reflux for 4 hr then 50° C. overnight. The mixture was cooled to RT, diluted with DCM, and washed with saturated sodium bicarbonate and brine. The organic fraction was dried over sodium sulfate and concentrated in vacuo. The residue was purified by silica gel chromatography using 5-40% Hexanes:EtOAc to afford 2-bromo-9-ethylidene-7-methoxy-9H-xanthene as a yellow oil, MH+=317.0/319.0@3.35 min.

Step 2: 2'-Bromo-7'-methoxy-5-methyl-5H-spiro[oxazole-4,9'-xanthen]-2-amine

A 50 ml RBF was charged with iodine (0.176 g, 0.695 mmol) and THF (3 mL) and the resulting solution was cooled to −20-−25° C. in a methanol-ice bath. Cyanatosilver (0.298 g, 1.986 mmol) was added in one portion and the resulting mixture was stirred for 20 min at −25 to −15° C. 2-Bromo-9-ethylidene-7-methoxy-9H-xanthene (0.210 g, 0.662 mmol) was added slowly as a solution in THF (2.5 mL) and the resulting mixture was stirred for 2 min at −15° C., then 20 min at 0° C. The yellow mixture was filtered through Celite with the aid of THF (5 ml) and to the filtrate ammonia (0.993 mL, 1.986 mmol) (2 M in i-PrOH) was added dropwise at RT. The solution was stirred for 48 hrs at RT before concentration in vacuo and adsorption onto silica gel. The material was purified by silica gel chromatography using 1-5% MeOH in CH$_2$Cl$_2$ with 1% NH$_4$OH to afford 2'-bromo-7'-methoxy-5-methyl-5H-spiro[oxazole-4,9'-xanthen]-2-amine as an orange solid. MH+=375.0/377.0@1.85 min.

Step 3:'(4R,5S)-2'-Methoxy-5-methyl-7'-(5-pyrimidinyl)spiro[1,3-oxazole-4,9'-xanthen]-2-amine To a mixture of sodium carbonate (0.636 g, 6.00 mmol), palladium tetrakistriphenylphosphine (0.185 g, 0.160 mmol), pyrimidin-5-ylboronic acid (0.322 g, 2.60 mmol) and 2'-bromo-7'-methoxy-5-methyl-5H-spiro[oxazole-4,9'-xanthen]-2-amine (0.750 g, 1.999 mmol) in a resealable pressure tube, was added DME (6 mL) and water (2 mL) at RT. The tube was sealed and heated to 85° C. After 2 hrs, the mixture was cooled to RT, diluted with EtOAc, and washed with brine. The organic fraction was dried with sodium sulfate and concentrated in vacuo. The residue was purified by silica gel chromatography using 2-8% MeOH in CH$_2$Cl$_2$ with 1% NH$_4$OH to afford a mixture of diastereomers as an off-white foam. MH+=375.2@1.54 min. Purification of the resulting racemic product mixture using Chiralpack AD-H (2×15 cm) 30% MeOH/CO$_2$, 100 bar, 70 ml/min afforded:

Diastereomer 1-'(4R,5S)-2'-methoxy-5-methyl-7'-(5-pyrimidinyl)spiro[1,3-oxazole-4,9'-xanthen]-2-amine (Example No. 125a);

Diastereomer 2-'(4S,5S)-2'-methoxy-5-methyl-7'-(5-pyrimidinyl)spiro[1,3-oxazole-4,9'-xanthen]-2-amine (Example No. 125b);

Diastereomer 3-'(4R,5R)-2'-methoxy-5-methyl-7'-(5-pyrimidinyl)spiro[1,3-oxazole-4,9'-xanthen]-2-amine (Example No. 125c);

Diastereomer 4-'(4S,5R)-2'-methoxy-5-methyl-7'-(5-pyrimidinyl)spiro[1,3-oxazole-4,9'-xanthen]-2-amine (Example No. 125d).

Example 126

Method RW2

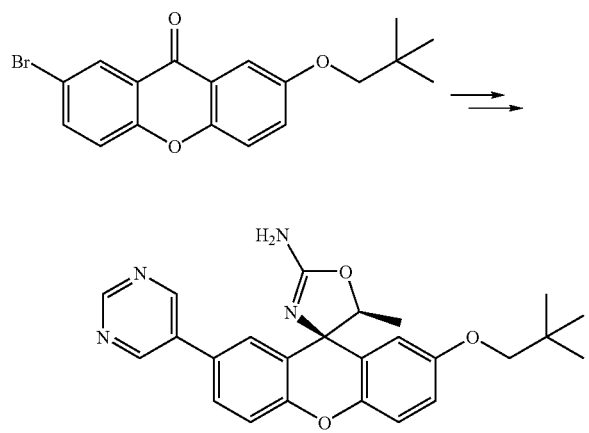

Synthesis of '(4R,5S)-2'-(2,2-dimethylpropoxy)-5-methyl-7'-(5-pyrimidinyl)spiro[1,3-oxazole-4,9'-xanthen]-2-amine The titled compound was prepared in a manner analogous to that described in Example 125 starting with 2-bromo-7-(neopentyloxy)-9H-xanthen-9-one.

Example 127

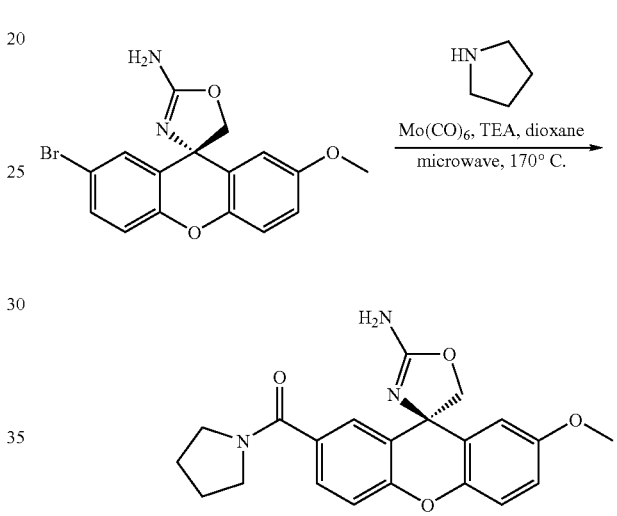

Synthesis of (R)-(2-amino-2'-methoxy-5H-spiro[oxazole-4,9'-xanthene]-7'-yl)(pyrrolidin-1-yl)methanone A microwave vial charged with (S)-2'-bromo-7'-methoxy-5H-spiro[oxazole-4,9'-xanthen]-2-amine (100 mg, 277 μmol), Mo(CO)$_6$ (Strem, 37 mg, 138 μmol), Herrmann's catalyst (Strem, 13 mg, 14 μmol), triethylamine (39 μL, 277 μmol), pyrrolidine (Fluka, 23 μL, 277 μmol), and 1,4-dioxane (0.5 mL, 5.8 mmol) was sealed and irradiated to 170° C. for 10 min. The mixture was diluted with EtOAc and saturated NaHCO$_3$, extracted 3× with EtOAc. The organic layers were combined and dried over Na$_2$SO$_4$ and concentrated in vacuo. The crude residue was purified by reverse phase prep HPLC: 35-100% CH$_3$CN (0.1% TFA)-water (0.1% TFA) in 15 min. The fractions were combined and neutralized with solid Na$_2$CO$_3$, extracted 3×CH$_2$Cl$_2$. The organic layer was dried over Na$_2$SO$_4$ and concentrated in vacuo. The product was obtained as a white solid. MS m/z=380 [M+H]$^+$.

Example 128

Method CB1

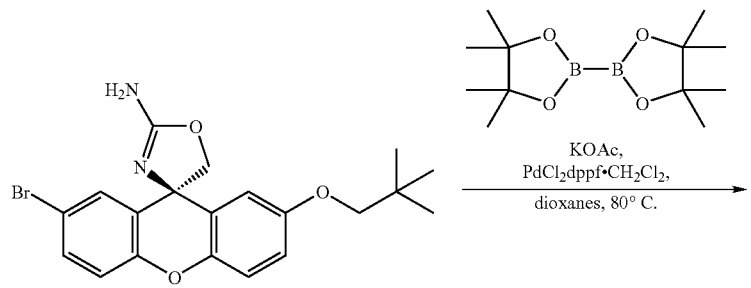

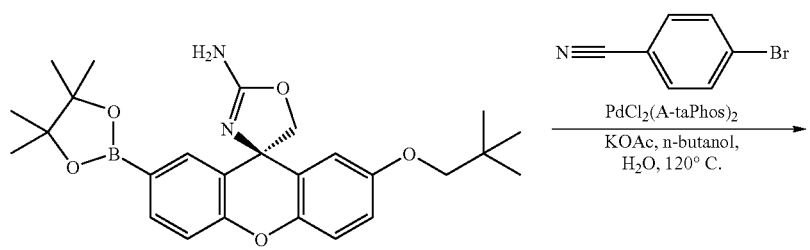

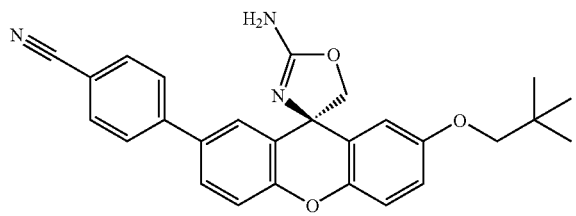

Synthesis of (R)-4-(2-amino-2'-(neopentyloxy)-5H-spiro[oxazole-4,9'-xanthene]-7'-yl)benzonitrile Step 1: (R)-2'-(Neopentyloxy)-7'-(4,4,5,5-tetramethyl-1,3,2-dioxaborolan-2-yl)-5H-spiro[oxazole-4,9'-xanthen]-2-amine A 250 mL RBF was charged with (S)-2'-bromo-7'-(neopentyloxy)-5H-spiro[oxazole-4,9'-xanthen]-2-amine (3 g, 7.2 mmol), Bis(pinacolate)diboron (3.65 g, 14.4 mmol), and potassium acetate (1.4 g, 14.4 mmol). Anhydrous dioxane (40 mL) was added and the mixture was purged with Ar. [1,1'-Bis(diphenylphosphino)-ferrocene]dichloropalladium (II) complex with dichloromethane (1:1) (587 mg, 719 µmol) was added and the reaction mixture was stirred under a reflux condenser under Ar in an 80° C. oil bath for 3 h followed by 3 h at 110° C. The reaction mixture was allowed to cool to RT and concentrated in vacuo to give a dark brown solid. The solid was resuspended between EtOAc (200 mL) and water (200 mL). The organic phase was washed with saturated aqueous sodium bicarbonate (100 mL) and brine (100 mL). The organic phase was then dried over magnesium sulfate, treated with decolorizing carbon, filtered through a pad of Celite, and concentrated in vacuo to give a brown residue. The residue was suspended in dichloromethane (30 mL), sonicated for 30 s, and then added to hexane (120 mL). The resulting precipitate was collected by suction filtration and air-dried to afford the crude desired product as a tan solid which was taken directly without further purification. MS m/z=464.8 [M+H]$^+$. Calc'd for $C_{26}H_{33}BN_2O_5$: 464.25

Step 2: (R)-4-(2-amino-2'-(neopentyloxy)-5H-spiro[oxazole-4,9'-xanthene]-7'-yl)benzonitrile A 2-mL microwave vial was charged with (R)-2'-(neopentyloxy)-7'-(4,4,5,5-tetramethyl-1,3,2-dioxaborolan-2-yl)-5H-spiro[oxazole-4,9'-xanthen]-2-amine (100 mg, 0.215 mmol) in n-butanol (1723 µL), 4-bromobenzonitrile (78 mg, 0.431 mmol), and potassium acetate (63.4 mg, 0.646 mmol) in water (431 µL). The vessel was purged with Argon gas. Bis(di-tert-butyl(4-dimethylaminophenyl)phosphine (dichloropalladium (II) (3.1 mg, 4.3 µmol) was added and the reaction was heated to 120° C. for 15 min in a Biotage microwave initiator. The reaction was then cooled to room temperature and purified by reverse-phase preparative HPLC using a Gemini NX C18 column (150×30 mm, 5 um), 0.1% trifluoroacetic acid in acetonitrile/water, gradient 10% to 70% over 10 min to give the desired product as the trifluoroacetic acid salt. MS m/z=440.0 [M+H]$^+$. Calc'd for $C_{27}H_{25}N_3O_3$: 439.19.

Example 129

Method CB2

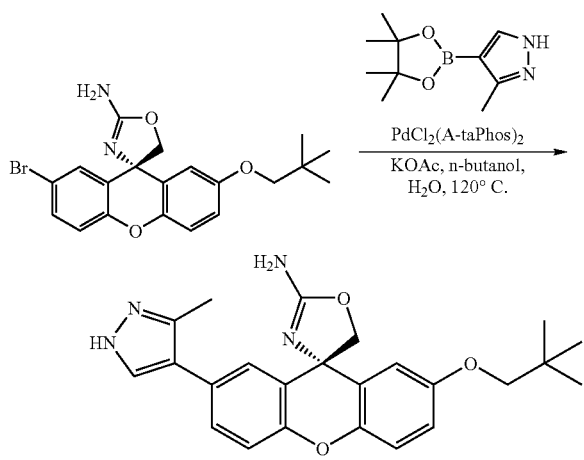

Synthesis of (S)-2'-(3-methyl-1H-pyrazol-4-yl)-7'-(neopentyloxy)-5H-spiro[oxazole-4,9'-xanthen]-2-amine 2,2,2-trifluoroacetate A 2-mL microwave vial was charged with (R)-2'-bromo-7'-(neopentyloxy)-5H-spiro[oxazole-4,9'-xanthen]-2-amine (50 mg, 120 μmol) in n-butanol (959 μL), 3-methyl-4-(4,4,5,5-tetramethyl-1,3,2-dioxaborolan-2-yl)-1H-pyrazole (49.9 mg, 240 μmol), and potassium acetate (35.3 mg, 359 μmol) in water (240 μL). The vessel was purged with Ar. Bis(di-tert-butyl(4-dimethylaminophenyl)phosphine(dichloropalladium (II) (1.7 mg, 2.4 μmol) was added and the reaction was heated to 120° C. for 30 min in a Biotage microwave initiator. The reaction was then cooled to room temperature and loaded an AccuBOND II SCX cartridge, washed with methanol (3 ml) and eluted with 2N ammonia in methanol (6 ml) to give the crude product. The crude mixture was then purified by reverse-phase preparative HPLC using a Gemini NX C18 column (150×30 mm, 5 um), 0.1% TFA in acetonitrile/water, gradient 10% to 90% over 10 min to give the desired product as the TFA salt. MS m/z=419.0 [M+H]$^+$. Calc'd for $C_{24}H_{26}N_4O_3$: 418.20.

Example 130

Method IM1

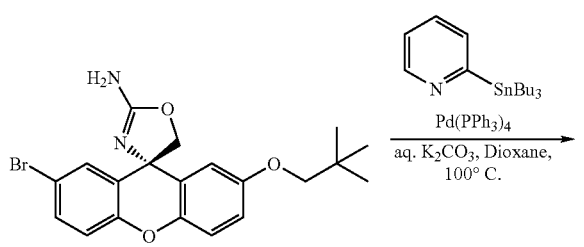

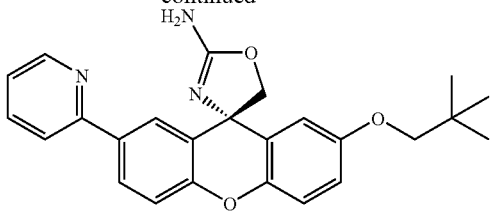

A vial was charged with (R)-2'-bromo-7'-(neopentyloxy)-5H-spiro[oxazole-4,9'-xanthen]-2-amine (0.050 g, 0.120 mmol), tetrakis(triphenylphosphine)palladium (0) (0.014 g, 0.012 mmol), 2-(tributylstannyl)pyridine (0.132 g, 0.359 mmol), and dioxane (0.6 mL). The reaction was stirred overnight at 100° C. The mixture was diluted with DMSO and filtered through a syringe filter, which was flushed with additional DMSO. The material was purified via Gilson HPLC (10-90% MeCN:H2O). The clean product fractions were partitioned between DCM and saturated sodium bicarbonate solution. The aqueous layer was extracted with DCM, and the combined organic layers were dried with sodium sulfate, filtered, and concentrated to afford (S)-2'-(neopentyloxy)-7'-(pyridin-2-yl)-5H-spiro[oxazole-4,9'-xanthen]-2-amine as a white solid. MS MH+ 416.4

Example 131

Method TAD1

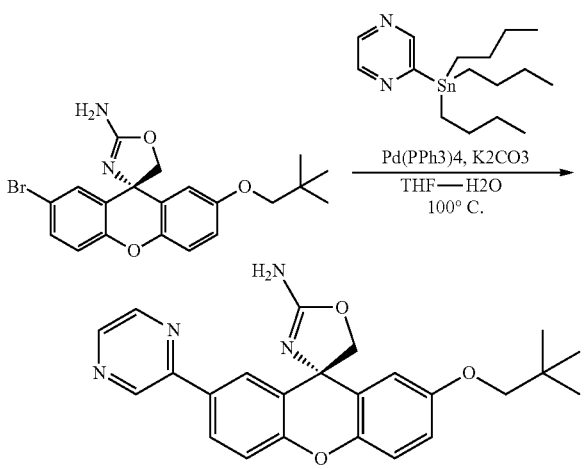

Synthesis of (S)-2'-(neopentyloxy)-7'-(pyrazin-2-yl)-5H-spiro[oxazole-4,9'-xanthen]-2-amine A vial was charged with (R)-2'-bromo-7'-(neopentyloxy)-5H-spiro[oxazole-4,9'-xanthen]-2-amine (55.6 mg, 0.133 mmol), tetrakis(triphenylphosphine)palladium (0) (15.40 mg, 0.013 mmol), 2-(tributylstannyl)pyrazine (148 mg, 0.400 mmol), and dioxane (0.7 mL). The vial was sealed under a blanket of Ar gas and placed in a 100° C. oil for 16 h. The mixture was then cooled and filtered through celite. The filtrate was evaporated, and the residue was purified by chromatography on a 12-g Redi-Sep column, eluting with 0-10% MeOH/DCM to give a brown oil. This oil was dissolved in MeOH and filtered through a 2 micron filter, then purified further by reverse-phase HPLC (10-90% CH$_3$CN/H$_2$O with 0.1% TFA). The product containing fractions were combined in saturated aqueous sodium bicarbonate solution with the aid of MeOH. The mixture was extracted with DCM (2×), and the combined organic extracts were dried over sodium sulfate, filtered, and evaporated to give (S)-2'-(neopentyloxy)-7'-(pyrazin-2-yl)-5H-spiro[oxazole-4,9'-xanthen]-2-amine as a white solid. MS m/z=417.2 [M+H]$^+$. Calc'd for C$_{24}$H$_{25}$N$_4$O$_3$: 417.19.

Example 132

Method IM2

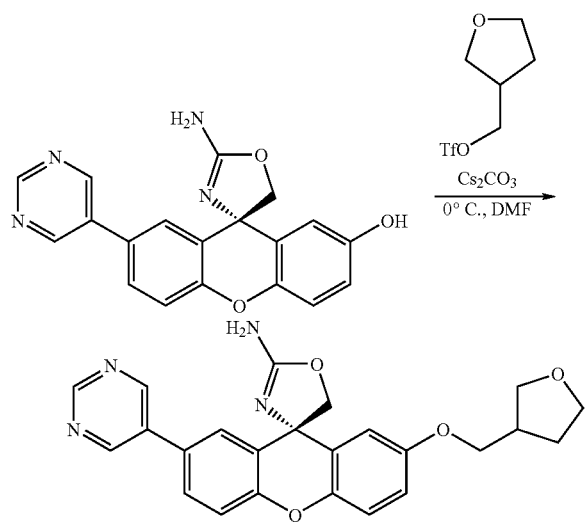

Synthesis of (S)-2'-(pyrimidin-5-yl)-7'-((tetrahydro-furan-3-yl)methoxy)-5H-spiro[oxazole-4,9'-xanthen]-2-amine Step 1: Preparation of (tetrahydrofuran-3-yl)methyl trifluoromethanesulfonate A 100 mL RBF was charged with tetrahydro-3-furan-methanol (0.500 mL, 4.79 mmol), DCM (19.15 mL), and pyridine (0.410 mL, 5.51 mmol). The solution was cooled for 10 minutes in an ice bath, then triflic anhydride (0.890 mL, 5.27 mmol) was added slowly dropwise. The resulting pink solution was stirred for one hour at 0° C. The reaction was decanted and the remaining salts were washed with DCM and decanted again. The combined organic layers were concentrated and purified via column chromatography (RediSep 40 g, gradient elution 0-40% EtOAc:Hex). The resulting oil was vacuum dried for one hour to afford (tetrahydrofuran-3-yl)methyl trifluoromethanesulfonate as a light brown oil. The material was used immediately in step 2.

Step 2: (S)-2'-(Pyrimidin-5-yl)-7'-((tetrahydrofuran-3-yl)methoxy)-5H-spiro[oxazole-4,9'-xanthen]-2-amine (S)-2-Amino-7'-(pyrimidin-5-yl)-5H-spiro[oxazole-4,9'-xanthen]-2'-ol (0.075 g, 0.217 mmol) and cesium carbonate (0.106 g, 0.325 mmol) were dissolved in DMF (0.7 mL) and stirred for five minutes before being cooled in an ice bath. (Tetrahydrofuran-3-yl)methyl trifluoromethanesulfonate (0.056 g, 0.238 mmol) was dissolved in DMF (0.15 mL) and added dropwise to the reaction, which was stirred for one hour. An additional equivalent of triflate was added and the reaction was stirred for five days. The reaction was cooled to 0° C. and 0.5 eq. of triflate was dissolved in 0.1 mL of DMF and added dropwise to the reaction. The reaction was stirred for two days. The reaction was diluted with EtOAc and washed with water. The aqueous layer was extracted with EtOAc, and the combined organic layers were washed with brine, dried with sodium sulfate, filtered, and concentrated. The material was purified via column chromatography (RediSep 40 g, gradient elution 0-10% MeOH:DCM) but the material was impure so the material was repurified via Gilson HPLC (10-90% MeCN:H2O). The product fractions were partitioned between DCM and saturated sodium bicarbonate solution. The aqueous layer was extracted with DCM, and the combined organic layers were dried with sodium sulfate, filtered, and concentrated to afford (S)-2'-(pyrimidin-5-yl)-7'-((tetrahydrofuran-3-yl)methoxy)-5H-spiro[oxazole-4,9'-xanthen]-2-amine as a white solid. LC-MS MH+ 431.4

Example 133

Method IM3

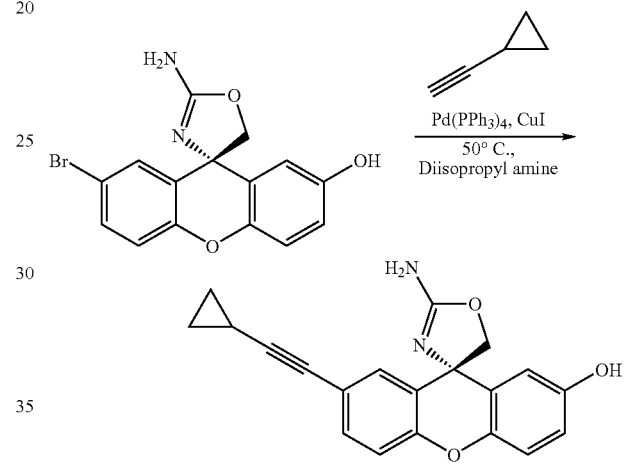

Synthesis of (R)-2-amino-2'-bromo-5H-spiro[oxazole-4,9'-xanthen]-7'-ol (1.00 g, 2.88 mmol) to (S)-2-amino-2'-(cyclopropylethynyl)-5H-spiro[oxazole-4,9'-xanthen]-7'-ol The titled compound was prepared by a method similar to that described in Example 40 (Method G). MS Found by LC-MS: MH+ 333.3

Example 134

Method TAD2

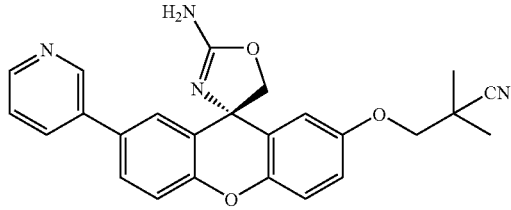 [SMILES: CC(C)(C#N)COc1ccc2c(c1)[C@]1(COC(N)=N1)c1cc(-c3cccnc3)ccc1O2]

Synthesis of (S)-3-(2-amino-2'-(pyridin-3-yl)-5H-spiro[oxazole-4,9'-xanthene]-7'-yloxy)-2,2-dimethyl-propanenitrile The titled compound was prepared by a method analogous to that described in Example 5 (Method A), except using (S)-2-amino-7'-(pyridin-3-yl)-5H-spiro[oxazole-4,9'-xanthen]-2'-ol as the starting material.

Example 135

Method TAD3

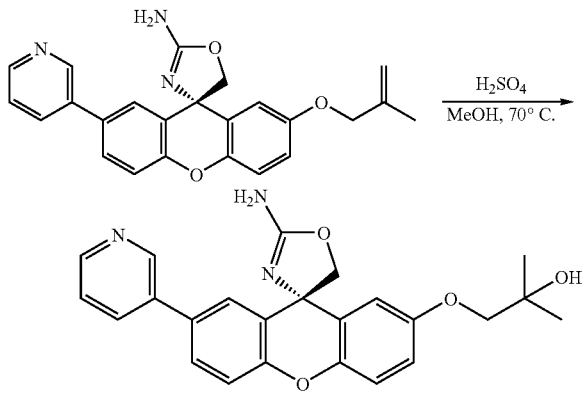

Synthesis of (S)-1-(2-amino-2'-(pyridin-3-yl)-5H-spiro[oxazole-4,9'-xanthene]-7'-yloxy)-2-methylpropan-2-ol A vial was charged with (S)-2'-(2-methylallyloxy)-7'-(pyridin-3-yl)-5H-spiro[oxazole-4,9'-xanthen]-2-amine (41.17 mg, 0.103 mmol) and water (0.5 mL) giving a suspension. Sulfuric acid (110 μL, 2.061 mmol) was added, and the mixture became a cloudy solution. The vial was sealed and placed in a 70° C. oil bath for 8 h. The mixture was cooled to RT, and potassium carbonate was added until bubbling ceased. The resulting suspension was extracted with DCM (3×). The combined organic extracts were dried over sodium sulfate, filtered, and evaporated. The residue was chromatographed on a 12-g Redi-Sep column eluting with 0-10% MeOH/DCM to give a white solid. The solid was dissolved in methanol and purified further by reverse-phase HPLC (10-90% $CH_3CN/H_2O$ with 0.1% TFA). The fractions containing product were combined in saturated aq. sodium bicarbonate solution and extracted with DCM (3×). The combined organic extracts were dried over sodium sulfate, filtered, and evaporated to give (S)-1-(2-amino-2'-(pyridin-3-yl)-5H-spiro[oxazole-4,9'-xanthene]-7'-yloxy)-2-methylpropan-2-ol as a white solid. MS m/z=418.2 $[M+H]^+$. Calculated Mass for $C_{24}H_{24}N_3O_4$: 418.2.

Examples 136a & 136b

Method WQ

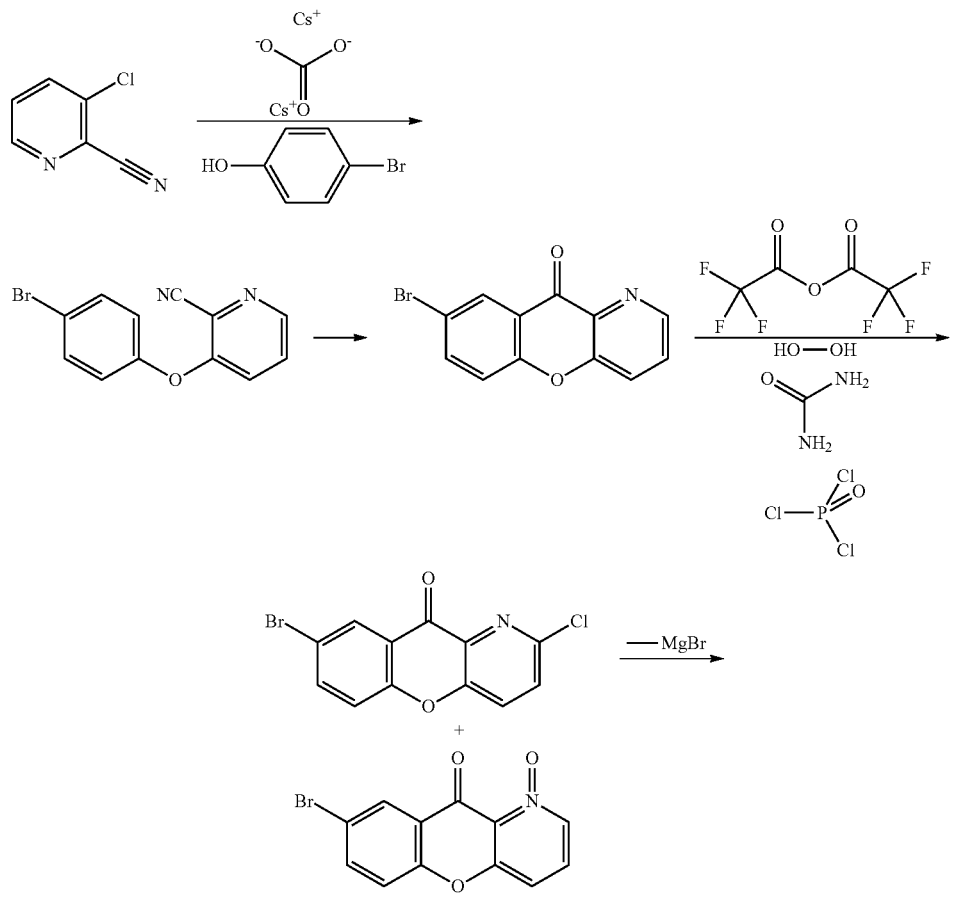

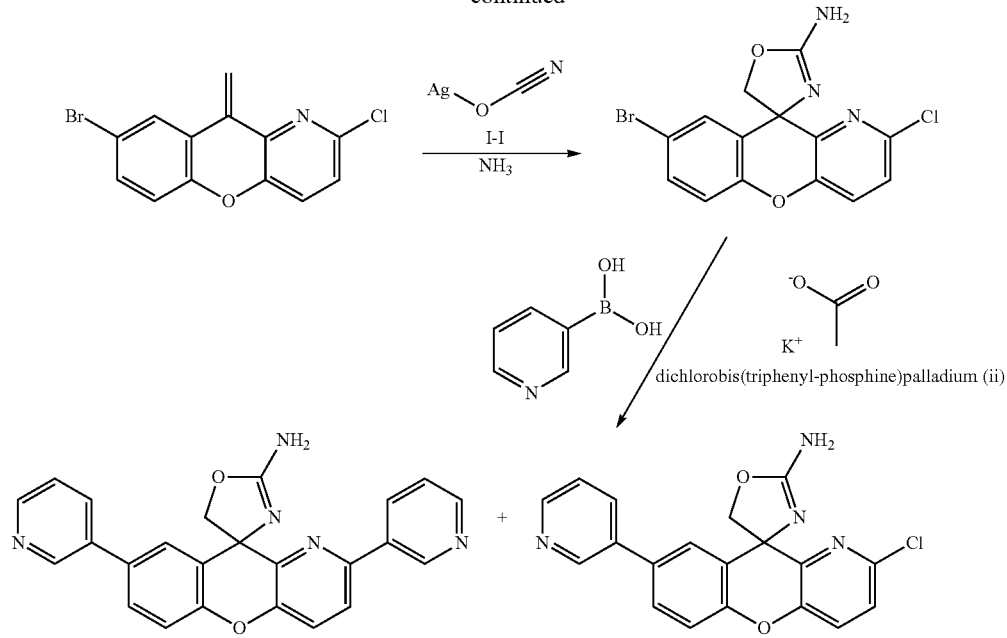

Synthesis of 2,8-di(pyridin-3-yl)-5'H-spiro[chromeno[3,2-b]pyridine-10,4'-oxazol]-2'-amine (136b) and 2-chloro-8-(pyridin-3-yl)-5'H-spiro[chromeno[3,2-b]pyridine-10,4'-oxazol]-2'-amine (136a)

Step 1:

A RBF was charged with 3-chloro-2-cyanopyridine (40 g, 289 mmol), 4-bromophenol (49.9 g, 289 mmol) and cesium carbonate (113 g, 346 mmol). The reactants were suspended in 50 mL of DMSO and allowed to stir at 85 C overnight. The reaction was cooled to RT and to it was added 600 mL of water. The reaction was filtered and the solid washed with water, air dried to provide 3-(4-bromophenoxy)picolinonitrile as a tan solid.

Step 2:

A mixture of 3-(4-bromophenoxy)picolinonitrile (57 g, 207 mmol) and 300 g of PPA was stirred at 190° C. for 2 h, followed by 180° C. overnight. After cooling to RT, the reaction mixture was poured into 500 g of ice water. After the PH was adjusted to 7 with KOH, the suspension was filtered. The solid was washed with large excess of water, followed by washing with methanol and acetone. The resulting solid was air dried to give 8-bromo-10H-chromeno[3,2-b]pyridin-10-one as a tan solid with >90% purity. The material was carried on to the next step.

Step 3:

To a solution of 8-bromo-10H-chromeno[3,2-b]pyridin-10-one (60 g, 217 mmol) and urea peroxide (42.9 g, 456 mmol) in 120 mL of DCM at 0° C. was added dropwise trifluoroacetic anhydride (63.9 mL, 456 mmol). The resulting reaction was stirred for 2 h. The reaction was quenched with 10% $Na_2S_2O_3$, extracted with DCM, dried over $Na_2SO_4$ and evaporated to dryness to give crude 8-bromo-10-oxo-10H-chromeno[3,2-b]pyridine 1-oxide as a pale yellow solid.

Step 4:

To a suspension of 8-bromo-10-oxo-10H-chromeno[3,2-b]pyridine 1-oxide in 100 mL of toluene at 0° C. was added dropwise phosphorus oxychloride (35.8 mL, 391 mmol) followed by 2 mL of DMF and the mixture was stirred at RT overnight. The solvent was evaporated under vacuum and the residue which crashed out of water, was filtered and washed with water, methanol and acetone in sequence. The solid was air dried to give 8-bromo-2-chloro-10H-chromeno[3,2-b]pyridin-10-one as a tan solid.

Step 5:

To a suspension of 8-bromo-2-chloro-10H-chromeno[3,2-b]pyridin-10-one (20 g, 64.4 mmol) in 500 mL of THF at −78° C. was added dropwise methylmagnesium bromide 3.0 M in diethyl ether (13.82 mL, 116 mmol). The reaction was allowed to slowly warmed up to 0° C. in about 2 h. The reaction was quenched with $NH_4Cl$ solution, extracted with EtOAc, dried over $Na_2SO_4$, filtered and evaporated to give the corresponding crude tertiary alcohol. This solid residue was re-dissolved in 100 mL of THF and treated with mL of chloroform and the resulting solution was evaporated on a 75° C. water bath for 10 min to give crude 8-bromo-2-chloro-10-methylene-10H-chromeno[3,2-b]pyridine as a brownish solid.

Step 6:

A solution of iodine (12.96 g, 51.0 mmol) in THF at −25° C. was treated with silver cyanate (21.86 g, 146 mmol). After 30 min, a solution of 8-bromo-2-chloro-10-methylene-10H-chromeno[3,2-b]pyridine (15 g, 48.6 mmol) in THF was added dropwise. The slurry was maintained at −25° C. for 2 h until LCMS showed complete consumption of starting material. The slurry was filtered through celite with ether. The brown solution was concentrated to dryness, taken up in THF, cooled to 0° C. and treated with ammonia, 2m solution in 2-propanol (4.22 mL, 194 mmol) (100 mL). The reaction was allowed to slowly warm to RT and stirred overnight. The solvents were evaporated and the residue was diluted with water, extracted with EtOAc and purified by column chromatography (SiO2, DCM to DCM/EA=3:1 to DCM/MeOH=100:2 to 100:5) to provide 8-bromo-2-chloro-5'H-spiro[chromeno[3,2-b]pyridine-10,4'-oxazol]-2'-amine (impure) as a brownish solid. MS (M+1): 365.9.

Step 7:

A mixture of the 8-bromo-2-chloro-5'H-spiro[chromeno[3,2-b]pyridine-10,4'-oxazol]-2'-amine (from step 6, 40.0 mg, 0.109 mmol), potassium acetate (27.3 μL, 0.436 mmol), dichlorobis(triphenyl-phosphine)palladium (ii) (3.83 mg, 5.46 μmol) and 3-pyridylboronic acid (40.2 mg, 0.327 mmol) in 1.5 ml of dioxane/water=2:1 was heated at 110° C. under microwave irradiation for 15 min. LCMS and TLC showed incomplete conversion after 15 min. The reaction was re-heated in the microwave at 130° C. for 20 additional min. After cooling, the reaction mixture was purified by column chromatography (SiO2, DCM to DCM/MeOH=100:1 to 100:5 to 100:10 to 100:20) to afford 2,8-di(pyridin-3-yl)-5'H-spiro[chromeno[3,2-b]pyridine-10,4'-oxazol]-2'-amine as a gum. MS (M+1): 408.0; and 2-chloro-8-(pyridin-3-yl)-5'H-spiro[chromeno[3,2-b]pyridine-10,4'-oxazol]-2'-amine also as a gum. MS (M+1): 365.0.

The following examples in Table III were prepared by methods and Steps analogous to those described in Examples 108-134 herein. Provided also is the mass spectral data and BACE enzyme and cell-based assay data ($IC_{50}$'s in uM ranges) for each example, where available.

TABLE III

| Ex. No. | Compound Name | Method | Observed MS | BACE1 FRET assay (uM) | HEK cell assay (uM) |
|---|---|---|---|---|---|
| 137 | 2',7'-di-5-pyrimidinylspiro[1,3-oxazole-4,9'-xanthen]-2-amine | OE8 | 409.2 | ++++ | +++ |
| 138 | (4R)-2'-(cyclohexylethynyl)-7'-(5-pyrimidinyl)spiro[1,3-oxazole-4,9'-xanthen]-2-amine | P | 437.0 | ++++ | +++ |
| 139 | (4S)-2'-((2-methyl-2-propen-1-yl)oxy)-7'-(5-pyrimidinyl)spiro[1,3-oxazole-4,9'-xanthen]-2-amine | A | 401.2 | ++++ | ++++ |
| 140 | (4S)-2'-((3-methyl-3-oxetanyl)methoxy)-7'-(5-pyrimidinyl)spiro[1,3-oxazole-4,9'-xanthen]-2-amine | B | 431.4 | ++++ | ++++ |
| 141 | 1-((4S)-2-amino-7'-(5-pyrimidinyl)spiro[1,3-oxazole-4,9'-xanthen]-2'-yl)-2-cyclohexylethanone | R | 455.0 | ++++ | +++ |
| 142 | 3-(((4S)-2-amino-7'-(5-pyrimidinyl)spiro[1,3-oxazole-4,9'-xanthen]-2'-yl)oxy)-2,2-dimethylpropanenitrile | A | 428.2 | ++++ | ++++ |
| 143 | (4S)-2'-(2-methoxy-2-methylpropoxy)-7'-(5-pyrimidinyl)spiro[1,3-oxazole-4,9'-xanthen]-2-amine | A | 433.2 | ++++ | ++++ |
| 131 | (4S)-2'-(2,2-dimethylpropoxy)-7'-(2-pyrazinyl)spiro[1,3-oxazole-4,9'-xanthen]-2-amine | TAD1 | 417.2 | ++++ | ++++ |
| 134 | 3-(((4S)-2-amino-7'-(3-pyridinyl)spiro[1,3-oxazole-4,9'-xanthen]-2'-yl)oxy)-2,2-dimethylpropanenitrile | TAD2 | 427.2 | ++++ | ++++ |
| 144 | (4S)-2'-((3-methyl-3-oxetanyl)methoxy)-7'-(3-pyridinyl)spiro[1,3-oxazole-4,9'-xanthen]-2-amine | TAD2 | 430.2 | ++++ | ++++ |
| 130 | (4S)-2'-(2,2-dimethylpropoxy)-7'-(2-pyridinyl)spiro[1,3-oxazole-4,9'-xanthen]-2-amine | IM1 | 416.4 | ++++ | +++ |
| 145 | (4S)-2'-(2,2-dimethylpropoxy)-7'-(4-pyridazinyl)spiro[1,3-oxazole-4,9'-xanthen]-2-amine | TAD1 | 417.2 | ++++ | +++ |
| 146 | (4S)-2'-((2-methyl-2-propen-1-yl)oxy)-7'-(3-pyridinyl)spiro[1,3-oxazole-4,9'-xanthen]-2-amine | TAD2 | 400.2 | ++++ | +++ |
| 116a | (4S)-2'-((1S)-1-fluoro-3,3-dimethylbutyl)-7'-(5-pyrimidinyl)spiro[1,3-oxazole-4,9'-xanthen]-2-amine | OE1 | 433.0 | ++++ | +++ |
| 116b | (4S)-2'-((1R)-1-fluoro-3,3-dimethylbutyl)-7'-(5-pyrimidinyl)spiro[1,3-oxazole-4,9'-xanthen]-2-amine | OE1 | 433.0 | ++++ | +++ |
| 147a | (4R)-2'-(3,3-dimethyl-1-butyn-1-yl)-7'-(6-fluoro-3-pyridinyl)spiro[1,3-oxazole-4,9'-xanthen]-2-amine | P | 428.2 | ++++ | +++ |
| 147b | (4S)-2'-(3,3-dimethyl-1-butyn-1-yl)-7'-(6-fluoro-3-pyridinyl)spiro[1,3-oxazole-4,9'-xanthen]-2-amine | P | 428.2 | ++++ | +++ |
| 148 | (4S)-2'-(2-fluoro-2-methylpropoxy)-7'-(3-pyridinyl)spiro[1,3-oxazole-4,9'-xanthen]-2-amine | TAD2 | 420.2 | ++++ | ++++ |
| 117a | (4R)-2'-(3-(dimethylamino)-1-propyn-1-yl)-7'-(5-pyrimidinyl)spiro[1,3-oxazole-4,9'-xanthen]-2-amine | OE2 | 412.0 | +++ | ++++ |
| 117b | (4S)-2'-(3-(dimethylamino)-1-propyn-1-yl)-7'-(5-pyrimidinyl)spiro[1,3-oxazole-4,9'-xanthen]-2-amine | OE2 | 412.0 | ++ | +++ |

TABLE III-continued

| Ex. No. | Compound Name | Method | Observed MS | BACE1 FRET assay (uM) | HEK cell assay (uM) |
|---|---|---|---|---|---|
| 118 | 4,4'-(2-aminospiro[1,3-oxazole-4,9'-xanthene]-2',7'-diyl)bis(2-methyl-3-butyn-2-ol) | OE3 | 417.2 | ++ | ++ |
| 132 | (4S)-2'-(5-pyrimidinyl)-7'-(tetrahydro-3-furanylmethoxy)spiro[1,3-oxazole-4,9'-xanthen]-2-amine | IM2 | 431.4 | ++ | + |
| 119 | 2',7'-bis(3-methoxy-3-methyl-1-butyn-1-yl)spiro[1,3-oxazole-4,9'-xanthen]-2-amine | OE4 | 445.2 | +++ | +++ |
| 149 | (4S)-2'-(2-methoxy-2-methylpropoxy)-7'-(3-pyridinyl)spiro[1,3-oxazole-4,9'-xanthen]-2-amine | TAD2 | 432.2 | ++++ | ++++ |
| 150a | 1-((4S)-2-amino-7'-(6-fluoro-3-pyridinyl)spiro[1,3-oxazole-4,9'-xanthen]-2'-yl)-3,3-dimethyl-1-butanone | R | 446.2 | ++++ | +++ |
| 150b | 1-((4R)-2-amino-7'-(6-fluoro-3-pyridinyl)spiro[1,3-oxazole-4,9'-xanthen]-2'-yl)-3,3-dimethyl-1-butanone | R | 446.2 | ++++ | +++ |
| 120 | 4-((4R)-2-amino-7'-(5-pyrimidinyl)spiro[1,3-oxazole-4,9'-xanthen]-2'-yl)-2-methyl-3-butyn-2-ol | OE5 | 413.0 | ++++ | ++++ |
| 120 | 4-((4S)-2-amino-7'-(5-pyrimidinyl)spiro[1,3-oxazole-4,9'-xanthen]-2'-yl)-2-methyl-3-butyn-2-ol | OE5 | 413.0 | +++ | ++ |
| 151a | 4-((4R)-2-amino-7'-(3-pyridinyl)spiro[1,3-oxazole-4,9'-xanthen]-2'-yl)-2-methyl-3-butyn-2-ol | OE5 | 412.0 | ++++ | ++++ |
| 151b | 4-((4S)-2-amino-7'-(3-pyridinyl)spiro[1,3-oxazole-4,9'-xanthen]-2'-yl)-2-methyl-3-butyn-2-ol | OE5 | 412.0 | ++++ | ++++ |
| 121 | (4R)-2'-(3-methoxy-3-methyl-1-butyn-1-yl)-7'-(5-pyrimidinyl)spiro[1,3-oxazole-4,9'-xanthen]-2-amine | OE6 | 427.0 | ++++ | ++++ |
| 121 | (4S)-2'-(3-methoxy-3-methyl-1-butyn-1-yl)-7'-(5-pyrimidinyl)spiro[1,3-oxazole-4,9'-xanthen]-2-amine | OE4 | 427.0 | ++++ | +++ |
| 152a | (4R)-4'-fluoro-7'-methoxy-2'-(5-pyrimidinyl)spiro[1,3-oxazole-4,9'-xanthen]-2-amine | JBH2 | 379.0 | +++ | ++ |
| 152b | (4S)-4'-fluoro-7'-methoxy-2'-(5-pyrimidinyl)spiro[1,3-oxazole-4,9'-xanthen]-2-amine | JBH2 | 379.0 | ++ | ++ |
| 153a | (4S)-2'-(3,3-dimethylbutyl)-7'-(6-fluoro-3-pyridinyl)spiro[1,3-oxazole-4,9'-xanthen]-2-amine | O | 432.0 | ++++ | +++ |
| 153b | (4R)-2'-(3,3-dimethylbutyl)-7'-(6-fluoro-3-pyridinyl)spiro[1,3-oxazole-4,9'-xanthen]-2-amine | O | 432.0 | ++++ | +++ |
| 154a | (4R)-3'-fluoro-2'-methoxy-7'-(5-pyrimidinyl)spiro[1,3-oxazole-4,9'-xanthen]-2-amine | JBH1 | 379.0 | + | + |
| 154b | (4S)-3'-fluoro-2'-methoxy-7'-(5-pyrimidinyl)spiro[1,3-oxazole-4,9'-xanthen]-2-amine | JBH1 | 379.0 | ++++ | +++ |
| 155a | (4S)-7'-(2,2-dimethylpropoxy)-4'-fluoro-2'-(5-pyrimidinyl)spiro[1,3-oxazole-4,9'-xanthen]-2-amine | JBH2 | 435.0 | ++++ | +++ |
| 155b | (4R)-7'-(2,2-dimethylpropoxy)-4'-fluoro-2'-(5-pyrimidinyl)spiro[1,3-oxazole-4,9'-xanthen]-2-amine | JBH2 | 435.0 | ++++ | +++ |
| 156a | (4R)-2'-(3-methoxy-1-propyn-1-yl)-7'-(5-pyrimidinyl)spiro[1,3-oxazole-4,9'-xanthen]-2-amine | OE6 | 399.0 | ++++ | ++++ |
| 156b | (4S)-2'-(3-methoxy-1-propyn-1-yl)-7'-(5-pyrimidinyl)spiro[1,3-oxazole-4,9'-xanthen]-2-amine | OE6 | 399.0 | +++ | +++ |
| 135 | 1-(((4S)-2-amino-7'-(3-pyridinyl)spiro[1,3-oxazole-4,9'-xanthen]-2'-yl)oxy)-2-methyl-2-propanol | TAD3 | 418.2 | ++++ | ++++ |
| 157 | (5R)-3,7-di-3-pyridinylspiro[chromeno[2,3-b]pyridine-5,4'-[1,3]oxazol]-2'-amine | MW4 | 408.2 | ++++ | ++++ |
| 158 | (4S)-2'-(2-tert-butoxyethoxy)-7'-(5-pyrimidinyl)spiro[1,3-oxazole-4,9'-xanthen]-2-amine | A | 447.2 | ++++ | ++++ |

TABLE III-continued

| Ex. No. | Compound Name | Method | Observed MS | BACE1 FRET assay (uM) | HEK cell assay (uM) |
|---|---|---|---|---|---|
| 159 | (4S)-2'-(2-tert-butoxyethoxy)-7'-(3-pyridinyl)spiro[1,3-oxazole-4,9'-xanthen]-2-amine | TAD2 | 446.2 | ++++ | +++ |
| 160 | (5S)-7-(3,3-dimethyl-1-butyn-1-yl)-3-(3-pyridinyl)spiro[chromeno[2,3-b]pyridine-5,4'-[1,3]oxazol]-2'-amine | MW1 | 411.2 | ++++ | ++++ |
| 161 | (5S)-7-(3,3-dimethylbutyl)-3-(3-pyridinyl)spiro[chromeno[2,3-b]pyridine-5,4'-[1,3]oxazol]-2'-amine | MW1 | 415.2 | ++++ | ++++ |
| 162a | 1-((4S)-2-amino-7'-(6-fluoro-3-pyridinyl)spiro[1,3-oxazole-4,9'-xanthen]-2'-yl)-3,3-dimethyl-1-butanol | S | 448.2 | +++ | +++ |
| 162b | 1-((4R)-2-amino-7'-(6-fluoro-3-pyridinyl)spiro[1,3-oxazole-4,9'-xanthen]-2'-yl)-3,3-dimethyl-1-butanol | S | 448.2 | +++ | +++ |
| 163 | (4S)-2'-(5-pyrimidinyl)-7'-(3,3,3-trifluoro-2-(trifluoromethyl)propoxy)spiro[1,3-oxazole-4,9'-xanthen]-2-amine | A | 511.2 | +++ | +++ |
| 126a | (4R,5S)-2'-(2,2-dimethylpropoxy)-5-methyl-7'-(5-pyrimidinyl)spiro[1,3-oxazole-4,9'-xanthen]-2-amine | RW2 | 431.0 | +++ | ++ |
| 126b | (4S,5S)-2'-(2,2-dimethylpropoxy)-5-methyl-7'-(5-pyrimidinyl)spiro[1,3-oxazole-4,9'-xanthen]-2-amine | RW2 | 431.0 | ++++ | +++ |
| 126c | (4R,5R)-2'-(2,2-dimethylpropoxy)-5-methyl-7'-(5-pyrimidinyl)spiro[1,3-oxazole-4,9'-xanthen]-2-amine | RW2 | 431.0 | +++ | ++ |
| 126d | (4S,5R)-2'-(2,2-dimethylpropoxy)-5-methyl-7'-(5-pyrimidinyl)spiro[1,3-oxazole-4,9'-xanthen]-2-amine | RW2 | 431.0 | ++++ | ++++ |
| 164 | (5R)-3-bromo-7-((3-methyl-3-oxetanyl)methoxy)spiro[chromeno[2,3-b]pyridine-5,4'-[1,3]oxazol]-2'-amine | N | 432 | +++ | ++ |
| 165 | (5R)-7-((3-methyl-3-oxetanyl)methoxy)-3-(3-pyridinyl)spiro[chromeno[2,3-b]pyridine-5,4'-[1,3]oxazol]-2'-amine | N | 431.2 | ++++ | ++++ |
| 166 | (5R)-7-((3-methyl-3-oxetanyl)methoxy)-3-(5-pyrimidinyl)spiro[chromeno[2,3-b]pyridine-5,4'-[1,3]oxazol]-2'-amine | N | 432.2 | ++++ | +++ |
| 167 | 3-(((5R)-2'-amino-3-(5-pyrimidinyl)spiro[chromeno[2,3-b]pyridine-5,4'-[1,3]oxazol]-7-yl)oxy)-2,2-dimethylpropanenitrile | N | 429.2 | ++++ | +++ |
| 168 | 3-(((5R)-2'-amino-3-(3-pyridinyl)spiro[chromeno[2,3-b]pyridine-5,4'-[1,3]oxazol]-7-yl)oxy)-2,2-dimethylpropanenitrile | N | 428.2 | ++++ | ++++ |
| 169 | methyl (2E)-3-((4S)-2-amino-7'-bromospiro[1,3-oxazole-4,9'-xanthen]-2'-yl)-2-propenoate | AA60 | 416 | ++ | + |
| 125a | (4R,5S)-2'-methoxy-5-methyl-7'-(5-pyrimidinyl)spiro[1,3-oxazole-4,9'-xanthen]-2-amine | RW1 | 375.2 | + | + |
| 125b | (4S,5S)-2'-methoxy-5-methyl-7'-(5-pyrimidinyl)spiro[1,3-oxazole-4,9'-xanthen]-2-amine | RW1 | 375.2 | +++ | +++ |
| 125c | (4R,5R)-2'-methoxy-5-methyl-7'-(5-pyrimidinyl)spiro[1,3-oxazole-4,9'-xanthen]-2-amine | RW1 | 375.2 | + | + |
| 125d | (4S,5R)-2'-methoxy-5-methyl-7'-(5-pyrimidinyl)spiro[1,3-oxazole-4,9'-xanthen]-2-amine | RW1 | 375.2 | +++ | +++ |
| 170 | (4S)-2'-(2-ethoxy-2-methylpropoxy)-7'-(5-pyrimidinyl)spiro[1,3-oxazole-4,9'-xanthen]-2-amine | A | 447.2 | ++++ | ++++ |
| 171 | (5R)-3-bromo-7-(2-fluoro-2-methylpropoxy)spiro[chromeno[2,3-b]pyridine-5,4'-[1,3]oxazol]-2'-amine | N | 422 | +++ | ++ |
| 111 | (5R)-3-(3,3-dimethyl-1-butyn-1-yl)-7-(3-pyridinyl)spiro[chromeno[2,3-b]pyridine-5,4'-[1,3]oxazol]-2'-amine | MW2 | 411.2 | ++++ | ++++ |
| 172 | (4S)-2'-(2-ethoxy-2-methylpropoxy)-7'-(3-pyridinyl)spiro[1,3-oxazole-4,9'-xanthen]-2-amine | TAD2 | 446.1 | ++++ | ++++ |

TABLE III-continued

| Ex. No. | Compound Name | Method | Observed MS | BACE1 FRET assay (uM) | HEK cell assay (uM) |
|---|---|---|---|---|---|
| 173 | 4-((5S)-2'-amino-3-bromospiro[chromeno[2,3-b]pyridine-5,4'-[1,3]oxazol]-7-yl)-2-methyl-3-butyn-2-ol | MW2 | 414 | ++ | + |
| 174 | (5R)-3-bromo-7-(3-pyridinyl)spiro[chromeno[2,3-b]pyridine-5,4'-[1,3]oxazol]-2'-amine | MW2 | 409 | ++++ | +++ |
| 175 | (4S)-2'-(5-pyrimidinyl)-7'-(tetrahydro-2H-pyran-4-ylmethoxy)spiro[1,3-oxazole-4,9'-xanthen]-2-amine | B | 445.2 | ++++ | ++++ |
| 122 | (4R)-2'-(3-methoxy-3-methylbutyl)-7'-(5-pyrimidinyl)spiro[1,3-oxazole-4,9'-xanthen]-2-amine | OE7 | 431.0 | ++++ | ++++ |
| 176 | (5R)-7-(2-fluoro-2-methylpropoxy)-3-(5-pyrimidinyl)spiro[chromeno[2,3-b]pyridine-5,4'-[1,3]oxazol]-2'-amine | N | 422.2 | ++++ | +++ |
| 123 | 2',7'-di-3-pyridinylspiro[1,3-oxazole-4,9'-xanthen]-2-amine | OE8 | 407.0 | ++++ | ++++ |
| 177 | (5R)-7-(2-fluoro-2-methylpropoxy)-3-(3-pyridinyl)spiro[chromeno[2,3-b]pyridine-5,4'-[1,3]oxazol]-2'-amine | N | 421.2 | ++++ | ++++ |
| 178 | 3-(((4S)-2-amino-7'-(cyclopropylethynyl)spiro[1,3-oxazole-4,9'-xanthen]-2'-yl)oxy)-2,2-dimethylpropanenitrile | IM3 | 414.3 | ++++ | +++ |
| 179 | (5S)-7-(3-methoxy-3-methyl-1-butyn-1-yl)-3-(3-pyridinyl)spiro[chromeno[2,3-b]pyridine-5,4'-[1,3]oxazol]-2'-amine | MW1 | 427.2 | ++++ | +++ |
| 180 | (4S)-2'-(2-(1-methylethoxy)ethoxy)-7'-(5-pyrimidinyl)spiro[1,3-oxazole-4,9'-xanthen]-2-amine | A | 433.2 | ++++ | +++ |
| 181 | (4S)-2'-(2-(1-methylethoxy)ethoxy)-7'-(3-pyridinyl)spiro[1,3-oxazole-4,9'-xanthen]-2-amine | TAD2 | 432.2 | ++++ | +++ |
| 124 | (4R)-2'-(3-pyridinyl)-7'-(5-pyrimidinyl)spiro[1,3-oxazole-4,9'-xanthen]-2-amine | OE9 | 408.0 | ++++ | ++++ |
| 182a | (5S)-7-(3,3-dimethylbutyl)-3-(3-pyridinyl)spiro[chromeno[2,3-b]pyridine-5,4'-[1,3]oxazol]-2'-amine | MW1 | 415.2 | ++++ | ++++ |
| 182b | (5R)-7-(3,3-dimethylbutyl)-3-(3-pyridinyl)spiro[chromeno[2,3-b]pyridine-5,4'-[1,3]oxazol]-2'-amine | MW1 | 415.2 | ++++ | +++ |
| 109 | (10R)-1-(3,3-dimethylbutoxy)-8-(5-pyrimidinyl)spiro[chromeno[3,2-c]pyridine-10,4'-[1,3]oxazol]-2'-amine | MM-1 | 432.0 | +++ | +++ |
| 110 | (5S)-7-(3-methoxy-3-methylbutyl)-3-(3-pyridinyl)spiro[chromeno[2,3-b]pyridine-5,4'-[1,3]oxazol]-2'-amine | MW1 | 431.2 | ++++ | +++ |
| 183 | 4-((4R)-2-amino-7'-(3-pyridinyl)spiro[1,3-oxazole-4,9'-xanthen]-2'-yl)-3-butyn-1-ol | OE5 | 398.0 | ++++ | ++++ |
| 184 | (5S)-3,7-di-3-pyridinylspiro[chromeno[2,3-c]pyridine-5,4'-[1,3]oxazol]-2'-amine | WQ | 408.0 | ++++ | ++++ |
| 185a | (5R)-3-(3,3-dimethyl-1-butyn-1-yl)-7-(3-pyridinyl)spiro[chromeno[2,3-b]pyridine-5,4'-[1,3]oxazol]-2'-amine | MW2 | 411.2 | +++ | ++ |
| 185b | (5S)-3-(3,3-dimethyl-1-butyn-1-yl)-7-(3-pyridinyl)spiro[chromeno[2,3-b]pyridine-5,4'-[1,3]oxazol]-2'-amine | MW2 | 411.2 | ++++ | ++++ |
| 186 | (4R)-2'-(2,2-dimethylpropoxy)-7'-(2-pyrimidinyl)spiro[1,3-oxazole-4,9'-xanthen]-2-amine | CB1 | 417.0 | ++++ | ++++ |
| 187 | (4R)-2'-(2,2-dimethylpropoxy)-7'-(1-methyl-1H-imidazol-5-yl)spiro[1,3-oxazole-4,9'-xanthen]-2-amine | CB1 | 419.0 | ++ | ++ |
| 188 | (4R)-2'-(2,2-dimethylpropoxy)-7'-(2-methoxy-5-pyrimidinyl)spiro[1,3-oxazole-4,9'-xanthen]-2-amine | CB1 | 447.0 | +++ | ++ |
| 189 | (4R)-2'-(3,5-dimethyl-4-isoxazolyl)-7'-(2,2-dimethylpropoxy)spiro[1,3-oxazole-4,9'-xanthen]-2-amine | CB1 | 434.0 | +++ | + |
| 190 | 1-(2-((4R)-2-amino-7'-(2,2-dimethylpropoxy)spiro[1,3-oxazole-4,9'-xanthen]-2'-yl)phenyl)ethanone | CB1 | 457.0 | +++ | + |

TABLE III-continued

| Ex. No. | Compound Name | Method | Observed MS | BACE1 FRET assay (uM) | HEK cell assay (uM) |
|---|---|---|---|---|---|
| 191 | 1-(3-((4R)-2-amino-7'-(2,2-dimethylpropoxy)spiro[1,3-oxazole-4,9'-xanthen]-2'-yl)phenyl)ethanone | CB1 | 457.0 | ++++ | ++ |
| 128 | 4-((4R)-2-amino-7'-(2,2-dimethylpropoxy)spiro[1,3-oxazole-4,9'-xanthen]-2'-yl)benzonitrile | CB1 | 440.0 | ++++ | +++ |
| 192 | (4R)-2'-(2,2-dimethylpropoxy)-7'-imidazo[1,2-a]pyridin-3-ylspiro[1,3-oxazole-4,9'-xanthen]-2-amine | CB1 | 455.0 | ++ | + |
| 193 | 4-((4R)-2-amino-7'-(3-pyridinyl)spiro[1,3-oxazole-4,9'-xanthen]-2'-yl)-2-methyl-2-butanol | OE7 | 416.0 | ++++ | ++++ |
| 194 | 4-((4R)-2-amino-7'-(3-pyridinyl)spiro[1,3-oxazole-4,9'-xanthen]-2'-yl)-1-butanol | OE7 | 402.0 | ++++ | ++++ |
| 195 | (4S)-2'-(cyclobutyloxy)-7'-(3-pyridinyl)spiro[1,3-oxazole-4,9'-xanthen]-2-amine | TAD2 | 400.2 | ++++ | +++ |
| 196 | 2',7'-bis(6-fluoro-3-pyridinyl)spiro[1,3-oxazole-4,9'-xanthen]-2-amine | OE 1 | 443.0 | ++++ | +++ |
| 197 | (4S)-2'-(cyclopropylethynyl)-7'-((3-methyl-3-oxetanyl)methoxy)spiro[1,3-oxazole-4,9'-xanthen]-2-amine | B | 417.3 | ++++ | ++++ |
| 198 | (4S)-2'-bromo-7'-(2-pyridinyloxy)spiro[1,3-oxazole-4,9'-xanthen]-2-amine | MW3 | 424 | +++ | ++ |
| 199 | (4S)-2'-(cyclobutyloxy)-7'-(5-pyrimidinyl)spiro[1,3-oxazole-4,9'-xanthen]-2-amine | B | 424.0 | ++++ | +++ |
| 114 | 4,4'-((5R)-2'-aminospiro[chromeno[2,3-b]pyridine-5,4'-[1,3]oxazole]-3,7-diyl)bis(2-methyl-3-butyn-2-ol) | MW5 | 418.2 | +++ | +++ |
| 200 | 1-(((4S)-2-amino-7'-(cyclopropylethynyl)spiro[1,3-oxazole-4,9'-xanthen]-2'-yl)oxy)-2-propanone | H | 389.4 | +++ | +++ |
| 201 | (4R)-2'-(3-methoxy-3-methyl-1-butyn-1-yl)-7'-(3-pyridinyl)spiro[1,3-oxazole-4,9'-xanthen]-2-amine | OE4 | 426.0 | ++++ | ++++ |
| 112 | (4R)-2'-(3,3-dimethyl-1-butyn-1-yl)-7'-(2-pyridinyloxy)spiro[1,3-oxazole-4,9'-xanthen]-2-amine | MW3 | 426.2 | ++++ | +++ |
| 202 | (4R)-2'-(3,6-dihydro-2H-pyran-4-yl)-7'-(5-pyrimidinyl)spiro[1,3-oxazole-4,9'-xanthen]-2-amine | OE9 | 413.2 | ++++ | ++++ |
| 203 | (5S)-3,7-di-3-pyridinylspiro[chromeno[2,3-b]pyridine-5,4'-[1,3]oxazol]-2'-amine | MW4 | 408.2 | +++ | ++ |
| 113 | (5R)-3,7-di-3-pyridinylspiro[chromeno[2,3-b]pyridine-5,4'-[1,3]oxazol]-2'-amine | MW4 | 408.2 | ++++ | ++++ |
| 204 | 4-((4R)-2-amino-7'-(3-pyridinyl)spiro[1,3-oxazole-4,9'-xanthen]-2'-yl)benzonitrile | OE9 | 431.0 | ++++ | ++++ |
| 205 | (4R)-2'-(3,3-dimethylbutyl)-7'-(2-pyridinyloxy)spiro[1,3-oxazole-4,9'-xanthen]-2-amine | MW3 | 430.2 | ++++ | +++ |
| 206 | (4R)-2'-bromo-7'-(2-pyridinyloxy)spiro[1,3-oxazole-4,9'-xanthen]-2-amine | A | 424.0 | + | +++ |
| 207 | (4S)-2'-(3-pyridinyl)-7'-(2-pyridinyloxy)spiro[1,3-oxazole-4,9'-xanthen]-2-amine | D | 423.2 | +++ | +++ |
| 208a | (5S)-7-(3-methoxy-3-methyl-1-butyn-1-yl)-3-(3-pyridinyl)spiro[chromeno[2,3-b]pyridine-5,4'-[1,3]oxazol]-2'-amine | MW1 | 427.2 | +++ | +++ |
| 208b | (5R)-7-(3-methoxy-3-methyl-1-butyn-1-yl)-3-(3-pyridinyl)spiro[chromeno[2,3-b]pyridine-5,4'-[1,3]oxazol]-2'-amine | MW1 | 427.2 | ++++ | ++++ |
| 209 | (4S)-2'-(2-pyridinyloxy)-7'-(5-pyrimidinyl)spiro[1,3-oxazole-4,9'-xanthen]-2-amine | D | 424.2 | ++++ | +++ |
| 210 | 1-(((4R)-2-amino-7'-bromospiro[1,3-oxazole-4,9'-xanthen]-2'-yl)oxy)-2-methyl-2-propanol | TAD3 | 419.2 | ++ | ++ |
| 211 | (4S)-2'-(cyclopropylethynyl)-7'-(2-pyridinyloxy)spiro[1,3-oxazole-4,9'-xanthen]-2-amine | G | 410.2 | +++ | ++ |
| 129 | (4S)-2'-(2,2-dimethylpropoxy)-7'-(3-methyl-1H-pyrazol-4-yl)spiro[1,3-oxazole-4,9'-xanthen]-2-amine | CB2 | 419.0 | +++ | + |

TABLE III-continued

| Ex. No. | Compound Name | Method | Observed MS | BACE1 FRET assay (uM) | HEK cell assay (uM) |
|---|---|---|---|---|---|
| 212 | (4S)-2'-(2,2-dimethylpropoxy)-7'-(2-(2-methyl-1H-imidazol-1-yl)-1,3-thiazol-4-yl)spiro[1,3-oxazole-4,9'-xanthen]-2-amine | CB2 | 302.0 | ++ | ++ |
| 213 | (4S)-2'-(2,2-dimethylpropoxy)-7'-(1,3,5-trimethyl-1H-pyrazol-4-yl)spiro[1,3-oxazole-4,9'-xanthen]-2-amine | CB2 | 447.1 | +++ | ++ |
| 214 | (4S)-2'-(2,2-dimethylpropoxy)-7'-(2-(1H-imidazol-1-yl)-1,3-thiazol-4-yl)spiro[1,3-oxazole-4,9'-xanthen]-2-amine | CB2 | 488.0 | +++ | ++ |
| 215 | (4S)-2'-(2,2-dimethylpropoxy)-7'-(2-(1-pyrrolidinyl)-1,3-thiazol-4-yl)spiro[1,3-oxazole-4,9'-xanthen]-2-amine | CB2 | 491.0 | ++ | + |
| 216 | 5-((4S)-2-amino-7'-(2,2-dimethylpropoxy)spiro[1,3-oxazole-4,9'-xanthen]-2'-yl)-3-pyridinecarbonitrile | CB2 | 441.0 | ++++ | ++++ |
| 217 | (4S)-2'-(2,2-dimethylpropoxy)-7'-(4-methoxy-3-pyridinyl)spiro[1,3-oxazole-4,9'-xanthen]-2-amine | CB2 | 446.0 | +++ | ++ |
| 218a | (4R)-2'-(2,2-dimethylpropoxy)-7'-(1-pyrrolidinylcarbonyl)spiro[1,3-oxazole-4,9'-xanthen]-2-amine | Ex127 | 436.0 | +++ | ++ |
| 218b | (4S)-2'-(2,2-dimethylpropoxy)-7'-(1-pyrrolidinylcarbonyl)spiro[1,3-oxazole-4,9'-xanthen]-2-amine | Ex127 | 436.0 | +++ | +++ |
| 219 | (4S)-2'-(2,2-dimethylpropoxy)-7'-(2-fluoro-3-pyridinyl)spiro[1,3-oxazole-4,9'-xanthen]-2-amine | M | 434.4 | ++++ | ++++ |
| 220 | (4R)-2'-(2-methylphenyl)-7'-(5-pyrimidinyl)spiro[1,3-oxazole-4,9'-xanthen]-2-amine | OE9 | 421.0 | ++++ | +++ |
| 221 | 1-(((4S)-2-amino-7'-phenylspiro[1,3-oxazole-4,9'-xanthen]-2'-yl)oxy)-2-methyl-2-propanol | D | 417.2 | ++++ | +++ |
| 222 | 1-(((4S)-2-amino-7'-(6-fluoro-3-pyridinyl)spiro[1,3-oxazole-4,9'-xanthen]-2'-yl)oxy)-2-methyl-2-propanol | D | 436.2 | ++++ | ++++ |
| 223 | 1-(((4S)-2-amino-7'-(5-methyl-3-pyridinyl)spiro[1,3-oxazole-4,9'-xanthen]-2'-yl)oxy)-2-methyl-2-propanol | D | 432.2 | ++++ | ++++ |
| 224 | 1-(((4S)-2-amino-7'-(5-fluoro-3-pyridinyl)spiro[1,3-oxazole-4,9'-xanthen]-2'-yl)oxy)-2-methyl-2-propanol | D | 436.2 | ++++ | ++++ |
| 225 | (4S)-2'-(3-pyridinyl)-7'-(5-pyrimidinyl)spiro[1,3-oxazole-4,9'-xanthen]-2-amine | OE9 | 408.0 | ++++ | ++++ |
| 226 | (4R)-2'-(4-methylphenyl)-7'-(5-pyrimidinyl)spiro[1,3-oxazole-4,9'-xanthen]-2-amine | OE9 | 421.0 | ++++ | ++++ |
| 127 | (4R)-2'-methoxy-7'-(1-pyrrolidinylcarbonyl)spiro[1,3-oxazole-4,9'-xanthen]-2-amine | QL1 | 380.0 | + | ++ |

The following are procedures for preparing intermediates, which in turn were used to prepare additional Exemplary compounds, representative of the present invention. The procedures and Methods hereforth were used to prepare the compounds in Table IV herein.

Example 227

Method AA1

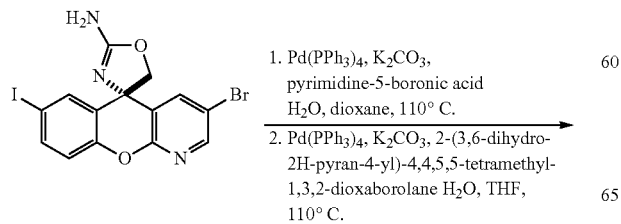

1. Pd(PPh₃)₄, K₂CO₃, pyrimidine-5-boronic acid H₂O, dioxane, 110° C.
2. Pd(PPh₃)₄, K₂CO₃, 2-(3,6-dihydro-2H-pyran-4-yl)-4,4,5,5-tetramethyl-1,3,2-dioxaborolane H₂O, THF, 110° C.

-continued

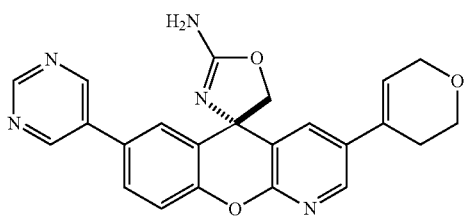

Synthesis of (S)-3-(3,6-dihydro-2H-pyran-4-yl)-7-(pyrimidin-5-yl)-5'H-spiro[chromeno[2,3-b]pyridine-5,4'-oxazol]-2'-amine Step 1:
A 10-20 mL microwave vial was charged with (S)-3-bromo-7-iodo-5'H-spiro[chromeno[2,3-b]pyridine-5,4'-oxazol]-2'-amine (503 mg, 1.098 mmol), pyrimidin-5-ylboronic acid (143 mg, 1.153 mmol), pd(ph3p)4 (127 mg, 0.110 mmol). The vial was flushed with Ar(g), then THF (5489 µL, 1.098 mmol) and potassium carbonate (1.5 M) (1464 µL, 2.195 mmol) (aq. solution) were added in sequence. The vial was sealed and heated at 110° C. for 2 hours. The mixture was diluted with water and extracted with 10% i-PrOH/EtOAc (3×). The combined organic extracts were dried over sodium sulfate, filtered, and evaporated. The residue was purified by chromatography on a 100-g SNAP column, eluting with 0-100% of a 90:10:1 mixture of DCM/MeOH/NH4OH in DCM to provide (S)-3-bromo-7-(pyrimidin-5-yl)-5'H-spiro[chromeno[2,3-b]pyridine-5,4'-oxazol]-2'-amine as an off-white solid.

Step 2:
A vial was charged with (S)-3-bromo-7-(pyrimidin-5-yl)-5'H-spiro[chromeno[2,3-b]pyridine-5,4'-oxazol]-2'-amine (68.1 mg, 0.166 mmol), 2-(3,6-dihydro-2H-pyran-4-yl)-4,4,5,5-tetramethyl-1,3,2-dioxaborolane (105 mg, 0.498 mmol), tetrakis(triphenylphosphine)palladium (19.18 mg, 0.017 mmol), THF (830 µL), and potassium carbonate (415 µL, 0.830 mmol) (as a 2.0 M aq. solution). The vial was sealed and placed in a 110° C. for 5 hours. The layers were separated, and the aqueous layer was extracted with EtOAc (2×). The combined organic extracts were dried over sodium sulfate, filtered, and evaporated. The residue was purified by chromatography on a 25-g SNAP column, eluting with 0-60% of a 90:10:1 mixture of DCM/MeOH/NH4OH in DCM to give (S)-3-(3,6-dihydro-2H-pyran-4-yl)-7-(pyrimidin-5-yl)-5'H-spiro[chromeno[2,3-b]pyridine-5,4'-oxazol]-2'-amine as a white solid Example 228

Method AA2

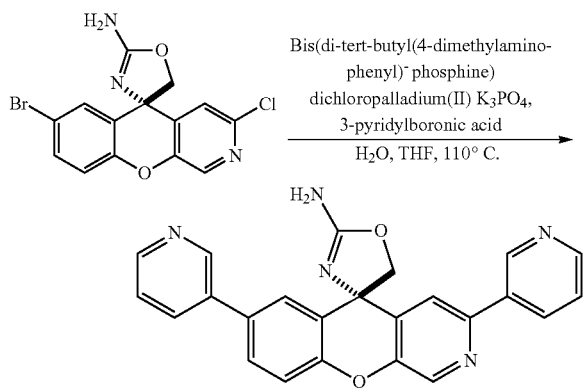

Synthesis of (S)-3,7-di(pyridin-3-yl)-5'H-spiro[chromeno[2,3-c]pyridine-5,4'-oxazol]-2'-amine A glass microwave reaction vessel was charged with (S)-7-bromo-3-chloro-5'H-spiro[chromeno[2,3-c]pyridine-5,4'-oxazol]-2'-amine (32 mg, 0.087 mmol), potassium phosphate (55.6 mg, 0.262 mmol), Amphos (1.525 mg, 2.153 µmol) and 3-pyridylboronic acid (32.2 mg, 0.262 mmol) in dioxane (0.6 mL) and water (0.200 mL). The reaction mixture was stirred and heated in a microwave at 100° C. for 30 min. The reaction mixture was diluted with water (mL) and extracted with EtOAc (2×5 mL). The organic extract was washed with saturated NH4Cl (2×5 mL) and dried over MgSO4. The solution was filtered and concentrated in vacuo to give the crude material as a yellow solid. The crude material was absorbed onto a plug of silica gel and purified by silica gel chromatography (0-10% MeOH in DCM) to provide (S)-3,7-di(pyridin-3-yl)-5'H-spiro[chromeno[2,3-c]pyridine-5,4'-oxazol]-2'-amine as white solid.

Example 229

Method AA3

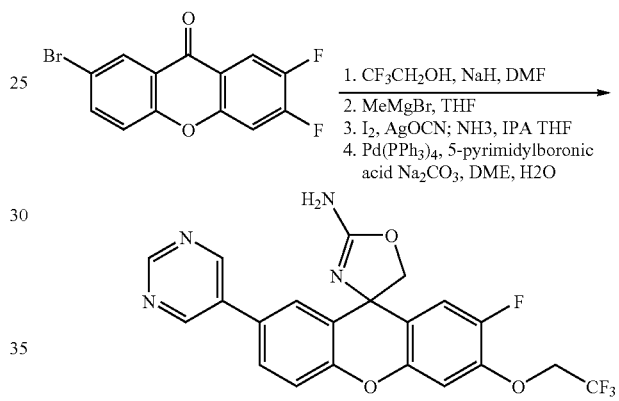

Step 1:
To a solution of 7-bromo-2,3-difluoro-9H-xanthen-9-one (3.1 g, 9.97 mmol) and 2,2,2-trifluoroethanol (1.445 mL, 19.93 mmol) in DMF (33 mL) at 0° C. was added sodium hydride (0.598 g, 14.95 mmol) slowly in portions. After addition, the mixture was stirred at RT for overnight. Then, H2O (100 mL) was added slowly and the mixture was extracted with EtOAc (1×100 mL). The organic layer was collected, dried over MgSO4, and concentrated. The residue was then washed with hexane (1×100 mL) to give 2.76 g of 7-bromo-2-fluoro-3-(2,2,2-trifluoroethoxy)-9H-xanthen-9-one as a light yellow solid. MS (ESI, positive ion) m/z: 390.9, 392.9 (M+1).

Step 2:
To a solution of 7-bromo-2-fluoro-3-(2,2,2-trifluoroethoxy)-9H-xanthen-9-one (2.00 g, 5.11 mmol) in THF (25 mL) at 0° C. was added methylmagnesium bromide 3.0 M in diethyl ether (3.41 mL, 10.23 mmol) slowly. After addition, the mixture was stirred at room temperature for overnight. Then, the mixture was cooled to 0° C. and saturated ammonium chloride (50 mL) was added slowly. The mixture was then stirred at RT for 15 min. Then, the organic layer was collected and the aqueous layer was extracted with EtOAc (1×50 mL). The combined organic extracts were dried over MgSO4, concentrated, and dried in vacuo to give 7-bromo-2-fluoro-9-methylene-3-(2,2,2-trifluoroethoxy)-9H-xanthene as a brown solid. MS (ESI, positive ion) m/z: 388.9, 390.9 (M+1).

Step 3:

To a solution of iodine (0.254 mL, 4.93 mmol) in THF (25 mL) at −20° C. was added silver cyanate (0.616 mL, 16.45 mmol). After addition, the mixture was stirred at −20° C. for 1 h. Then, a solution of 7-bromo-2-fluoro-9-methylene-3-(2,2,2-trifluoroethoxy)-9H-xanthene (1.600 g, 4.11 mmol) in THF (1.5 mL) was added and the mixture was stirred at 0° C. for 2 h. Then, the mixture was filtered through celite with the aid of THF (15 mL). Then, ammonia (6.17 mL, 12.33 mmol) (2 M in i-PrOH) was added dropwise to the filtrate. The resulting mixture was stirred at RT for overnight. Then, saturated $Na_2O_3S_2$ (5 mL) was added followed by saturated $NaHCO_3$ (5 mL). The mixture was stirred at room temperature for 5 min. The organic layer was collected, dried over $MgSO_4$, and concentrated. The residue was then mixed with silica gel and the solid mixture was purified by silica gel column chromatography using ISCO instrument (solid loading, 0%-20% MeOH/DCM) to give 7'-bromo-2'-fluoro-3'-(2,2,2-trifluoroethoxy)-5H-spiro[oxazole-4,9'-xanthen]-2-amine as a light yellow solid. MS (ESI, positive ion) m/z: 446.9, 448.9 (M+1).

Step 4:

To a solution of 7'-bromo-2'-fluoro-3'-(2,2,2-trifluoroethoxy)-5H-spiro[oxazole-4,9'-xanthen]-2-amine (0.250 g, 0.559 mmol) in 1,2-Dimethoxyethane (2.5 mL) at RT was added sodium carbonate monohydrate crystals (0.070 mL, 1.677 mmol), 5-pyrimidinylboronic acid (0.104 g, 0.839 mmol), tetrakis(triphenylphosphine)palladium (0.052 g, 0.045 mmol), and $H_2O$ (0.5 mL). The resulting mixture was then heated to 90° C. for 5 h. Then, the mixture was cooled to RT and EtOAc (5 mL) was added. The mixture was stirred at RT for 1 min. The organic layer was collected, dried over $MgSO_4$, and concentrated. The residue was then dissolved in DMSO (2 mL) and the solution mixture was then purified by preparative HPLC (0%-100% MeCN 0.1% TFA/$H_2O$ 0.1% TFA) to give a desired product in a solution of MeCN 0.1% TFA/$H_2O$ 0.1% TFA. Then, solution mixture was neutralized by saturated $NaHCO_3$ and MeCN was removed in vacuo. Then saturated $NaHCO_3$ (2 mL) was added and the mixture was extracted with EtOAc (2×15 mL). The combined organic extracts were dried over $MgSO_4$, concentrated, and dried in vacuo to give the product depicted above as a colorless solid. MS (ESI, positive ion) m/z: 447 (M+1).

Example 230

Method AA4

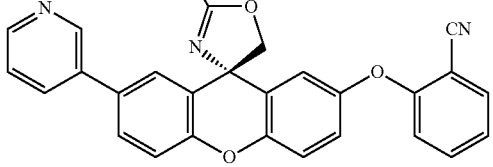

Synthesis of (S)-2-(2-amino-2'-(pyridin-3-yl)-5H-spiro[oxazole-4,9'-xanthene]-7'-yloxy)benzonitrile Step 1:

A vial was charged with (R)-2-amino-2'-bromo-5H-spiro[oxazole-4,9'-xanthen]-7'-ol (210 mg, 0.605 mmol), cesium carbonate (237 mg, 0.726 mmol), and DMF (4033 µL). The mixture was stirred for 15 min, then 2-fluorobenzonitrile (81 µL, 0.665 mmol) was added. The mixture was heated at 85° C. overnight. The reaction was diluted with water and EtOAc. The aqueous layer was extracted with EtOAc (2×). The combined organic extracts were dried over sodium sulfate, filtered, and evaporated. The residue was chromatographed on a 40-g Redi-Sep column, eluting with 0-100% of a 90:10:1 mix of DCM/MeOH/$NH_4OH$ in DCM. The product isolated this way was impure, so the material was resubjected to chromatography on a 40-g Redi-Sep column, this time eluting with 0-100% EtOAc/Hexane. This gave (R)-2-(2-amino-2'-bromo-5H-spiro[oxazole-4,9'-xanthene]-7'-yloxy)benzonitrile as 94% pure by HPLC. It was a yellow solid after evaporation from DCM/hexane.

Step 2:

A vial was charged with (R)-2-(2-amino-2'-bromo-5H-spiro[oxazole-4,9'-xanthene]-7'-yloxy)benzonitrile (75 mg, 0.167 mmol), pyridin-3-ylboronic acid (51.4 mg, 0.418 mmol), tetrakis(triphenylphosphine)palladium(0) (9.67 mg, 8.37 µmol), THF (837 µL), and potassium carbonate (418 µL, 0.837 mmol) (as a 2.0 M aq. solution). The vial was sealed and heated to 100° C. in a shaker overnight. The mixture was diluted with EtOAc and the layers were separated. The aqueous layer was extracted with EtOAc (2×). The combined organic extracts were evaporated, and the residue was chromatographed on a 25-g SNAP column, eluting with 0-80% of a 90:10:1 mix of DCM/MeOH/$NH_4OH$ in DCM to give (S)-2-(2-amino-2'-(pyridin-3-yl)-5H-spiro[oxazole-4,9'-xanthene]-7'-yloxy)benzonitrile as a pale-yellow solid.

Example 231

Method AA5

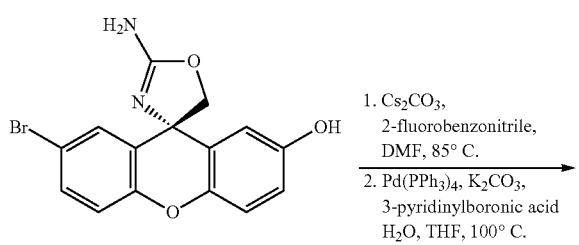

1. $Cs_2CO_3$, 2-fluorobenzonitrile, DMF, 85° C.
2. Pd(PPh3)4, $K_2CO_3$, 3-pyridinylboronic acid $H_2O$, THF, 100° C.

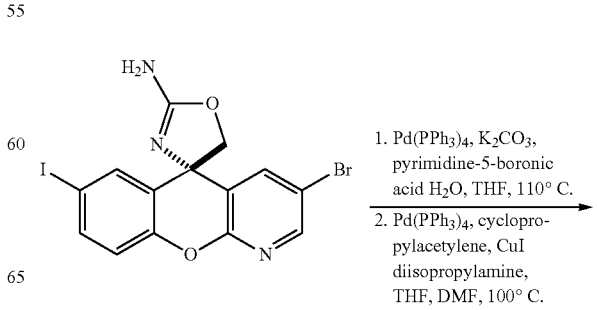

1. Pd(PPh3)4, $K_2CO_3$, pyrimidine-5-boronic acid $H_2O$, THF, 110° C.
2. Pd(PPh3)4, cyclopropylacetylene, CuI diisopropylamine, THF, DMF, 100° C.

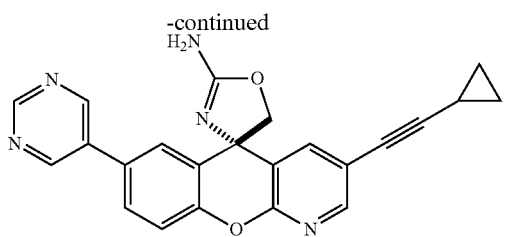

Synthesis of (S)-3-(3,3-dimethylbut-1-ynyl)-7-(pyrimidin-5-yl)-5'H-spiro[chromeno[2,3-b]pyridine-5,4'-oxazol]-2'-amine Step 1:

A sealable tube was charged with (S)-3-bromo-7-iodo-5'H-spiro[chromeno[2,3-b]pyridine-5,4'-oxazol]-2'-amine (2.000 g, 4.37 mmol), pd(ph3p)4 (0.504 g, 0.437 mmol), pyrimidin-5-ylboronic acid (0.568 g, 4.58 mmol) and THF (21.83 mL, 4.37 mmol). The mixture was flushed with Ar then a solution of potassium carbonate (1.5 M) (5.82 mL, 8.73 mmol) was added. The reaction was heated at 110° C. for 2 hours before being diluted with water 50 mL and poured into a separatory funnel containing ethyl acetate 50 mL. The layers were separated and the aqueous layer was extracted with ethyl acetate 3×100 mL. The aqeuous layer was then extracted with DCM (3×100 mL). The combined organic layers were washed with brine, dried over sodium sulfate, filtered and concentrated in vacuo to provide a brown oil that was purified by silica gel chromatography (Redi-Sep pre-packed silica gel column (80 g), 0-10% methanol in methylenechloride with 0.1% ammonium hydroxide) to provide (S)-3-bromo-7-(pyrimidin-5-yl)-5'H-spiro[chromeno[2,3-b]pyridine-5,4'-oxazol]-2'-amine as a light yellow foam.

Step 2:

Combined (S)-3-bromo-7-(pyrimidin-5-yl)-5'H-spiro[chromeno[2,3-b]pyridine-5,4'-oxazol]-2'-amine (75 mg, 0.183 mmol), tetrakis(triphenylphosphine)palladium (21.13 mg, 0.018 mmol), copper iodide (3.48 mg, 0.018 mmol), THF (366 µL, 0.183 mmol) and DMF (366 µL, 0.183 mmol) in a reaction vial. To the mixture was added diisopropyl amine (512 µL, 3.66 mmol) then ethynylcyclopropane (60.4 mg, 0.914 mmol). The reaction vial was sealed and heated at 110° C. for 1.5 hours. The reaction was allowed to cool to RT before being diluted with water (15 mL) and poured into a separatory funnel containing ethyl acetate (50 mL). The layers were separated and the aqueous layer was extracted with ethyl acetate (1×25 mL). The combined organic layers were washed with water and then brine, dried over sodium sulfate, filtered and concentrated in vacuo to provide a brown foam that was purified by silica gel chromatography (Redi-Sep pre-packed silica gel column (12 g), 0-10% methanol in methylenechloride with 0.1% ammonium hydroxide) to provide (S)-3-(3,3-dimethylbut-1-ynyl)-7-(pyrimidin-5-yl)-5'H-spiro[chromeno[2,3-b]pyridine-5,4'-oxazol]-2'-amine as an orange solid.

Example 232

Method AA6

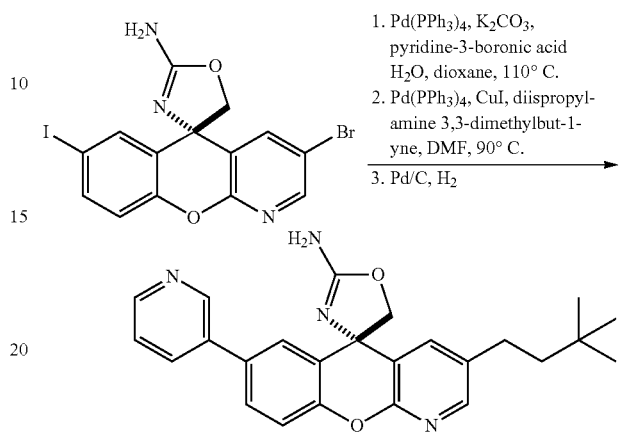

Synthesis of (S)-3-(3,3-dimethylbutyl)-7-(pyridin-3-yl)-5'H-spiro[chromeno[2,3-b]pyridine-5,4'-oxazol]-2'-amine Step 1:

A sealable tube was charged with (S)-3-bromo-7-iodo-5'H-spiro[chromeno[2,3-b]pyridine-5,4'-oxazol]-2'-amine (600 mg, 1.310 mmol), Pd(PPh$_3$)$_4$ (151 mg, 0.131 mmol), pyridin-3-ylboronic acid (161 mg, 1.310 mmol) and THF (6550 µL, 1.310 mmol). The mixture was purged with Ar for 2 minutes then a solution of potassium carbonate (1747 µL, 2.62 mmol) was added. The tube was sealed and heated at 110° C. for 2 hours.

The reaction was diluted with water 50 mL and poured into a separatory funnel containing ethyl acetate 50 mL. The layers were separated and the aqueous layer was extracted with ethyl acetate 4×50 mL. The combined organic layers were washed with brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide (S)-3-bromo-7-(pyridin-3-yl)-5'H-spiro[chromeno[2,3-b]pyridine-5,4'-oxazol]-2'-amine as a light yellow foam.

Step 2:

Combined (S)-3-bromo-7-(pyridin-3-yl)-5'H-spiro[chromeno[2,3-b]pyridine-5,4'-oxazol]-2'-amine (250 mg, 0.611 mmol), Pd(PPh$_3$)$_4$ (70.6 mg, 0.061 mmol), copper(i) iodide (23.27 mg, 0.122 mmol) and DMF (4073 µL, 0.611 mmol) in a sealable tube. Added (201 mg, 2.444 mmol) and diisopropylamine (4353 µL, 30.5 mmol), flushed with argon, sealed and heated at 90° C. overnight. The reaction was diluted with water (25 mL) and poured into a separatory funnel containing ethyl acetate (50 mL). The layers were separated and the aqueous layer was extracted with ethyl acetate (1×100 mL). The combined organic layers were washed with water, dried over sodium sulfate, filtered and concentrated in vacuo to provide a brown foam that was purified by silica gel chromatography (Redi-Sep pre-packed silica gel column (12 g), 0-10% methanol in methylenechloride with 0.1% ammonium hydroxide) to provide (S)-3-(3,3-dimethylbut-1-ynyl)-7-(pyridin-3-yl)-5'H-spiro[chromeno[2,3-b]pyridine-5,4'-oxazol]-2'-amine as a brown solid Step 3:

To a solution of (S)-3-(3,3-dimethylbut-1-ynyl)-7-(pyridin-3-yl)-5'H-spiro[chromeno[2,3-b]pyridine-5,4'-oxazol]-2'-amine (60 mg, 0.146 mmol) in 5 mL of methanol was added Pd/C (5%) (156 mg, 1.462 mmol). The mixture was maintained under an atmosphere of hydrogen gas for 20 hours before being filtered through a celite plug, washing well with methanol. The filtrate was concentrated and the derived residue was purified by silical gel chromatography (12 g, 0-10% methanol in methylenechloride with 0.1% ammonium hydroxide) to provide (S)-3-(3,3-dimethylbutyl)-7-(pyridin-3-yl)-5'H-spiro[chromeno[2,3-b]pyridine-5,4'-oxazol]-2'-amine as a white solid.

Example 233

Method AA7

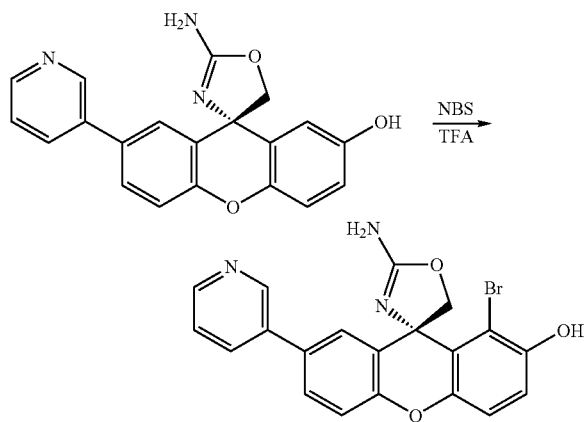

A vial was charged with (S)-2-amino-7'-(pyridin-3-yl)-5H-spiro[oxazole-4,9'-xanthen]-2'-ol (106 mg, 0.308 mmol) and TFA (1540 μL) to give an orange solution. The vial was submerged in an ice-bath for 15 min, and n-bromosuccinimide (54.8 mg, 0.308 mmol) was added in a single portion. Stirred the mixture for 1 hour, then it was diluted with methanol and evaporated under reduced pressure. The residue was dissolved in methanol and loaded onto a 2-g SCX-2 acidic column. The column was first eluted with methanol to remove impurities, then with 2 M ammonia in methanol to elute the product. The filtrate was evaporated in vacuo to give a brown oil. This oil was chromatographed on a 40-g HP (high performance) Redi-Sep column, eluting with 0-100% of a 90:10:1 mix of DCM/MeOH/DCM in DCM to provide the title compound as a yellow solid.

Example 234

Method AA8

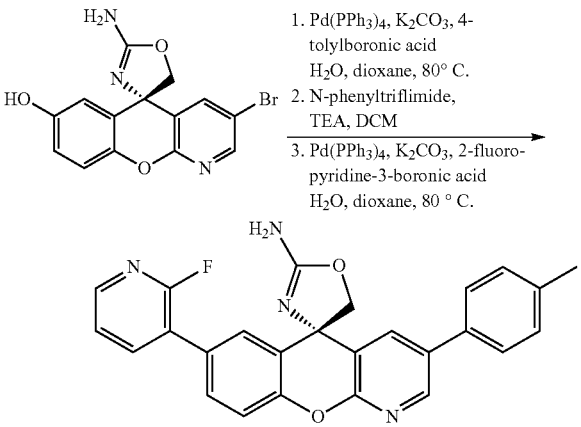

Synthesis of (S)-7-(2-fluoropyridin-3-yl)-3-p-tolyl-5'H-spiro[chromeno[2,3-b]pyridine-5,4'-oxazol]-2'-amine Step 1:

A vial was charged (S)-2'-amino-3-bromo-5'H-spiro[chromeno[2,3-b]pyridine-5,4'-oxazol]-7-ol (282 mg, 0.809 mmol), p-tolylboronic acid (220 mg, 1.618 mmol), potassium carbonate (559 mg, 4.04 mmol), Pd(PPh$_3$)$_4$ (46.7 mg, 0.040 mmol). The vial was flushed with Ar (g), then Dioxane (4044 μL) and water (2 mL) were added in sequence. The vial was sealed and placed in an 80° C. oil bath. After stirring for 50 minutes, the mixture was partitioned between brine and 10% iPrOH/EtOAc. The layers were separated, and the aq. layer was extracted with EtOAc. The combined organic extracts were dried over sodium sulfate, filtered, and evaporated. The residue was chromatographed on an 80-g Redi-Sep column, eluting with 0-80% of a 90:10:1 mix of DCM/MeOH/NH$_4$OH in DCM to give (S)-2'-amino-3-p-tolyl-5'H-spiro[chromeno[2,3-b]pyridine-5,4'-oxazol]-7-ol (259.36 mg, 0.722 mmol, 89% yield) as an orange solid.

Step 2:

A 25-mL flask was charged with (S)-2'-amino-3-p-tolyl-5'H-spiro[chromeno[2,3-b]pyridine-5,4'-oxazol]-7-ol (259.36 mg, 0.722 mmol) in DCM (7217 μL) to give an clear, orange solution. triethylamine (201 μL, 1.443 mmol) and 1,1,1-trifluoro-N-phenyl-N-(trifluoromethylsulfonyl)methanesulfonamide (271 mg, 0.758 mmol) were added in sequence. The mixture was stirred for 4 hours before being loaded directly onto a 25-g silica gel loading column with the aid of DCM. The column was eluted onto a prequilibrated 40-g Redi-Sep column with 0-5% MeOH/DCM to give (S)-2'-amino-3-p-tolyl-5'H-spiro[chromeno[2,3-b]pyridine-5,4'-oxazole]-7-yl trifluoromethanesulfonate (317.34 mg, 0.646 mmol, 89% yield) as a cream-colored solid Step 3:

A vial was charged with (S)-2'-amino-3-p-tolyl-5'H-spiro[chromeno[2,3-b]pyridine-5,4'-oxazole]-7-yl trifluoromethanesulfonate (45.0 mg, 0.092 mmol), 2-fluoropyridin- 3-ylboronic acid (38.7 mg, 0.275 mmol), potassium carbonate (229 µL, 0.458 mmol), and Pd(PPh$_3$)$_4$ (5.29 mg, 4.58 µmol). The vial was flushed with Ar (g), then dioxane (458 µL) (actual amount as 1 mL) and water (0.5 mL) were added in sequence. The vial was sealed and placed in an 80° C. oil bath for 2 hours. The mixture was diluted with EtOAc, washed with brine, dried over sodium sulfate, filtered, and evaporated. The residue was chromatographed on a 12-g Redi-Sep column with 0-5% MeOH/DCM to give (S)-7-(2-fluoropyridin-3-yl)-3-p-tolyl-5'H-spiro[chromeno[2,3-b]pyridine-5,4'-oxazol]-2'-amine (29.53 mg, 0.067 mmol, 73.6% yield) as a tan solid.

Example 235

Method AA9

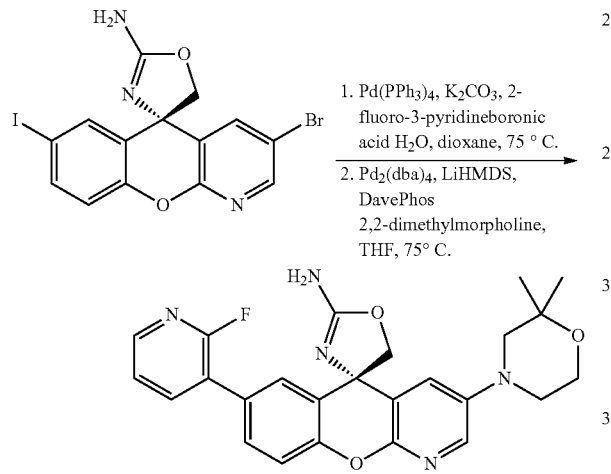

Synthesis of (S)-3-(2,2-dimethylmorpholino)-7-(2-fluoropyridin-3-yl)-5'H-spiro[chromeno[2,3-b]pyridine-5,4'-oxazol]-2'-amine Step 1:
A vial was charged with (S)-3-bromo-7-iodo-5'H-spiro[chromeno[2,3-b]pyridine-5,4'-oxazol]-2'-amine (302.9 mg, 0.661 mmol), 2-fluoro-3-pyridineboronic acid (102 mg, 0.727 mmol), potassium carbonate (457 mg, 3.31 mmol), and tetrakis(triphenylphosphine)palladium(0) (38.2 mg, 0.033 mmol). The vial was flushed with Ar (g), then dioxane (3306 µL) and water (1.7 mL) were added in sequence. The vial was sealed and placed in a 75° C. oil bath for 2 hours. The mixture was diluted with EtOAc (15 mL) and brine (15 mL). The layers were separated, and the aq. layer was extracted with EtOAc (2×15 mL). The combined organic extracts were dried over sodium sulfate, filtered, and evaporated. The residue was purified by chromatography on a 40-g Redi-Sep column, eluting with 0-60% of a 90:10:1 mix of DCM/MeOH/NH$_4$OH in DCM to give (S)-3-bromo-7-(2-fluoropyridin-3-yl)-5'H-spiro[chromeno[2,3-b]pyridine-5,4'-oxazol]-2'-amine as an off-white solid.
Step 2:
A vial was charged with (S)-3-bromo-7-(2-fluoropyridin-3-yl)-5'H-spiro[chromeno[2,3-b]pyridine-5,4'-oxazol]-2'-amine (110 mg, 0.257 mmol), DavePhos (12.16 mg, 0.031 mmol), and tris(dibenzylideneacetone)dipalladium(0) (11.79 mg, 0.013 mmol). The vessel was flushed with Ar(g), then lithium bis(trimethylsilyl)amide (772 µL, 0.772 mmol) (1.0 M solution in THF) and 2,2-dimethylmorpholine (61.8 µL, 0.515 mmol) were added in sequence. The vial was sealed and placed in a 75° C. oil bath for two hours. The mixture was diluted with saturated aq. ammonium chloride solution (20 mL) and water (10 mL). The mixture was extracted with DCM (3×20 mL), leaving behind a dark oily solid. The combined organic extracts were dried over sodium sulfate, filtered, and evaporated. The residue was chromatographed on an 24-g Redi-Sep Gold column with 0-70% of a 90:10:1 mix of DCM/MeOH/NH$_4$OH in DCM to give (S)-3-(2,2-dimethylmorpholino)-7-(2-fluoropyridin-3-yl)-5'H-spiro[chromeno[2,3-b]pyridine-5,4'-oxazol]-2'-amine as a yellow solid.

Example 236

Method AA10

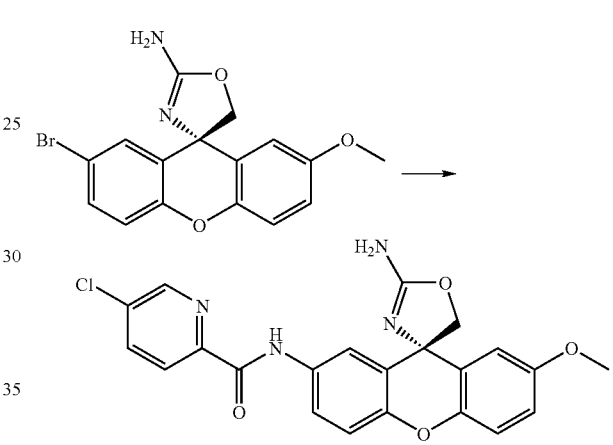

Synthesis of N-((4S)-2-amino-7'-methoxyspiro[1,3-oxazole-4,9'-xanthen]-2'-yl)-5-chloro-2-pyridinecarboxamide Step 1:
A 5 mL smith synthesizer vial was charged with (R)-2'-bromo-7'-methoxy-5H-spiro[oxazole-4,9'-xanthen]-2-amine (1.248 g, 3.46 mmol), sodium azide (0.684 g, 10.52 mmol), L-ascorbic acid sodium salt (0.057 g, 0.288 mmol), copper(I) iodide (0.131 g, 0.688 mmol), and (1R,2R)—N1,N2-dimethylcyclohexane-1,2-diamine (0.116 mL, 0.736 mmol) in EtOH (6.0 mL), water (2.6 mL) and the reaction was heated to 100° C. in the microwave for 35 minutes. The reaction vial was cooled to RT and concentrated on the rotary evaporator and the resulting residue was taken up in ethyl acetate (125 mL), water (50 mL) the organic layer was separated. The organic layer was dried over sodium sulfate and concentrated to yield the crude product which was purified by silica gel flash column chromatography (using a 40G ISCO silica gel cartridge), and eluted using hexanes/ethyl acetate gradient. The fractions were combined and concentrated to yield (S)-2'-azido-7'-methoxy-5H-spiro[oxazole-4,9'-xanthen]-2-amine as a yellowish solid. MS (ESI pos. ion) m/z: 324 (M+1).
Step 2:
A solution of (S)-2'-azido-7'-methoxy-5H-spiro[oxazole-4,9'-xanthen]-2-amine (1.162 g, 3.59 mmol) in dichloromethane (25 mL) was treated with pyridine (0.775 mL, 9.50 mmol) followed by trifluoroaceticacid anhydride (0.9 mL, 6.43 mmol) at RT. The reaction was allowed to stir for 2 hours during which formation of desired product was detected (M+H~420) along with traces of unreacted starting material. The reaction was allowed to stir for another 6 hours and diluted with DCM (75 mL), water (20 mL), and separated the organic layer. The organic layer was dried over anhydrous sodium sulfate, and concentrated to yield (S)—N-(2'-azido-7'-methoxy-5H-spiro[oxazole-4,9'-xanthene]-2-yl)-2,2,2-trifluoroacetamide as a yellowish solid. MS (ESI pos. ion) m/z: 420 (M+1).

Step 3:
A solution of (S)—N-(2'-azido-7'-methoxy-5H-spiro[oxazole-4,9'-xanthene]-2-yl)-2,2,2-trifluoroacetamide (0.410 g, 0.978 mmol) in ethanol (12 mL) and THF (8 mL) was stirred with palladium hydroxide, 20 wt % pd (dry basis) on carbon, wet, degussa type e101 ne/w (0.136 g, 0.978 mmol) under hydrogen at atmospheric pressure and RT for 2 hours. The catalyst was removed by filtration over a celite-pad, washed with ethanol (15 mL). The combined filtrates were concentrated to yield the crude product (104584-37-2). The product (S)—N-(2'-amino-7'-methoxy-5H-spiro[oxazole-4,9'-xanthene]-2-yl)-2,2,2-trifluoroacetamide was obtained as an off-white solid. MS (ESI pos. ion) m/z: 394 (M+1).

Step 4:
A 25 mL RBF containing a solution of (S)—N-(2'-amino-7'-methoxy-5H-spiro[oxazole-4,9'-xanthene]-2-yl)-2,2,2-trifluoroacetamide (0.058 g, 0.147 mmol), 5-chloropyridine-2-carboxylic acid (0.030 g, 0.190 mmol), 1-(3-dimethylaminopropyl)-3-ethylcarbodiimide hydrochloride (0.045 g, 0.235 mmol) in DCM (4 mL) and DMF (0.25 mL) was treated with 1-hydroxy-1H-benzotriazole (0.014 g, 0.104 mmol) and stirred for 1.5 hrs at RT. The reaction was diluted with DCM (50 mL) and water (15 mL). The DCM layer was separated, dried over anhydrous sodium sulfate, and concentrated to dryness to yield (S)-5-chloro-N-(2'-methoxy-2-(2,2,2-trifluoroacetamido)-5H-spiro[oxazole-4,9'-xanthene]-7'-yl)picolinamide as a brownish solid. MS (ESI pos. ion) m/z: 533 (M+1).

Step 5:
A solution of (S)-5-chloro-N-(2'-methoxy-2-(2,2,2-trifluoroacetamido)-5H-spiro[oxazole-4,9'-xanthene]-7'-yl)picolinamide (0.054 g, 0.101 mmol) in methanol (3.5 mL) was treated with potassium carbonate anhydrous (0.045 g, 0.326 mmol) and stirred at RT for 30 minutes. The catalyst was removed by filtration and the filtrate was concentrated to yield the crude product as a yellowish gummy solid. The crude product was purified by preparative HPLC [gradient 10-90% MeCN (0.1% TFA)/H$_2$O (0.1% TFA)] to give pure product which was dissolved in methanol (5 mL) and neutralized by passing the solution through a Polymer Lab-HCO$_3$ macroporous resin cartridge, and the filtrate was concentrated to give N-((4S)-2-amino-7'-methoxyspiro[1,3-oxazole-4,9'-xanthen]-2'-yl)-5-chloro-2-pyridinecarboxamide as an off-white solid. MS (ESI pos. ion) m/z: 437 (M+1).

Example 237

Method AA11

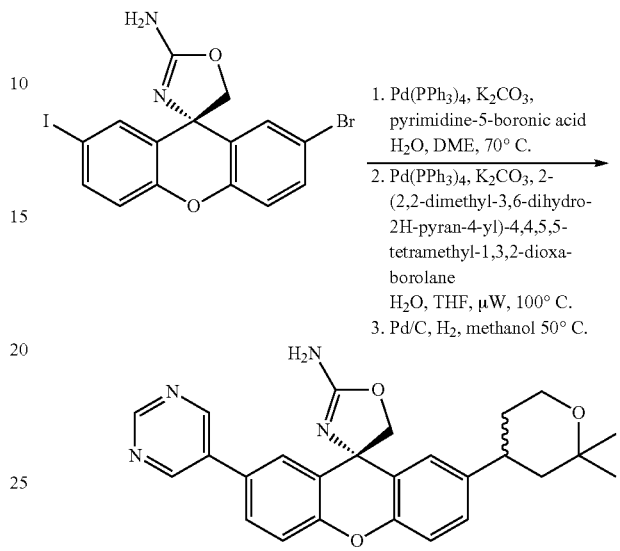

1. Pd(PPh$_3$)$_4$, K$_2$CO$_3$, pyrimidine-5-boronic acid H$_2$O, DME, 70° C.
2. Pd(PPh$_3$)$_4$, K$_2$CO$_3$, 2-(2,2-dimethyl-3,6-dihydro-2H-pyran-4-yl)-4,4,5,5-tetramethyl-1,3,2-dioxaborolane H$_2$O, THF, μW, 100° C.
3. Pd/C, H$_2$, methanol 50° C.

Synthesis of R)-2'-(2,2-dimethyltetrahydro-2H-pyran-4-yl)-7'-(pyrimidin-5-yl)-5H-spiro[oxazole-4,9'-xanthen]-2-amine Step 1:
A 100 ml RBF was charged with (R)-2'-bromo-7'-iodo-5H-spiro[oxazole-4,9'-xanthen]-2-amine (3.3 g, 7.22 mmol), pyrimidin-5-ylboronic acid (1.163 g, 9.39 mmol), and tetrakis(triphenylphosphine)palladium(0) (0.834 g, 0.722 mmol). To this were added DME (51.6 mL) followed by sodium carbonate (10.83 mL, 21.66 mmol) (2M solution) and the mixture was heated at 70° C. for 24 hrs. The mixture was diluted with water and ethyl acetate, filtered and organic layer was separated and concentrated. The crude material was purified by FC on 80 g RediSep column using 5-70% gradient of DCM/MeOH/NH4OH in DCM to give (S)-2'-bromo-7'-(pyrimidin-5-yl)-5H-spiro[oxazole-4,9'-xanthen]-2-amine).

Step 2:
A 15 ml resealable vial was charged with (S)-2'-bromo-7'-(pyrimidin-5-yl)-5H-spiro[oxazole-4,9'-xanthen]-2-amine (700 mg, 1.711 mmol), 2-(2,2-dimethyl-3,6-dihydro-2H-pyran-4-yl)-4,4,5,5-tetramethyl-1,3,2-dioxaborolane (652 mg, 2.74 mmol), 1.5:1 mixture of regioisomers of the double bond, major shown, which contains significant amount of bis-pinaclborane. Potassium carbonate (709 mg, 5.13 mmol) and AmPhos (60.6 mg, 0.086 mmol), 1,4-Dioxane (9978 μL) and Water (1425 μL) were added, the vial was sealed and heated in microwave reactor for 1 hr at 100° C. The mixture was diluted with ethyl acetate, filtered through celite and concentrated, the residue was 1 purified by flash chromatography (20-60% gradient of DCM/MeOH/NH4OH (90:10:1) in DCM) to afford a 450 mg (60% yield) of 1:1 mixture of (R)-2'-(6,6-dimethyl-3,6-dihydro-2H-pyran-4-yl)-7'-(pyrimidin-5-yl)-5H-spiro[oxazole-4,9'-xanthen]-2-amine and (R)-2'-(2,2-dimethyl-3,6-dihydro-2H-pyran-4-yl)-7'-(pyrimidin-5-yl)-5H-spiro[oxazole-4,9'-xanthen]-2-amine.

Step 3:

To a solution of (R)-2'-(2,2-dimethyl-3,6-dihydro-2H-pyran-4-yl)-7'-(pyrimidin-5-yl)-5H-spiro[oxazole-4,9'-xanthen]-2-amine (55 mg, 0.125 mmol) in MeOH (2 mL) palladium on carbon (66.4 mg, 0.062 mmol) was added and the mixture was hydrogenated at 50° C. (1 atm of hydrogen gas) for 30 min. Another 20 mg of Pd/C was added and hydrogenation was continued for 1.5 hr at 50° C. The mixture was filtered through a plug of celite and purified by silica gel chromatography (10-80% DCM/MeOH/NH4OH in DCM) to afford (R)-2'-(2,2-dimethyltetrahydro-2H-pyran-4-yl)-7'-(pyrimidin-5-yl)-5H-spiro[oxazole-4,9'-xanthen]-2-amine.

Example 238

Method AA12

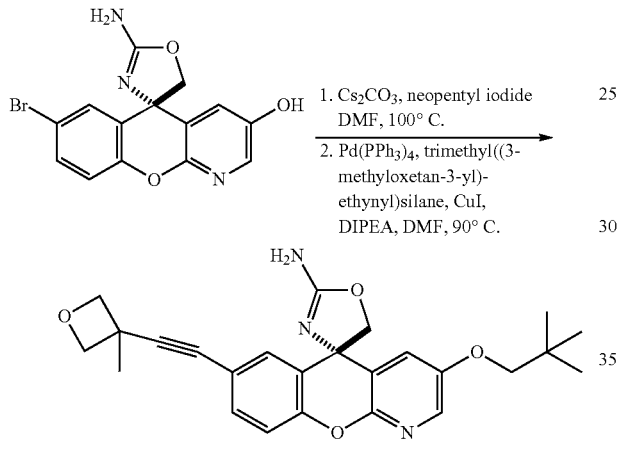

Synthesis of (S)-7-((3-methyloxetan-3-yl)ethynyl)-3-(neopentyloxy)-5'H-spiro[chromeno[2,3-b]pyridine-5,4'-oxazol]-2'-amine Step 1:

To a solution of (S)-2'-amino-7-bromo-5'H-spiro[chromeno[2,3-b]pyridine-5,4'-oxazol]-3-ol (390 mg, 1.120 mmol) in DMF (4481 µL, 1.120 mmol) in a sealed tube was added cesium carbonate (912 mg, 2.80 mmol). After stirring for 1 minute neopentyl iodide (223 µL, 1.680 mmol) was added, the reaction vessel was sealed and heated at 100° C. for 2.5 hours. Reaction was cooled to RT to prevent over alkylation. The reaction was diluted with water (25 mL) and 10 mL of ethyl acetate and stirred for 30 minutes before being poured into a separatory funnel containing ethyl acetate (100 mL) and water (250 mL). The layers were separated and the aqueous layer was extracted with ethyl acetate (3×50 mL). The aqueous layer was then extracted with DCM (3×50 mL). The organic layers were each washed with water and then brine, at which point all the organics were combined, dried over sodium sulfate, filtered and concentrated in vacuo to provide a brown foam that was purified by silica gel chromatography (Redi-Sep pre-packed silica gel column (40 g), 0-10% methanol in methylenechloride with 0.1% ammonium hydroxide) to provide (S)-7-bromo-3-(neopentyloxy)-5'H-spiro[chromeno[2,3-b]pyridine-5,4'-oxazol]-2'-amine as a yellow solid.

Step 2:

A sealable tube was charged with (S)-7-bromo-3-(neopentyloxy)-5'H-spiro[chromeno[2,3-b]pyridine-5,4'-oxazol]-2'-amine (75 mg, 0.179 mmol), copper iodide (3.38 mg, 0.018 mmol), tetrakis(triphenylphosphine)palladium (20.53 mg, 0.018 mmol). To this mixture was added DMF (355 µL, 0.178 mmol), diisopropylamine (498 µL, 3.55 mmol) and trimethyl((3-methyloxetan-3-yl)ethynyl)silane (90 mg, 0.533 mmol). The tube was flushed with argon, sealed and heated to 90° C. for 12 hours. The reaction was diluted with water (100 mL) and poured into a separatory funnel containing ethyl acetate (50 mL). The layers were separated and the aqueous layer was extracted with ethyl acetate (2×50 mL). The combined organic layers were washed with water and then brine, dried over sodium sulfate, filtered and concentrated in vacuo to provide a brown oil that was purified by silica gel chromatography (Redi-Sep pre-packed silica gel column (12 g), 0-10% methanol in methylenechloride with 0.1% ammonium hydroxide) to provide (S)-7-((3-methyloxetan-3-yl)ethynyl)-3-(neopentyloxy)-5'H-spiro[chromeno[2,3-b]pyridine-5,4'-oxazol]-2'-amine as a yellow solid.

Example 239

Method AA13

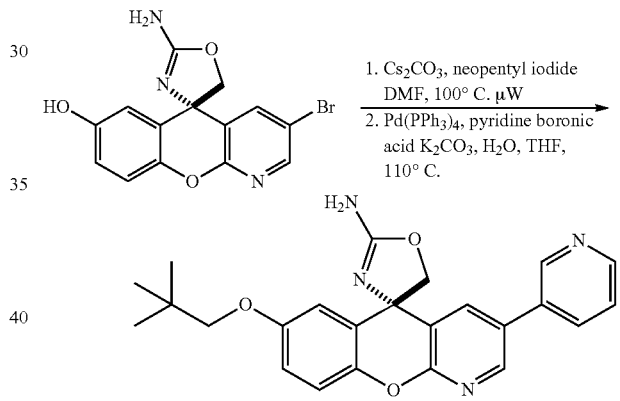

Synthesis of (R)-7-(neopentyloxy)-3-(pyridin-3-yl)-5'H-spiro[chromeno[2,3-b]pyridine-5,4'-oxazol]-2'-amine Step 1:

A 350 mL sealable flask was charged with (R)-2'-amino-3-bromo-5'H-spiro[chromeno[2,3-b]pyridine-5,4'-oxazol]-7-ol (12.10 g, 34.8 mmol) and DMF (99 mL, 34.8 mmol). To this solution was added cesium carbonate (28.3 g, 87 mmol). The resulting brown slurry was stirred at rt for 3 minutes before neopentyl iodide (9.21 mL, 69.5 mmol) was added in one portion. The reaction vessel was sealed and heated at 100° C. After heating for 4 hours another 1 mL of neopentyl iodide was added and heating at 100° C. was continued for another 1 hour at which point the reaction was allowed to cool to room temperature. The reaction was diluted with ethyl acetate (500 mL) and poured into water (2000 mL) before being transferred into a separatory funnel containing ethyl acetate (500 mL). The layers were separated and the aqueous layer was extracted with ethyl acetate (3×500 mL). The combined organic layers were washed with water and then brine. The aqeuous layer was combined with the above brined wash and was then extracted with DCM (2×500 mL). The organic layers were washed with water and then brine. All of the organigs were combined, dried over sodium sulfate, filtered and concentrated in vacuo to provide a brown foam that was purified by silica gel chromatography (Redi-Sep pre-packed silica gel column (330 g), 0-10% methanol in methylenechloride with 0.1% ammonium hydroxide) to provide (R)-3-bromo-7-(neopentyloxy)-5'H-spiro[chromeno[2,3-b]pyridine-5,4'-oxazol]-2'-amine as a light yellow solid.

Step 2:

Combined (R)-3-bromo-7-(neopentyloxy)-5'H-spiro[chromeno[2,3-b]pyridine-5,4'-oxazol]-2'-amine (9.15 g, 21.88 mmol), tetrakis(triphenylphosphine)palladium (2.53 g, 2.188 mmol) and 3-pyridylboronic acid (6.72 g, 54.7 mmol). Added THF (146 mL, 21.88 mmol) followed by potassium carbonate (1.5 M) (58.3 mL, 88 mmol). Flushed reaction tube with argon, sealed and heated at 110° C. for 2.5 hours. The reaction was allowed to cool to room temperature before being poured into a separatory funnel containing ethyl acetate (500 mL). Water (1000 mL) was added and, the layers were separated and the aqueous layer was extracted with ethyl acetate (3×500 mL). The combined organic layers were washed with brine, dried over sodium sulfate, filtered and concentrated in vacuo to provide a brown foam. This foam was purified by silica gel chromatography (Redi-Sep pre-packed silica gel column (330 g), 0-10% methanol in methylenechloride with 0.1% ammonium hydroxide) to provide (R)-7-(neopentyloxy)-3-(pyridin-3-yl)-5'H-spiro[chromeno[2,3-b]pyridine-5,4'-oxazol]-2'-amine as a light yellow solid.

Example 240

Method AA14

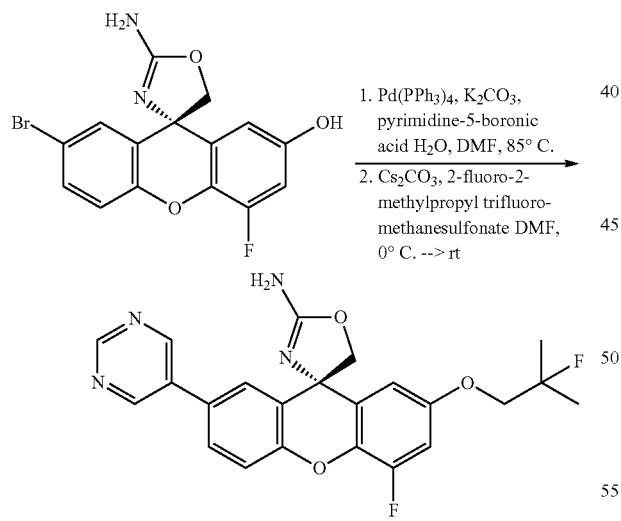

Synthesis of (S)-4'-fluoro-2'-(2-fluoro-2-methylpropoxy)-7'-(pyrimidin-5-yl)-5H-spiro[oxazole-4,9'-xanthen]-2-amine Step 1:

A 25 ml RBF was charged with (S)-2-amino-7'-bromo-4'-fluoro-5H-spiro[oxazole-4,9'-xanthen]-2'-ol (629 mg, 1.723 mmol), tetrakis(triphenylphosphine)palladium (199 mg, 0.172 mmol), and pyrimidin-5-ylboronic acid (320 mg, 2.58 mmol). DMF (8613 µL) and sodium carbonate (2M solution) (2584 µL, 5.17 mmol) were added and the mixture was stirred at 85° C. for 2.5 hrs. The mixture was cooled to RT, water (~5 ml) was added and stirring was continued for 10 min. The precipitate was filtered out, washed with water (3×5 mL), 1:1 i-PrOH/water to remove color and dried in vacuo to afford (S)-2-amino-4'-fluoro-7'-(pyrimidin-5-yl)-5H-spiro[oxazole-4,9'-xanthen]-2'-ol as yellow solid.

Step 2:

A vial was charged with (S)-2-amino-4'-fluoro-7'-(pyrimidin-5-yl)-5H-spiro[oxazole-4,9'-xanthen]-2'-ol (61.0 mg, 0.167 mmol), cesium carbonate (82 mg, 0.251 mmol), and DMF (670 µL). The resulting mixture was stirred vigorously for 10 min, then the vial was placed in large ice-bath for 10 min and 2-fluoro-2-methylpropyl trifluoromethanesulfonate (33.3 µL, 0.201 mmol) was added dropwise. The ice bath was removed after 5 minutes and the mixture was stirred at RT for 6 hours before being diluted with water (10 mL) and extracted with EtOAc (3×5 mL). The combined organic extracts were dried over sodium sulfate, filtered, and evaporated. The residue was chromatographed on a 12 g Redi-Sep column, eluting with 5-60% gradient of DCM/MeOH/NH4OH (90:10:1) in DCM to give (S)-4'-fluoro-2'-(2-fluoro-2-methylpropoxy)-7'-(pyrimidin-5-yl)-5H-spiro[oxazole-4,9'-xanthen]-2-amine as an off-white solid.

Example 241

Method AA16

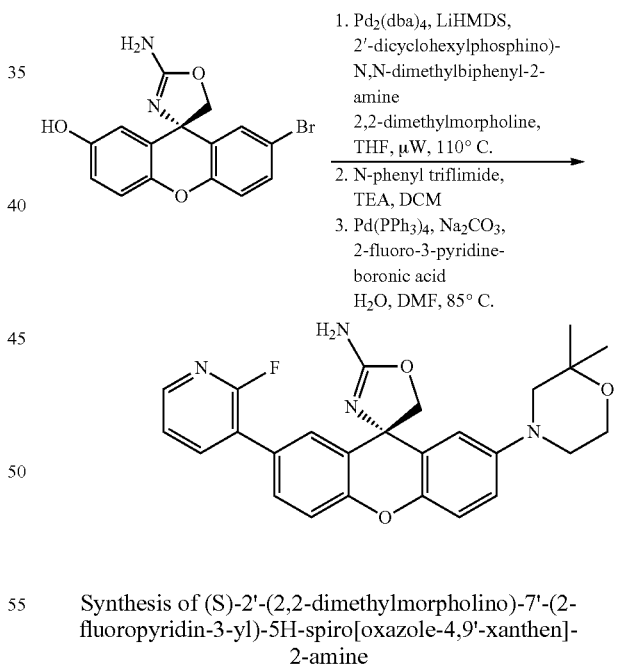

Synthesis of (S)-2'-(2,2-dimethylmorpholino)-7'-(2-fluoropyridin-3-yl)-5H-spiro[oxazole-4,9'-xanthen]-2-amine Step 1:

A 2-5 ml microwave vial was charged with (S)-2-amino-2'-bromo-5H-spiro[oxazole-4,9'-xanthen]-7'-ol (300 mg, 0.864 mmol) (104780-26-0), Pd₂dba₃ (39.6 mg, 0.043 mmol), 2'-(dicyclohexylphosphino)-N,N-dimethylbiphenyl-2-amine (40.8 mg, 0.104 mmol) and 2,2-dimethylmorpholine (299 mg, 2.59 mmol). The mixture was capped with argon and LiHMDS (1M in THF) (4321 µL, 4.32 mmol) was added and the vial was sealed and heated at 110° C. in microwave reactor for 1 hr. The reaction mixture was quenched by addition of 2 ml water and EtOAc, then saturated NH₄Cl was added. The organic layer was filtered through Celite, concentrated in vacuo and purified on a 40 g RediSep column using 15-80% DCM/MeOH/NH4OH in DCM to afford (R)-2-amino-2'-(2,2-dimethylmorpholino)-5H-spiro[oxazole-4,9'-xanthen]-7'-ol.

Step 2:

To a solution of (R)-2-amino-2'-(2,2-dimethylmorpholino)-5H-spiro[oxazole-4,9'-xanthen]-7'-ol (370 mg, 0.970 mmol) in DCM (4850 μL), were added triethylamine (270 μL, 1.940 mmol) and 1,1,1-trifluoro-N-phenyl-N-(trifluoromethylsulfonyl)methanesulfonamide (520 mg, 1.455 mmol). After stirring at room temperature for 60 hours the mixture was directly loaded onto 12 g RediSep column and purified using 15-60% DCM/MeOH/NH4OH to afford (R)-2-amino-2'-(2,2-dimethylmorpholino)-5H-spiro[oxazole-4,9'-xanthene]-7'-yl trifluoromethanesulfonate.

Step 3:

A 25 mL RB flask was charged with (R)-2-amino-2'-(2,2-dimethylmorpholino)-5H-spiro[oxazole-4,9'-xanthene]-7'-yl trifluoromethanesulfonate (270 mg, 0.526 mmol), tetrakis(triphenylphosphine)palladium(0) (60.8 mg, 0.053 mmol), 2-fluoropyridin-3-ylboronic acid (119 mg, 0.841 mmol), DMF (2629 μL) and sodium carbonate (2M solution) (789 μL, 1.577 mmol). The mixture was stirred under argon for 2 hrs at 85° C. The mixture was diluted with water (2 ml) and extracted with 10 ml of EtOAc. Organic layer was washed with water, brine, passed through plug of Celite and concentrated. The dark residue was purified by silica gel chromatography (5-70% DCM/MeOH/NH4OH in DCM) to afford (S)-2'-(2,2-dimethylmorpholino)-7'-(2-fluoropyridin-3-yl)-5H-spiro[oxazole-4,9'-xanthen]-2-amine.

Example 242

Method AA17

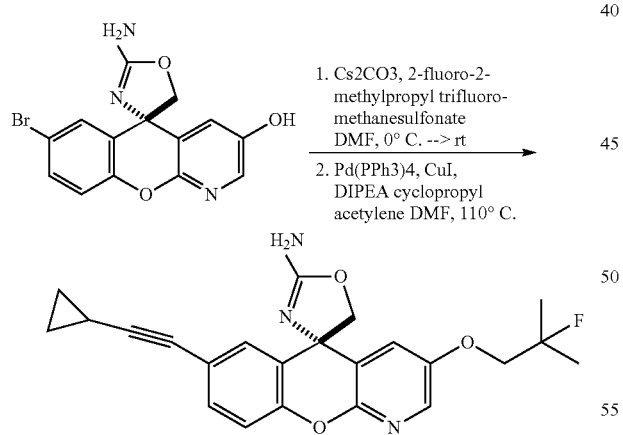

Synthesis of (S)-7-(cyclopropylethynyl)-3-(2-fluoro-2-methylpropoxy)-5'H-spiro[chromeno[2,3-b]pyridine-5,4'-oxazol]-2'-amine Step 1:

A vial was charged with (S)-2'-amino-7-bromo-5'H-spiro[chromeno[2,3-b]pyridine-5,4'-oxazol]-3-ol (750 mg, 2.154 mmol), DMF (8617 μL, 2.154 mmol) and cesium carbonate (2106 mg, 6.46 mmol). The mixture was cooled to 0° C. and 2-fluoro-2-methylpropyl trifluoromethanesulfonate (966 mg, 4.31 mmol) was added. The reaction was removed from the ice bath and stirred at RT for 45 minutes. The reaction was diluted with water (250 mL) and poured into a separatory funnel containing ethyl acetate (250 mL). The layers were separated and the aqueous layer was extracted with ethyl acetate (3×100 mL). The combined organic layers were washed with water and then brine, dried over sodium sulfate, filtered and concentrated in vacuo to provide a light yellow solid that was purified by silica gel chromatography (RediSep pre-packed silica gel column (40 g), 0-10% methanol in methylenechloride with 0.1% ammonium hydroxide) to provide (S)-7-bromo-3-(2-fluoro-2-methylpropoxy)-5'H-spiro[chromeno[2,3-b]pyridine-5,4'-oxazol]-2'-amine as a light yellow solid.

Step 2:

A sealable tube was charged with (S)-7-bromo-3-(2-fluoro-2-methylpropoxy)-5'H-spiro[chromeno[2,3-b]pyridine-5,4'-oxazol]-2'-amine (75 mg, 0.178 mmol), copper(i) iodide (3.38 mg, 0.018 mmol), tetrakis(triphenylphosphine)palladium (20.53 mg, 0.018 mmol). Added DMF (355 μL, 0.178 mmol), diisopropylamine (498 μL, 3.55 mmol) and cyclopropylacetylene (75 μL, 0.888 mmol) and the tube was flushed with argon, sealed and heated to 110° C. for 2 hours. More copper iodide (3.38 mg, 0.018 mmol), tetrakis(triphenylphosphine)palladium (20.53 mg, 0.018 mmol), diisopropylamine (498 μL, 3.55 mmol) and cyclopropylacetylene (75 μL, 0.888 mmol) were added and the black mixture was heated at 110° C. for 3 hours. The reaction was diluted with water (100 mL) and poured into a separatory funnel containing ethyl acetate (50 mL). The layers were separated and the aqueous layer was extracted with ethyl acetate (2×50 mL). The combined organic layers were washed with water and then brine, dried over sodium sulfate, filtered and concentrated in vacuo to provide a brown oil that was purified by silica gel chromatography (Redi-Sep pre-packed silica gel column (12 g), 0-10% methanol in methylenechloride with 0.1% ammonium hydroxide) to provide (S)-7-(cyclopropylethynyl)-3-(2-fluoro-2-methylpropoxy)-5'H-spiro[chromeno[2,3-b]pyridine-5,4'-oxazol]-2'-amine as a tan solid.

Example 243

Method AA18

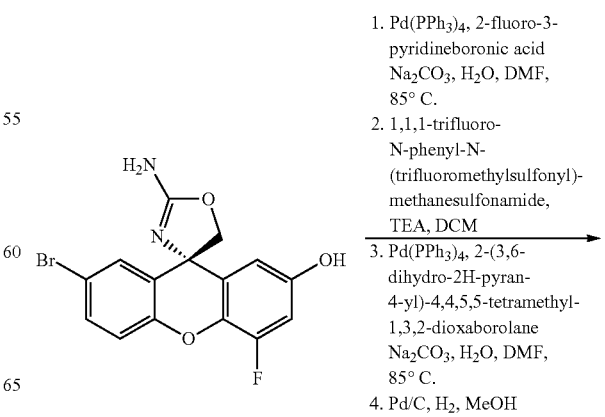

-continued

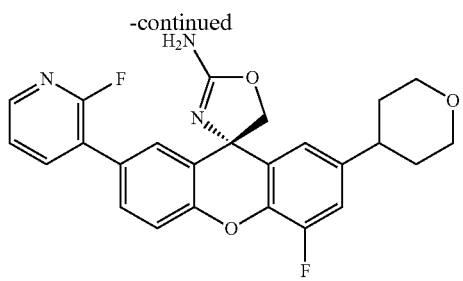

Synthesis of (S)-4'-fluoro-7'-(2-fluoropyridin-3-yl)-2'-(tetrahydro-2H-pyran-4-yl)-5H-spiro[oxazole-4,9'-xanthen]-2-amine Step 1:

A RBF was charged with sodium carbonate (2 M, 2 mL), tetrakis(triphenylphosphine)palladium (0.237 g, 0.205 mmol), (S)-2-amino-7'-bromo-4'-fluoro-5H-spiro[oxazole-4,9'-xanthen]-2'-ol (0.75 g, 2.054 mmol), and 2-fluoro-3-pyridineboronic acid (0.579 g, 4.11 mmol) and DMF (5 ml). The solution was heated at 85° C. overnight. The solution was diluted with water (25 ml) and filtered. The solids were triturated with methanol and dried under vacuum to afford (S)-2-amino-4'-fluoro-7'-(2-fluoropyridin-3-yl)-5H-spiro[oxazole-4,9'-xanthen]-2'-ol as a tan solid.

Step 2:

A flask was charged with (S)-2-amino-4'-fluoro-7'-(2-fluoropyridin-3-yl)-5H-spiro[oxazole-4,9'-xanthen]-2'-ol (300 mg, 0.787 mmol), TEA (0.219 ml, 1.573 mmol), DCM (5 mL) and 1,1,1-trifluoro-N-phenyl-N-(trifluoromethylsulfonyl)methanesulfonamide (337 mg, 0.944 mmol). The solution was stirred at RT overnight. The solution was loaded directly on a silica column. The product was purified via silica gel column chromatography (RediSep 12 g column) using 5-25% 90/10/1 (DCM/MeOH/ammonia) in DCM to afford (S)-2-amino-5'-fluoro-2'-(2-fluoropyridin-3-yl)-5H-spiro[oxazole-4,9'-xanthene]-7'-yl trifluoromethanesulfonate as a yellow solid.

Step 3:

A flask was charged with tetrakis(triphenylphosphine)palladium (29.3 mg, 0.025 mmol), 2-(3,6-dihydro-2H-pyran-4-yl)-4,4,5,5-tetramethyl-1,3,2-dioxaborolane (106 mg, 0.506 mmol), (S)-2-amino-5'-fluoro-2'-(2-fluoropyridin-3-yl)-5H-spiro[oxazole-4,9'-xanthene]-7'-yl trifluoromethanesulfonate (130 mg, 0.253 mmol), sodium carbonate (saturated) (0.253 mL, 1.266 mmol) and DMF (2 ml). The solution was heated at 85° C. for 18 hours. The product was purified via Gilson HPLC (gradient elution 20-90% MeCN/H₂O, 0.1% TFA) to afford (S)-2'-(3,6-dihydro-2H-pyran-4-yl)-4'-fluoro-7'-(2-fluoropyridin-3-yl)-5H-spiro[oxazole-4,9'-xanthen]-2-amine.

Step 4:

(S)-2'-(3,6-dihydro-2H-pyran-4-yl)-4'-fluoro-7'-(2-fluoropyridin-3-yl)-5H-spiro[oxazole-4,9'-xanthen]-2-amine (30 mg, 0.067 mmol) and palladium on carbon (7.14 mg, 0.067 mmol) were combined in 10 ml of MeOH and stirred under an atmosphere of hydrogen overnight. The solution was filtered and concentrated to afford (S)-4'-fluoro-7'-(2-fluoropyridin-3-yl)-2'-(tetrahydro-2H-pyran-4-yl)-5H-spiro[oxazole-4,9'-xanthen]-2-amine as a white solid.

Example 244

Method AA19

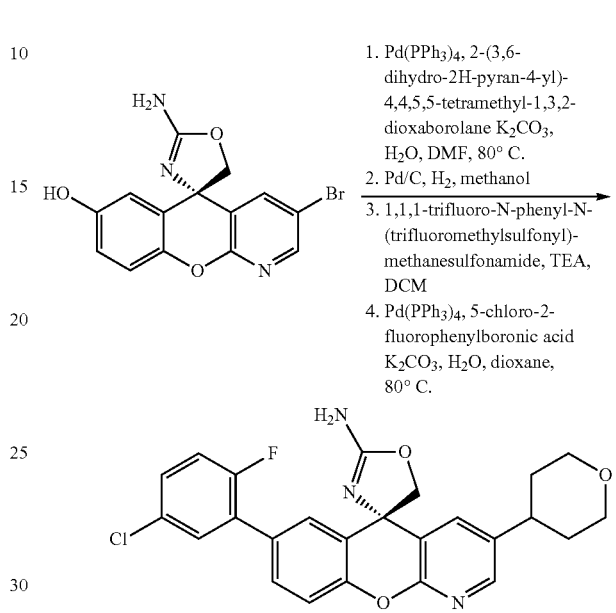

Synthesis of (S)-7-(5-chloro-2-fluorophenyl)-3-(tetrahydro-2H-pyran-4-yl)-5'H-spiro[chromeno[2,3-b]pyridine-5,4'-oxazol]-2'-amine Step 1:

A vial was charged with (S)-2'-amino-3-bromo-5'H-spiro[chromeno[2,3-b]pyridine-5,4'-oxazol]-7-ol (380 mg, 1.091 mmol), potassium carbonate (754 mg, 5.46 mmol), 2-(3,6-dihydro-2H-pyran-4-yl)-4,4,5,5-tetramethyl-1,3,2-dioxaborolane (688 mg, 3.27 mmol), pd(ph3p)4 (126 mg, 0.109 mmol), DMF (5457 μL), and water (2.5 mL). The vial was sealed, placed in 80° C. and heated overnight. The mixture was diluted with water (35 mL) and extracted with EtOAc (3×15 mL). The combined organic extract was dried over sodium sulfate, filtered, and evaporated. The residue was purified by chromatography on a 80-g Redi-Sep column, eluting with 0-100% of a 90:10:1 mix of DCM/MeOH/NH₄OH in DCM to give (S)-2'-amino-3-(3,6-dihydro-2H-pyran-4-yl)-5'H-spiro[chromeno[2,3-b]pyridine-5,4'-oxazol]-7-ol as an orange solid.

Step 2:

A 25-mL flask was charged with (S)-2'-amino-3-(3,6-dihydro-2H-pyran-4-yl)-5'H-spiro[chromeno[2,3-b]pyridine-5,4'-oxazol]-7-ol (211 mg, 0.601 mmol) and MeOH (7507 μL). The mixture was sonicated for 1 min to give an opaque mixture. Palladium on carbon (63.9 mg, 0.060 mmol) was added, and H₂ (g) was bubbled through the mixture for 1 min. The mixture was stirred further under a balloon of H₂ (g) for 60 hours. The mixture was filtered through celite with the aid of methanol. The filtrate was evaporated, and the residue was chromatographed on a 40-g Redi-Sep column with 0-100% of a 90:10:1 mix of DCM/MeOH/NH₄OH to give (S)-2'-amino-3-(tetrahydro-2H-pyran-4-yl)-5'H-spiro[chromeno[2,3-b]pyridine-5,4'-oxazol]-7-ol as an off-white solid.

Step 3:

A 25-mL RBF was charged with [Reactants] and triethylamine (194 μL, 1.392 mmol) in DCM (2.5 mL) to give an opaque mixture. n-phenyltrifluoromethanesulfonimide (261 mg, 0.731 mmol) was added, and the mixture was stirred for 2 hours before an additional portion of triflimide (50 mg) was added. After an additional 2 hours the mixture was diluted with DCM (20 mL) and saturated aq. sodium bicarbonate solution (20 mL). The layers were separated, and the aq. layer was extracted with DCM (2×10 mL). The combined organic extracts were dried over sodium sulfate, filtered, and evaporated. The residue was chromatographed on a 40-g Redi-Sep column with 0-70% MeOH/DCM to give (S)-2'-amino-3-(tetrahydro-2H-pyran-4-yl)-5'H-spiro[chromeno[2,3-b]pyridine-5,4'-oxazole]-7-yl trifluoromethanesulfonate as a white solid.

Step 4:

A vial was charged with (S)-2'-amino-3-(tetrahydro-2H-pyran-4-yl)-5'H-spiro[chromeno[2,3-b]pyridine-5,4'-oxazole]-7-yl trifluoromethanesulfonate (70.0 mg, 0.144 mmol), 5-chloro-2-fluorophenylboronic acid (75 mg, 0.433 mmol), potassium carbonate (100 mg, 0.721 mmol), and Pd(PPh$_3$)$_4$ (8.33 mg, 7.21 μmol). The vial was flushed with Ar (g), then Dioxane (721 μL) and water (0.3 mL) were added in sequence. The vial was sealed and placed in an 80° C. for 1.5 hours. The mixture was diluted with brine (20 mL) and extracted with EtOAc (2×15 mL). The combined organic extracts were dried over sodium sulfate, filtered, and evaporated. The residue was chromatographed on a 24-g Redi-Sep Gold column with 0-60% of a 90:10:1 mix of DCM/MeOH/NH$_4$OH in DCM to give (S)-7-(5-chloro-2-fluorophenyl)-3-(tetrahydro-2H-pyran-4-yl)-5'H-spiro[chromeno[2,3-b]pyridine-5,4'-oxazol]-2'-amine.

Example 245

Method AA20

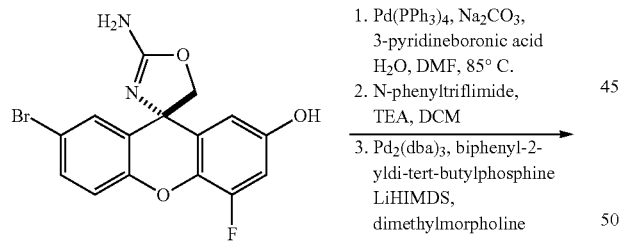

1. Pd(PPh$_3$)$_4$, Na$_2$CO$_3$, 3-pyridineboronic acid H$_2$O, DMF, 85° C.
2. N-phenyltriflimide, TEA, DCM
3. Pd$_2$(dba)$_3$, biphenyl-2-yldi-tert-butylphosphine LiHIMDS, dimethylmorpholine Synthesis of (S)-2'-(2,2-dimethylmorpholino)-4'-fluoro-7'-(pyridin-3-yl)-5H-spiro[oxazole-4,9'-xanthen]-2-amine 2,2,2-trifluoroacetate Step 1:

A 25 ml RB flask was charged with (S)-2-amino-7'-bromo-4'-fluoro-5H-spiro[oxazole-4,9'-xanthen]-2'-ol (629 mg, 1.723 mmol), tetrakis(triphenylphosphine)palladium(0) (199 mg, 0.172 mmol), and pyrimidin-5-ylboronic acid (320 mg, 2.58 mmol). DMF (8613 μL) and sodium carbonate (2 M solution) (2584 μL, 5.17 mmol) were added and the mixture was stirred at 85° C. for 2.5 hrs The mixture was cooled to room temperature, water (~5 ml) was added and stirring was continued for 10 min. The precipitate was filtered out, washed with water (3×5 mL), 1:1 i-PrOH/water to remove color and dried in vacuo to afford (S)-2-amino-4'-fluoro-7'-(pyrimidin-5-yl)-5H-spiro[oxazole-4,9'-xanthen]-2'-ol as yellow solid.

Step 2:

To a solution of (S)-2-amino-4'-fluoro-7'-(pyrimidin-5-yl)-5H-spiro[oxazole-4,9'-xanthen]-2'-ol (374 mg, 1.027 mmol) in DCM (5133 μL), triethylamine (286 μL, 2.053 mmol) and 1,1,1-trifluoro-N-phenyl-N-(trifluoromethylsulfonyl)methanesulfonamide (550 mg, 1.540 mmol) were added and the mixture was stirred overnight at room temperature. Additional N-phenyltriflimide (100 mg) and TEA (0.1 ml) were and the stirring continued for 4 hrs. The mixture was directly loaded onto 12 g RediSep column and purified using 15-60% DCM/MeOH/NH4OH to afford (S)-2-amino-5'-fluoro-2'-(pyrimidin-5-yl)-5H-spiro[oxazole-4,9'-xanthene]-7'-yl trifluoromethanesulfonate.

Step 3:

0.5-2 ml microwave vial was charged with, Pd$_2$dba$_3$ (7.39 mg, 8.07 μmol), biphenyl-2-yldi-tert-butylphosphine (5.78 mg, 0.019 mmol) and. The solids were capped with argon and 2,2-dimethylmorpholine (55.8 mg, 0.484 mmol) and LiHMDS (1 M in THF) (0.646 mL, 0.646 mmol) were added and the vial sealed and heated at 110° C. in microwave reactor for 1 hr. The mixture was quenched with 1 ml of water, diluted with EtOAc and saturated NH$_4$Cl. The organic layer was filtered through Celite and concentrated. The residue was purified by Prep HPLC (Gilson, 15-90% MeCN in 0.1% aq. TFA) to afford (S)-2'-(2,2-dimethylmorpholino)-4'-fluoro-7'-(pyridin-3-yl)-5H-spiro[oxazole-4,9'-xanthen]-2-amine 2,2,2-trifluoroacetate.

Example 246

Method AA21

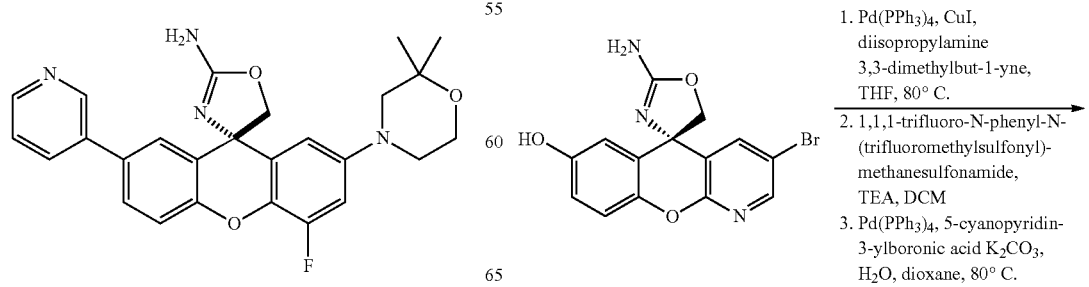

1. Pd(PPh$_3$)$_4$, CuI, diisopropylamine 3,3-dimethylbut-1-yne, THF, 80° C.
2. 1,1,1-trifluoro-N-phenyl-N-(trifluoromethylsulfonyl)-methanesulfonamide, TEA, DCM
3. Pd(PPh$_3$)$_4$, 5-cyanopyridin-3-ylboronic acid K$_2$CO$_3$, H$_2$O, dioxane, 80° C.

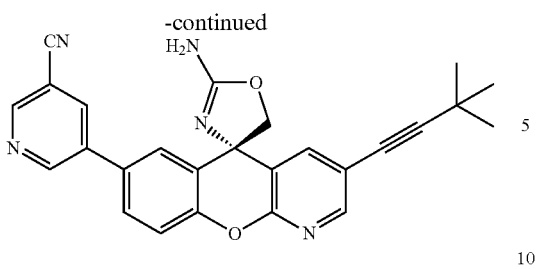

Synthesis of (S)-5-(2'-amino-3-(3,3-dimethylbut-1-ynyl)-5'H-spiro[chromeno[2,3-b]pyridine-5,4'-oxazole]-7-yl)nicotinonitrile Step 1:

A vial charged with (S)-2'-amino-3-bromo-5'H-spiro[chromeno[2,3-b]pyridine-5,4'-oxazol]-7-ol (0.250 g, 0.718 mmol), Pd(PPh₃)₄ (0.083 g, 0.072 mmol), and copper(i) iodide (0.014 g, 0.072 mmol), was treated with 1 mL THF followed by diisopropylamine (1.535 mL, 10.77 mmol). The solution was degassed with argon and 3,3-dimethylbut-1-yne (0.295 g, 3.59 mmol) was added and the vial heated to 80° C. overnight. The reaction mixture was purified directly by column chromatography yielding (S)-2'-amino-3-(3,3-dimethylbut-1-ynyl)-5'H-spiro[chromeno[2,3-b]pyridine-5,4'-oxazol]-7-ol.

Step 2:

A vial charged with (S)-2'-amino-3-(3,3-dimethylbut-1-ynyl)-5'H-spiro[chromeno[2,3-b]pyridine-5,4'-oxazol]-7-ol (0.200 g, 0.572 mmol) and potassium carbonate (0.087 g, 0.630 mmol) was treated with 2 mL DMF and was allowed to stir for 15 minutes. The reaction mixture was cooled to 0° C. and n-phenyltriflamide (0.245 g, 0.630 mmol) was added. After stirring for one hour the reaction mixture was poured into water and extracted with EtOAc. The organics were dried over MgSO4 and concentrated. Purification of the crude residue by column chromatography gave (S)-2'-amino-3-(3,3-dimethylbut-1-ynyl)-5'H-spiro[chromeno[2,3-b]pyridine-5,4'-oxazole]-7-yl trifluoromethanesulfonate (0.183 g, 0.380 mmol, 66.4% yield)

Step 3:

A vial charged with 5-cyanopyridin-3-ylboronic acid (0.030 g, 0.206 mmol), palladiumtetrakis (10.80 mg, 9.35 μmol), potassium carbonate (0.129 g, 0.935 mmol), and (S)-2'-amino-3-(3,3-dimethylbut-1-ynyl)-5'H-spiro[chromeno[2,3-b]pyridine-5,4'-oxazole]-7-yl trifluoromethanesulfonate (0.090 g, 0.187 mmol) was treated with 1 mL of dioxane followed by 0.4 mL water. The vial was flushed with argon and was heated to 80° C. for 4 hours. The reaction mixture was diluted with EtOAc and dried over MgSO₄. The organics were then concentrated, and the crude residue was purified by column chromatography yielding (S)-5-(2'-amino-3-(3,3-dimethylbut-1-ynyl)-5'H-spiro[chromeno[2,3-b]pyridine-5,4'-oxazole]-7-yl)nicotinonitrile.

Example 247

Method AA22

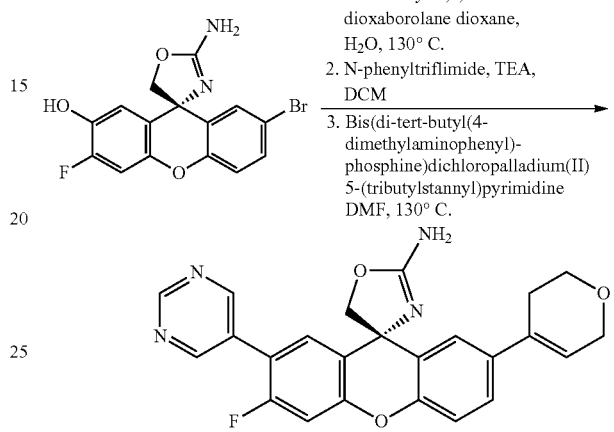

Synthesis of (R)-7'-(3,6-dihydro-2H-pyran-4-yl)-3'-fluoro-2'-(pyrimidin-5-yl)-5H-spiro[oxazole-4,9'-xanthen]-2-amine Step 1:

A mixture of 2-(3,6-dihydro-2H-pyran-4-yl)-4,4,5,5-tetramethyl-1,3,2-dioxaborolane (276 mg, 1.315 mmol), (S)-2-amino-7'-bromo-3'-fluoro-5H-spiro[oxazole-4,9'-xanthen]-2'-ol (300 mg, 0.822 mmol), potassium phosphate (523 mg, 2.465 mmol) and Cl₂Pdbis(di-tert-butyl(phenyl)phosphine) (15.28 mg, 0.025 mmol) in 3 ml of dioxane/water=2:1 was heated at 110° C. microwave for 30 min. The reaction mixture was purified by silica gel chromatography (DCM to DCM/MeOH=100:1 to 100:6) to give (R)-2-amino-7'-(3,6-dihydro-2H-pyran-4-yl)-3'-fluoro-5H-spiro[oxazole-4,9'-xanthen]-2'-ol as a white solid.

Step 2:

To a suspension of (R)-2-amino-7'-(3,6-dihydro-2H-pyran-4-yl)-3'-fluoro-5H-spiro[oxazole-4,9'-xanthen]-2'-ol (150 mg, 0.407 mmol) and n-phenyltrifluoromethanesulfonimide (218 mg, 0.611 mmol) in 15 mL of dry DCM was added TEA (142 μL, 1.018 mmol). After stirring at RT overnight the solution was evaporated to dryness and the residue was purified by silica gel chromatography (DCM to DCM/EA=4:1 to 3:1 to 2:1 to 1:1) to give (R)-2-amino-2'-(3,6-dihydro-2H-pyran-4-yl)-6'-fluoro-5H-spiro[oxazole-4,9'-xanthene]-7'-yl trifluoromethanesulfonate as a white solid.

Step 3:

A mixture of 5-(tributylstannyl)pyrimidine (73.8 mg, 0.200 mmol), AmPhos (4.24 mg, 5.99 μmol) and (R)-2-amino-2'-(3,6-dihydro-2H-pyran-4-yl)-6'-fluoro-5H-spiro[oxazole-4,9'-xanthene]-7'-yl trifluoromethanesulfonate (50 mg, 0.100 mmol) in 0.3 mL of DMF was heated at 130° C. for 1 hour. After cooling and evaporation of the solvent under high vacuum, the mixture was purified by silica gel chromatography (DCM to DCM/EA=1:1 to 1:2 to pure EA to EA/MeOH=100:5 to 100:10) to provide (R)-7'-(3,6-dihydro-2H-pyran-4-yl)-3'-fluoro-2'-(pyrimidin-5-yl)-5H-spiro[oxazole-4,9'-xanthen]-2-amine as an off-white solid.

Example 248

Method AA23

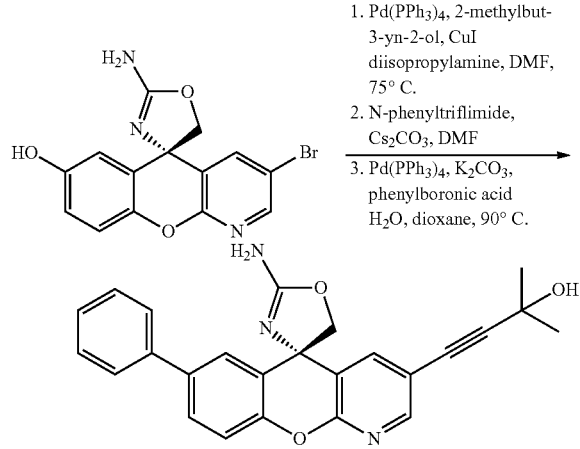

Synthesis of (S)-4-(2'-amino-7-phenyl-5'H-spiro[chromeno[2,3-b]pyridine-5,4'-oxazole]-3-yl)-2-methylbut-3-yn-2-ol Step 1:
A 25-mL flask was charged with (S)-2'-amino-3-bromo-5'H-spiro[chromeno[2,3-b]pyridine-5,4'-oxazol]-7-ol (1.012 g, 2.91 mmol), copper(i) iodide (0.055 g, 0.291 mmol), and tetrakis(triphenylphosphine)palladium (0.034 g, 0.029 mmol). The vial was flushed with Ar(g), then a septum was attached. DMF (5.81 mL), diisopropylamine (6.11 mL, 43.6 mmol), and 2-methylbut-3-yn-2-ol (1.137 mL, 11.63 mmol) were added in sequence to give a clear, brown solution. A reflux condenser was attached, and the flask was placed in a 75° C. oil bath for 4 hours. The mixture was diluted with water (35 mL) and extracted with DCM (4×20 mL). The combined organic extracts were dried over sodium sulfate, filtered, and evaporated. The residue, which contained a considerable amount of DMF, was loaded onto a 10-g SCX-2 column with the aid of methanol. The column was eluted with methanol to remove impurities, then with 2M ammonia in methanol to elute the product. The filtrate was evaporated, and the residue was chromatographed on an 80-g Redi-Sep column, eluting with 0-10% MeOH/DCM to give (S)-2'-amino-3-(3-hydroxy-3-methylbut-1-ynyl)-5'H-spiro[chromeno[2,3-b]pyridine-5,4'-oxazol]-7-ol.
Step 2:
A 10-mL pear flask was charged with (S)-2'-amino-3-(3-hydroxy-3-methylbut-1-ynyl)-5'H-spiro[chromeno[2,3-b]pyridine-5,4'-oxazol]-7-ol (111 mg, 0.316 mmol), cesium carbonate (113 mg, 0.348 mmol), and DMF (1580 µL). The resulting mixture was stirred for 5 min, then placed in an ice-bath for 5 min. 1,1,1-trifluoro-N-phenyl-N-(trifluoromethylsulfonyl)methanesulfonamide (124 mg, 0.348 mmol) was added, the ice-bath was removed and stirring was continued for 1 hour. The mixture was partitioned between water (15 mL) and EtOAc (15 mL), with a small amount of brine to break up an emulsion. The layers were separated, and the aqueous layer was extracted with EtOAc (15 mL). The combined organic extracts were dried over sodium sulfate, filtered, and evaporated. The residue was chromatographed on a 12-g Redi-Sep column eluting with 0-6% MeOH/DCM to give (S)-2'-amino-3-(3-hydroxy-3-methylbut-1-ynyl)-5'H-spiro[chromeno[2,3-b]pyridine-5,4'-oxazole]-7-yl trifluoromethanesulfonate as a feathery-white solid.
Step 3:
A 0.5-2 mL vial was charged with (S)-2'-amino-3-(3-hydroxy-3-methylbut-1-ynyl)-5'H-spiro[chromeno[2,3-b]pyridine-5,4'-oxazole]-7-yl trifluoromethanesulfonate (72.4 mg, 0.150 mmol), phenylboronic acid (54.8 mg, 0.449 mmol), potassium carbonate (103 mg, 0.748 mmol), and tetrakis(triphenylphosphine)palladium (8.64 mg, 7.48 µmol). The vial was purged with Ar(g), then Dioxane (748 µL) and water (0.37 mL) were added in sequence. The vial was sealed and placed in a 90° C. oil bath for 1 hour. The mixture was diluted with water (15 mL), and extracted with EtOAc (3×10 mL). The combined organic extracts were dried over sodium sulfate, filtered, and evaporated. The residue was chromatographed on a 40-g Redi-Sep column eluting with 0-6% MeOH/DCM to give (S)-4-(2'-amino-7-phenyl-5'H-spiro[chromeno[2,3-b]pyridine-5,4'-oxazole]-3-yl)-2-methylbut-3-yn-2-ol as a slightly tan solid Example 249

Method AA24

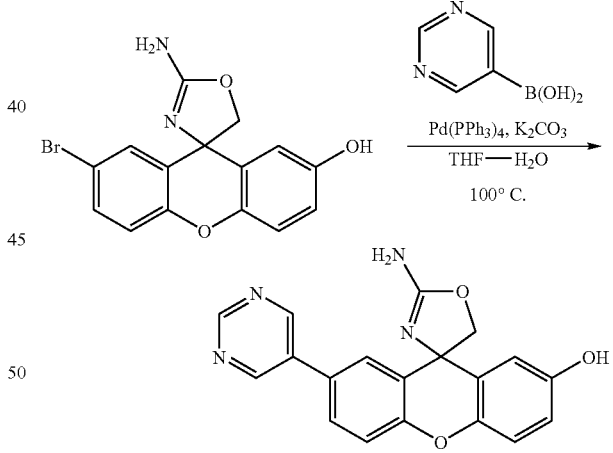

A 150-mL pressure vessel was charged with 2'-bromo-7'-hydroxyspiro[1,3-oxazole-4,9'-xanthen]-2-amine (845 mg, 2434 µmol) in THF (24 mL), pyrimidin-5-ylboronic acid (754 mg, 6085 µmol), tetrakis(triphenylphosphine)palladium(0) (281 mg, 243 µmol), and potassium carbonate (10.1 mL of a 1.2 M aqueous solution, 12.1 mmol). The vessel was sealed and placed in a 100° C. oil bath at for 4 h. The reaction mixture was cooled to RT and partitioned between EtOAc (50 mL) and water (50 mL). The aqueous layer was extracted with EtOAc (50 mL), and the combined organic extracts were dried over sodium sulfate, filtered, and evaporated. The crude material was purified by chromatography on silica gel (eluting with 30-100% of a 90:10:1 DCM/MeOH/NH4OH solution in DCM) to give 2'-hydroxy-7'-(5-pyrimidinyl)spiro[1,3-oxazole-4,9'-xanthen]-2-amine as an off-white solid.

Example 250

Method AA25

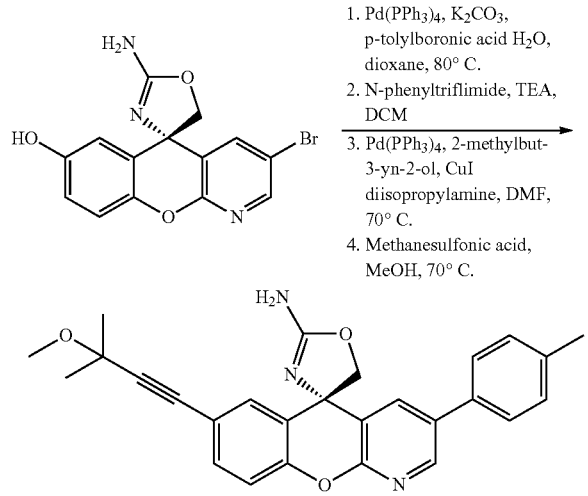

Synthesis of (S)-7-(3-methoxy-3-methylbut-1-ynyl)-3-p-tolyl-5'H-spiro[chromeno[2,3-b]pyridine-5,4'-oxazol]-2'-amine Step 1:

A vial was charged (S)-2'-amino-3-bromo-5'H-spiro[chromeno[2,3-b]pyridine-5,4'-oxazol]-7-ol (282 mg, 0.809 mmol), p-tolylboronic acid (220 mg, 1.618 mmol), potassium carbonate (559 mg, 4.04 mmol), tetrakis(triphenylphosphine)palladium (46.7 mg, 0.040 mmol). The vial was flushed with Ar (g), then Dioxane (4044 µL) and water (2 mL) were added in sequence. The vial was sealed and placed in an 80° C. oil bath for 1 hour. The mixture was partitioned between brine and 10% iPrOH/EtOAc. The layers were separated, and the aq. layer was extracted with EtOAc. The combined organic extracts were dried over sodium sulfate, filtered, and evaporated. The residue was chromatographed on an 80-g Redi-Sep column, eluting with 0-80% of a 90:10:1 mix of DCM/MeOH/NH$_4$OH in DCM to give (S)-2'-amino-3-p-tolyl-5'H-spiro[chromeno[2,3-b]pyridine-5,4'-oxazol]-7-ol as an orange solid.

Step 2:

A 25-mL flask was charged with (S)-2'-amino-3-p-tolyl-5'H-spiro[chromeno[2,3-b]pyridine-5,4'-oxazol]-7-ol (259.36 mg, 0.722 mmol) in DCM (7217 µL) to give an clear, orange solution. triethylamine (201 µL, 1.443 mmol) and 1,1,1-trifluoro-N-phenyl-N-(trifluoromethylsulfonyl)methanesulfonamide (271 mg, 0.758 mmol) were added in sequence and stirred for 4 hours. The reaction mixture was loaded directly onto a 25-g silica gel loading column with the aid of DCM. The column was eluted onto a prequilibrated 40-g Redi-Sep column with 0-5% MeOH/DCM to give (S)-2'-amino-3-p-tolyl-5'H-spiro[chromeno[2,3-b]pyridine-5,4'-oxazol]-7-yl trifluoromethanesulfonate as a cream-colored solid.

Step 3:

A vial was charged with (S)-2'-amino-3-p-tolyl-5'H-spiro[chromeno[2,3-b]pyridine-5,4'-oxazole]-7-yl trifluoromethanesulfonate (209 mg, 0.426 mmol), copper(i) iodide (8.11 mg, 0.043 mmol), and tetrakis(triphenylphosphine)palladium (49.2 mg, 0.043 mmol). The vial was flushed with Ar (g), then DMF (1704 µL, 0.426 mmol), diisopropylamine (1194 µL, 8.52 mmol), and 2-methylbut-3-yn-2-ol (208 µL, 2.130 mmol) were added in sequence. The vial was sealed and placed in a 70° C. oil bath for 2 hours. The mixture was diluted with EtOAc (15 mL), washed with water (10 mL), washed with brine (15 mL), dried over sodium sulfate, filtered, and evaporated. The residue was taken up in DCM/MeOH (not completely soluble) and chromatographed on a 40-g Redi-Sep column, eluting with 0-8% MeOH/DCM (product came out in a streak) to give (S)-4-(2'-amino-3-p-tolyl-5'H-spiro[chromeno[2,3-b]pyridine-5,4'-oxazole]-7-yl)-2-methylbut-3-yn-2-ol as a light yellow solid Step 4:

A vial was charged with (S)-4-(2'-amino-3-p-tolyl-5'H-spiro[chromeno[2,3-b]pyridine-5,4'-oxazole]-7-yl)-2-methylbut-3-yn-2-ol (134.5 mg, 0.316 mmol), MeOH (3161 µL), and methanesulfonic acid (103 µL, 1.581 mmol). The vial was sealed and placed in a 70° C. oil bath for 4 hours. The mixture was poured into saturated aq. sodium bicarbonate solution (30 mL) and extracted with EtOAc (2×25 mL). The combined organic extracts were dried over sodium sulfate, filtered, and evaporated. The residue was chromatographed on a 40-g Redi-Sep column to give a impure material that was dissolved in methanol and purified by reverse-phase HPLC (10-90% CH$_3$CN/H$_2$O with 0.1% TFA). The fractions containing product were combined in saturated aq. sodium bicarbonate solution with the aid of methanol, and the mixture was extracted with DCM (3×). The combined organic extracts were dried over sodium sulfate, filtered, and evaporated to give (S)-7-(3-methoxy-3-methylbut-1-ynyl)-3-p-tolyl-5'H-spiro[chromeno[2,3-b]pyridine-5,4'-oxazol]-2'-amine.

Example 251

Method AA26

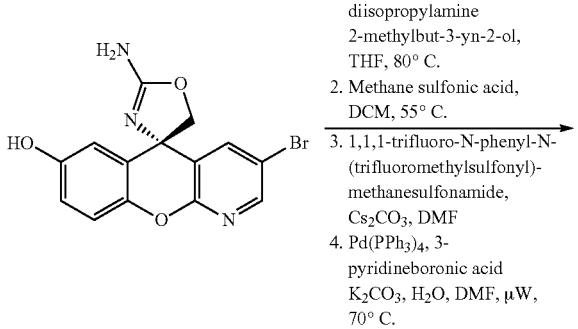

-continued

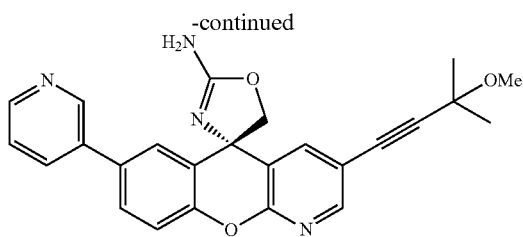

Synthesis of (S)-3-(3-methoxy-3-methylbut-1-ynyl)-7-(pyridin-3-yl)-5'H-spiro[chromeno[2,3-b]pyridine-5,4'-oxazol]-2'-amine Step 1:
Combined (S)-2'-amino-3-bromo-5'H-spiro[chromeno[2,3-b]pyridine-5,4'-oxazol]-7-ol (1.260 g, 3.62 mmol), tetrakis(triphenylphosphine)palladium (0.418 g, 0.362 mmol), copper(i) iodide (0.069 g, 0.362 mmol) and THF (14.48 mL, 3.62 mmol) and DMF (14.48 mL, 3.62 mmol) in a sealable reaction tube. Added diisopropylamine (10.14 mL, 72.4 mmol) then 2-methylbut-3-yn-2-ol (1.768 mL, 18.10 mmol) and flushed the reaction tube with argon. Sealed and heated at 110° C. for 3 hours. The mixture was diluted with water (150 mL) and 10% iPrOH/EtOAc (50 mL). The layers were separated, and the aqueous layer was extracted with 10% iPrOH/EtOAc (2×50 mL). The organic layers were combined, washed with water (60 mL), washed with brine (60 mL), dried over sodium sulfate, filtered, and evaporated. The residue was purified by chromatography on a 100-g SNAP column, eluting with 0-100% of a 90:10:1 mixture of DCM/MeOH/NH$_4$OH in DCM to (S)-2'-amino-3-(3-hydroxy-3-methylbut-1-ynyl)-5'H-spiro[chromeno[2,3-b]pyridine-5,4'-oxazol]-7-ol as a brown solid.

Step 2:
A vessel was charged with (S)-2'-amino-3-(3-hydroxy-3-methylbut-1-ynyl)-5'H-spiro[chromeno[2,3-b]pyridine-5,4'-oxazol]-7-ol (0.512 g, 1.457 mmol) in methanol (17.73 mL, 437 mmol). Methane sulfonic acid (0.945 mL, 14.57 mmol) was added, and the vial was sealed and placed in a 55° C. oil bath overnight. Potassium carbonate was added to quench the acid, and the mixture was filtered with the aid of DCM. The filtrate was evaporated, and the residue was soluble in MeOH/DCM, but some potassium carbonate still came through. The residue was purified by chromatography on a 50-g SNAP column, eluting with 0-100% of a 90:10:1 mixture of DCM/MeOH/NH$_4$OH in DCM. The material thus obtained was rechromatographed to under the same conditions to give (S)-2'-amino-3-(3-methoxy-3-methylbut-1-ynyl)-5'H-spiro[chromeno[2,3-b]pyridine-5,4'-oxazol]-7-ol as a pale-yellow solid.

Step 3:
A 15-mL RBF was charged with cesium carbonate (358 mg, 1.099 mmol) and (S)-2'-amino-3-(3-methoxy-3-methylbut-1-ynyl)-5'H-spiro[chromeno[2,3-b]pyridine-5,4'-oxazol]-7-ol (365.01 mg, 0.999 mmol) in DMF (4995 µL). The resulting mixture was stirred for 10 min, then the flask was submerged in an ice-bath for 5 min. n-phenyltrifluoromethanesulfonimide (393 mg, 1.099 mmol) was added as a single portion. The mixture was stirred for 2 min, then the ice-bath was removed and stirring was continued for 1 hour. The mixture was diluted with water (and a small amount of brine to clear an emulsion) and extracted with EtOAc (3×). The combined organic extracts were dried over sodium sulfate, filtered, and evaporated. The residue was purified by chromatography on a 50-g SNAP column, eluting with 0-60% of a 90:10 mixture of DCM/MeOH in DCM. The obtained residue was taken up in water (total 20 mL) and extracted with EtOAc (2×15 mL). The combined organic extracts were dried over sodium sulfate, filtered, and evaporated to give (S)-2'-amino-3-(3-methoxy-3-methylbut-1-ynyl)-5'H-spiro[chromeno[2,3-b]pyridine-5,4'-oxazole]-7-yl trifluoromethanesulfonate.

Step 4:
A vial was charged with (S)-2'-amino-3-(3-methoxy-3-methylbut-1-ynyl)-5'H-spiro[chromeno[2,3-b]pyridine-5,4'-oxazole]-7-yl trifluoromethanesulfonate (104 mg, 0.210 mmol), pyridin-3-ylboronic acid (77 mg, 0.629 mmol), and tetrakis(triphenylphosphine)palladium (24.22 mg, 0.021 mmol). The vial was purged with Ar (g), then DMF (1048 µL) and potassium carbonate (524 µL, 1.048 mmol) (as a 2.0 M aq. solution) were added in sequence. The vial was capped and heated in a Biotage Initiator microwave reactor for 1.5 h at 70° C. The mixture was diluted with water (10 mL) and extracted with EtOAc (2×10 mL). The combined organic extracts were dried over sodium sulfate, filtered, and evaporated. The residue was purified by chromatography on a 25-g SNAP column, eluting with 0-60% of a 90:10:1 mixture of DCM/MeOH/NH$_4$OH in DCM to give (S)-3-(3-methoxy-3-methylbut-1-ynyl)-7-(pyridin-3-yl)-5'H-spiro[chromeno[2,3-b]pyridine-5,4'-oxazol]-2'-amine.

Example 252

Method AA27

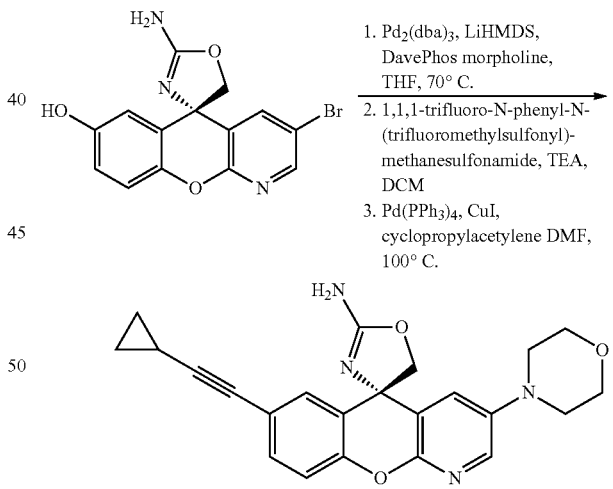

Synthesis of (S)-3-(3,3-dimethylbut-1-ynyl)-7-(pyrazin-2-yl)-5'H-spiro[chromeno[2,3-b]pyridine-5,4'-oxazol]-2'-amine Step 1:
A vial was charged with (S)-2'-amino-3-bromo-5'H-spiro[chromeno[2,3-b]pyridine-5,4'-oxazol]-7-ol (0.647 g, 1.858 mmol), DavePhos (0.088 g, 0.223 mmol), and tris(dibenzylideneacetone)dipalladium(0) (0.085 g, 0.093 mmol). The vessel was flushed with Ar(g), then lithium bis(trimethylsilyl) amide (1.0 M in THF) (9.29 mL, 9.29 mmol) and morpholine (0.486 mL, 5.58 mmol) were added in sequence. The vial was sealed and heated at 70° C. for one hour at which point the mixture was diluted with water and saturated ammonium chloride. The mixture was extracted with DCM (3×30 mL). The aq. layer was extracted with ethyl acetate and 10% iPrOH/EtOAc, and the solid was taken with the organic layer. The different organic layers were combined, dried over sodium sulfate, filtered, and evaporated. The material was purified via column chromatography (RediSep 40 g, gradient elution 0-10% MeOH:DCM w/1% NH4OH) to afford (S)-2'-amino-3-morpholino-5'H-spiro[chromeno[2,3-b]pyridine-5,4'-oxazol]-7-ol as an orange solid.

Step 2:

A 25-mL RBF was charged with cesium carbonate (0.371 g, 1.138 mmol) and (S)-2'-amino-3-morpholino-5'H-spiro[chromeno[2,3-b]pyridine-5,4'-oxazol]-7-ol (0.336 g, 0.948 mmol) in DMF (4.74 mL). The resulting mixture was stirred for 10 min, then the flask was submerged in an ice-bath for 5 min. n-phenyltrifluoromethanesulfonimide (0.373 g, 1.043 mmol) was added as a single portion and the reaction was allowed to warm to RT overnight. The reaction was cooled in an ice bath and 150 mg of cesium carbonate was added. The reaction was stirred for 10 minutes, then 40 mg of n-phenyl-trifluoromethanesulfonimide was added and the reaction was stirred for one hour. The mixture was diluted with water and extracted twice with EtOAc (a little brine was added to help with emulsion). The combined organic extracts were dried over sodium sulfate, filtered, and evaporated. The material was purified via column chromatography (RediSep 40 g, gradient elution 0-7% MeOH:DCM w/1% NH4OH) to afford (S)-2'-amino-3-morpholino-5'H-spiro[chromeno[2,3-b]pyridine-5,4'-oxazole]-7-yl trifluoromethanesulfonate as an off-white solid.

Step 3:

A vial was charged with (S)-2'-amino-3-morpholino-5'H-spiro[chromeno[2,3-b]pyridine-5,4'-oxazole]-7-yl trifluoromethanesulfonate (0.120 g, 0.247 mmol), tetrakis(triphenylphosphine)palladium (2.85 mg, 2.467 μmol), and copper (i) iodide (4.70 mg, 0.025 mmol). The vial was flushed with Ar (g), then DMF (0.987 mL), diisopropylamine (0.692 mL, 4.93 mmol), and ethynylcyclopropane (0.104 mL, 1.233 mmol) were added in sequence to give a yellow solution. The vial was sealed and heated to 70° C. for two hours at which point 8 mg of tetrakis(triphenylphosphine)palladium and 0.1 mL of cyclopropylacetylene were added and the reaction was heated to 100° C. and stirred for two hours. The vial was purged with Ar (g), then DMF (1.039 mL) and 2-(tributylstannyl)pyrazine (0.197 mL, 0.623 mmol) were added in sequence. The vial was sealed and heated to 110° C. for one hour. The mixture was loaded onto a 2-g SCX-2 column and eluted 4× with methanol to remove impurities. The product was then eluted with 2M ammonia in methanol. The filtrate was evaporated, and the residue was purified via column chromatography (RediSep 40 g, gradient elution 0-5% MeOH:DCM) to afford (S)-3-(3,3-dimethylbut-1-ynyl)-7-(pyrazin-2-yl)-5'H-spiro[chromeno[2,3-b]pyridine-5,4'-oxazol]-2'-amine as a white solid.

Example 253

Method AA30

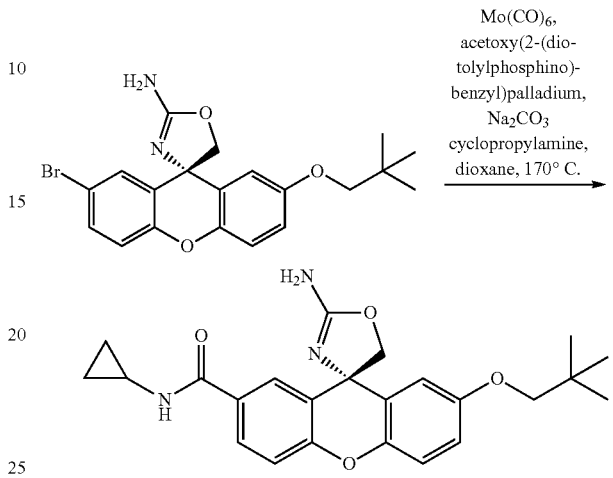

A 0.5-2 mL microwave vial charged with (R)-2'-bromo-7'-(neopentyloxy)-5H-spiro[oxazole-4,9'-xanthen]-2-amine (0.1000 g, 0.240 mmol), Mo(CO)$_6$ (0.063 g, 0.240 mmol), acetoxy(2-(dio-tolylphosphino)benzyl)palladium (0.011 g, 0.012 mmol), sodium carbonate (0.025 g, 0.240 mmol), cyclopropylamine (0.025 mL, 0.359 mmol), and 1,4-dioxane (0.443 mL, 5.03 mmol) was sealed and heated to 170° C. for 30 minutes. The mixture was diluted with EtOAc and water and filtered through celite. The celite was washed with EtOAc and MeOH. The aqueous phase was extracted with EtOAc three times. The organic layer was dried over Na$_2$SO$_4$ and concentrated in vacuo. The crude was purified by silica gel chromatography (2-10% MeOH—CH$_2$Cl$_2$, then 10% MeOH—CH$_2$Cl$_2$). The product was purified again by reverse phase prep HPLC: 10-55% CH3CN (0.1% TFA)-water (0.1% TFA) in 26 min. The fractions were combined and neutralized with solid Na$_2$CO$_3$, extracted three times with DCM. The organic layer was concentrated to provide (S)-2-amino-N-cyclopropyl-7'-(neopentyloxy)-5H-spiro[oxazole-4,9'-xanthene]-2'-carboxamide.

Example 254

Method AA31

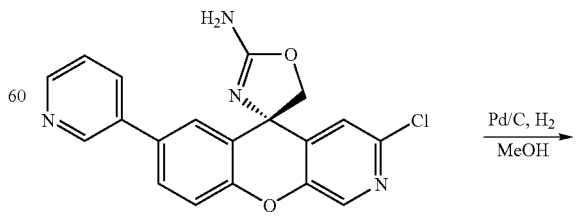

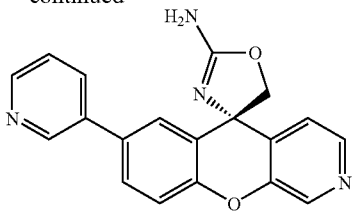

To the solution of (S)-3-chloro-7-(pyridin-3-yl)-5'H-spiro[chromeno[2,3-c]pyridine-5,4'-oxazol]-2'-amine (23 mg, 0.063 mmol) in MeOH (2 mL) was added 10% Pd on Carbon (10 mg, 0.073 mmol). The mixture was hydrogenated under 1 atm of $H_2$ for 24 h. After filtration and concentration, the crude material was absorbed onto a plug of silica gel and purified by chromatography through a Redi-Sep pre-packed silica gel column (12 g), eluting with isocratic % to 20% MeOH in CH2CL2, to provide (S)-7-(pyridin-3-yl)-5'H-spiro[chromeno[2,3-c]pyridine-5,4'-oxazol]-2'-amine as white solid.

Example 255

Method AA32

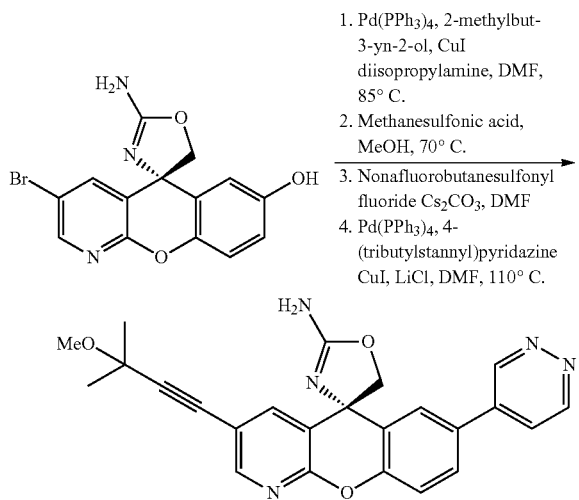 [SMILES: NC1=N[C@]2(CO1)c1cc(O)ccc1Oc1ncc(Br)cc12 ; COC(C)(C)C#Cc1cnc2c(c1)[C@@]1(COC(N)=N1)c1cc(-c3ccnnc3)ccc1O2]

Synthesis of (R)-3-(3-methoxy-3-methylbut-1-ynyl)-7-(pyridazin-4-yl)-5'H-spiro[chromeno[2,3-b]pyridine-5,4'-oxazol]-2'-amine Step 1:

Combined (R)-2'-amino-3-bromo-5'H-spiro[chromeno[2,3-b]pyridine-5,4'-oxazol]-7-ol (2.259 g, 6.49 mmol), tetrakis(triphenylphosphine)palladium (0.750 g, 0.649 mmol), copper(i) iodide (0.124 g, 0.649 mmol) and THF (26.0 mL, 6.49 mmol) and DMF (26.0 mL, 6.49 mmol) in a reaction tube. Added diisopropylamine (18.19 mL, 130 mmol) then 2-methylbut-3-yn-2-ol (3.17 mL, 32.4 mmol) and flushed the reaction tube with argon. Sealed and heated at 85° C. for 3 hours. The mixture was diluted with water (100 mL) and extracted with DCM (1×100 mL, 2×50 mL). The combined organic extracts were dried over sodium sulfate, filtered, and evaporated. The resulting liquid was poured onto a 25-g SCX-2 column and eluted with methanol. The product was then eluted with 2M ammonia in methanol. The filtrate was evaporated and purified by chromatography on a 120-g Redi-Sep column, eluting with 0-100% of a 90:10:1 mixture of DCM/MeOH/NH4OH in DCM to give (R)-2'-amino-3-(3-hydroxy-3-methylbut-1-ynyl)-5'H-spiro[chromeno[2,3-b]pyridine-5,4'-oxazol]-7-ol as a tan solid.

Step 2:

A vessel was charged with (S)-2'-amino-3-(3-hydroxy-3-methylbut-1-ynyl)-5'H-spiro[chromeno[2,3-b]pyridine-5,4'-oxazol]-7-ol (0.679 g, 1.933 mmol) in methanol (23.51 mL, 580 mmol). methane sulfonic acid (0.627 mL, 9.66 mmol) was added, and the vial was sealed and placed in a 70° C. oil bath for 5 hours. The volatiles were evaporated, and the residue was loaded onto a silica gel cartridge in MeOH/DCM. The column was eluted onto an 80-g Redi-Sep column with 30-100% of a 90:10:1 mixture of DCM/MeOH/NH4OH in DCM. This was not the best strategy as it clogged the column for a while. The fractions containing product were evaporated to give (S)-2'-amino-3-(3-methoxy-3-methylbut-1-ynyl)-5'H-spiro[chromeno[2,3-b]pyridine-5,4'-oxazol]-7-ol as an off-white solid.

Step 3:

A 25-mL flask was charged with (R)-2'-amino-3-(3-methoxy-3-methylbut-1-ynyl)-5'H-spiro[chromeno[2,3-b]pyridine-5,4'-oxazol]-7-ol (577.53 mg, 1.581 mmol), cesium carbonate (566 mg, 1.739 mmol), and DMF (7903 µL). The resulting mixture was stirred for 10 min, then the vial was submerged in an ice-bath for 10 min. nonafluorobutanesulfonyl fluoride (306 µL, 1.739 mmol) was added dropwise over 2 minutes. Stirred for 2 hours before the mixture was quenched with saturated aqueous ammonium chloride (10 mL). The mixture was partitioned between water (15 mL) and EtOAc (15 mL). The layers were separated, and the aqueous layer was extracted with EtOAc (15 mL). The combined organic layers were washed with brine, dried over sodium sulfate, filtered, and evaporated. The residue was purified by chromatography on an 80-g Redi-Sep column, eluting with 0-50% of a 90:10 mixture of DCM/MeOH in DCM to give (R)-2'-amino-3-(3-methoxy-3-methylbut-1-ynyl)-5'H-spiro[chromeno[2,3-b]pyridine-5,4'-oxazole]-7-yl 1,1,2,2,3,3,4,4,4-nonafluorobutane-1-sulfonate as a white solid.

Step 4:

A vial was charged with (R)-2'-amino-3-(3-methoxy-3-methylbut-1-ynyl)-5'H-spiro[chromeno[2,3-b]pyridine-5,4'-oxazole]-7-yl 1,1,2,2,3,3,4,4,4-nonafluorobutane-1-sulfonate (102 mg, 0.158 mmol), copper(i) iodide (3.01 mg, 0.016 mmol), tetrakis(triphenylphosphine)palladium (18.24 mg, 0.016 mmol), and lithium chloride (10.96 mg, 1.579 mmol). The vial was purged with Ar (g), then DMF (790 µL) and 4-(tributylstannyl)pyridazine (146 µL, 0.474 mmol) were added in sequence. The vial was sealed and placed in a 110° C. oil bath for 4 hours. The mixture loaded onto a 2-g SCX-2 column and eluted 4× with methanol to remove impurities. The product was then eluted with 2M ammonia in methanol. The filtrate was evaporated, and the residue was chromatographed on a 40-g Redi-Sep column, eluting with 0-100% EtOAc/Hexane, then with 0-10% MeOH/DCM. The resulting material was still impure, so the material was dissolved in methanol and purified by reverse-phase HPLC (15-80% CH3CN/H2O with 0.1% TFA). The fractions containing product were combined in saturated aq. sodium bicarbonate solution with the aid of methanol and extracted with DCM (3×). The combined organic extracts were dried over sodium sulfate, filtered, and evaporated to give (R)-3-(3-methoxy-3- methylbut-1-ynyl)-7-(pyridazin-4-yl)-5'H-spiro[chromeno[2,3-b]pyridine-5,4'-oxazol]-2'-amine as a white solid.

Example 256

Method AA33

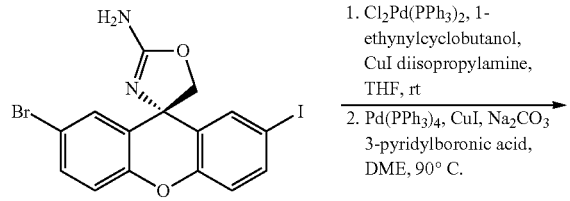

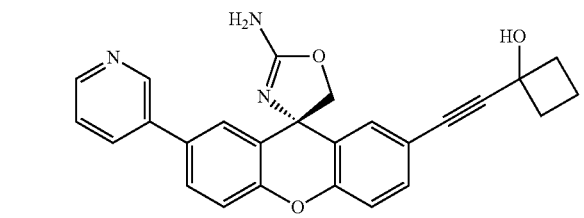

Step 1:

To a solution of (S)-2'-bromo-7'-iodo-5H-spiro[oxazole-4,9'-xanthen]-2-amine (0.250 g, 0.547 mmol) in THF (4.5 mL) was added dichlorobis(triphenylphosphine)palladium (ii) (0.077 g, 0.109 mmol), 1-ethynylcyclobutanol (0.079 g, 0.820 mmol), copper(i) iodide (3.71 µL, 0.109 mmol), and diisopropyl amine (0.613 mL, 4.38 mmol). The resulting mixture was then stirred at RT for 2 h. EtOAc (7 mL) was added and the mixture was filtered. The solid was washed with EtOAc (1×5 mL). The combined filtrates were concentrated. The residue was mixed with silica gel and the solid mixture was purified by silica gel column chromatography (solid loading, 0%-20% MeOH/DCM) to give the alkynylated product as a brown solid.

Step 2:

To a solution of (R)-1-((2-amino-2'-bromo-5H-spiro[oxazole-4,9'-xanthene]-7'-yl)ethynyl)cyclobutanol (0.290 g, 0.682 mmol) in DME (5.5 mL) was added 3-pyridylboronic acid (0.084 g, 0.682 mmol), tetrakis(triphenylphosphine)palladium(o) (0.063 g, 0.055 mmol), sodium carbonate monohydrate crystals (0.217 g, 2.046 mmol), and H₂O (1.0 mL). The resulting mixture was then heated to 90° C. for 5 h. Then, the mixture was cooled to room temperature and EtOAc (10 mL) was added. The mixture was stirred at room temperature for 2 min. The organic layer was collected, dried over MgSO4, and concentrate. The residue was mixed with silica gel and the solid mixture was purified by silica gel column chromatography (solid loading, 0%-20% MeOH/DCM) to give the depicted product as a brown solid.

Example 257

Method AA34

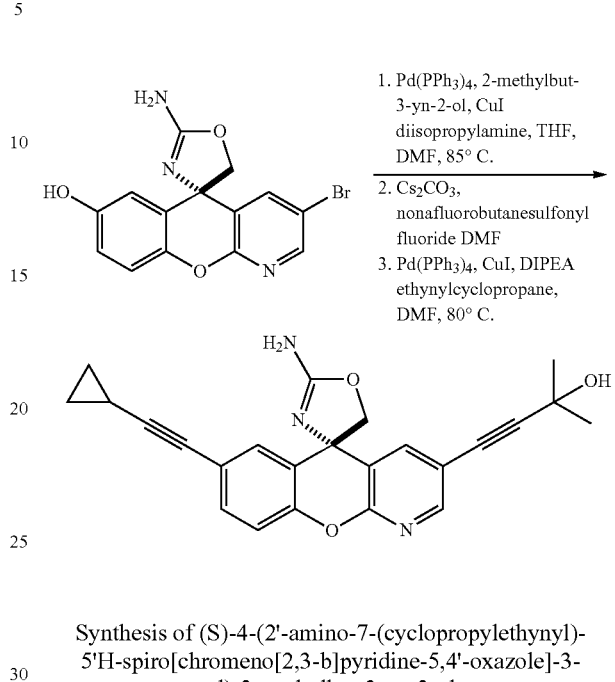

Synthesis of (S)-4-(2'-amino-7-(cyclopropylethynyl)-5'H-spiro[chromeno[2,3-b]pyridine-5,4'-oxazole]-3-yl)-2-methylbut-3-yn-2-ol Step 1:

Combined (R)-2'-amino-3-bromo-5'H-spiro[chromeno[2,3-b]pyridine-5,4'-oxazol]-7-ol (2.259 g, 6.49 mmol), tetrakis(triphenylphosphine)palladium (0.750 g, 0.649 mmol), copper(i) iodide (0.124 g, 0.649 mmol) and THF (26.0 mL, 6.49 mmol) and DMF (26.0 mL, 6.49 mmol). Added diisopropylamine (18.19 mL, 130 mmol) then 2-methylbut-3-yn-2-ol (3.17 mL, 32.4 mmol) and flushed the reaction tube with argon. Sealed and heated at 85° C. for 3 hours. The mixture was diluted with water (100 mL) and extracted with DCM (1×100 mL, 2×50 mL). (DCM was used because this product is partially soluble in water and EtOAc is not as good a solvent for it). The combined organic extracts were dried over sodium sulfate, filtered, and evaporated. The resulting liquid was poured onto a 25-g SCX-2 column and eluted with methanol. The product was then eluted with 2M ammonia in methanol. The filtrate was evaporated and purified by chromatography on a 120-g Redi-Sep column, eluting with 0-100% of a 90:10:1 mixture of DCM/MeOH/NH₄OH in DCM to give (R)-2'-amino-3-(3-hydroxy-3-methylbut-1-ynyl)-5'H-spiro[chromeno[2,3-b]pyridine-5,4'-oxazol]-7-ol as a tan solid.

Step 2:

A 25-mL flask was charged with (S)-2'-amino-3-(3-hydroxy-3-methylbut-1-ynyl)-5'H-spiro[chromeno[2,3-b]pyridine-5,4'-oxazol]-7-ol (437.24 mg, 1.244 mmol), cesium carbonate (446 mg, 1.369 mmol), and DMF (6222 µL). The resulting mixture was stirred for 10 min, then the vial was submerged in an ice-bath for 10 min. nonafluorobutanesulfonyl fluoride (241 µL, 1.369 mmol) was added dropwise over 1 min. The mixture was stirred for 3 hours before being diluted with water (20 mL) and a small amount of brine. This mixture was extracted with EtOAc (2×20 mL). The combined organic extracts were washed with brine, dried over sodium sulfate, filtered, and evaporated. The residue was purified by chromatography on an 80-g Redi-Sep column, eluting with 0-60% of a 90:10 mixture of DCM/MeOH in DCM to give (S)-2'-amino-3-(3-hydroxy-3-methylbut-1-ynyl)-5'H-spiro[chromeno[2,3-b]pyridine-5,4'-oxazole]-7-yl 1,1,2,2,3,3,4,4,4-nonafluorobutane-1-sulfonate as a white solid.

Step 3:

A 0.5-2 mL vial was charged with (S)-2'-amino-3-(3-hydroxy-3-methylbut-1-ynyl)-5'H-spiro[chromeno[2,3-b]pyridine-5,4'-oxazole]-7-yl 1,1,2,2,3,3,4,4,4-nonafluorobutane-1-sulfonate (106 mg, 0.167 mmol), and copper(i) iodide (3.19 mg, 0.017 mmol). The vial was flushed with Ar (g), then DMF (669 µL, 0.167 mmol), diisopropylamine (469 µL, 3.35 mmol), and ethynylcyclopropane (70.8 µL, 0.836 mmol) were added in sequence to give a yellow solution. The vial was sealed and heated overnight in at 80° C. The mixture was diluted with water (15 mL) and extracted with EtOAc (3×10 mL). The combined organic extracts were washed with brine, dried over sodium sulfate, filtered, and evaporated. The residue was purified by chromatography on a 40-g Redi-Sep column, eluting with 0-50% of a 90:10:1 mixture of DCM/MeOH/NH$_4$OH in DCM to give (S)-4-(2'-amino-7-(cyclopropylethynyl)-5'H-spiro[chromeno[2,3-b]pyridine-5,4'-oxazole]-3-yl)-2-methylbut-3-yn-2-ol as a tan solid after evaporation from DCM/hexanes.

Example 258

Method AA36

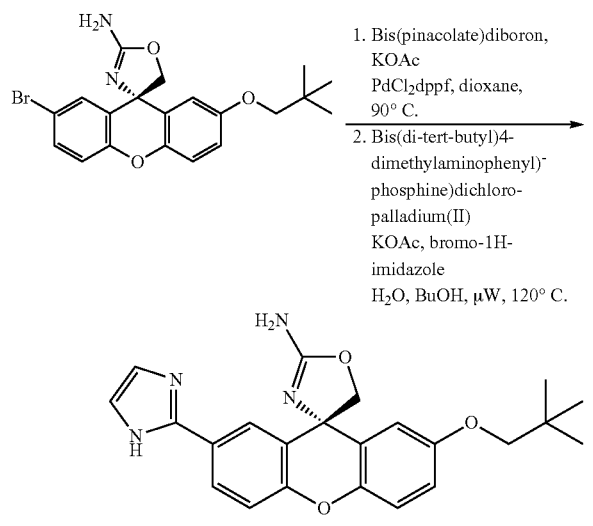

Synthesis of (S)-2'-(1H-imidazol-2-yl)-7'-(neopentyloxy)-5H-spiro[oxazole-4,9'-xanthen]-2-amine Step 1:

(R)-2'-Bromo-7'-(neopentyloxy)-5H-spiro[oxazole-4,9'-xanthen]-2-amine (1170 mg, 2.80 mmol), Bis(pinacolate)diboron (1780 mg, 7.01 mmol), Potassium acetate (550 mg, 5.61 mmol) and PdCl$_2$ dppf with DCM (229 mg, 0.280 mmol) were combined in a 20 ml microwave vial. Dioxane (14 ml) was added, Ar gas was bubbled through, and the vial was sealed and heated to 90° C. After 3 days, the reaction mixture was concentrated and brought up in DMF (~10 ml). To the dark brown solution was added H$_2$O and a precipitate formed. The solution was filtered to give a brown solid. The filtrate was diluted with DCM and washed with sat'd aqueous NaHCO$_3$. The precipitate was brought up in DCM (1 ml) and sonicated for 30 s. Addition of hexanes crashed out minimal amounts of the desired product and the precipitate and solution were combined with the organic layer from before and concentrated. The crude mixture was diluted with H$_2$O and filtered to give the crude product as a brown solid that was brought up in minimal DCM, sonicated for 20s, diluted with hexanes, filtered and washed with hexanes to provide (S)-2'-(neopentyloxy)-7'-(4,4,5,5-tetramethyl-1,3,2-dioxaborolan-2-yl)-5H-spiro[oxazole-4,9'-xanthen]-2-amine as a brown solid.

Step 2:

A solution of (S)-2'-(neopentyloxy)-7'-(4,4,5,5-tetramethyl-1,3,2-dioxaborolan-2-yl)-5H-spiro[oxazole-4,9'-xanthen]-2-amine (50 mg, 0.108 mmol) in BuOH (861 µL), 2-bromo-1H-imidazole (0.129 mmol), and KOAc (31.7 mg, 0.323 mmol) in Water (215 µL) was purged with Ar in a sealed tube. AmPhos (1.525 mg, 2.153 µmol) was added and the reaction was heated to 120° C. for 30 min in the microwave. The reaction was cooled to rt, diluted with MeOH (3 ml), loaded onto an AccuBOND II SCX cartridge, washed with MeOH (3 ml) and eluted with 2N NH3 in MeOH (6 ml) to give the crude product which was purified by reverse-phase preparative HPLC using a Gemini NX c!8 column (150*30 mm, 5 um), 0.1% TFA in CH3CN/H2O, gradient 0% to 70% over 10 min to provide (S)-2'-(1H-imidazol-2-yl)-7'-(neopentyloxy)-5H-spiro[oxazole-4,9'-xanthen]-2-amine.

Example 259

Method AA37

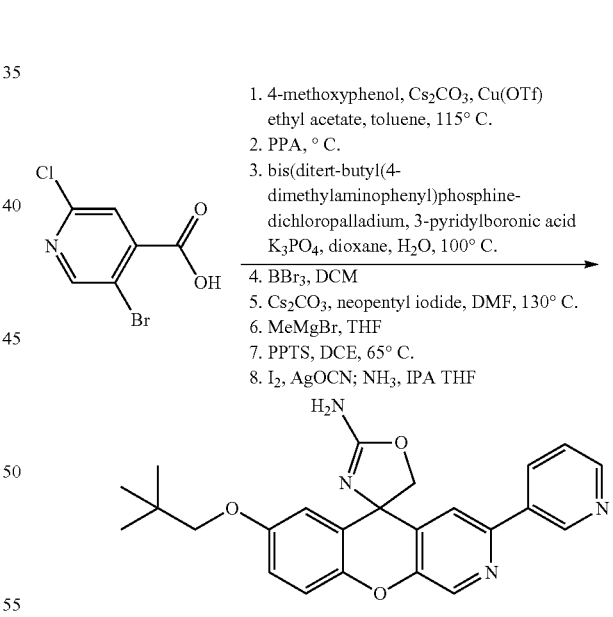

Step 1:

To a solution of 5-bromo-2-chloroisonicotinic acid (14.0 g, 59.2 mmol) in toluene (200 mL) was added 4-methoxyphenol (6.16 mL, 77 mmol), and cesium carbonate (38.6 g, 118 mmol). The resulting mixture was stirred at RT and was flushed with N$_2$. Then, copper (trifluoromethane) (0.919 g, 1.776 mmol) and EtOAc (0.6 mL) were added. The mixture was then heated to 115° C. for 17 h. Then, the mixture was cooled to RT and was concentrated to ⅒th of the original volume. The residue was then dissolved in EtOAc (400 mL) and water (400 mL). The organic layer was separated and the aqueous layer was collected. The aqueous layer was carefully adjusted to pH=4.0 using concentrated HCl at 0° C. Then, EtOAc (400 mL) was added and the mixture was stirred at RT for 15 min. A brown precipitation (not product) was observed. The mixture was filtered and the filtrate was collected and concentrated. Then, MeOH (200 mL) was added to the residue and a light brown precipitation was observed. The mixture was filtered and the solid was collected. Then, the solid was dissolved in DCM (1000 mL). The mixture was filtered and the filtrate was concentrated to give the product as light yellow solid. MS (ESI, positive ion) m/z: 280, 282 (M+1).

Step 2:
To a RBF was added 2-chloro-5-(4-methoxyphenoxy) isonicotinic acid (1.1 g, 3.93 mmol) and polyphosphoric acid (56 g). The resulting mixture was then heated to 150° C. for 1 h. Then, the mixture was carefully poured to a beaker containing ice and water. Then, the mixture was adjusted to pH=7 using NaHCO$_3$ (s). Then, the mixture was extracted with EtOAc (2×200 mL). The combined organic extracts were dried over MgSO$_4$, concentrated, and dried in vacuo to give the product as a yellow solid. MS (ESI, positive ion) m/z: 262, 264 (M+1).

Step 3:
To a solution of 3-chloro-7-methoxy-5H-chromeno[2,3-c]pyridin-5-one (0.410 g, 1.567 mmol) in 1,4-Dioxane (7.0 mL) and Water (2.333 mL) was added 3-pyridylboronic acid (0.289 g, 2.350 mmol), potassium phosphate (0.998 g, 4.70 mmol), and bis(ditert-butyl(4-dimethylaminophenyl)phosphinedichloropalladium II (0.111 g, 0.157 mmol). The resulting mixture was then subjected to a microwave irradiation at 100° C. for 15 min. Then, DCM (10 mL) and H$_2$O (5 mL) were added to the mixture. The mixture was then stirred at RT for 5 min. The organic layer was collected and the aqueous layer was extracted with DCM (1×10 mL). The combined organic extracts were dried over MgSO$_4$ and concentrated. Then, MeOH (5 mL) was added to the residue. A yellow precipitation was observed. The mixture was filtered, and the yellow solid was collected and dried in vacuo to give the product as a light yellow solid. MS (ESI, positive ion) m/z: 305 (M+1).

Step 4:
To a solution of 7-methoxy-3-(pyridin-3-yl)-5H-chromeno[2,3-c]pyridin-5-one (363 mg, 1.193 mmol) in DCM (6 mL) was added boron tribromide, 1.0M in DCM (2.98 mL, 2.98 mmol) drop wise. After addition, the mixture was stirred at RT for overnight. Then, the mixture was carefully quenched with MeOH (50 mL). The mixture was then concentrated and DCM (10 mL) was added. A yellow precipitation was observed. The mixture was filtered and the yellow solid was collected. Then, MeOH (200 mL) was added to the yellow solid and the mixture was stirred at RT for 2 h. The mixture was filtered and the yellow solid was collected and dried in vacuo to the product as a yellow solid. MS (ESI, positive ion) m/z: 291 (M+1).

Step 5:
To a microwave vial was added 7-hydroxy-3-(pyridin-3-yl)-5H-chromeno[2,3-c]pyridin-5-one (0.312 g, 1.075 mmol), DMF (7.5 mL), cesium carbonate (0.525 g, 1.612 mmol), and neopentyl iodide (0.513 mL, 3.87 mmol). The resulting mixture was then subjected to a microwave irradiation at 130° C. for 15 min. Then, EtOAc (30 mL) and H$_2$O (30 mL) were added. The mixture was then stirred at RT for 5 min. A yellow precipitation was observed. The mixture was filtered, and the yellow solid was collected and dried in vacuo to give the product as a yellow solid. MS (ESI, positive ion) m/z: 361 (M+1).

Step 6:
To a solution of 7-(neopentyloxy)-3-(pyridin-3-yl)-5H-chromeno[2,3-c]pyridin-5-one (0.230 g, 0.638 mmol) in THF (4 mL) at 0° C. was added methylmagnesium chloride, 3.0M solution in THF (0.425 mL, 1.276 mmol). After addition, the mixture was stirred at RT for 4 h. Then, saturated ammonium chloride (10 mL) and EtOAc (20 mL) were added. The mixture was stirred at RT for 5 min. Then, the organic layer was collected, dried over MgSO$_4$, and concentrated to give 240 mg of the product as a light brown solid. MS (ESI, positive ion) m/z: 377 (M+1).

Step 7:
A solution of 5-methyl-7-(neopentyloxy)-3-(pyridin-3-yl)-5H-chromeno[2,3-c]pyridin-5-ol (0.240 g, 0.638 mmol) in 1,2-dichloroethane (2.0 mL) was added pyridinium 4-toluenesulfonate (6.41 mg, 0.026 mmol). The resulting mixture was then heated to 65° C. for 6 h. Then, saturated NaHCO$_3$ (5 mL) was added to the mixture and the mixture was extracted with DCM (2×10 mL). The combined organic extracts were dried over MgSO$_4$ and concentrated. The residue was then dissolved in a solution of EtOAc/hexane. A light brown precipitation was observed. The mixture was filtered and the light brown solid was washed with hexane (2×5 mL) to give the desired product, which was used in the next step. MS (ESI, positive ion) m/z: 359 (M+1).

Step 8:
To a solution of iodine (0.178 g, 0.703 mmol) in THF (4 mL) at −20° C. was added silver cyanate (0.287 g, 1.917 mmol). After addition, the mixture was stirred at −20° C. for 1 h. Then, 5-methylene-7-(neopentyloxy)-3-(pyridin-3-yl)-5H-chromeno[2,3-c]pyridine (0.229 g, 0.639 mmol) was added and the mixture was stirred at 0° C. for 2 h. Then, the mixture was filtered through celite with the aid of THF (7 mL). Then, ammonia (0.958 mL, 1.917 mmol) (2 M in i-PrOH) was added drop wise to the filtrate at 0° C. The resulting mixture was stirred at RT for overnight. Then, saturated Na$_2$S$_2$O$_3$ (1.0 mL) was added followed by saturated NaHCO$_3$ (1.0 mL). The mixture was stirred at RT for 15 min. The organic layer was collected, dried over MgSO$_4$, and concentrated. The residue was mixed with silica gel and the solid mixture was purified by silica gel column chromatography using ISCO instrument (solid loading, 0%-20% MeOH/DCM) to give the depicted product as a brown solid, which was then purified by preparative HPLC (0%-100% MeCN 0.1% TFA/H$_2$O 0.1% TFA) to give a desired product in a solution of MeCN 0.1% TFA/H$_2$O. The solvent, MeCN was removed and saturated NaHCO$_3$ (4 mL) was added. The mixture was then extracted with EtOAc (2×10 mL). The combined organic extracts were then dried over MgSO$_4$, concentrated, and dried in vacuo to give the depicted product as a white solid. MS (ESI, positive ion) m/z: 417 (M+1).

Example 260

Method AA39

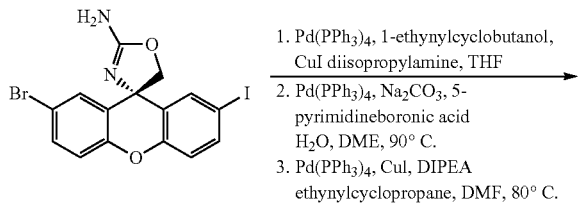

1. Pd(PPh$_3$)$_4$, 1-ethynylcyclobutanol, CuI diisopropylamine, THF
2. Pd(PPh$_3$)$_4$, Na$_2$CO$_3$, 5-pyrimidineboronic acid H$_2$O, DME, 90° C.
3. Pd(PPh$_3$)$_4$, CuI, DIPEA ethynylcyclopropane, DMF, 80° C.

163

-continued

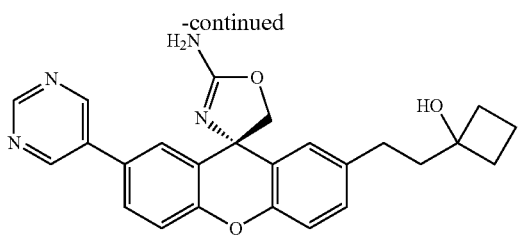

164

-continued

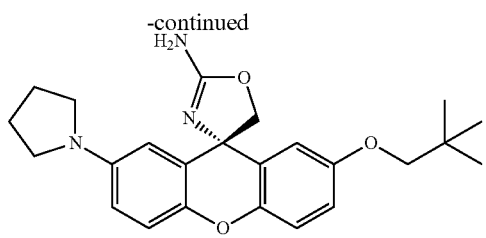

Synthesis of (S)-2'-(neopentyloxy)-7'-(pyrrolidin-1-yl)-5H-spiro[oxazole-4,9'-xanthen]-2-amine A vial was charged with (R)-2'-bromo-7'-(neopentyloxy)-5H-spiro[oxazole-4,9'-xanthen]-2-amine (0.100 g, 0.240 mmol), 2'-(dicyclohexylphosphino)-N,N-dimethylbiphenyl-2-amine (1.132 mg, 2.88 μmol), Pd$_2$(dba)$_3$ (1.097 mg, 1.198 μmol), LiHMDS (1.0 M in THF) (0.959 mL, 0.959 mmol), and pyrrolidine (0.059 mL, 0.719 mmol). The vial was sealed and heated to 100° C. overnight. Additional Pd$_2$ (dba)$_3$ (1.097 mg, 1.198 μmol), 2'-(dicyclohexylphosphino)-N,N-dimethylbiphenyl-2-amine (1.132 mg, 2.88 μmol), LiHMDS (1.0 M in THF) (0.480 mL, 0.480 mmol) and pyrrolidine (0.059 mL, 0.719 mmol) were added and the reaction was at 100° C. for 2 hours. The reaction mixture was diluted with a saturated aqueous ammonium chloride solution (10 mL) and extracted three times with DCM. The combined organic extracts were dried over sodium sulfate, filtered, and evaporated. The material was purified via Gilson HPLC (20-90% MeCN:H$_2$O). The product fractions were partitioned between DCM and saturated sodium bicarbonate solution. The aqueous layer was extracted with DCM, and the combined organic layers were dried with sodium sulfate, filtered, and concentrated to afford (S)-2'-(neopentyloxy)-7'-(pyrrolidin-1-yl)-5H-spiro[oxazole-4,9'-xanthen]-2-amine as a white solid.

Example 262

Method AA41

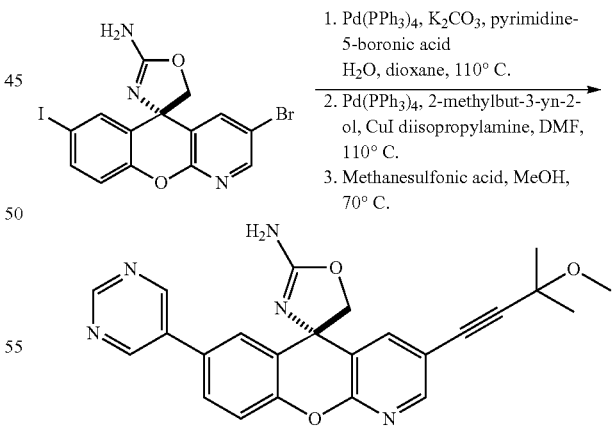

Synthesis of (S)-3-(3-methoxy-3-methylbut-1-ynyl)-7-(pyrimidin-5-yl)-5'H-spiro[chromeno[2,3-b]pyridine-5,4'-oxazol]-2'-amine Step 1:
A 10-20 mL microwave vial was charged with (S)-3-bromo-7-iodo-5'H-spiro[chromeno[2,3-b]pyridine-5,4'-ox- Step 1:
To a solution of (S)-2'-bromo-7'-iodo-5H-spiro[oxazole-4,9'-xanthen]-2-amine (1.070 g, 2.341 mmol) in THF (20 mL) was added 1-ethynylcyclobutanol (0.338 g, 3.51 mmol), copper(i) iodide (0.016 mL, 0.468 mmol), dichlorobis(triphenylphosphine)palladium (ii) (0.329 g, 0.468 mmol), and DIPA (2.62 mL, 18.73 mmol). The resulting mixture was then stirred at RT overnight. EtOAc (30 mL) was added and the mixture was filtered. The solid was washed with EtOAc (1×5 mL). The combined filtrates were concentrated. The residue was mixed with silica gel and the solid mixture was purified by silica gel column chromatography (solid loading, 0%-20% MeOH/DCM) to give the product as a light brown solid Step 2:
To a solution of (R)-1-((2-amino-2'-bromo-5H-spiro[oxazole-4,9'-xanthene]-7'-yl)ethynyl)cyclobutanol (883 mg, 2.076 mmol) in DME (7 mL) and H$_2$O (2.333 mL) was added tetrakis(triphenylphosphine)palladium(o) (192 mg, 0.166 mmol), 5-pyrimidinylboronic acid (283 mg, 2.284 mmol), and sodium carbonate (0.087 mL, 2.076 mmol). The resulting mixture was then heated to 90° C. for 5 h. The mixture was cooled to RT and EtOAc (20 mL) was added. The mixture was stirred at RT for 5 min. The organic layer was collected, dried over MgSO$_4$, and concentrated. The residue was then dissolved in a solution of DMSO (2 mL) and MeOH (2 mL). The solution was then purified by preparative HPLC (0%-100% MeCN 0.1% NH$_4$OH/H$_2$O 0.1% NH$_4$OH) to give the product as a light yellow solid Step 3:
To a solution of (R)-1-((2-amino-2'-(pyrimidin-5-yl)-5H-spiro[oxazole-4,9'-xanthene]-7'-yl)ethynyl)cyclobutanol (0.134 g, 0.316 mmol) in MeOH (2 mL) was added palladium hydroxide (20 mg). The resulting mixture was then stirred at RT under H$_2$ overnight. The mixture was filtered through celite and washed with MeOH (2×5 mL). The combined filtrates were concentrated and the residue was dissolved in MeOH (2 mL). The solution was then purified by preparative HPLC (0%-90% MeCN 0.1% NH$_4$OH/H$_2$O 0.1% NH$_4$OH) to give the title compound as a white solid.

Example 261

Method AA40

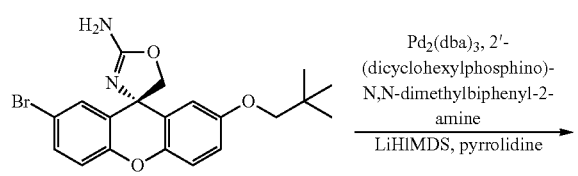

azol]-2'-amine (503 mg, 1.098 mmol), pyrimidin-5-ylboronic acid (143 mg, 1.153 mmol), tetrakis(triphenylphosphine)palladium (127 mg, 0.110 mmol). The vial was flushed with Ar(g), then THF (5489 μL, 1.098 mmol) and potassium carbonate (1.5 M) (1464 μL, 2.195 mmol) (aq. solution) were added in sequence. The vial was sealed and heated at 110° C. for 2 hours. The mixture was diluted with water and extracted with 10% i-PrOH/EtOAc (3×). The combined organic extracts were dried over sodium sulfate, filtered, and evaporated. The residue was purified by chromatography on a 100-g SNAP column, eluting with 0-100% of a 90:10:1 mixture of DCM/MeOH/NH₄OH in DCM to provide (S)-3-bromo-7-(pyrimidin-5-yl)-5'H-spiro[chromeno[2,3-b]pyridine-5,4'-oxazol]-2'-amine as an off-white solid.

Step 2:

Combined (S)-3-bromo-7-(pyrimidin-5-yl)-5'H-spiro[chromeno[2,3-b]pyridine-5,4'-oxazol]-2'-amine (99 mg, 0.242 mmol), tetrakis(triphenylphosphine)palladium (28.0 mg, 0.024 mmol), copper(i) iodide (4.61 mg, 0.024 mmol) and THF (969 μL, 0.242 mmol) and DMF (969 μL, 0.242 mmol). Added diisopropylamine (679 μL, 4.85 mmol) then 2-methylbut-3-yn-2-ol (118 μL, 1.211 mmol) and flushed the reaction tube with argon. Sealed and heated at 110° C. for 2 hours. The mixture was diluted with water and extracted with EtOAc (3×). The combined organic extracts were dried over sodium sulfate, filtered, and evaporated. The residue was purified by chromatography on a 25-g SNAP column, eluting with 0-100% of a 90:10:1 mixture of DCM/MeOH/NH₄OH to give (S)-4-(2'-amino-7-(pyrimidin-5-yl)-5'H-spiro[chromeno[2,3-b]pyridine-5,4'-oxazole]-3-yl)-2-methylbut-3-yn-2-ol as a white solid after evaporation from DCM/hexane.

Step 3:

To a solution of (S)-4-(2'-amino-7-(pyrimidin-5-yl)-5'H-spiro[chromeno[2,3-b]pyridine-5,4'-oxazole]-3-yl)-2-methylbut-3-yn-2-ol (58 mg, 0.140 mmol) in MeOH (1703 μL, 42.1 mmol) was added methane sulfonic acid (91 μL, 1.403 mmol) in a vial. The vial was sealed and placed in a 70° C. oil bath for 3 hours. The mixture was poured into saturated aqueous sodium bicarbonate solution (20 mL) and extracted with DCM (3×10 mL). The combined organic extracts were dried over sodium sulfate, filtered, and evaporated. The residue was purified by chromatography on a 25-g SNAP column, eluting with 0-70% of a 90:10:1 mixture of DCM/MeOH/NH₄OH in DCM to give (S)-3-(3-methoxy-3-methylbut-1-ynyl)-7-(pyrimidin-5-yl)-5'H-spiro[chromeno[2,3-b]pyridine-5,4'-oxazol]-2'-amine as a white solid after evaporation from DCM/hexane.

Example 263

Method AA42

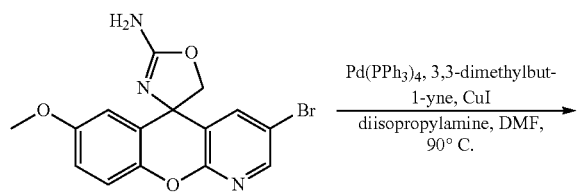

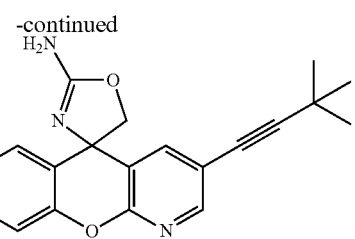

Synthesis of 3-(3,3-dimethylbut-1-ynyl)-7-methoxy-5'H-spiro[chromeno[2,3-b]pyridine-5,4'-oxazol]-2'-amine Combined 3-bromo-7-methoxy-5'H-spiro[chromeno[2,3-b]pyridine-5,4'-oxazol]-2'-amine (104186-10-peak 1) (500 mg, 1.381 mmol), tetrakis(triphenylphosphine)palladium (160 mg, 0.138 mmol), copper(i) iodide (52.6 mg, 0.276 mmol). Added DMF (6903 μL, 1.381 mmol), 3,3-dimethylbut-1-yne (340 mg, 4.14 mmol) and diisopropylamine (4837 μL, 34.5 mmol), flushed with argon, sealed and heated at 90° C. for 2 hours. The reaction was diluted with water (100 mL) and poured into a separatory funnel containing ethyl acetate (100 mL). The layers were separated and the aqueous layer was extracted with ethyl acetate (3×50 mL). The combined organic layers were washed with water and then brine, dried over sodium sulfate, filtered and concentrated in vacuo to provide a brown oil that was purified by silica gel chromatography (Redi-Sep pre-packed silica gel column (40 g), 0-10% methanol in methylenechloride with 0.1% ammonium hydroxide) to provide the desired product contaminated with triphenylphosphine. The yellow solid was suspended in 25 mL of ether, resulting in the formation of a fine white precipitate. Decanted ether and washed the solid with 10 mL of ether. Dried under reduced pressure to provide 3-(3,3-dimethylbut-1-ynyl)-7-methoxy-5'H-spiro[chromeno[2,3-b]pyridine-5,4'-oxazol]-2'-amine as a white solid.

Example 264

Method AA43

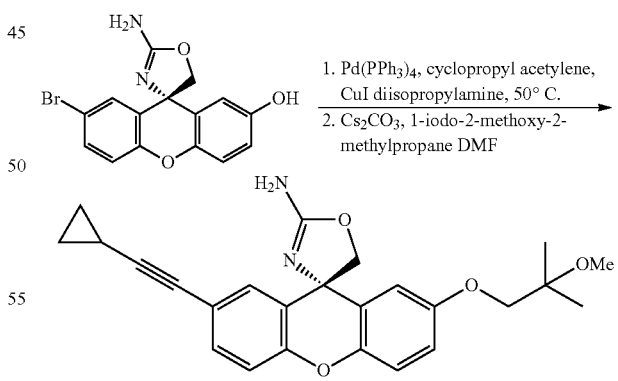

Synthesis of (S)-2'-(cyclopropylethynyl)-7'-(2-methoxy-2-methylpropoxy)-5H-spiro[oxazole-4,9'-xanthen]-2-amine Step 1:

A vial was charged with (R)-2-amino-2'-bromo-5H-spiro[oxazole-4,9'-xanthen]-7'-ol (1.00 g, 2.88 mmol), cyclopropyl acetylene (0.732 mL, 8.64 mmol), copper(i) iodide (0.110 g, 0.576 mmol), and diisopropylamine (14.40 mL). tetrakis(triphenylphosphine)palladium(0) (0.333 g, 0.288 mmol) was added, the vial was flushed with argon, and the reaction was heated to 50° C. and stirred overnight. The reaction was diluted with ethyl acetate and filtered through Celite. The solution was concentrated and purified via column chromatography (RediSep 40 g, gradient elution 0-10% MeOH:DCM) to afford (S)-2-amino-2'-(cyclopropylethynyl)-5H-spiro[oxazole-4,9'-xanthen]-7'-ol as a tan solid.

Step 2:

A 2-5 mL microwave vial was charged with (S)-2-amino-2'-(cyclopropylethynyl)-5H-spiro[oxazole-4,9'-xanthen]-7'-ol (0.250 g, 0.752 mmol), cesium carbonate (0.980 g, 3.01 mmol), and DMF (3.01 mL). The mixture was stirred vigorously for 5 min, then 1-iodo-2-methoxy-2-methylpropane (0.303 mL, 2.257 mmol) was added via syringe. The vial was sealed and the reaction was microwaved at 110° C. for two hours. The mixture was diluted with water and EtOAc and the layers were separated, and the aqueous layer was extracted twice with EtOAc. The combined organic extracts were dried over sodium sulfate, filtered, and evaporated. The residue was purified by chromatography on a 12-g Redi-Sep column, eluting with 0-10% MeOH/DCM to provide (S)-2'-(cyclopropylethynyl)-7'-(2-methoxy-2-methylpropoxy)-5H-spiro[oxazole-4,9'-xanthen]-2-amine as an off-white solid.

Example 265

Method AA44

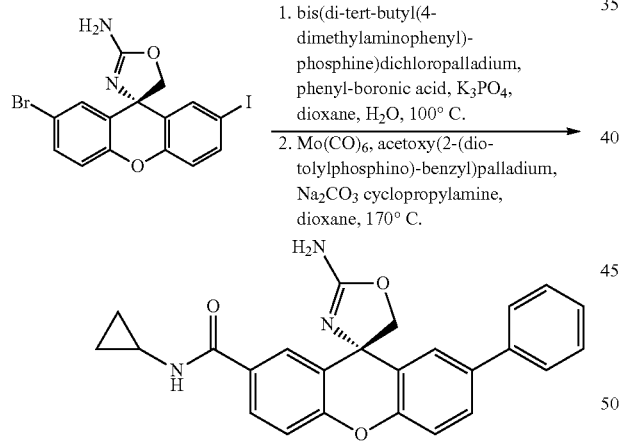

Step 1:

A 100 ml RBF vial was charged with (S)-2'-bromo-7'-iodo-5H-spiro[oxazole-4,9'-xanthen]-2-amine (3.37 g, 7.37 mmol) in dioxane (30 mL), water (15 mL), phenylboronic acid (0.965 g, 7.91 mmol), bis(di-tert-butyl(4-dimethylaminophenyl)phosphine)dichloropalladium(II) (0.106 g, 0.150 mmol), and potassium phosphate-tribasic (3.17 g, 14.93 mmol). The reaction was heated to 100° C. in an oil-bath for 8 hours. The reaction was diluted with ethyl acetate (100 mL), water (25 mL), and the ethyl acetate layer was separated and dried over anhydrous sodium sulfate. Concentration and purification by silica gel flash column chromatography (hexanes/ethyl acetate) provided (R)-2'-bromo-7'-phenyl-5H-spiro[oxazole-4,9'-xanthen]-2-amine.

Step 2:

A 0.5-2 mL microwave vial charged with (R)-2'-bromo-7'-phenyl-5H-spiro[oxazole-4,9'-xanthen]-2-amine (0.1000 g, 0.246 mmol), Mo(CO)$_6$ (0.065 g, 0.246 mmol), acetoxy(2-(dio-tolylphosphino)benzyl)palladium (0.012 g, 0.012 mmol), sodium carbonate (0.026 g, 0.246 mmol), cyclopropanamine (0.026 mL, 0.368 mmol), and 1,4-dioxane (0.541 mL, 6.14 mmol) was sealed and heated to 170° C. for 30 min. The mixture was diluted with EtOAc and water. The aqueous phase was extracted with EtOAc three times. The organic layer was dried over Na$_2$SO$_4$ and concentrated in vacuo. The crude was purified by silica gel chromatography (12 g, 2-10% MeOH—CH$_2$Cl$_2$, then 10-20% MeOH (2 M NH$_3$)—CH$_2$Cl$_2$). The product was purified again by reverse phase prep HPLC: 15-60% CH$_3$CN (0.1% TFA)-water (0.1% TFA) in 26 min. The fractions were combined and neutralized with solid Na$_2$CO$_3$, extracted three times with CH$_2$Cl$_2$. The organic layer was dried over Na$_2$SO$_4$ and concentrated in vacuo. The depicted product was obtained as a white solid.

Example 266

Method AA45

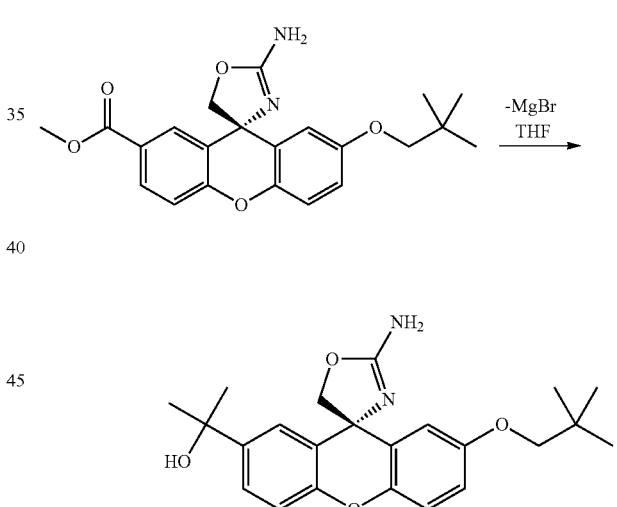

Synthesis of (S)-2-(2-amino-2'-(neopentyloxy)-5H-spiro[oxazole-4,9'-xanthene]-7'-yl)propan-2-ol To a solution of (S)-methyl 2-amino-7'-(neopentyloxy)-5H-spiro[oxazole-4,9'-xanthene]-2'-carboxylate (50 mg, 0.13 mmol) in THF (1 mL) was added methylmagnesium bromide (Aldrich, 0.76 mL, 0.76 mmol) at 0° C. The cooling bath was removed after the addition. After 1 h, the reaction was quenched with saturated NH$_4$Cl. The mixture was extracted with EtOAc three times. The organic phase was dried over Na$_2$SO$_4$, and concentrated in vacuo. The residue was purified by silica gel chromatography (12 g, 2-10% in 10 min, then 10% MeOH—CH₂Cl₂). The product was obtained as a white solid. MS: 397 (M+1).

Example 267

Method AA46

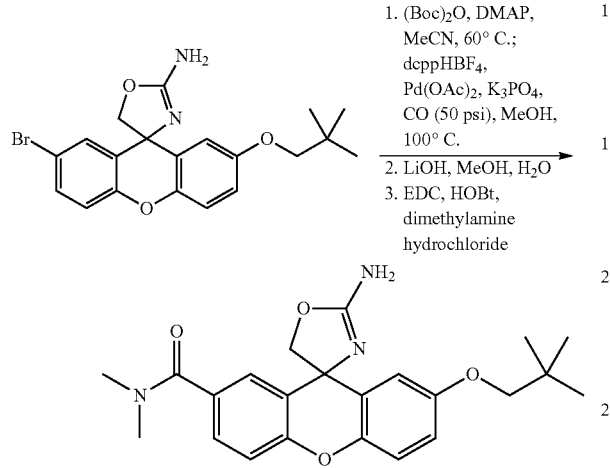

Step 1:
The mixture of 2'-bromo-7'-(neopentyloxy)-5H-spiro[oxazole-4,9'-xanthen]-2-amine (1.00 g, 2.4 mmol), CH₃CN (15 mL), di-tert-butyl dicarbonate (Aldrich, 0.63 g, 2.9 mmol), and DMAP (Aldrich, 0.015 g, 0.12 mmol) was heated to 60° C. overnight. LCMS showed the product. di-tert-butyl dicarbonate (70 mg) was added and the reaction was continued overnight. LC didn't show further improvement in conversion. The mixture was diluted with EtOAc and washed with saturated Na₂CO₃, water and brine. The organic layer was dried over Na₂SO₄ and concentrated in vacuo. The residue was purified by silica gel chromatography (40 g, 0-10%, then 10% MeOH—CH₂Cl₂). The Boc-protected 2'-bromo-7'-(neopentyloxy)-5H-spiro[oxazole-4,9'-xanthen]-2-amine was obtained as a white solid. MS: 517, 519, 462 (M+1). The mixture of the above product (70 mg, 0.14 mmol), potassium phosphate (115 mg, 0.54 mmol), dcppHBF₄ (0.41 mg, 0.68 µmol), palladium acetate (0.12 mg, 0.54 µmol), and MeOH (3 mL) was pressurized with carbon monoxide, purged twice with CO gas (40 psi) and then heated to 100° C. (50 psi) overnight. The reaction mixture was concentrated in vacuo. The residue was diluted with EtOAc and water. The aqueous phase was extracted with EtOAc three times. The organic layer was dried over Na₂SO₄ and concentrated in vacuo. The crude was purified by prep TLC: 8% MeOH—CH₂Cl₂. The product was obtained as a white solid. MS: 397 (M+1).

Step 2:
To a mixture of methyl 2-amino-7'-(neopentyloxy)-5H-spiro[oxazole-4,9'-xanthene]-2'-carboxylate (33 mg, 83 µmol) and lithium hydroxide hydrate (Aldrich, 7 mg, 166 µmol) was added THF:MeOH:water (3:2:1, 1 mL). The mixture was stirred at RT for 5 h, then at 40° C. for 2 h. The mixture was concentrated in vacuo. The residue was neutralized with 1N HCl (2 mL). Ether was added to the mixture and stirred at RT for 10 min. The solid was filtered, washed with ether and dried in vacuum oven. The product was obtained as a white solid. MS: 383 (M+1).

Step 3:
A mixture of 2-amino-7'-(neopentyloxy)-5H-spiro[oxazole-4,9'-xanthene]-2'-carboxylic acid (17 mg, 44 µmol), EDC (Aldrich, 13 mg, 67 µmol), HOBt (Ana Spec, 3 mg, 22 µmol), TEA (Aldrich, 37 µL, 267 µmol), dimethylamine.HCl (Alfa Aesar, 33 mg, 400 µmol) and DMF (0.5 mL) was stirred at RT overnight. The mixture was diluted with EtOAc and washed with saturated Na₂CO₃. The organic layer was dried over Na₂SO₄ and concentrated in vacuo. The crude was purified by silica gel chromatography (4 g, 0-10% MeOH—CH₂Cl₂). The depicted product was obtained as colorless film. MS: 410 (M+1).

Example 268

Method AA47

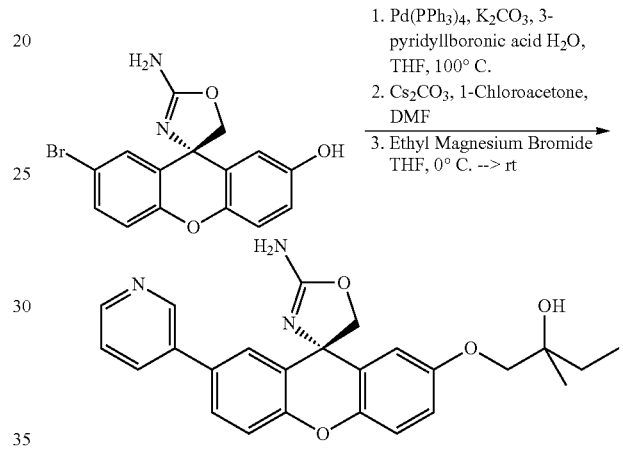

Synthesis of 1-((S)-2-amino-2'-(pyridin-3-yl)-5H-spiro[oxazole-4,9'-xanthene]-7'-yloxy)-2-methylbutan-2-ol Step 1:
A 350-mL pressure vessel was charged with (R)-2-amino-2'-bromo-5H-spiro[oxazole-4,9'-xanthen]-7'-ol (4.00 g, 11.52 mmol), 3-pyridylboronic acid (3.54 g, 28.8 mmol), tetrakis(triphenylphosphine)palladium(0) (1.331 g, 1.152 mmol), THF (57.6 mL), and potassium carbonate (2.0M aq. solution) (28.8 mL, 57.6 mmol). The vessel was sealed and heated to 100° C. and stirred for 2 hours. The layers were partitioned between EtOAc (20 mL) and water (20 mL). The layers were separated, and the aqueous layer was extracted with EtOAc (2×20 mL). The combined organic layers were washed with brine (emulsion!), dried over sodium sulfate and filtered with the aid of 10% MeOH/DCM. The filtrate was evaporated to give a yellow solid. This solid was taken up in minimal DCM and sonicated for 5 min. The solid was filtered and washed with DCM (30 mL). Filtering and washing with DCM afforded (S)-2-amino-7'-(pyridin-3-yl)-5H-spiro[oxazole-4,9'-xanthen]-2'-ol as a pale-yellow solid Step 2:
A vial was charged with (S)-2-amino-7'-(pyridin-3-yl)-5H-spiro[oxazole-4,9'-xanthen]-2'-ol (0.300 g, 0.869 mmol), cesium carbonate (0.425 g, 1.303 mmol). DMF (3.47 mL) was added, the vial was sonicated for 30 s, and the mixture was stirred vigorously for 20 min, at which time some white solid still remained. The vial was cooled in an ice-bath for 10 min, then 1-chloroacetone (0.083 mL, 1.042 mmol) was added dropwise and the reaction was stirred over the weekend, during which the bath warmed to RT. The reaction was cooled back to 0° C. and 1-chloroacetone (0.083 mL, 1.042 mmol) was added. The reaction was stirred for two hours before 0.5 equivalents of cesium carbonate and chloroacetone were added at one hour intervals until the reaction was complete. The mixture was partitioned between water and EtOAc. The layers were separated, and the aqueous layer was extracted with EtOAc (2×). The combined organic extracts were dried over sodium sulfate, filtered, and evaporated. The material was purified via column chromatography (RediSep 40 g, gradient elution 0-5% MeOH:DCM) to afford (S)-1-(2-amino-2'-(pyridin-3-yl)-5H-spiro[oxazole-4,9'-xanthene]-7'-yloxy)propan-2-one as a white solid. The remaining fractions were combined and concentrated to afford impure material as an off-white solid.

Step 3:

(S)-1-(2-amino-2'-(pyridin-3-yl)-5H-spiro[oxazole-4,9'-xanthene]-7'-yloxy)propan-2-one (0.050 g, 0.125 mmol) was dissolved in THF (1.246 mL) and cooled to 0° C. ethylmagnesium bromide 1.0 M solution in THF (0.374 mL, 0.374 mmol) was added and the reaction was stirred for one hour. Additional ethylmagnesium bromide 1.0 M solution in THF (0.374 mL, 0.374 mmol) was added again and the reaction was stirred overnight at RT. The reaction was diluted with ethyl acetate and washed with water. The aqueous layer was extracted with ethyl acetate, and the combined organic layers were dried with sodium sulfate, filtered, and concentrated. The material was purified via Gilson HPLC (25-90% MeCN: $H_2O$). The product fractions were partitioned between DCM and saturated sodium bicarbonate solution. The aqueous layer was extracted with DCM, and the combined organic layers were dried with sodium sulfate, filtered, and concentrated to afford 1-((S)-2-amino-2'-(pyridin-3-yl)-5H-spiro[oxazole-4,9'-xanthene]-7'-yloxy)-2-methylbutan-2-ol as a white solid.

Example 269

Method AA48

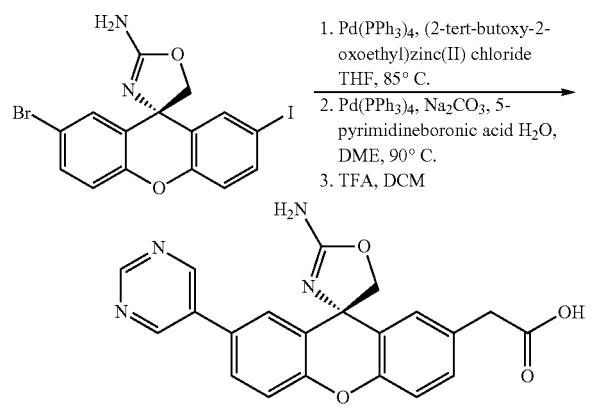

Step 1:

To a solution of (S)-2'-bromo-7'-iodo-5H-spiro[oxazole-4,9'-xanthen]-2-amine (0.978 g, 2.140 mmol) in THF (5 mL) was added (2-tert-butoxy-2-oxoethyl)zinc(II) chloride (17.12 mL, 8.56 mmol) and tetrakis(triphenylphosphine)palladium (o) (0.124 g, 0.107 mmol). The resulting mixture was then heated to 85° C. overnight. Saturated ammonium chloride (50 mL) and EtOAc (100 mL) were added and the mixture was stirred at room temperature overnight. The mixture was filtered and the organic layer was collected, dried over $MgSO_4$, and concentrated. The residue was mixed silica gel and the solid mixture was purified by silica gel column chromatography (solid loading, 0%-100% ammonia in methanol 2M/DCM) to give the product as a brown solid.

Step 2:

To a solution of (R)-tert-butyl 2-(2-amino-2'-bromo-5H-spiro[oxazole-4,9'-xanthene]-7'-yl)acetate (0.505 g, 1.134 mmol) in 1,2-Dimethoxyethane (7 mL) was added 5-pyrimidinylboronic acid (0.155 g, 1.247 mmol), sodium carbonate monohydrate (0.142 mL, 3.40 mmol), tetrakis(triphenylphosphine)palladium(o) (0.105 g, 0.091 mmol), and $H_2O$ (1.4 mL). The resulting mixture was then heated to 90° C. for 10 h. The mixture was cooled to room temperature, EtOAc (20 mL) and sat. $NaHCO_3$ (5 mL) were added. The mixture was stirred at room temperature for 5 minutes then the organic layer was collected, dried over $MgSO_4$, and concentrated. The residue was then dissolved in a solution of DMSO (1 mL) and MeOH (1 mL). The solution mixture was then purified by preparative HPLC (0%-90% MeCN 0.1% $NH_4OH/H_2O$ 0.1% $NH_4OH$) to give the product as a light yellow solid.

Step 3:

A solution of (R)-tert-butyl 2-(2-amino-2'-(pyrimidin-5-yl)-5H-spiro[oxazole-4,9'-xanthene]-7'-yl)acetate (14 mg, 0.031 mmol) in 30% TFA in DCM (0.5 mL) was stirred at room temperature for 1 h. A saturated $NaHCO_3$ solution was added slowly to the mixture at 0° C. to adjust the pH to 7. Then, solvents were removed and the residue was dissolved in a solution of MeOH (0.5 mL), $H_2O$ (0.1 mL), and DMF (0.3 mL). The solution mixture was then purified by preparative HPLC (0%-100% MeCN 0.1% $NH_4OH/H_2O$ 0.1% $NH_4OH$) to give the depicted product as a white solid.

Example 270

Method AA49

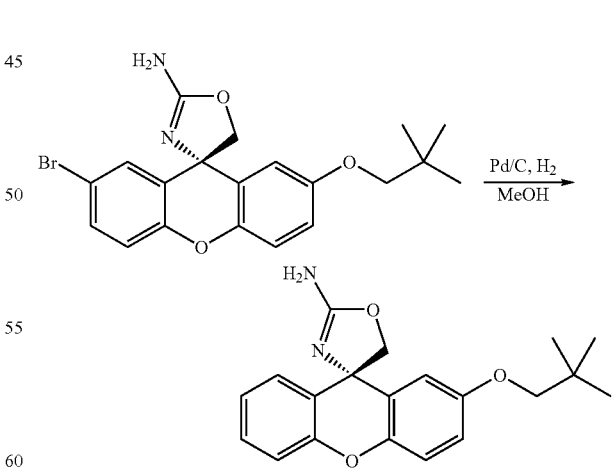

A mixture of (R)-2'-bromo-7'-(neopentyloxy)-5H-spiro[oxazole-4,9'-xanthen]-2-amine (0.0500 g, 0.120 mmol), ethanol (2 mL), and palladium 10% on activated carbon (0.013 g, 0.012 mmol) was stirred under 1 atm of $H_2$ gas overnight. The catalyst was filtered through celite and the Example 271

Method AA50

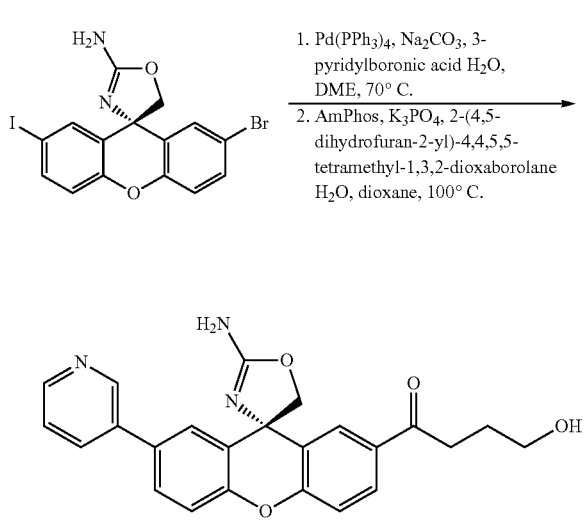

Synthesis of (S)-1-(2-amino-2'-(pyridin-3-yl)-5H-spiro[oxazole-4,9'-xanthene]-7'-yl)-4-hydroxybutan-1-one Step 1:

A 250 ml RB flask was charged with (R)-2'-bromo-7'-iodo-5H-spiro[oxazole-4,9'-xanthen]-2-amine (4.06 g, 8.88 mmol), pyridin-3-ylboronic acid (1.419 g, 11.55 mmol), tetrakis(triphenylphosphine)palladium(0) (1.026 g, 0.888 mmol). DME (63.4 mL) and sodium carbonate (13.32 mL, 26.6 mmol) (2M solution) were added and the mixture was heated at 70° C. for 15 hrs. The mixture was diluted with water and ethyl acetate, filtered and organic layer was separated and concentrated. The crude material was purified by silica gel chromatography (0-50% gradient of 90/10/1 DCM/MeOH/NH4OH in DCM) to give (S)-2'-bromo-7'-(pyridin-3-yl)-5H-spiro[oxazole-4,9'-xanthen]-2-amine as an off-white solid.

Step 2:

A 2-5 ml microwave vial was charged with (S)-2'-bromo-7'-(pyridin-3-yl)-5H-spiro[oxazole-4,9'-xanthen]-2-amine (96 mg, 0.235 mmol), potassium phosphate (150 mg, 0.705 mmol), 2-(4,5-dihydrofuran-2-yl)-4,4,5,5-tetramethyl-1,3,2-dioxaborolane (92 mg, 0.470 mmol) and AmPhos (16.65 mg, 0.024 mmol). 1,4-Dioxane (1176 μL) and water (392 μL) were added and the vial was sealed and heated in microwave reactor for 1 hr at 100° C. The mixture was diluted with ethyl acetate, filtered through celite, and concentrated on 2 g of silica gel. Purification by flash chromatography on 12 g rediSep column using 5-50% gradient of DCM/MeOH/NH4OH (90:10:1) in DCM provided (S)-1-(2-amino-2'-(pyridin-3-yl)-5H-spiro[oxazole-4,9'-xanthene]-7'-yl)-4-hydroxybutan-1-one as an off-white solid.

Example 272

Method AA51

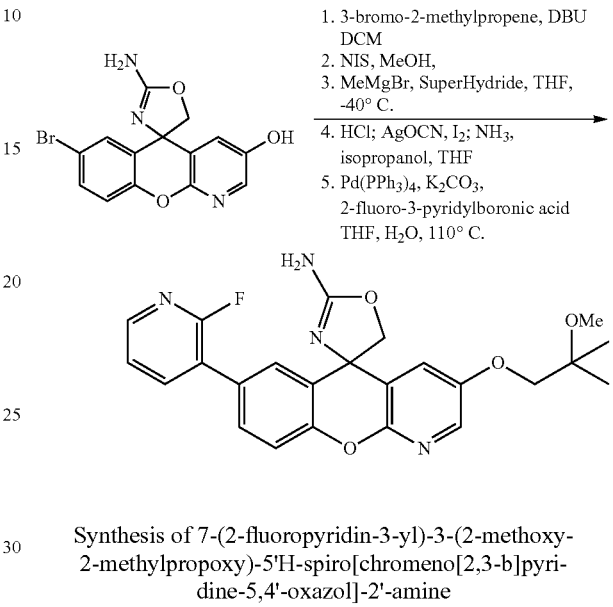

Synthesis of 7-(2-fluoropyridin-3-yl)-3-(2-methoxy-2-methylpropoxy)-5'H-spiro[chromeno[2,3-b]pyridine-5,4'-oxazol]-2'-amine Step 1:

A solution of 2'-amino-7-bromo-5'H-spiro[chromeno[2,3-b]pyridine-5,4'-oxazol]-3-ol (15.00 g, 51.4 mmol) in 100 mL DCM was treated with DBU (9.68 mL, 64.2 mmol) and was allowed to stir for 10 minutes. 3-Bromo-2-methylpropene (5.44 mL, 53.9 mmol) was added, and the reaction mixture was allowed to stir at RT for an additional 1 hour. The reaction mixture was quenched with 200 mL 0.5 N citric acid and was concentrated to remove the organics. The resulting solid was filtered, washed with 1:1 water/acetone, and was dried. The solid was purified by column chromatography yielding 7-bromo-3-(2-methylallyloxy)-5H-chromeno[2,3-b]pyridin-5-one.

Step 2:

A suspension of 7-bromo-3-(2-methylallyloxy)-5H-chromeno[2,3-b]pyridin-5-one (4.50 g, 13.00 mmol) in 100 mL MeOH was treated with NIS (5.85 g, 26.0 mmol) and was allowed to stir at room temperature for 48 hours. The reaction mixture was poured into 1:1 water/brine and was extracted with ether and then DCM. The organics were dried over MgSO4 and concentrated. Purification of the crude residue by column chromatography gave 7-bromo-3-(3-iodo-2-methoxy-2-methylpropoxy)-5H-chromeno[2,3-b]pyridin-5-one as a yellow solid.

Step 3:

A solution of 7-bromo-3-(3-iodo-2-methoxy-2-methylpropoxy)-5H-chromeno[2,3-b]pyridin-5-one (4.10 g, 8.13 mmol) in 100 mL THF was cooled to −40° C. and was treated with methylmagnesium chloride (5.42 mL, 16.27 mmol). After stirring for two hours, the reaction mixture was allowed to warm to room temperature and superhydride (40.7 mL, 40.7 mmol) was added. After stirring for an additional 2 hours the reaction mixture was cooled to 0° C. and was quenched with MeOH. The reaction mixture was poured into saturated NH₄Cl solution and was extracted with EtOAc. The organics were washed with water, brine, dried over MgSO4 and concentrated yielding 7-bromo-3-(2-methoxy-2-methylpropoxy)-5-methyl-5H-chromeno[2,3-b]pyridin-5-ol.

Step 4:

A solution of 7-bromo-3-(2-methoxy-2-methylpropoxy)-5-methyl-5H-chromeno[2,3-b]pyridin-5-ol (1.780 g, 4.51 mmol) in 50 mL THF was treated with HCl 4N in dioxane (0.113 mL, 0.451 mmol) and was heated to 50° C. for one hour. The reaction mixture was cooled to 0° C. and added to the mixture below.

A separate solution of iodine (1.260 g, 4.97 mmol) in 50 mL THF was prepared and cooled to −40° C. Silver cyanate (1.692 g, 11.29 mmol) was added, and the reaction mixture was allowed to stir for one hour. The above solution was then added via cannula and the reaction mixture was allowed to stir for an additional hour before ammonia 2N in IPA (13.54 mL, 27.1 mmol) was added, and the reaction mixture was allowed to warm to room temperature and stir 3 hours. The reaction mixture was quenched with 10% sodium thiosulfate solution, and was allowed to stir at room temperature for one hour. The organics were separated, washed with water, brine, dried over MgSO₄ and concentrated. Purification of the crude residue by column chromatography gave 7-bromo-3-(2-methoxy-2-methylpropoxy)-5'H-spiro[chromeno[2,3-b]pyridine-5,4'-oxazol]-2'-amine.

Step 5:

A vial charged with 2-fluoropyridin-3-ylboronic acid (0.156 g, 1.105 mmol), palladiumtetrakis (0.043 g, 0.037 mmol), potassium carbonate (0.255 g, 1.842 mmol), and 7-bromo-3-(2-methoxy-2-methylpropoxy)-5'H-spiro[chromeno[2,3-b]pyridine-5,4'-oxazol]-2'-amine (0.160 g, 0.368 mmol) was dissolved in 3 mL THF and 0.5 mL water and was heated to 110° C. 2 hours. The reaction mixture was diluted with EtOAc and dried over MgSO₄. The organics were concentrated then purified directly by column chromatography yielding 7-(2-fluoropyridin-3-yl)-3-(2-methoxy-2-methylpropoxy)-5'H-spiro[chromeno[2,3-b]pyridine-5,4'-oxazol]-2'-amine.

Example 273

Method AA52

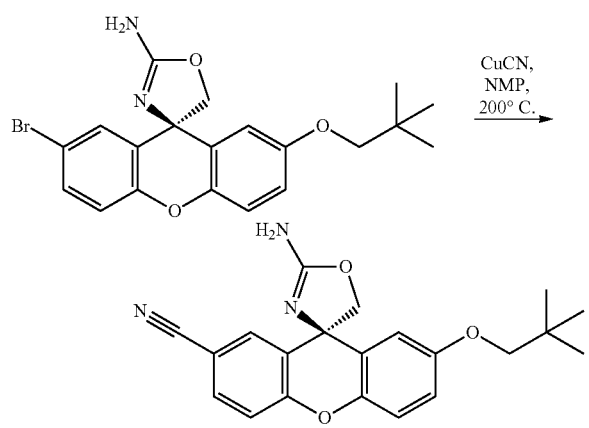

Synthesis fo (R)-2-amino-7'-(neopentyloxy)-5H-spiro[oxazole-4,9'-xanthene]-2'-carbonitrile (S)-2'-bromo-7'-(neopentyloxy)-5H-spiro[oxazole-4,9'-xanthen]-2-amine (250 mg, 0.599 mmol) and CuCN (268 mg, 3.00 mmol) were brought up in NMP (1997 μL) and heated to 200° C. in the microwave. The reactions were cooled to rt, filtered and purified by reverse-phase preparative HPLC using a Gemini NX c!8 column (150*30 mm, 5 um), 0.1% TFA in CH₃CN/H₂O, gradient 0% to 70% over 10 min to provide the product. Solvent was removed by evaporation and the product was brought up in sat's aqueous NaHCO₃ and DCM and extracted with DCM. The organic washes were combined, dried over Na₂SO₄, filtered and concentrated to give (R)-2-amino-7'-(neopentyloxy)-5H-spiro[oxazole-4,9'-xanthene]-2'-carbonitrile.

Example 274

Method AA54

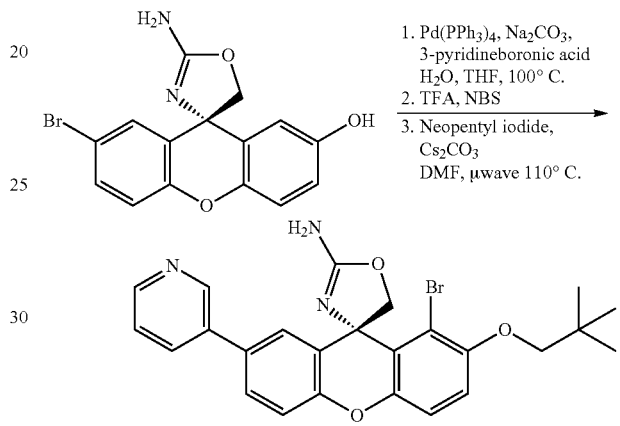

Synthesis of (S)-1'-bromo-2'-(neopentyloxy)-7'-(pyridin-3-yl)-5H-spiro[oxazole-4,9'-xanthen]-2-amine Step 1:

A 75-mL pressure vessel was charged with starting material (3.25 g, 9.36 mmol), pyridin-3-ylboronic acid (2.88 g, 23.40 mmol), tetrakis(triphenylphosphine)palladium(0) (1.081 g, 0.936 mmol), THF (46.8 mL), and potassium carbonate (23.40 mL, 46.8 mmol) (as a 2.0 M aq. solution). The vessel was sealed and placed in a 100° C. oil bath for 5 hours. The mixture was partitioned between EtOAc (50 mL) and water (50 mL). The layers were separated, and the aqueous layer was extracted with EtOAc (2×30 mL). The combined mixture was dried over sodium sulfate and filtered with the aid of 10% MeOH/DCM. The filtrate was evaporated to give a yellow solid. This solid was taken up in DCM (80 mL) and sonicated for 5 min. The solid was filtered and washed with DCM (2×40 mL), then air-dried on the filter. The filtrate was evaporated and again taken up in DCM (80 mL). The mixture was sonicated for 10 min, then filtered and washed with DCM (30 mL). The solid was air-dried and combined with the first solid to give (S)-2-amino-7'-(pyridin-3-yl)-5H-spiro[oxazole-4,9'-xanthen]-2'-ol.

Step 2:

A 50-mL RBF was charged with (S)-2-amino-7'-(pyridin-3-yl)-5H-spiro[oxazole-4,9'-xanthen]-2'-ol (1.426 g, 4.13 mmol) and TFA (20.65 mL). The mixture was stirred for 30 min and sonicated for 2 min, but it did not become a clear solution. An additional portion of TFA (5 mL) was added, giving an orange mixture. The flask was cooled in an ice-bath for 15 min. n-bromosuccinimide (0.735 g, 4.13 mmol) was added in one portion. After stirring for 2 hour the mixture was diluted with methanol and evaporated in vacuo. The residue was dissolved in methanol and loaded onto a 10-g SCX-2 column. The column was eluted with methanol to remove impurities, then with 2M ammonia in methanol to give the product. The filtrate was evaporated, and the residue was purified by chromatography on a 100-g SNAP column, eluting with 0-100% of a 90:10:1 mix of a DCM/MeOH/NH$_4$OH in DCM. The product came out in two peaks which were combined to give (S)-2-amino-1'-bromo-7'-(pyridin-3-yl)-5H-spiro[oxazole-4,9'-xanthen]-2'-ol as an off-white powder. NMR matched that of the product.

Step 3:

A vial was charged with (S)-2-amino-1'-bromo-7'-(pyridin-3-yl)-5H-spiro[oxazole-4,9'-xanthen]-2'-ol (163 mg, 0.384 mmol), cesium carbonate (375 mg, 1.152 mmol), and DMF (2.0 mL). The mixture was stirred for 10 min, then 1-iodo-2,2-dimethylpropane (102 µL, 0.768 mmol) was added. The vial was sealed and heated in a Biotage Initiator microwave reactor for 2 h at 110° C. LCMS at this time shows no starting material and mainly desired product. The mixture was partitioned between water and EtOAc. Brine was added to break up the emulsion that formed and this was partially successful. The aqueous layer was extracted with EtOAc (2×), and the combined organic extracts were dried over sodium sulfate, filtered, and evaporated. The residue was chromatographed on a 50-g SNAP column, eluting with 0-70% of a 90:10:1 mix of DCM/MeOH/NH$_4$OH in DCM to give (S)-1'-bromo-2'-(neopentyloxy)-7'-(pyridin-3-yl)-5H-spiro[oxazole-4,9'-xanthen]-2-amine as an off-white solid after evaporation from DCM/hexane.

Example 275

Method AA55

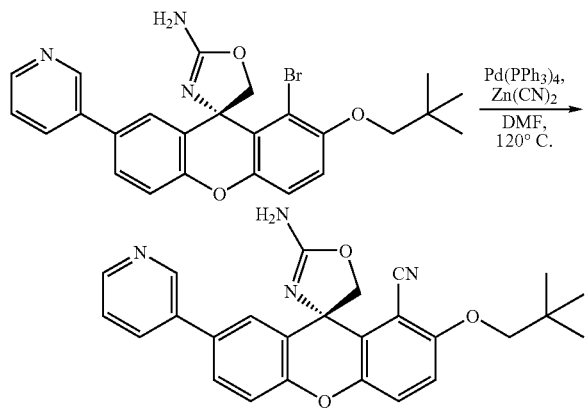

Synthesis of (S)-2-amino-2'-(neopentyloxy)-7'-(pyridin-3-yl)-5H-spiro[oxazole-4,9'-xanthene]-1'-carbonitrile A vial was charged with (S)—1'-bromo-2'-(neopentyloxy)-7'-(pyridin-3-yl)-5H-spiro[oxazole-4,9'-xanthen]-2-amine (68.1 mg, 0.138 mmol), dicyanozinc (81 mg, 0.689 mmol), tetrakis(triphenylphosphine)palladium(0) (31.8 mg, 0.028 mmol), and DMF (689 µL). The vial was sealed and placed in a 120° C. oil bath for 12 hours. The mixture was diluted with water and extracted with DCM (3×). The combined organic extracts were dried over sodium sulfate, filtered, and evaporated. The residue was chromatographed on a 25-g SNAP column, eluting with a 90:10:1 mix of DCM/MeOH/NH$_4$OH in DCM. This gave ca. 40 mg of a white powder that was impure by HPLC. The solid was combined with 104487-6-2 in DMSO/MeOH and purified by reverse-phase HPLC (10-90% CH$_3$CN/H$_2$O with 0.1% TFA). The fractions containing product were combined in saturated aq. sodium bicarbonate solution with the aid of methanol and extracted with DCM (3×). The combined organic extracts were dried over sodium sulfate, filtered, and evaporated to give (S)-2-amino-2'-(neopentyloxy)-7'-(pyridin-3-yl)-5H-spiro[oxazole-4,9'-xanthene]-1'-carbonitrile as an off-white powder after evaporation from DCM/hexane.

Example 276

Method AA56

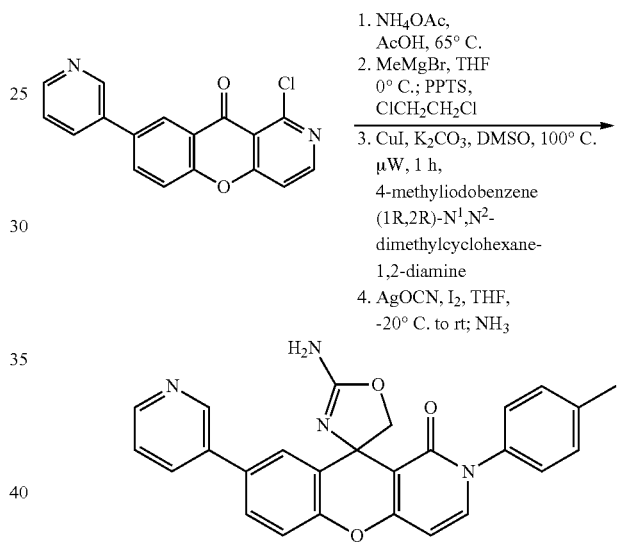

Step 1:

A resealable tube was charged with 1-chloro-8-(pyridin-3-yl)-10H-chromeno[3,2-c]pyridin-10-one (0.500 g, 1.620 mmol) and acetic acid (12.5 mL). Ammonium acetate (1.248 g, 16.20 mmol) was added, the system was purged with argon, and the tube was sealed. The mixture stirred at 65° C. for 20 h. The reaction mixture was filtered and washed with water. The filter cake was concentrated down from heptanes to afford 8-(pyridin-3-yl)-1H-chromeno[3,2-c]pyridine-1,10 (2H)-dione as an off-white solid. MS m/z=291.0 [M+H]$^+$. Calcd for C$_{17}$H$_{10}$N$_2$O$_3$: 290.07.

Step 2:

A solution of 8-(pyridin-3-yl)-1H-chromeno[3,2-c]pyridine-1,10(2H)-dione (0.100 g, 0.345 mmol) in THF (3.00 mL) was cooled to 0° C. and methylmagnesium bromide (3.0 M in diethyl ether) (0.345 mL, 1.034 mmol) was added dropwise. The mixture stirred at 0° C. for 1 h. The mixture was quenched at 0° C. with saturated aqueous ammonium chloride solution and diluted with ethyl acetate. The aqueous phase was separated and extracted with ethyl acetate. The combined organic phases were washed with brine, dried over anhydrous sodium sulfate, filtered, and concentrated to afford a tan solid. The material was dissolved in 1,2-dichloroethane (3.00 mL), pyridinium p-toluenesulfonate (8.66 mg, 0.034 mmol) was added, and the mixture was heated at reflux for 2 h to afford a tan suspension. This mixture was filtered, and the solids were washed with 1,2 dichloroethane and dried to afford 10-methylene-8-(pyridin-3-yl)-2,10-dihydro-1H-chromeno[3,2-c]pyridin-1-one as a tan solid. MS m/z=289.0 [M+H]+. Calcd for $C_{18}H_{12}N_2O_2$: 288.1.

Step 3:

A resealable tube was charged with (1R,2R)-diaminomethylcyclohexane (9.77 mg, 0.069 mmol), copper(I) iodide (8.72 mg, 0.046 mmol), 10-methylene-8-(pyridin-3-yl)-2,10-dihydro-1H-chromeno[3,2-c]pyridin-1-one (0.066 g, 0.229 mmol), 4-iodotoluene (0.055 g, 0.252 mmol), potassium carbonate (0.063 g, 0.458 mmol), and DMSO (2.5 mL). The system was purged with argon and the tube was sealed. The mixture stirred in an Initiator microwave reactor (Personal Chemistry, Biotage AB, Inc., Upssala, Sweden) at 100° C. for 2 h. The reaction mixture was diluted with dichloromethane and filtered through a pad of celite. The filtrate was concentrated and partitioned between dichloromethane and water. The aqueous phase was separated and extracted with dichloromethane. The combined organic phases were washed with brine, dried over anhydrous sodium sulfate, filtered, and concentrated to afford 10-methylene-8-(pyridin-3-yl)-2-p-tolyl-2,10-dihydro-1H-chromeno[3,2-c]pyridin-1-one. MS m/z=379.0 [M+H]+. Calcd for $C_{25}H_{18}N_2O_2$: 378.4.

Step 4:

A solution of iodine (0.061 g, 0.239 mmol) in THF (2.5 mL) was cooled to −25° C. and silver cyanate (0.102 g, 0.682 mmol) was added. The mixture stirred at −25° C. for 30 min and then a −25° C. solution of 10-methylene-8-(pyridin-3-yl)-2-p-tolyl-2,10-dihydro-1H-chromeno[3,2-c]pyridin-1-one (0.086 g, 0.227 mmol) in THF (2.5 mL) was added via cannula. The mixture stirred at −20° C. for 1 h. The reaction mixture was cooled to −40° C. and ammonia, 2.0 M in 2-propanol (0.568 mL, 1.136 mmol) was added dropwise. The reaction mixture was allowed to warm to RT overnight. The reaction mixture was filtered through celite and washed with ethyl acetate. The filtrate was partitioned between ethyl acetate and saturated aqueous sodium thiosulfate solution. The aqueous phase was separated and extracted with ethyl acetate. The combined organic phases were washed with brine, dried over anhydrous sodium sulfate, filtered, and concentrated to afford a yellow solid. This material was purified via column chromatography on silica gel (RediSep 40 g column, gradient elution with 50-100% ((90:10:1, dichloromethane/methanol/ammonium hydroxide)-dichloromethane) to afford 2'-amino-8-(pyridin-3-yl)-2-p-tolyl-5'H-spiro[chromeno[3,2-c]pyridine-10,4'-oxazol]-1(2H)-one. MS m/z=437.0 [M+H]+. Calcd for $C_{26}H_{20}N_4O_3$: 436.2.

Example 277

Method AA57

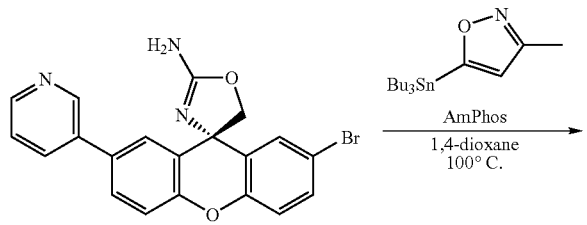

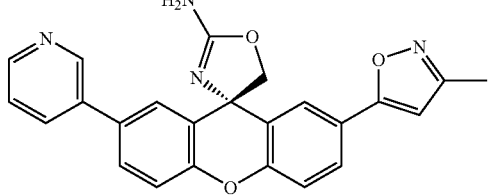

Synthesis of (S)-2'-(2-fluoropyridin-3-yl)-7'-(3-methylisoxazol-5-yl)-5H-spiro[oxazole-4,9'-xanthen]-2-amine A resealable was charged with (S)-2'-bromo-7'-(2-fluoropyridin-3-yl)-5H-spiro[oxazole-4,9'-xanthen]-2-amine (300 mg, 0.704 mmol), 3-methyl-5-(tributylstannyl)isoxazole (786 mg, 2.111 mmol), amphos (18.68 mg, 0.070 mmol) and argon purged dry dioxane (3 mL). The tube was purged with argon, sealed and heated with microwave at 100° C. for 1 h. The solution was concentrated. The crude product was purified via silica gel column chromatography (RediSep 12 g column) using 10-50% 90/10/1 DCM/MeOH/ammonia in DCM to afford (S)-2'-(2-fluoropyridin-3-yl)-7'-(3-methylisoxazol-5-yl)-5H-spiro[oxazole-4,9'-xanthen]-2-amine as a white solid. MS m/z=429.2 [M+H]+. Calcd for $C_{24}H_{17}FN_4O_3$: 428.42.

Example 278

Method AA60

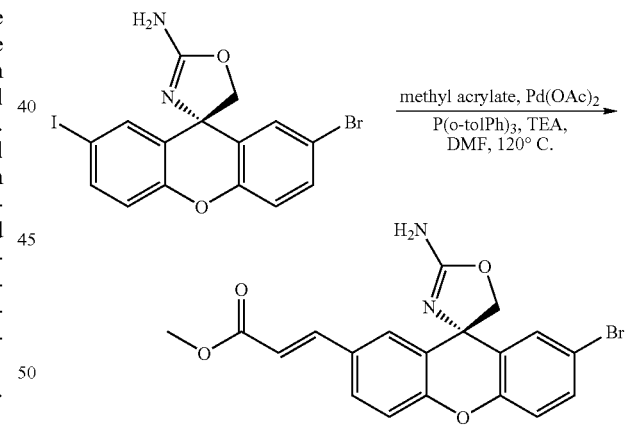

Synthesis of (S,E)-methyl 3-(2-amino-2'-bromo-5H-spiro[oxazole-4,9'-xanthene]-7'-yl)acrylate A mixture of (R)-2'-bromo-7'-iodo-5H-spiro[oxazole-4,9'-xanthen]-2-amine (3.00 g, 6.56 mmol), methyl acrylate (0.621 mL, 6.89 mmol), phosphine, tri-o-tolyl (0.400 g, 1.313 mmol), palladium(ii) acetate (0.295 g, 1.313 mmol), and triethylamine 99.5% (1.826 mL, 13.13 mmol) in DMF (12 mL) in a microwave vial was purged with argon for 5 min, capped, and heated to 120° C. for 40 min in a microwave. The reaction mixture was diluted with EtOAc (100 mL) and washed with water, dried over Na2SO4, and concentrated. The product was purified with ISCO using 0-70% EtOAc in hexanes to give (S,E)-methyl 3-(2-amino-2'-bromo-5H-spiro[oxazole-4,9'-xanthene]-7'-yl)acrylate. MS (ESI pos. ion) m/z: 416.9 (M+1).

Example 279

Method AA62

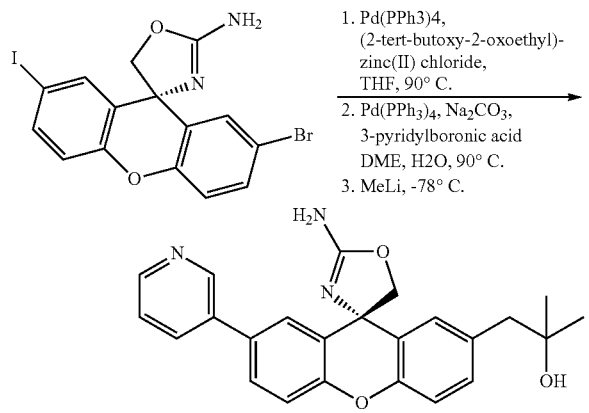

Step 1:

To a solution of (R)-2'-bromo-7'-iodo-5H-spiro[oxazole-4,9'-xanthen]-2-amine (1.5 g, 3.28 mmol) in THF (7.5 mL) was added (2-tert-butoxy-2-oxoethyl)zinc(II) chloride (21.00 mL, 10.50 mmol) (0.5 M in diethyl ether) and tetrakis(triphenylphosphine)palladium(o) (0.190 g, 0.164 mmol). The resulting mixture was then heated to 85-90° C. for overnight. Then, the mixture was cooled to RT and saturated NaHCO₃ solution (50 mL) was added. The mixture was then extracted with EtOAc (2×50 mL). The combined organic extracts were dried over MgSO₄ and concentrated. The residue was then dissolved in DCM. The solution mixture was then purified by silica gel column chromatography using ISCO instrument (solid loading, 0%-30% MeOH/DCM) to give the product as a light brown solid. MS (ESI, positive ion) m/z: 444.9, 446.9 (M+1).

Step 2:

To a solution of (R)-tert-butyl 2-(2-amino-2'-bromo-5H-spiro[oxazole-4,9'-xanthene]-7'-yl)acetate (0.663 g, 1.489 mmol) in 1,2-dimethoxyethane (7 mL) was added 3-pyridineboronic acid (0.220 g, 1.787 mmol), tetrakis(triphenylphosphine)palladium(o) (0.138 g, 0.119 mmol), bisodium carbonate (0.062 mL, 1.489 mmol), and water (2.333 mL). The resulting mixture was then heated to 85-90° C. for 5 h. Then, the mixture was cooled to room temperature and was diluted with EtOAc (10 mL). Then, saturated NaHCO₃ (3 mL) was added and the mixture was stirred at room temperature for 5 min. The organic layer was collected, dried over MgSO₄, and concentrated. The residue was then dissolved in a solution of DMSO (1 mL) and MeOH (2 mL). The solution mixture was then purified by preparative HPLC (0%-100% MeCN 0.1% TFA/H₂O 0.1% TFA) to give a desired product in a solution of MeCN/H₂O 0.1% TFA. The solution mixture was neutralized by saturated NaHCO₃. The solvent, MeCN was removed and saturated NaHCO₃ (10 mL) was added and the mixture was extracted with EtOAc (2×20 mL). The combined organic extracts were dried over MgSO₄, concentrated, and dried in vacuo to give the product both as a white solid and as an orange solid (<95% pure). MS (ESI, positive ion) m/z: 444 (M+1).

Step 3:

To a solution of (R)-tert-butyl 2-(2-amino-2'-(pyridin-3-yl)-5H-spiro[oxazole-4,9'-xanthene]-7'-yl)acetate (95 mg, 0.214 mmol) in THF (1 mL) at −78° C. was added methyllithium, 1.6M solution in diethyl ether (0.669 mL, 1.071 mmol). The resulting mixture was then stirred at −78° C. for 2 h. Then, the mixture was quenched with saturated ammonium chloride (1 mL). Then, saturated NaHCO₃ (5 mL) and EtOAc (10 mL) were added. The mixture was then extracted with EtOAc (2×10 mL). The combined organic extracts were dried over MgSO₄ and concentrated. The residue was then dissolved in a solution of DMSO (1 mL) and MeOH (1 mL). The solution mixture was then purified by preparative HPLC (0%-100% MeCN 0.1% TFA/H₂O 0.1% TFA) to give two products: R)-1-(2-amino-2'-(pyridin-3-yl)-5H-spiro[oxazole-4,9'-xanthene]-7'-yl)-2-methylpropan-2-ol and (R)-1-(2-amino-2'-(pyridin-3-yl)-5H-spiro[oxazole-4,9'-xanthene]-7'-yl)propan-2-one in a solution of MeCN/H₂O 0.1% TFA. The solution was then neutralized by saturated NaHCO₃. Then, the solvents were removed, and saturated NaHCO₃ (2 mL) and EtOAc (5 mL) were added. The mixture was then stirred at RT for 15 min. The organic layer was collected, dried over MgSO₄, concentrated, and dried in vacuo to give the depicted product as a white solid. MS (ESI, positive ion) m/z: 402 (M+1).

Example 280

Method AA63

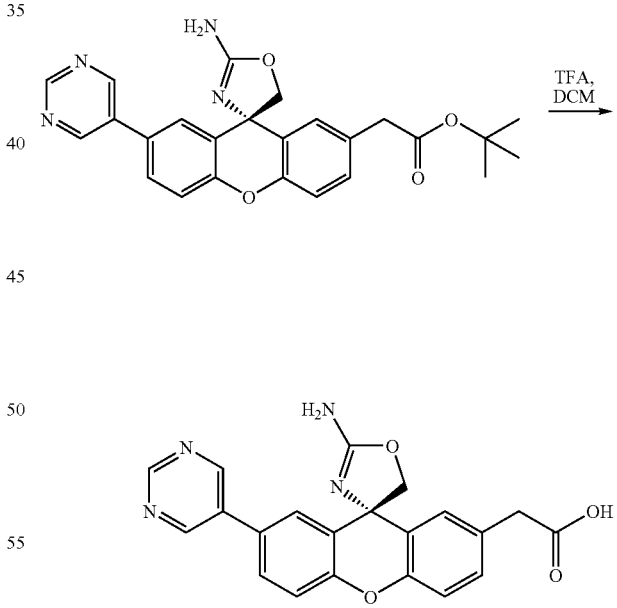

A solution of (R)-tert-butyl 2-(2-amino-2'-(pyrimidin-5-yl)-5H-spiro[oxazole-4,9'-xanthene]-7'-yl)acetate (14 mg, 0.031 mmol) in 30% TFA in DCM (0.5 mL) was stirred at room temperature for 1 h. Then, saturated NaHCO₃ solution was added slowly to the mixture at 0° C. until pH=7.0. Then, solvents were removed and the residue was dissolved in a solution of MeOH (0.5 mL), H₂O (0.1 mL), and DMF (0.3 mL). The solution mixture was then purified by preparative HPLC (0%-100% MeCN 0.1% NH₄OH/H₂O 0.1% NH₄OH) to give the acid adduct as a white solid. MS (ESI, positive ion) m/z: 389 (M+1).

Example 281

Method AA64

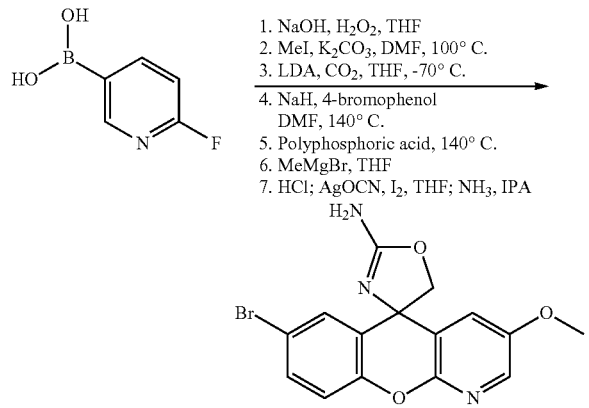

1. NaOH, H₂O₂, THF
2. MeI, K₂CO₃, DMF, 100° C.
3. LDA, CO₂, THF, -70° C.
4. NaH, 4-bromophenol DMF, 140° C.
5. Polyphosphoric acid, 140° C.
6. MeMgBr, THF
7. HCl; AgOCN, I₂, THF; NH₃, IPA Step 1:

A three neck 3-L flask equipped with an overhead stirred was charged with 6-fluoropyridin-3-ylboronic acid (105 g, 745 mmol) and 1 L of THF. The mixture was cooled to 0° C. and NaOH 6N (373 mL, 2235 mmol) was added. To the resulting mixture was added hydrogen peroxide 30% (126 mL, 4098 mmol), dropwise via an addition funnel over the course of 30 minutes. After stirring at 0° C. for 2 hours the mixture was removed from the ice bath and maintained at RT for 30 minutes. The reaction was acidified to pH 7 with 6 N HCl (ca. 300 mL) and diluted with 500 mL of ether. The aqueous layer was extracted with ether (2×1 L) and the combined organic layers were washed with water (1.5 L) then brine before being dried over sodium sulfate. Filtration and concentration provided a white solid that was dried on high vac overnight to provide 6-fluoropyridin-3-ol.

Step 2:

To a solution of 6-fluoropyridin-3-ol (75 g, 663 mmol) in DMF (265 mL, 663 mmol) were added potassium carbonate (59.7 g, 995 mmol) and iodomethane (108 g, 763 mmol). The resulting slurry was heated at 100° C. for 3 hours. The reaction was diluted with water (1000 mL) and poured into a separatory funnel containing diethyl ether (1000 mL). The layers were separated and the aqueous layer was extracted with diethyl ether (4×500 mL). The combined organic layers were washed with water and then brine, dried over sodium sulfate, filtered and concentrated in vacuo to provide a yellow oil. This oil was diluted with 500 mL of DCM and concentrated to provide a yellow oil with a large amount of an off white precipitate. The mixture was filtered and the derived solid was washed well with DCM. The filtrate was concentrate to provide a mixture consisting of a yellow oil and an off white solid. The solid eas filtered, washing with DCM. Repeat this procedure again and then concentrated the filtrate to provide a yellow oil. The oil was taken up in 100 mL of ether and flashed through a plug of silica gel with 10:1 hexanes:ether to provide 2-fluoro-5-methoxypyridine as a yellow oil.

Step 3:

To a solution of DIPA (54.0 mL, 385 mmol) in THF (1101 mL, 385 mmol) at −60° C. was added BuLi, 2.5 M in hexanes (154 mL, 385 mmol) over 5 minutes such that the internal temperature was maintained below −60° C. After stirring for 45 minutes at −65° C. a solution of 2-fluoro-5-methoxypyridine (49 g, 385 mmol) in 200 mL of THF was added over the course of 2 minutes maintaining an internal temperature < −65° C. The reaction was stirred at −70° C. for 1.5 hours then reaction was poured into a 3 L flask containing 1200 g of crushed dry ice. The reaction was allowed to warm to 0° C. and then poured into 1000 mL of water. The organics were removed under reduced pressure and the aqueous layer was acidified with 1100 mL of 2 N HCl. The resulting thick white slurry was stirred for 1 hour then filtered to provide 2-fluoro-5-methoxynicotinic acid as a white solid.

Step 4:

To a slurry of sodium hydride (60% dispersion) (21.74 g, 543 mmol) in DMF (351 mL, 175 mmol) at 0° C. was added 4-bromophenol (60.7 g, 351 mmol) over the course of 5 minutes. Stirred at 0° C. for two minutes then removed from the ice bath and stirred for an additional 5 minutes at room temperature. Added 2-fluoro-5-methoxynicotinic acid (30 g, 175 mmol) portionwise over 10 minutes and heated the resulting slurry at 140° C. After cooling to room temperature the mixture was then poured onto 1 kg of ice and was quenched with acetic acid (50.2 mL, 877 mmol) and then 75 mL of 6 N HCl. Stirred vigorously for 1 hour, leading to the formation of a red slurry containing a very fine white precipitate. Filtered the slurry to provide 2-(4-bromophenoxy)-5-methoxynicotinic acid.

Step 5:

A 2 L flask charged with polyphosphoric acid (115% H₃PO₄) (300 g, 89 mmol) was heated to 140° C. at which point 2-(4-bromophenoxy)-5-methoxynicotinic acid (29 g, 89 mmol) was introduced. The thick viscous mixture is slowly stirred while heating at 140° C. After heating for 2.5 hours the solution was cooled to 100° C. and then poured onto 1 kg of ice, leading to the formation of a yellow taffy mixture. The slurry was vigorously stirred for 1 hour leading to the formation of a fine white precipitate. Filtration of this mixture proceeded slowly to provide an off white solid. This solid was washed well with DCM. The filtrate, which contained the desired product, was washed with brine and concentrated to provide 7-bromo-3-methoxy-5H-chromeno[2,3-b]pyridin-5-one as an off-white solid.

Step 6:

To a slurry of 7-bromo-3-methoxy-5H-chromeno[2,3-b]pyridin-5-one (23 g, 75 mmol) in THF (751 mL, 75 mmol) at −40° C. was added methylmagnesium chloride, 3.0 M solution in THF (88 mL, 263 mmol) over 2 minutes such that the temperature did not rise above −35° C. The resulting red slurry was maintained at −30° C. After 1 hour the reaction, which was now homogeneous, was quenched with 50 mL of ethyl acetate. The solution was then carefully quenched with 800 mL of 50% ammonium chloride. The mixture was poured into a separatory funnel containing ethyl acetate (100 mL). The layers were separated and the organics were washed with brined, dried over sodium sulfate, filtered and concentrated. The aqueous layer was extracted with ethyl acetate (3×500 mL). The combined organic layers were washed with water and then brine, dried over sodium sulfate, filtered, and combined with the above derived oil. This organic solution was washed with brined, dried over sodium sulfate, filtered and concentrated to provide 7-bromo-3-methoxy-5-methyl-5H-chromeno[2,3-b]pyridin-5-ol as a yellow solid.

Step 7:

To a solution of 7-bromo-3-methoxy-5-methyl-5H-chromeno[2,3-b]pyridin-5-ol (23.5 g, 72.9 mmol) in THF (729 mL, 72.9 mmol) was added HCl (1 M in ether) (0.729 mL, 0.729 mmol). The resulting solution was heated at 45° C. for 1 hour. The light yellow solution was cooled to −25° C. and added to the slurry below.

In a separate 2 L flask was added iodine (20.37 g, 80 mmol) and 400 mL of THF. This solution was cooled to −15° C. and silver cyanate (32.8 g, 219 mmol) was added. The resulting slurry was maintained at −40° C. for 25 minutes before the above solution was added via cannula over 15 minutes maintaining the temperature below −35° C. The derived slurry was maintained at −30° C. for 1 hour at which it was filtered through a pad of celite, washing well with 200 mL of THF. The derived brown solution was cooled to −20° C. and treated with ammonia, 2.0 M solution in 2-propanol (219 mL, 438 mmol). The resulting solution was allowed to slowly warm to rt overnight. To the reaction was added 700 mL of 10% sodium thiosulfate and the resulting light orange solution was stirred for minutes before being poured into a separatory funnel containing 250 mL of ethyl acetate. The layers were separated and the organics were washed with brine and then concentrated in vacuo. This mixture was combined with the organic extracts obtained below.

The aqueous layer was extracted with ethyl acetate (2×500 mL). These organics were combined with the organics obtained and poured into a separatory funnel. The layers were separated and the aqueous layer was extracted with ethyl acetate (2×100 mL). The combined organic layers were washed with brine, dried over sodium sulfate, filtered and concentrated in vacuo to provide 25 g of 7-bromo-3-methoxy-5'H-spiro[chromeno[2,3-b]pyridine-5,4'-oxazol]-2'-amine as a brown solid.

Example 282

Method CK01

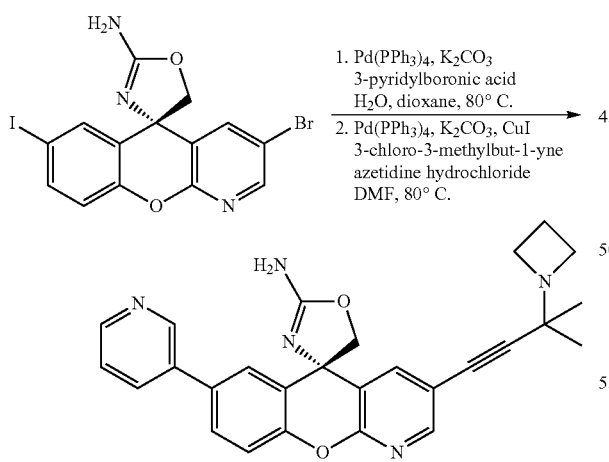

Synthesis of (S)-3-(3-(azetidin-1-yl)-3-methylbut-1-ynyl)-7-(pyridin-3-yl)-5'H-spiro[chromeno[2,3-b]pyridine-5,4'-oxazol]-2'-amine Step 1:

A vial charged with pyridin-3-ylboronic acid (0.295 g, 2.401 mmol), palladiumtetrakis (0.126 g, 0.109 mmol), potassium carbonate (1.509 g, 10.92 mmol), and (S)-3-bromo-7-iodo-5'H-spiro[chromeno[2,3-b]pyridine-5,4'-oxazol]-2'-amine (1.000 g, 2.183 mmol) was treated with 11 mL dioxane followed by 4.5 mL water. The vial was flushed with argon and was heated to 80° C. for 4 hours. The reaction mixture was diluted with EtOAc and dried over MgSO$_4$. The organics were then concentrated, and the crude residue was purified by column chromatography yielding (S)-3-bromo-7-(pyridin-3-yl)-5'H-spiro[chromeno[2,3-b]pyridine-5,4'-oxazol]-2'-amine.

Step 2:

A vial charged with potassium carbonate (0.338 g, 2.444 mmol), (S)-3-bromo-7-(pyridin-3-yl)-5'H-spiro[chromeno[2,3-b]pyridine-5,4'-oxazol]-2'-amine (0.100 g, 0.244 mmol), azetidine hydrochloride (0.209 g, 3.67 mmol), copper (i) iodide (4.65 mg, 0.024 mmol), and palladiumtetrakistriphenylphosphine (0.028 g, 0.024 mmol) was treated with 2 mL DMF and was thoroughly degassed with argon gas. 3-chloro-3-methylbut-1-yne (0.125 g, 1.222 mmol) was added, the vial was placed under argon, and was heated to 80° C. for 4 hours. The reaction mixture was poured into water and was extracted with EtOAc. The organics were washed with brine, dried over MgSO$_4$ and concentrated. Purification of the crude residue by column chromatography gave (S)-3-(3-(azetidin-1-yl)-3-methylbut-1-ynyl)-7-(pyridin-3-yl)-5'H-spiro[chromeno[2,3-b]pyridine-5,4'-oxazol]-2'-amine.

Example 283

Method OE10

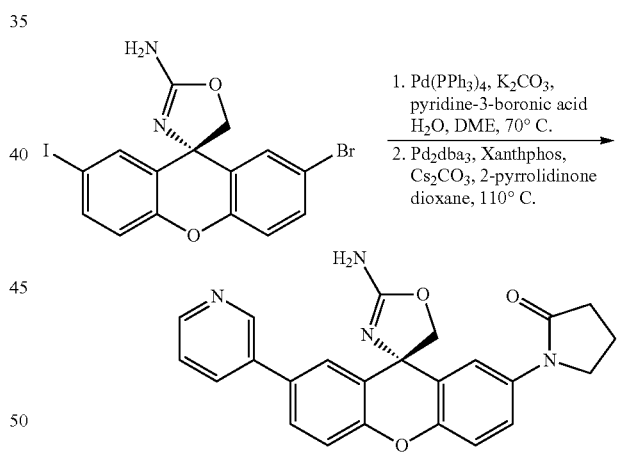

Step 1:

A 100 ml RB flask was charged with (R)-2'-bromo-7'-iodo-5H-spiro[oxazole-4,9'-xanthen]-2-amine (3.3 g, 7.22 mmol), pyridin-3-ylboronic acid (1.163 g, 9.39 mmol), and tetrakis(triphenylphosphine)palladium(0) (0.834 g, 0.722 mmol). To this were added DME (51.6 mL) followed by sodium carbonate (10.83 mL, 21.66 mmol) (2M solution) and the mixture was heated at 70° C. for 24 hrs. The mixture was diluted with water and ethyl acetate, filtered and organic layer was separated and concentrated. The crude material was purified by FC on 80 g RediSep column using 5-70% gradient of DCM/MeOH/NH4OH in DCM to give (S)-2'-bromo-7'-(pyridin-3-yl)-5H-spiro[oxazole-4,9'-xanthen]-2-amine (1.82 g, 4.45 mmol, 61.6% yield).

Step 2:

A microwave vial was charged with (S)-2'-bromo-7'-(pyridin-3-yl)-5H-spiro[oxazole-4,9'-xanthen]-2-amine (100 mg, 0.245 mmol), cesium carbonate (120 mg, 0.367 mmol), Xanthphos (42.5 mg, 0.073 mmol), $Pd_2(dba)_3$ (22.43 mg, 0.024 mmol). Dioxane (1 mL) and 2-pyrrolidinone (23 μL, 0.294 mmol) were added and the vial was sealed and heated at 110° C. for 3 hrs. The mixture was diluted with ethyl acetate filtered through celite and concentrated The material was redissolved in MeOH and repurified by reverse phase HPLC using 15-90% MeCN in 0.1% aq TFA. The fractions containing product were concentrated and liophilized over weekend to afford (S)-1-(2-amino-2'-(pyridin-3-yl)-5H-spiro[oxazole-4,9'-xanthene]-7'-yl)pyrrolidin-2-one 2,2,2-trifluoroacetate (57 mg, 0.108 mmol, 44.2% yield).

Example 284

Method TAD10

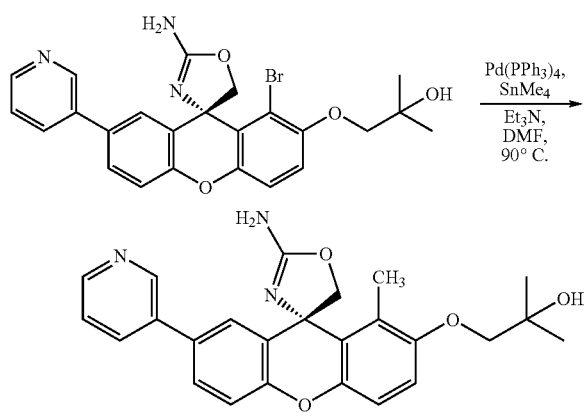

Synthesis of (S)-1-(2-amino-1'-methyl-7'-(pyridin-3-yl)-5H-spiro[oxazole-4,9'-xanthene]-2'-yloxy)-2-methylpropan-2-ol A vial was charged with (S)-1-(2-amino-1'-bromo-7'-(pyridin-3-yl)-5H-spiro[oxazole-4,9'-xanthene]-2'-yloxy)-2-methylpropan-2-ol (150 mg, 0.302 mmol), tetrakis(triphenylphosphine)palladium(0) (34.9 mg, 0.030 mmol), TEA (168 μL, 1.209 mmol), and tetramethyltin (617 μL, 4.53 mmol). The vial was sealed and heated in a 90° C. oil bath 16 h. The mixture was cooled to RT, diluted with water, and extracted with EtOAc (3×). The combined organic extracts were dried over sodium sulfate, filtered, and evaporated. The residue was dissolved in methanol and filtered through a 0.2 micron filter. The filtrate was purified by reverse-phase HPLC (10-40% $CH_3CN/H_2O$ with 0.1% TFA). The fractions containing product combined in saturated aq. sodium bicarbonate solution with the aid of methanol and extracted with DCM (3×). The combined organic extracts were dried over sodium sulfate, filtered, and evaporated to give (S)-1-(2-amino-1'-methyl-7'-(pyridin-3-yl)-5H-spiro[oxazole-4,9'-xanthene]-2'-yloxy)-2-methylpropan-2-ol as a white solid. MS m/z=432.0. Calc'd for $C_{25}H_{26}N_3O_4$: 432.19.

Example 284

Method WQ 1

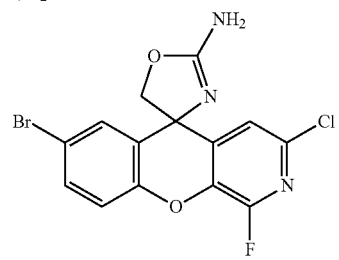

1. 2,6dibromobenzoic acid, $Cs_2CO_3$ CuOTf, ethyl acetate, toluene, 120° C.
2. Diethylamine, TBTU, DMF
3. Urea hydrogen peroxide, TFAA
4. $POCl_3$
5. LDA, THF, -78° C.
6. MeMgBr, THF; $I_2$, AgOCN; $NH_3$
7. Amphos, $K_3PO_4$, 3-pyridineboronic acid dioxane, $H_2O$ Synthesis of 1-fluoro-3,7-di(pyridin-3-yl)-5'H-spiro[chromeno[2,3-c]pyridine-5,4'-oxazol]-2'-amine Step 1:

A 500 mL RBF was charged with 2-fluoro-3-hydroxypyridine (3487 mg, 30.8 mmol), 2,5-dibromobenzoic acid (8630 mg, 30.8 mmol), copper (I) trifluoromethane-sulfonate toluene complex (2:1) (399 mg, 0.771 mmol) and cesium carbonate (2.01E+04 mg, 61.7 mmol). To this was added 100 mL of toluene and the mixture was azeotroped to remove about 20 mL of toluene under reduced pressure. Reaction mixture was then flushed with N2 and was heated to 120° C. for 2 hours. LC-MS analysis showed formation of the desired product along with significant impurities. The reaction mixture was cooled to RT and concentrated to give a gummy residue. The residue was taken up in ethyl acetate (100 mL) and water (75 mL). The aqueous layer was neutralized with 1N HCl to pH ~2.0-3.0. The aqueous layer was extracted with ethyl acetate (2×150 mL), separated, dried over anhydrous sodium sulfate, and concentrated to yield the crude product as a brown solid which was used directly in the next step.

Step 2:

A mixture of crude 5-bromo-2-(2-fluoropyridin-3-yloxy)benzoic acid (8.00 g, 25.6 mmol), diethylamine (6.63 mL, 64.1 mmol) and TBTU (8.23 g, 25.6 mmol) in 8 mL of DMF was stirred overnight. The reaction was quenched with Sat. NaHCO3, extracted with EA/H=2:1, washed with brine, dried over Na2SO4, filtered and evaporated to dryness. CC (DCM to DCM/EA 100:5 to 100:10 to 100:20 to 3:1) gave 5-bromo-N,N-diethyl-2-(2-fluoropyridin-3-yloxy)benzamide as a yellow solid.

Step 3:

To a solution of 5-bromo-N,N-diethyl-2-(2-fluoropyridin-3-yloxy)benzamide (1.4 g, 3.81 mmol) and urea peroxide (1.076 g, 11.44 mmol) in 10 mL of DCM at 0 C was added dropwise trifluoroacetic anhydride (1.601 mL, 11.44 mmol) and the resulting reaction was stirred overnight. LCMS showed only less than 50% of desired conversion. The mixture was evaporated to dryness, quenched with Sat. NaHCO₃, extracted with EA, dried over Na₂SO₄, filtered and evaporated to dryness. CC (DCM to DCM/EA=3:1 to DCM/MeOH=100:2 to 100:5 to 100:10) gave 3-(4-bromo-2-(diethylcarbamoyl)phenoxy)-2-fluoropyridine 1-oxide as an offwhite solid.

Step 4:

To a solution of 3-(4-bromo-2-(diethylcarbamoyl)phenoxy)-2-fluoropyridine 1-oxide (420 mg, 1.096 mmol) in 15 mL of DCM was added dropwise phosphorus oxychloride (301 μL, 3.29 mmol) followed by 2 drops of DMF. After stirring at rt for 1 h, the reaction was quenched with sat. NaHCO₃, extracted with EA, dried over Na2SO4, filtered and evaporated to dryness. CC (DCM to DCM/EA=10:1 to 5:1 to 3:1) gave 5-bromo-2-(6-chloro-2-fluoropyridin-3-yloxy)-N,N-diethylbenzamide as a colorless gum.

Step 5:

To a solution of 5-bromo-2-(6-chloro-2-fluoropyridin-3-yloxy)-N,N-diethylbenzamide (120 mg, 0.299 mmol) in 5 mL of dry THF at −78 C was added dropwise lithium diisopropylamide, 2.0 m heptane/tetrahydrofuran/ethylbenzene (158 μL, 1.195 mmol) (0.6 mL of 2M solution) and the reaction was stirred at −78 C for 3 h. The reaction was quenched at −78 C with sat. NH₄Cl and was allowed to warm up to RT. The reaction was extracted with EA, dried over Na₂SO₄, filtered and evaporated to dryness. CC (hexane to H/DCM=1:1 to DCM) gave 7-bromo-3-chloro-1-fluoro-5H-chromeno[2,3-c]pyridin-5-one as an offwhite solid. MS (M+1): 328.

Step 6:

To a solution of 7-bromo-3-chloro-1-fluoro-5H-chromeno[2,3-c]pyridin-5-one (50 mg, 0.152 mmol) in 5 mL of dry THF at −78 C was added methylmagnesium chloride, 3.0 m solution in tetrahydrofuran (16.87 μL, 0.228 mmol) (0.07 mL) and the reaction was slowly warmed up to −30 C. Only half of conversion was detected. To this was added another batch of methylmagnesium chloride, 3.0 m solution in THF (16.87 μL, 0.228 mmol) (0.07 mL). The reaction was quenched at −30 C with sat. NH₄Cl, extracted with EA, dried over Na₂SO₄, filtered and evaporated to dryness. It was then treated with 1 mg of PPTS in DCM at 25 C for 0.5 h. After cooling, 0.1 g of NaHCO₃ was added the solvent was evaporated to dryness to give crude 7-bromo-3-chloro-1-fluoro-5-methylene-5H-chromeno[2,3-c]pyridine which was directly used in the next step.

A solution of iodine (8.23 μL, 0.160 mmol) in THF at −25 C was treated with silver cyanate (22.81 μL, 0.609 mmol). After 30 min, a solution of crude 7-bromo-3-chloro-1-fluoro-5-methylene-5H-chromeno[2,3-c]pyridine in THF was added dropwise. The slurry was maintained at −25 C for 2 h until LCMS showed complete consumption of starting material. The slurry was filtered through celite with ether. The brown solution was concentrated to dryness, taken up in THF, cooled to 0 C and treated with ammonia, 2 m solution in 2-propanol (13.21 μL, 0.609 mmol) (0.4 mL). The reaction was allowed to slowly warm to RT and stirred overnight. Half the solvent was evaporated and the residue was diluted with water, extracted with EA, dried over Na₂SO₄, filtered and evaporated to dryness. The residue was filtered, washed with DCM and air dried to give 7-bromo-3-chloro-1-fluoro-5'H-spiro[chromeno[2,3-c]pyridine-5,4'-oxazol]-2'-amine as a yellow solid. MS (M+1): 384.

Step 7:

A mixture of 7-bromo-3-chloro-1-fluoro-5'H-spiro[chromeno[2,3-c]pyridine-5,4'-oxazol]-2'-amine (40.0 mg, 0.104 mmol), pyridin-3-ylboronic acid (21.73 mg, 0.177 mmol), bis-(di-tert-butyl(4-dimethylaminophenyl)phosphine)dichloropalladium(ii) (2.95 mg, 4.16 μmol) and potassium phosphate (66.2 mg, 0.312 mmol) in 1.5 ml of dioxane/water=2:1 was heated at 120 C microwave for 20 min. LCMS showed mostly conversion to the mono coupling product. 10 mg of pyridin-3-ylboronic acid (21.73 mg, 0.177 mmol) was added and the reaction was heated at 140 C under microwave for 20 min.

The reaction mixture was directly loaded to CC (SiO2, DCM to DCM/MeOH=100:1 to 100:6) to give crude final product which was further purified by prep TLC (DCM/MeOH) to give 1-fluoro-3,7-di(pyridin-3-yl)-5'H-spiro[chromeno[2,3-c]pyridine-5,4'-oxazol]-2'-amine as a white solid. MS (M+1): 426.

Example 285

Method RR1

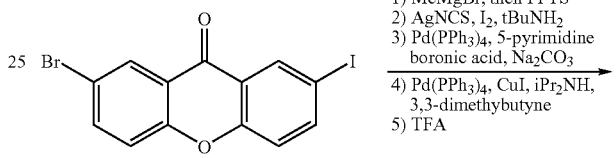

1) MeMgBr, then PPTS
2) AgNCS, I₂, tBuNH₂
3) Pd(PPh₃)₄, 5-pyrimidine boronic acid, Na₂CO₃
4) Pd(PPh₃)₄, CuI, iPr₂NH, 3,3-dimethybutyne
5) TFA

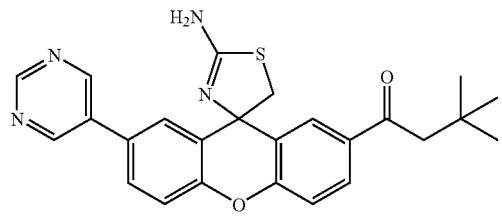

Synthesis of (R) and (S)-1-(2-amino-2'-(pyrimidin-5-yl)-5H-spiro[thiazole-4,9'-xanthene]-7'-yl)-3,3-dimethylbutan-1-one Step 1:

A 500 ml RB flask was charged with 2-bromo-7-iodo-9H-xanthen-9-one (16.030 g, 40.0 mmol) and THF (150 mL). The mixture was stirred for 10 min at RT and the resulting suspension was placed in water-ice bath for another 10 min. Methylmagnesium bromide, 3.0 M in Et2O (20.0 ml, 60.0 mmol) was added dropwise. After 1 hr, the mixture was carefully quenched with sat NH4Cl (150 mL) at 0° C. and diluted with EtOAc. The organic layer was washed with brine, dried with sodium sulfate, and concentrated in vacuo. The material was dissolved in 100 mL of methylene chloride, treated with PPTS (0.201 g, 0.800 mmol), and heated to reflux for 2 hr. The mixture was cooled to RT, diluted with DCM, and washed with saturated sodium bicarbonate and brine. The organic fraction was dried over sodium sulfate and concentrated in vacuo to afford crude 2-bromo-7-iodo-9-methylene-9H-xanthene as a light orange solid that was advanced without further purification. MS: MH+=399.0/401.0.

Step 2:

A 100 mL flask was charged with iodine (1.002 g, 3.95 mmol) and THF (30 mL) and the resulting solution was cooled to −20° C. in a methanol-ice bath. Thiocyanatosilver (1.872 g, 11.28 mmol) was added in one portion and the resulting mixture was stirred for 0.5 hr at ca. −15° C. Crude 2-bromo-7-iodo-9-methylene-9H-xanthene (1.500 g, 3.76 mmol) was added as a solid in one portion and the resulting mixture was stirred for 5 min @−15° C., then at 0° C. for 1 hr. The yellow mixture was filtered through celite with the aid of THF (5 ml) and to the filtrate was dropwise added 2-methyl-propan-2-amine (1.195 mL, 11.28 mmol) at RT. After 20 hrs, the solution was concentrated in vacuo, taken up in DCM, and adsorbed onto silica gel. The material was purified by silica gel chromatography using 15-30% Hexanes:EtOAc to afford 2'-bromo-N-tert-butyl-7'-iodo-5H-spiro[thiazole-4,9'-xanthen]-2-amine as a yellow solid. MS: MH+=529.8/530.8.

Step 3:

To a mixture of sodium carbonate (1.562 g, 14.74 mmol), palladium tetrakistriphenylphosphine (0.454 g, 0.393 mmol), pyrimidin-5-ylboronic acid (0.791 g, 6.39 mmol) and 2'-bromo-N-tert-butyl-7'-iodo-5H-spiro[thiazole-4,9'-xanthen]-2-amine (2.600 g, 4.91 mmol) in a resealable pressure tube, was added DME (15 mL) and water (5 mL) at RT. The tube was sealed and heated to 80° C. After 24 hrs, the mixture was cooled to RT, diluted with EtOAc, and washed with water and brine. The organic fraction was adsorbed onto silica gel and purified by silica gel chromatography using 40% hexanes:EtOAc to afford 2'-bromo-N-tert-butyl-7'-(pyrimidin-5-yl)-5H-spiro[thiazole-4,9'-xanthen]-2-amine. MH+=481.0/483.0.

Step 4:

A resealable tube was charged with (t-4)-tetrakis(triphenylphosphine)palladium (27.1 mg, 0.023 mmol), copper(i) iodide (8.94 mg, 0.047 mmol),2'-bromo-N-tert-butyl-7'-(pyrimidin-5-yl)-5H-spiro[thiazole-4,9'-xanthen]-2-amine (113 mg, 0.235 mmol), 3,3-dimethylbut-1-yne (144 μL, 1.174 mmol), diisopropylamine (669 μL, 4.69 mmol) and DMF (1.9 mL). The mixture was heated at 80° C. After 18 hrs, the mixture was cooled to RT, filtered through celite with EtOAc, and concentrated in vacuo. The residue was adsorbed onto silica gel and purified by silica gel chromatography using 30-75% Hexanes:EtOAc to afford N-tert-butyl-2'-(3,3-dimethylbut-1-ynyl)-7'-(pyrimidin-5-yl)-5H-spiro[thiazole-4,9'-xanthen]-2-amine as an off-white foam. MH+=483.2.

Step 5:

A resealable tube charged with N-tert-butyl-2'-(3,3-dimethylbut-1-ynyl)-7'-(pyrimidin-5-yl)-5H-spiro[thiazole-4,9'-xanthen]-2-amine (0.113 g, 0.234 mmol) and TFA (2 mL) was sealed and heated to 160° C. After 3 hrs, the solvent was removed in vacuo and the residue taken up in 2 mL DCM. TEA (ca. 0.1 mL) was added and the solution was loaded onto a silica gel plug and purified by silica gel chromatography using 2-4% MeOH:DCM w/1% NH$_4$OH to afford crude, racemic product that was resolved by chiral column chromatography to give both (R) and (S)-1-(2-amino-2'-(pyrimidin-5-yl)-5H-spiro[thiazole-4,9'-xanthene]-7'-yl)-3,3-dimethylbutan-1-one. MS Found: MH+=445.2.

Example 285

Method RR2

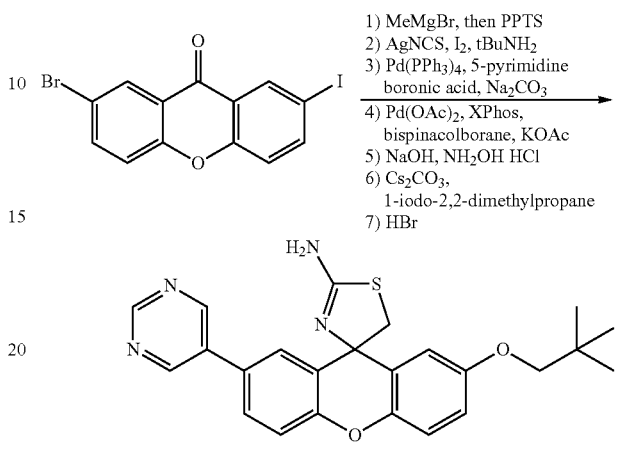

Synthesis of (R) and (S)-2'-(neopentyloxy)-7'-(pyrimidin-5-yl)-5H-spiro[thiazole-4,9'-xanthen]-2-amine Step 1:

A 500 ml RB flask was charged with 2-bromo-7-iodo-9H-xanthen-9-one (16.030 g, 40.0 mmol) and THF (150 mL). The mixture was stirred for 10 min at RT and the resulting suspension was placed in water-ice bath for another 10 min. Methylmagnesium bromide, 3.0 M in Et$_2$O (20.0 ml, 60.0 mmol) was added dropwise. After 1 hr, the mixture was carefully quenched with sat NH$_4$Cl (150 mL) at 0° C. and diluted with EtOAc. The organic layer was washed with brine, dried with sodium sulfate, and concentrated in vacuo. The material was dissolved in 100 mL of methylene chloride, treated with PPTS (0.201 g, 0.800 mmol), and heated to reflux for 2 hr. The mixture was cooled to RT, diluted with methylene chloride, and washed with saturated sodium bicarbonate and brine. The organic fraction was dried over sodium sulfate and concentrated in vacuo to afford crude 2-bromo-7-iodo-9-methylene-9H-xanthene as a light orange solid that was advanced without further purification. MS: MH+=399.0/401.0.

Step 2:

A 100 mL flask was charged with iodine (1.002 g, 3.95 mmol) and THF (30 mL) and the resulting solution was cooled to −20° C. in a methanol-ice bath. Thiocyanatosilver (1.872 g, 11.28 mmol) was added in one portion and the resulting mixture was stirred for 0.5 hr at ca. −15° C. Crude 2-bromo-7-iodo-9-methylene-9H-xanthene (1.500 g, 3.76 mmol) was added as a solid in one portion and the resulting mixture was stirred for 5 min @−15° C., then at 0° C. for 1 hr. The yellow mixture was filtered through celite with the aid of THF (5 ml) and to the filtrate was dropwise added 2-methyl-propan-2-amine (1.195 mL, 11.28 mmol) at RT. After 20 hrs, the solution was concentrated in vacuo, taken up in CH2Cl2, and adsorbed onto silica gel. The material was purified by silica gel chromatography using 15-30% Hexanes:EtOAc to afford 2'-bromo-N-tert-butyl-7'-iodo-5H-spiro[thiazole-4,9'-xanthen]-2-amine as a yellow solid. MH+=529.8/530.8.

Step 3:

To a mixture of sodium carbonate (1.562 g, 14.74 mmol), palladium tetrakistriphenylphosphine (0.454 g, 0.393 mmol), pyrimidin-5-ylboronic acid (0.791 g, 6.39 mmol) and 2'-bromo-N-tert-butyl-7'-iodo-5H-spiro[thiazole-4,9'-xanthen]-2-amine (2.600 g, 4.91 mmol) in a resealable pressure tube, was added DME (15 mL) and water (5 mL) at RT. The tube was sealed and heated to 80° C. After 24 hrs, the mixture was cooled to RT, diluted with EtOAc, and washed with water and brine. The organic fraction was adsorbed onto silica gel and purified by silica gel chromatography using 40% hexanes:EtOAc to afford 2'-bromo-N-tert-butyl-7'-(pyrimidin-5-yl)-5H-spiro[thiazole-4,9'-xanthen]-2-amine. MS: MH+=481.0/483.0.

Step 4:

A pressure tubel was charged with 2'-bromo-N-tert-butyl-7'-(pyrimidin-5-yl)-5H-spiro[thiazole-4,9'-xanthen]-2-amine (0.150 g, 0.312 mmol), 4,4,4',4',5,5,5',5'-octamethyl-2,2'-bi(1,3,2-dioxaborolane) (0.237 g, 0.935 mmol), potassium acetate (0.092 g, 0.935 mmol), XPhos (0.030 g, 0.062 mmol), diacetoxypalladium (7.00 mg, 0.031 mmol), and 1,4-dioxane (3.0 mL, 0.312 mmol). The tube was purged with Argon, sealed, and heated to 100° C. After 18 hrs the dark mixture was filtered over celite with EtOAc. The filtrate was concentrated in vacuo and purified by silica gel chromatography using 25-50% Hexanes:EtOAc to afford N-tert-butyl-2'-(pyrimidin-5-yl)-7'-(4,4,5,5-tetramethyl-1,3,2-dioxaborolan-2-yl)-5H-spiro[thiazole-4,9'-xanthen]-2-amine as a white foam. MH+=529.2.

Step 5:

To a mixture of N-tert-butyl-2'-(pyrimidin-5-yl)-7'-(4,4,5,5-tetramethyl-1,3,2-dioxaborolan-2-yl)-5H-spiro[thiazole-4,9'-xanthen]-2-amine (0.475 g, 0.899 mmol), NaOH solid (0.062 mL, 3.33 mmol), and hydroxyammonium chloride (0.120 mL, 2.88 mmol) was added Ethanol (8 mL). The mixture was stirred at RT. After 48 hrs, the mixture was concentrated in vacuo and the residue partioned between DCM and water. The aqueous layer was acidified to ca. pH=7 and extracted with CH$_2$Cl$_2$. The combined organic fractions were adsorbed onto silica gel and purified by silica gel chromatography using 40-80% Hexanes:EtOAc to give 2-(tert-butylamino)-7'-(pyrimidin-5-yl)-5H-spiro[thiazole-4,9'-xanthen]-2'-ol as an off-white solid. MS: MH+=419.2.

Step 6:

To a solution of 2-(tert-butylamino)-7'-(pyrimidin-5-yl)-5H-spiro[thiazole-4,9'-xanthen]-2'-ol (0.075 g, 0.179 mmol) in DMF (2 mL) was added cesium carbonate (0.175 g, 0.538 mmol) followed by 1-iodo-2,2-dimethylpropane (0.048 mL, 0.358 mmol). The mixture was heated to 100° C. After 6 hrs the mixture was cooled to RT, diluted with EtOAc, and washed with water and brine. The organic fraction was concentrated in vacuo and purified by silica gel chromatography using 40-60% Hexanes:EtOAc to afford N-tert-butyl-2'-(neopentyloxy)-7'-(pyrimidin-5-yl)-5H-spiro[thiazole-4,9'-xanthen]-2-amine as an off-white foam. MS: MH+=489.2.

Step 7:

A resealable tube charged with a solution of N-tert-butyl-2'-(neopentyloxy)-7'-(pyrimidin-5-yl)-5H-spiro[thiazole-4,9'-xanthen]-2-amine (0.033 g, 0.068 mmol) in 48% HBr (1.00 mL, 18.42 mmol) was heated to 80° C. After 3 hrs, the solution was cooled and evaporated to dryness with a stream of N2. The residue was treated with CH2Cl2 (2 mL) and TEA (0.1 mL). The solution was loaded onto a silica gel column and purified with 1-5% MeOH:CH2Cl2 w/1% NH4OH (Rf=0.5 in 10% MeOH:CH2Cl2 w/1% NH4OH) to afford racemic material that was resolved by chiral chromatography to give both (R) and (S)-2'-(neopentyloxy)-7'-(pyrimidin-5-yl)-5H-spiro[thiazole-4,9'-xanthen]-2-amine. MS Found: MH+=433.2.

Example 286

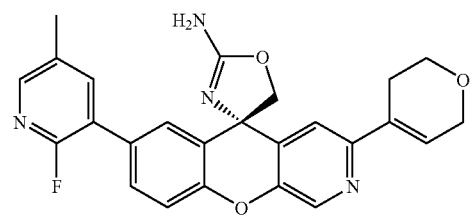 [SMILES: Cc1cnc(F)c(-c2ccc3c(c2)[C@@]2(COC(N)=N2)c2cc(C4=CCOCC4)ncc2O3)c1]

A glass microwave reaction vessel was charged with (S)-3-chloro-7-(2-fluoro-5-methylpyridin-3-yl)-5'H-spiro[chromeno[2,3-c]pyridine-5,4'-oxazol]-2'-amine (0.100 g, 0.252 mmol), potassium phosphate (0.160 g, 0.756 mmol), 2-(3,6-dihydro-2H-pyran-4-yl)-4,4,5,5-tetramethyl-1,3,2-dioxaborolane (0.106 g, 0.504 mmol) and Bis(di-tert-butyl(4-dimethylaminophenyl)phosphine)dichloropalladium (II) (8.92 mg, 0.013 mmol) in dioxane (1.2 mL) and water (0.40 mL). The reaction mixture was stirred and heated in microwave at 120° C. for 30 minutes before being diluted with EtOAc and saturated Na$_2$CO$_3$. The organic layer was washed twice with saturated Na$_2$CO$_3$, dried over Na2SO4 and concentrated in vacuo. The crude was purified by silica gel chromatography (2-10% MeOH—CH$_2$Cl$_2$), followed by preparative HPLC (15-60% CH$_3$CN (with 0.1% TFA)-water (with 0.1% TFA) in 20 min) to provide (S)-3-(3,6-dihydro-2H-pyran-4-yl)-7-(2-fluoro-5-methylpyridin-3-yl)-5'H-spiro[chromeno[2,3-c]pyridine-5,4'-oxazol]-2'-amine as a white solid (MS: MH+=445).

Example 287

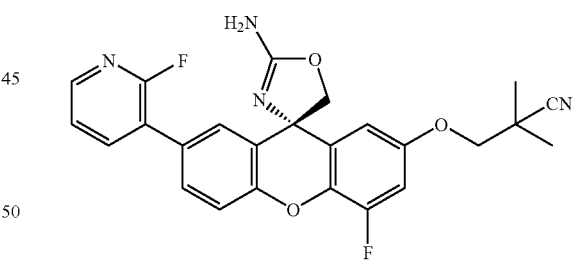

A vial was charged with (S)-2-amino-4'-fluoro-7'-(2-fluoropyridin-3-yl)-5H-spiro[oxazole-4,9'-xanthen]-2'-ol (45.0 mg, 0.118 mmol), cesium carbonate (57.7 mg, 0.177 mmol), and DMF (787 μL). The mixture was stirred vigorously for 15 min, then 2-cyano-2-methylpropyl trifluoromethanesulfonate (22.56 μL, 0.130 mmol) was added via syringe. The resulting mixture was stirred at room temperature for 19 hours before being diluted with water (10 mL) and EtOAc (10 mL). The layers were separated, and the aqueous layer was extracted with EtOAc (2×10 mL). The combined organic extracts were dried over sodium sulfate, filtered, and evaporated. The residue was purified by chromatography on a 12 g Redi-Sep column, eluting with 5-60% MeOH/DCM to give (S)-3-(2-amino-5'-fluoro-2'-(2-fluoropyridin-3-yl)-5H-spiro

[oxazole-4,9'-xanthene]-7'-yloxy)-2,2-dimethylpropanenitrile as an off-white solid. (MS: MH+=463).

Example 288

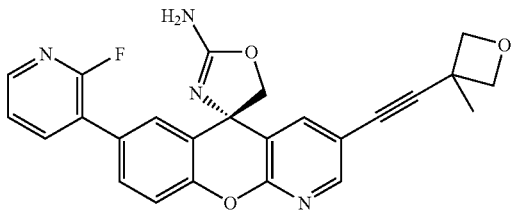 [SMILES: CC1(C#Cc2cnc3c(c2)[C@]2(COC(N)=N2)c2cc(-c4cccnc4F)ccc2O3)COC1]

A vial was charged with (S)-2'-amino-3-((3-methyloxetan-3-yl)ethynyl)-5'H-spiro[chromeno[2,3-b]pyridine-5,4'-oxazole]-7-yl trifluoromethanesulfonate (50.0 mg, 0.101 mmol), 2-fluoropyridin-3-ylboronic acid (21.33 mg, 0.151 mmol), potassium carbonate (69.7 mg, 0.505 mmol), and Pd(PPh₃)₄ (11.66 mg, 10.09 µmol). The vial was flushed with Ar (g), then dioxane (505 µL) and water (0.25 mL) were added in sequence. The vial was sealed and placed in a 70° C. oil for 1 hour. The mixture was diluted with EtOAc and washed with brine. The organic layer was dried over sodium sulfate, filtered, and evaporated. The residue was chromatographed on a 12-g Redi-Sep column with 0-60% of a 90:10:1 mix of DCM/MeOH/NH₄OH in DCM to give a pink solid. The solid was dissolved in MeOH and loaded onto a 500-mg SCX-2 column. The column was first eluted with methanol, then with 2N ammonia in methanol to remove the product. The filtrate was evaporated to give (S)-7-(2-fluoropyridin-3-yl)-3-((3-methyloxetan-3-yl)ethynyl)-5'H-spiro[chromeno[2,3-b]pyridine-5,4'-oxazol]-2'-amine as pale yellow solid. Found MS: MH+=443.0.

Example 289

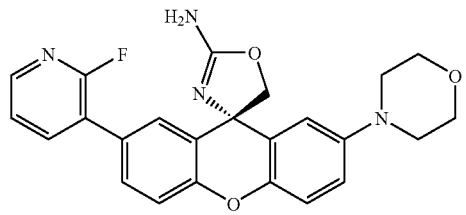 [SMILES: NC1=N[C@@]2(CO1)c1cc(-c3cccnc3F)ccc1Oc1ccc(N3CCOCC3)cc12]

A 0.5-2 ml microwave vial was charged with potassium carbonate (59.8 mg, 0.433 mmol), 2-fluoropyridin-3-ylboronic acid (34.5 mg, 0.245 mmol) and AmPhos (5.11 mg, 7.21 µmol). A solution of (R)-2-amino-2'-morpholino-5H-spiro[oxazole-4,9'-xanthene]-7'-yl trifluoromethanesulfonate (70 mg, 0.144 mmol) in dioxane (841 µL) was added followed by water (120 µL). Rhe vial was sealed and heated in microwave reactor at 100° C. for 1 hr. Tetrakis(triphenylphosphine)palladium(0) (16.66 mg, 0.014 mmol) and 2-fluoropyridin-3-ylboronic acid (34.5 mg, 0.245 mmol) were added and the mixture was heated for 30 min at 110 C in the microwave reactor. The dark brown mixture was diluted with 3 ml of ethyl acetate, filtered through celite and concentrated. The mixture was purified by silica gel chromatography on 12 g RediSep column using 15-60% DCM/MeOH/NH₄OH in DCM. The derived residue was then purified by reverse phase HPLC (15-90% MeCN in 0.1% aq. TFA) to afford (S)-2'-(2-fluoropyridin-3-yl)-7'-morpholino-5H-spiro[oxazole-4,9'-xanthen]-2-amine 2,2,2-trifluoroacetate as an off white solid. Found MS: MH+=441.

Example 290

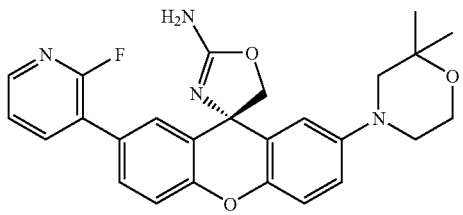 [SMILES: CC1(C)CN(c2ccc3c(c2)[C@]2(COC(N)=N2)c2cc(-c4cccnc4F)ccc2O3)CCO1]

A 25 mL RB flask was charged with (R)-2-amino-2'-(2,2-dimethylmorpholino)-5H-spiro[oxazole-4,9'-xanthene]-7'-yl trifluoromethanesulfonate (270 mg, 0.526 mmol), tetrakis (triphenylphosphine)palladium(0) (60.8 mg, 0.053 mmol), 2-fluoropyridin-3-ylboronic acid (119 mg, 0.841 mmol), DMF (2629 µL) and sodium carbonate (2M solution) (789 µL, 1.577 mmol). The mixture was stirred under argon for 2 hrs at 85° C. The mixture was diluted with water (2 ml) and extracted with 10 ml of EtOAc. The organic layer was washed with water, brine, passed through plug of Celite and concentrated. Dark residue was purified by silica gel chromatography on a 12 g RediSep column using 5-70% DCM/MeOH/NH₄OH in DCM to afford (S)-2'-(2,2-dimethylmorpholino)-7'-(2-fluoropyridin-3-yl)-5H-spiro[oxazole-4,9'-xanthen]-2-amine. Found MS: MH+=461.

Example 291

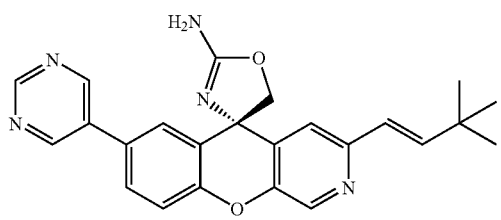 [SMILES: CC(C)(C)/C=C/c1cc2c(cn1)Oc1ccc(-c3cncnc3)cc1[C@@]21COC(N)=N1]

Synthesis of (S,E)-3-(3,3-dimethylbut-1-enyl)-7-(pyrimidin-5-yl)-5'H-spiro[chromeno[2,3-c]pyridine-5,4'-oxazol]-2'-amine A mixture of (S)-3-chloro-7-(pyrimidin-5-yl)-5'H-spiro[chromeno[2,3-c]pyridine-5,4'-oxazol]-2'-amine (0.967 g, 2.64 mmol), trans-(3,3-dimethylbutenyl)boronic acid pinacol ester (1.389 g, 6.61 mmol), AmPhos (0.094 g, 0.132 mmol), and potassium phosphate hydrate (1.218 g, 5.29 mmol) in 10 mL dioxane/water (1:1) was heated in the microwave at 130° C. for 1 h. After cooling to rt, the reaction was concentrated and the residue purified by silica gel chromatography using 0-5% MeOH/DCM to give (S,E)-3-(3,3-dimethylbut-1- enyl)-7-(pyrimidin-5-yl)-5'H-spiro[chromeno[2,3-c]pyridine-5,4'-oxazol]-2'-amine. Found MS: MH+=414.

Example 292

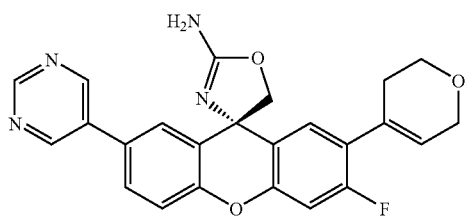 [SMILES: NC1=N[C@@]2(CO1)c1cc(-c3cncnc3)ccc1Oc1cc(F)c(C3=CCOCC3)cc12]

Synthesis of (S)-2'-(3,6-dihydro-2H-pyran-4-yl)-3'-fluoro-7'-(pyrimidin-5-yl)-5H-spiro[oxazole-4,9'-xanthen]-2-amine A 0.5-2 ml microwave vial was charged with tetrakis(triphenylphosphine)palladium(0) (27.9 mg, 0.024 mmol), 2-(3,6-dihydro-2H-pyran-4-yl)-4,4,5,5-tetramethyl-1,3,2-dioxaborolane (86 mg, 0.411 mmol). A solution of (S)-2-amino-6'-fluoro-2'-(pyrimidin-5-yl)-5H-spiro[oxazole-4,9'-xanthene]-7'-yl trifluoromethanesulfonate (120 mg, 0.242 mmol) in DMF (1612 µL) was added followed by sodium carbonate (2M solution) (363 µL, 0.725 mmol). The vial was sealed and heated in microwave reactor at 85° C. for 1 hr. The mixture was diluted with water and extracted with EtOAc. The organic layer was washed with water, brine, filtered through celite and concentrated to leve brown oil. The crude material was purified by silica gel chromatography on 12 g RediSep column using (15-60% DCM/MeOH/NH4OH 90:10:1 in DCM) to afford (S)-2'-(3,6-dihydro-2H-pyran-4-yl)-3'-fluoro-7'-(pyrimidin-5-yl)-5H-spiro[oxazole-4,9'-xanthen]-2-amine. Found MS: MH+=431.

Example 293

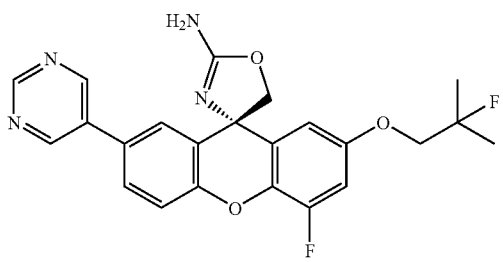 [SMILES: CC(C)(F)COc1cc(F)c2c(c1)[C@]1(COC(N)=N1)c1cc(-c3cncnc3)ccc1O2]

Synthesis of (S)-4'-fluoro-2'-(2-fluoro-2-methylpropoxy)-7'-(pyrimidin-5-yl)-5H-spiro[oxazole-4,9'-xanthen]-2-amine A vial was charged with (S)-2-amino-4'-fluoro-7'-(pyrimidin-5-yl)-5H-spiro[oxazole-4,9'-xanthen]-2'-ol (61.0 mg, 0.167 mmol), cesium carbonate (82 mg, 0.251 mmol), and DMF (670 µL). The resulting mixture was stirred vigorously for 10 min, then the vial was placed in large ice-bath for 10 min. 2-fluoro-2-methylpropyl trifluoromethanesulfonate (33.3 µL, 0.201 mmol) was added dropwise and the ice-bath was removed after 5 minutes. The mixture was stirred at for 6 hours, then the mixture was diluted with water (10 mL) and extracted with EtOAc (3×5 mL). The combined organic extracts were dried over sodium sulfate, filtered, and evaporated. The residue was chromatographed on a 12 g Redi-Sep column, eluting with 5-60% gradient of DCM/MeOH/NH4OH (90:10:1) in DCM to give (S)-4'-fluoro-2'-(2-fluoro-2-methylpropoxy)-7'-(pyrimidin-5-yl)-5H-spiro[oxazole-4,9'-xanthen]-2-amine as an off-white solid. Found MS: MH+=439.

Example 294

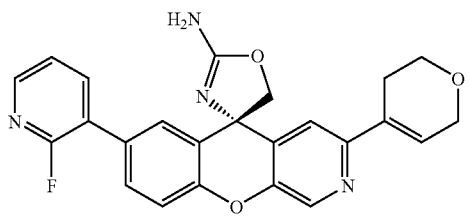 [SMILES: NC1=N[C@@]2(CO1)c1cc(-c3cccnc3F)ccc1Oc1cnc(C3=CCOCC3)cc12]

Synthesis of (S)-3-(3,6-dihydro-2H-pyran-4-yl)-7-(2-fluoropyridin-3-yl)-5'H-spiro[chromeno[2,3-c]pyridine-5,4'-oxazol]-2'-amine A glass microwave reaction vessel was charged with (S)-3-chloro-7-(2-fluoropyridin-3-yl)-5'H-spiro[chromeno[2,3-c]pyridine-5,4'-oxazol]-2'-amine (0.075 g, 0.196 mmol), potassium phosphate (0.125 g, 0.588 mmol), 2-(3,6-dihydro-2H-pyran-4-yl)-4,4,5,5-tetramethyl-1,3,2-dioxaborolane (0.082 g, 0.392 mmol) and Bis(di-tert-butyl(4-dimethylaminophenyl)phosphine)dichloropalladium (II) (0.014 g, 0.020 mmol) in dioxane (1.2 mL) and water (0.40 mL). The reaction mixture was stirred and heated in microwave at 120° C. for 30 min. The mixture was diluted with EtOAc and saturated Na2CO3. The organic layer was washed twice with saturated Na2CO3, dried over Na2SO4 and concentrated in vacuo. The crude was purified by silica gel chromatography (12 g, 2-10% MeOH-DCM, then 10% MeOH—DCM) provided (S)-3-(3,6-dihydro-2H-pyran-4-yl)-7-(2-fluoropyridin-3-yl)-5'H-spiro[chromeno[2,3-c]pyridine-5,4'-oxazol]-2'-amine as a grey solid. Found MS: MH+=431.

Example 295

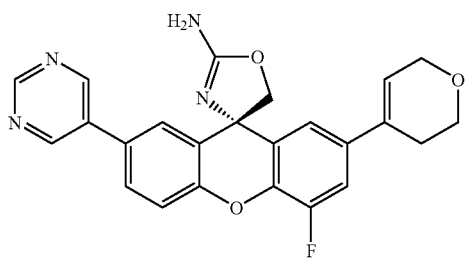 [SMILES: NC1=N[C@@]2(CO1)c1cc(-c3cncnc3)ccc1Oc1c(F)cc(C3=CCOCC3)cc12]

Synthesis of (R)-2'-(3,6-dihydro-2H-pyran-4-yl)-4'-fluoro-7'-(pyrimidin-5-yl)-5H-spiro[oxazole-4,9'-xanthen]-2-amine A vial was charged with 2-amino-2'-(3,6-dihydro-2H-pyran-4-yl)-4'-fluoro-5H-spiro[oxazole-4,9'-xanthene]-7'-yl trifluoromethanesulfonate (150 mg, 0.300 mmol), pyrimidin-5-ylboronic acid (111 mg, 0.899 mmol), and Pd(PPh₃)₄ (34.6 mg, 0.030 mmol). The vial was purged with Ar (g), then DMF (2 mL) and potassium carbonate (0.749 mL, 1.499 mmol) (as a 2.0 M aq. solution) were added in sequence. The vial was capped and heated in a Biotage Initiator microwave reactor for 1.5 h at 75° C. The product was purified via Gilson HPLC (gradient elution 20-90% MeCN/H₂O, 0.1% TFA) to afford (R)-2'-(3,6-dihydro-2H-pyran-4-yl)-4'-fluoro-7'-(pyrimidin-5-yl)-5H-spiro[oxazole-4,9'-xanthen]-2-amine as an off white solid. Found MS: MH+=431.

Example 296

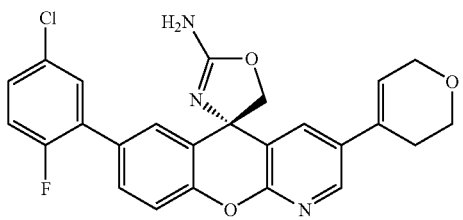 [SMILES: NC1=N[C@@]2(CO1)c1cc(-c3cc(Cl)ccc3F)ccc1Oc1ncc(C3=CCOCC3)cc12]

Synthesis of (S)-7-(5-chloro-2-fluorophenyl)-3-(3,6-dihydro-2H-pyran-4-yl)-5'H-spiro[chromeno[2,3-b]pyridine-5,4'-oxazol]-2'-amine A vial was charged with (S)-2'-amino-3-(3,6-dihydro-2H-pyran-4-yl)-5'H-spiro[chromeno[2,3-b]pyridine-5,4'-oxazole]-7-yl trifluoromethanesulfonate (0.050 g, 0.103 mmol), 5-chloro-2-fluorophenylboronic acid (0.054 g, 0.310 mmol), and Pd(PPh₃)₄ (5.97 mg, 5.17 µmol). The vial was purged with Ar (g). Then, DMF (0.517 mL) and potassium carbonate (0.259 mL, 0.517 mmol) (as a 2.0 M aq. solution) were added in sequence. The vial was sealed and stirred at 70° C. for one hour. The reaction was diluted with ethyl acetate and washed with water. The aqueous layer was extracted with ethyl acetate, and the combined organic layers were dried with sodium sulfate, filtered, and concentrated. The material was purified via column chromatography (RediSep 40 g, gradient elution 0-7% MeOH in DCM) to afford (S)-7-(5-chloro-2-fluorophenyl)-3-(3,6-dihydro-2H-pyran-4-yl)-5'H-spiro[chromeno[2,3-b]pyridine-5,4'-oxazol]-2'-amine as a white solid. Found MS: MH+=464.

Example 297

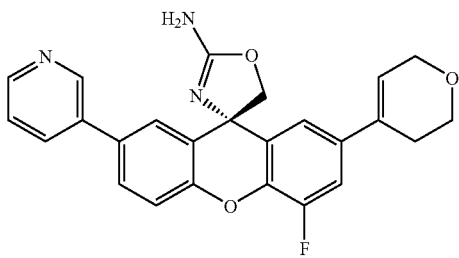 [SMILES: NC1=N[C@@]2(CO1)c1cc(-c3cccnc3)ccc1Oc1c(F)cc(C3=CCOCC3)cc12]

Synthesis of (R)-2'-(3,6-dihydro-2H-pyran-4-yl)-4'-fluoro-7'-(pyridin-3-yl)-5H-spiro[oxazole-4,9'-xanthen]-2-amine A vial was charged with 2-amino-2'-(3,6-dihydro-2H-pyran-4-yl)-4'-fluoro-5H-spiro[oxazole-4,9'-xanthene]-7'-yl trifluoromethanesulfonate (150 mg, 0.300 mmol), pyridin-3-ylboronic acid (111 mg, 0.899 mmol), and Pd(PPh₃)₄ (34.6 mg, 0.030 mmol). The vial was purged with Ar (g), then DMF (2 mL) and potassium carbonate (0.749 mL, 1.499 mmol) (as a 2.0 M aq. solution) were added in sequence. The vial was capped and heated in a Biotage Initiator microwave reactor for 1.5 h at 75° C. The product was purified via Gilson HPLC (gradient elution 20-90% MeCN/H₂O, 0.1% TFA) to afford (R)-2'-(3,6-dihydro-2H-pyran-4-yl)-4'-fluoro-7'-(pyridin-3-yl)-5H-spiro[oxazole-4,9'-xanthen]-2-amine as an off white solid. Found MS: MH+=430.

Example 298

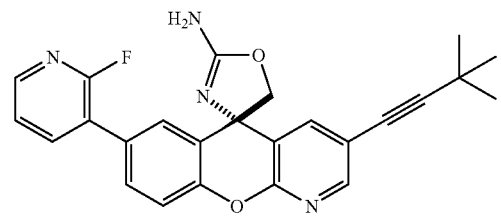

Synthesis of (S)-3-(3,3-dimethylbut-1-ynyl)-7-(2-fluoropyridin-3-yl)-5'H-spiro[chromeno[2,3-b]pyridine-5,4'-oxazol]-2'-amine Combined (S)-3-bromo-7-(2-fluoropyridin-3-yl)-5'H-spiro[chromeno[2,3-b]pyridine-5,4'-oxazol]-2'-amine (80 mg, 0.187 mmol), tetrakis(triphenylphosphine)palladium (21.64 mg, 0.019 mmol), copper(i) iodide (3.57 mg, 0.019 mmol) and THF (749 µL, 0.187 mmol) and DMF (749 µL, 0.187 mmol) in a reaction tube. Added DIPA (525 µL, 3.75 mmol) then 3,3-dimethylbut-1-yne (115 µL, 0.936 mmol) and flushed the reaction tube with argon. Sealed and heated at 110° C. for 3 hours. The mixture was partioned between water (10 mL) and EtOAc (10 mL). The layers were separated, and the aqueous layer was extracted with EtOAc (2×10 mL). The combined organic extracts were dried over sodium sulfate, filtered, and evaporated. The residue was purified by chromatography on a 25-g SNAP column, eluting with 0-70% of a 90:10:1 mixture of DCM/MeOH/NH₄OH in DCM. The derived residue was then purified by reverse-phase HPLC (10-90% CH₃CN/H₂O with 0.1% TFA) to give (S)-3-(3,3-dimethylbut-1-ynyl)-7-(2-fluoropyridin-3-yl)-5'H-spiro

[chromeno[2,3-b]pyridine-5,4'-oxazol]-2'-amine as a white powder after evaporation from DCM/hexane. Found MS: MH+=429.

Example 299

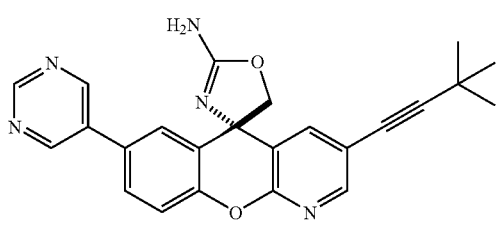

Synthesis of (S)-3-(3,3-dimethylbut-1-ynyl)-7-(pyrimidin-5-yl)-5'H-spiro[chromeno[2,3-b]pyridine-5,4'-oxazol]-2'-amine Combined (S)-3-bromo-7-(pyrimidin-5-yl)-5'H-spiro[chromeno[2,3-b]pyridine-5,4'-oxazol]-2'-amine (120 mg, 0.293 mmol), tetrakis(triphenylphosphine)palladium (33.8 mg, 0.029 mmol), copper(i) iodide (11.14 mg, 0.059 mmol) and DMF (1950 µL, 0.293 mmol). Added 3,3-dimethylbut-1-yne (96 mg, 1.170 mmol) and DIPA (2085 µL, 14.63 mmol), flushed with argon, sealed and heated at 90° C. overnight. The reaction was diluted with water (25 mL) and poured into a separatory funnel containing ethyl acetate (25 mL). The layers were separated and the aqueous layer was extracted with ethyl acetate (2×50 mL). The combined organic layers were washed with water, dried over sodium sulfate, filtered and concentrated in vacuo to provide a brown oil that was purified by silica gel chromatography (Redi-Sep pre-packed silica gel column (12 g), 0-10% methanol in DCM with 0.1% ammonium hydroxide) to provide (S)-3-(3,3-dimethylbut-1-ynyl)-7-(pyrimidin-5-yl)-5'H-spiro[chromeno[2,3-b]pyridine-5,4'-oxazol]-2'-amine as a tan solid. Found MS: MH+=412.2.

Example 300

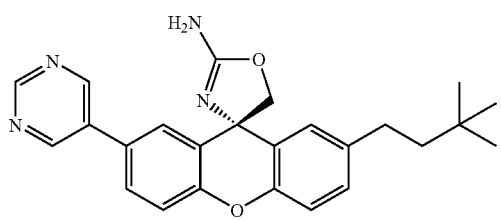 [SMILES: CC(C)(C)CCc1ccc2c(c1)[C@]1(COC(N)=N1)c1cc(-c3cncnc3)ccc1O2]

Synthesis of (R)-2'-(3,3-dimethylbutyl)-7'-(pyrimidin-5-yl)-5H-spiro[oxazole-4,9'-xanthen]-2-amine (R)-2'-(3,3-dimethylbut-1-ynyl)-7'-(pyrimidin-5-yl)-5H-spiro[oxazole-4,9'-xanthen]-2-amine (400 mg, 0.974 mmol) and palladium on carbon (104 mg, 0.974 mmol) were combined in 20 ml of ethanol and stirred under an atmosphere of hydrogen for 12 hours. The solution is filtered thru celite and concentrated. The product is purified via silica gel column chromatography (RediSep 80 g column) using 0-10% methanol in ethyl acetate to afford (R)-2'-(3,3-dimethylbutyl)-7'-(pyrimidin-5-yl)-5H-spiro[oxazole-4,9'-xanthen]-2-amine as a white crystalline solid. Found MS: MH+=415.2.

The following intermediates were used in preparing exemplary compounds of the present invention. The codes for each intermediate relate to the compounds in Table IV below.

| Intermediate Structure | code | procedure |
|---|---|---|
| ![structure with Br, I, H2N, oxazole, xanthene] | II1 | Example 115 |
| ![structure with Br, Cl, H2N, oxazole, chromenopyridine] | II2 | Method C4 |
| ![structure with I, Br, H2N, oxazole, chromenopyridine] | II3 | Example 45; Method N; Steps 1-4 |

-continued

| Intermediate Structure | code | procedure |
|---|---|---|
| (structure with H₂N-oxazoline spiro, HO- and Br- substituents, pyridine O) | II4 | Example 45; Method N; Step 5 |
| (structure with H₂N-oxazoline spiro, Br- and OH- substituents, pyridine O) | II5 | Example 45; Method N; Step 5 |
| (structure with H₂N-oxazoline spiro, MeO- and Br- substituents, pyridine O) | II7 | Example 45; Method N; Steps 1-4 |
| (structure with H₂N-oxazoline spiro, Br- and Cl- substituents, pyridine) | II8 | Example 136 |
| (structure with H₂N-oxazoline spiro, Br-, OH- and F- substituents, xanthene) | II9 | Example 109 |
| (structure with H₂N-oxazoline spiro, Br-, OH- and F- substituents, xanthene) | II10 | Example 109 |

-continued
| Intermediate Structure | code | procedure |
|---|---|---|
| 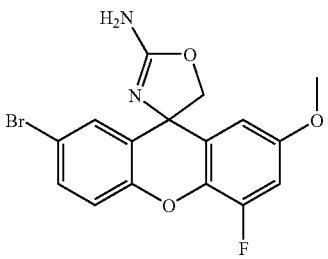 [SMILES: COc1cc(F)c2c(c1)C1(COC(N)=N1)c1cc(Br)ccc1O2] | II11 | Example 109 |
| 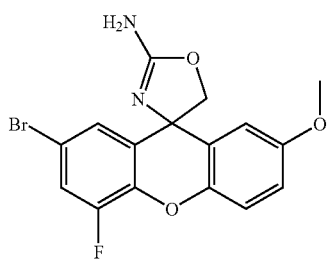 [SMILES: COc1ccc2c(c1)C1(COC(N)=N1)c1cc(Br)cc(F)c1O2] | II12 | Example 115 |
| 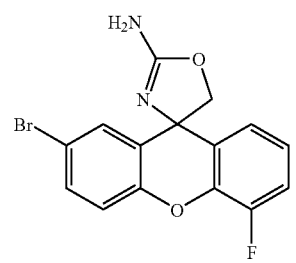 [SMILES: NC1=NC2(CO1)c1cc(Br)ccc1Oc1c(F)cccc12] | II13 | Example 115 |
| 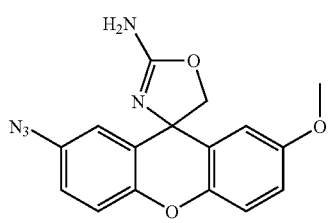 [SMILES: COc1ccc2c(c1)C1(COC(N)=N1)c1cc(N=[N+]=[N-])ccc1O2] | II14 | AA10 |
| 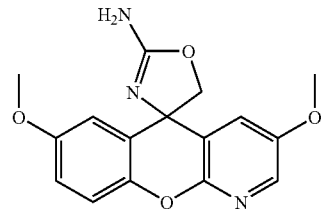 [SMILES: COc1ccc2c(c1)C1(COC(N)=N1)c1cc(OC)cnc1O2] | II16 | Example 45; Method N |
| 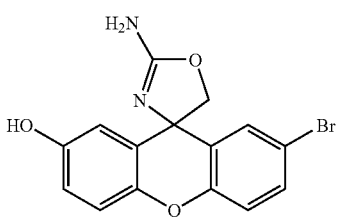 [SMILES: NC1=NC2(CO1)c1cc(O)ccc1Oc1ccc(Br)cc12] | II18 | Example 115 |

-continued
| Intermediate Structure | code | procedure |
|---|---|---|
| 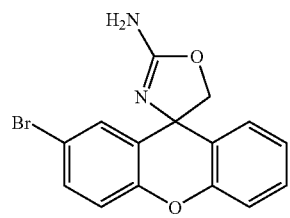 [SMILES: NC1=NC2(CO1)c1ccccc1Oc1ccc(Br)cc12] | II19 | Example 115 |
| 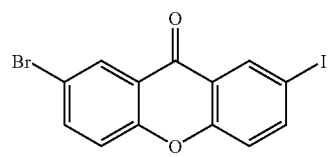 [SMILES: O=c1c2cc(Br)ccc2oc2ccc(I)cc12] | II38 | Scheme1 |
| 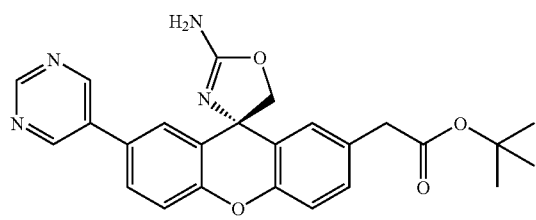 [SMILES: CC(C)(C)OC(=O)Cc1ccc2c(c1)[C@]1(COC(N)=N1)c1cc(-c3cncnc3)ccc1O2] | II39 | AA48 |
| 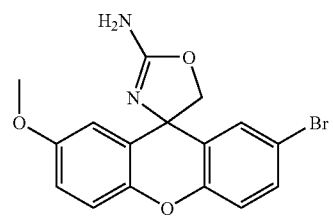 [SMILES: COc1ccc2c(c1)C1(COC(N)=N1)c1cc(Br)ccc1O2] | II17 | Example 115 |
| 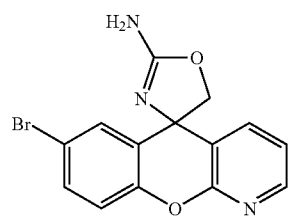 [SMILES: NC1=NC2(CO1)c1cc(Br)ccc1Oc1ncccc12] | II20 | Example 115 |
| 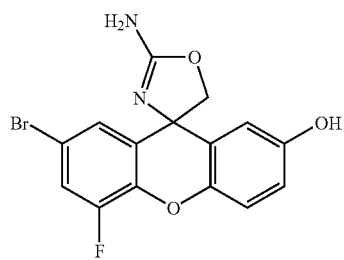 [SMILES: NC1=NC2(CO1)c1cc(O)ccc1Oc1c(F)cc(Br)cc12] | II21 | Example 109 |
| 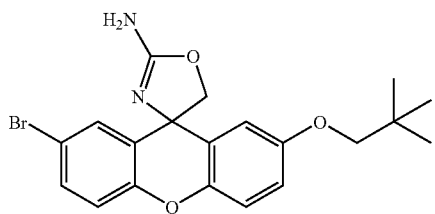 [SMILES: CC(C)(C)COc1ccc2c(c1)C1(COC(N)=N1)c1cc(Br)ccc1O2] | II22 | Example 44 |

-continued

| Intermediate Structure | code | procedure |
|---|---|---|
| (structure) | II23 | Example 136 |
| (structure) | II24 | Scheme 1 |
| (structure) | II25 | Example 109 |
| (structure) | II26 | AA7 |
| (structure) | II27 | Example 115 |
| (structure) | II28 | Example 109 (also Method MM1) |
| (structure) | II29 | Scheme 1 |
| (structure) | II31 | Example 109 (also Method MM1) |

-continued

| Intermediate Structure | code | procedure |
|---|---|---|
| | II32 | Example 115 |
| | II33 | AA64 |
| | II34 | Example 109 |
| | II35 | Example 109 |
| | II36 | Scheme 1 |
| | II37 | Scheme 1 |
| | II6 | AA64 |

-continued

| Intermediate Structure | code | procedure |
|---|---|---|
| 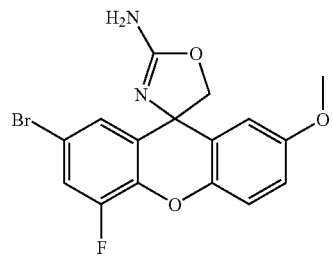 [SMILES: COc1ccc2c(c1)C1(COC(N)=N1)c1cc(Br)cc(F)c1O2] | II12 | Example 109 |

The following compounds in Table IV are additional representative examples of compounds of Formulas I-IV provided by the present invention. The methods and intermediates used to prepare each exemplary compound are also included in the Table, along with the biological data (enzyme and cell assay data) where available.

TABLE IV

| Ex. No. | Compound Name | Observed Mass | Method | Intermediate used | BACE1 FRET assay (uM) | HEK cell assay (uM) |
|---|---|---|---|---|---|---|
| 301 | 1-fluoro-3,7-di(pyridin-3-yl)-5'H-spiro[chromeno[2,3-c]pyridine-5,4'-oxazol]-2'-amine | 426 | WQ1 | | ++++ | ++++ |
| 302 | (5S)-7-(5-chloro-3-pyridinyl)-3-(4-pyridinyl)spiro[chromeno[2,3-c]pyridine-5,4'-[1,3]oxazol]-2'-amine | 442 | AA1 | II2 | ++++ | |
| 303 | (5S)-7-(5-chloro-3-pyridinyl)-3-(3-pyridinyl)spiro[chromeno[2,3-c]pyridine-5,4'-[1,3]oxazol]-2'-amine | 442 | AA1 | II2 | ++++ | |
| 304 | (4S)-4'-fluoro-7'-methoxy-2'-(4-morpholinyl)spiro[1,3-oxazole-4,9'-xanthen]-2-amine | 386 | AA40 | II12 | +++ | |
| 305 | (5S)-7-(5-methyl-3-pyridinyl)-3-(4-pyridinyl)spiro[chromeno[2,3-c]pyridine-5,4'-[1,3]oxazol]-2'-amine | 422 | AA1 | II2 | ++++ | |
| 306 | (5S)-7-(5-methyl-3-pyridinyl)-3-(3-pyridinyl)spiro[chromeno[2,3-c]pyridine-5,4'-[1,3]oxazol]-2'-amine | 422 | AA1 | II2 | ++++ | |
| 307 | (5S)-3-(2-methyl-4-pyridinyl)-7-(5-methyl-3-pyridinyl)spiro[chromeno[2,3-c]pyridine-5,4'-[1,3]oxazol]-2'-amine | 436 | AA2 | II2 | ++++ | |
| 308 | (5S)-7-(5-methyl-3-pyridinyl)-3-(tetrahydro-2H-pyran-4-yl)spiro[chromeno[2,3-c]pyridine-5,4'-[1,3]oxazol]-2'-amine | 429 | AA11 | II2 | ++++ | |
| 309 | (5S)-7-(5-chloro-3-pyridinyl)-3-(3,6-dihydro-2H-pyran-4-yl)spiro[chromeno[2,3-c]pyridine-5,4'-[1,3]oxazol]-2'-amine | 447 | AA1 | II2 | ++++ | |
| 310 | (5S)-3-chloro-7-(6-fluoro-3-pyridinyl)spiro[chromeno[2,3-c]pyridine-5,4'-[1,3]oxazol]-2'-amine | 383 | AA24 | II2 | +++ | |
| 311 | (5S)-3-(2-fluoro-4-pyridinyl)-7-(6-fluoro-3-pyridinyl)spiro[chromeno[2,3-c]pyridine-5,4'-[1,3]oxazol]-2'-amine | 444 | AA1 | II2 | ++++ | |
| 312 | (5S)-7-(2-fluoro-3-pyridinyl)-3-(6-fluoro-3-pyridinyl)spiro[chromeno[2,3-c]pyridine-5,4'-[1,3]oxazol]-2'-amine | 444 | AA1 | II2 | ++++ | |
| 313 | (5S)-7-(6-fluoro-3-pyridinyl)-3-(2-methyl-4-pyridinyl)spiro[chromeno[2,3-c]pyridine-5,4'-[1,3]oxazol]-2'-amine | 440 | AA1 | II2 | ++++ | |
| 314 | (5S)-7-(3-chlorophenyl)-3-((3-methyl-3-oxetanyl)ethynyl)spiro[chromeno[2,3-b]pyridine-5,4'-[1,3]oxazol]-2'-amine | 458.2 | AA23 | II4 | ++++ | |
| 315 | (5S)-3-((3-methyl-3-oxetanyl)ethynyl)-7-(3-pyridinyl)spiro[chromeno[2,3-b]pyridine-5,4'-[1,3]oxazol]-2'-amine | 425.2 | AA21 | II4 | ++++ | |
| 316 | (5S)-3-(3,3-dimethyl-1-pyrrolidinyl)-7-(2-fluoro-3-pyridinyl)spiro[chromeno[2,3-b]pyridine-5,4'-[1,3]oxazol]-2'-amine | 446 | AA9 | II3 | ++++ | |

TABLE IV-continued

| Ex. No. | Compound Name | Observed Mass | Method | Intermediate used | BACE1 FRET assay (uM) | HEK cell assay (uM) |
|---|---|---|---|---|---|---|
| 317 | 5-((5S)-2'-amino-3-(3,3-dimethyl-1-butyn-1-yl)spiro[chromeno[2,3-b]pyridine-5,4'-[1,3]oxazol]-7-yl)-3-pyridinecarbonitrile | 436 | AA21 | II4 | ++++ | |
| 318 | 3-((5S)-2'-amino-3-(3,3-dimethyl-1-butyn-1-yl)spiro[chromeno[2,3-b]pyridine-5,4'-[1,3]oxazol]-7-yl)benzonitrile | 435 | AA5 | II4 | ++++ | |
| 319 | 3-(((5S)-2'-amino-3-(3,3-dimethyl-1-butyn-1-yl)spiro[chromeno[2,3-b]pyridine-5,4'-[1,3]oxazol]-7-yl)oxy)-2,2-dimethylpropanenitrile | 431.2 | AA12 | II4 | ++++ | |
| 320 | (5S)-3-(3-(1-azetidinyl)-3-methyl-1-butyn-1-yl)-7-(3-pyridinyl)spiro[chromeno[2,3-b]pyridine-5,4'-[1,3]oxazol]-2'-amine | 452.2 | CK01 | II3 | ++++ | |
| 321 | (5S)-7-(2,4-difluoro-3-pyridinyl)-3-(3,6-dihydro-2H-pyran-4-yl)spiro[chromeno[2,3-b]pyridine-5,4'-[1,3]oxazol]-2'-amine | 449 | AA36 | II4 | ++++ | |
| 322 | (5S)-7-(3-chlorophenyl)-3-(3,6-dihydro-2H-pyran-4-yl)spiro[chromeno[2,3-b]pyridine-5,4'-[1,3]oxazol]-2'-amine | 446 | AA8 | II4 | ++++ | |
| 323 | (5S)-3-(2,2-dimethylpropoxy)-7-((3-methyl-3-oxetanyl)ethynyl)spiro[chromeno[2,3-b]pyridine-5,4'-[1,3]oxazol]-2'-amine | 434.2 | AA12 | II4 | ++++ | |
| 324 | N-((4R)-2-amino-7'-(3,3-dimethyl-1-butyn-1-yl)spiro[1,3-oxazole-4,9'-xanthen]-2'-yl)-2-methoxyacetamide | 420 | AA10 | II14 | ++++ | +++ |
| 325 | (5S)-7-(5-methyl-3-pyridinyl)-3-(4-morpholinyl)spiro[chromeno[2,3-c]pyridine-5,4'-[1,3]oxazol]-2'-amine | 430 | AA9 | II2 | ++++ | ++++ |
| 326 | (5S)-3-(3,6-dihydro-2H-pyran-4-yl)-7-(5-methyl-3-pyridinyl)spiro[chromeno[2,3-c]pyridine-5,4'-[1,3]oxazol]-2'-amine | 427 | AA1 | II2 | ++++ | ++++ |
| 327 | (5S)-3-chloro-7-(5-methyl-3-pyridinyl)spiro[chromeno[2,3-c]pyridine-5,4'-[1,3]oxazol]-2'-amine | 379 | AA24 | II2 | +++ | ++ |
| 328 | (5S)-3-(1-methyl-1H-pyrazol-4-yl)-7-(3-(1-methyl-1H-pyrazol-4-yl)phenyl)spiro[chromeno[2,3-c]pyridine-5,4'-[1,3]oxazol]-2'-amine | 490 | AA1 | II2 | ++++ | +++ |
| 329 | (5S)-7-(3-chlorophenyl)-3-(1-methyl-1H-pyrazol-4-yl)spiro[chromeno[2,3-c]pyridine-5,4'-[1,3]oxazol]-2'-amine | 444 | AA1 | II2 | ++++ | ++++ |
| 330 | (5S)-7-(5-chloro-2-fluorophenyl)-3-(4-pyridinyl)spiro[chromeno[2,3-c]pyridine-5,4'-[1,3]oxazol]-2'-amine | 459 | AA1 | II2 | ++++ | ++++ |
| 331 | (5S)-7-(5-fluoro-3-pyridinyl)-3-(tetrahydro-2H-pyran-4-yl)spiro[chromeno[2,3-c]pyridine-5,4'-[1,3]oxazol]-2'-amine | 433 | AA11 | II2 | ++++ | ++++ |
| 332 | (5S)-7-(2-fluoro-5-methyl-3-pyridinyl)-3-(tetrahydro-2H-pyran-4-yl)spiro[chromeno[2,3-c]pyridine-5,4'-[1,3]oxazol]-2'-amine | 447 | AA11 | II2 | ++++ | ++++ |
| 333 | (5S)-7-(2-fluoro-3-pyridinyl)-3-(1-methyl-1H-pyrazol-4-yl)spiro[chromeno[2,3-c]pyridine-5,4'-[1,3]oxazol]-2'-amine | 429 | AA1 | II2 | ++++ | ++++ |
| 334 | (10S)-2-(4-morpholinyl)-8-(3-pyridinyl)spiro[chromeno[3,2-b]pyridine-10,4'-[1,3]oxazol]-2'-amine | 416 | AA9 | II8 | +++ | +++ |
| 335 | (5S)-3-(4-morpholinyl)-7-(3-pyridinyl)spiro[chromeno[2,3-c]pyridine-5,4'-[1,3]oxazol]-2'-amine | 416 | AA9 | II2 | ++++ | ++++ |
| 336 | (5S)-3-(4-morpholinyl)-7-(2-(4-morpholinyl)-3-pyridinyl)spiro[chromeno[2,3-c]pyridine-5,4'-[1,3]oxazol]-2'-amine | 501 | AA9 | II2 | ++++ | +++ |
| 337 | (5S)-3-chloro-7-(2-(4-morpholinyl)-3-pyridinyl)spiro[chromeno[2,3-c]pyridine-5,4'-[1,3]oxazol]-2'-amine | 450 | AA9 | II2 | ++ | + |
| 338 | (10S)-8-(2-fluoro-3-pyridinyl)-2-(tetrahydro-2H-pyran-4- | 433 | AA11 | II8 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| | yl)spiro[chromeno[3,2-b]pyridine-10,4'-[1,3]oxazol]-2'-amine | | | | | |
| 339 | (5S)-7-(2-fluoro-3-pyridinyl)-3-(6-methyl-3-pyridinyl)spiro[chromeno[2,3-b]pyridine-5,4'-[1,3]oxazol]-2'-amine | 440 | AA1 | II3 | ++++ | |
| 340 | 4-((5S)-2'-amino-7-(2-cyano-2-methylpropoxy)spiro[chromeno[2,3-b]pyridine-5,4'-[1,3]oxazol]-3-yl)benzonitrile | 452.1 | AA13 | II4 | ++++ | |
| 341 | 3-(((5S)-2'-amino-3-(6-methoxy-3-pyridinyl)spiro[chromeno[2,3-b]pyridine-5,4'-[1,3]oxazol]-7-yl)oxy)-2,2-dimethylpropanenitrile | 458.2 | AA13 | II4 | ++++ | |
| 342 | 3-(((5S)-2'-amino-3-(4-(trifluoromethoxy)phenyl)spiro[chromeno[2,3-b]pyridine-5,4'-[1,3]oxazol]-7-yl)oxy)-2,2-dimethylpropanenitrile | 511.1 | AA13 | II4 | ++++ | |
| 343 | (5S)-7-(2-fluoro-3-pyridinyl)-3-(2-methyl-4-pyridinyl)spiro[chromeno[2,3-b]pyridine-5,4'-[1,3]oxazol]-2'-amine | 449 | AA1 | II3 | ++++ | |
| 344 | (5S)-7-(2-fluoro-3-pyridinyl)-3-(6-methoxy-3-pyridinyl)spiro[chromeno[2,3-b]pyridine-5,4'-[1,3]oxazol]-2'-amine | 456.2 | AA1 | II3 | ++++ | |
| 345 | (5S)-7-(3-chlorophenyl)-3-(4-pyridinyl)spiro[chromeno[2,3-b]pyridine-5,4'-[1,3]oxazol]-2'-amine | 441 | AA8 | II3 | ++++ | |
| 346 | (5S)-7-(2-fluoro-3-pyridinyl)-3-(1-methyl-1H-pyrazol-4-yl)spiro[chromeno[2,3-b]pyridine-5,4'-[1,3]oxazol]-2'-amine | 429 | AA1 | II3 | ++++ | |
| 347 | (5S)-3-(3-ethoxy-3-methyl-1-butyn-1-yl)-7-(3-pyridinyl)spiro[chromeno[2,3-b]pyridine-5,4'-[1,3]oxazol]-2'-amine | 441 | AA41 | II3 | ++++ | ++++ |
| 348 | (5S)-7-(3-pyridinyl)-3-((trimethylsilyl)ethynyl)spiro[chromeno[2,3-b]pyridine-5,4'-[1,3]oxazol]-2'-amine | 427 | AA5 | II3 | ++++ | ++++ |
| 349 | (5R)-3-(2-methoxy-2-methylpropoxy)-7-phenylspiro[chromeno[2,3-b]pyridine-5,4'-[1,3]oxazol]-2'-amine | 432.2 | AA51 | II5 | +++ | ++ |
| 350 | (5S)-3-(2-methoxy-2-methylpropoxy)-7-phenylspiro[chromeno[2,3-b]pyridine-5,4'-[1,3]oxazol]-2'-amine | 432.3 | AA51 | II5 | ++++ | ++++ |
| 351 | (5R)-7-(2-fluoro-3-pyridinyl)-3-(2-methoxy-2-methylpropoxy)spiro[chromeno[2,3-b]pyridine-5,4'-[1,3]oxazol]-2'-amine | 451.2 | AA51 | II5 | +++ | +++ |
| 352 | (5S)-7-(2-fluoro-3-pyridinyl)-3-(2-methoxy-2-methylpropoxy)spiro[chromeno[2,3-b]pyridine-5,4'-[1,3]oxazol]-2'-amine | 451.2 | AA51 | II5 | ++++ | ++++ |
| 353 | (4S)-3'-fluoro-2'-(2-fluoro-2-methylpropoxy)-7'-(3-pyridinyl)spiro[1,3-oxazole-4,9'-xanthen]-2-amine | 438 | AA14 | II9 | ++++ | ++++ |
| 354 | (4S)-4'-fluoro-7'-(2-fluoro-3-pyridinyl)-2'-(1-methyl-1H-pyrazol-4-yl)spiro[1,3-oxazole-4,9'-xanthen]-2-amine | 446 | AA8 | II10 | ++++ | ++++ |
| 355 | (4S)-4'-fluoro-2'-(2-fluoro-2-methylpropoxy)-7'-(2-fluoro-3-pyridinyl)spiro[1,3-oxazole-4,9'-xanthen]-2-amine | 456 | AA14 | II10 | ++++ | ++++ |
| 356 | (5S)-7-(2-fluoro-3-pyridinyl)-3-(2-fluoro-4-pyridinyl)spiro[chromeno[2,3-b]pyridine-5,4'-[1,3]oxazol]-2'-amine | 444 | AA1 | II3 | ++++ | ++++ |
| 357 | 3-((5S)-2'-amino-3-(2-fluoro-2-methylpropoxy)spiro[chromeno[2,3-b]pyridine-5,4'-[1,3]oxazol]-7-yl)benzonitrile | 445 | AA13 | II5 | ++++ | ++++ |
| 358 | 3-((5S)-2'-amino-3-(2,2-dimethylpropoxy)spiro[chromeno[2,3-b]pyridine-5,4'-[1,3]oxazol]-7-yl)benzonitrile | 441 | AA13 | II5 | ++++ | ++++ |
| 359 | (4S)-2'-((2S)-2-(2-methylpropyl)-4-morpholinyl)-7'-(3-pyridinyl)spiro[1,3-oxazole-4,9'-xanthen]-2-amine | 472 | AA9 | II1 | +++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 360 | (4S)-2'-((2R)-2-(2-methylpropyl)-4-morpholinyl)-7'-(3-pyridinyl)spiro[1,3-oxazole-4,9'-xanthen]-2-amine | 472 | AA9 | II1 | +++ | +++ |
| 361 | (4S)-2'-((2S)-2-(2-methoxyethyl)-4-morpholinyl)-7'-(3-pyridinyl)spiro[1,3-oxazole-4,9'-xanthen]-2-amine | 473 | AA9 | II1 | +++ | ++++ |
| 362 | (4S)-2'-((2R)-2-(2-methoxyethyl)-4-morpholinyl)-7'-(3-pyridinyl)spiro[1,3-oxazole-4,9'-xanthen]-2-amine | 473 | AA9 | II1 | +++ | +++ |
| 363 | (4R)-2'-(3,6-dihydro-2H-pyran-4-yl)-4'-fluoro-7'-methoxyspiro[1,3-oxazole-4,9'-xanthen]-2-amine | 383 | AA24 | II12 | + | + |
| 364 | (4S)-2'-(3,6-dihydro-2H-pyran-4-yl)-4'-fluoro-7'-methoxyspiro[1,3-oxazole-4,9'-xanthen]-2-amine | 383 | AA24 | II12 | +++ | ++ |
| 365 | (4S)-2'-(2-fluoro-3-pyridinyl)-7'-((2R)-tetrahydro-2H-pyran-2-yl)spiro[1,3-oxazole-4,9'-xanthen]-2-amine | 432 | AA11 | II1 | ++++ | ++++ |
| 366 | (5S)-3,7-bis(3-fluorophenyl)spiro[chromeno[2,3-c]pyridine-5,4'-[1,3]oxazol]-2'-amine | 442 | AA2 | II2 | ++++ | +++ |
| 367 | (5S)-7-(5-chloro-2-fluorophenyl)-3-(3-pyridinyl)spiro[chromeno[2,3-c]pyridine-5,4'-[1,3]oxazol]-2'-amine | 459 | AA1 | II2 | ++++ | ++++ |
| 368 | (5S)-3-(3,6-dihydro-2H-pyran-4-yl)-7-(5-fluoro-3-pyridinyl)spiro[chromeno[2,3-c]pyridine-5,4'-[1,3]oxazol]-2'-amine | 431 | AA1 | II2 | ++++ | ++++ |
| 369 | (5S)-3-chloro-7-(5-fluoro-3-pyridinyl)spiro[chromeno[2,3-c]pyridine-5,4'-[1,3]oxazol]-2'-amine | 383 | AA24 | II2 | +++ | ++ |
| 370 | (5S)-7-(2-fluoro-3-pyridinyl)-3-((2R)-tetrahydro-2H-pyran-2-yl)spiro[chromeno[2,3-c]pyridine-5,4'-[1,3]oxazol]-2'-amine | 433 | AA11 | II2 | ++++ | ++++ |
| 371 | (5S)-3-(3,4-dihydro-2H-pyran-6-yl)-7-(2-fluoro-3-pyridinyl)spiro[chromeno[2,3-c]pyridine-5,4'-[1,3]oxazol]-2'-amine | 431 | AA1 | II2 | ++++ | ++++ |
| 372 | 4-((5S)-2'-amino-7-(2-fluoro-3-pyridinyl)spiro[chromeno[2,3-c]pyridine-5,4'-[1,3]oxazol]-3-yl)benzonitrile | 450 | AA1 | II2 | ++++ | ++++ |
| 373 | 3-((5S)-2'-amino-7-(2-fluoro-3-pyridinyl)spiro[chromeno[2,3-c]pyridine-5,4'-[1,3]oxazol]-3-yl)benzonitrile | 450 | AA1 | II2 | ++++ | ++++ |
| 374 | N-((4S)-2-amino-7'-methoxyspiro[1,3-oxazole-4,9'-xanthen]-2'-yl)-2-phenoxyacetamide | 432 | AA10 | II14 | +++ | ++ |
| 375 | N-((4S)-2-amino-7'-(2,2-dimethylpropoxy)spiro[1,3-oxazole-4,9'-xanthen]-2'-yl)-2-methoxyacetamide | 426 | AA10 | II14 | ++++ | +++ |
| 376 | N-((4S)-2-amino-7'-methoxyspiro[1,3-oxazole-4,9'-xanthen]-2'-yl)-2-ethoxyacetamide | 384 | AA10 | II14 | +++ | +++ |
| 377 | (4R)-2'-bromo-4'-fluoro-7'-methoxyspiro[1,3-oxazole-4,9'-xanthen]-2-amine | 380 | JBH2 | II12 | + | ++ |
| 378 | (4S)-2'-bromo-4'-fluoro-7'-methoxyspiro[1,3-oxazole-4,9'-xanthen]-2-amine | 380 | JBH2 | II12 | ++ | + |
| 379 | (5S)-3-((1E)-3,3-dimethyl-1-buten-1-yl)-7-(5-pyrimidinyl)spiro[chromeno[2,3-b]pyridine-5,4'-[1,3]oxazol]-2'-amine | 414 | AA1 | II3 | ++++ | ++++ |
| 380 | (5S)-3-((1E)-3,3-dimethyl-1-buten-1-yl)-7-(2-fluoro-3-pyridinyl)spiro[chromeno[2,3-b]pyridine-5,4'-[1,3]oxazol]-2'-amine | 431 | AA1 | II3 | ++++ | ++++ |
| 381 | (4S)-4'-fluoro-2'-(2-fluoro-2-methylpropoxy)-7'-(3-pyridinyl)spiro[1,3-oxazole-4,9'-xanthen]-2-amine | 438 | AA14 | II10 | ++++ | ++++ |
| 382 | (5S)-7-(cyclopropylethynyl)-3-(2-fluoro-2-methylpropoxy)spiro[chromeno[2,3-b]pyridine-5,4'-[1,3]oxazol]-2'-amine | 408 | AA17 | II5 | ++++ | ++++ |
| 383 | (5S)-3-(2,2-dimethylpropoxy)-7-(5-methoxy-3-pyridinyl)spiro[chromeno[2,3-b]pyridine-5,4'-[1,3]oxazol]-2'-amine | 447.2 | AA13 | II5 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 384 | (4S)-2'-(3-(1-methylethoxy)-1-azetidinyl)-7'-(3-pyridinyl)spiro[1,3-oxazole-4,9'-xanthen]-2-amine | 443 | AA9 | II1 | ++++ | ++++ |
| 385 | (4S)-4'-fluoro-7'-(2-fluoro-3-pyridinyl)-2'-(tetrahydro-2H-pyran-4-yl)spiro[1,3-oxazole-4,9'-xanthen]-2-amine | 450 | AA18 | II10 | ++++ | ++++ |
| 386 | (4S)-2'-(3,6-dihydro-2H-pyran-4-yl)-4'-fluoro-7'-(2-fluoro-3-pyridinyl)spiro[1,3-oxazole-4,9'-xanthen]-2-amine | 448 | AA8 | II10 | ++++ | ++++ |
| 387 | 2-(((4S)-2-amino-4'-fluoro-7'-(3-pyridinyl)spiro[1,3-oxazole-4,9'-xanthen]-2'-yl)oxy)-1-cyclopropylethanone | 446 | AA14 | II10 | ++++ | ++++ |
| 388 | (5S)-7-bromo-3-(2,2-dimethylpropoxy)spiro[chromeno[2,3-b]pyridine-5,4'-[1,3]oxazol]-2'-amine | 418 | AA13 | II5 | +++ | ++ |
| 389 | (5S)-3-(2,2-dimethylpropoxy)-7-(5-fluoro-3-pyridinyl)spiro[chromeno[2,3-b]pyridine-5,4'-[1,3]oxazol]-2'-amine | 435 | AA13 | II5 | ++++ | ++++ |
| 390 | 4-((4R)-2-amino-7'-(3-pyridinyl)spiro[1,3-oxazole-4,9'-xanthen]-2'-yl)-6-methyl-2H-pyran-2-one | 438 | AA36 | II1 | ++++ | ++++ |
| 391 | (4S)-2'-(4-morpholinyl)-7'-(2-(4-morpholinyl)-3-pyridinyl)spiro[1,3-oxazole-4,9'-xanthen]-2-amine | 500 | AA9 | II1 | +++ | ++ |
| 392 | (10S)-2-chloro-8-(2-fluoro-3-pyridinyl)spiro[chromeno[3,2-b]pyridine-10,4'-[1,3]oxazol]-2'-amine | 383 | AA24 | II8 | +++ | +++ |
| 393 | (10S)-2-chloro-8-(3-pyridinyl)spiro[chromeno[3,2-b]pyridine-10,4'-[1,3]oxazol]-2'-amine | 365 | AA24 | II8 | +++ | ++ |
| 394 | (5S)-3-(2,2-dimethylpropoxy)-7-(5-pyrimidinyl)spiro[chromeno[2,3-b]pyridine-5,4'-[1,3]oxazol]-2'-amine | 418.2 | AA13 | II5 | ++++ | ++++ |
| 395 | (5S)-3-(2,2-dimethylpropoxy)-7-(2-fluoro-3-pyridinyl)spiro[chromeno[2,3-b]pyridine-5,4'-[1,3]oxazol]-2'-amine | 435 | AA13 | II5 | ++++ | ++++ |
| 396 | (4-((5S)-2'-amino-7-(3-pyridinyl)spiro[chromeno[2,3-c]pyridine-5,4'-[1,3]oxazol]-3-yl)-1-piperazinyl)acetic acid | 473 | AA9 | II2 | ++++ | +++ |
| 397 | (5S)-3-((1E)-3,3-dimethyl-1-buten-1-yl)-7-(3-pyridinyl)spiro[chromeno[2,3-c]pyridine-5,4'-[1,3]oxazol]-2'-amine | 413 | AA1 | II2 | ++++ | ++++ |
| 398 | (10S)-2-((1E)-3,3-dimethyl-1-buten-1-yl)-8-(3-pyridinyl)spiro[chromeno[3,2-b]pyridine-10,4'-[1,3]oxazol]-2'-amine | 413 | AA1 | II8 | ++++ | ++++ |
| 399 | (10S)-8-(2-fluoro-3-pyridinyl)-2-(2-fluoro-4-pyridinyl)spiro[chromeno[3,2-b]pyridine-10,4'-[1,3]oxazol]-2'-amine | 444 | AA1 | II8 | ++++ | +++ |
| 400 | (10S)-2-(3,6-dihydro-2H-pyran-4-yl)-8-(2-fluoro-3-pyridinyl)spiro[chromeno[3,2-b]pyridine-10,4'-[1,3]oxazol]-2'-amine | 431 | AA1 | II8 | ++++ | ++++ |
| 401 | (10S)-8-(2-fluoro-3-pyridinyl)-2-(2-methyl-4-pyridinyl)spiro[chromeno[3,2-b]pyridine-10,4'-[1,3]oxazol]-2'-amine | 440 | AA1 | II8 | +++ | ++++ |
| 402 | (10S)-8-(2-fluoro-3-pyridinyl)-2-(4-pyridinyl)spiro[chromeno[3,2-b]pyridine-10,4'-[1,3]oxazol]-2'-amine | 426 | AA1 | II8 | ++++ | ++++ |
| 403 | (5S)-7-(2-fluoro-3-pyridinyl)-3-(4-pyridinyl)spiro[chromeno[2,3-b]pyridine-5,4'-[1,3]oxazol]-2'-amine | 426.3 | AA8 | II4 | ++++ | ++++ |
| 404 | (5S)-7-(5-chloro-2-fluorophenyl)-3-(tetrahydro-2H-pyran-4-yl)spiro[chromeno[2,3-b]pyridine-5,4'-[1,3]oxazol]-2'-amine | 466 | AA19 | II3 | ++++ | ++++ |
| 405 | (5S)-7-(2-fluoro-3-pyridinyl)-3-(tetrahydro-2H-pyran-4-yl)spiro[chromeno[2,3-b]pyridine-5,4'-[1,3]oxazol]-2'-amine | 433 | AA19 | II3 | ++++ | ++++ |
| 406 | (4S)-2'-bromo-4'-fluoro-7'-methoxyspiro[1,3-oxazole-4,9'-xanthen]-2-amine | 380 | JBH2 | II12 | + | + |

TABLE IV-continued

| Ex. No. | Compound Name | Observed Mass | Method | Intermediate used | BACE1 FRET assay (uM) | HEK cell assay (uM) |
|---|---|---|---|---|---|---|
| 407 | 3-(((5S)-2'-amino-7-(2,5-difluorophenyl)spiro[chromeno[2,3-b]pyridine-5,4'-[1,3]oxazol]-3-yl)oxy)-2,2-dimethylpropanenitrile | 463 | AA13 | II5 | ++++ | ++++ |
| 408 | 3-(((5S)-2'-amino-7-(2-fluorophenyl)spiro[chromeno[2,3-b]pyridine-5,4'-[1,3]oxazol]-3-yl)oxy)-2,2-dimethylpropanenitrile | 445 | AA13 | II5 | ++++ | ++++ |
| 409 | 3-(((5S)-2'-amino-7-phenylspiro[chromeno[2,3-b]pyridine-5,4'-[1,3]oxazol]-3-yl)oxy)-2,2-dimethylpropanenitrile | 427 | AA13 | II5 | ++++ | +++ |
| 410 | 3-(((5S)-2'-amino-7-(3-pyridinyl)spiro[chromeno[2,3-b]pyridine-5,4'-[1,3]oxazol]-3-yl)oxy)-2,2-dimethylpropanenitrile | 428 | AA13 | II5 | ++++ | ++++ |
| 411 | (5S)-7-(2,6-difluorophenyl)-3-((3-methyl-3-oxetanyl)methoxy)spiro[chromeno[2,3-b]pyridine-5,4'-[1,3]oxazol]-2'-amine | 466 | AA13 | II5 | ++++ | ++++ |
| 412 | (5S)-7-(2,5-difluorophenyl)-3-((3-methyl-3-oxetanyl)methoxy)spiro[chromeno[2,3-b]pyridine-5,4'-[1,3]oxazol]-2'-amine | 466 | AA13 | II5 | ++++ | ++++ |
| 413 | (5S)-7-(2,3-difluorophenyl)-3-((3-methyl-3-oxetanyl)methoxy)spiro[chromeno[2,3-b]pyridine-5,4'-[1,3]oxazol]-2'-amine | 466 | AA13 | II5 | ++++ | ++++ |
| 414 | (5S)-7-(2-chlorophenyl)-3-((3-methyl-3-oxetanyl)methoxy)spiro[chromeno[2,3-b]pyridine-5,4'-[1,3]oxazol]-2'-amine | 464 | AA13 | II5 | ++++ | +++ |
| 415 | (4S)-2'-(3-ethoxy-1-azetidinyl)-7'-(3-pyridinyl)spiro[1,3-oxazole-4,9'-xanthen]-2-amine | 429 | AA9 | II1 | ++++ | ++++ |
| 416 | (4S)-4'-fluoro-7'-(2-fluoro-3-pyridinyl)-2'-((1S,4S)-2-oxa-5-azabicyclo[2.2.1]hept-5-yl)spiro[1,3-oxazole-4,9'-xanthen]-2-amine | 463 | AA20 | II10 | ++++ | ++++ |
| 417 | (4S)-4'-fluoro-7'-(5-pyrimidinyl)-2'-(tetrahydro-2H-pyran-4-ylmethoxy)spiro[1,3-oxazole-4,9'-xanthen]-2-amine | 463 | AA13 | II10 | ++++ | ++++ |
| 418 | (4S)-4'-fluoro-7'-(3-pyridinyl)-2'-(tetrahydro-2H-pyran-4-ylmethoxy)spiro[1,3-oxazole-4,9'-xanthen]-2-amine | 462 | AA13 | II10 | ++++ | ++++ |
| 419 | (4S)-2'-(4-oxa-7-azaspiro[2.5]oct-7-yl)-7'-(3-pyridinyl)spiro[1,3-oxazole-4,9'-xanthen]-2-amine | 441 | AA9 | II1 | ++++ | ++++ |
| 420 | (4R)-2'-(5-pyrimidinyl)-7'-((3S)-tetrahydro-3-furanyl)spiro[1,3-oxazole-4,9'-xanthen]-2-amine | 401 | AA11 | II1 | ++++ | +++ |
| 421 | (4S)-2'-((2R)-2-(2-methoxyethyl)-4-morpholinyl)-7'-(3-pyridinyl)spiro[1,3-oxazole-4,9'-xanthen]-2-amine | 473 | AA9 | II1 | +++ | +++ |
| 422 | (4S)-2'-((2R)-2-(2-methylpropyl)-4-morpholinyl)-7'-(5-pyrimidinyl)spiro[1,3-oxazole-4,9'-xanthen]-2-amine | 472 | AA9 | II1 | +++ | +++ |
| 423 | (5S)-3-(3,6-dihydro-2H-pyran-4-yl)-7-(5-(3,6-dihydro-2H-pyran-4-yl)-2-fluorophenyl)spiro[chromeno[2,3-c]pyridine-5,4'-[1,3]oxazol]-2'-amine | 512 | AA1 | II2 | ++++ | +++ |
| 424 | (5S)-7-(5-chloro-2-fluorophenyl)-3-(3,6-dihydro-2H-pyran-4-yl)spiro[chromeno[2,3-c]pyridine-5,4'-[1,3]oxazol]-2'-amine | 464 | AA1 | II2 | ++++ | ++++ |
| 425 | (5S)-3-chloro-7-(2-fluorophenyl)spiro[chromeno[2,3-c]pyridine-5,4'-[1,3]oxazol]-2'-amine | 382 | AA24 | II2 | +++ | + |
| 426 | (5S)-3-(3,6-dihydro-2H-pyran-4-yl)-7-(2-fluorophenyl)spiro[chromeno[2,3-c]pyridine-5,4'-[1,3]oxazol]-2'-amine | 430 | AA1 | II2 | ++++ | +++ |
| 427 | (5S)-7-(3-chlorophenyl)-3-(3,6-dihydro-2H-pyran-4-yl)spiro[chromeno[2,3-c]pyridine-5,4'-[1,3]oxazol]-2'-amine | 446 | AA1 | II2 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 428 | (5S)-7-(2-fluoro-3-pyridinyl)-3-(2-fluoro-4-pyridinyl)spiro[chromeno[2,3-c]pyridine-5,4'-[1,3]oxazol]-2'-amine | 444 | AA1 | II2 | ++++ | ++++ |
| 429 | (5S)-7-(2-fluoro-3-pyridinyl)-3-(2-methyl-4-pyridinyl)spiro[chromeno[2,3-c]pyridine-5,4'-[1,3]oxazol]-2'-amine | 440 | AA1 | II2 | ++++ | ++++ |
| 430 | (5S)-7-(2-fluoro-3-pyridinyl)-3-(2-methoxy-4-pyridinyl)spiro[chromeno[2,3-c]pyridine-5,4'-[1,3]oxazol]-2'-amine | 456 | AA1 | II2 | ++++ | +++ |
| 431 | (5S)-3-(3,6-dihydro-2H-pyran-4-yl)-7-(6-fluoro-3-pyridinyl)spiro[chromeno[2,3-c]pyridine-5,4'-[1,3]oxazol]-2'-amine | 431 | AA1 | II2 | ++++ | ++++ |
| 432 | (5S)-3-((4R)-2,2-dimethyltetrahydro-2H-pyran-4-yl)-7-(2-fluoro-3-pyridinyl)spiro[chromeno[2,3-c]pyridine-5,4'-[1,3]oxazol]-2'-amine | 461 | AA11 | II2 | ++++ | ++++ |
| 433 | (5S)-3,7-bis(6-fluoro-3-pyridinyl)spiro[chromeno[2,3-c]pyridine-5,4'-[1,3]oxazol]-2'-amine | 444 | AA2 | II2 | ++++ | +++ |
| 434 | (5S)-3-(2,2-dimethyl-3,6-dihydro-2H-pyran-4-yl)-7-(2-fluoro-3-pyridinyl)spiro[chromeno[2,3-c]pyridine-5,4'-[1,3]oxazol]-2'-amine | 459 | AA1 | II2 | ++++ | ++++ |
| 435 | (5S)-3-(6,6-dimethyl-3,6-dihydro-2H-pyran-4-yl)-7-(2-fluoro-3-pyridinyl)spiro[chromeno[2,3-c]pyridine-5,4'-[1,3]oxazol]-2'-amine | 459 | AA1 | II2 | ++++ | ++++ |
| 436 | (5S)-3-(2,2-dimethyl-3,6-dihydro-2H-pyran-4-yl)-7-(3-pyridinyl)spiro[chromeno[2,3-c]pyridine-5,4'-[1,3]oxazol]-2'-amine | 441 | AA1 | II2 | ++++ | ++++ |
| 437 | (5S)-3-(6,6-dimethyl-3,6-dihydro-2H-pyran-4-yl)-7-(3-pyridinyl)spiro[chromeno[2,3-c]pyridine-5,4'-[1,3]oxazol]-2'-amine | 441 | AA1 | II2 | ++++ | ++++ |
| 438 | methyl (4-((5S)-2'-amino-7-(3-pyridinyl)spiro[chromeno[2,3-c]pyridine-5,4'-[1,3]oxazol]-3-yl)-1-piperazinyl)acetate | 487 | AA9 | II2 | ++++ | ++++ |
| 439 | (5S)-3-(1-piperazinyl)-7-(3-pyridinyl)spiro[chromeno[2,3-c]pyridine-5,4'-[1,3]oxazol]-2'-amine | 415 | AA9 | II2 | ++++ | ++++ |
| 440 | (5S)—N~3~-(2,2-dimethylpropyl)-7-(3-pyridinyl)spiro[chromeno[2,3-c]pyridine-5,4'-[1,3]oxazole]-2',3-diamine | 416 | AA9 | II2 | ++++ | ++++ |
| 441 | (5S)-3-(4-methyl-1-piperidinyl)-7-(3-pyridinyl)spiro[chromeno[2,3-c]pyridine-5,4'-[1,3]oxazol]-2'-amine | 428 | AA9 | II2 | ++++ | ++++ |
| 442 | 1-((5S)-2'-amino-7-(3-pyridinyl)spiro[chromeno[2,3-c]pyridine-5,4'-[1,3]oxazol]-3-yl)-4-piperidinone | 428 | AA9 | II2 | ++++ | ++++ |
| 443 | (5S)-3-(1,4-dioxa-8-azaspiro[4.5]dec-8-yl)-7-(3-pyridinyl)spiro[chromeno[2,3-c]pyridine-5,4'-[1,3]oxazol]-2'-amine | 472 | AA9 | II2 | ++++ | ++++ |
| 444 | (5S)-3-(4-methyl-1-piperazinyl)-7-(3-pyridinyl)spiro[chromeno[2,3-c]pyridine-5,4'-[1,3]oxazol]-2'-amine | 428 | AA9 | II2 | ++++ | ++++ |
| 445 | (5S)-3-(1-piperidinyl)-7-(3-pyridinyl)spiro[chromeno[2,3-c]pyridine-5,4'-[1,3]oxazol]-2'-amine | 414 | AA9 | II2 | ++++ | ++++ |
| 446 | (5S)-7-(3-pyridinyl)spiro[chromeno[2,3-c]pyridine-5,4'-[1,3]oxazole]-2',3-diamine | 346 | AA9 | II2 | +++ | +++ |
| 447 | (5S)-3-(1-azetidinyl)-7-(3-pyridinyl)spiro[chromeno[2,3-c]pyridine-5,4'-[1,3]oxazol]-2'-amine | 386 | AA9 | II2 | ++++ | +++ |
| 448 | (4S)-2'-(2,5-dihydro-3-furanyl)-7'-(5-pyrimidinyl)spiro[1,3-oxazole-4,9'-xanthen]-2-amine | 399 | AA1 | II1 | ++++ | ++++ |
| 449 | (5S)-3-(2-fluoro-2-methylpropoxy)-7-(2-fluoro-3-pyridinyl)spiro[chromeno[2,3-b]pyridine-5,4'-[1,3]oxazol]-2'-amine | 439 | AA13 | II5 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 450 | (5S)-3-(2-fluoro-2-methylpropoxy)-7-(3-pyridinyl)spiro[chromeno[2,3-b]pyridine-5,4'-[1,3]oxazol]-2'-amine | 421 | AA13 | II5 | ++++ | ++++ |
| 451 | (5S)-3-(2-fluoro-2-methylpropoxy)-7-(6-fluoro-3-pyridinyl)spiro[chromeno[2,3-b]pyridine-5,4'-[1,3]oxazol]-2'-amine | 439 | AA13 | II5 | ++++ | ++++ |
| 452 | (5S)-3-(2-fluoro-2-methylpropoxy)-7-phenylspiro[chromeno[2,3-b]pyridine-5,4'-[1,3]oxazol]-2'-amine | 420 | AA13 | II5 | ++++ | +++ |
| 453 | (5S)-7-(2,5-difluorophenyl)-3-((1S,4S)-2-oxa-5-azabicyclo[2.2.1]hept-5-yl)spiro[chromeno[2,3-b]pyridine-5,4'-[1,3]oxazol]-2'-amine | 463 | AA16 | II4 | ++++ | ++++ |
| 454 | (5S)-3-((1S,4S)-2-oxa-5-azabicyclo[2.2.1]hept-5-yl)-7-phenylspiro[chromeno[2,3-b]pyridine-5,4'-[1,3]oxazol]-2'-amine | 427 | AA16 | II4 | ++++ | ++++ |
| 455 | (5S)-3-(3,3-dimethylbutyl)-7-(5-pyrimidinyl)spiro[chromeno[2,3-c]pyridine-5,4'-[1,3]oxazol]-2'-amine | 416 | AA11 | II2 | ++++ | ++++ |
| 456 | (5S)-7-(2,5-difluorophenyl)-3-(3-methoxy-1-azetidinyl)spiro[chromeno[2,3-b]pyridine-5,4'-[1,3]oxazol]-2'-amine | 451 | AA9 | II3 | ++++ | ++++ |
| 457 | (5S)-7-(5-chloro-2-fluorophenyl)-3-(4-morpholinyl)spiro[chromeno[2,3-b]pyridine-5,4'-[1,3]oxazol]-2'-amine | 467 | AA16 | II4 | ++++ | ++++ |
| 458 | (5S)-7-(2-fluorophenyl)-3-((3-methyl-3-oxetanyl)methoxy)spiro[chromeno[2,3-b]pyridine-5,4'-[1,3]oxazol]-2'-amine | 448.2 | AA13 | II5 | ++++ | ++++ |
| 459 | (5S)-3-((3-methyl-3-oxetanyl)methoxy)-7-phenylspiro[chromeno[2,3-b]pyridine-5,4'-[1,3]oxazol]-2'-amine | 430 | AA13 | II5 | ++++ | ++++ |
| 460 | (5S)-7-(2-fluorophenyl)-3-(4-morpholinyl)spiro[chromeno[2,3-b]pyridine-5,4'-[1,3]oxazol]-2'-amine | 433 | AA16 | II4 | ++++ | +++ |
| 461 | (5S)-7-(2,5-difluorophenyl)-3-(4-morpholinyl)spiro[chromeno[2,3-b]pyridine-5,4'-[1,3]oxazol]-2'-amine | 451 | AA16 | II4 | ++++ | ++++ |
| 462 | (4S)-2'-(6-oxa-9-azaspiro[4.5]dec-9-yl)-7'-(5-pyrimidinyl)spiro[1,3-oxazole-4,9'-xanthen]-2-amine | 470 | AA9 | II1 | ++++ | +++ |
| 463 | (5S)-3-(2,2-dimethyl-4-morpholinyl)-7-(2-fluoro-3-pyridinyl)spiro[chromeno[2,3-b]pyridine-5,4'-[1,3]oxazol]-2'-amine | 462 | AA9 | II3 | ++++ | ++++ |
| 464 | (4S)-2'-(4-methoxy-1-piperidinyl)-7'-(3-pyridinyl)spiro[1,3-oxazole-4,9'-xanthen]-2-amine | 443 | AA9 | II1 | ++++ | ++++ |
| 465 | (4S)-2'-(2,2-dimethyl-3,6-dihydro-2H-pyran-4-yl)-4'-fluoro-7'-(5-pyrimidinyl)spiro[1,3-oxazole-4,9'-xanthen]-2-amine | 459 | AA8 | II10 | ++++ | ++++ |
| 466 | (4S)-2'-(6,6-dimethyl-3,6-dihydro-2H-pyran-4-yl)-4'-fluoro-7'-(5-pyrimidinyl)spiro[1,3-oxazole-4,9'-xanthen]-2-amine | 459 | AA8 | II10 | ++++ | ++++ |
| 467 | (4S)-2'-(2,2-diethyl-4-morpholinyl)-7'-(5-pyrimidinyl)spiro[1,3-oxazole-4,9'-xanthen]-2-amine | 472 | AA9 | II1 | ++++ | +++ |
| 468 | (5S)-7-(2,5-difluorophenyl)-3-(2,2-dimethyl-4-morpholinyl)spiro[chromeno[2,3-b]pyridine-5,4'-[1,3]oxazol]-2'-amine | 479 | AA9 | II3 | ++++ | ++++ |
| 469 | (5S)-3-(2,2-dimethylpropoxy)-7-phenylspiro[chromeno[2,3-b]pyridine-5,4'-[1,3]oxazol]-2'-amine | 416.2 | AA13 | II5 | ++++ | +++ |
| 470 | (5S)-3-(2,2-dimethylpropoxy)-7-(6-fluoro-3-pyridinyl)spiro[chromeno[2,3-b]pyridine-5,4'-[1,3]oxazol]-2'-amine | 435 | AA13 | II5 | ++++ | ++++ |
| 471 | (5R)-3-(2,2-dimethylpropoxy)-7-(2-fluoro-3-pyridinyl)spiro[chromeno[2,3-b]pyridine-5,4'-[1,3]oxazol]-2'-amine | 435.1 | AA13 | II5 | +++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 472 | (5S)-3-(3,3-dimethylbutyl)-7-(5-pyrimidinyl)spiro[chromeno[2,3-b]pyridine-5,4'-[1,3]oxazol]-2'-amine | 416 | AA6 | II3 | ++++ | ++++ |
| 473 | 4-((5S)-2'-amino-7-(5-pyrimidinyl)spiro[chromeno[2,3-b]pyridine-5,4'-[1,3]oxazol]-3-yl)benzonitrile | 433 | AA8 | II4 | ++++ | ++++ |
| 474 | (4S)-4'-fluoro-2'-(3-methoxy-1-azetidinyl)-7'-(3-pyridinyl)spiro[1,3-oxazole-4,9'-xanthen]-2-amine | 433 | AA20 | II10 | ++++ | ++++ |
| 475 | (4S)-4'-fluoro-2'-((3-methyl-3-oxetanyl)ethynyl)-7'-(5-pyrimidinyl)spiro[1,3-oxazole-4,9'-xanthen]-2-amine | 443 | AA21 | II10 | ++++ | ++++ |
| 476 | (4S)-2'-(3,6-dihydro-2H-pyran-4-yl)-3'-fluoro-7'-(3-pyridinyl)spiro[1,3-oxazole-4,9'-xanthen]-2-amine | 430 | AA8 | II9 | ++++ | ++++ |
| 477 | (4S)-4'-fluoro-2'-((3-methyl-3-oxetanyl)methoxy)-7'-(3-pyridinyl)spiro[1,3-oxazole-4,9'-xanthen]-2-amine | 448 | AA14 | II10 | ++++ | ++++ |
| 478 | (5S)-3-(6,6-dimethyl-3,6-dihydro-2H-pyran-4-yl)-7-(5-pyrimidinyl)spiro[chromeno[2,3-b]pyridine-5,4'-[1,3]oxazol]-2'-amine | 442 | AA8 | II4 | ++++ | ++++ |
| 479 | (5S)-3-(6,6-dimethyl-3,6-dihydro-2H-pyran-4-yl)-7-(2-fluoro-3-pyridinyl)spiro[chromeno[2,3-b]pyridine-5,4'-[1,3]oxazol]-2'-amine | 459 | AA8 | II4 | ++++ | ++++ |
| 480 | 4-((5S)-2'-amino-7-(2-fluoro-3-pyridinyl)spiro[chromeno[2,3-b]pyridine-5,4'-[1,3]oxazol]-3-yl)benzonitrile | 450 | AA8 | II4 | ++++ | ++++ |
| 481 | (5S)-3-(6,6-dimethyl-3,6-dihydro-2H-pyran-4-yl)-7-(3-pyridinyl)spiro[chromeno[2,3-b]pyridine-5,4'-[1,3]oxazol]-2'-amine | 441 | AA8 | II4 | ++++ | ++++ |
| 482 | (4R)-2'-((4R)-2,2-dimethyltetrahydro-2H-pyran-4-yl)-7'-(5-pyrimidinyl)spiro[1,3-oxazole-4,9'-xanthen]-2-amine | 443 | AA11 | II1 | ++++ | ++++ |
| 483 | (4S)-2'-((2R,6S)-2,6-dimethyl-4-morpholinyl)-4'-fluoro-7'-(3-pyridinyl)spiro[1,3-oxazole-4,9'-xanthen]-2-amine | 461 | AA20 | II10 | ++++ | ++++ |
| 484 | (4S)-2'-(2,2-dimethyl-4-morpholinyl)-4'-fluoro-7'-(3-pyridinyl)spiro[1,3-oxazole-4,9'-xanthen]-2-amine | 461 | AA20 | II10 | ++++ | ++++ |
| 485 | (5S)-3-(3,6-dihydro-2H-pyran-4-yl)-7-(3-fluorophenyl)spiro[chromeno[2,3-c]pyridine-5,4'-[1,3]oxazol]-2'-amine | 430 | AA1 | II2 | ++++ | ++++ |
| 486 | (5S)-7-(2,5-difluorophenyl)-3-(3,6-dihydro-2H-pyran-4-yl)spiro[chromeno[2,3-c]pyridine-5,4'-[1,3]oxazol]-2'-amine | 448 | AA1 | II2 | ++++ | ++++ |
| 487 | (5S)-7-(2,5-difluorophenyl)-3-(3,6-dihydro-2H-pyran-4-yl)spiro[chromeno[2,3-b]pyridine-5,4'-[1,3]oxazol]-2'-amine | 448 | AA8 | II4 | ++++ | ++++ |
| 488 | (5S)-3-(3,6-dihydro-2H-pyran-4-yl)-7-(2-fluorophenyl)spiro[chromeno[2,3-b]pyridine-5,4'-[1,3]oxazol]-2'-amine | 430 | AA8 | II4 | ++++ | ++++ |
| 489 | (5S)-3-(2,2-dimethyl-4-morpholinyl)-7-(2-fluoro-3-pyridinyl)spiro[chromeno[2,3-c]pyridine-5,4'-[1,3]oxazol]-2'-amine | 462 | AA9 | II2 | ++++ | ++++ |
| 490 | (5S)-3-(2,2-dimethyl-4-morpholinyl)-7-(3-pyridinyl)spiro[chromeno[2,3-c]pyridine-5,4'-[1,3]oxazol]-2'-amine | 444 | AA9 | II2 | ++++ | ++++ |
| 491 | (4R)-2-amino-7'-(3,6-dihydro-2H-pyran-4-yl)-3'-fluorospiro[1,3-oxazole-4,9'-xanthen]-2'-ol | 369 | AA24 | II10 | +++ | ++ |
| 492 | (4R)-7'-(3,6-dihydro-2H-pyran-4-yl)-3'-fluoro-2'-(3-pyridinyl)spiro[1,3-oxazole-4,9'-xanthen]-2-amine | 430 | AA8 | II9 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 493 | (5S)-7-(3-pyridinyl)-3-(1-pyrrolidinyl)spiro[chromeno[2,3-c]pyridine-5,4'-[1,3]oxazol]-2'-amine | 400 | AA9 | II2 | ++++ | ++++ |
| 286 | (5S)-3-(3,6-dihydro-2H-pyran-4-yl)-7-(2-fluoro-5-methyl-3-pyridinyl)spiro[chromeno[2,3-c]pyridine-5,4'-[1,3]oxazol]-2'-amine | 445 | AA1 | II2 | ++++ | ++++ |
| 494 | (5S)-7-(2-fluoro-3-pyridinyl)-3-phenylspiro[chromeno[2,3-c]pyridine-5,4'-[1,3]oxazol]-2'-amine | 425 | AA1 | II2 | ++++ | ++++ |
| 495 | (5S)-7-(2-fluoro-3-pyridinyl)-3-(tetrahydro-2H-pyran-4-yl)spiro[chromeno[2,3-c]pyridine-5,4'-[1,3]oxazol]-2'-amine | 433 | AA11 | II2 | ++++ | ++++ |
| 486 | (5S)-7-(2-fluoro-3-pyridinyl)-3-(6-methyl-3-pyridinyl)spiro[chromeno[2,3-c]pyridine-5,4'-[1,3]oxazol]-2'-amine | 440 | AA1 | II2 | ++++ | ++++ |
| 291 | (5S)-3-((1E)-3,3-dimethyl-1-buten-1-yl)-7-(5-pyrimidinyl)spiro[chromeno[2,3-c]pyridine-5,4'-[1,3]oxazol]-2'-amine | 414 | AA1 | II2 | ++++ | ++++ |
| 497 | (5R)-7-(3,6-dihydro-2H-pyran-4-yl)-3-(2-fluoro-3-pyridinyl)spiro[chromeno[2,3-c]pyridine-5,4'-[1,3]oxazol]-2'-amine | 431 | AA1 | II2 | ++++ | ++++ |
| 498 | (5R)-7-(3,6-dihydro-2H-pyran-4-yl)-3-(2-fluorophenyl)spiro[chromeno[2,3-c]pyridine-5,4'-[1,3]oxazol]-2'-amine | 430 | AA1 | II2 | ++++ | +++ |
| 499 | (5R)-3-chloro-7-(3,6-dihydro-2H-pyran-4-yl)spiro[chromeno[2,3-c]pyridine-5,4'-[1,3]oxazol]-2'-amine | 370 | AA24 | II2 | ++ | + |
| 500 | (5S)-3-chloro-7-(5-pyrimidinyl)spiro[chromeno[2,3-c]pyridine-5,4'-[1,3]oxazol]-2'-amine | 365.9 | AA24 | II2 | +++ | ++ |
| 501 | (4S)-2'-((2R,6S)-2,6-dimethyl-4-morpholinyl)-4'-fluoro-7'-(5-pyrimidinyl)spiro[1,3-oxazole-4,9'-xanthen]-2-amine | 462 | AA20 | II10 | ++++ | ++++ |
| 502 | (4S)-2'-(6,6-dimethyl-3,6-dihydro-2H-pyran-4-yl)-3'-fluoro-7'-(5-pyrimidinyl)spiro[1,3-oxazole-4,9'-xanthen]-2-amine | 459 | AA8 | II9 | ++++ | ++++ |
| 503 | (10R)-2'-amino-2-(4-methylphenyl)-8-(3-pyridinyl)spiro[chromeno[3,2-c]pyridine-10,4'-[1,3]oxazol]-1(2H)-one | 437 | AA56 | II28 | + | ++ |
| 504 | (10S)-2'-amino-2-(4-methylphenyl)-8-(3-pyridinyl)spiro[chromeno[3,2-c]pyridine-10,4'-[1,3]oxazol]-1(2H)-one | 437 | AA56 | II28 | +++ | +++ |
| 505 | (4S)-2'-(2,2-dimethyl-4-morpholinyl)-4'-fluoro-7'-(5-pyrimidinyl)spiro[1,3-oxazole-4,9'-xanthen]-2-amine | 462 | AA20 | II10 | ++++ | ++++ |
| 506 | (4R)-2'-(2,2-dimethyl-4-morpholinyl)-4'-fluoro-7'-(5-pyrimidinyl)spiro[1,3-oxazole-4,9'-xanthen]-2-amine | 462 | AA20 | II10 | +++ | ++ |
| 287 | 3-(((4S)-2-amino-4'-fluoro-7'-(2-fluoro-3-pyridinyl)spiro[1,3-oxazole-4,9'-xanthen]-2'-yl)oxy)-2,2-dimethylpropanenitrile | 463 | AA14 | II10 | ++++ | ++++ |
| 507 | (4S)-2'-((2,2-difluorocyclopropyl)methoxy)-4'-fluoro-7'-(5-pyrimidinyl)spiro[1,3-oxazole-4,9'-xanthen]-2-amine | 455 | AA14 | II10 | ++++ | ++++ |
| 508 | (4S)-2'-(3,3-difluoro-1-azetidinyl)-7'-(5-pyrimidinyl)spiro[1,3-oxazole-4,9'-xanthen]-2-amine | 422 | AA9 | II1 | ++++ | ++++ |
| 509 | (4S)-4'-fluoro-2'-(1-methyl-1H-pyrazol-4-yl)-7'-(3-pyridinyl)spiro[1,3-oxazole-4,9'-xanthen]-2-amine | 428 | AA8 | II10 | ++++ | ++++ |
| 510 | tert-butyl 2-((4S)-2-amino-5'-fluorospiro[1,3-oxazole-4,9'-xanthen]-2'-yl)-1H-pyrrole-1-carboxylate | 436 | AA24 | II13 | ++ | ++ |
| 511 | (4S)-4'-fluoro-2'-(1-methyl-1H-pyrazol-4-yl)-7'-(5-pyrimidinyl)spiro[1,3-oxazole-4,9'-xanthen]-2-amine | 429 | AA8 | II10 | ++++ | ++++ |
| 512 | (5S)-3-(3,3-dimethyl-1-butyn-1-yl)-7-(5-pyrimidinyl)spiro[chromeno[2,3-c]pyridine-5,4'-[1,3]oxazol]-2'-amine | 412 | AA1 | II2 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 293 | (4S)-4'-fluoro-2'-(2-fluoro-2-methylpropoxy)-7'-(5-pyrimidinyl)spiro[1,3-oxazole-4,9'-xanthen]-2-amine | 439 | AA14 | II10 | ++++ | ++++ |
| 513 | (4S)-4'-fluoro-7'-(2-fluoro-3-pyridinyl)-2'-((3-methyl-3-oxetanyl)methoxy)spiro[1,3-oxazole-4,9'-xanthen]-2-amine | 466 | AA14 | II10 | ++++ | ++++ |
| 514 | (5S)-3-((1E)-3,3-dimethyl-1-buten-1-yl)-7-(2-fluoro-3-pyridinyl)spiro[chromeno[2,3-c]pyridine-5,4'-[1,3]oxazol]-2'-amine | 431 | AA1 | II2 | ++++ | ++++ |
| 515 | (5S)-7-(2-fluoro-3-pyridinyl)-3-(4-pyridinyl)spiro[chromeno[2,3-c]pyridine-5,4'-[1,3]oxazol]-2'-amine | 426 | AA1 | II2 | ++++ | ++++ |
| 516 | (5S)-7-(2-fluoro-3-pyridinyl)-3-(2-pyridinyl)spiro[chromeno[2,3-c]pyridine-5,4'-[1,3]oxazol]-2'-amine | 426 | AA1 | II2 | ++++ | ++++ |
| 517 | (5S)-7-(2-fluoro-3-pyridinyl)-3-(3-pyridinyl)spiro[chromeno[2,3-c]pyridine-5,4'-[1,3]oxazol]-2'-amine | 426 | AA1 | II2 | ++++ | ++++ |
| 518 | (4R)-2-amino-N-cyclopropyl-7'-phenylspiro[1,3-oxazole-4,9'-xanthene]-2'-carboxamide | 412 | AA44 | II1 | ++++ | ++++ |
| 519 | (5S)-7-(2,5-difluorophenyl)-3-((3-methyl-3-oxetanyl)ethynyl)spiro[chromeno[2,3-b]pyridine-5,4'-[1,3]oxazol]-2'-amine | 460 | AA23 | II4 | ++++ | ++++ |
| 520 | (5S)-7-(2-fluorophenyl)-3-((3-methyl-3-oxetanyl)ethynyl)spiro[chromeno[2,3-b]pyridine-5,4'-[1,3]oxazol]-2'-amine | 442 | AA23 | II4 | ++++ | ++++ |
| 290 | (4S)-2'-(2,2-dimethyl-4-morpholinyl)-7'-(2-fluoro-3-pyridinyl)spiro[1,3-oxazole-4,9'-xanthen]-2-amine | 461 | AA16 | II18 | ++++ | ++++ |
| 521 | (5S)-7-(5-chloro-2-fluorophenyl)-3-((3-methyl-3-oxetanyl)ethynyl)spiro[chromeno[2,3-b]pyridine-5,4'-[1,3]oxazol]-2'-amine | 476.2 | AA23 | II4 | ++++ | ++++ |
| 288 | (5S)-7-(2-fluoro-3-pyridinyl)-3-((3-methyl-3-oxetanyl)ethynyl)spiro[chromeno[2,3-b]pyridine-5,4'-[1,3]oxazol]-2'-amine | 443 | AA5 | II3 | ++++ | ++++ |
| 522 | N-(2-amino-7'-(2,2-dimethylpropoxy)spiro[1,3-oxazole-4,9'-xanthen]-2'-yl)-5-chloro-2-pyridinecarboxamide | 493 | AA10 | II20 | ++++ | ++++ |
| 523 | 4-((10R)-2'-amino-1-oxo-8-(3-pyridinyl)spiro[chromeno[3,2-c]pyridine-10,4'-[1,3]oxazol]-2(1H)-yl)benzonitrile | 448 | AA56 | II28 | ++ | ++ |
| 524 | 4-((4S)-2-amino-3'-fluoro-7'-(5-pyrimidinyl)spiro[1,3-oxazole-4,9'-xanthen]-2'-yl)-6,6-dimethyl-5,6-dihydro-2H-pyran-2-one | 473 | AA8 | II9 | ++++ | ++++ |
| 525 | (10S)-8-(5-pyrimidinyl)spiro[chromeno[3,2-b]pyridine-10,4'-[1,3]oxazol]-2'-amine | 332 | AA24 | II8 | + | + |
| 526 | (10S)-2-(3,3-dimethyl-1-butyn-1-yl)-8-(5-pyrimidinyl)spiro[chromeno[3,2-b]pyridine-10,4'-[1,3]oxazol]-2'-amine | 412 | AA5 | II8 | +++ | +++ |
| 527 | (10R)-8-(5-pyrimidinyl)spiro[chromeno[3,2-b]pyridine-10,4'-[1,3]oxazol]-2'-amine | 332 | AA24 | II8 | +++ | +++ |
| 528 | (10R)-2-(3,3-dimethyl-1-butyn-1-yl)-8-(5-pyrimidinyl)spiro[chromeno[3,2-b]pyridine-10,4'-[1,3]oxazol]-2'-amine | 412 | AA5 | II8 | ++++ | ++++ |
| 529 | (4R)-7'-(3,6-dihydro-2H-pyran-4-yl)-3'-fluoro-2'-(5-pyrimidinyl)spiro[1,3-oxazole-4,9'-xanthen]-2-amine | 431 | AA22 | II9 | ++++ | ++++ |
| 530 | (4S)-3'-fluoro-2'-(2-fluoro-2-methylpropoxy)-7'-(5-pyrimidinyl)spiro[1,3-oxazole-4,9'-xanthen]-2-amine | 439 | AA14 | II9 | ++++ | ++++ |
| 531 | (4S)-3'-fluoro-2'-(1-methyl-1H-pyrazol-4-yl)-7'-(3-pyridinyl)spiro[1,3-oxazole-4,9'-xanthen]-2-amine | 428.1 | AA8 | II9 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 532 | 2',7'-diphenylspiro[1,3-oxazole-4,9'-xanthen]-2-amine | 405 | AA2 | II1 | ++++ | +++ |
| 533 | N-((4R)-2-amino-7'-phenylspiro[1,3-oxazole-4,9'-xanthen]-2'-yl)-2-methoxyacetamide | 416 | AA10 | II1 | ++++ | ++++ |
| 534 | N-((4S)-2-amino-7'-methoxyspiro[1,3-oxazole-4,9'-xanthen]-2'-yl)-4-chloro-2-pyridinecarboxamide | 437 | AA10 | II14 | ++ | + |
| 535 | (2S)—N-((4S)-2-amino-7'-methoxyspiro[1,3-oxazole-4,9'-xanthen]-2'-yl)-2-methoxypropanamide | 384 | AA10 | II14 | ++ | ++ |
| 536 | (2R)—N-((4S)-2-amino-7'-methoxyspiro[1,3-oxazole-4,9'-xanthen]-2'-yl)-2-methoxypropanamide | 384 | AA10 | II14 | +++ | +++ |
| 537 | (5S)-3-(3,3-dimethyl-1-butyn-1-yl)-9-fluoro-7-(5-pyrimidinyl)spiro[chromeno[2,3-b]pyridine-5,4'-[1,3]oxazol]-2'-amine | 430.2 | AA23 | II33 | ++++ | +++ |
| 538 | (5R)-3-(3,3-dimethyl-1-butyn-1-yl)-9-fluoro-7-(5-pyrimidinyl)spiro[chromeno[2,3-b]pyridine-5,4'-[1,3]oxazol]-2'-amine | 430.2 | AA23 | II33 | +++ | +++ |
| 539 | (5S)-3-(4-morpholinyl)-7-(3-pyridinyl)spiro[chromeno[2,3-b]pyridine-5,4'-[1,3]oxazol]-2'-amine | 416 | AA16 | II4 | ++++ | ++++ |
| 540 | (4S)-2'-(3,3-difluoro-1-azetidinyl)-7'-(3-pyridinyl)spiro[1,3-oxazole-4,9'-xanthen]-2-amine | 421 | AA9 | II1 | ++++ | ++++ |
| 541 | (5R)-3,7-dimethoxyspiro[chromeno[2,3-b]pyridine-5,4'-[1,3]oxazol]-2'-amine | 314 | Method N | II16 | + | ++ |
| 542 | (5S)-7-bromo-3-methoxyspiro[chromeno[2,3-b]pyridine-5,4'-[1,3]oxazol]-2'-amine | 362 | AA64 | II5 | ++ | + |
| 543 | (5R)-7-bromo-3-methoxyspiro[chromeno[2,3-b]pyridine-5,4'-[1,3]oxazol]-2'-amine | 362 | AA64 | II5 | + | + |
| 292 | (4S)-2'-(3,6-dihydro-2H-pyran-4-yl)-3'-fluoro-7'-(5-pyrimidinyl)spiro[1,3-oxazole-4,9'-xanthen]-2-amine | 431 | AA8 | II9 | ++++ | ++++ |
| 544 | (4S)-3'-fluoro-2'-(2-methoxy-2-methylpropoxy)-7'-(3-pyridinyl)spiro[1,3-oxazole-4,9'-xanthen]-2-amine | 450 | AA14 | II9 | ++++ | ++++ |
| 289 | (4S)-2'-(2-fluoro-3-pyridinyl)-7'-(4-morpholinyl)spiro[1,3-oxazole-4,9'-xanthen]-2-amine | 441 | AA16 | II18 | ++++ | ++++ |
| 545 | (5S)-3-(3,6-dihydro-2H-pyran-4-yl)-7-phenylspiro[chromeno[2,3-c]pyridine-5,4'-[1,3]oxazol]-2'-amine | 412 | AA1 | II2 | ++++ | ++++ |
| 546 | (5S)-3-phenyl-7-(5-pyrimidinyl)spiro[chromeno[2,3-c]pyridine-5,4'-[1,3]oxazol]-2'-amine | 408 | AA1 | II2 | ++++ | ++++ |
| 547 | 3-(((4S)-2-amino-3'-fluoro-7'-(3-pyridinyl)spiro[1,3-oxazole-4,9'-xanthen]-2'-yl)oxy)-2,2-dimethylpropanenitrile | 445 | AA14 | II9 | ++++ | ++++ |
| 548 | (5S)-7-bromo-3-chlorospiro[chromeno[2,3-c]pyridine-5,4'-[1,3]oxazol]-2'-amine | 366, 368 | Method C4 | II2 | + | + |
| 549 | (5R)-7-bromo-3-chlorospiro[chromeno[2,3-c]pyridine-5,4'-[1,3]oxazol]-2'-amine | 366, 368 | Method C4 | II2 | + | + |
| 294 | (5S)-3-(3,6-dihydro-2H-pyran-4-yl)-7-(2-fluoro-3-pyridinyl)spiro[chromeno[2,3-c]pyridine-5,4'-[1,3]oxazol]-2'-amine | 431 | AA1 | II2 | ++++ | ++++ |
| 541 | (5R)-3,7-dimethoxyspiro[chromeno[2,3-b]pyridine-5,4'-[1,3]oxazol]-2'-amine | 314 | Method N | II16 | + | ++ |
| 550 | (5S)-3,7-bis(2-fluoro-3-pyridinyl)spiro[chromeno[2,3-c]pyridine-5,4'-[1,3]oxazol]-2'-amine | 444 | AA2 | II2 | ++++ | +++ |
| 551 | (5S)-3-chloro-7-(2-fluoro-3-pyridinyl)spiro[chromeno[2,3-c]pyridine-5,4'-[1,3]oxazol]-2'-amine | 383 | AA24 | II2 | +++ | +++ |
| 552 | (4R)-5'-fluoro-2'-(5-pyrimidinyl)spiro[1,3-oxazole-4,9'-xanthen]-2-amine | 349 | AA24 | II13 | + | + |

TABLE IV-continued

| Ex. No. | Compound Name | Observed Mass | Method | Intermediate used | BACE1 FRET assay (uM) | HEK cell assay (uM) |
|---|---|---|---|---|---|---|
| 553 | (4S)-5'-fluoro-2'-(5-pyrimidinyl)spiro[1,3-oxazole-4,9'-xanthen]-2-amine | 349 | AA24 | II13 | ++++ | +++ |
| 554 | (4S)-2'-(1-methyl-1H-imidazol-4-yl)-7'-(3-pyridinyl)spiro[1,3-oxazole-4,9'-xanthen]-2-amine | 410 | AA1 | II1 | +++ | ++++ |
| 555 | (4S)-3'-fluoro-2'-((3-methyl-3-oxetanyl)methoxy)-7'-(3-pyridinyl)spiro[1,3-oxazole-4,9'-xanthen]-2-amine | 448 | AA14 | II9 | ++++ | ++++ |
| 556 | (10R)-8-(3-pyridinyl)spiro[chromeno[3,2-c]pyridine-10,4'-[1,3]oxazol]-2'-amine | 331.2 | AA49 | II30 | +++ | +++ |
| 557 | (10S)-8-(3-pyridinyl)spiro[chromeno[3,2-c]pyridine-10,4'-[1,3]oxazol]-2'-amine | 331.2 | AA49 | II30 | + | ++ |
| 558 | (4S)-2'-bromo-5'-fluorospiro[1,3-oxazole-4,9'-xanthen]-2-amine | 350 | JBH2 | II13 | ++ | + |
| 559 | (4R)-2'-bromo-5'-fluorospiro[1,3-oxazole-4,9'-xanthen]-2-amine | 350 | JBH2 | II13 | + | + |
| 561 | (4S)-2'-(3,3-dimethyl-1-azetidinyl)-7'-(5-pyrimidinyl)spiro[1,3-oxazole-4,9'-xanthen]-2-amine | 414 | AA9 | II1 | ++++ | ++++ |
| 562 | (5R)-7-bromo-3-methoxyspiro[chromeno[2,3-b]pyridine-5,4'-[1,3]oxazol]-2'-amine | 362 | AA64 | II5 | + | + |
| 563 | (4S)-2'-(2-fluoro-3-pyridinyl)-7'-(3-methyl-5-isoxazolyl)spiro[1,3-oxazole-4,9'-xanthen]-2-amine | 429.2 | AA57 | II1 | ++++ | ++++ |
| 564 | (4S)-2'-((1S,4S)-2-oxa-5-azabicyclo[2.2.1]hept-5-yl)-7'-(3-pyridinyl)spiro[1,3-oxazole-4,9'-xanthen]-2-amine | 427 | AA9 | II1 | ++++ | ++++ |
| 565 | (4S)-2'-(6-fluoro-3-pyridinyl)-7'-(3-methyl-5-isoxazolyl)spiro[1,3-oxazole-4,9'-xanthen]-2-amine | 429.2 | AA57 | II1 | ++++ | +++ |
| 566 | (10R)-2'-amino-2-(4-methylphenyl)-8-(3-pyridinyl)spiro[chromeno[3,2-c]pyridine-10,4'-[1,3]oxazol]-1(2H)-one | 437 | AA56 | II28 | +++ | +++ |
| 567 | (4R)-2'-(1H-indol-2-yl)spiro[1,3-oxazole-4,9'-xanthen]-2-amine | 368 | AA24 | II19 | ++ | + |
| 568 | tert-butyl 2-((4R)-2-aminospiro[1,3-oxazole-4,9'-xanthen]-2'-yl)-1H-indole-1-carboxylate | 468 | AA24 | II19 | + | + |
| 569 | (4R)-3'-fluoro-2'-(3-pyridinyl)spiro[1,3-oxazole-4,9'-xanthen]-2-amine | 348 | AA1 | II19 | +++ | +++ |
| 570 | (5S)-7-(2-fluoro-3-pyridinyl)spiro[chromeno[2,3-b]pyridine-5,4'-[1,3]oxazol]-2'-amine | 349 | AA24 | II20 | ++++ | +++ |
| 571 | (5S)-7-(2-fluoro-5-methyl-3-pyridinyl)spiro[chromeno[2,3-b]pyridine-5,4'-[1,3]oxazol]-2'-amine | 363 | AA24 | II20 | +++ | +++ |
| 572 | (5S)-7-imidazo[1,2-a]pyridin-6-ylspiro[chromeno[2,3-b]pyridine-5,4'-[1,3]oxazol]-2'-amine | 370 | AA24 | II20 | + | ++ |
| 573 | (4S)-5'-fluoro-2'-(5-pyrimidinyl)spiro[1,3-oxazole-4,9'-xanthen]-2-amine | 349 | AA24 | II13 | ++++ | +++ |
| 574 | (4R)-5'-fluoro-2'-(2-fluoro-3-pyridinyl)spiro[1,3-oxazole-4,9'-xanthen]-2-amine | 366 | AA24 | II13 | ++++ | +++ |
| 575 | (4R)-2'-bromo-5'-fluorospiro[1,3-oxazole-4,9'-xanthen]-2-amine | 350 | JBH2 | II13 | + | + |
| 576 | (5S)-7-(2-fluoro-3-pyridinyl)-3-(4-methylphenyl)spiro[chromeno[2,3-b]pyridine-5,4'-[1,3]oxazol]-2'-amine | 439 | AA8 | II4 | ++++ | ++++ |
| 577 | (5S)-7-(3-methoxy-3-methyl-1-butyn-1-yl)-3-(4-methylphenyl)spiro[chromeno[2,3-b]pyridine-5,4'-[1,3]oxazol]-2'-amine | 440 | AA25 | II4 | ++++ | ++++ |
| 578 | (5S)-3-(4-methylphenyl)-7-(5-pyrimidinyl)spiro[chromeno[2,3-b]pyridine-5,4'-[1,3]oxazol]-2'-amine | 422 | AA8 | II4 | ++++ | ++++ |
| 579 | 4-((5S)-2'-amino-3-(4-methylphenyl)spiro[chromeno[2,3-b]pyridine-5,4'-[1,3]oxazol]-7-yl)-2-methyl-3-butyn-2-ol | 426.3 | AA21 | II4 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 580 | (5S)-3-(3,6-dihydro-2H-pyran-4-yl)-7-phenylspiro[chromeno[2,3-b]pyridine-5,4'-[1,3]oxazol]-2'-amine | 412 | AA8 | II4 | ++++ | ++++ |
| 581 | (4S)-4'-fluoro-2'-methoxy-7'-(5-pyrimidinyl)spiro[1,3-oxazole-4,9'-xanthen]-2-amine | 379 | AA24 | II11 | ++++ | ++++ |
| 582 | (4R)-4'-fluoro-2'-methoxy-7'-(5-pyrimidinyl)spiro[1,3-oxazole-4,9'-xanthen]-2-amine | 379 | AA24 | II11 | ++ | + |
| 296 | (5S)-7-(5-chloro-2-fluorophenyl)-3-(3,6-dihydro-2H-pyran-4-yl)spiro[chromeno[2,3-b]pyridine-5,4'-[1,3]oxazol]-2'-amine | 464 | AA1 | II3 | ++++ | ++++ |
| 583 | (5S)-3-(3,6-dihydro-2H-pyran-4-yl)-7-(4-fluorophenyl)spiro[chromeno[2,3-b]pyridine-5,4'-[1,3]oxazol]-2'-amine | 430 | AA8 | II4 | ++++ | ++++ |
| 584 | (5R)-9-fluoro-7-methoxy-3-(5-pyrimidinyl)spiro[chromeno[2,3-b]pyridine-5,4'-[1,3]oxazol]-2'-amine | 380.2 | AA24 | II33 | ++ | + |
| 585 | (5S)-9-fluoro-7-methoxy-3-(5-pyrimidinyl)spiro[chromeno[2,3-b]pyridine-5,4'-[1,3]oxazol]-2'-amine | 380.2 | AA24 | II33 | + | + |
| 586 | (5S)-3-(3-methoxy-3-methyl-1-butyn-1-yl)-7-(2-pyrazinyl)spiro[chromeno[2,3-b]pyridine-5,4'-[1,3]oxazol]-2'-amine | 428 | MW2 | II4 | ++++ | ++++ |
| 587 | (4S)-2'-(1-benzofuran-2-yl)spiro[1,3-oxazole-4,9'-xanthen]-2-amine | 369 | AA24 | II19 | ++ | ++ |
| 588 | (4S)-2'-(5-isoquinolinyl)-7'-methoxyspiro[1,3-oxazole-4,9'-xanthen]-2-amine | 410 | AA24 | II17 | +++ | ++ |
| 589 | (4S)-2'-methoxy-7'-(4-quinolinyl)spiro[1,3-oxazole-4,9'-xanthen]-2-amine | 410 | AA24 | II17 | ++ | ++ |
| 590 | (4S)-2'-methoxy-7'-(8-quinolinyl)spiro[1,3-oxazole-4,9'-xanthen]-2-amine | 410 | AA24 | II17 | ++ | ++ |
| 591 | (4S)-2'-methoxy-7'-(5-quinolinyl)spiro[1,3-oxazole-4,9'-xanthen]-2-amine | 410 | AA24 | II17 | ++ | ++ |
| 592 | (4S)-5'-fluoro-2'-(3-pyridinyl)spiro[1,3-oxazole-4,9'-xanthen]-2-amine | 348 | AA24 | II13 | ++++ | +++ |
| 593 | (5R)-7-(3-pyridinyl)spiro[chromeno[2,3-b]pyridine-5,4'-[1,3]oxazol]-2'-amine | 331 | AA24 | II20 | +++ | +++ |
| 594 | (5S)-7-(3-pyridinyl)spiro[chromeno[2,3-b]pyridine-5,4'-[1,3]oxazol]-2'-amine | 331 | AA24 | II20 | + | + |
| 595 | (5R)-7-(3-(trifluoromethoxy)phenyl)spiro[chromeno[2,3-b]pyridine-5,4'-[1,3]oxazol]-2'-amine | 414 | AA24 | II20 | +++ | ++ |
| 596 | (5R)-7-(3-methylphenyl)spiro[chromeno[2,3-b]pyridine-5,4'-[1,3]oxazol]-2'-amine | 344 | AA24 | II20 | +++ | ++ |
| 597 | (4S)-2'-(5-pyrimidinyl)-7'-(trifluoromethyl)spiro[1,3-oxazole-4,9'-xanthen]-2-amine | 399 | AA24 | II32 | +++ | +++ |
| 598 | (5R)-7-phenylspiro[chromeno[2,3-b]pyridine-5,4'-[1,3]oxazol]-2'-amine | 330 | AA24 | II20 | ++ | + |
| 599 | (4R)-2'-(2,4-difluoro-3-pyridinyl)spiro[1,3-oxazole-4,9'-xanthen]-2-amine | 366 | AA24 | II36 | +++ | ++ |
| 600 | (5R)-7-bromospiro[chromeno[2,3-b]pyridine-5,4'-[1,3]oxazol]-2'-amine | 332 | Example 115 | II20 | + | + |
| 601 | (5S)-7-bromospiro[chromeno[2,3-b]pyridine-5,4'-[1,3]oxazol]-2'-amine | 332 | Example 115 | II20 | + | + |
| 602 | (5S)-3-(3-methoxy-3-methyl-1-butyn-1-yl)-7-(5-methoxy-3-pyridinyl)spiro[chromeno[2,3-b]pyridine-5,4'-[1,3]oxazol]-2'-amine | 457 | AA26 | II4 | ++++ | ++++ |
| 603 | (5S)-3-(3-methoxy-3-methyl-1-butyn-1-yl)-7-(3-pyridinyl)spiro[chromeno[2,3-b]pyridine-5,4'-[1,3]oxazol]-2'-amine | 427 | AA26 | II4 | ++++ | ++++ |
| 604 | (4S)-2'-(3-methoxy-1-azetidinyl)-7'-(3-pyridinyl)spiro[1,3-oxazole-4,9'-xanthen]-2-amine | 415 | AA9 | II1 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 605 | (4S)-4'-fluoro-7'-((3-methyl-3-oxetanyl)methoxy)-2'-(3-pyridinyl)spiro[1,3-oxazole-4,9'-xanthen]-2-amine | 448 | AA13 | II21 | ++++ | ++++ |
| 606 | (4R)-4'-fluoro-7'-((3-methyl-3-oxetanyl)methoxy)-2'-(3-pyridinyl)spiro[1,3-oxazole-4,9'-xanthen]-2-amine | 448 | AA13 | II21 | ++++ | +++ |
| 607 | (5S)-7-(cyclopropylethynyl)-3-(4-morpholinyl)spiro[chromeno[2,3-b]pyridine-5,4'-[1,3]oxazol]-2'-amine | 403 | AA27 | II4 | ++++ | ++++ |
| 608 | (4S)-2'-(1-azetidinylcarbonyl)-7'-(2,2-dimethylpropoxy)spiro[1,3-oxazole-4,9'-xanthen]-2-amine | 422 | AA30 | II22 | +++ | +++ |
| 609 | (5R)-7-(2-methylphenyl)spiro[chromeno[2,3-b]pyridine-5,4'-[1,3]oxazol]-2'-amine | 344 | AA24 | II20 | + | + |
| 610 | 3-((5R)-2'-aminospiro[chromeno[2,3-b]pyridine-5,4'-[1,3]oxazol]-7-yl)benzonitrile | 355 | AA24 | II20 | +++ | ++ |
| 611 | 5-((4R)-2-amino-7'-(3-pyridinyl)spiro[1,3-oxazole-4,9'-xanthen]-2'-yl)-1-methyl-2(1H)-pyridinone | 437 | AA1 | II1 | ++++ | +++ |
| 612 | 1-((5S)-2'-amino-7-(3-pyridinyl)spiro[chromeno[2,3-c]pyridine-5,4'-[1,3]oxazol]-3-yl)-5-hydroxy-1-pentanone | 431 | AA50 | II2 | ++++ | +++ |
| 613 | N-((4S)-2-amino-7'-methoxyspiro[1,3-oxazole-4,9'-xanthen]-2'-yl)-2-methoxyacetamide | 370 | AA10 | II14 | +++ | +++ |
| 614 | N-((4S)-2-amino-7'-methoxyspiro[1,3-oxazole-4,9'-xanthen]-2'-yl)tetrahydro-2-furancarboxamide | 396 | AA10 | II14 | +++ | +++ |
| 615 | N-((4S)-2-amino-7'-methoxyspiro[1,3-oxazole-4,9'-xanthen]-2'-yl)-2-pyridinecarboxamide | 403 | AA10 | II14 | +++ | +++ |
| 616 | N-((4S)-2-amino-7'-methoxyspiro[1,3-oxazole-4,9'-xanthen]-2'-yl)benzamide | 402 | AA10 | II14 | ++ | ++ |
| 617 | N-((4S)-2-amino-7'-methoxyspiro[1,3-oxazole-4,9'-xanthen]-2'-yl)-6-chloro-3-pyridinecarboxamide | 437 | AA10 | II14 | ++ | ++ |
| 618 | (5R)-7-(1-benzothiophen-2-yl)spiro[chromeno[2,3-b]pyridine-5,4'-[1,3]oxazol]-2'-amine | 386 | AA24 | II20 | + | ++ |
| 619 | (4S)-2'-(2-chloro-5-fluoro-3-pyridinyl)spiro[1,3-oxazole-4,9'-xanthen]-2-amine | 382 | AA24 | II19 | ++ | +++ |
| 620 | (4R)-2-amino-N-(cyclohexylmethyl)spiro[1,3-oxazole-4,9'-xanthene]-2'-carboxamide | 392 | AA30 | II19 | + | + |
| 621 | (4R)-2-amino-N-cyclohexylspiro[1,3-oxazole-4,9'-xanthene]-2'-carboxamide | 378 | AA30 | II19 | + | + |
| 622 | (4S)-2'-(2-tert-butyl-1,3-thiazol-4-yl)-7'-(3-pyridinyl)spiro[1,3-oxazole-4,9'-xanthen]-2-amine | 469.2 | AA1 | II1 | ++++ | +++ |
| 623 | (4S)-2'-(4-isoxazolyl)-7'-(3-pyridinyl)spiro[1,3-oxazole-4,9'-xanthen]-2-amine | 397.2 | AA1 | II1 | ++++ | ++++ |
| 624 | (4S)-2'-(3-pyridinyl)-7'-(2-(1-pyrrolidinyl)-1,3-thiazol-4-yl)spiro[1,3-oxazole-4,9'-xanthen]-2-amine | 482.2 | AA1 | II11 | +++ | ++ |
| 625 | (5S)-7-(2-fluoro-3-pyridinyl)-3-(4-morpholinyl)spiro[chromeno[2,3-b]pyridine-5,4'-[1,3]oxazol]-2'-amine | 434 | AA16 | II4 | ++++ | ++++ |
| 626 | (5S)-3-(4-morpholinyl)-7-phenylspiro[chromeno[2,3-b]pyridine-5,4'-[1,3]oxazol]-2'-amine | 415 | AA16 | II4 | ++++ | ++++ |
| 627 | (4R)-2'-(5-quinolinyl)spiro[1,3-oxazole-4,9'-xanthen]-2-amine | 380 | AA24 | II19 | + | + |
| 628 | (4S)-2'-(3-quinolinyl)spiro[1,3-oxazole-4,9'-xanthen]-2-amine | 380 | AA24 | II19 | + | + |
| 629 | (4R)-2'-(4-isoquinolinyl)spiro[1,3-oxazole-4,9'-xanthen]-2-amine | 380 | AA24 | II19 | ++ | + |

TABLE IV-continued

| Ex. No. | Compound Name | Observed Mass | Method | Intermediate used | BACE1 FRET assay (uM) | HEK cell assay (uM) |
|---|---|---|---|---|---|---|
| 630 | (4R)-2'-(8-quinolinyl)spiro[1,3-oxazole-4,9'-xanthen]-2-amine | 380 | AA24 | II19 | ++ | + |
| 631 | (4S)-2'-(6-fluoro-3-pyridinyl)-7'-(1-methyl-1H-pyrazol-4-yl)spiro[1,3-oxazole-4,9'-xanthen]-2-amine | 428.2 | AA1 | II1 | ++++ | ++++ |
| 632 | (4S)-2'-(2-cyclopropyl-1,3-thiazol-4-yl)-7'-(3-pyridinyl)spiro[1,3-oxazole-4,9'-xanthen]-2-amine | 453.2 | AA1 | II1 | ++++ | +++ |
| 633 | (4S)-2'-methoxy-7'-(3-quinolinyl)spiro[1,3-oxazole-4,9'-xanthen]-2-amine | 410 | AA24 | II17 | ++ | ++ |
| 634 | (4S)-2'-(4-isoquinolinyl)-7'-methoxyspiro[1,3-oxazole-4,9'-xanthen]-2-amine | 410 | AA24 | II17 | +++ | ++ |
| 635 | (5R)-7-(3-pyridinyl)spiro[chromeno[2,3-b]pyridine-5,4'-[1,3]oxazol]-2'-amine | 331 | AA24 | II20 | +++ | +++ |
| 636 | (5R)-7-bromospiro[chromeno[2,3-b]pyridine-5,4'-[1,3]oxazol]-2'-amine | 332 | Example 115 | II20 | + | + |
| 295 | (4S)-2'-(3,6-dihydro-2H-pyran-4-yl)-4'-fluoro-7'-(5-pyrimidinyl)spiro[1,3-oxazole-4,9'-xanthen]-2-amine | 431 | AA8 | II10 | ++++ | ++++ |
| 637 | (4R)-2'-(3,6-dihydro-2H-pyran-4-yl)-4'-fluoro-7'-(5-pyrimidinyl)spiro[1,3-oxazole-4,9'-xanthen]-2-amine | 431 | AA8 | II10 | ++ | +++ |
| 638 | (4R)-2'-bromo-7'-(1-methyl-1H-pyrazol-4-yl)spiro[1,3-oxazole-4,9'-xanthen]-2-amine | 413 | AA24 | II1 | +++ | ++ |
| 639 | (4S)-2'-(1-piperidinylcarbonyl)spiro[1,3-oxazole-4,9'-xanthen]-2-amine | 364 | AA30 | II19 | + | + |
| 640 | (4S)-2'-(3-pyridinyl)spiro[1,3-oxazole-4,9'-xanthen]-2-amine | 330 | AA24 | II19 | ++ | ++ |
| 641 | (4S)-2'-(2-fluoro-3-pyridinyl)spiro[1,3-oxazole-4,9'-xanthen]-2-amine | 348 | AA24 | II19 | +++ | ++ |
| 642 | (4R)-2'-(2-fluoro-3-pyridinyl)-7'-(1-methyl-1H-pyrazol-4-yl)spiro[1,3-oxazole-4,9'-xanthen]-2-amine | 428.2 | AA1 | II1 | ++++ | ++++ |
| 643 | (5S)-3-(3,3-dimethyl-1-butyn-1-yl)-7-(5-methoxy-3-pyridinyl)spiro[chromeno[2,3-b]pyridine-5,4'-[1,3]oxazol]-2'-amine | 441 | AA23 | II4 | ++++ | ++++ |
| 644 | (4R)-2'-(3,6-dihydro-2H-pyran-4-yl)-4'-fluoro-7'-(3-pyridinyl)spiro[1,3-oxazole-4,9'-xanthen]-2-amine | 430 | AA8 | II10 | +++ | ++ |
| 297 | (4S)-2'-(3,6-dihydro-2H-pyran-4-yl)-4'-fluoro-7'-(3-pyridinyl)spiro[1,3-oxazole-4,9'-xanthen]-2-amine | 430 | AA8 | II10 | ++++ | ++++ |
| 645 | (4R)-4'-fluoro-7'-(6-fluoro-3-pyridinyl)-2'-(3-methoxy-3-methyl-1-butyn-1-yl)spiro[1,3-oxazole-4,9'-xanthen]-2-amine | 462 | AA26 | II10 | +++ | ++ |
| 646 | (4S)-4'-fluoro-7'-(6-fluoro-3-pyridinyl)-2'-(3-methoxy-3-methyl-1-butyn-1-yl)spiro[1,3-oxazole-4,9'-xanthen]-2-amine | 462 | AA26 | II10 | ++++ | ++++ |
| 647 | 4-((5S)-2'-amino-7-phenylspiro[chromeno[2,3-b]pyridine-5,4'-[1,3]oxazol]-3-yl)-2-methyl-3-butyn-2-ol | 412 | AA23 | II4 | ++++ | ++++ |
| 648 | 8-(3-pyridinyl)spiro[chromeno[3,2-c]pyridine-10,4'-[1,3]oxazol]-2'-amine | 331.2 | AA49 | II30 | ++ | ++ |
| 649 | (4S)-2'-(2,2-dimethylpropoxy)-7'-(3-pyridazinyl)spiro[1,3-oxazole-4,9'-xanthen]-2-amine | 417.2 | AA36 | II22 | ++++ | +++ |
| 650 | 1-((4S)-2-amino-7'-(3-pyridinyl)spiro[1,3-oxazole-4,9'-xanthen]-2'-yl)-4-hydroxy-1-butanone | 416.2 | AA50 | II1 | ++++ | +++ |
| 651 | N-((4S)-2-amino-7'-methoxyspiro[1,3-oxazole-4,9'-xanthen]-2'-yl)-2,2,2-trifluoroacetamide | 394 | AA10 | II14 | +++ | ++ |
| 652 | N-((4S)-2-amino-7'-methoxyspiro[1,3-oxazole-4,9'-xanthen]-2'-yl)-5-chloro-2-pyridinecarboxamide | 437 | AA10 | II14 | ++++ | +++ |
| 653 | (5S)-3-(3,3-dimethyl-1-butyn-1-yl)-7-(4-pyridazinyl)spiro[chromeno[2,3-b]pyridine-5,4'-[1,3]oxazol]-2'-amine | 412 | MW2 | II4 | ++++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 654 | (5S)-3-(3,3-dimethyl-1-butyn-1-yl)-7-(2-pyrazinyl)spiro[chromeno[2,3-b]pyridine-5,4'-[1,3]oxazol]-2'-amine | 412 | MW2 | II4 | ++++ | ++++ |
| 655 | (4S)-2'-(2,2-dimethylpropoxy)spiro[1,3-oxazole-4,9'-xanthen]-2-amine | 339 | AA49 | II22 | ++ | + |
| 656 | (4S)-2'-(2,2-dimethylpropoxy)-7'-(tetrahydro-2H-pyran-2-yl)spiro[1,3-oxazole-4,9'-xanthen]-2-amine | 423 | Method O | II22 | ++++ | +++ |
| 657 | (4S)-2-amino-7'-(2,2-dimethylpropoxy)-N-propylspiro[1,3-oxazole-4,9'-xanthene]-2'-carboxamide | 424 | AA30 | II22 | ++++ | +++ |
| 658 | 1-((4R)-2-amino-7'-(3-pyridinyl)spiro[1,3-oxazole-4,9'-xanthen]-2'-yl)-2-propanone | 386 | AA62 | II1 | +++ | +++ |
| 659 | 1-((4R)-2-amino-7'-(3-pyridinyl)spiro[1,3-oxazole-4,9'-xanthen]-2'-yl)-2-methyl-2-propanol | 402 | AA62 | II1 | +++ | +++ |
| 660 | (4S)-2'-(3-pyridinyl)-7'-(1,3-thiazol-5-yl)spiro[1,3-oxazole-4,9'-xanthen]-2-amine | 413.2 | AA36 | II1 | ++++ | ++++ |
| 661 | (5R)-3-(5-pyrimidinyl)spiro[chromeno[2,3-b]pyridine-5,4'-[1,3]oxazol]-2'-amine | 332 | AA24 | II20 | +++ | +++ |
| 662 | (4S)-2'-((2R,6S)-2,6-dimethyl-4-morpholinyl)-7'-(3-pyridinyl)spiro[1,3-oxazole-4,9'-xanthen]-2-amine | 443 | AA9 | II1 | ++++ | ++++ |
| 663 | (4S)-2'-(2,2-dimethyl-4-morpholinyl)-7'-(3-pyridinyl)spiro[1,3-oxazole-4,9'-xanthen]-2-amine | 443.2 | AA9 | II1 | ++++ | ++++ |
| 664 | (5S)-3-(3,6-dihydro-2H-pyran-4-yl)-7-(3-pyridinyl)spiro[chromeno[2,3-b]pyridine-5,4'-[1,3]oxazol]-2'-amine | 413 | AA8 | II4 | ++++ | ++++ |
| 665 | (4R)-2'-(2,2-dimethylpropoxy)spiro[1,3-oxazole-4,9'-xanthen]-2-amine | 339 | AA49 | II22 | +++ | ++ |
| 666 | (4S)-2'-(3-pyridinyl)-7'-(1,3-thiazol-2-yl)spiro[1,3-oxazole-4,9'-xanthen]-2-amine | 413.2 | AA57 | II1 | ++++ | ++++ |
| 667 | (5S)-3-(6-ethoxy-3-pyridinyl)-7-methoxyspiro[chromeno[2,3-b]pyridine-5,4'-[1,3]oxazol]-2'-amine | 405 | AA24 | II7 | +++ | +++ |
| 668 | (5S)-3-(6-(cyclopropylmethoxy)-3-pyridinyl)-7-methoxyspiro[chromeno[2,3-b]pyridine-5,4'-[1,3]oxazol]-2'-amine | 431.2 | AA24 | II7 | +++ | +++ |
| 669 | (5S)-7-methoxy-3-(5-pyrimidinyl)spiro[chromeno[2,3-b]pyridine-5,4'-[1,3]oxazol]-2'-amine | 362 | AA24 | II7 | ++ | ++ |
| 670 | (5S)-7-methoxy-3-(3-pyridinyl)spiro[chromeno[2,3-b]pyridine-5,4'-[1,3]oxazol]-2'-amine | 361 | AA24 | II7 | +++ | ++ |
| 671 | (4S)-2'-(3-pyridinyl)-7'-(1,3-thiazol-4-yl)spiro[1,3-oxazole-4,9'-xanthen]-2-amine | 413.2 | AA57 | II1 | ++++ | ++++ |
| 672 | (4S)-2'-(3-pyridinyl)-7'-(3-thiophenyl)spiro[1,3-oxazole-4,9'-xanthen]-2-amine | 412.2 | AA1 | II1 | ++++ | ++++ |
| 673 | (4S)-4'-fluoro-2'-(3-methoxy-3-methyl-1-butyn-1-yl)-7'-(5-pyrimidinyl)spiro[1,3-oxazole-4,9'-xanthen]-2-amine | 445.2 | AA26 | II21 | ++++ | ++++ |
| 674 | (4R)-4'-fluoro-2'-(3-methoxy-3-methyl-1-butyn-1-yl)-7'-(5-pyrimidinyl)spiro[1,3-oxazole-4,9'-xanthen]-2-amine | 445.2 | AA26 | II21 | +++ | ++ |
| 675 | (5S)-7-(3-pyridinyl)spiro[chromeno[2,3-c]pyridine-5,4'-[1,3]oxazol]-2'-amine | 331 | AA31 | II2 | +++ | ++ |
| 676 | (5S)-3-chloro-7-(3-pyridinyl)spiro[chromeno[2,3-c]pyridine-5,4'-[1,3]oxazol]-2'-amine | 365 | AA24 | II2 | +++ | ++ |
| 677 | (5R)-3-(2,2-dimethylcyclopropyl)-7-(3-pyridinyl)spiro[chromeno[2,3-c]pyridine-5,4'-[1,3]oxazol]-2'-amine | 399 | AA1 | II2 | ++++ | +++ |
| 678 | (5R)-3-cyclopropyl-7-(3-pyridinyl)spiro[chromeno[2,3-c]pyridine-5,4'-[1,3]oxazol]-2'-amine | 371 | AA1 | II2 | ++++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 679 | (4S)-2'-(2-methyl-1,3-thiazol-4-yl)-7'-(3-pyridinyl)spiro[1,3-oxazole-4,9'-xanthen]-2-amine | 427.2 | AA1 | II1 | ++++ | ++++ |
| 680 | (5S)-3-bromo-7-methoxyspiro[chromeno[2,3-b]pyridine-5,4'-[1,3]oxazol]-2'-amine | 362 | Method N | II4 | + | + |
| 681 | (5R)-3-(3-methoxy-3-methyl-1-butyn-1-yl)-7-(4-pyridazinyl)spiro[chromeno[2,3-b]pyridine-5,4'-[1,3]oxazol]-2'-amine | 428 | AA32 | II4 | ++ | + |
| 682 | 3-(((4R)-2-amino-7'-bromospiro[1,3-oxazole-4,9'-xanthen]-2'-yl)ethynyl)-3-oxetanol | 427.9 | AA42 | II1 | ++ | + |
| 683 | 5-((4S)-2-amino-7'-(3-pyridinyl)spiro[1,3-oxazole-4,9'-xanthen]-2'-yl)-2-pyridinecarbonitrile | 432.2 | AA36 | II1 | ++++ | ++++ |
| 684 | (4R)-2'-(3-pyridinyl)spiro[1,3-oxazole-4,9'-xanthen]-2-amine | 330 | AA31 | II1 | +++ | +++ |
| 685 | 3-(((4R)-2-amino-7'-(3-pyridinyl)spiro[1,3-oxazole-4,9'-xanthen]-2'-yl)ethynyl)-3-oxetanol | 426 | AA33 | II1 | ++++ | ++++ |
| 686 | (4S)-2'-bromo-7'-(5-pyrimidinyl)spiro[1,3-oxazole-4,9'-xanthen]-2-amine | 408.9 | AA24 | II1 | +++ | +++ |
| 687 | (5S)-7-(2-fluoro-4-pyridinyl)-3-(3-methoxy-3-methyl-1-butyn-1-yl)spiro[chromeno[2,3-b]pyridine-5,4'-[1,3]oxazol]-2'-amine | 445 | AA26 | II4 | ++ | + |
| 688 | (4R)-2'-(2,2-dimethyl-3,6-dihydro-2H-pyran-4-yl)-7'-(5-pyrimidinyl)spiro[1,3-oxazole-4,9'-xanthen]-2-amine | 441 | AA2 | II1 | ++++ | ++++ |
| 689 | (4R)-2'-(6,6-dimethyl-3,6-dihydro-2H-pyran-4-yl)-7'-(5-pyrimidinyl)spiro[1,3-oxazole-4,9'-xanthen]-2-amine | 441 | AA1 | II1 | ++++ | ++++ |
| 690 | (5R)-3-(3,6-dihydro-2H-pyran-4-yl)-7-(3-fluorophenyl)spiro[chromeno[2,3-b]pyridine-5,4'-[1,3]oxazol]-2'-amine | 430 | AA8 | II4 | ++ | + |
| 691 | (5R)-3-(3,6-dihydro-2H-pyran-4-yl)-7-(4-fluorophenyl)spiro[chromeno[2,3-b]pyridine-5,4'-[1,3]oxazol]-2'-amine | 430 | AA8 | II4 | ++ | ++ |
| 692 | (5R)-3-(3-methoxy-3-methyl-1-butyn-1-yl)-7-(4-pyridinyl)spiro[chromeno[2,3-b]pyridine-5,4'-[1,3]oxazol]-2'-amine | 427 | AA26 | II4 | + | + |
| 693 | (4S)-2'-(3-methyl-5-isoxazolyl)-7'-(3-pyridinyl)spiro[1,3-oxazole-4,9'-xanthen]-2-amine | 411.2 | AA57 | II1 | ++++ | ++++ |
| 694 | (5R)-3-(3-methoxy-3-methyl-1-butyn-1-yl)-7-(2-pyrazinyl)spiro[chromeno[2,3-b]pyridine-5,4'-[1,3]oxazol]-2'-amine | 428 | AA32 | II4 | ++ | + |
| 695 | (5S)-3-(2-cyclopropylethyl)-7-(3-pyridinyl)spiro[chromeno[2,3-c]pyridine-5,4'-[1,3]oxazol]-2'-amine | 399 | AA11 | II2 | ++++ | +++ |
| 696 | (5S)-7-(3-pyridinyl)-3-((2S)-tetrahydro-2H-pyran-2-yl)spiro[chromeno[2,3-c]pyridine-5,4'-[1,3]oxazol]-2'-amine | 415 | AA11 | II2 | ++++ | ++++ |
| 697 | (10R)-8-(3,3-dimethyl-1-butyn-1-yl)-2-(3-pyridinyl)spiro[chromeno[3,2-b]pyridine-10,4'-[1,3]oxazol]-2'-amine | 411 | AA33 | II8 | +++ | ++ |
| 698 | (2S)-4-((4R)-2-amino-7'-(3-pyridinyl)spiro[1,3-oxazole-4,9'-xanthen]-2'-yl)-1,1,1-trifluoro-2-methyl-3-butyn-2-ol | 466 | AA33 | II1 | ++++ | ++++ |
| 699 | (5R)-7-(5-fluoro-3-pyridinyl)-3-(3-methoxy-3-methyl-1-butyn-1-yl)spiro[chromeno[2,3-b]pyridine-5,4'-[1,3]oxazol]-2'-amine | 445.2 | AA26 | II4 | +++ | ++ |
| 700 | (4S)-2'-bicyclo[2.2.1]hept-2-yl-7'-(2,2-dimethylpropoxy)spiro[1,3-oxazole-4,9'-xanthen]-2-amine | 433 | Method O | II22 | +++ | + |
| 701 | (4S)-2'-cyclopentyl-7'-(2,2-dimethylpropoxy)spiro[1,3-oxazole-4,9'-xanthen]-2-amine | 407 | Method O | II22 | ++++ | ++ |
| 702 | (4S)-2-amino-N-cyclobutyl-7'-(2,2-dimethylpropoxy)spiro[1,3-oxazole-4,9'-xanthene]-2'-carboxamide | 436 | AA30 | II22 | ++++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 703 | (4S)-2-amino-7'-(2,2-dimethylpropoxy)-N-(1-methylethyl)spiro[1,3-oxazole-4,9'-xanthene]-2'-carboxamide | 424 | AA30 | II22 | ++++ | ++++ |
| 704 | (4S)-2'-(3,5-dimethyl-4-isoxazolyl)-7'-(3-pyridinyl)spiro[1,3-oxazole-4,9'-xanthen]-2-amine | 425.2 | AA1 | II1 | +++ | +++ |
| 705 | 4-((5R)-2'-amino-7-(cyclopropylethynyl)spiro[chromeno[2,3-b]pyridine-5,4'-[1,3]oxazol]-3-yl)-2-methyl-3-butyn-2-ol | 400 | AA34 | II4 | + | + |
| 706 | tert-butyl ((4R)-2-amino-7'-(3-pyridinyl)spiro[1,3-oxazole-4,9'-xanthen]-2'-yl)acetate | 444 | AA62 | II1 | +++ | +++ |
| 707 | tert-butyl ((4R)-2-amino-7'-bromospiro[1,3-oxazole-4,9'-xanthen]-2'-yl)acetate | 446 | AA62 | II1 | + | + |
| 708 | (4S)-2'-(1-(2-methylpropyl)-1H-pyrazol-4-yl)-7'-(3-pyridinyl)spiro[1,3-oxazole-4,9'-xanthen]-2-amine | 452.2 | AA1 | II1 | ++++ | +++ |
| 709 | 4-((5R)-2'-amino-7-phenylspiro[chromeno[2,3-b]pyridine-5,4'-[1,3]oxazol]-3-yl)-2-methyl-3-butyn-2-ol | 412 | AA23 | II4 | ++ | + |
| 710 | (4S)-2'-(1-methyl-1H-pyrazol-4-yl)-7'-(3-pyridinyl)spiro[1,3-oxazole-4,9'-xanthen]-2-amine | 410.2 | AA1 | II1 | ++++ | ++++ |
| 711 | (4S)-2'-(5-methoxy-2-furanyl)-7'-(3-pyridinyl)spiro[1,3-oxazole-4,9'-xanthen]-2-amine | 426.2 | AA1 | II1 | ++++ | +++ |
| 712 | (4S)-3'-fluoro-2'-((3-methyl-3-oxetanyl)methoxy)-7'-(5-pyrimidinyl)spiro[1,3-oxazole-4,9'-xanthen]-2-amine | 449 | AA13 | II9 | ++++ | ++++ |
| 713 | (4R)-3'-fluoro-2'-((3-methyl-3-oxetanyl)methoxy)-7'-(5-pyrimidinyl)spiro[1,3-oxazole-4,9'-xanthen]-2-amine | 449 | AA13 | II9 | +++ | +++ |
| 714 | (4R)-2'-(1-(1-methylethyl)-1,2,3,6-tetrahydro-4-pyridinyl)-7'-(5-pyrimidinyl)spiro[1,3-oxazole-4,9'-xanthen]-2-amine | 454 | AA36 | II1 | +++ | ++++ |
| 715 | (4R)-2'-(3,6-dihydro-2H-pyran-4-yl)-7'-(3-pyridinyl)spiro[1,3-oxazole-4,9'-xanthen]-2-amine | 412 | AA2 | II1 | ++++ | ++++ |
| 716 | (5R)-3-(3,6-dihydro-2H-pyran-4-yl)-7-(6-fluoro-3-pyridinyl)spiro[chromeno[2,3-b]pyridine-5,4'-[1,3]oxazol]-2'-amine | 431 | AA8 | II4 | ++ | ++ |
| 717 | (5R)-3-(3,6-dihydro-2H-pyran-4-yl)-7-(2-fluoro-3-pyridinyl)spiro[chromeno[2,3-b]pyridine-5,4'-[1,3]oxazol]-2'-amine | 431 | AA8 | II4 | +++ | ++ |
| 718 | (5R)-3-(3,6-dihydro-2H-pyran-4-yl)-7-phenylspiro[chromeno[2,3-b]pyridine-5,4'-[1,3]oxazol]-2'-amine | 412 | AA8 | II4 | ++ | ++ |
| 719 | (5R)-3-(3-methoxy-3-methyl-1-butyn-1-yl)-7-(3-pyridinyl)spiro[chromeno[2,3-b]pyridine-5,4'-[1,3]oxazol]-2'-amine | 427 | AA26 | II4 | +++ | +++ |
| 720 | (4S)-2'-(2,2-dimethylpropoxy)-7'-(5-pyrimidinyl)spiro[1,3-thiazole-4,9'-xanthen]-2-amine | 433.2 | RR2 | II38 | ++++ | ++++ |
| 721 | (4R)-2'-(2,2-dimethylpropoxy)-7'-(5-pyrimidinyl)spiro[1,3-thiazole-4,9'-xanthen]-2-amine | 433.2 | RR2 | II38 | ++++ | ++ |
| 722 | methyl 5-((4S)-2-amino-7'-(3-pyridinyl)spiro[1,3-oxazole-4,9'-xanthen]-2'-yl)-2-thiophenecarboxylate | 470.2 | AA1 | II1 | ++++ | ++++ |
| 723 | (5R)-7-(6-fluoro-3-pyridinyl)-3-(3-methoxy-3-methyl-1-butyn-1-yl)spiro[chromeno[2,3-b]pyridine-5,4'-[1,3]oxazol]-2'-amine | 445 | AA26 | II4 | +++ | ++ |
| 724 | (5R)-7-(2-fluoro-3-pyridinyl)-3-(3-methoxy-3-methyl-1-butyn-1-yl)spiro[chromeno[2,3-b]pyridine-5,4'-[1,3]oxazol]-2'-amine | 445 | AA26 | II4 | +++ | ++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 725 | ethyl 5-((4S)-2-amino-7'-(3-pyridinyl)spiro[1,3-oxazole-4,9'-xanthen]-2'-yl)-2-furancarboxylate | 468.2 | AA1 | II1 | ++++ | +++ |
| 726 | (4S)-2'-(4-methyl-2-thiophenyl)-7'-(3-pyridinyl)spiro[1,3-oxazole-4,9'-xanthen]-2-amine | 426.2 | AA1 | II1 | ++++ | +++ |
| 727 | 3-chloro-8-(3-pyridinyl)spiro[chromeno[3,2-c]pyridine-10,4'-[1,3]oxazol]-2'-amine | 365.2 | MM1 | II34 | ++ | + |
| 728 | (5S)-3-((E)-2-cyclopropylethenyl)-7-(3-pyridinyl)spiro[chromeno[2,3-c]pyridine-5,4'-[1,3]oxazol]-2'-amine | 397 | AA1 | II2 | ++++ | ++++ |
| 729 | (5S)-3-(3,4-dihydro-2H-pyran-6-yl)-7-(3-pyridinyl)spiro[chromeno[2,3-c]pyridine-5,4'-[1,3]oxazol]-2'-amine | 413 | AA1 | II2 | ++++ | ++++ |
| 730 | (4S)-2'-bicyclo[2.2.1]hept-2-en-2-yl-7'-(2,2-dimethylpropoxy)spiro[1,3-oxazole-4,9'-xanthen]-2-amine | 431 | AA24 | II1 | ++++ | ++ |
| 731 | (4S)-2'-(1-cyclopenten-1-yl)-7'-(2,2-dimethylpropoxy)spiro[1,3-oxazole-4,9'-xanthen]-2-amine | 405 | AA24 | II22 | +++ | ++ |
| 732 | (10R)-2-(2,2-dimethylpropoxy)-8-(5-pyrimidinyl)spiro[chromeno[3,2-b]pyridine-10,4'-[1,3]oxazol]-2'-amine | 418 | AA24 | II23 | ++ | ++ |
| 733 | (10S)-2-(2,2-dimethylpropoxy)-8-(5-pyrimidinyl)spiro[chromeno[3,2-b]pyridine-10,4'-[1,3]oxazol]-2'-amine | 418 | AA24 | II23 | ++++ | ++++ |
| 734 | (10R)-8-bromo-2-(2,2-dimethylpropoxy)spiro[chromeno[3,2-b]pyridine-10,4'-[1,3]oxazol]-2'-amine | 418 | Example 115 | II23 | + | + |
| 735 | (10S)-8-bromo-2-(2,2-dimethylpropoxy)spiro[chromeno[3,2-b]pyridine-10,4'-[1,3]oxazol]-2'-amine | 418 | Example 115 | II23 | ++ | ++ |
| 736 | (10R)-8-bromo-2-(2,2-dimethylpropoxy)spiro[chromeno[3,2-b]pyridine-10,4'-[1,3]oxazol]-2'-amine | 418 | Example 115 | II23 | ++ | + |
| 737 | (4S)-2'-(5-(difluoromethyl)-3-thiophenyl)-7'-(2,2-dimethylpropoxy)spiro[1,3-oxazole-4,9'-xanthen]-2-amine | 471 | AA36 | II22 | ++++ | +++ |
| 738 | (4S)-2'-(2,2-dimethylpropoxy)-7'-(4-methyl-3-thiophenyl)spiro[1,3-oxazole-4,9'-xanthen]-2-amine | 435 | AA24 | II22 | +++ | ++ |
| 739 | (4S)-2'-(2,2-dimethylpropoxy)-7'-(2-methyl-3-furanyl)spiro[1,3-oxazole-4,9'-xanthen]-2-amine | 419 | AA24 | II22 | +++ | ++ |
| 740 | (5S)-7-(2,2-dimethylpropoxy)-3-(6-(2,2,2-trifluoroethoxy)-3-pyridinyl)spiro[chromeno[2,3-b]pyridine-5,4'-[1,3]oxazol]-2'-amine | 515.1 | AA13 | II4 | ++++ | ++++ |
| 741 | (5S)-3-(6-(cyclopropylmethoxy)-3-pyridinyl)-7-(2,2-dimethylpropoxy)spiro[chromeno[2,3-b]pyridine-5,4'-[1,3]oxazol]-2'-amine | 487.2 | AA13 | II4 | ++++ | ++++ |
| 742 | (5S)-3-(cyclopropylethynyl)-7-(5-pyrimidinyl)spiro[chromeno[2,3-b]pyridine-5,4'-[1,3]oxazol]-2'-amine | 396.1 | AA5 | II3 | ++++ | ++++ |
| 743 | (5S)-3-(3-methyl-1-butyn-1-yl)-7-(5-pyrimidinyl)spiro[chromeno[2,3-b]pyridine-5,4'-[1,3]oxazol]-2'-amine | 398 | AA5 | II3 | ++++ | ++++ |
| 744 | (5S)-3-(2,2-dimethylpropoxy)-7-(3-pyridinyl)spiro[chromeno[2,3-b]pyridine-5,4'-[1,3]oxazol]-2'-amine | 417.2 | AA13 | II5 | ++++ | ++++ |
| 745 | (5R)-3-(2,2-dimethylpropoxy)-7-(3-pyridinyl)spiro[chromeno[2,3-b]pyridine-5,4'-[1,3]oxazol]-2'-amine | 417.2 | AA13 | II5 | +++ | +++ |
| 746 | (5R)-3-(2-fluorophenyl)-7-((3-methyl-3-oxetanyl)methoxy)spiro[chromeno[2,3-b]pyridine-5,4'-[1,3]oxazol]-2'-amine | 448.2 | AA13 | II4 | ++++ | +++ |
| 747 | (4S)-2'-(2,2-dimethylpropoxy)-7'-(tetrahydro-2H-pyran-4-yl)spiro[1,3-oxazole-4,9'-xanthen]-2-amine | 423 | Method O | II22 | +++ | ++ |
| 748 | (4R)-2'-(6,6-dimethyl-3,6-dihydro-2H-pyran-4-yl)-7'-(5-pyrimidinyl)spiro[1,3-oxazole-4,9'-xanthen]-2-amine | 441 | AA2 | II1 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 749 | 1-((4S)-2-amino-7'-(3-pyridinyl)spiro[1,3-oxazole-4,9'-xanthen]-2'-yl)-4,4-dimethyl-2-pyrrolidinone | 441 | OE1 | II1 | ++++ | ++++ |
| 750 | (5R)-7-(2,2-dimethylpropoxy)-3-(3-pyridinyl)spiro[chromeno[2,3-c]pyridine-5,4'-[1,3]oxazol]-2'-amine | 417 | AA37 | II2 | ++++ | +++ |
| 751 | ((4R)-2-amino-7'-(5-pyrimidinyl)spiro[1,3-oxazole-4,9'-xanthen]-2'-yl)acetic acid | 389 | AA62, AA63 | II1 | +++ | + |
| 752 | (5S)-7-(2,2-dimethylpropoxy)-3-(2-fluoro-4-pyridinyl)spiro[chromeno[2,3-b]pyridine-5,4'-[1,3]oxazol]-2'-amine | 435 | AA13 | II4 | ++++ | ++++ |
| 753 | (5S)-7-(2,2-dimethylpropoxy)-3-(5-fluoro-3-pyridinyl)spiro[chromeno[2,3-b]pyridine-5,4'-[1,3]oxazol]-2'-amine | 435.2 | AA13 | II4 | ++++ | ++++ |
| 754 | (4S)-2'-(2,2-dimethylcyclopropyl)-7'-(2,2-dimethylpropoxy)spiro[1,3-oxazole-4,9'-xanthen]-2-amine | 407 | AA13 | II1 | ++++ | +++ |
| 755 | (4S)-2'-(3,6-dihydro-2H-pyran-4-yl)-7'-(2,2-dimethylpropoxy)spiro[1,3-oxazole-4,9'-xanthen]-2-amine | 421 | AA13 | II1 | +++ | ++ |
| 756 | (4S)-2'-cyclopropyl-7'-(3,6-dihydro-2H-pyran-4-yl)spiro[1,3-oxazole-4,9'-xanthen]-2-amine | 375.1 | AA1 | II1 | +++ | ++ |
| 757 | 2',7'-di-3,6-dihydro-2H-pyran-4-ylspiro[1,3-oxazole-4,9'-xanthen]-2-amine | 417 | AA2 | II1 | +++ | +++ |
| 758 | (4R)-2'-cyclopropyl-7'-(3-pyridinyl)spiro[1,3-oxazole-4,9'-xanthen]-2-amine | 370.1 | AA1 | II1 | ++++ | +++ |
| 759 | (4S)-2'-cyclopropyl-7'-(2,2-dimethylpropoxy)spiro[1,3-oxazole-4,9'-xanthen]-2-amine | 379.1 | AA13 | II22 | +++ | ++ |
| 760 | 2',7'-dicyclopropylspiro[1,3-oxazole-4,9'-xanthen]-2-amine | 333.1 | AA2 | II1 | ++ | ++ |
| 761 | 1-((4S)-2-amino-7'-(5-pyrimidinyl)spiro[1,3-thiazole-4,9'-xanthen]-2'-yl)-3,3-dimethyl-1-butanone | 445.2 | RR1 | II38 | ++++ | +++ |
| 762 | 1-((4R)-2-amino-7'-(5-pyrimidinyl)spiro[1,3-thiazole-4,9'-xanthen]-2'-yl)-3,3-dimethyl-1-butanone | 445.2 | RR1 | II38 | +++ | ++ |
| 763 | (4S)-2'-(2,2-dimethyl-4-morpholinyl)-7'-(5-pyrimidinyl)spiro[1,3-oxazole-4,9'-xanthen]-2-amine | 444 | AA9 | II1 | ++++ | ++++ |
| 764 | (4S)-2'-(4-morpholinyl)-7'-(3-pyridinyl)spiro[1,3-oxazole-4,9'-xanthen]-2-amine | 415 | AA9 | II1 | ++++ | ++++ |
| 765 | tert-butyl ((4R)-2-amino-7'-(5-pyrimidinyl)spiro[1,3-oxazole-4,9'-xanthen]-2'-yl)acetate | 445 | AA62 | II1 | +++ | +++ |
| 766 | (5S)-3-(3,3-dimethyl-1-butyn-1-yl)-7-(6-fluoro-3-pyridinyl)spiro[chromeno[2,3-b]pyridine-5,4'-[1,3]oxazol]-2'-amine | 429 | AA5 | II3 | ++++ | ++++ |
| 767 | (5S)-3-(3-methoxy-3-methyl-1-butyn-1-yl)-7-(6-methoxy-3-pyridinyl)spiro[chromeno[2,3-b]pyridine-5,4'-[1,3]oxazol]-2'-amine | 457 | AA41 | II3 | +++ | +++ |
| 768 | 1-(((4S)-2-amino-7'-(3-methoxy-3-methyl-1-butyn-1-yl)spiro[1,3-oxazole-4,9'-xanthen]-2'-yl)oxy)-2-methyl-2-propanol | 437 | AA47 | II18 | +++ | +++ |
| 769 | (11S)-2-ethyl-9-(5-pyrimidinyl)spiro[furo[3',2':5,6]chromeno[2,3-b]pyridine-11,4'-[1,3]oxazol]-2'-amine | 400 | AA38 | II4 | +++ | ++ |
| 770 | 1-(((4S)-2-amino-7'-(3-pyridinyl)spiro[1,3-oxazole-4,9'-xanthen]-2'-yl)oxy)-2-methyl-2-butanol | 432 | AA47 | II18 | ++++ | ++++ |
| 771 | (4S)-7'-(5-pyrimidinyl)-N~2~'-(tetrahydro-2H-pyran-4-yl)spiro[1,3-oxazole-4,9'-xanthene]-2,2'-diamine | 430 | AA9 | II1 | +++ | +++ |
| 772 | (5S)-3-(3-chlorophenyl)-7-((3-methyl-3-oxetanyl)methoxy)spiro[chromeno[2,3-b]pyridine-5,4'-[1,3]oxazol]-2'-amine | 464 | AA13 | II4 | ++++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 773 | (4R)-2'-(4-(difluoromethoxy)phenyl)-7'-(5-pyrimidinyl)spiro[1,3-oxazole-4,9'-xanthen]-2-amine | 473 | AA2 | II1 | ++++ | +++ |
| 774 | (5S)-3-(3-fluorophenyl)-7-((3-methyl-3-oxetanyl)methoxy)spiro[chromeno[2,3-b]pyridine-5,4'-[1,3]oxazol]-2'-amine | 448.2 | AA13 | II4 | ++++ | ++++ |
| 775 | (5S)-3-(4-fluorophenyl)-7-((3-methyl-3-oxetanyl)methoxy)spiro[chromeno[2,3-b]pyridine-5,4'-[1,3]oxazol]-2'-amine | 448 | AA13 | II4 | ++++ | ++++ |
| 776 | (4S)-2'-(3-oxetanyloxy)-7'-(5-pyrimidinyl)spiro[1,3-oxazole-4,9'-xanthen]-2-amine | 403 | AA13 | II18 | +++ | +++ |
| 777 | (4S)-2'-(3-oxetanyloxy)-7'-(3-pyridinyl)spiro[1,3-oxazole-4,9'-xanthen]-2-amine | 402 | AA13 | II18 | +++ | +++ |
| 778 | (4R)-2'-(2,2-dimethylpropoxy)-7'-(4-methoxy-3-pyridinyl)spiro[1,3-oxazole-4,9'-xanthen]-2-amine | 446.2 | AA36 | II22 | ++ | ++ |
| 779 | (4R)-2'-(2,2-dimethylpropoxy)-7'-(5-methoxy-3-pyridinyl)spiro[1,3-oxazole-4,9'-xanthen]-2-amine | 447.2 | AA36 | II22 | + | + |
| 780 | (4R)-2'-(2-(dimethylamino)-5-pyrimidinyl)-7'-(2,2-dimethylpropoxy)spiro[1,3-oxazole-4,9'-xanthen]-2-amine | 460.2 | AA36 | II22 | +++ | ++ |
| 781 | (4R)-2'-(2,2-dimethylpropoxy)-7'-(1,3-thiazol-5-yl)spiro[1,3-oxazole-4,9'-xanthen]-2-amine | 422.1 | AA36 | II22 | ++++ | +++ |
| 782 | 5-((4R)-2-amino-7'-(2,2-dimethylpropoxy)spiro[1,3-oxazole-4,9'-xanthen]-2'-yl)-2-pyridinecarbonitrile | 441.2 | AA36 | II22 | ++++ | +++ |
| 783 | (4R)-2'-(5-(difluoromethyl)-3-thiophenyl)-7'-(2,2-dimethylpropoxy)spiro[1,3-oxazole-4,9'-xanthen]-2-amine | 471.1 | AA36 | II22 | ++++ | ++ |
| 784 | (4R)-2'-(2,2-dimethylpropoxy)-7'-(4-((methylamino)methyl)phenyl)spiro[1,3-oxazole-4,9'-xanthen]-2-amine | 458.2 | AA36 | II22 | +++ | ++ |
| 785 | (4R)-2'-(2,2-dimethylpropoxy)-7'-(6-fluoro-3-pyridinyl)spiro[1,3-oxazole-4,9'-xanthen]-2-amine | 434.1 | AA36 | II22 | + | + |
| 786 | (4R)-2'-(2,2-dimethylpropoxy)-7'-(6-methyl-3-pyridinyl)spiro[1,3-oxazole-4,9'-xanthen]-2-amine | 430.2 | AA36 | II22 | +++ | +++ |
| 787 | (4R)-2'-(2,2-dimethylpropoxy)-7'-(4-(methylsulfanyl)phenyl)spiro[1,3-oxazole-4,9'-xanthen]-2-amine | 461.2 | AA36 | II22 | ++++ | ++ |
| 788 | 2-(((4S)-2-amino-7'-(3-pyridinyl)spiro[1,3-oxazole-4,9'-xanthen]-2'-yl)oxy)-N-methoxy-N-methylacetamide | 447 | AA14 | II18 | ++ | ++ |
| 789 | (5S)-3-(1-cyclohexen-1-yl)-7-(3-pyridinyl)spiro[chromeno[2,3-c]pyridine-5,4'-[1,3]oxazol]-2'-amine | 411 | AA1 | II2 | ++++ | ++++ |
| 790 | (5S)-3-(3,6-dihydro-2H-pyran-4-yl)-7-(3-pyridinyl)spiro[chromeno[2,3-c]pyridine-5,4'-[1,3]oxazol]-2'-amine | 413 | AA1 | II2 | ++++ | ++++ |
| 791 | (5S)-3-cyclohexyl-7-(3-pyridinyl)spiro[chromeno[2,3-c]pyridine-5,4'-[1,3]oxazol]-2'-amine | 413 | AA11 | II2 | ++++ | +++ |
| 792 | (11S)-2-(2-methylpropyl)-9-(5-pyrimidinyl)spiro[furo[3',2':5,6]chromeno[2,3-b]pyridine-11,4'-[1,3]oxazol]-2'-amine | 428.1 | AA38 | II4 | +++ | ++ |
| 794 | 4-((5S)-2'-amino-7-(6-fluoro-3-pyridinyl)spiro[chromeno[2,3-b]pyridine-5,4'-[1,3]oxazol]-3-yl)-2-methyl-3-butyn-2-ol | 431 | AA5 | II3 | ++++ | ++++ |
| 795 | (4S)-4'-fluoro-7'-((3-methyl-3-oxetanyl)methoxy)-2'-(5-pyrimidinyl)spiro[1,3-oxazole-4,9'-xanthen]-2-amine | 449 | AA13 | II21 | ++++ | ++++ |
| 796 | (4R)-4'-fluoro-7'-((3-methyl-3-oxetanyl)methoxy)-2'-(5- | 449 | AA13 | II21 | ++++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| | pyrimidinyl)spiro[1,3-oxazole-4,9'-xanthen]-2-amine | | | | | |
| 797 | 1-(2-((4R)-2-amino-7'-(5-pyrimidinyl)spiro[1,3-oxazole-4,9'-xanthen]-2'-yl)ethyl)cyclobutanol | 429 | AA39 | II1 | ++++ | ++++ |
| 798 | (4S)-2-amino-N-cyclopropyl-7'-(2,2-dimethylpropoxy)spiro[1,3-oxazole-4,9'-xanthene]-2'-carboxamide | 422 | AA30 | II22 | ++++ | ++++ |
| 799 | (4R)-2-amino-7'-(2,2-dimethylpropoxy)-N,N-dimethylspiro[1,3-oxazole-4,9'-xanthene]-2'-carboxamide | 410 | AA46 | II22 | +++ | +++ |
| 800 | (5R)-3-(3,6-dihydro-2H-pyran-4-yl)-7-(3,3-dimethyl-1-butyn-1-yl)spiro[chromeno[2,3-c]pyridine-5,4'-[1,3]oxazol]-2'-amine | 416 | AA1 | II2 | +++ | ++ |
| 801 | (5S)-7-(3-pyridinyl)-3-(tetrahydro-2H-pyran-4-yl)spiro[chromeno[2,3-c]pyridine-5,4'-[1,3]oxazol]-2'-amine | 415 | AA11 | II2 | ++++ | ++++ |
| 802 | (4S)-2'-cyclohexyl-7'-(2,2-dimethylpropoxy)spiro[1,3-oxazole-4,9'-xanthen]-2-amine | 421 | Method O | II22 | ++++ | +++ |
| 803 | (4S)-2'-(1-cyclohexen-1-yl)-7'-(2,2-dimethylpropoxy)spiro[1,3-oxazole-4,9'-xanthen]-2-amine | 419 | AA24 | II22 | ++++ | ++ |
| 804 | (5S)-7-(2,2-dimethylpropoxy)-3-(6-ethoxy-3-pyridinyl)spiro[chromeno[2,3-b]pyridine-5,4'-[1,3]oxazol]-2'-amine | 461.2 | AA13 | 114 | ++++ | ++++ |
| 805 | (5S)-3-(3,6-dihydro-2H-pyran-4-yl)-7-(5-pyrimidinyl)spiro[chromeno[2,3-b]pyridine-5,4'-[1,3]oxazol]-2'-amine | 414 | AA1 | II3 | ++++ | ++++ |
| 806 | (5S)-3-(3-methoxy-3-methyl-1-butyn-1-yl)-7-(2-methoxy-3-pyridinyl)spiro[chromeno[2,3-b]pyridine-5,4'-[1,3]oxazol]-2'-amine | 457 | AA41 | II3 | ++++ | ++++ |
| 298 | (5S)-3-(3,3-dimethyl-1-butyn-1-yl)-7-(2-fluoro-3-pyridinyl)spiro[chromeno[2,3-b]pyridine-5,4'-[1,3]oxazol]-2'-amine | 429 | AA5 | II3 | ++++ | ++++ |
| 807 | (5S)-7-(2,2-dimethylpropoxy)-3-phenylspiro[chromeno[2,3-b]pyridine-5,4'-[1,3]oxazol]-2'-amine | 416.2 | AA13 | II4 | ++++ | ++++ |
| 808 | (5S)-7-(2,2-dimethylpropoxy)-3-(4-pyridinyl)spiro[chromeno[2,3-b]pyridine-5,4'-[1,3]oxazol]-2'-amine | 417.2 | AA13 | II4 | ++++ | ++++ |
| 809 | (4R)-2'-(5-pyrimidinyl)-7'-(3-(trifluoromethyl)phenyl)spiro[1,3-oxazole-4,9'-xanthen]-2-amine | 475 | AA2 | II1 | ++++ | +++ |
| 810 | (4R)-2'-(3-pyridinyl)-7'-(1,2,3,6-tetrahydro-4-pyridinyl)spiro[1,3-oxazole-4,9'-xanthen]-2-amine | 411 | AA2 | II1 | ++++ | ++++ |
| 811 | (4R)-2'-(5-pyrimidinyl)-7'-(4-(trifluoromethyl)phenyl)spiro[1,3-oxazole-4,9'-xanthen]-2-amine | 475 | AA2 | II1 | ++++ | +++ |
| 812 | (4S)-2'-(2,2-dimethylpropoxy)-7'-(4-methyl-1-piperazinyl)spiro[1,3-oxazole-4,9'-xanthen]-2-amine | 437 | AA40 | II22 | ++ | +++ |
| 813 | (4S)-2'-(2,2-dimethylpropoxy)-7'-(1-piperidinyl)spiro[1,3-oxazole-4,9'-xanthen]-2-amine | 422 | AA40 | II22 | +++ | +++ |
| 814 | (4R)-1'-fluoro-7'-methoxy-2'-(5-pyrimidinyl)spiro[1,3-oxazole-4,9'-xanthen]-2-amine | 379 | AA24 | II29 | ++++ | +++ |
| 815 | (4S)-2'-(2,2-dimethylpropoxy)-7'-(1-pyrrolidinyl)spiro[1,3-oxazole-4,9'-xanthen]-2-amine | 408 | AA40 | II22 | +++ | ++ |
| 816 | (4S)-1'-fluoro-7'-methoxy-2'-(5-pyrimidinyl)spiro[1,3-oxazole-4,9'-xanthen]-2-amine | 379 | AA24 | II29 | + | + |
| 817 | 3-(((5S)-2'-amino-3-phenylspiro[chromeno[2,3-b]pyridine-5,4'-[1,3]oxazol]-7-yl)oxy)-2,2-dimethylpropanenitrile | 427.2 | AA13 | II4 | ++++ | ++++ |
| 818 | (5S)-7-(2-methoxy-2-methylpropoxy)-3-phenylspiro[chromeno[2,3-b]pyridine-5,4'-[1,3]oxazol]-2'-amine | 432.2 | AA13 | II4 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 819 | tert-butyl 4-((4R)-2-amino-7'-(3-pyridinyl)spiro[1,3-oxazole-4,9'-xanthen]-2'-yl)-3,6-dihydro-1(2H)-pyridinecarboxylate | 511 | AA2 | II1 | ++++ | +++ |
| 820 | (4S)-2'-(5-methyl-2-thiophenyl)-7'-(5-pyrimidinyl)spiro[1,3-oxazole-4,9'-xanthen]-2-amine | 427 | AA2 | II1 | ++++ | ++++ |
| 821 | 4-((5S)-2'-amino-7-(2-fluoro-3-pyridinyl)spiro[chromeno[2,3-b]pyridine-5,4'-[1,3]oxazol]-3-yl)-2-methyl-3-butyn-2-ol | 431 | AA5 | II3 | ++++ | ++++ |
| 822 | (5S)-3-(3-methoxy-3-methyl-1-butyn-1-yl)-7-(5-pyrimidinyl)spiro[chromeno[2,3-b]pyridine-5,4'-[1,3]oxazol]-2'-amine | 428 | AA41 | II3 | ++++ | ++++ |
| 823 | 4-((5S)-2'-amino-7-(5-pyrimidinyl-[chromeno[2,3-b]pyridine-5,4'-[1,3]oxazol]-3-yl)-2-methyl-3-butyn-2-ol | 414 | AA5 | II3 | ++++ | ++++ |
| 824 | (5R)-7-(3,3-dimethyl-1-butyn-1-yl)-3-(3-pyridinyl)spiro[chromeno[2,3-c]pyridine-5,4'-[1,3]oxazol]-2'-amine | 411 | AA33 | II2 | ++++ | +++ |
| 825 | ethyl (2E)-3-((4R)-2-amino-7'-(5-pyrimidinyl)spiro[1,3-oxazole-4,9'-xanthen]-2'-yl)-2-propenoate | 429 | AA1 | II1 | +++ | +++ |
| 826 | tert-butyl 3-((4R)-2-amino-7'-(5-pyrimidinyl)spiro[1,3-oxazole-4,9'-xanthen]-2'-yl)propanoate | 459 | Method O | II1 | +++ | ++ |
| 827 | 2-((4S)-2-amino-7'-(2,2-dimethylpropoxy)spiro[1,3-oxazole-4,9'-xanthen]-2'-yl)-2-propanol | 397 | AA45 | II22 | +++ | ++ |
| 828 | ((4S)-2-amino-7'-(2,2-dimethylpropoxy)spiro[1,3-oxazole-4,9'-xanthen]-2'-yl)methanol | 369 | AA45 | II22 | ++ | ++ |
| 829 | (4R)-2'-(6-methoxy-3-pyridinyl)-7'-(5-pyrimidinyl)spiro[1,3-oxazole-4,9'-xanthen]-2-amine | 438 | AA2 | II1 | ++++ | ++++ |
| 830 | (4R)-2'-(3,4-dimethoxyphenyl)-7'-(5-pyrimidinyl)spiro[1,3-oxazole-4,9'-xanthen]-2-amine | 467 | AA2 | II1 | ++++ | +++ |
| 831 | (4R)-2'-(3,6-dihydro-2H-thiopyran-4-yl)-7'-(5-pyrimidinyl)spiro[1,3-oxazole-4,9'-xanthen]-2-amine | 429 | AA2 | II1 | ++++ | ++++ |
| 832 | (4S)-2'-(2,2-dimethylpropoxy)-7'-(2-(1-methylethyl)-1,3-thiazol-4-yl)spiro[1,3-oxazole-4,9'-xanthen]-2-amine | 464 | AA36 | II22 | +++ | ++ |
| 833 | (4S)-2'-(2,2-dimethylpropoxy)-7'-(3-thiophenyl)spiro[1,3-oxazole-4,9'-xanthen]-2-amine | 421 | AA36 | II22 | ++++ | ++ |
| 834 | (4S)-2'-(2,2-dimethylpropoxy)-7'-(2-thiophenyl)spiro[1,3-oxazole-4,9'-xanthen]-2-amine | 421 | AA36 | II22 | ++++ | ++ |
| 835 | 1-(3-((4S)-2-amino-7'-(2,2-dimethylpropoxy)spiro[1,3-oxazole-4,9'-xanthen]-2'-yl)-2-thiophenyl)ethanone | 464 | AA36 | II22 | ++ | + |
| 836 | 1-(4-((4S)-2-amino-7'-(2,2-dimethylpropoxy)spiro[1,3-oxazole-4,9'-xanthen]-2'-yl)-2-thiophenyl)ethanone | 464 | AA36 | II22 | ++ | ++ |
| 837 | (4S)-2'-(2,2-dimethylpropoxy)-7'-(2,4-dimethyl-1,3-thiazol-5-yl)spiro[1,3-oxazole-4,9'-xanthen]-2-amine | 450 | AA36 | II22 | +++ | + |
| 838 | (4S)-2'-(2-(dimethylamino)-5-pyrimidinyl)-7'-(2,2-dimethylpropoxy)spiro[1,3-oxazole-4,9'-xanthen]-2-amine | 461 | AA36 | II22 | + | + |
| 839 | (4R)-2'-(5-pyrimidinyl)-7'-(3-(trifluoromethoxy)phenyl)spiro[1,3-oxazole-4,9'-xanthen]-2-amine | 491 | AA2 | II1 | ++++ | ++ |
| 840 | (4R)-2'-(5-pyrimidinyl)-7'-(4-(trifluoromethoxy)phenyl)spiro[1,3-oxazole-4,9'-xanthen]-2-amine | 491 | AA2 | II1 | ++++ | +++ |
| 841 | (4R)-2'-(2,2-dimethyl-2,3-dihydro-1-benzofuran-5-yl)-7'-(5-pyrimidinyl)spiro[1,3-oxazole-4,9'-xanthen]-2-amine | 477 | AA2 | II1 | ++++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 842 | (10S)-1-((4-methylpentyl)oxy)-8-(3-pyridinyl)spiro[chromeno[3,2-c]pyridine-10,4'-[1,3]oxazol]-2'-amine | 431 | MM1 | II28 | +++ | +++ |
| 843 | (10R)-1-((4-methylpentyl)oxy)-8-(3-pyridinyl)spiro[chromeno[3,2-c]pyridine-10,4'-[1,3]oxazol]-2'-amine | 431 | MM1 | II28 | + | + |
| 844 | (4S)-2'-(5-pyrimidinyl)spiro[1,3-oxazole-4,9'-xanthen]-2-amine | 331.2 | AA24 | II19 | +++ | +++ |
| 845 | (5S)-3-(3,3-dimethyl-1-butyn-1-yl)-7-(3-pyridinyl)spiro[chromeno[2,3-c]pyridine-5,4'-[1,3]oxazol]-2'-amine | 411 | AA5 | II2 | ++++ | ++++ |
| 846 | (5R)-3-chloro-7-(3,3-dimethyl-1-butyn-1-yl)spiro[chromeno[2,3-c]pyridine-5,4'-[1,3]oxazol]-2'-amine | 368 | AA42 | II2 | ++ | + |
| 847 | (5R)-3,7-bis(3,3-dimethyl-1-butyn-1-yl)spiro[chromeno[2,3-c]pyridine-5,4'-[1,3]oxazol]-2'-amine | 414 | AA42 | II2 | +++ | ++ |
| 848 | (5S)-3-(1-cyclohexen-1-yl)-7-(3-pyridinyl)spiro[chromeno[2,3-c]pyridine-5,4'-[1,3]oxazol]-2'-amine | 411 | AA1 | II2 | ++++ | ++++ |
| 849 | (5S)-3-(3,6-dihydro-2H-pyran-4-yl)-7-(3-pyridinyl)spiro[chromeno[2,3-c]pyridine-5,4'-[1,3]oxazol]-2'-amine | 413 | AA1 | II2 | ++++ | ++++ |
| 850 | methyl (4S)-2-amino-7'-(2,2-dimethylpropoxy)spiro[1,3-oxazole-4,9'-xanthene]-2'-carboxylate | 397 | AA45 | II22 | +++ | ++ |
| 851 | (5S)-3-(4-(1-methylethoxy)phenyl)-7-(3-pyridinyl)spiro[chromeno[2,3-c]pyridine-5,4'-[1,3]oxazol]-2'-amine | 465 | AA1 | II2 | ++++ | +++ |
| 852 | 3-chloro-8-(5-pyrimidinyl)spiro[chromeno[3,2-c]pyridine-10,4'-[1,3]oxazol]-2'-amine | 366.2 | MM1 | II35 | ++ | + |
| 853 | (4S)-2'-(2,4-difluoro-3-pyridinyl)-7'-(2,2-dimethylpropoxy)spiro[1,3-oxazole-4,9'-xanthen]-2-amine | 452 | AA36 | II22 | ++++ | ++++ |
| 854 | (10S)-2-(3,3-dimethyl-1-butyn-1-yl)-8-(3-pyridinyl)spiro[chromeno[3,2-b]pyridine-10,4'-[1,3]oxazol]-2'-amine | 411 | AA5 | II8 | ++++ | ++++ |
| 855 | (10S)-8-bromo-2-chlorospiro[chromeno[3,2-b]pyridine-10,4'-[1,3]oxazol]-2'-amine | 366 | Example 136 | II8 | + | + |
| 856 | (10R)-8-bromo-2-chlorospiro[chromeno[3,2-b]pyridine-10,4'-[1,3]oxazol]-2'-amine | 366 | Example 136 | II8 | + | + |
| 857 | (3E)-4-((4R)-2-amino-7'-(5-pyrimidinyl)spiro[1,3-oxazole-4,9'-xanthen]-2'-yl)-3-buten-2-one | 399.1 | A60 | II1 | ++++ | +++ |
| 858 | tert-butyl ((4S)-2-amino-7'-bromospiro[1,3-oxazole-4,9'-xanthen]-2'-yl)acetate | 446 | AA62 | II1 | + | + |
| 859 | 1-(2-((4R)-2-amino-7'-(3-pyridinyl)spiro[1,3-oxazole-4,9'-xanthen]-2'-yl)ethyl)cyclobutanol | 428 | AA39 | II1 | ++++ | ++++ |
| 861 | (4S)-2-amino-7'-(2,2-dimethylpropoxy)spiro[1,3-oxazole-4,9'-xanthene]-2'-carboxylic acid | 383 | AA46 | II22 | ++ | + |
| 863 | 1-((4S)-2-amino-7'-(3-pyridinyl)spiro[1,3-oxazole-4,9'-xanthen]-2'-yl)-2-pyrrolidinone | 413 | OE10 | II1 | ++++ | +++ |
| 864 | 1-(((5S)-2'-amino-3-(3-pyridinyl)spiro[chromeno[2,3-b]pyridine-5,4'-[1,3]oxazol]-7-yl)oxy)-2-propanone | 403 | AA13 | II4 | +++ | +++ |
| 865 | 1-(((5R)-2'-amino-3-(3-pyridinyl)spiro[chromeno[2,3-b]pyridine-5,4'-[1,3]oxazol]-7-yl)oxy)-2-propanone | 403 | AA13 | II4 | ++ | ++ |
| 866 | 1-(((4S)-2-amino-7'-(3-pyridinyl)spiro[1,3-oxazole-4,9'-xanthen]-2'-yl)oxy)-3-methyl-2-butanol | 432 | AA47 | II18 | ++++ | +++ |
| 867 | 1-(((4S)-2-amino-7'-(3-pyridinyl)spiro[1,3-oxazole-4,9'-xanthen]-2'-yl)oxy)-2,3-dimethyl-2-butanol | 446 | AA47 | II18 | ++++ | ++++ |
| 868 | (5S)-7-(2,2-dimethylpropoxy)-3-(6-fluoro-3-pyridinyl)spiro[chromeno[2,3-b]pyridine-5,4'-[1,3]oxazol]-2'-amine | 435.2 | AA13 | II4 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 869 | (5R)-7-(2,2-dimethylpropoxy)-3-(6-fluoro-3-pyridinyl)spiro[chromeno[2,3-b]pyridine-5,4'-[1,3]oxazol]-2'-amine | 435.2 | AA13 | II4 | +++ | ++ |
| 870 | (5S)-7-(2,2-dimethylpropoxy)-3-(2-fluoro-3-pyridinyl)spiro[chromeno[2,3-b]pyridine-5,4'-[1,3]oxazol]-2'-amine | 435.2 | AA13 | II4 | ++++ | ++++ |
| 871 | (5R)-7-(2,2-dimethylpropoxy)-3-(2-fluoro-3-pyridinyl)spiro[chromeno[2,3-b]pyridine-5,4'-[1,3]oxazol]-2'-amine | 435.2 | AA13 | II4 | ++++ | +++ |
| 872 | (4R)-2'-(3-pyridinyl)-7'-(1-pyrrolidinylcarbonyl)spiro[1,3-oxazole-4,9'-xanthen]-2-amine | 427 | AA44 | II1 | +++ | +++ |
| 873 | (4S)-2'-(2,2-dimethylpropoxy)-7'-(1-piperidinylcarbonyl)spiro[1,3-oxazole-4,9'-xanthen]-2-amine | 450 | AA30 | II22 | +++ | +++ |
| 874 | (4S)-2-amino-N-cyclopentyl-7'-(2,2-dimethylpropoxy)spiro[1,3-oxazole-4,9'-xanthene]-2'-carboxamide | 450 | AA30 | II22 | +++ | ++ |
| 875 | methyl (4S)-2-amino-7'-(2,2-dimethylpropoxy)spiro[1,3-oxazole-4,9'-xanthene]-2'-carboxylate | 397 | AA46 | II22 | ++++ | +++ |
| 876 | (4R)-2'-bromo-7'-(3-pyridinyl)spiro[1,3-oxazole-4,9'-xanthen]-2-amine | 408, 410 | AA24 | II1 | +++ | ++ |
| 877 | methyl 3-((4R)-2-amino-7'-(5-pyrimidinyl)spiro[1,3-oxazole-4,9'-xanthen]-2'-yl)propanoate | 417.1 | Method O | II1 | +++ | +++ |
| 880 | (4S)-2'-(5-methyl-2-furanyl)-7'-(5-pyrimidinyl)spiro[1,3-oxazole-4,9'-xanthen]-2-amine | 411 | AA2 | II1 | ++++ | ++++ |
| 881 | (4S)-2'-(2-chloro-5-pyrimidinyl)-7'-(2,2-dimethylpropoxy)spiro[1,3-oxazole-4,9'-xanthen]-2-amine | 451 | AA36 | II22 | ++++ | +++ |
| 882 | 5-((4S)-2-amino-7'-(2,2-dimethylpropoxy)spiro[1,3-oxazole-4,9'-xanthen]-2'-yl)-2-pyridinecarbonitrile | 441 | AA36 | II22 | ++++ | ++ |
| 883 | (4S)-2'-(4-chloro-3-pyridinyl)-7'-(2,2-dimethylpropoxy)spiro[1,3-oxazole-4,9'-xanthen]-2-amine | 450 | AA36 | II22 | ++++ | +++ |
| 884 | 5-((4S)-2-amino-7'-(2,2-dimethylpropoxy)spiro[1,3-oxazole-4,9'-xanthen]-2'-yl)-4-pyrimidinol | 433 | AA36 | II22 | +++ | ++ |
| 885 | (4S)-2'-(2,2-dimethylpropoxy)-7'-(2-pyrimidinyl)spiro[1,3-oxazole-4,9'-xanthen]-2-amine | 417 | AA36 | II22 | +++ | ++ |
| 886 | (4S)-2'-(2-(dimethylamino)ethoxy)-7'-(3-pyridinyl)spiro[1,3-oxazole-4,9'-xanthen]-2-amine | 417 | AA14 | II18 | +++ | ++++ |
| 887 | (4S)-2'-(6-chloro-3-pyridinyl)-7'-(2,2-dimethylpropoxy)spiro[1,3-oxazole-4,9'-xanthen]-2-amine | 450 | AA24 | II22 | ++++ | +++ |
| 888 | 1-(4-((4R)-2-amino-7'-(5-pyrimidinyl)spiro[1,3-oxazole-4,9'-xanthen]-2'-yl)phenyl)ethanone | 449 | AA2 | II1 | ++++ | ++++ |
| 889 | 1-(3-((4R)-2-amino-7'-(5-pyrimidinyl)spiro[1,3-oxazole-4,9'-xanthen]-2'-yl)phenyl)ethanone | 449 | AA2 | II1 | ++++ | ++++ |
| 890 | 4-((4R)-2-amino-7'-(5-pyrimidinyl)spiro[1,3-oxazole-4,9'-xanthen]-2'-yl)phenol | 423 | AA2 | II1 | ++++ | +++ |
| 891 | 3-((4R)-2-amino-7'-(5-pyrimidinyl)spiro[1,3-oxazole-4,9'-xanthen]-2'-yl)phenol | 423 | AA2 | II1 | ++++ | +++ |
| 892 | (4R)-2'-(4-methoxyphenyl)-7'-(5-pyrimidinyl)spiro[1,3-oxazole-4,9'-xanthen]-2-amine | 437 | AA2 | II1 | ++++ | ++++ |
| 893 | (4R)-2'-(3-methoxyphenyl)-7'-(5-pyrimidinyl)spiro[1,3-oxazole-4,9'-xanthen]-2-amine | 437 | AA2 | II1 | ++++ | +++ |
| 894 | 2-((((4S)-2-amino-7'-(3-pyridinyl)spiro[1,3-oxazole-4,9'-xanthen]-2'-yl)oxy)methyl)-1,1,1,3,3,3-hexafluoro-2-propanol | 526 | AA14 | II18 | ++++ | +++ |
| 895 | (5S)-7-(3,3-dimethyl-1-butyn-1-yl)-3-(3-pyridinyl)spiro[chromeno[2,3-b]pyridine-5,4'-[1,3]oxazol]-2'-amine | 411 | AA33 | II3 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 896 | (5R)-7-(3,3-dimethyl-1-butyn-1-yl)-3-(3-pyridinyl)spiro[chromeno[2,3-b]pyridine-5,4'-[1,3]oxazol]-2'-amine | 411 | AA33 | II3 | +++ | ++ |
| 897 | (5S)-3,7-bis(3,3-dimethyl-1-butyn-1-yl)spiro[chromeno[2,3-b]pyridine-5,4'-[1,3]oxazol]-2'-amine | 414.2 | AA42 | II3 | ++++ | +++ |
| 898 | (5R)-3,7-bis(3,3-dimethyl-1-butyn-1-yl)spiro[chromeno[2,3-b]pyridine-5,4'-[1,3]oxazol]-2'-amine | 414.2 | AA42 | II3 | +++ | + |
| 899 | (4S)-1'-fluoro-7'-methoxy-2'-(5-pyrimidinyl)spiro[1,3-oxazole-4,9'-xanthen]-2-amine | 379 | AA24 | II29 | +++ | ++ |
| 900 | (5R)-3-(2,2-dimethylpropoxy)-7-(3-pyridinyl)spiro[chromeno[2,3-b]pyridine-5,4'-[1,3]oxazol]-2'-amine | 417 | AA13 | II5 | ++++ | ++++ |
| 901 | (5R)-7-methoxy-3-(3-methoxy-3-methyl-1-butyn-1-yl)spiro[chromeno[2,3-b]pyridine-5,4'-[1,3]oxazol]-2'-amine | 380.2 | AA42 | II7 | ++ | + |
| 902 | (5S)-3,7-di-3-pyridinylspiro[chromeno[2,3-c]pyridine-5,4'-[1,3]oxazol]-2'-amine | 408 | AA2 | II2 | ++++ | ++++ |
| 903 | 4-((5R)-2'-amino-7-methoxyspiro[chromeno[2,3-b]pyridine-5,4'-[1,3]oxazol]-3-yl)-2-methyl-3-butyn-2-ol | 366.3 | AA42 | II6 | + | + |
| 904 | (5R)-3-(3,3-dimethyl-1-butyn-1-yl)-7-methoxyspiro[chromeno[2,3-b]pyridine-5,4'-[1,3]oxazol]-2'-amine | 364.2 | AA42 | II6 | + | +++ |
| 905 | (4S)-2'-(4-morpholinyl)-7'-(5-pyrimidinyl)spiro[1,3-oxazole-4,9'-xanthen]-2-amine | 416 | AA9 | II1 | ++++ | ++++ |
| 906 | 1-(((4S)-2-amino-7'-(2-fluoro-3-pyridinyl)spiro[1,3-oxazole-4,9'-xanthen]-2'-yl)oxy)-2-methyl-2-propanol | 436 | AA14 | II18 | ++++ | ++++ |
| 907 | 1-(((4S)-2-amino-1'-methyl-7'-(3-pyridinyl)spiro[1,3-oxazole-4,9'-xanthen]-2'-yl)oxy)-2-methyl-2-propanol | 432 | TAD10 | II18 | ++++ | ++++ |
| 908 | (4S)-2'-(2,2-dimethylpropoxy)-7'-(5-methoxy-3-pyridinyl)spiro[1,3-oxazole-4,9'-xanthen]-2-amine | 446 | AA24 | II22 | ++++ | ++++ |
| 909 | (4S)-2'-(2,6-dimethoxy-3-pyridinyl)-7'-(2,2-dimethylpropoxy)spiro[1,3-oxazole-4,9'-xanthen]-2-amine | 476 | AA24 | II22 | +++ | + |
| 910 | (4S)-2'-(2,2-dimethylpropoxy)-7'-(4-(methylsulfonyl)phenyl)spiro[1,3-oxazole-4,9'-xanthen]-2-amine | 493 | AA24 | II22 | ++ | ++ |
| 911 | (4S)-2'-(2,2-dimethylpropoxy)-7'-(2-(trifluoromethyl)-3-pyridinyl)spiro[1,3-oxazole-4,9'-xanthen]-2-amine | 484 | AA24 | II22 | +++ | + |
| 912 | (4S)-2'-(2,2-dimethylpropoxy)-7'-(6-(4-morpholinyl)-3-pyridinyl)spiro[1,3-oxazole-4,9'-xanthen]-2-amine | 501 | AA24 | II22 | ++ | + |
| 913 | (4S)-2'-(2-chloro-3-pyridinyl)-7'-(2,2-dimethylpropoxy)spiro[1,3-oxazole-4,9'-xanthen]-2-amine | 450 | AA24 | II22 | ++++ | +++ |
| 914 | (4S)-2'-(2,2-dimethylpropoxy)-7'-(1-methyl-1H-indol-5-yl)spiro[1,3-oxazole-4,9'-xanthen]-2-amine | 468 | AA24 | II22 | +++ | + |
| 915 | (4S)-2'-(2,2-dimethylpropoxy)-7'-(3-(methylsulfonyl)phenyl)spiro[1,3-oxazole-4,9'-xanthen]-2-amine | 493 | AA24 | II22 | ++++ | ++ |
| 916 | (4S)-2'-(2,2-dimethylpropoxy)-7'-(5-quinolinyl)spiro[1,3-oxazole-4,9'-xanthen]-2-amine | 466 | AA24 | II22 | +++ | ++ |
| 917 | (2E)-3-((4R)-2-amino-7'-(5-pyrimidinyl)spiro[1,3-oxazole-4,9'-xanthen]-2'-yl)-N,N-dimethyl-2-propenamide | 428 | A60 | II1 | ++++ | +++ |
| 918 | methyl (2E)-3-((4S)-2-amino-7'-(3-pyridinyl)spiro[1,3-oxazole-4,9'-xanthen]-2'-yl)-2-propenoate | 414 | AA60 | II1 | +++ | +++ |
| 919 | (2E)-3-((4R)-2-amino-7'-bromospiro[1,3-oxazole-4,9'-xanthen]-2'-yl)-2-propenoic acid | 402.9 | AA63 | II39 | ++ | + |

TABLE IV-continued

| Ex. No. | Compound Name | Observed Mass | Method | Intermediate used | BACE1 FRET assay (uM) | HEK cell assay (uM) |
|---|---|---|---|---|---|---|
| 920 | (4S)-3'-fluoro-7'-(6-fluoro-3-pyridinyl)-2'-propoxyspiro[1,3-oxazole-4,9'-xanthen]-2-amine | 424.2 | AA13 | II9 | ++++ | +++ |
| 921 | (4R)-3'-fluoro-7'-(6-fluoro-3-pyridinyl)-2'-propoxyspiro[1,3-oxazole-4,9'-xanthen]-2-amine | 424.2 | AA13 | II9 | +++ | ++ |
| 922 | (5S)-3-(3,3-dimethylbutyl)-7-(3-pyridinyl)spiro[chromeno[2,3-b]pyridine-5,4'-[1,3]oxazol]-2'-amine | 415.2 | AA6 | II3 | ++++ | ++++ |
| 923 | 1-(((4S)-2-amino-7'-(3-pyridinyl)spiro[1,3-oxazole-4,9'-xanthen]-2'-yl)oxy)-2-propanone | 402 | AA14 | II18 | ++++ | ++++ |
| 924 | (2S)-3-(((4S)-2-amino-7'-(3-pyridinyl)spiro[1,3-oxazole-4,9'-xanthen]-2'-yl)oxy)-1,1,1-trifluoro-2-propanol | 458 | AA14 | II18 | ++++ | +++ |
| 925 | (2R)-3-(((4S)-2-amino-7'-(3-pyridinyl)spiro[1,3-oxazole-4,9'-xanthen]-2'-yl)oxy)-1,1,1-trifluoro-2-propanol | 458 | AA14 | II18 | ++++ | +++ |
| 926 | 1-(((5S)-2'-amino-3-(3-pyridinyl)spiro[chromeno[2,3-b]pyridine-5,4'-[1,3]oxazol]-7-yl)oxy)-2-propanone | 403 | AA14 | II4 | +++ | +++ |
| 927 | (5R)-3-(3,3-dimethyl-1-butyn-1-yl)-7-(2-pyridinyloxy)spiro[chromeno[2,3-b]pyridine-5,4'-[1,3]oxazol]-2'-amine | 427.2 | AA4 | II4 | +++ | ++ |
| 929 | (4S)-2-amino-2'-(2-hydroxy-2-methylpropoxy)-7'-(3-pyridinyl)spiro[1,3-oxazole-4,9'-xanthene]-1'-carbonitrile | 443 | AA55 | II26 | ++++ | +++ |
| 930 | 2',7'-bis(3,3-dimethyl-1-butyn-1-yl)spiro[1,3-oxazole-4,9'-xanthen]-2-amine | 413 | AA42 | II1 | +++ | ++ |
| 931 | (10R)-1-(3,3-dimethylbutoxy)-8-(3-pyridinyl)spiro[chromeno[3,2-c]pyridine-10,4'-[1,3]oxazol]-2'-amine | 431 | MM1 | II28 | ++ | + |
| 932 | (10S)-1-(3,3-dimethylbutoxy)-8-(3-pyridinyl)spiro[chromeno[3,2-c]pyridine-10,4'-[1,3]oxazol]-2'-amine | 431 | MM1 | II28 | +++ | +++ |
| 933 | (4S)-2'-(3-pyridinyl)-7'-(tetrahydro-2H-pyran-4-ylmethoxy)spiro[1,3-oxazole-4,9'-xanthen]-2-amine | 445 | AA14 | II18 | ++++ | ++++ |
| 934 | (5S)-3,7-bis(3-methoxy-3-methyl-1-butyn-1-yl)spiro[chromeno[2,3-b]pyridine-5,4'-[1,3]oxazol]-2'-amine | 446 | AA42 | II3 | ++++ | ++++ |
| 935 | 4,4'-((5S)-2'-aminospiro[chromeno[2,3-b]pyridine-5,4'-[1,3]oxazole]-3,7-diyl)bis(2-methyl-3-butyn-2-ol) | 418.2 | AA42 | II3 | +++ | +++ |
| 936 | (5S)-3-bromo-7-(2-pyridinyloxy)spiro[chromeno[2,3-b]pyridine-5,4'-[1,3]oxazol]-2'-amine | 425 | AA4 | II4 | + | + |
| 937 | 1-(((4S)-2-amino-7'-(cyclopropylethynyl)spiro[1,3-oxazole-4,9'-xanthen]-2'-yl)oxy)-2-methyl-2-propanol | 405 | AA47 | II18 | ++++ | +++ |
| 938 | (4S)-3'-fluoro-2'-propoxy-7'-(3-pyridinyl)spiro[1,3-oxazole-4,9'-xanthen]-2-amine | 406 | AA13 | II9 | ++++ | ++++ |
| 939 | (4R)-3'fluoro-2'-propoxy-7'-(3-pyridinyl)spiro[1,3-oxazole-4,9'-xanthen]-2-amine | 406 | AA13 | II9 | +++ | +++ |
| 940 | (4S)-3'-fluoro-2'-propoxy-7'-(5-pyrimidinyl)spiro[1,3-oxazole-4,9'-xanthen]-2-amine | 407 | AA13 | II9 | ++++ | ++++ |
| 941 | (4R)-3'-fluoro-2'-propoxy-7'-(5-pyrimidinyl)spiro[1,3-oxazole-4,9'-xanthen]-2-amine | 407 | AA13 | II9 | +++ | ++ |
| 942 | 1-(((4R)-2-amino-7'-(3-pyridinyl)spiro[1,3-oxazole-4,9'-xanthen]-2'-yl)ethynyl)cyclobutanol | 424 | AA33 | II1 | ++++ | ++++ |
| 943 | (4S)-2-amino-2'-(2,2-dimethylpropoxy)-7'-(3-pyridinyl)spiro[1,3-oxazole-4,9'-xanthene]-1'-carbonitrile | 441 | AA55 | II26 | ++++ | +++ |
| 944 | 1-(((4S)-2-amino-1'-bromo-7'-(3-pyridinyl)spiro[1,3-oxazole-4,9'-xanthen]-2'-yl)oxy)-2-methyl-2-propanol | 496 | AA54 | II18 | ++++ | ++++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 945 | (4S)-2'-(3-pyridinyl)-7'-(1-pyrrolidinylcarbonyl)spiro[1,3-oxazole-4,9'-xanthen]-2-amine | 427 | AA44 | II1 | +++ | +++ |
| 946 | methyl(2E)-3-((4S)-2-amino-7'-(5-pyrimidinyl)spiro[1,3-oxazole-4,9'-xanthen]-2'-yl)-propenoate | 415 | AA60 | II1 | +++ | +++ |
| 947 | methyl(2E)-3-((4R)-2-amino-7'-(3-pyridinyl)spiro[1,3-oxazole-4,9'-xanthen]-2'-yl)-propenoate | 414 | AA60 | II1 | +++ | +++ |
| 948 | (2E)-3-((4R)-2-amino-7'-(5-pyrimidinyl)spiro[1,3-oxazole-4,9'-xanthen]-2'-yl)-2-propenoic acid | 401 | AA63 | II1 | +++ | + |
| 949 | (2E)-3-((4R)-2-amino-7'-(3-pyridinyl)spiro[1,3-oxazole-4,9'-xanthen]-2'-yl)-2-propenoic acid | 400 | AA63 | II39 | ++++ | + |
| 950 | methyl(2E)-3-((4S)-2-amino-7'-bromospiro[1,3-oxazole-4,9'-xanthen]-2'-yl)-2-propenoate | 416.9 | AA62 | II1 | ++ | + |
| 951 | (5S)-7-(2,2-dimethylpropoxy)-3-(6-fluoro-3-pyridinyl)spiro[chromeno[2,3-b]pyridine-5,4'-[1,3]oxazol]-2'-amine | 435.2 | AA13 | II4 | ++++ | ++++ |
| 952 | (5S)-7-(2,2-dimethylpropoxy)-3-(2-fluoro-3-pyridinyl)spiro[chromeno[2,3-b]pyridine-5,4'-[1,3]oxazol]-2'-amine | 435.2 | AA13 | II4 | ++++ | ++++ |
| 953 | (5R)-3-chloro-7-(3-pyridinyl)spiro[chromeno[2,3-c]pyridine-5,4'-[1,3]oxazol]-2'-amine | 365 | AA24 | II2 | +++ | ++ |
| 954 | (5R)-3,7-di-3-pyridinylspiro[chromeno[2,3-c]pyridine-5,4'-[1,3]oxazol]-2'-amine | 408 | AA2 | II2 | ++++ | +++ |
| 955 | (5R)-3-chloro-7-(3-pyridinyl)spiro[chromeno[2,3-c]pyridine-5,4'-[1,3]oxazol]-2'-amine | 365 | AA24 | II2 | ++ | + |
| 956 | 1-(((4R)-2-amino-7'-(5-pyrimidinyl)spiro[1,3-oxazole-4,9'-xanthen]-2'-yl)ethynyl)cyclobutanol | 425 | AA33 | II1 | ++++ | ++++ |
| 957 | 1-(((4R)-2-amino-7'-bromospiro[1,3-oxazole-4,9'-xanthen]-2'-yl)ethynyl)cyclobutanol | 426 | AA42 | II1 | ++ | + |
| 958 | (4S)-1'-bromo-2'-(2,2-dimethylpropoxy)-7'-(3-pyridinyl)spiro[1,3-oxazole-4,9'-xanthen]-2-amine | 404 | AA54 | II18 | ++++ | ++++ |
| 959 | (4S)-2-amino-7'-(2,2-dimethylpropoxy)spiro[1,3-oxazole-4,9'-xanthene]-2'-carbonitrile | 364 | AA53 | II22 | +++ | ++ |
| 960 | (4S)-2'-bromo-7'-(3-pyridinyl)spiro[1,3-oxazole-4,9'-xanthen]-2-amine | 408, 410 | AA24 | II1 | +++ | ++ |
| 961 | 3-((4R)-2-amino-7'-(3-pyridinyl)spiro[1,3-oxazole-4,9'-xanthen]-2'-yl)benzonitrile | 431 | AA2 | II1 | ++++ | ++++ |
| 962 | 2-((4R)-2-amino-7'-(3-pyridinyl)spiro[1,3-oxazole-4,9'-xanthen]-2'-yl)benzonitrile | 431 | AA2 | II1 | ++++ | +++ |
| 963 | (4R)-2'-((1E)-3,3-dimethyl-1-buten-1-yl)-7'-(5-pyrimidinyl)spiro[1,3-oxazole-4,9'-xanthen]-2-amine | 413.2 | AA2 | II1 | ++++ | ++++ |
| 964 | (4R)-2'-(5-pyrimidinyl)-7'-(1,2,3,6-tetrahydro-4-pyridinyl)spiro[1,3-oxazole-4,9'-xanthen]-2-amine | 412 | AA2 | II1 | ++++ | ++++ |
| 299 | (5S)-3-(3,3-dimethyl-1-butyn-1-yl)-7-(5-pyrimidinyl)spiro[chromeno[2,3-b]pyridine-5,4'-[1,3]oxazol]-2'-amine | 412.2 | AA5 | II3 | ++++ | ++++ |
| 965 | 2-(((4S)-2-amino-7'-(5-pyrimidinyl)spiro[1,3-oxazole-4,9'-xanthen]-2'-yl)oxy)benzonitrile | 448.2 | AA4 | II18 | +++ | + |
| 966 | (5S)-7-((3-methyl-3-oxetanyl)methoxy)-3-phenylspiro[chromeno[2,3-b]pyridine-5,4'-[1,3]oxazol]-2'-amine | 430.2 | AA13 | II4 | ++++ | ++++ |
| 967 | (5S)-3-(cyclopropylethynyl)-7-((3-methyl-3-oxetanyl)methoxy)spiro[chromeno[2,3-b]pyridine-5,4'-[1,3]oxazol]-2'-amine | 418.2 | AA17 | II4 | ++++ | +++ |
| 968 | tert-butyl 4-((4R)-2-amino-7'-(5-pyrimidinyl)spiro[1,3-oxazole-4,9'- | 512.2 | AA2 | II1 | ++++ | +++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| | xanthen]-2'-yl)-3,6-dihydro-1(2H)-pyridinecarboxylate | | | | | |
| 969 | (4S)-2'-(6-fluoro-3-pyridinyl)-7'-(3-pyridinyl)spiro[1,3-oxazole-4,9'-xanthen]-2-amine | 425 | AA1 | II1 | ++++ | ++++ |
| 970 | (4S)-2'-(6-bromo-3-pyridazinyl)-7'-(2,2-dimethylpropoxy)spiro[1,3-oxazole-4,9'-xanthen]-2-amine | 496.9 | AA36 | II22 | +++ | + |
| 971 | (4S)-2'-(2,2-dimethylpropoxy)-7'-(1,3-thiazol-5-yl)spiro[1,3-oxazole-4,9'-xanthen]-2-amine | 422 | AA36 | II22 | ++++ | ++ |
| 972 | 4-((4S)-2-amino-7'-(2,2-dimethylpropoxy)spiro[1,3-oxazole-4,9'-xanthen]-2'-yl)benzonitrile | 440 | AA36 | II22 | +++ | + |
| 973 | 1-(3-((4S)-2-amino-7'-(2,2-dimethylpropoxy)spiro[1,3-oxazole-4,9'-xanthen]-2'-yl)phenyl)ethanone | 457 | AA36 | II22 | +++ | ++ |
| 974 | 1-(2-((4S)-2-amino-7'-(2,2-dimethylpropoxy)spiro[1,3-oxazole-4,9'-xanthen]-2'-yl)phenyl)ethanone | 457 | AA36 | II22 | +++ | ++ |
| 975 | (4S)-2'-(2,2-dimethylpropoxy)-7'-imidazo[1,2-a]pyridin-3-ylspiro[1,3-oxazole-4,9'-xanthen]-2-amine | 455.1 | AA36 | II22 | +++ | +++ |
| 976 | (4S)-2'-(3,5-dimethyl-4-isoxazolyl)-7'-(2,2-dimethylpropoxy)spiro[1,3-oxazole-4,9'-xanthen]-2-amine | 434 | AA36 | II22 | +++ | + |
| 977 | (4S)-2'-(2,2-dimethylpropoxy)-7'-(2-methoxy-5-pyrimidinyl)spiro[1,3-oxazole-4,9'-xanthen]-2-amine | 447 | AA36 | II22 | +++ | ++ |
| 978 | (4S)-2'-(2,2-dimethylpropoxy)-7'-(1H-imidazol-4-yl)spiro[1,3-oxazole-4,9'-xanthen]-2-amine | 405 | AA36 | II22 | +++ | ++ |
| 979 | (4S)-2'-(2,2-dimethylpropoxy)-7'-(1H-imidazol-2-yl)spiro[1,3-oxazole-4,9'-xanthen]-2-amine | 405 | AA36 | II22 | +++ | ++ |
| 980 | 5-((4S)-2-amino-7'-(2,2-dimethylpropoxy)spiro[1,3-oxazole-4,9'-xanthen]-2'-yl)-2(1H)-pyridinone | 432 | AA36 | II22 | +++ | ++ |
| 981 | (((4S)-2-amino-7'-(3-pyridinyl)spiro[1,3-oxazole-4,9'-xanthen]-2'-yl)oxy)acetonitrile | 385 | AA14 | II18 | +++ | ++ |
| 982 | (4S)-2'-(cyclopropylethynyl)-7'-(2-methoxy-2-methylpropoxy)spiro[1,3-oxazole-4,9'-xanthen]-2-amine | 419 | AA43 | II18 | ++++ | +++ |
| 983 | (5S)-7-(2-methoxy-2-methylpropoxy)-3-(3-pyridinyl)spiro[chromeno[2,3-b]pyridine-5,4'-[1,3]oxazol]-2'-amine | 433.2 | AA13 | II4 | ++++ | ++++ |
| 984 | (10S)-1-(3,3-dimethylbutoxy)-8-(5-pyrimidinyl)spiro[chromeno[3,2-c]pyridine-10,4'-[1,3]oxazol]-2'-amine | 432 | MM1 | II31 | +++ | +++ |
| 985 | (10R)-1-(3,3-dimethylbutoxy)-8-(5-pyrimidinyl)spiro[chromeno[3,2-c]pyridine-10,4'-[1,3]oxazol]-2'-amine | 432 | MM1 | II31 | +++ | + |
| 986 | 2-(((4S)-2-amino-7'-(3-pyridinyl)spiro[1,3-oxazole-4,9'-xanthen]-2'-yl)oxy)benzonitrile | 447.2 | AA4 | II18 | +++ | ++ |
| 987 | (4S)-2'-fluoro-7'-(5-pyrimidinyl)-3'-(2,2,2-trifluoroethoxy)spiro[1,3-oxazole-4,9'-xanthen]-2-amine | 447 | AA3 | II24 | + | + |
| 988 | (10S)-2-chloro-8-(3-pyridinyl)spiro[chromeno[3,2-b]pyridine-10,4'-[1,3]oxazol]-2'-amine | 365 | AA24 | II8 | ++ | ++ |
| 989 | (10S)-2,8-di-3-pyridinylspiro[chromeno[3,2-b]pyridine-10,4'-[1,3]oxazol]-2'-amine | 408 | AA2 | II8 | +++ | +++ |
| 990 | (4R)-2-amino-7'-(2,2-dimethylpropoxy)spiro[1,3-oxazole-4,9'-xanthene]-2'-carbonitrile | 364 | AA53 | II22 | +++ | ++ |
| 991 | (4R)-2'-(6-fluoro-3-pyridinyl)-7'-(5-pyrimidinyl)spiro[1,3-oxazole-4,9'-xanthen]-2-amine | 426.2 | AA1 | II1 | ++++ | ++++ |
| 992 | (4R)-2'-(2,2-dimethylpropoxy)-7'-(1-pyrrolidinylcarbonyl)spiro[1,3-oxazole-4,9'-xanthen]-2-amine | 436 | AA30 | II22 | +++ | ++ |

TABLE IV-continued

| Ex. No. | Compound Name | Observed Mass | Method | Intermediate used | BACE1 FRET assay (uM) | HEK cell assay (uM) |
|---|---|---|---|---|---|---|
| 993 | methyl (2E)-3-((4R)-2-amino-7'-(5-pyrimidinyl)spiro[1,3-oxazole-4,9'-xanthen]-2'-yl)-2-propenoate | 415.1 | AA60 | II1 | ++++ | +++ |
| 994 | tert-butyl (2E)-3-((4R)-2-amino-7'-(5-pyrimidinyl)spiro[1,3-oxazole-4,9'-xanthen]-2'-yl)-2-propenoate | 457.1 | AA60 | II1 | +++ | ++ |
| 995 | tert-butyl (2E)-3-((4R)-2-amino-7'-(3-pyridinyl)spiro[1,3-oxazole-4,9'-xanthen]-2'-yl)-2-propenoate | 456.1 | AA60 | II1 | +++ | ++ |
| 996 | tert-butyl (2E)-3-((4R)-2-amino-7'-bromospiro[1,3-oxazole-4,9'-xanthen]-2'-yl)-2-propenoate | 458 | AA62 | II1 | + | + |
| 997 | 2-(((4R)-2-amino-7'-bromospiro[1,3-oxazole-4,9'-xanthen]-2'-yl)oxy)benzonitrile | 448 | AA4 | II18 | + | + |
| 998 | (4R)-2'-(3-methylphenyl)-7'-(5-pyrimidinyl)spiro[1,3-oxazole-4,9'-xanthen]-2-amine | 421 | AA2 | II1 | ++++ | ++++ |
| 999 | (4S)-3'-(2,2-dimethylpropoxy)-2'-fluoro-7'-(5-pyrimidinyl)spiro[1,3-oxazole-4,9'-xanthen]-2-amine | 435 | AA3 | II24 | ++ | + |
| 1000 | (5S)-3,7-bis(3,3-dimethyl-1-butyn-1-yl)spiro[chromeno[2,3-b]pyridine-5,4'-[1,3]oxazol]-2'-amine | 414 | AA42 | II3 | ++++ | +++ |
| 1001 | (4R)-2'-(3-methoxy-3-methylbutyl)-7'-(3-pyridinyl)spiro[1,3-oxazole-4,9'-xanthen]-2-amine | 430.2 | AA6 | II1 | ++++ | ++++ |

The following compound in Table 5 contain additional representative examples of Formulas I-IV provided by the present invention.

TABLE 5

| Ex. No. | $R^2$ | $A^1$ | $R^7$ | Y | Z |
|---|---|---|---|---|---|
| 1002 | $CH_3$—O—$CH_2$— | CH | pyrimidine | $CH_2$ | $CH_2$ |
| 1003 | $CH_3$—S—$CH_2$— | CH | pyrimidine | S | absent |
| 1004 | $CH_3$—NH—$CH_2$— | CH | pyrimidine | O | absent |
| 1005 | $CH_3$—N($CH_3$)—$CH_2$— | CH | pyridine | NH | $CH_2$ |
| 1006 | $CH_3CH_2$—$CH_2$—O— | CH | pyridine | S | $CH_2$ |
| 1007 | $CH_3$—O—$CH_2CH_2$— | N | 3-NH($CH_3$)-phenyl | O | $CH_2$ |
| 1008 | $CH_3$—O—CH($CF_3$)— | N | pyridine | $SO_2$ | absent |
| 1009 | $CH_2(CF_3)$—O—$CH_2$— | N | pyrazine | N-Me | $CH_2$ |
| 1010 | $(CH_3)_2CHCH_2O$— | N | pyridazine | S | $CH_2$ |
| 1011 | $CH_3CH_2$—S—$CH_2$— | N | pyrimidine | O | $CH_2$ |
| 1012 | $CH_3CH_2$—NH—$CH_2$— | CH | pyridine | $SO_2$ | absent |
| 1013 | $(CH_3)_2NCH_2$—O— | CH | pyrimidine | N-Et | $CH_2$ |
| 1014 | $CH_3$—$CH_2$—O— | CH | pyrazine | NH | $CH_2$ |
| 1015 | $CH_3$—$CH_2$—S— | CH | pyridazine | S | absent |
| 1016 | $CH_3$—$CH_2$—NH | CH | triazine | O | absent |
| 1017 | $CH_3$—N($CH_3$)—$CH_2$—O | N | thiophene | $SO_2$ | absent |
| 1018 | $CH_3CH_2$—$CH_2$—O— | N | benzothiophene | N-Me | absent |
| 1019 | $CH_3$—O—$CH_2CH_2$— | N | benzimidazole | S | absent |
| 1020 | $CH_3$—O—CH($CF_3$)— | N | benzopyrazole | O | absent |
| 1021 | $CH_2(CF_3)$—O—$CH_2$— | N | pyrazole | NH | $CH_2$ |

Additional examples representative of the invention include the following:

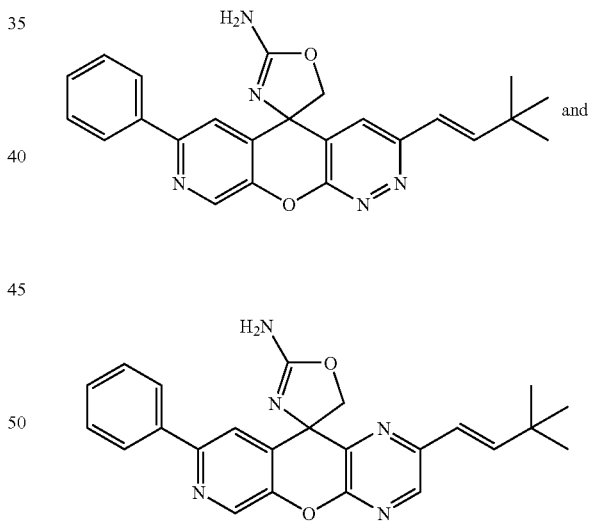

which may be prepared using procedures similar to those described in *Journal of Heterocyclic Chemistry* (1990), 27, (5), 1377-81; *Journal of Heterocyclic Chemistry*, 27(5), 1377-81 (1990); *Archiv der Pharmazie* (Weinheim, Germany), 320(12), 1222-6; 1987; and/or *Synthesis* (11), 881-4 (1988).

The present invention also provides methods for making compounds of Formulas I-IV. In another embodiment of the invention, there is provided a method of making a compound of Formula I, the method comprising the step of reacting a compound 20

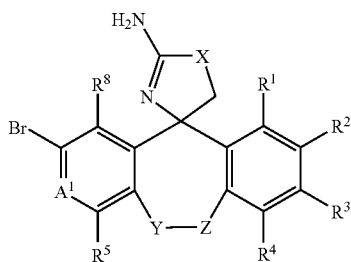

20 wherein $A^1$, $R^1$, $R^2$, $R^3$, $R^4$, $R^5$, $R^8$, X, Y and Z of Formula I are as defined herein, with a compound having the structure $R^7$—$B(OH)_2$ wherein $R^7$ is as defined herein, to make a compound of Formulas I, II, III or IV.

The present invention also provides methods for making compounds of Formulas I-IV. In another embodiment of the invention, there is provided a method of making a compound of Formula I, the method comprising the step of reacting a compound 20

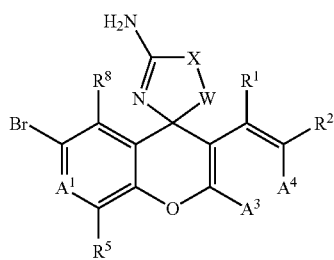

20 wherein $A^1$, $A^3$, $A^4$, $R^1$, $R^2$, $R^3$, $R^4$, $R^5$, $R^8$, W and X of Formula I are as defined herein, with a compound having the structure $R^7$—$B(OH)_2$ wherein $R^7$ is as defined herein, to make a compound of Formulas I, II, III or IV.

The present invention also provides methods for making compounds of Formulas I-IV. In another embodiment of the invention, there is provided a method of making a compound of Formula I, the method comprising the step of reacting a compound 20

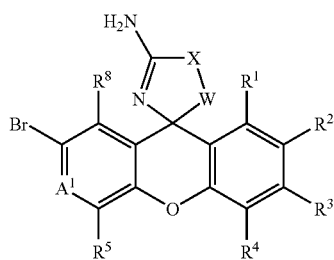

20 wherein $A^1$, $R^1$, $R^2$, $R^3$, $R^4$, $R^5$, $R^8$, W and X of Formula I are as defined herein, with a compound having the structure $R^7$—$B(OH)_2$ wherein $R^7$ is as defined herein, to make a compound of Formulas I, II, III or IV.

In another embodiment of the invention, there is provided a method of making a compound of Formula II, the method comprising the step of reacting a compound 20-A

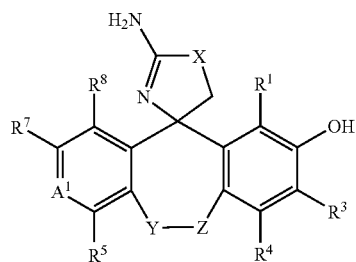

20-A wherein $A^1$, $R^1$, $R^3$, $R^4$, $R^5$, $R^7$, $R^8$, X, Y and Z of Formula I, II, III or IV are as defined herein, with an $R^{10}$-halide wherein the halide is either an I or Br, to prepare the compound of Formula I, II, III or IV.

In yet another embodiment of the invention, there is provided a method of making a compound of Formula II, the method comprising the step of reacting a compound 20-A

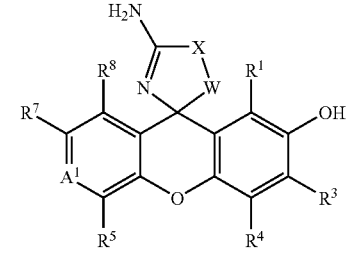

20-A wherein $A^1$, $R^1$, $R^3$, $R^4$, $R^5$, $R^7$, $R^8$, W and X of Formula I, II, III or IV are as defined herein, with an $R^{10}$-halide wherein the halide is either an I or Br, to prepare the compound of Formula I, II, III or IV.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent (s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-IV, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$ (deuterium), $^3H$ (tritium), $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Deuterated ($^2H$), Tritiated ($^3H$) and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

Biological Evaluation

The compounds of the invention may be modified by appending appropriate functionalities to enhance selective biological properties. Surprisingly, the compounds of the present invention exhibit improved pharmacokinetics and pharmacodynamics, which relate, directly and indirectly, to the ability of the compound to be effective for its intended use. For example, the compounds have been found to possess favorable clearance and efflux properties, which readily lend themselves to projecting in-vivo PK and PD properties, which in turn assist in projection of therapeutic target coverage for the compounds and projected efficacious dosages via in-vivo absorption, distribution, metabolism and excretion properties. Increased biological penetration into a given biological compartment (e.g., blood, lymphatic system, central nervous system), increase oral availability, increase solubility to allow administration by injection and alter clearance, metabolism and/or rate of excretion are important factors for discovering which compound may be a useful drug and which may not.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in the Example Tables I, II, III & IV)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Of the compounds tested, the in-vitro BACE FRET enzyme data for each of Examples 5-7, 9-226 and 301-1001 is provided in Tables I, II, III and IV. Data key for the in-vitro BACE FRET assay is as follows:

"+" means the compound example has an $IC_{50}$ value of=to or >5 uM;

"++" means the compound example has an $IC_{50}$ value in the range from 1.0 uM-5.0 uM (<5.0 uM to = or >1.0 uM);

"+++" means the compound example has an $IC_{50}$ value in the range from 100 nM-1.0 uM (<1.0 uM to = or >0.1 uM); and "++++" means the compound example has an $IC_{50}$ value in the range less than 100 nM (<0.1 uM).

In Vitro BACE Cell-based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Of the compounds tested, the cell based assay data for each of Examples 5-7 9-226 and 301-1001 is provided in Tables I, II, III and IV. Data key for the BACE1 cell-based assay is as follows:

"+" means the compound example has an $IC_{50}$ value of=to or >5 uM;

"++" means the compound example has an $IC_{50}$ value in the range from 1.0 uM-5.0 uM (<5.0 uM to = or >1.0 uM);

"+++" means the compound example has an $IC_{50}$ value in the range from 100 nM-1.0 uM (<1.0 uM to = or >0.1 uM); and "++++" means the compound example has an $IC_{50}$ value in the range less than 100 nM (<0.1 uM).

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76,173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2

IV: 5% EtOH, 45% Propylene glycol in 5% Dextrose

The compounds of the invention have generally been shown to reduce the formation and/or deposition of amyloid beta peptide in the cerebrospinal fluid as well as in the brain of a mouse or rat at both 10 mpk (mpk=mg compound per kg animal) and 30 mpk dosing concentrations after 4 hrs. For instance, Example Nos. 490, 286, 495, 291, 287, 293, 513, 515, 517, 290, 288, 531, 540, 292, 289, 545, 294, 563, 296, 586, 295, 297, 662, 663, 673, 689, 744, 763, 289, 808, 817, 956, 299, 51, 56, 58, 61, 65, 47, 92, 104, 143, 185b and 202 exhibited a 28% and 9%; 73% and 57%; 72% and 57% (both @30 mpk); 62% and 32%; 48% and 32%; 73% and 63%; 18% and 13%; 56% and 39%; 56% and 36%; 63% and 33%; 69% and 48%; 45% and 25%; 40% and 7%; 57% and 29%; 49% and 23%; 73% and 58% (both @30 mpk); 86% and 73% (both @30 mpk); 54% and 41%; 61% and 40%; 32% and 11%; 78% and 66% (both @30 mpk); 69% and 54% (both @30 mpk); 53% and 34% (both @30 mpk); 57% and 44% (both @30 mpk); 81% and 63% (Both @30 mpk); 69% and 41% (both @30 mpk); 37% and 26%; 69% and 59% (both @30 mpk); 69% and 52% (both @30 mpk); 55% and 43% (both @30 mpk); 44% and 25% (both @30 mpk); 25% and 8% (both @30 mpk); 84% and 81% (both @30 mpk); 47% and 25%; 76% and 35% (both @30 mpk); 45% and 29%; 50% and 18%; 48% and 21%; 39% and 2%; 62% and 49% (both @30 mpk); 58% and 43%; 69% and 37% (both @30 mpk); 72% and 58% (both @30 mpk) and 67% and 55% (both @30 mpk) percent reduction in CSF and brain A-beta levels at 10 mpk (except where 30 mpk indicated), respectively.

Indications

Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I-IV. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I, II, II-A, III, III-A, III-B, IV, IV-A, IV-B and IV-C. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-IV with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-IV with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I and II may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I:

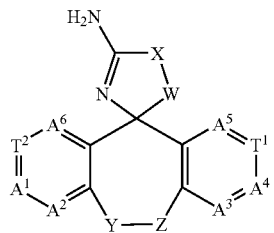

or a stereoisomer, tautomer or pharmaceutically acceptable salt thereof, wherein
$A^1$ is $CR^6$;
$A^2$ is $CR^5$;
$A^3$ is $CR^4$ or N;
$A^4$ is $CR^3$ or N;
$A^5$ is $CR^1$ or N;
$A^6$ is $CR^8$;
$T^1$ is $CR^2$;
$T^2$ is $CR^7$, provided that (1) no more than two of $A^3$, $A^4$ and $A^5$, is N, such that the fused ring comprising $A^3$, $A^4$, $A^5$ and $T^1$ form a fused benzene, pyridine or pyridazine ring;
each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$ $C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;
each of $R^2$ and $R^7$, independently, is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 9- or 10-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;
each of $R^3$ and $R^6$, independently, is H, halo, haloalkyl, haloalkoxyl, $C_{1-6}$-alkyl, CN, OH, $OC_{1-6}$-alkyl, $S(O)_o$ $C_{1-6}$-alkyl, $NHC_{1-6}$-alkyl or $C(O)C_{1-6}$-alkyl;

each R⁹, independently, is —C(O)R¹⁰, —S(O)₂R¹⁰, —C(O)NHR¹⁰, —NHC(O)R¹⁰, —NHC(O)NHR¹⁰, —S(O)₂NHR¹⁰ or —NHS(O)₂R¹⁰;

each R¹⁰, independently, is H, halo, haloalkyl, CN, OH, NO₂, NH₂, acetyl, oxo, C₁₋₁₀-alkyl, C₂₋₁₀-alkenyl, C₂₋₁₀-alkenyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C₁₋₁₀-alkyl, C₂₋₁₀-alkenyl, C₂₋₁₀-alkynyl, C₃₋₁₀-cycloalkyl, C₄₋₁₀-cycloalkenyl, C₁₋₁₀-alkylamino-, C₁₋₁₀-dialkylamino-, C₁₋₁₀-alkoxyl, C₁₋₁₀-thioalkoxyl and ring of said ring system is optionally substituted independently with 1-5 substituents of halo, haloalkyl, haloalkoxyl, CN, NO₂, NH₂, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, C₁₋₁₀-alkylamino-, C₁₋₁₀-dialkylamino-, C₁₋₁₀-thioalkoxyl, benzyl or phenyl;

W is CR¹R¹;
X is O;
Y is O; and
Z is absent.

2. The compound of claim 1, or a pharmaceutically acceptable salt thereof, wherein
one of R² and R⁷, independently, is a fully saturated or partially or fully unsaturated 4-, 5- or 6-membered monocyclic or 9- or 10-membered bicyclic ring formed of carbon atoms, said ring optionally including 1-4 heteroatoms selected from O, N, or S and optionally substituted, independently with 1-5 substituents of R⁹ or R¹⁰;
the other of R² and R⁷, independently, is H, halo, haloalkyl, haloalkoxyl, C₁₋₆-alkyl, C₂₋₆alkenyl, C₂₋₆-alkynyl, C₃₋₈-cycloalkyl, C₄₋₈-cycloalkenyl, CN, OR¹⁰, SR¹⁰, NR¹⁰R¹⁰, C(O)R¹⁰, S(O)₂R¹⁰, NR¹⁰C(O)R¹⁰, C(O)NR¹⁰R¹⁰, NR¹⁰S(O)₂R¹⁰, S(O)₂NR¹⁰, NR¹⁰C(O)NR¹⁰R¹⁰, wherein the C₁₋₆-alkyl, C₂₋₆-alkenyl, C₂₋₆-alkynyl, C₃₋₈-cycloalkyl, C₄₋₈-cycloalkenyl are optionally substituted, independently, with 1-5 substituents of R⁹ or R¹⁰; and
each of R¹, R⁴, R⁵ and R⁸, independently, is H, F, Cl, CF₃, OCF₃, methyl, ethyl, CN, OH, OCH₃, SCH₃, NHCH₃ or C(O)CH₃;
each of R³ and R⁶, independently, is H, halo, haloalkyl, haloalkoxyl, C₁₋₆-alkyl, CN, OH, OC₁₋₆-alkyl, SC₁₋₆-alkyl, NHC₁₋₆-alkyl or C(O)C₁₋₆-alkyl;
Y is O; and
Z is absent.

3. The compound of claim 2 wherein R⁷ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted, independently, with 1-5 substituents of R⁹ or R¹⁰.

4. The compound of claim 1, or a pharmaceutically acceptable salt thereof, wherein
R² is halo, haloalkyl, haloalkoxyl, C₁₋₆-alkyl, C₂₋₆alkenyl, C₂₋₆-alkynyl, C₃₋₈-cycloalkyl, OR¹⁰, SR¹⁰, NR¹⁰R¹⁰ or a ring selected from phenyl, pyridine, pyrimidine, dihydropyran, morpholine, oxazole, isoxazole, azetidine, pyran, pyrazole and imidazole, wherein the C₁₋₆-alkyl, C₂₋₆-alkenyl, C₂₋₆-alkynyl, C₃₋₈-cycloalkyl and ring are optionally substituted with 1-5 substituents of R⁹ or R¹⁰; and each of R¹, R⁴, R⁵ and R⁸, independently, is H, F, Cl, CF₃, methyl, CN, OH, OCH₃, SCH₃ or NHCH₃; and
each of R³ and R⁶, independently, is H, halo, haloalkyl, haloalkoxyl, C₁₋₆-alkyl, CN, OH, OC₁₋₆-alkyl, SC₁₋₆-alkyl, NHC₁₋₆-alkyl or C(O)C₁₋₆-alkyl;
R⁷ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, or R⁷ is —OC₁₋₁₀alkyl, said ring and —OC₁₋₁₀alkyl optionally substituted, independently, with 1-5 substituents of R⁹ or R¹⁰;
Y is O; and
Z is absent.

5. The compound of claim 1, or a pharmaceutically acceptable salt thereof, wherein
R² is halo, haloalkyl, haloalkoxyl, C₁₋₆-alkyl, C₂₋₆alkenyl, C₂₋₆-alkynyl, OR¹⁰ or SR¹⁰, wherein the C₁₋₆-alkyl, C₂₋₆-alkenyl, C₂₋₆-alkynyl and C₃₋₈-cycloalkyl are optionally substituted, independently, with 1-5 substituents of R⁹ or R¹⁰;
each of R¹, R⁴, R⁵ and R⁸, independently, is H, F, methyl, CN or OH;
each of R³ and R⁶, independently, is H, F, Cl, CF₃, methyl, CN, OH, OCH₃, SCH₃ or NHCH₃;
R⁷ is a ring selected from phenyl, pyridyl, pyrimidyl, pyridazinyl, pyrazinyl, triazinyl or thiophenyl, said ring optionally substituted, independently, with 1-5 substituents of R⁹ or R¹⁰;
W is CH₂, —CHF or —CCH₃;
X is O;
Y is O; and
Z is absent.

6. The compound of claim 1, or a stereoisomer, tautomer or pharmaceutically acceptable salt thereof, having a general formula IV-A

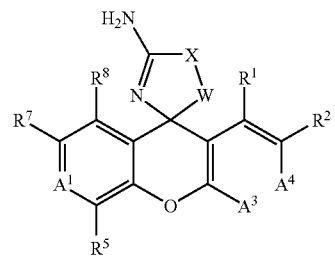

IV-A wherein
A¹ is CR⁶;
A³ is CR⁴ or N;
A⁴ is CR³ or N; provided no more than one of A³ and A⁴ is N;
each of R¹, R⁴, R⁵ and R⁸, independently, is H, F, Cl, Br, CF₃, OCF₃, CH₃, C₂H₅, CN, OH, OCH₃;
each of R² and R⁷, independently, is H, halo, haloalkyl, haloalkoxyl, C₁₋₆-alkyl, C₂₋₆alkenyl, C₂₋₆-alkynyl, C₃₋₈- cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 5- or 6-membered monocyclic or 9- or 10-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHC_{1-3}$alkyl; and

X is O.

7. The compound of claim 6, or a stereoisomer or pharmaceutically acceptable salt thereof, wherein $A^1$ is $CR^6$;
$A^3$ is $CR^4$;
$A^4$ is $CR^3$;

each of $R^1$, $R^4$, $R^5$ and $R^8$, independently, is H, F, Cl, Br, $CF_3$, $OCF_3$, $CH_3$, $C_2H_5$, CN, OH, $OCH_3$;

$R^2$ is H, halo, haloalkyl, haloalkoxyl, $C_{1-6}$-alkyl, $C_{2-6}$-alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a 5- or 6-membered monocyclic or 9- to 10-membered bicyclic heterocyclic, aryl or heteroaryl ring, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;

each of $R^3$ and $R^6$, independently, is H, halo, haloalkyl, haloalkoxyl, $C_{1-6}$-alkyl, CN, OH, $OC_{1-6}$-alkyl, $SC_{1-6}$-alkyl, $NHC_{1-6}$-alkyl or $C(O)C_{1-6}$-alkyl;

$R^7$ is phenyl, pyridyl or pyrimidyl, each of which is optionally substituted with 1-5 substituents of F, Cl, Br, I, $CF_3$, $C_2F_5$, haloalkoxyl, $C_{1-6}$-alkyl, CN, OH, $OC_{1-6}$-alkyl, $SC_{1-6}$-alkyl, $NC_{1-6}$-alkyl, $S(O)_oC_{1-6}$-alkyl wherein o is 0, 1 or 2, $NHC_{1-6}$-alkyl or $C(O)C_{1-6}$-alkyl, each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;

each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a 5- or 6-membered monocyclic or 7- to 11-membered bicyclic heterocyclic, aryl or heteroaryl ring, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

W is $CH_2$, —CHF or —$CHCH_3$; and

X is O.

8. The compound of claim 1, or a stereoisomer or pharmaceutically acceptable salt thereof, selected from 2'-(2,2-dimethylpropoxy)-7'-(5-pyrimidinyl)spiro[1,3-oxazole-4,9'-xanthen]-2-amine;

(4S)-2'-propoxy-7'-(5-pyrimidinyl)spiro[1,3-oxazole-4,9'-xanthen]-2-amine;

2'-(2-methylpropoxy)-7'-(5-pyrimidinyl)spiro[1,3-oxazole-4,9'-xanthen]-2-amine;

2'-propoxy-7'-(5-pyrimidinyl)spiro[1,3-oxazole-4,9'-xanthen]-2-amine;

(4S)-2'-methoxy-7'-(5-pyrimidinyl)spiro[1,3-oxazole-4,9'-xanthen]-2-amine;

(4S)-2'-propoxy-7'-(5-pyrimidinyl)spiro[1,3-oxazole-4,9'-xanthen]-2-amine;

(4S)-2'-(5-chloro-2-fluorophenyl)-7'-methoxyspiro[1,3-oxazole-4,9'-xanthen]-2-amine trifluoroacetic acid;

2'-chloro-7'-(5-pyrimidinyl)spiro[1,3-oxazole-4,9'-xanthen]-2-amine;

2'-methoxy-7'-(5-pyrimidinyl)spiro[1,3-oxazole-4,9'-xanthen]-2-amine;

2'-(2-fluoro-5-methoxyphenyl)-7'-methoxyspiro[1,3-oxazole-4,9'-xanthen]-2-amine;

(4S)-2'-(2,2-dimethylpropoxy)-7'-(5-pyrimidinyl)spiro[1,3-oxazole-4,9'-xanthen]-2-amine;

(4S)-2'-(2-methylpropoxy)-7'-(5-pyrimidinyl)spiro[1,3-oxazole-4,9'-xanthen]-2-amine;

(4S)-2'-(5-pyrimidinyl)-7'-(2,2,2-trifluoroethoxy)spiro[1,3-oxazole-4,9'-xanthen]-2-amine;

(4S)-2'-(3,3-dimethylbutyl)-7'-(5-pyrimidinyl)spiro[1,3-oxazole-4,9'-xanthen]-2-amine;

(4S)-2'-(cyclopropylmethoxy)-7'-(5-pyrimidinyl)spiro[1,3-oxazole-4,9'-xanthen]-2-amine;

(4S)-2'-(3,3-dimethyl-1-butyn-1-yl)-7'-(5-pyrimidinyl)spiro[1,3-oxazole-4,9'-xanthen]-2-amine;

(4S)-2'-(((1S)-2,2-difluorocyclopropyl)methoxy)-7'-(5-pyrimidinyl)spiro[1,3-oxazole-4,9'-xanthen]-2-amine;

(4S)-2'-(((1R)-2,2-difluorocyclopropyl)methoxy)-7'-(5-pyrimidinyl)spiro[1,3-oxazole-4,9'-xanthen]-2-amine;

(4S)-7-(2,2-dimethylpropoxy)-3-(3-pyridinyl)spiro[chromeno[2,3-b]pyridine-5,4'-[1,3]oxazol]-2'-amine;

(4S)-2'-(2-fluoro-2-methylpropoxy)-7'-(5-pyrimidinyl)spiro[1,3-oxazole-4,9'-xanthen]-2-amine;

(4S)-2'-(2-methoxy-2-methylpropoxy)-7'-(5-pyrimidinyl)spiro[1,3-oxazole-4,9'-xanthen]-2-amine;

3-(((4S)-2-amino-7'-(3-pyridinyl)spiro[1,3-oxazole-4,9'-xanthen]-2'-yl)oxy)-2,2-dimethylpropanenitrile;

(4S)-2'-((3-methyl-3-oxetanyl)methoxy)-7'-(3-pyridinyl)spiro[1,3-oxazole-4,9'-xanthen]-2-amine;

(5S)-7-((3-methyl-3-oxetanyl)methoxy)-3-phenylspiro[chromeno[2,3-b]pyridine-5,4'-[1,3]oxazol]-2'-amine;

(5S)-3-(3,3-dimethyl-1-butyn-1-yl)-7-(3-pyridinyl)spiro[chromeno[2,3-b]pyridine-5,4'-[1,3]oxazol]-2'-amine;

3-(((5S)-2'-amino-3-(5-pyrimidinyl)spiro[chromeno[2,3-b]pyridine-5,4'-[1,3]oxazol]-7-yl)oxy)-2,2-dimethylpropanenitrile;

(4R)-2'-(3,6-dihydro-2H-pyran-4-yl)-7'-(5-pyrimidinyl)spiro[1,3-oxazole-4,9'-xanthen]-2-amine;

(4R)-2'-(3-methoxy-3-methyl-1-butyn-1-yl)-7'-(5-pyrimidinyl)spiro[1,3-oxazole-4,9'-xanthen]-2-amine;

(5S)-3-(3,3-dimethyl-1-butyn-1-yl)-7-(5-pyrimidinyl)spiro[chromeno[2,3-b]pyridine-5,4'-[1,3]oxazol]-2'-amine;

1-(((4R)-2-amino-7'-(5-pyrimidinyl)spiro[1,3-oxazole-4,9'-xanthen]-2'-yl)ethynyl)cyclobutanol;

N-(3-((4S)-2-amino-4-methyl-5,6-dihydro-4H-1,3-thiazin-4-yl)-4-fluorophenyl)-5-methyl-2-pyrazinecarboxamide;

N-(3-((4S)-2-amino-4-methyl-5,6-dihydro-4H-1,3-thiazin-4-yl)-4-fluorophenyl)-5-methoxy-2-pyrazinecarboxamide;

3-(((5S)-2'-amino-3-phenylspiro[chromeno[2,3-b]pyridine-5,4'-[1,3]oxazol]-7-yl)oxy)-2,2-dimethylpropanenitrile;

(5S)-7-(2,2-dimethylpropoxy)-3-(4-pyridinyl)spiro[chromeno[2,3-b]pyridine-5,4'-[1,3]oxazol]-2'-amine;

(5S)-3-(3,3-dimethyl-1-butyn-1-yl)-7-(2-fluoro-3-pyridinyl)spiro[chromeno[2,3-b]pyridine-5,4'-[1,3]oxazol]-2'-amine;

(4S)-2'-(2,2-dimethyl-4-morpholinyl)-7'-(5-pyrimidinyl)spiro[1,3-oxazole-4,9'-xanthen]-2-amine;

(4S)-2'-(2,2-dimethyl-4-morpholinyl)-7'-(3-pyridinyl)spiro[1,3-oxazole-4,9'-xanthen]-2-amine;

(4S)-2'-((2R,6S)-2,6-dimethyl-4-morpholinyl)-7'-(3-pyridinyl)spiro[1,3-oxazole-4,9'-xanthen]-2-amine;

(4R)-2'-(6,6-dimethyl-3,6-dihydro-2H-pyran-4-yl)-7'-(5-pyrimidinyl)spiro[1,3-oxazole-4,9'-xanthen]-2-amine;

(4S)-4'-fluoro-2'-(3-methoxy-3-methyl-1-butyn-1-yl)-7'-(5-pyrimidinyl)spiro[1,3-oxazole-4,9'-xanthen]-2-amine;

(5S)-3-(3,3-dimethyl-1-butyn-1-yl)-7-(3-pyridinyl)spiro[chromeno[2,3-b]pyridine-5,4'-[1,3]oxazol]-2'-amine;

(4S)-2'-(3,6-dihydro-2H-pyran-4-yl)-4'-fluoro-7'-(3-pyridinyl)spiro [1,3-oxazole-4,9'-xanthen]-2-amine;

(5S)-7-(5-chloro-2-fluorophenyl)-3-(3,6-dihydro-2H-pyran-4-yl)spiro[chromeno[2,3-b]pyridine-5,4'-[1,3]oxazol]-2'-amine;

(4S)-2'-(3,6-dihydro-2H-pyran-4-yl)-4'-fluoro-7'-(5-pyrimidinyl)spiro[1,3-oxazole-4,9'-xanthen]-2-amine;

(5S)-3-(3,6-dihydro-2H-pyran-4-yl)-7-phenylspiro[chromeno[2,3-c]pyridine-5,4'-[1,3]oxazol]-2'-amine;

(5S)-3-(3,6-dihydro-2H-pyran-4-yl)-7-(2-fluoro-3-pyridinyl)spiro[chromeno[2,3-c]pyridine-5,4'-[1,3]oxazol]-2'-amine;

(5S)-3-(3-methoxy-3-methyl-1-butyn-1-yl)-7-(2-pyrazinyl)spiro[chromeno[2,3-b]pyridine-5,4'-[1,3]oxazol]-2'-amine;

(4S)-2'-(2-fluoro-3-pyridinyl)-7'-(3-methyl-5-isoxazolyl)spiro[1,3-oxazole-4,9'-xanthen]-2-amine;

(5S)-3-(2,2-dimethylpropoxy)-7-(3-pyridinyl)spiro[chromeno[2,3-b]pyridine-5,4'-[1,3]oxazol]-2'-amine;

(4S)-4'-fluoro-2'-(2-fluoro-2-methylpropoxy)-7'-(5-pyrimidinyl)spiro[1,3-oxazole-4,9'-xanthen]-2-amine;

(4S)-2'-(3,3-difluoro-1-azetidinyl)-7'-(3-pyridinyl)spiro[1,3-oxazole-4,9'-xanthen]-2-amine;

(4S)-2'-(3,6-dihydro-2H-pyran-4-yl)-3'-fluoro-7'-(5-pyrimidinyl)spiro[1,3-oxazole-4,9'-xanthen]-2-amine;

(4S)-3'-fluoro-2'-(1-methyl-1H-pyrazol-4-yl)-7'-(3-pyridinyl)spiro[1,3-oxazole-4,9'-xanthen]-2-amine;

(5S)-3-((1E)-3,3-dimethyl-1-buten-1-yl)-7-(5-pyrimidinyl)spiro[chromeno[2,3-c]pyridine-5,4'-[1,3]oxazol]-2'-amine;

(4S)-2'-(2,2-dimethyl-4-morpholinyl)-7'-(2-fluoro-3-pyridinyl)spiro[1,3-oxazole-4,9'-xanthen]-2-amine;

(5S)-7-(2-fluoro-3-pyridinyl)-3-(3-pyridinyl)spiro[chromeno[2,3-c]pyridine-5,4'-[1,3]oxazol]-2'-amine;

(5S)-7-(2-fluoro-3-pyridinyl)-3-(4-pyridinyl)spiro[chromeno[2,3-c]pyridine-5,4'-[1,3]oxazol]-2'-amine;

(4S)-2'-(2-fluoro-3-pyridinyl)-7'-(4-morpholinyl)spiro[1,3-oxazole-4,9'-xanthen]-2-amine;

(5S)-7-(2-fluoro-3-pyridinyl)-3-(tetrahydro-2H-pyran-4-yl)spiro[chromeno[2,3-c]pyridine-5,4'-[1,3]oxazol]-2'-amine;

(5S)-3-(2,2-dimethyl-4-morpholinyl)-7-(3-pyridinyl)spiro[chromeno[2,3-c]pyridine-5,4'-[1,3]oxazol]-2'-amine;

(5S)-7-(2-fluoro-3-pyridinyl)-3-((3-methyl-3-oxetanyl)ethynyl)spiro[chromeno[2,3-b]pyridine-5,4'-[1,3]oxazol]-2'-amine;

3-(((4S)-2-amino-4'-fluoro-7'-(2-fluoro-3-pyridinyl)spiro[1,3-oxazole-4,9'-xanthen]-2'-yl)oxy)-2,2-dimethylpropanenitrile;

(5S)-3-(3,6-dihydro-2H-pyran-4-yl)-7-(2-fluoro-5-methyl-3-pyridinyl)spiro[chromeno[2,3-c]pyridine-5,4'-[1,3]oxazol]-2'-amine;

(4S)-4'-fluoro-7'-(2-fluoro-3-pyridinyl)-2'-((3-methyl-3-oxetanyl)methoxy)spiro[1,3-oxazole-4,9'-xanthen]-2-amine;

(5S)-7-(5-chloro-2-fluorophenyl)-3-((3-methyl-3-oxetanyl)ethynyl)spiro[chromeno[2,3-b]pyridine-5,4'-[1,3]oxazol]-2'-amine;

(5S)-7-(3-chlorophenyl)-3-(3,6-dihydro-2H-pyran-4-yl)spiro[chromeno[2,3-c]pyridine-5,4'-[1,3]oxazol]-2'-amine;

(4S)-4'-fluoro-2'-(1-methyl-1H-pyrazol-4-yl)-7'-(3-pyridinyl)spiro[1,3-oxazole-4,9'-xanthen]-2-amine;

(4S)-2'-(3,6-dihydro-2H-pyran-4-yl)-4'-fluoro-7'-(2-fluoro-3-pyridinyl)spiro[1,3-oxazole-4,9'-xanthen]-2-amine;

(5S)-3-(3,6-dihydro-2H-pyran-4-yl)-7-(5-fluoro-3-pyridinyl)spiro[chromeno[2,3-c]pyridine-5,4'-[1,3]oxazol]-2'-amine;

(5S)-3-(6,6-dimethyl-3,6-dihydro-2H-pyran-4-yl)-7-(3-pyridinyl)spiro[chromeno[2,3-c]pyridine-5,4'-[1,3]oxazol]-2'-amine;

(5S)-3-(3,6-dihydro-2H-pyran-4-yl)-7-(6-fluoro-3-pyridinyl)spiro[chromeno[2,3-c]pyridine-5,4'-[1,3]oxazol]-2'-amine;

(4S)-4'-fluoro-7'-(2-fluoro-3-pyridinyl)-2'-(tetrahydro-2H-pyran-4-yl)spiro[1,3-oxazole-4,9'-xanthen]-2-amine;

(4S)-4'-fluoro-7'-(2-fluoro-3-pyridinyl)-2'-(1-methyl-1H-pyrazol-4-yl)spiro[1,3-oxazole-4,9'-xanthen]-2-amine;

(4S)-3'-fluoro-2'-(2-fluoro-2-methylpropoxy)-7'-(3-pyridinyl)spiro[1,3-oxazole-4,9'-xanthen]-2-amine; and (5S)-3-(3,3-dimethyl-1-butyn-1-yl)-7-(5-pyrimidinyl)spiro[chromeno[2,3-c]pyridine-5,4'-[1,3]oxazol]-2'-amine.

9. A pharmaceutical composition comprising a compound according to claim 1 and a pharmaceutically acceptable excipient.

10. A process for preparing a compound of claim 1, the process comprising the step of reacting a compound 20

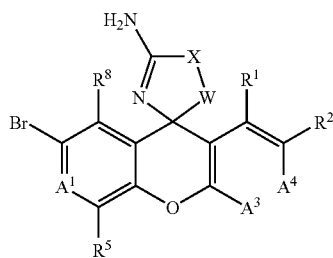

wherein
$A^1$ is $CR^6$;
$A^3$ is $CR^4$ or N;
$A^4$ is $CR^3$ or N;
each of $R^1$, $R^4$, $R^5$ and $R^8$, independently, is H, F, Cl, Br, $CF_3$, $OCF_3$, $C_{1-6}$-alkyl, CN, OH, —$OC_{1-6}$-alkyl, —$S(O)_o$ $C_{1-6}$-alkyl, —$NHC_{1-6}$-alkyl or —$C(O)C_{1-6}$-alkyl, wherein the $C_{1-6}$-alkyl and $C_{1-6}$-alkyl portion of —$OC_{1-6}$-alkyl, —$S(O)_oC_{1-6}$-alkyl, —$NHC_{1-6}$-alkyl and —$C(O)C_{1-6}$-alkyl are optionally substituted with 1-3 substituents of F, oxo or OH;
$R^2$ is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, Se, $NR^{10}R^{10}$, $C(O)R^{10}$, $S(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 9- or 10-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$;
each of $R^3$ and $R^6$, independently, is H, halo, haloalkyl, haloalkoxyl, $C_{1-6}$-alkyl, CN, OH, $OC_{1-6}$-alkyl, $S(O)_o$ $C_{1-6}$-alkyl, $NHC_{1-6}$-alkyl or $C(O)C_{1-6}$-alkyl;
each $R^9$, independently, is —$C(O)R^{10}$, —$S(O)_2R^{10}$, —$C(O)NHR^{10}$, —$NHC(O)R^{10}$, —$NHC(O)NHR^{10}$, —$S(O)_2NHR^{10}$ or —$NHS(O)_2R^{10}$;
each $R^{10}$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;
W is $CR^1R^1$; and
X is O,
with a compound having the structure $R^7$—$B(OH)_2$ wherein $R^7$ is H, halo, haloalkyl, haloalkoxyl, $C_{1-6}$-alkyl, $C_{2-6}$alkenyl, $C_{2-6}$-alkynyl, $C_{3-8}$-cycloalkyl, $C_{4-8}$-cycloalkenyl, CN, $OR^{10}$, $SR^{10}$, $NR^{10}R^{10}$, $C(O)R^{10}$, $S(O)R^{10}$, $S(O)_2R^{10}$, $NR^{10}C(O)R^{10}$, $C(O)NR^{10}R^{10}$, $NR^{10}S(O)_2R^{10}$, $S(O)_2NR^{10}$, $NR^{10}C(O)NR^{10}R^{10}$, or a fully saturated or partially or fully unsaturated 4-, 5-, 6- or 7-membered monocyclic or 9- or 10-membered bicyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl, $C_{4-8}$-cycloalkenyl and ring are optionally substituted, independently, with 1-5 substituents of $R^9$ or $R^{10}$,
to prepare the compound of claim 1.

11. The compound of claim 6, or a stereoisomer, tautomer or pharmaceutically acceptable salt thereof, wherein
each of $R^1$, $R^4$, $R^5$ and $R^8$, independently, is H, F, Cl, Br, $CF_3$, $CH_3$ or CN;
$R^2$ is halo, haloalkyl, haloalkoxyl, $C_{1-6}$-alkyl, $C_{2-6}$alkenyl, $C_{2-6}$-alkynyl, $C_{3-8}$-cycloalkyl, CN, $OR^{10}$, $SR^{10}$, $NR^{10}R^{10}$ or a fully saturated or partially or fully unsaturated 5- or 6-membered monocyclic ring formed of carbon atoms, said ring optionally including 1-4 heteroatoms selected from O, N, or S, wherein the $C_{1-6}$-alkyl, $C_{2-6}$-alkenyl, $C_{2-6}$-alkynyl, $C_{3-8}$-cycloalkyl and ring are optionally substituted, independently, with 1-5 substituents of $R^9$ or $R^{10}$;
each of $R^3$ and $R^6$, independently, is H, F, Cl, Br, $CF_3$, $OCF_3$, $CH_3$, $C_2H_5$, CN, OH, $OCH_3$;
$R^7$ is halo, haloalkyl, CN, $OR^{10}$, $SR^{10}$, $NR^{10}R^{10}$, $C(O)R^{10}$, $S(O)_2R^{10}$, $NR^{10}C(O)R^{10}$, $C(O)NR^{10}R^{10}$ or a fully saturated or partially or fully unsaturated 5- or 6-membered monocyclic ring formed of carbon atoms, said ring optionally including 1-4 heteroatoms selected from O, N, or S, and optionally substituted, independently, with 1-5 substituents of $R^9$ or $R^{10}$.

12. The compound of claim 6, or a stereoisomer, tautomer or pharmaceutically acceptable salt thereof, wherein
$A^1$ is CH, CF or N;
$A^3$ is CH, CF or N;
$A^4$ is CH, CF or N;
each of $R^1$, $R^5$ and $R^8$, independently, is H, F, Cl, Br, $CF_3$, $CH_3$ or CN;
$R^2$ is F, $CF_3$, $OCF_3$, $C_{1-6}$-alkyl or $OR^{10}$, wherein the $C_{1-6}$-alkyl is optionally substituted, independently, with 1-5 substituents of $R^9$ or $R^{10}$, or
$R^2$ is a ring selected from phenyl, pyridyl, pyrimidyl, pyridazinyl, pyrazinyl, triazinyl, thiophenyl, furyl, dihydrofuranyl, pyrrolyl, pyrazolyl, imidazolyl, imidazopyridiyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl, pyranyl, tetrahydropyranyl, duhydropyranyl, 2-oxo-5-aza-bicycloheptanyl, azetetinyl, pyridinonyl, pyrrolidinonyl, cyclopropyl, cyclobutyl, cyclopentyl, cyclohexyl, cyclohexenyl, tetrahydropyridinyl, dihydropyridinyl, thiopyranyl, dihydrothiopyranyl, benzofuranyl, dihydrobenzofuranyl, benzimidazolyl, benzopyrazolyl, said ring optionally substituted, independently, with 1-5 substituents of $R^9$ or $R^{10}$; and $R^7$ is $OR^{10}$, $SR^{10}$, $NR^{10}R^{10}$, $NR^{10}C(O)R^{10}$, $C(O)NR^{10}R^{10}$ or a ring selected from phenyl, naphthyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, quinolinyl, isoquinolinyl, naphthyridinyl, benzofuranyl, benzimidazolyl, benzopyrazolyl, morpholinyl, piperidinyl, piperazinyl and pyranyl, said ring optionally substituted, independently, with 1-5 substituents of $R^9$ or $R^{10}$.

13. The compound of claim 6 or a stereoisomer, tautomer or pharmaceutically acceptable salt thereof, wherein $A^1$ is CH;
$A^3$ is CH, CF or N;
$A^4$ is CH, CF or N;
each of $R^1$, $R^5$ and $R^8$, independently, is H or F;
$R^2$ is F, $CF_3$, $OCF_3$, $C_{1-6}$-alkyl or $OR^{10}$, wherein the $C_{1-6}$-alkyl is optionally substituted, independently, with 1-5 substituents of $R^9$ or $R^{10}$, or $R^2$ is a ring selected from 3-pyridyl, 4-pyridyl, 4-morpholinyl, tetrahydro-2H-pyran-4-yl, tetrahydro-2H-pyran-2-yl, dihydro-2H-pyran-2-yl, dihydro-2H-pyran-4-yl, -oxetanyl-ethynyl; 1-pyrrolidinyl, pyrrolidinon-2-yl, butyn-1-yl, methoxyl, ethoxyl, propoxyl, pyrazol-4-yl, phenyl, 3-ethoxy-3-methyl-butyn-1-yl, trimethylsilylethyn-1-yl, dimethylpropoxyl, 3,3-dimethyl-1-buten-1-yl, azetidin-1-yl, 6-methyl-pyran-2-one, piperizin-1-yl, 2,2-dimethylpropanitrile, tetrahydrofuran-3-yl, dihydrofuran-3-yl, 2,2dimethylpropylamino, piperidin-1-yl, isoxazol-5-yl, pyridinonyl, 1,3-thiazol-4-yl, 1,3-thiazol-2-yl, 1,3-thiazol-5-yl, 1,3-oxazol-4-yl, thien-3-yl, pyrazin-2-yl, 2-cyclopropylethyl, furan-2-yl, tetrahydropyridin-4-yl, 2-cyclopropylethenyl, cyclopropylethynyl, cyclopropyl and pyrimidin-5-yl, each of which is optionally substituted, independently, with 1-5 substituents of $R^9$ or $R^{10}$; and $R^7$ is $OR^{10}$, $SR^{10}$, $NR^{10}R^{10}$, $NR^{10}C(O)R^{10}$, $C(O)NR^{10}R^{10}$ or a ring selected from pyridin-3-yl, methoxyl, phenyl, 3-methyl-3-oxetanylethynyl, methoxyacetamido, 2-cyano-2-methylpropoxyl, cyclopropylethynyl, pyrimidin-5-yl, pyrimidin-2-yl, cyclopropylcarboxamido, 2-pyridylcarboxamido, 2-methoxypropanamido, 1-azetidinylcarbonyl, 2-tetrahydrofurancarboxamido, 2-pyridinecarboxamido, 3-pyridinecarboxamido, benzamido, 3-pyridazinyl, 2-pyrazinyl, N-cyclobutylcarboxamido, 3-thienyl, 3-furanyl, 2,2-dimethylpropoxyl, tetrahydropyran-4-yl, 1,3-thiazol-5-yl, 1,3-thiazol-4-yl and pyrrolidin-1-yl, each of which is optionally substituted, independently, with 1-5 substituents of $R^9$ or $R^{10}$.

14. The compound of claim 6, or a stereoisomer, tautomer or pharmaceutically acceptable salt thereof, selected from

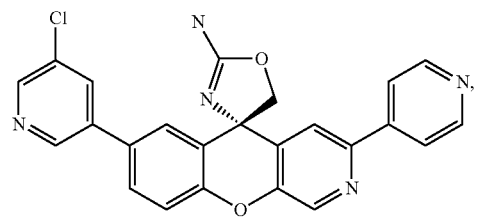

-continued

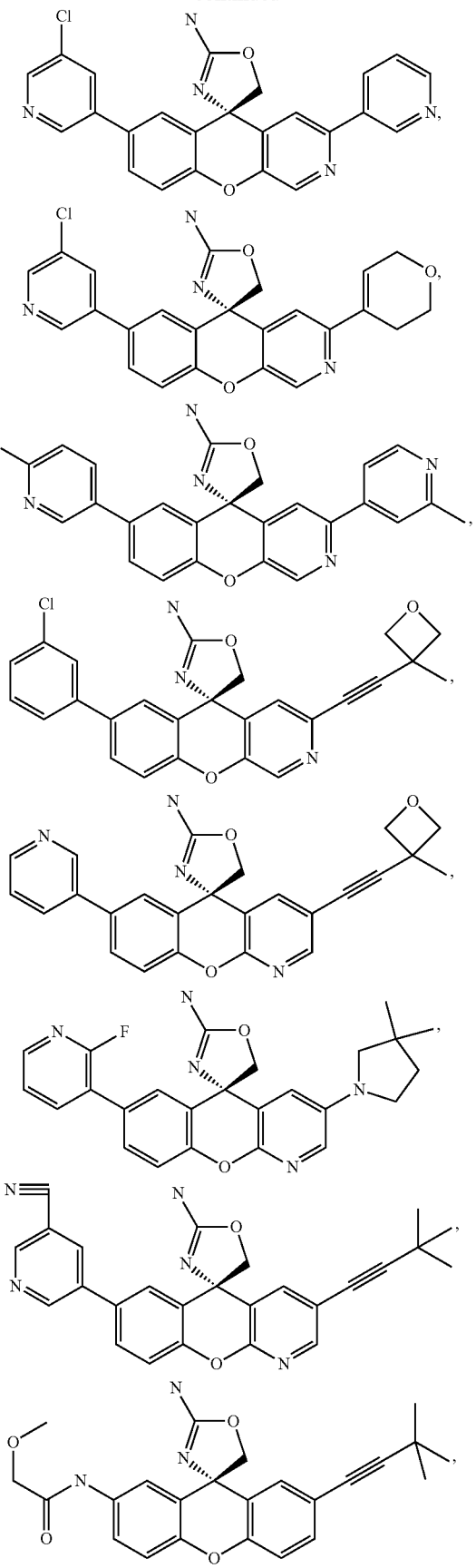

297
-continued
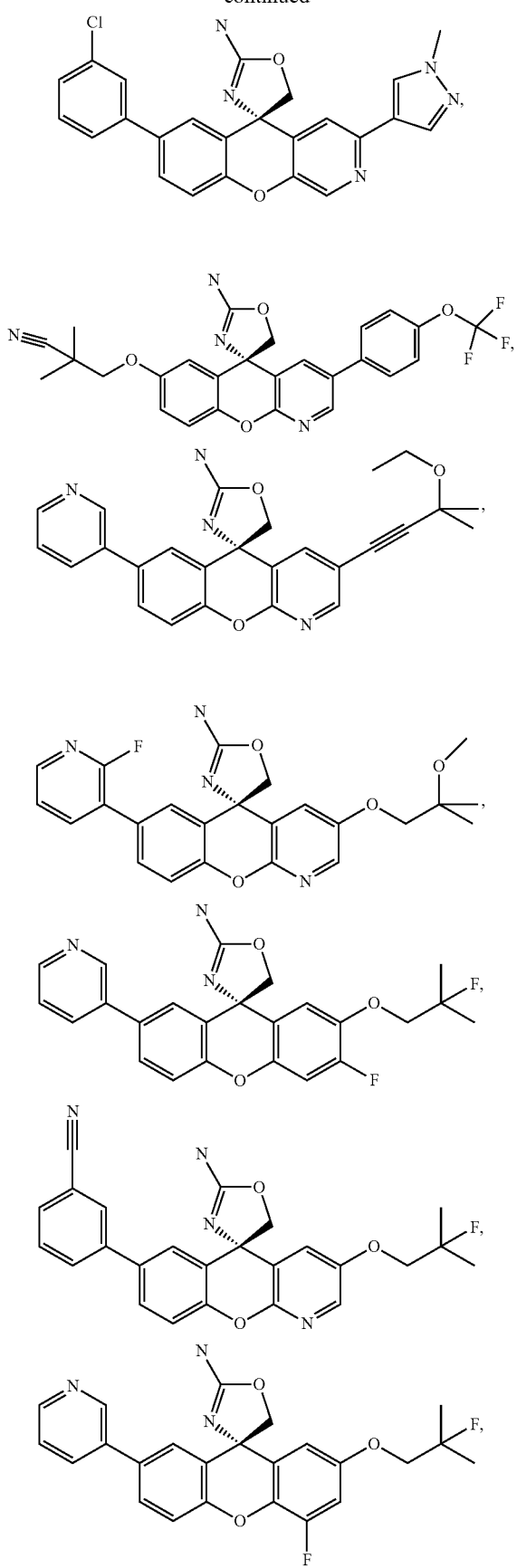
298
-continued
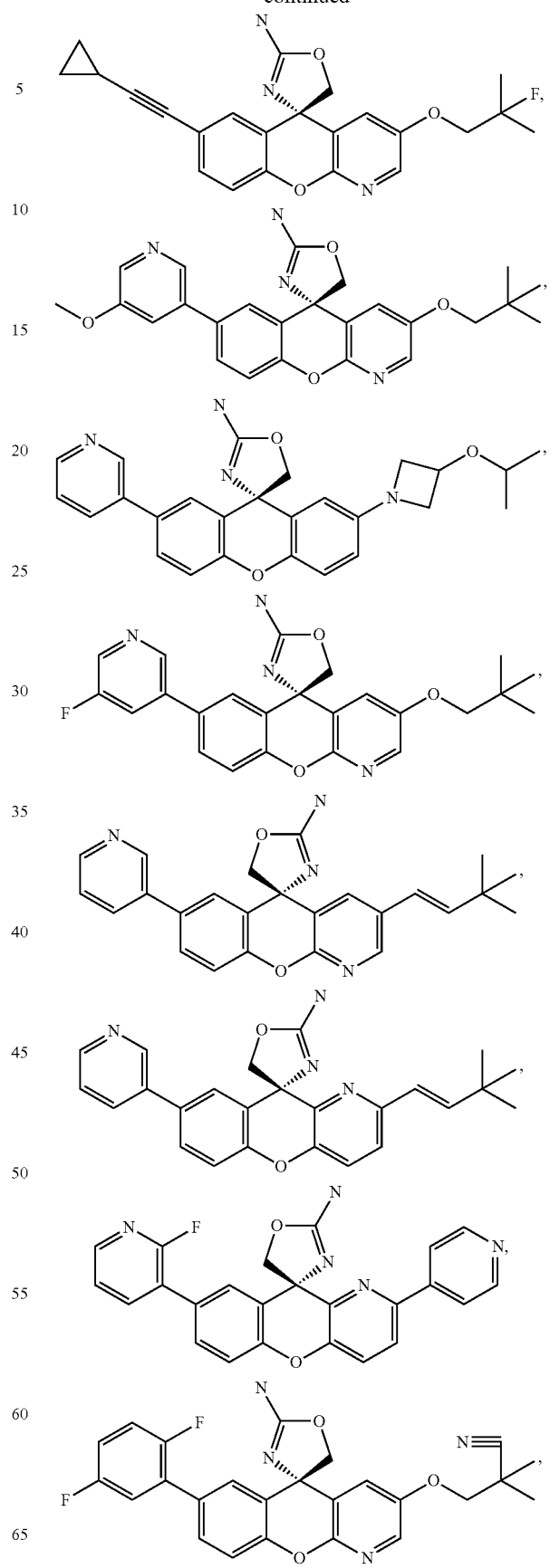

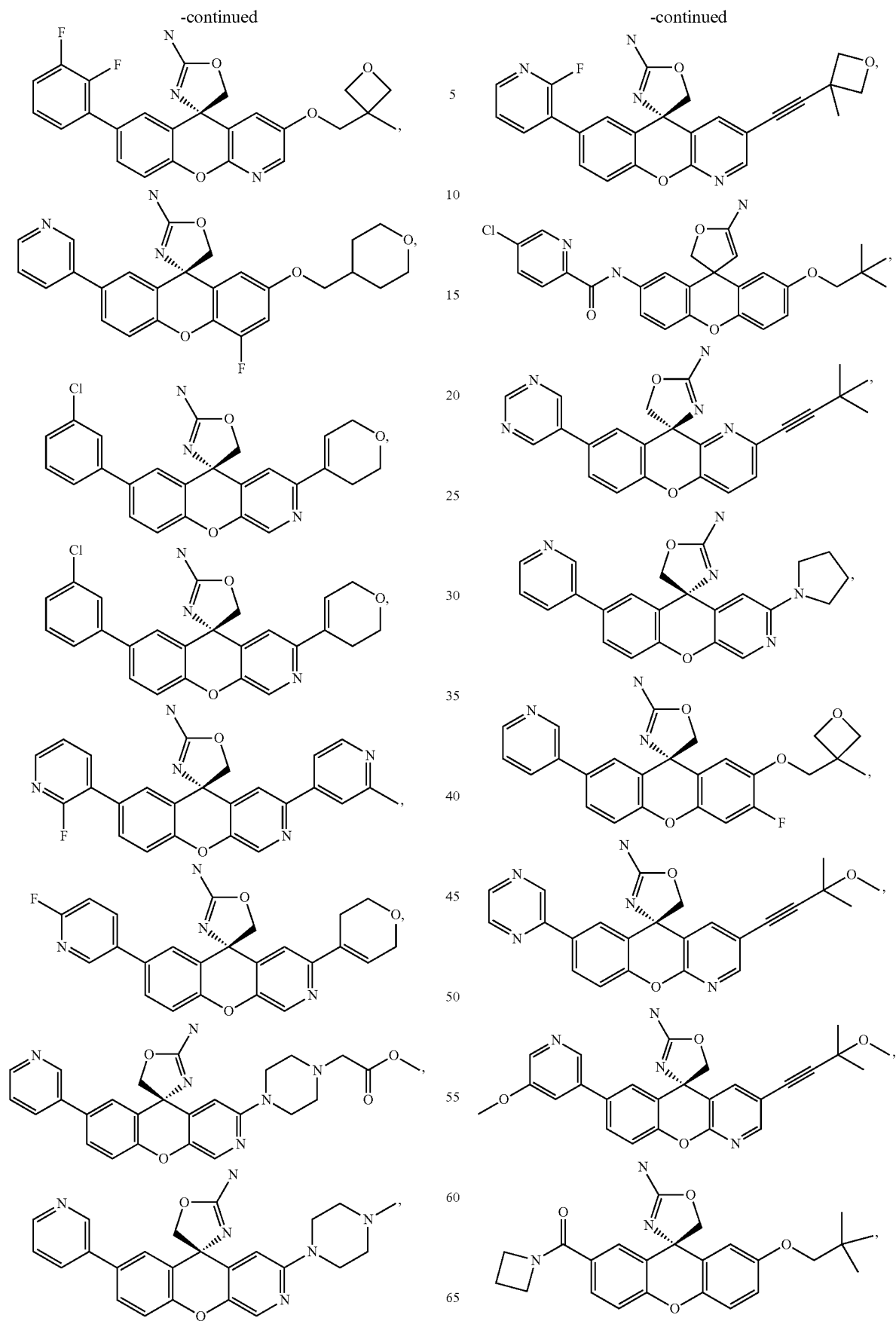

-continued

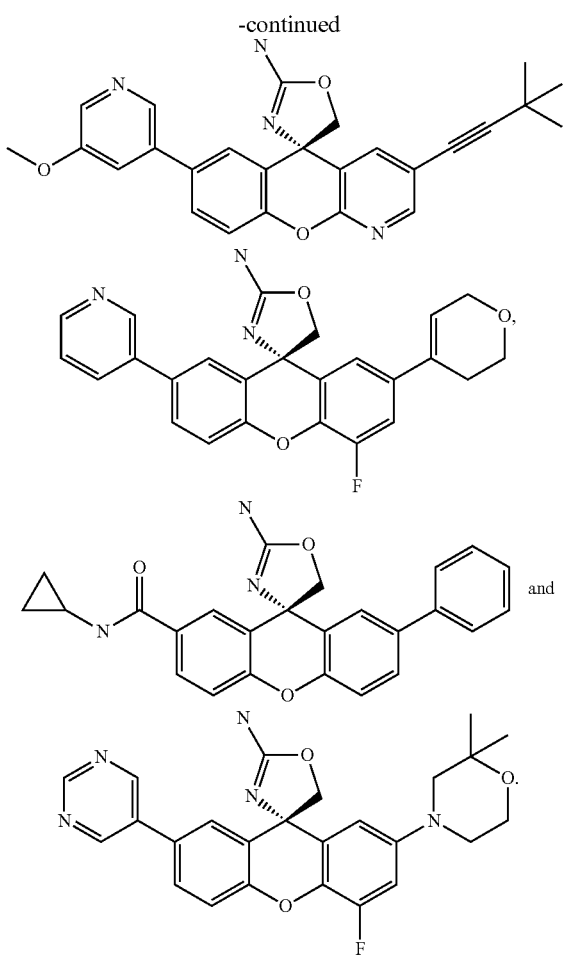

and

15. The compound of claim 14, or a pharmaceutically acceptable salt thereof, that is

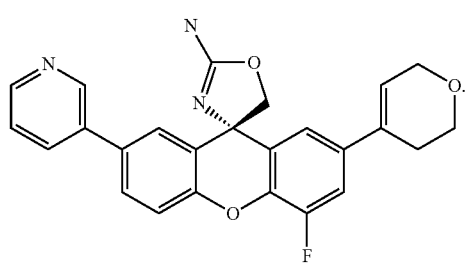 [SMILES: NC1=N[C@@]2(CO1)c1cc(-c3cccnc3)ccc1Oc1c(F)cc(C3=CCOCC3)cc12]

16. The compound of claim 14, or a pharmaceutically acceptable salt thereof, that is

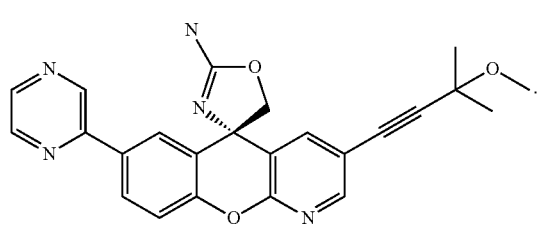 [SMILES: COC(C)(C)C#Cc1cnc2c(c1)[C@]1(COC(N)=N1)c1cc(-c3cnccn3)ccc1O2]

17. The compound of claim 14, or a pharmaceutically acceptable salt thereof, that is

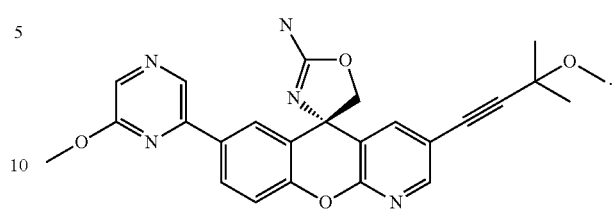

18. The compound of claim 14, or a pharmaceutically acceptable salt thereof, that is

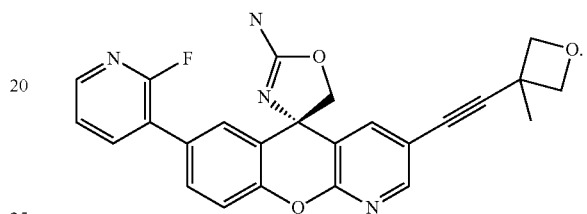

19. The compound of claim 14, or a pharmaceutically acceptable salt thereof, that is

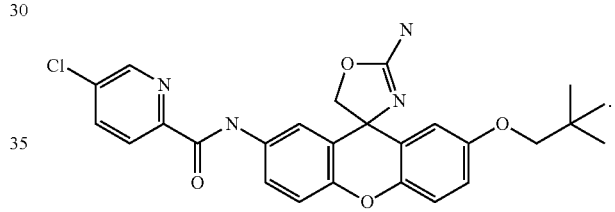

20. The compound of claim 14, or a pharmaceutically acceptable salt thereof, that is

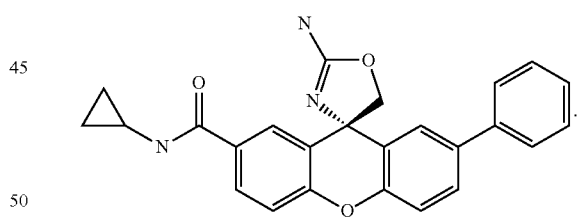

21. The compound of claim 14, or a pharmaceutically acceptable salt thereof, that is

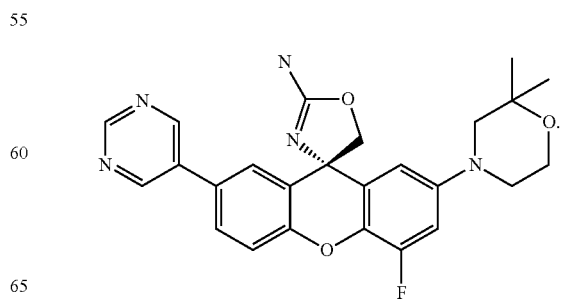

22. A pharmaceutical composition comprising the compound, or a pharmaceutically acceptable salt thereof, according to any one of claims 14-21 and a pharmaceutically acceptable excipient.

* * * * *